(12) United States Patent
Schroeder et al.

(10) Patent No.: US 9,445,596 B2
(45) Date of Patent: Sep. 20, 2016

(54) SMALL MOLECULE COMPOUNDS FOR THE CONTROL OF NEMATODES

(75) Inventors: Frank C. Schroeder, Ithaca, NY (US); Stephan H. von Reuss, Jena (DE); Andrea Choe, Los Angeles, CA (US); Paul W. Sternberg, Pasadena, CA (US)

(73) Assignees: California Institute of Technology, Pasadena, CA (US); Boyce Thompson Institute for Plant Research, Ithaca, NY (US)

( * ) Notice: Subject to any disclaimer, the term of this patent is extended or adjusted under 35 U.S.C. 154(b) by 233 days.

(21) Appl. No.: 14/237,774

(22) PCT Filed: Aug. 8, 2012

(86) PCT No.: PCT/US2012/050016
§ 371 (c)(1),
(2), (4) Date: Jun. 25, 2014

(87) PCT Pub. No.: WO2013/022985
PCT Pub. Date: Feb. 14, 2013

(65) Prior Publication Data
US 2014/0303360 A1 Oct. 9, 2014

Related U.S. Application Data

(60) Provisional application No. 61/521,295, filed on Aug. 8, 2011, provisional application No. 61/620,348, filed on Apr. 4, 2012.

(51) Int. Cl.
| | | |
|---|---|---|
| *C07H 15/04* | (2006.01) | |
| *C07H 15/10* | (2006.01) | |
| *C07H 15/18* | (2006.01) | |
| *A01N 63/02* | (2006.01) | |
| *A01N 47/36* | (2006.01) | |
| *A01N 37/46* | (2006.01) | |
| *A61K 31/7076* | (2006.01) | |
| *A61K 31/708* | (2006.01) | |
| *A01N 43/90* | (2006.01) | |
| *C07H 19/16* | (2006.01) | |
| *A01N 43/16* | (2006.01) | |
| *A01N 43/38* | (2006.01) | |

(52) U.S. Cl.
CPC ............... *A01N 43/90* (2013.01); *A01N 37/46* (2013.01); *A01N 43/16* (2013.01); *A01N 43/38* (2013.01); *A01N 47/36* (2013.01); *A01N 63/02* (2013.01); *A61K 31/708* (2013.01); *A61K 31/7076* (2013.01); *C07H 15/04* (2013.01); *C07H 15/10* (2013.01); *C07H 15/18* (2013.01); *C07H 19/16* (2013.01)

(58) Field of Classification Search
None
See application file for complete search history.

(56) References Cited

U.S. PATENT DOCUMENTS

| | | | |
|---|---|---|---|
| 5,945,445 A | 8/1999 | Barringer et al. | |
| 6,444,686 B1 | 9/2002 | Ko et al. | |
| 8,318,146 B1* | 11/2012 | Teal ..................... | C07H 15/04 424/84 |
| 2005/0075389 A1 | 4/2005 | Paik et al. | |
| 2008/0188646 A1 | 8/2008 | Jung et al. | |
| 2010/0048497 A1 | 2/2010 | Andersch et al. | |
| 2010/0056469 A1 | 3/2010 | Langewald et al. | |
| 2014/0303102 A1* | 10/2014 | Choe ..................... | A61K 31/454 514/25 |
| 2014/0364386 A1* | 12/2014 | Choe ..................... | A61K 31/454 514/32 |
| 2014/0364586 A1 | 12/2014 | Watts et al. | |
| 2015/0018291 A1* | 1/2015 | Choe ..................... | A61K 31/454 514/25 |

FOREIGN PATENT DOCUMENTS

| | | |
|---|---|---|
| KR | 10-2009-0088496 | 8/2009 |
| WO | WO-96/19920 | 7/1996 |
| WO | WO-2009/102736 | 8/2009 |
| WO | WO-2013/022996 A2 | 2/2013 |
| WO | WO-2013/022997 A2 | 2/2013 |
| WO | WO-2013/023000 A2 | 2/2013 |

OTHER PUBLICATIONS

Von Reuss et al., "Comparative Metabolomics Reveals Biogenesis of Ascarosides, a Modular Library of Small-Molecule Signals in C. elegans" Journal of the American Chemical Society (2012) vol. 134 pp. 1817-1824.*
Srinivasan et al., "A blend of small molecules regulates both mating and development in Caenorhabditis elegans" Nature (2008) vol. 454 pp. 1115-1119.*
Cheng et al., "Insertional Mutagenesis of a Fungal Biocontrol Agent Led to Discovery of a Rare Cellobiose Lipid with Antifungal Activity" Applied and Environmental Microbiology (2003) vol. 69 No. 5 pp. 2595-2602.*
Bose et al., "Complex Small-Molecule Architectures Regulate Phenotypic Plasticity in a Nematode" Angewandte Chem int ed. (2012) vol. 51 pp. 12438-12443.*
Jeong et al., "Chemical structure and biological activity of the Caenorhabditis elegans dauer-inducing pheromone" Nature (2005) vol. 433, pp. 541-545.*
International Search Report dated Jul. 25, 2013 from PCT/US2012/050016 .
International Search Report dated May 2, 2013 from PCT/US2012/050032.
Choe et al., "Ascaroside Signaling is Widely Conserved Among Nematodes," Curr Biol., 22(9):772-780 (2012).

(Continued)

*Primary Examiner* — Eric Olson
(74) *Attorney, Agent, or Firm* — Foley Hoag LLP; David P. Halstead

(57) ABSTRACT

The present invention relates to compounds involved in nematode signaling.

7 Claims, 145 Drawing Sheets

(56) References Cited

OTHER PUBLICATIONS

Gallo et al., "Effects of a Caenorhabditis elegans dauer pheromone ascaroside on physiology and signal transduction pathways," J. Chem. Ecol., 35(2):272-279 (2009).
Jeong et al., "Chemical structure and biological activity of the Caenorhabditis elegans dauer-inducing pheromone," Nature, 433(7025):541-545 (2005).
Noh et al., "Quantitative determination of daumone in rat plasma by liquid chromatography-mass spectrometry," J. Pharm. Biomed. Anal., 56(1):114-117 (2011).
Butcher, Rebecca A., et al. "An Indole-Containing Dauer Pheromone Component with Unusual Dauer Inhibitory Activity at Higher Concentrations," Organic Letters 11(14): 3100-3103 (May 9, 2009).
Butcher, R.A., et al. "Biosynthesis of the Caenorhabditis elegans dauer pheromone," Proceedings of the National Academy of Sciences, 106(6): 1875-1879 (Feb. 10, 2009).
Butcher, R. A. "Small-molecule pheromones that control dauer development in Caenorhabditus elegans," J. Nat. Chem. Biol. 3(7): 420-422 (2007).
Choe, Andrea, "Pheromones in Free-Living and Parasitic Nematodes," Thesis for California Institute of Technology, (Jun. 17, 2011) (Made publically available Dec. 2, 2013).
Chuman, T., et al. "Identification and Characterization of Nematode Pheromones," National High Magnetic Field Laboratory (Jan. 1, 2009).
European C. elegans Neurobiology Meeting; Oct. 9, 2010. (http://ww.worms.gr/ewnm2010/files/abstracts.pdf).
Kaplan, F., et al. "Ascaroside Expression in *Caenorhabditis elegans* Is Strongly Dependent on Diet and Developmental Stage," PLOSOne, 6(3): e17804 (Mar. 2011).
Martin, R., et al. "Improved Synthesis of an Ascaroside Pheromone Controlling Dauer Larva Development in *Caenorhabditis Elegans*," Synthesis, 20: 3488 (2009).
Pungaliya, C., et al. "A shortcut to identifying small molecule signals that regulate behavior and development in Caenorhabditis elegans," Proceedings of the National Academy of Sciences, 106(19): 7708-7713 (May 12, 2009).
Von Reuss, Stephan H., et al. "Comparative Metabolomics Reveals Biogenesis of Ascarosides, a Modular Library of Small-Molecule Signals in *C. elegans*," Journal of the American Chemical Society, 134(3): 1817-1824; (Jan. 25, 2012).
European Extended Search Report for EP Patent Application: 12822518.2 dated Jan. 30, 2015.
Ben-Yakir, D. et al., "Evaluation of entomopathogenic nematodes for biocontrol of the European Corn Borer, *Ostrinia nubilalis*, on sweet corn in Israel," Phytoparasitica, 26(2):101-8 (1998).
Lacey, L.A. et al., "Insect pathogens as biological control agents: Do they have a future?" Biol Control, 21:230-48 (2001).
Riga, E. et al., "In vitro effect of marigold seed exudates on plant parasitic nematodes," Phytoprotection, 86:31-5 (2004).

* cited by examiner

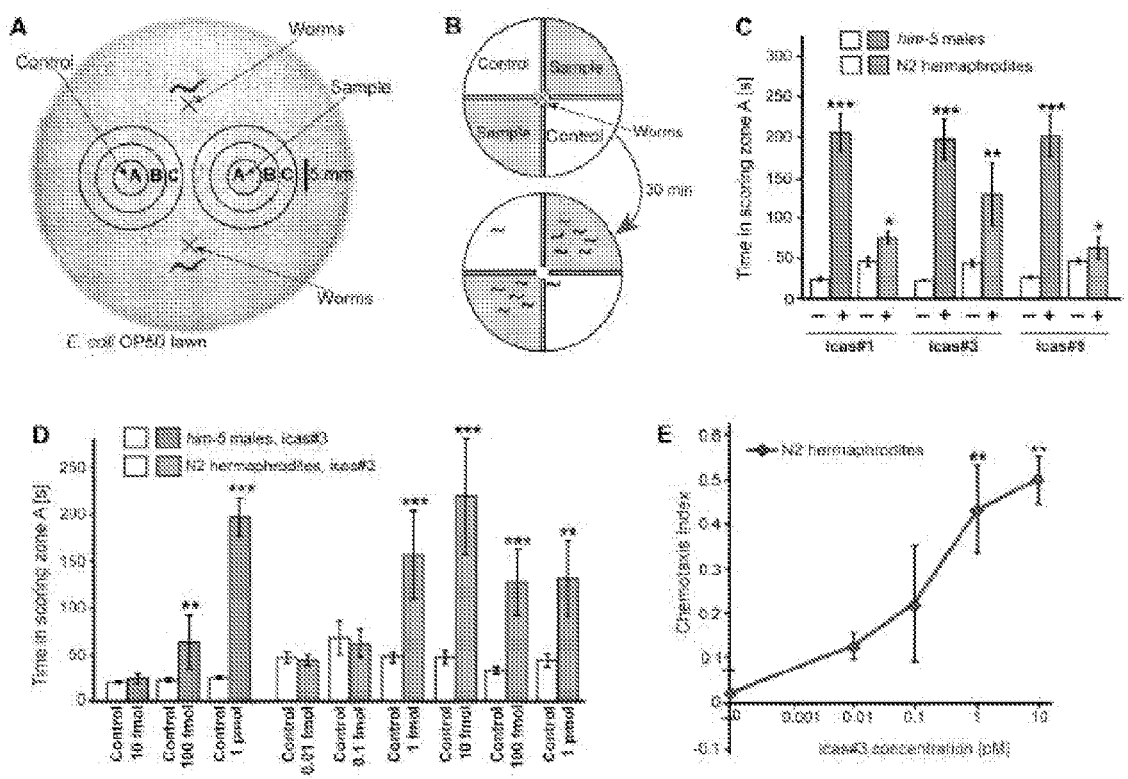
Figures 1A–E

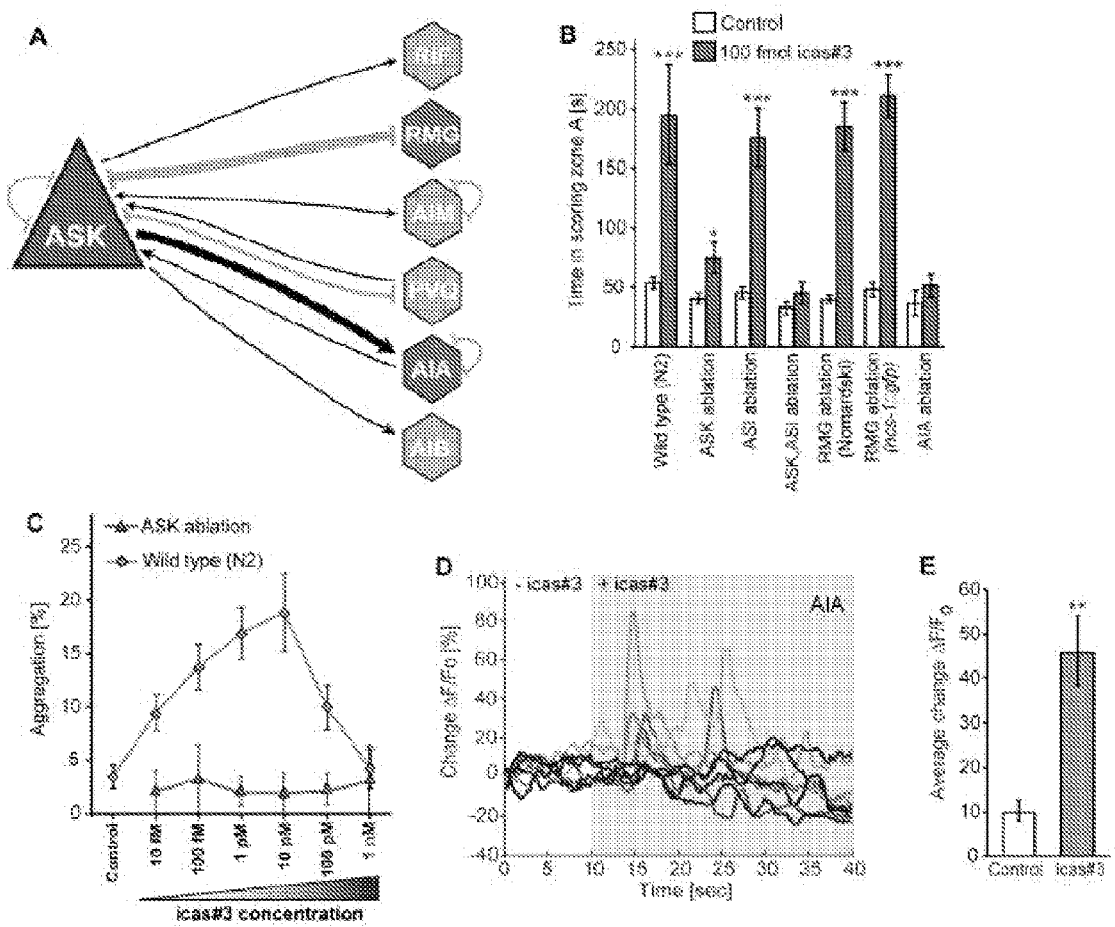
Figures 2A–E

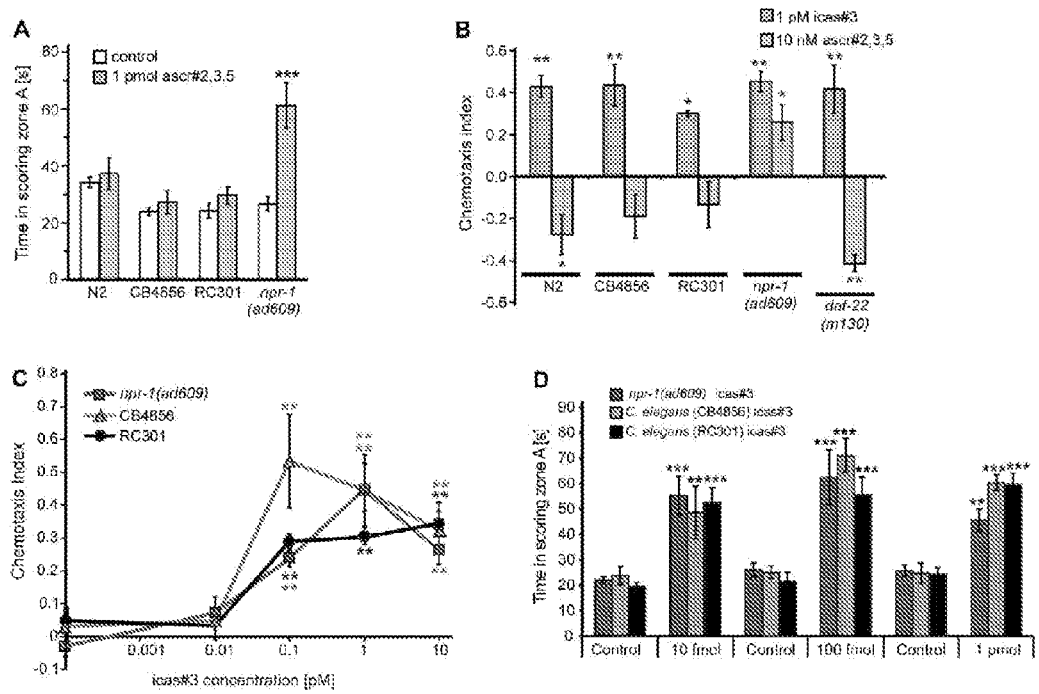
Figures 3A–D
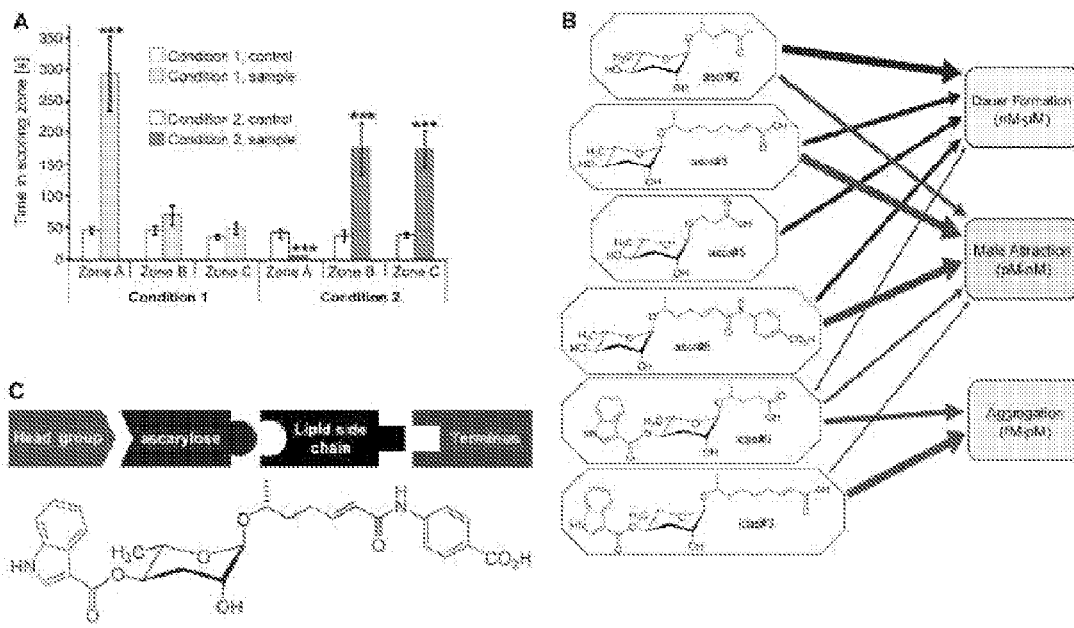
Figures 4A–C

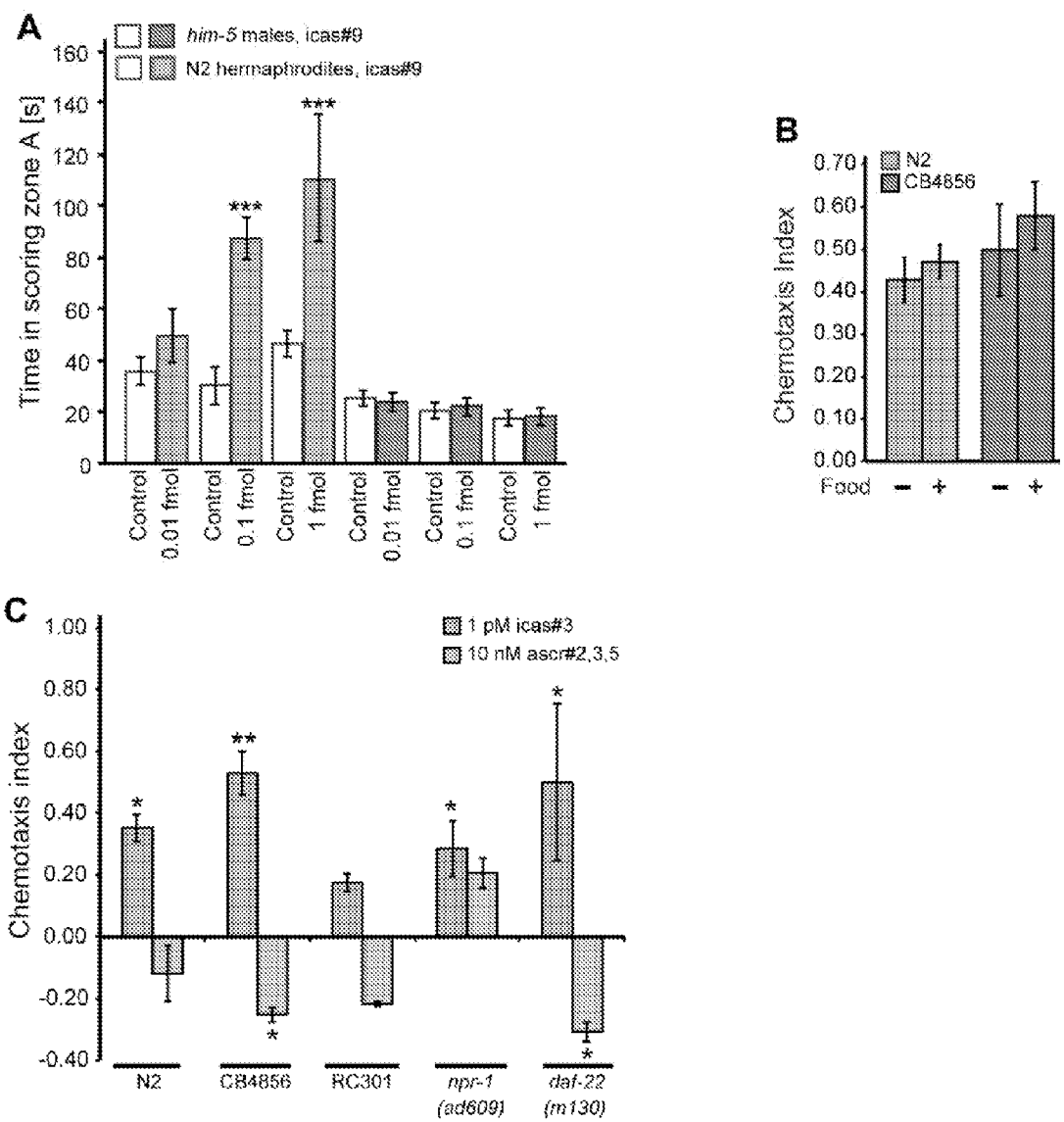
Figures 5A–C

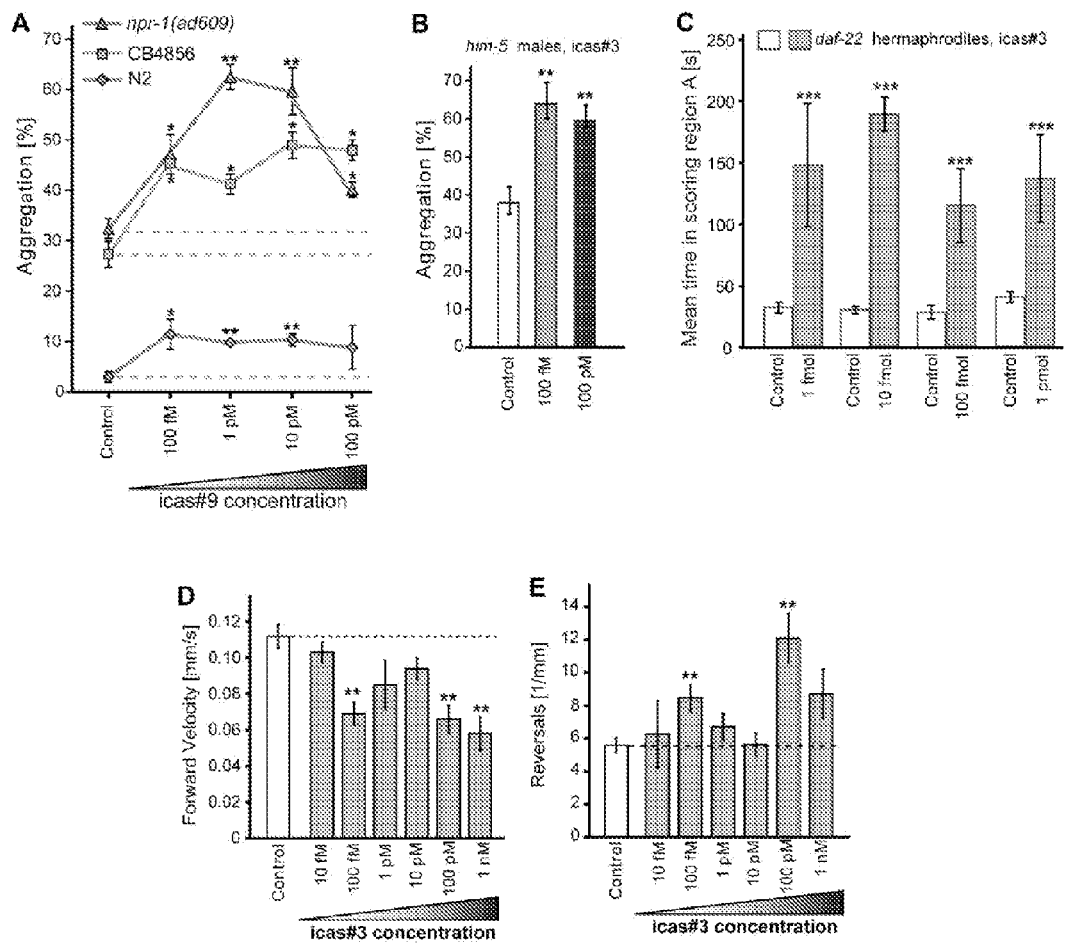
Figures 6A–E

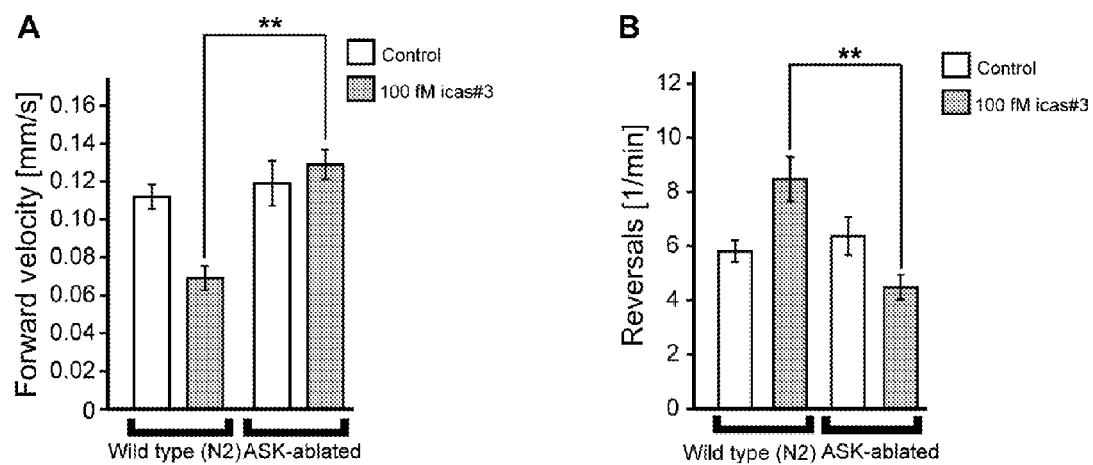
Figures 7A-B

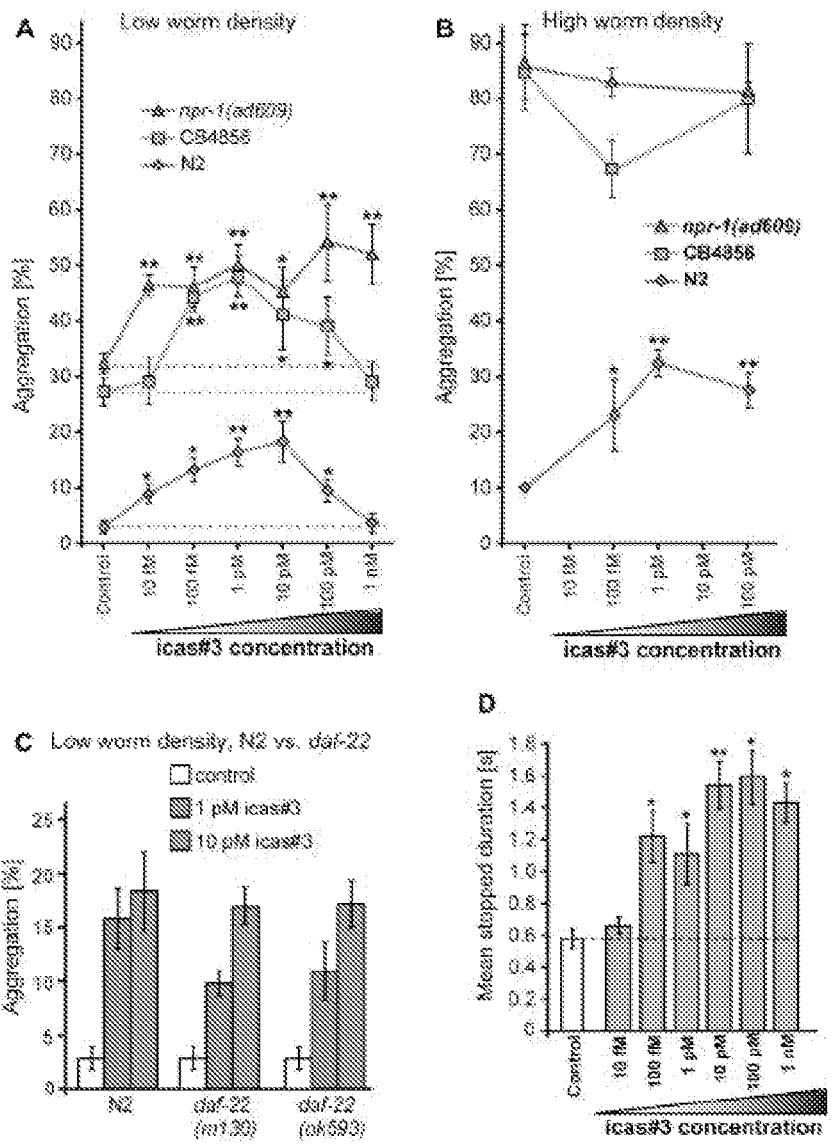
Figures 8A–D

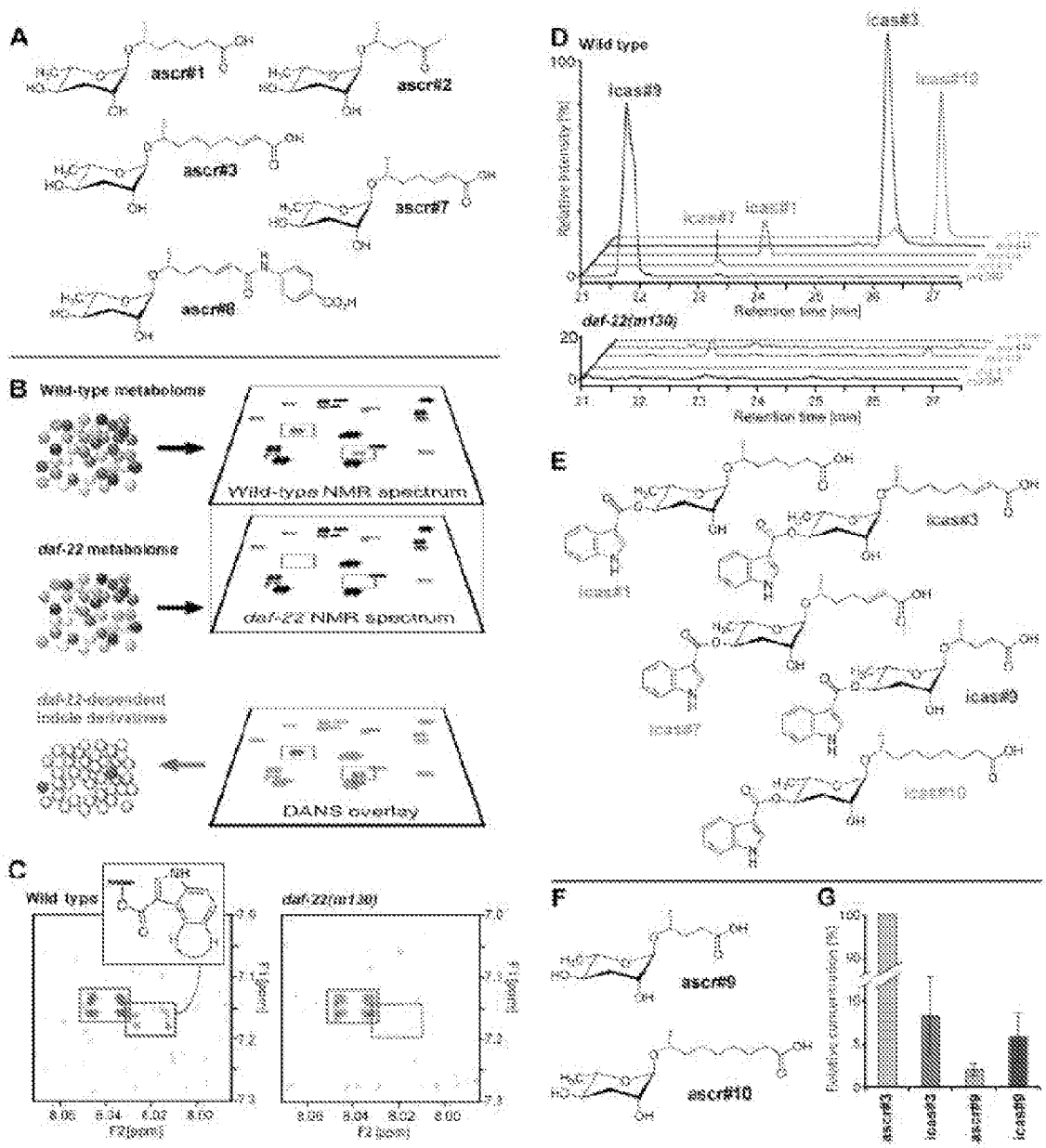
Figures 9A–G

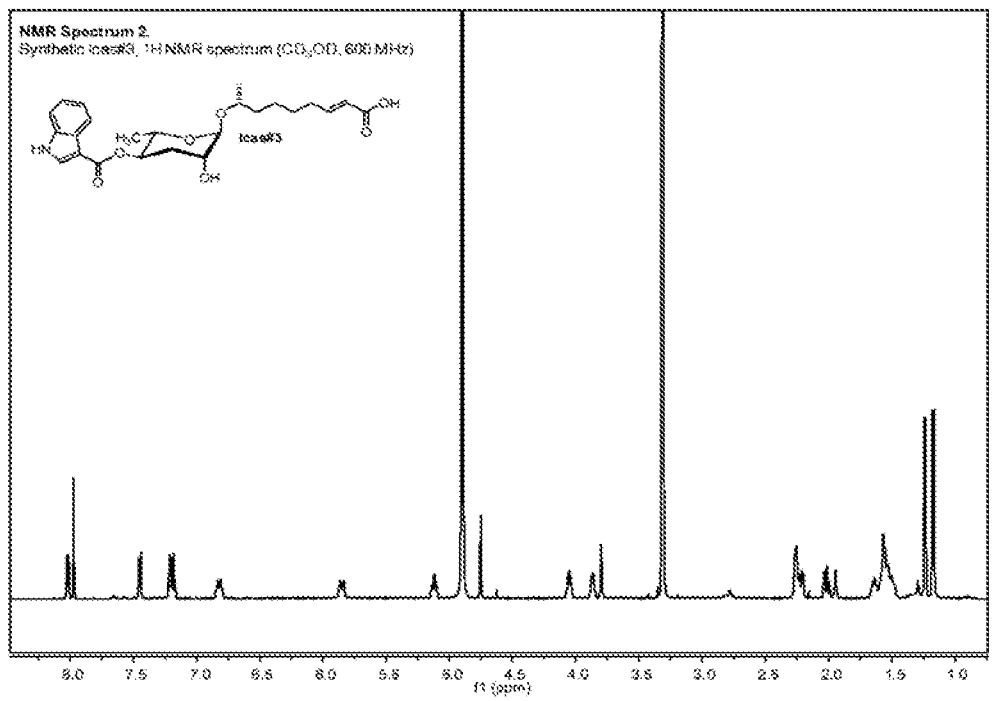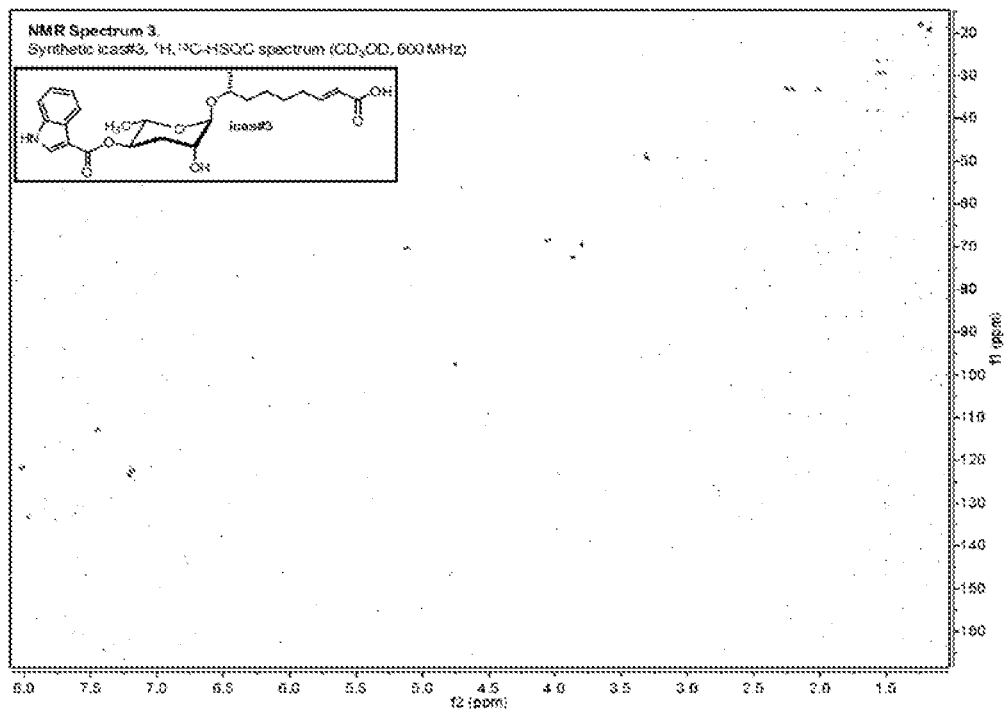
Figures 11A-B

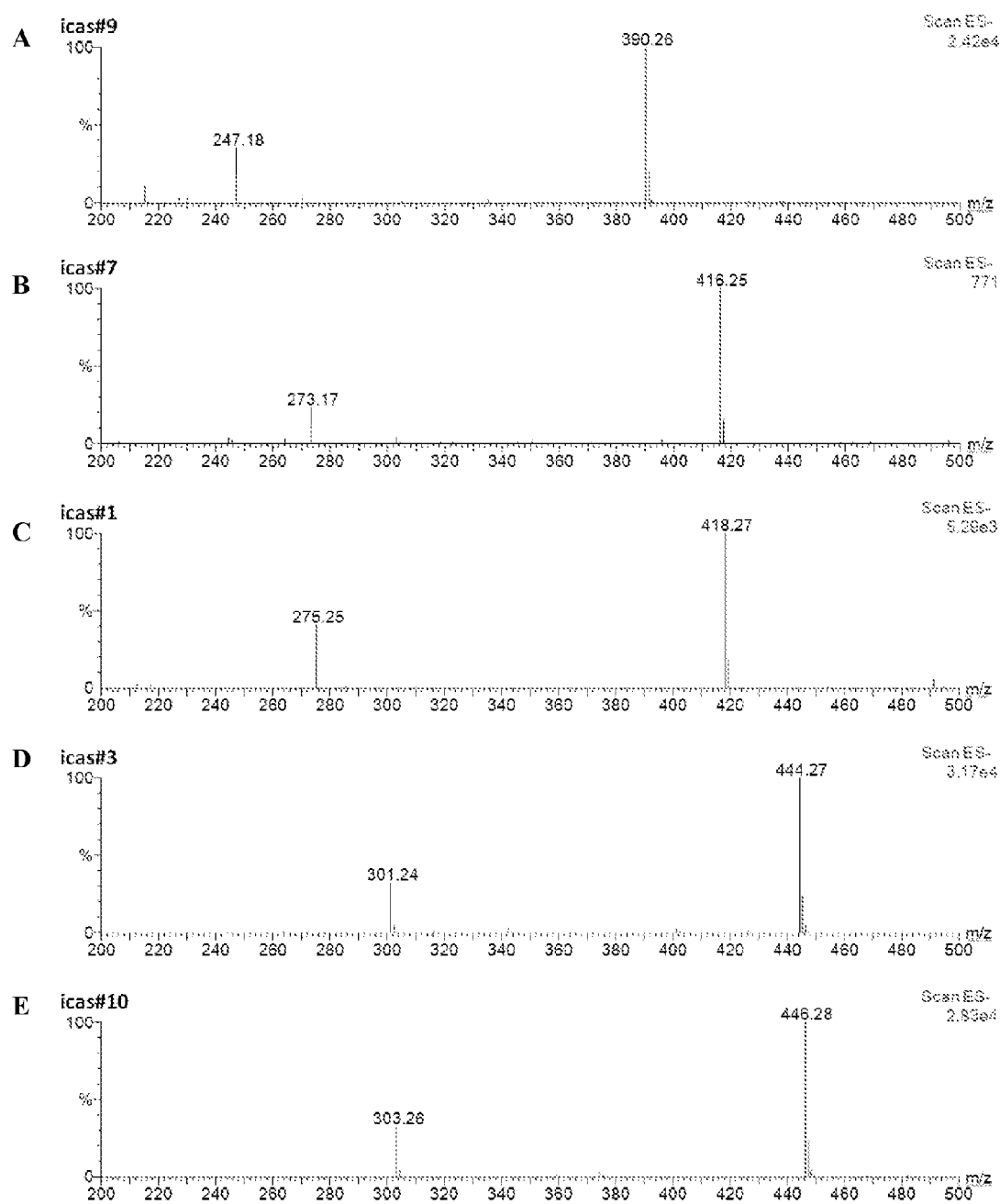
Figures 12A–E

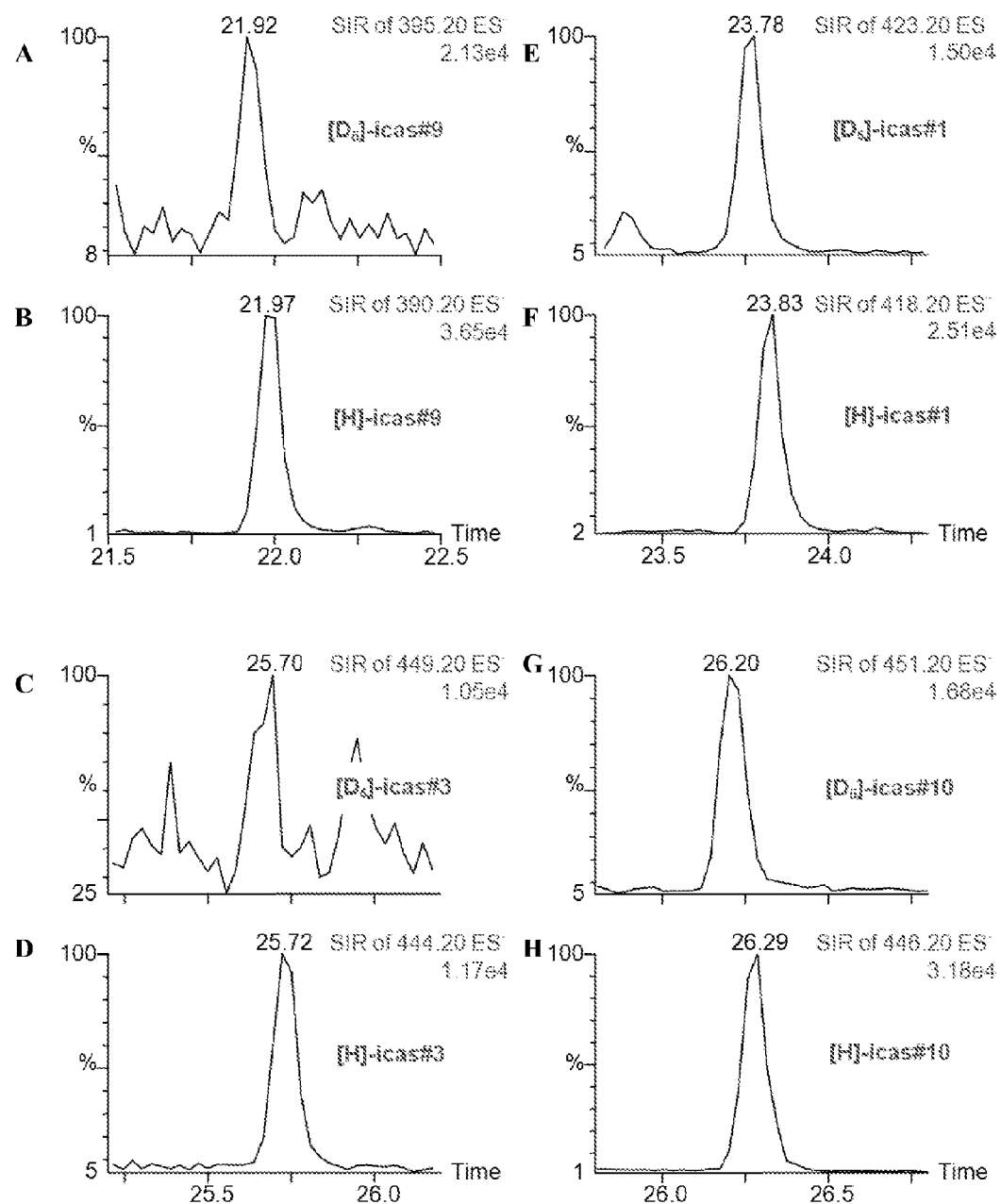
Figures 13A–H

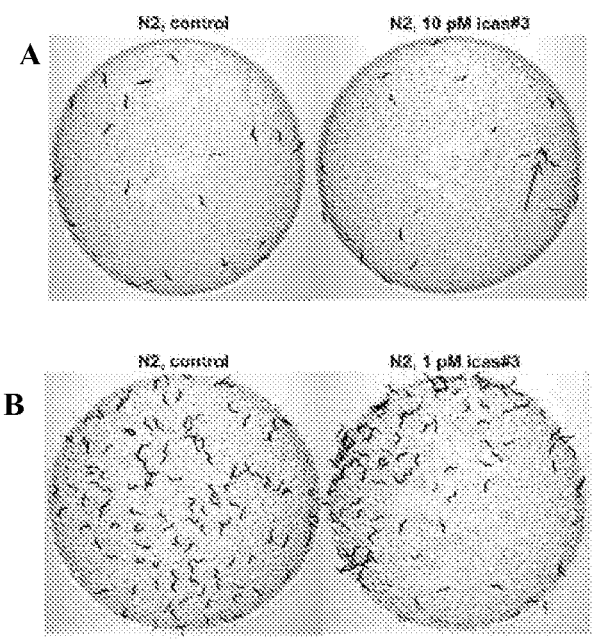
Figures 14A-B
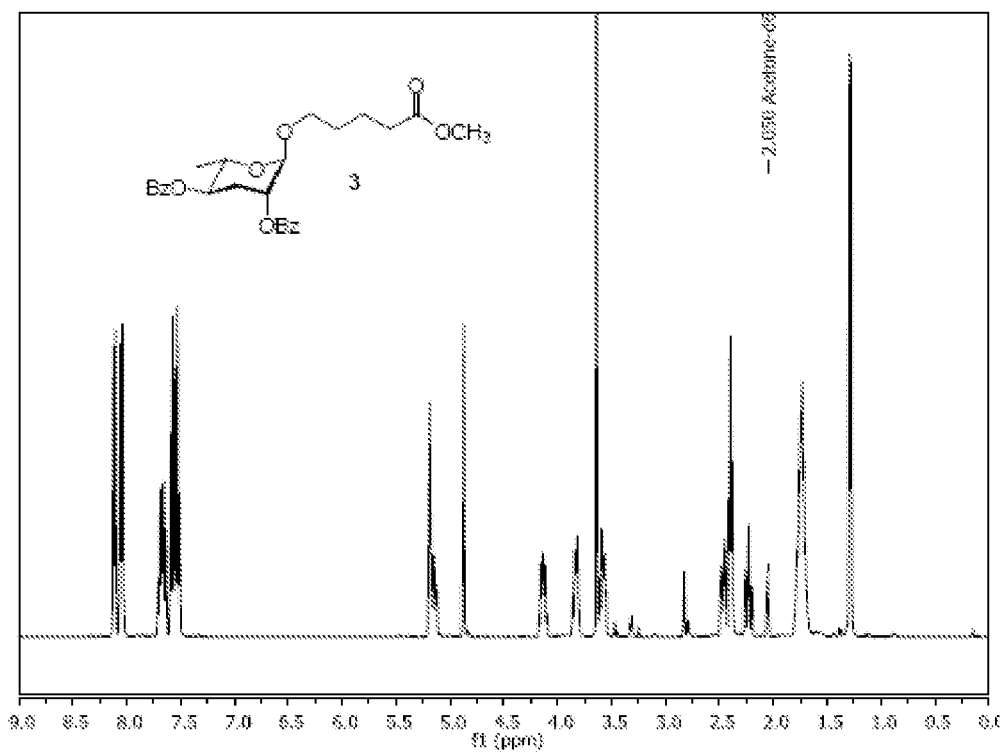
Figure 15A

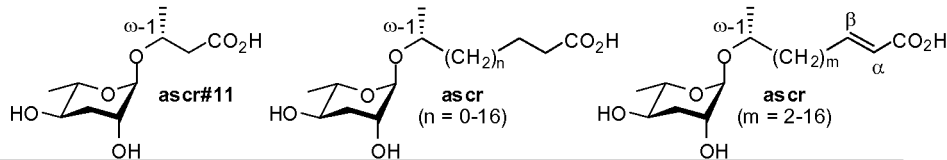

| Side chain Length (n, m) | SMID[S] | Molecular formula | Molecular Weight amu | m/z M-H- calculated | m/z M-H- observed | Retention time min ±SD |
|---|---|---|---|---|---|---|
| C4 | ascr#11* | C10H18O6 | 234.1103 | 233.1025 | 233.1031 | 10.21 ±0.03 |
| C5, n=0 | ascr#9*[4] | C11H20O6 | 248.1260 | 247.1182 | 247.1189 | 11.69 ±0.01 |
| C6, n=1 | ascr#12 | C12H22O6 | 262.1416 | 261.1338 | 261.1343 | 13.09 ±0.02 |
| ΔC7, m=2 | ascr#7*[2] | C13H22O6 | 274.1416 | 273.1339 | 273.1337 | 13.96 ±0.07 |
| C7, n=2 | ascr#1*[5] | C13H24O6 | 276.1573 | 275.1495 | 275.1497 | 14.52 ±0.04 |
| ΔC8, m=3 | ascr#13 | C14H24O6 | 288.1573 | 287.1495 | 287.1481 | 15.61 ±0.18 |
| C8, n=3 | ascr#14 | C14H26O6 | 290.1729 | 289.1651 | 289.1647 | 15.96 ±0.03 |
| ΔC9, m=4 | ascr#3*[6] | C15H26O6 | 302.1729 | 301.1651 | 301.1652 | 16.90 ±0.02 |
| C9, n=4 | ascr#10*[4] | C15H28O6 | 304.1886 | 303.1808 | 303.1800 | 17.44 ±0.02 |
| ΔC10, m=5 | ascr#15 | C16H28O6 | 316.1886 | 315.1808 | 315.1817 | 18.34 ±0.02 |
| C10, n=5 | ascr#16 | C16H30O6 | 318.2042 | 317.1964 | 317.1959 | 18.98 ±0.05 |
| ΔC11, m=6 | ascr#17 | C17H30O6 | 330.2042 | 329.1964 | 329.1957 | 19.75 ±0.02 |
| C11, n=6 | ascr#18 | C17H32O6 | 332.2199 | 331.2121 | 331.2130 | 20.43 ±0.02 |
| ΔC12, m=7 | ascr#19[7] | C18H32O6 | 344.2199 | 343.2121 | 343.2120 | 21.36 ±0.03 |
| C12, n=7 | ascr#20 | C18H34O6 | 346.2355 | 345.2277 | 345.2278 | 21.97 ±0.03 |
| ΔC13, m=8 | ascr#21[7] | C19H34O6 | 358.2355 | 357.2277 | 357.2273 | 22.83 ±0.02 |
| C13, n=8 | ascr#22 | C19H36O6 | 360.2512 | 359.2434 | 359.2437 | 23.58 ±0.02 |
| ΔC14, m=9 | ascr#23[7] | C20H36O6 | 372.2512 | 371.2434 | 371.2444 | 24.46 ±0.01 |
| C14, n=9 | ascr#24 | C20H38O6 | 374.2668 | 373.2590 | 373.2596 | 25.29 ±0.03 |
| ΔC15, m=10 | ascr#25[7] | C21H38O6 | 386.2668 | 385.2590 | 385.2598 | 26.15 ±0.02 |
| C15, n=10 | ascr#26 | C21H40O6 | 388.2825 | 387.2747 | 387.2743 | 27.09 ±0.02 |
| ΔC16, m=11 | ascr#27 | C22H40O6 | 400.2825 | 399.2747 | 399.2734 | 27.89 ±0.03 |
| C16, n=11 | ascr#28 | C22H42O6 | 402.2981 | 401.2903 | 401.2901 | 28.97 ±0.04 |
| ΔC17, m=12 | ascr#29 | C23H42O6 | 414.2981 | 413.2903 | 413.2891 | 29.80 ±0.03 |
| C17, n=12 | ascr#30 | C23H44O6 | 416.3138 | 415.3060 | 415.3067 | 30.96 ±0.03 |
| ΔC18, m=13 | ascr#31 | C24H44O6 | 428.3138 | 427.3060 | 427.3075 | 31.78 ±0.03 |
| C18, n=13 | ascr#32 | C24H46O6 | 430.3294 | 429.3216 | 429.3221 | 33.02 ±0.02 |
| ΔC19, m=14 | ascr#33 | C25H46O6 | 442.3294 | 441.3216 | 441.3215 | 33.74 ±0.03 |
| C19, n=14 | ascr#34 | C25H48O6 | 444.3451 | 443.3373 | 443.3374 | 35.12 ±0.08 |
| ΔC20, m=15 | ascr#35 | C26H48O6 | 456.3451 | 455.3373 | 455.3371 | 35.59 ±0.06 |
| C20, n=15 | ascr#36 | C26H50O6 | 458.3607 | 457.3529 | 457.3501 | 37.14 ±0.07 |
| ΔC21, m=16 | ascr#37 | C27H50O6 | 470.3607 | 469.3529 | 469.3519 | 37.71 ±0.13 |
| C21, n=16 | ascr#38 | C27H52O6 | 472.3764 | 471.3686 | 471.3697 | 39.15 ±0.06 |

[2.] Pungaliya et al., *Proc. Nat'l Acad. Sci. U.S.A.* 106:7708–13 (2009), which is hereby incorporated by reference in its entirety.
[4.] Srinivasan et al., *Pub. Lib. Sci. Biol.* 10:e1001237 (2012), which is hereby incorporated by reference in its entirety.
[5.] Jeong et al., *Nature* 433:541–45 (2005), which is hereby incorporated by reference in its entirety.
[6.] Butcher et al., *Nat. Chem. Biol.* 3:420–22 (2007), which is hereby incorporated by reference in its entirety.
[7.] Butcher et al., *Proc. Nat'l Acad. Sci. U.S.A.* 106:1875–79 (2009), which is hereby incorporated by reference in its entirety.

Figure 37A

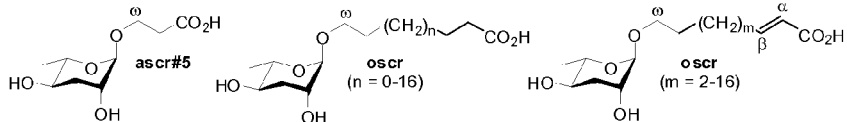

| Side chain length (n, m) | SMID[S] | Molecular formula | Molecular weight amu | m/z M-H- calculated | m/z M-H- observed | Retention time min ±SD |
|---|---|---|---|---|---|---|
| C3 | ascr#5*[8] | C9H16O6 | 220.0947 | 219.0869 | 219.0871 | 6.53 ±0.07 |
| C5, n=0 | oscr#9* | C11H20O6 | 248.1260 | 247.1182 | 247.1192 | 11.88 ±0.02 |
| C6, n=1 | oscr#12 | C12H22O6 | 262.1416 | 261.1338 | 261.1345 | 13.40 ±0.02 |
| ΔC7, m=2 | oscr#7 | C13H22O6 | 274.1416 | 273.1339 | 273.1350 | 14.67 ±0.02 |
| C7, n=2 | oscr#1 | C13H24O6 | 276.1573 | 275.1495 | 275.1503 | 14.95 ±0.03 |
| C8, n=3 | oscr#14 | C14H26O6 | 290.1729 | 289.1651 | 289.1672 | 16.45 ±0.02 |
| ΔC9, n=4 | oscr#3 | C15H26O6 | 302.1729 | 301.1651 | 301.1636 | 17.58 ±0.03 |
| C9, n=4 | oscr#10* | C15H28O6 | 304.1886 | 303.1808 | 303.1814 | 18.00 ±0.02 |
| ΔC10, m=5 | oscr#15 | C16H28O6 | 316.1886 | 315.1808 | 315.1816 | 18.91 ±0.06 |
| C10, n=5 | oscr#16 | C16H30O6 | 318.2042 | 317.1964 | 317.1967 | 19.48 ±0.03 |
| ΔC11, m=6 | oscr#17 | C17H30O6 | 330.2042 | 329.1964 | 329.1956 | 20.39 ±0.01 |
| C11, n=6 | oscr#18 | C17H32O6 | 332.2199 | 331.2121 | 331.2124 | 20.98 ±0.08 |
| ΔC12, m=7 | oscr#19 | C18H32O6 | 344.2199 | 343.2121 | 343.2125 | 21.86 ±0.06 |
| C12, n=7 | oscr#20 | C18H34O6 | 346.2355 | 345.2277 | 345.2302 | 22.54 ±0.03 |
| ΔC13, m=8 | oscr#21 | C19H34O6 | 358.2355 | 357.2277 | 357.2271 | 23.41 ±0.02 |
| C13, n=8 | oscr#22 | C19H36O6 | 360.2512 | 359.2434 | 359.2452 | 24.19 ±0.02 |
| ΔC14, m=9 | oscr#23 | C20H36O6 | 372.2512 | 371.2434 | 371.2436 | 25.04 ±0.03 |
| C14, n=9 | oscr#24 | C20H38O6 | 374.2668 | 373.2590 | 373.2589 | 25.91 ±0.02 |
| ΔC15, m=10 | oscr#25 | C21H38O6 | 386.2668 | 385.2590 | 385.2567 | 26.74 ±0.01 |
| C15, n=10 | oscr#26 | C21H40O6 | 388.2825 | 387.2747 | 387.2739 | 27.73 ±0.05 |
| ΔC16, m=11 | oscr#27 | C22H40O6 | 400.2825 | 399.2747 | 399.2728 | 28.54 ±0.03 |
| C16, n=11 | oscr#28 | C22H42O6 | 402.2981 | 401.2903 | 401.2905 | 29.67 ±0.02 |
| ΔC17, m=12 | oscr#29 | C23H42O6 | 414.2981 | 413.2903 | 413.2900 | 30.42 ±0.02 |
| C17, n=12 | oscr#30 | C23H44O6 | 416.3138 | 415.3060 | 415.3080 | 31.68 ±0.04 |
| ΔC18, m=13 | oscr#31 | C24H44O6 | 428.3138 | 427.3060 | 427.3053 | 32.44 ±0.02 |
| C18, n=13 | oscr#32 | C24H46O6 | 430.3294 | 429.3216 | 429.3207 | 33.78 ±0.02 |
| ΔC19, n=14 | oscr#33 | C25H46O6 | 442.3294 | 441.3216 | 441.3218 | 34.44 ±0.05 |
| C19, n=14 | oscr#34 | C25H48O6 | 444.3451 | 443.3373 | 443.3372 | 35.86 ±0.05 |
| ΔC20, m=15 | oscr#35 | C26H48O6 | 456.3451 | 455.3373 | 455.3384 | 36.23 ±0.05 |
| C20, n=15 | oscr#36 | C26H50O6 | 458.3607 | 457.3529 | 457.3545 | 37.96 ±0.05 |
| ΔC21, m=16 | oscr#37 | C27H50O6 | 470.3607 | 469.3529 | 469.3504 | 38.08 ±0.19 |
| C21, n=16 | oscr#38 | C27H52O6 | 472.3764 | 471.3686 | 471.3679 | 40.19 ±0.13 |

[8.] Butcher et al., *Proc. Nat'l Acad. Sci. U.S.A.* 105:14288–92 (2008), which is hereby incorporated by reference in its entirety.

Figure 37B

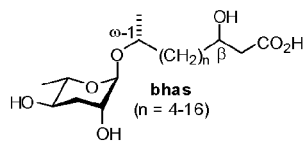

| Side chain length (n) | SMID[S] | Molecular formula | Molecular weight amu | m/z M-H- calculated | m/z M-H- observed | Retention time min ±SD |
|---|---|---|---|---|---|---|
| $C_9$, n=4 | bhas#10* | $C_{15}H_{28}O_7$ | 320.1835 | 319.1757 | 319.1764 | 13.98 ±0.03 |
| $C_{10}$, n=5 | bhas#16 | $C_{16}H_{30}O_7$ | 334.1992 | 333.1913 | 333.1909 | 15.55 ±0.03 |
| $C_{11}$, n=6 | bhas#18 | $C_{17}H_{32}O_7$ | 348.2148 | 347.2070 | 347.2058 | 16.72 ±0.02 |
| $C_{12}$, n=7 | bhas#20 | $C_{18}H_{34}O_7$ | 362.2305 | 361.2226 | 361.2235 | 18.02 ±0.02 |
| $C_{13}$, n=8 | bhas#22* | $C_{19}H_{36}O_7$ | 376.2461 | 375.2383 | 375.2371 | 19.39 ±0.02 |
| $C_{14}$, n=9 | bhas#24[7] | $C_{20}H_{38}O_7$ | 390.2618 | 389.2539 | 389.2537 | 20.74 ±0.03 |
| $C_{15}$, n=10 | bhas#26[7] | $C_{21}H_{40}O_7$ | 404.2774 | 403.2696 | 403.2693 | 22.19 ±0.03 |
| $C_{16}$, n=11 | bhas#28[7] | $C_{22}H_{42}O_7$ | 418.2931 | 417.2852 | 417.2852 | 23.66 ±0.03 |
| $C_{17}$, n=12 | bhas#30[7] | $C_{23}H_{44}O_7$ | 432.3087 | 431.3009 | 431.3009 | 25.32 ±0.02 |
| $C_{18}$, n=13 | bhas#32 | $C_{24}H_{46}O_7$ | 446.3244 | 445.3165 | 445.3164 | 27.07 ±0.03 |
| $C_{19}$, n=14 | bhas#34 | $C_{25}H_{48}O_7$ | 460.3400 | 459.3322 | 459.3316 | 28.97 ±0.02 |
| $C_{20}$, n=15 | bhas#36 | $C_{26}H_{50}O_7$ | 474.3557 | 473.3478 | 473.3471 | 30.97 ±0.03 |
| $C_{21}$, n=16 | bhas#38 | $C_{27}H_{52}O_7$ | 488.3713 | 487.3635 | 487.3629 | 33.12 ±0.06 |

[7.] Butcher et al., *Proc. Nat'l Acad. Sci. U.S.A.* 106:1875–79 (2009), which is hereby incorporated by reference in its entirety.

Figure 37C

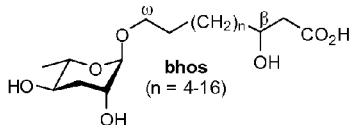

| Side chain length (n) | SMID$^S$ | Molecular formula | Molecular weight amu | m/z M-H- calculated | m/z M-H- observed | Retention time min ±SD |
|---|---|---|---|---|---|---|
| $C_9$, n=4 | bhos#10 | $C_{15}H_{28}O_7$ | 320.1835 | 319.1757 | 319.1781 | 14.44 ±0.01 |
| $C_{10}$, n=5 | bhos#16 | $C_{16}H_{30}O_7$ | 334.1992 | 333.1913 | 333.1902 | 15.82 ±0.01 |
| $C_{11}$, n=6 | bhos#18 | $C_{17}H_{32}O_7$ | 348.2148 | 347.2070 | 347.2054 | 17.17 ±0.02 |
| $C_{12}$, n=7 | bhos#20 | $C_{18}H_{34}O_7$ | 362.2305 | 361.2226 | 361.2224 | 18.51 ±0.01 |
| $C_{13}$, n=8 | bhos#22 | $C_{19}H_{36}O_7$ | 376.2461 | 375.2383 | 375.2370 | 19.86 ±0.02 |
| $C_{14}$, n=9 | bhos#24 | $C_{20}H_{38}O_7$ | 390.2618 | 389.2539 | 389.2537 | 21.23 ±0.03 |
| $C_{15}$, n=10 | bhos#26* | $C_{21}H_{40}O_7$ | 404.2774 | 403.2696 | 403.2691 | 22.70 ±0.01 |
| $C_{16}$, n=11 | bhos#28 | $C_{22}H_{42}O_7$ | 418.2931 | 417.2852 | 417.2849 | 24.28 ±0.06 |
| $C_{17}$, n=12 | bhos#30 | $C_{23}H_{44}O_7$ | 432.3087 | 431.3009 | 431.3005 | 25.95 ±0.07 |
| $C_{18}$, n=13 | bhos#32 | $C_{24}H_{46}O_7$ | 446.3244 | 445.3165 | 445.3164 | 27.73 ±0.02 |
| $C_{19}$, n=14 | bhos#34 | $C_{25}H_{48}O_7$ | 460.3400 | 459.3322 | 459.3318 | 29.68 ±0.03 |
| $C_{20}$, n=15 | bhos#36 | $C_{26}H_{50}O_7$ | 474.3557 | 473.3478 | 473.3473 | 31.76 ±0.03 |
| $C_{21}$, n=16 | bhos#38 | $C_{27}H_{52}O_7$ | 488.3713 | 487.3635 | 487.3640 | 33.96 ±0.08 |

Figure 37D

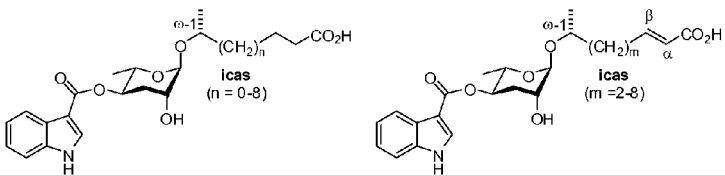

| Side chain Length (n, m) | SMID$^S$ | Molecular formula | Molecular weight amu | m/z M-H- calculated | m/z M-H- observed | Retention time min ±SD | WT (N2) | acox-1 (ok2557) | maoc-1 (hj13) | dhs-28 (hj8) | daf-22 (ok693) |
|---|---|---|---|---|---|---|---|---|---|---|---|
| $C_5$, n=0 | icas#9*$^9$ | $C_{20}H_{25}NO_7$ | 391.1631 | 390.1553 | 390.1555 | 20.18 ±0.02 | + | + | - | - | - |
| $C_6$, n=1 | icas#12 | $C_{21}H_{27}NO_7$ | 405.1788 | 404.1709 | 404.1703 | 21.02 ±0.03 | + | + | - | - | - |
| $\Delta C_7$, m=2 | icas#7*$^4$ | $C_{22}H_{27}NO_7$ | 417.1788 | 416.1709 | 416.1719 | 21.74 ±0.03 | + | - | - | - | - |
| $C_7$, n=2 | icas#1*$^4$ | $C_{22}H_{29}NO_7$ | 419.1944 | 418.1866 | 418.1864 | 22.06 ±0.03 | + | + | - | - | - |
| $C_8$, n=3 | icas#14 | $C_{23}H_{31}NO_7$ | 433.2101 | 432.2022 | 432.2013 | 23.20 ±0.04 | + | + | - | - | - |
| $\Delta C_9$, m=4 | icas#3*$^4$ | $C_{24}H_{31}NO_7$ | 445.2101 | 444.2022 | 444.2029 | 23.94 ±0.03 | + | - | + | - | - |
| $C_9$, n=4 | icas#10$^4$ | $C_{24}H_{33}NO_7$ | 447.2257 | 446.2179 | 446.2185 | 24.55 ±0.03 | + | + | + | + | - |
| $\Delta C_{10}$, m=5 | icas#15 | $C_{25}H_{33}NO_7$ | 459.2257 | 458.2179 | 458.2198 | 25.21 ±0.05 | - | - | + | + | - |
| $C_{10}$, n=5 | icas#16 | $C_{25}H_{35}NO_7$ | 461.2414 | 460.2335 | 460.2369 | 25.89 ±0.04 | + | + | + | + | - |
| $\Delta C_{11}$, m=6 | icas#17 | $C_{26}H_{35}NO_7$ | 473.2414 | 472.2335 | 472.2344 | 26.68 ±0.04 | - | - | + | + | - |
| $C_{11}$, n=6 | icas#18 | $C_{26}H_{37}NO_7$ | 475.2570 | 474.2492 | 474.2494 | 27.44 ±0.03 | + | + | + | + | - |
| $\Delta C_{12}$, m=7 | icas#19 | $C_{27}H_{37}NO_7$ | 487.2570 | 486.2492 | 486.2486 | 28.20 ±0.06 | - | - | + | + | - |
| $C_{12}$, n=7 | icas#20 | $C_{27}H_{39}NO_7$ | 489.27265 | 488.2648 | 488.2628 | 28.98 ±0.03 | + | + | + | + | - |
| $\Delta C13$, m=8 | icas#21 | $C_{28}H_{39}NO_7$ | 501.27265 | 500.2648 | 500.2640 | 29.71 ±0.04 | - | - | + | + | - |
| $C_{13}$, n=8 | icas#22 | $C_{28}H_{41}NO_7$ | 503.28830 | 502.2805 | 502.2807 | 30.66 ±0.03 | - | + | + | + | - |

$^4$ Srinivasan et al., *Pub. Lib. Sci. Biol.* 10:e1001237 (2012), which is hereby incorporated by reference in its entirety.
$^9$ Butcher et al., *Org. Lett.* 11:3100-03 (2009), which is hereby incorporated by reference in its entirety.

Figure 37E

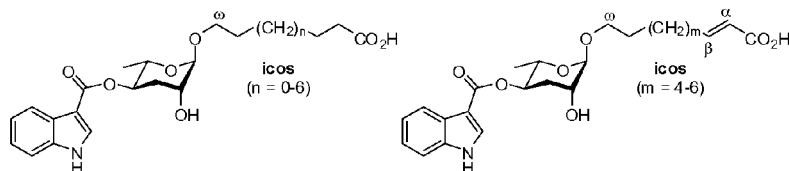

| Side chain length (n, m) | SMID$^S$ | Molecular formula | Molecular weight amu | m/z M-H– calculated | m/z M-H– observed | Retention time min ±SD | WT (N2) | acox-1 (*ok2557*) | maoc-1 (*hj13*) | dhs-28 (*hj8*) | daf-22 (*ok693*) |
|---|---|---|---|---|---|---|---|---|---|---|---|
| $C_5$, n=0 | icos#9 | $C_{20}H_{25}NO_7$ | 391.1631 | 390.1553 | 390.1541 | 20.48 ±0.03 | - | + | - | - | - |
| $C_7$, n=2 | icos#1 | $C_{22}H_{29}NO_7$ | 419.1944 | 418.1866 | 418.1858 | 22.63 ±0.03 | + | + | - | - | - |
| $\Delta C_9$, m=4 | icos#3 | $C_{24}H_{31}NO_7$ | 445.2101 | 444.2022 | 444.2049 | 24.66 ±0.04 | - | - | + | - | - |
| $C_9$, n=4 | icos#10* | $C_{24}H_{33}NO_7$ | 447.2257 | 446.2179 | 446.2171 | 25.29 ±0.03 | - | + | + | + | - |
| $\Delta C_{10}$, m=5 | icos#15 | $C_{25}H_{33}NO_7$ | 459.2257 | 458.2179 | 458.2170 | 26.02 ±0.05 | - | - | + | + | - |
| $C_{10}$, n=5 | icos#16 | $C_{25}H_{35}NO_7$ | 461.2414 | 460.2335 | 460.2350 | 26.73 ±0.04 | - | - | + | + | - |
| $\Delta C_{11}$, m=6 | icos#17 | $C_{26}H_{35}NO_7$ | 473.2414 | 472.2335 | 472.2325 | 27.45 ±0.03 | - | - | + | + | - |
| $C_{11}$, n=6 | icos#18 | $C_{26}H_{37}NO_7$ | 475.2570 | 474.2492 | 474.2490 | 28.21 ±0.04 | - | + | + | + | - |

Figure 37F

| Side chain length (n) | SMID$^S$ | Molecular formula | Molecular Weight amu | m/z M-H– calculated | m/z M-H– observed | Retention Time min ±SD | WT (N2) | acox-1 (*ok2557*) | maoc-1 (*hj13*) | dhs-28 (*hj8*) | daf-22 (*ok693*) |
|---|---|---|---|---|---|---|---|---|---|---|---|
| $C_9$, n=4 | ibha#10 | $C_{24}H_{35}NO_8$ | 463.2206 | 462.2128 | 462.2113 | 20.72 ±0.03 | - | - | - | + | - |
| $C_{10}$, n=5 | ibha#16 | $C_{25}H_{37}NO_8$ | 477.2363 | 476.2284 | 476.2251 | 21.81 ±0.04 | - | - | - | + | - |
| $C_{11}$, n=6 | ibha#18 | $C_{26}H_{39}NO_8$ | 491.2519 | 490.2441 | 490.2476 | 23.08 ±0.04 | - | - | + | + | - |
| $C_{12}$, n=7 | ibha#20 | $C_{27}H_{39}NO_8$ | 505.2676 | 504.2597 | 504.2582 | 24.38 ±0.03 | - | - | + | + | - |
| $C_{13}$, n=8 | ibha#22 | $C_{28}H_{41}NO_8$ | 519.2832 | 518.2754 | 518.2726 | 25.86 ±0.03 | - | - | + | + | - |
| $C_{14}$, n=9 | ibha#24 | $C_{29}H_{43}NO_8$ | 533.2989 | 532.2910 | 532.2938 | 27.30 ±0.04 | - | - | - | + | - |
| $C_{15}$, n=10 | ibha#26 | $C_{30}H_{45}NO_8$ | 547.3145 | 546.3067 | 546.3033 | 28.96 ±0.04 | - | - | - | + | + |
| $C_{16}$, n=11 | ibha#28 | $C_{31}H_{47}NO_8$ | 561.3302 | 560.3223 | 560.3201 | 30.63 ±0.05 | - | - | - | + | - |
| $C_{17}$, n=12 | ibha#30 | $C_{32}H_{49}NO_8$ | 575.3458 | 574.3380 | 574.3347 | 32.46 ±0.01 | - | - | - | + | - |

Figure 37G

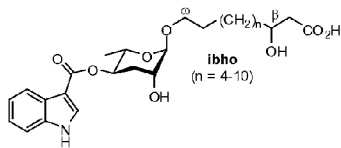

| Side chain length (n) | SMID[S] | Molecular formula | Molecular weight amu | m/z M-H- calculated | m/z M-H- observed | Retention Time min ±SD | WT (N2) | acox-1 (ok2557) | maoc-1 (hj13) | dhs-28 (hj8) | daf-22 (ok693) |
|---|---|---|---|---|---|---|---|---|---|---|---|
| C$_9$, n=4 | ibho#10 | C$_{24}$H$_{33}$NO$_8$ | 463.2206 | 462.2128 | 462.2114 | 21.39 ±0.03 | - | - | - | + | - |
| C$_{10}$, n=5 | ibho#16 | C$_{25}$H$_{35}$NO$_8$ | 477.2363 | 476.2284 | 476.2252 | 22.56 ±0.03 | - | - | - | + | - |
| C$_{11}$, n=6 | ibho#18 | C$_{26}$H$_{37}$NO$_8$ | 491.2519 | 490.2441 | 490.2438 | 23.79 ±0.03 | - | - | + | + | - |
| C$_{12}$, n=7 | ibho#20 | C$_{27}$H$_{39}$NO$_8$ | 505.2676 | 504.2597 | 504.2580 | 25.15 ±0.03 | - | - | - | + | - |
| C$_{13}$, n=8 | ibho#22 | C$_{28}$H$_{41}$NO$_8$ | 519.2832 | 518.2754 | 518.2719 | 26.58 ±0.03 | - | - | - | + | - |
| C$_{14}$, n=9 | ibho#24 | C$_{29}$H$_{43}$NO$_8$ | 533.2989 | 532.2910 | 532.2886 | 27.94 ±0.03 | - | - | - | + | - |
| C$_{15}$, n=10 | ibho#26 | C$_{30}$H$_{45}$NO$_8$ | 547.3145 | 546.3067 | 546.3094 | 29.65 ±0.03 | - | - | - | + | + |

Figure 37H

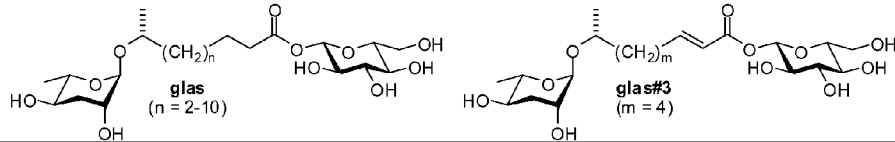

| Side chain length (n,m) | SMID[S] | Molecular formula | Molecular weight amu | m/z M-H- calculated | m/z M-H- observed | Retention Time min ±SD | WT (N2) | acox-1 (ok2557) | maoc-1 (hj13) | dhs-28 (hj8) | daf-22 (ok693) |
|---|---|---|---|---|---|---|---|---|---|---|---|
| C$_7$, n=2 | glas#1 | C$_{19}$H$_{32}$O$_{11}$ | 438.2101 | 473.1795 | 473.1803 | 11.99 ±0.04 | + | - | - | - | - |
| ΔC$_9$, m=4 | glas#3 | C$_{21}$H$_{36}$O$_{11}$ | 464.2258 | 499.1952 | 499.1932 | 14.64 ±0.03 | + | - | - | - | - |
| C$_9$, n=4 | glas#10* | C$_{21}$H$_{38}$O$_{11}$ | 466.2414 | 501.2108 | 501.2112 | 15.05 ±0.03 | + | + | - | - | - |
| C$_{10}$, n=5 | glas#16 | C$_{22}$H$_{40}$O$_{11}$ | 480.2571 | 515.2265 | 515.2269 | 16.19 ±0.05 | - | + | - | - | - |
| C$_{11}$, n=6 | glas#18 | C$_{23}$H$_{42}$O$_{11}$ | 494.2727 | 529.2421 | 529.2402 | 17.34 ±0.04 | + | + | - | - | - |
| C$_{12}$, n=7 | glas#20 | C$_{24}$H$_{44}$O$_{11}$ | 508.2884 | 543.2578 | 543.2551 | 18.41 ±0.04 | - | + | - | - | - |
| C$_{13}$, n=8 | glas#22 | C$_{25}$H$_{46}$O$_{11}$ | 522.3040 | 557.2734 | 557.2720 | 19.49 ±0.05 | - | + | - | - | - |
| C$_{14}$, n=9 | glas#24 | C$_{26}$H$_{48}$O$_{11}$ | 536.3197 | 571.2891 | 571.2896 | 20.59 ±0.04 | - | + | - | - | - |
| C$_{15}$, n=10 | glas#26 | C$_{27}$H$_{50}$O$_{11}$ | 550.3353 | 585.3047 | 585.3095 | 21.77 ±0.04 | - | + | - | - | - |

Figure 37I

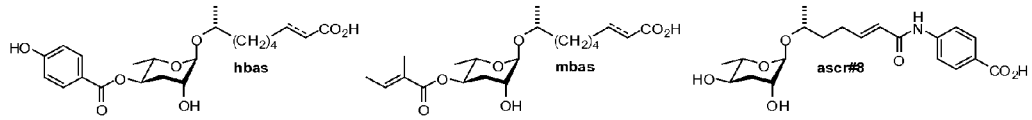

| Side chain length (n) | SMID[S] | Molecular formula | Molecular weight amu | m/z M-H- calculated | m/z M-H- observed | Retention Time min ±SD | WT (N2) | acox-1 (ok2557) | maoc-1 (hj13) | dhs-28 (hj8) | daf-22 (ok693) |
|---|---|---|---|---|---|---|---|---|---|---|---|
| ΔC$_7$ | ascr#8*2 | C$_{20}$H$_{27}$NO$_7$ | 393.1788 | 392.1709 | 392.1712 | 16.77 ±0.04 | + | - | - | - | - |
| ΔC$_9$ | hbas#3* | C$_{22}$H$_{30}$O$_8$ | 422.1941 | 421.1862 | 421.1866 | 22.41 ±0.03 | + | - | - | - | - |
| C$_9$ | hbas#10 | C$_{22}$H$_{32}$O$_8$ | 424.2097 | 423.2019 | 423.2018 | 22.94 ±0.04 | - | + | - | - | - |
| ΔC$_9$ | mbas#3* | C$_{20}$H$_{32}$O$_7$ | 384.2148 | 383.2070 | 383.2079 | 25.66 ±0.04 | + | - | - | - | - |
| C$_9$ | mbas#10 | C$_{20}$H$_{34}$O$_7$ | 386.2305 | 385.2226 | 385.2239 | 26.38 ±0.04 | - | + | - | - | - |

Figure 37J

| Side chain length (n) | SMID[S] | Molecular formula | Molecular weight amu | m/z M-H- calculated | m/z M-H- observed | Retention Time min ±SD |
|---|---|---|---|---|---|---|
| C$_6$ | ascr#2*[1] | C$_{12}$H$_{22}$O$_5$ | 246.1467 | 269.1365 | 269.1371 | 13.06 ±0.03 |
| C$_6$ | ascr#6*[2] | C$_{12}$H$_{24}$O$_5$ | 248.1624 | 271.1521 | 271.1532 | 12.72 ±0.04 |

[1]. Pungaliya et al., *Proc. Natl. Acad. Sci. U.S.A.* 106:7708–13 (2009), which is hereby incorporated by reference in its entirety.
[2]. Butcher et al., *Nat. Chem. Biol.* 3:420–22 (2007), which is hereby incorporated by reference in its entirety.

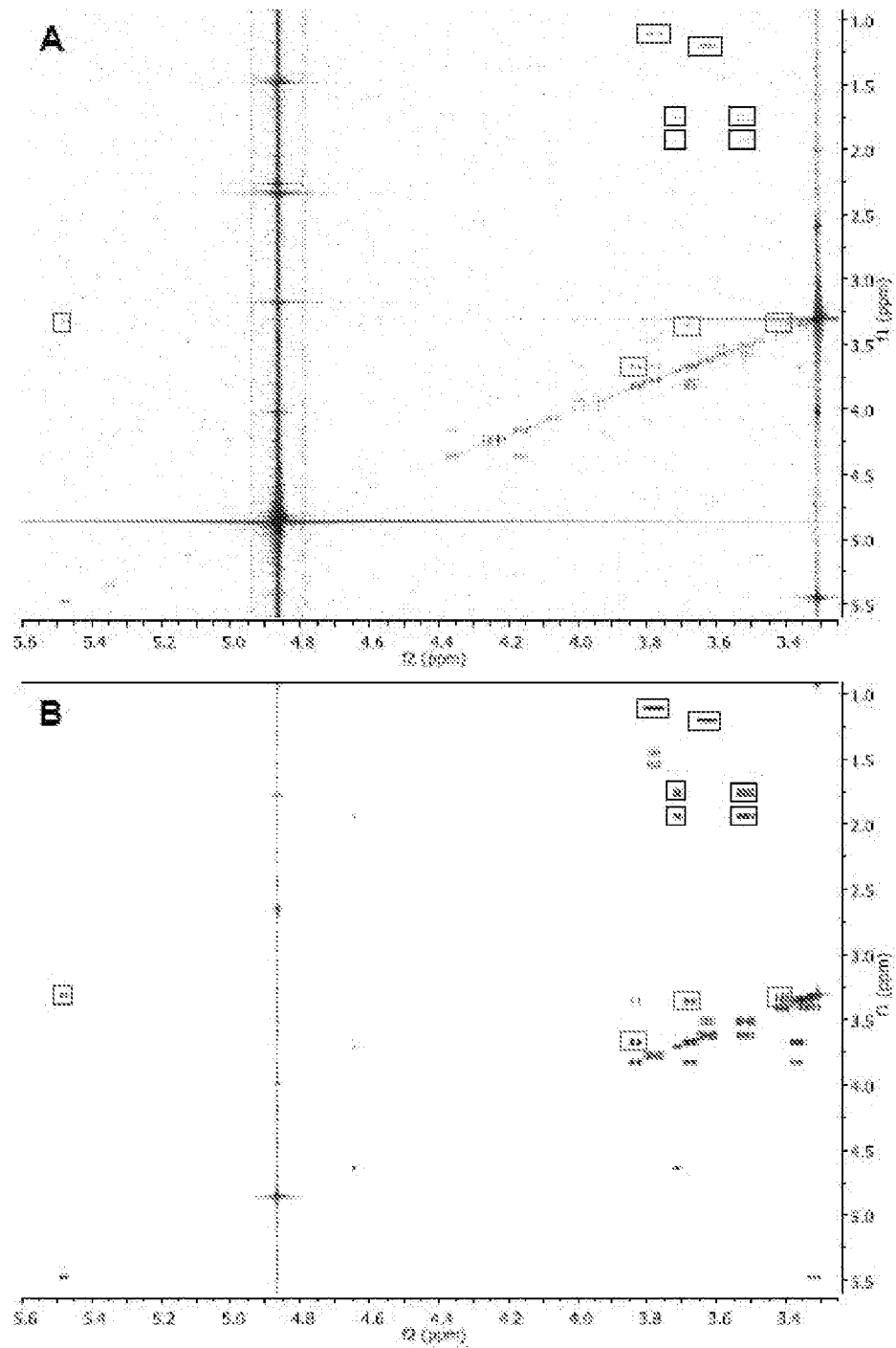
Figures 43A–B

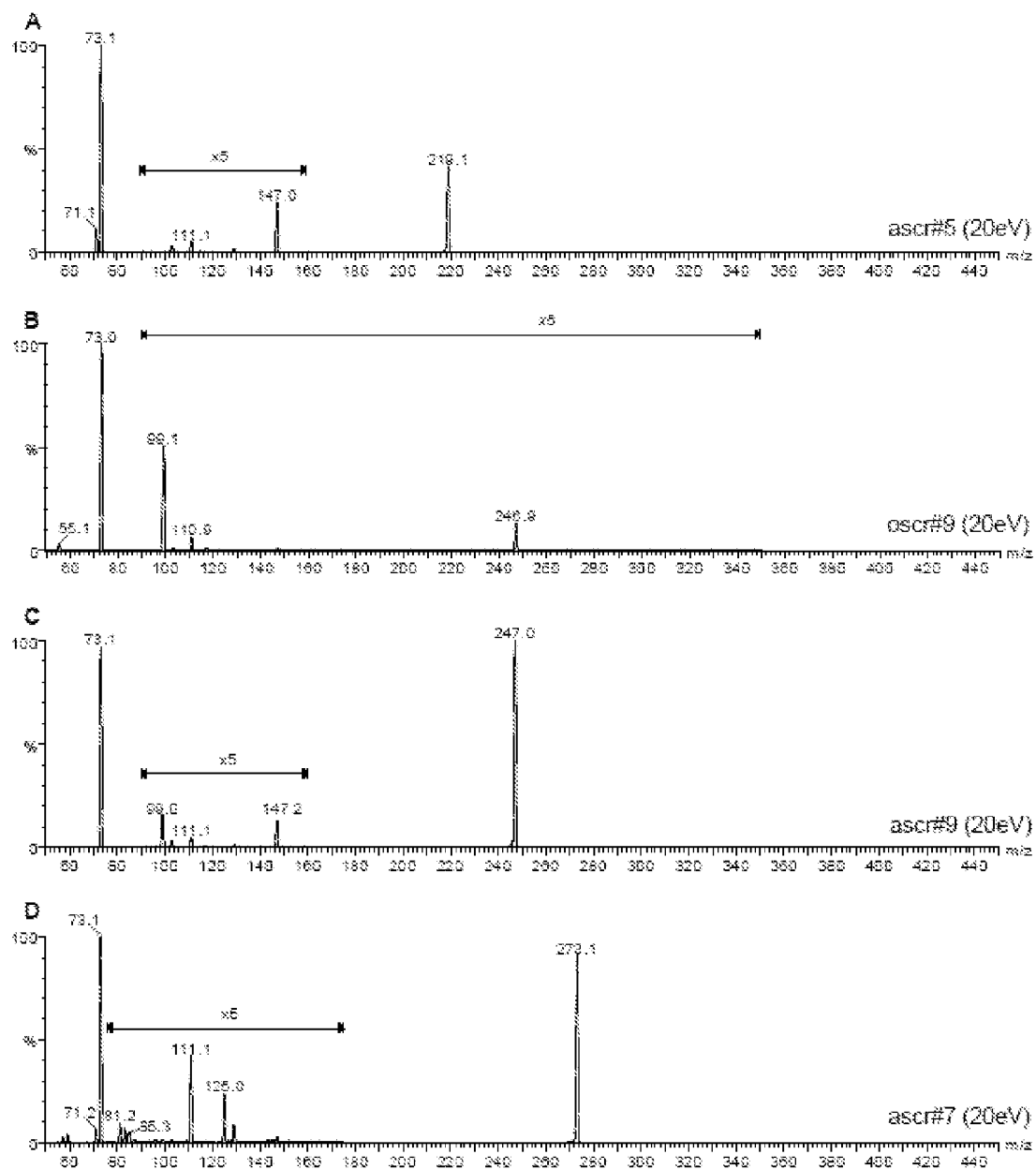
Figures 44A–D

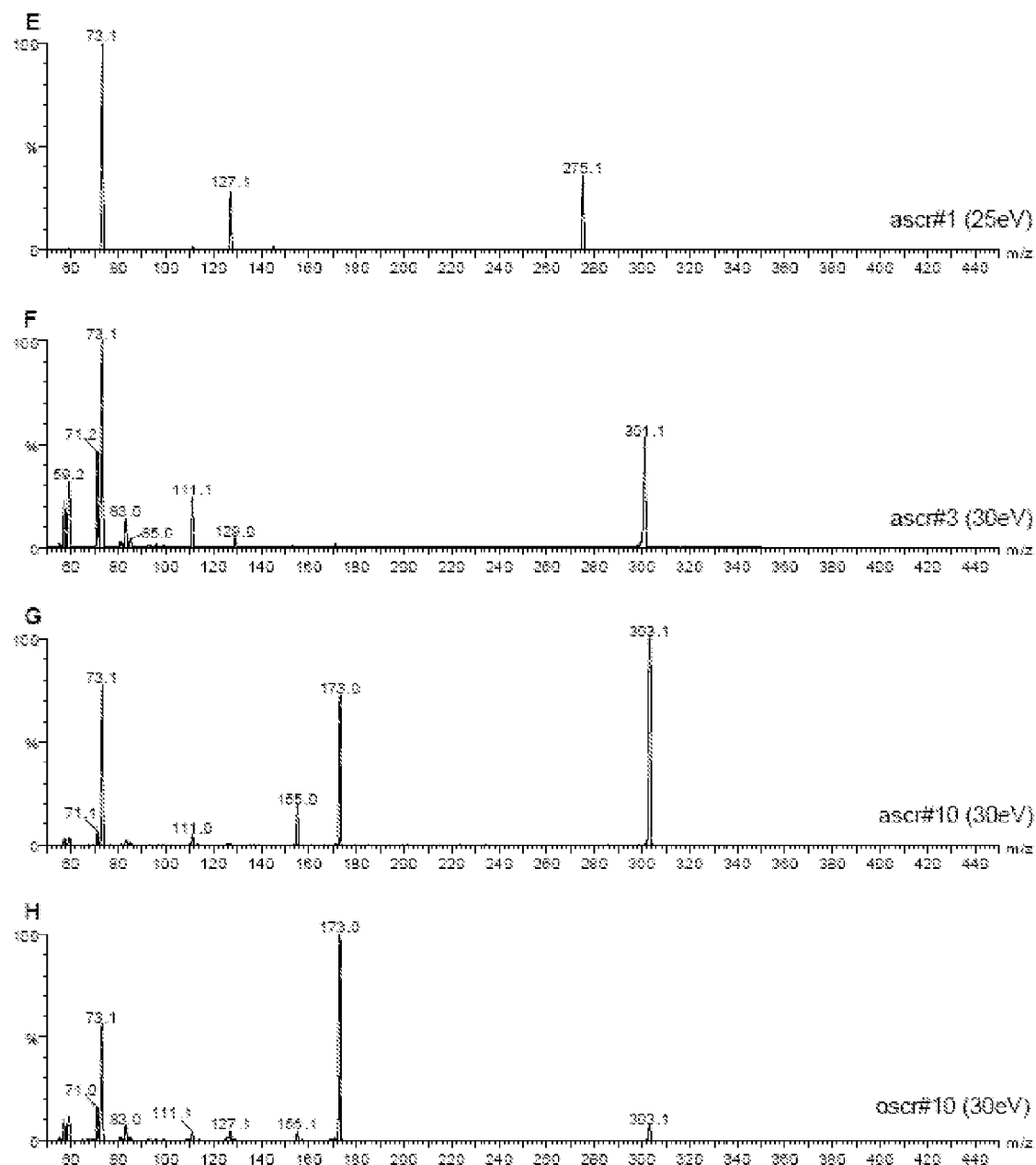
Figures 44E–H

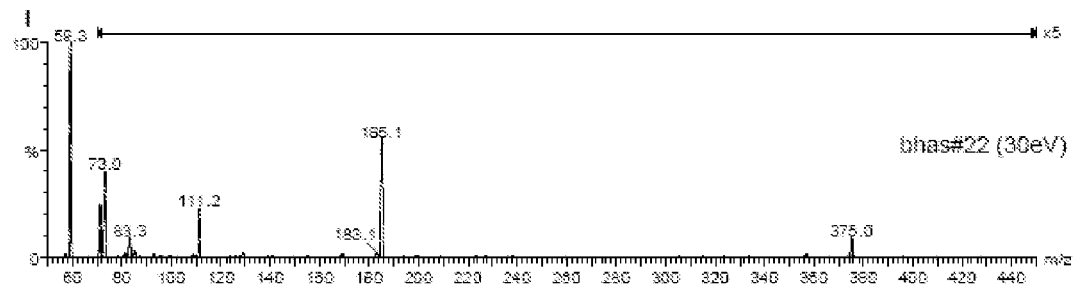
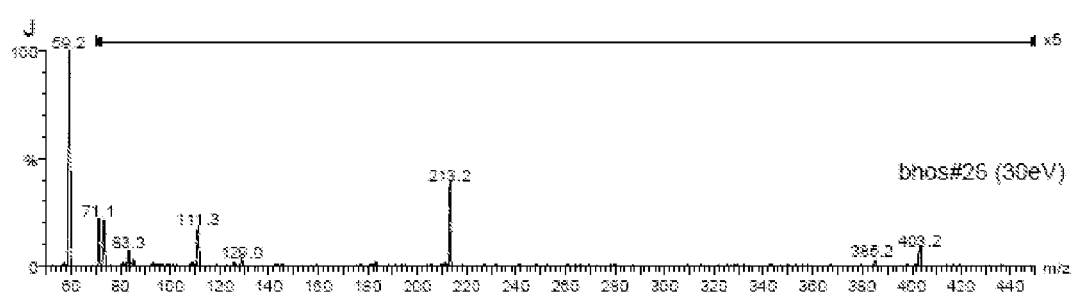
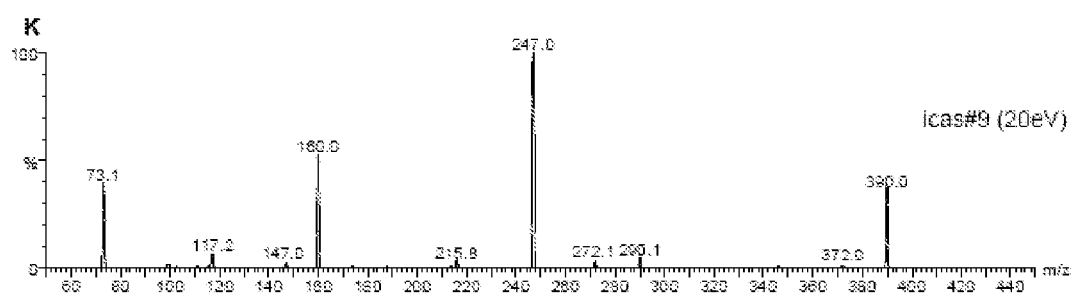
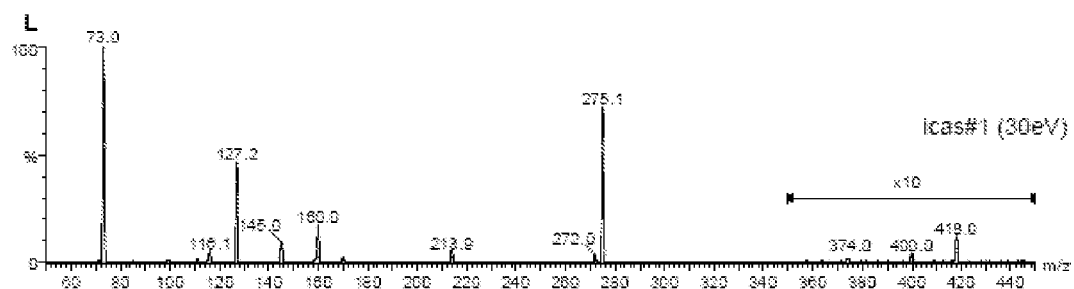
Figures 44I–L

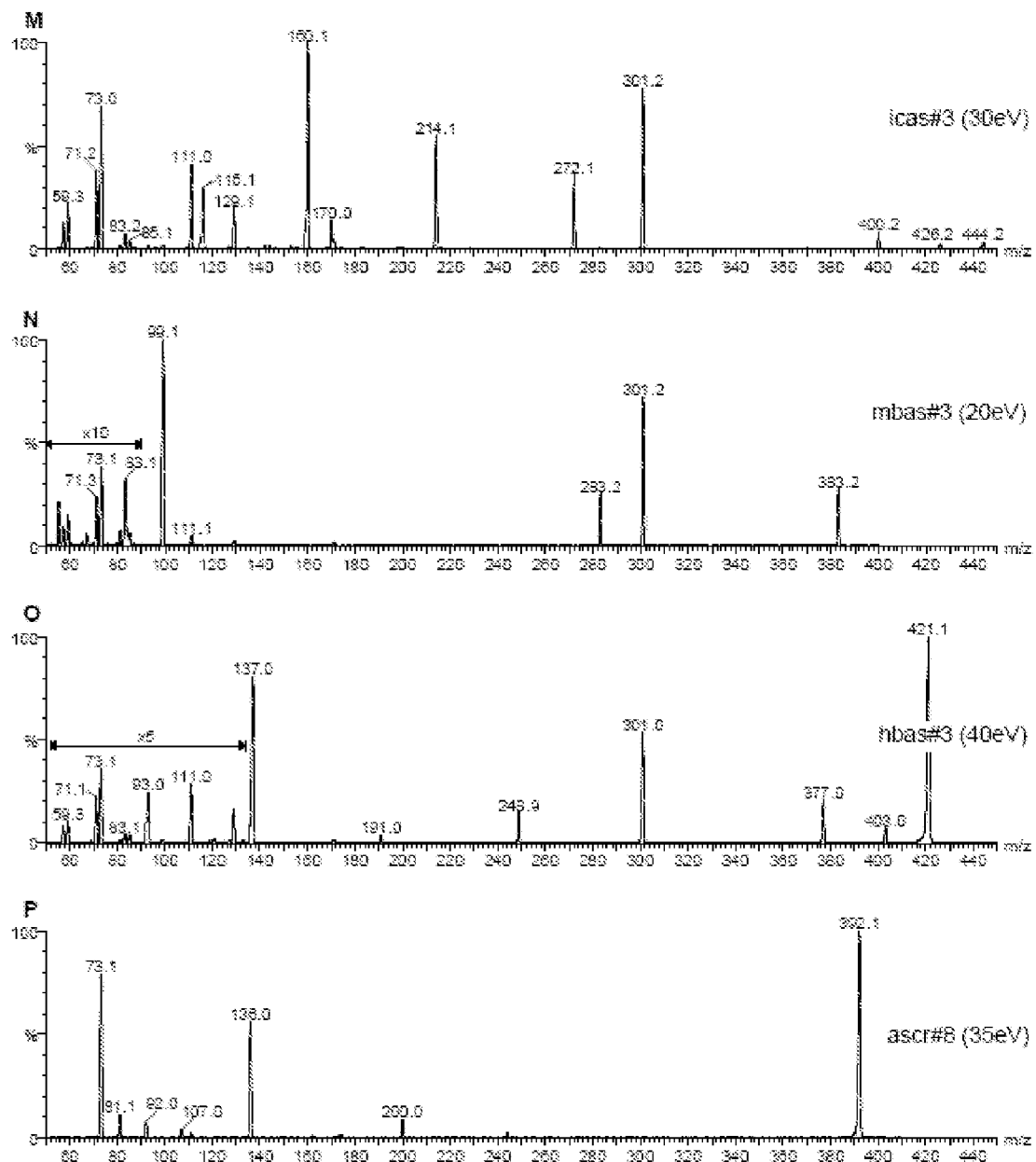
Figures 44M–P

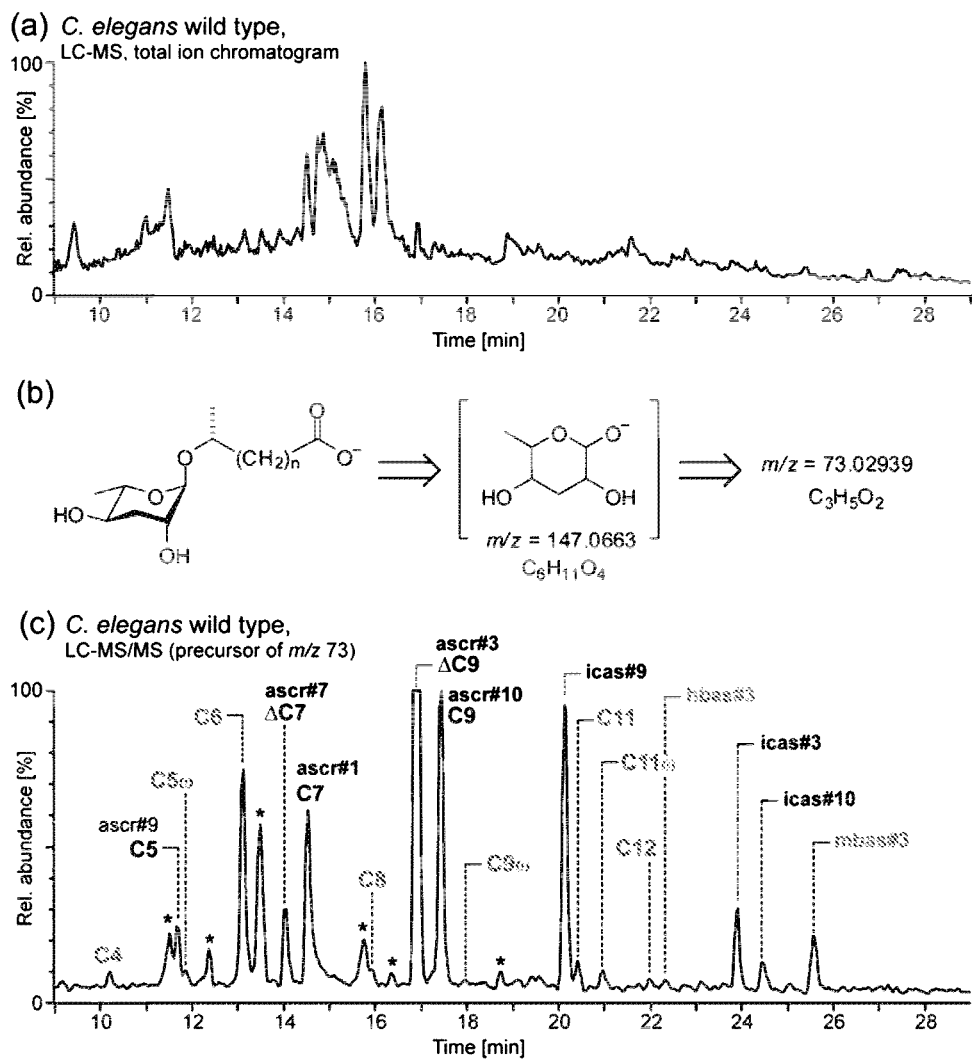
Figures 46A–C

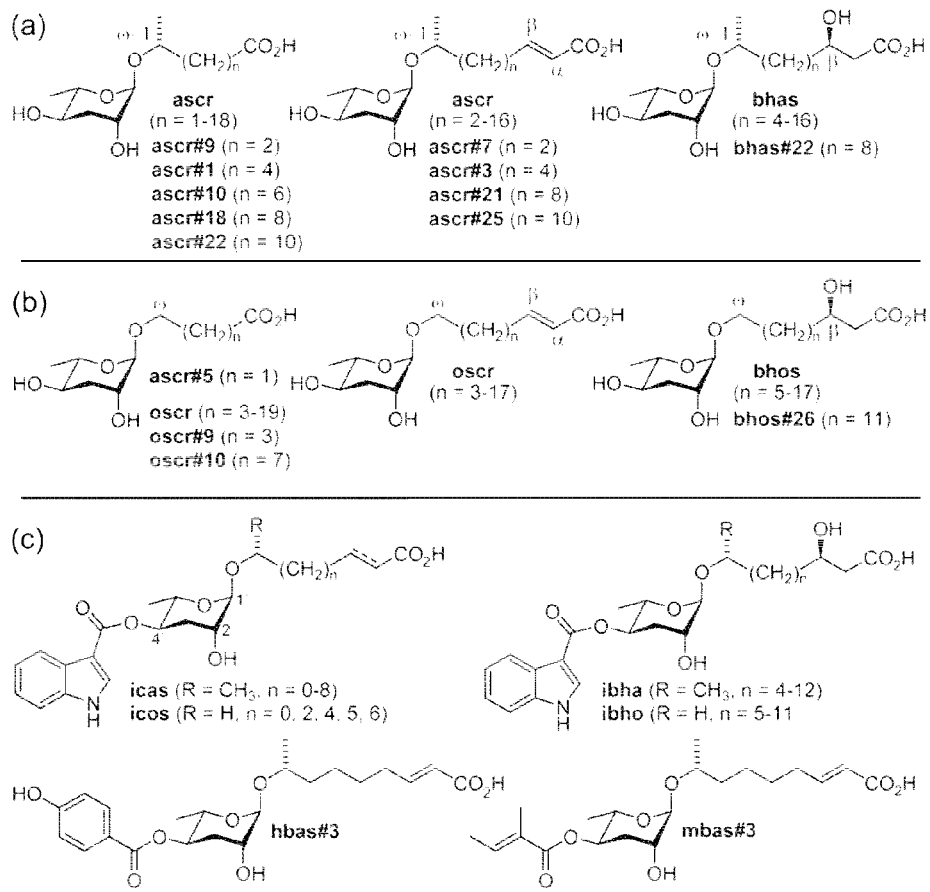
Figures 47A–C
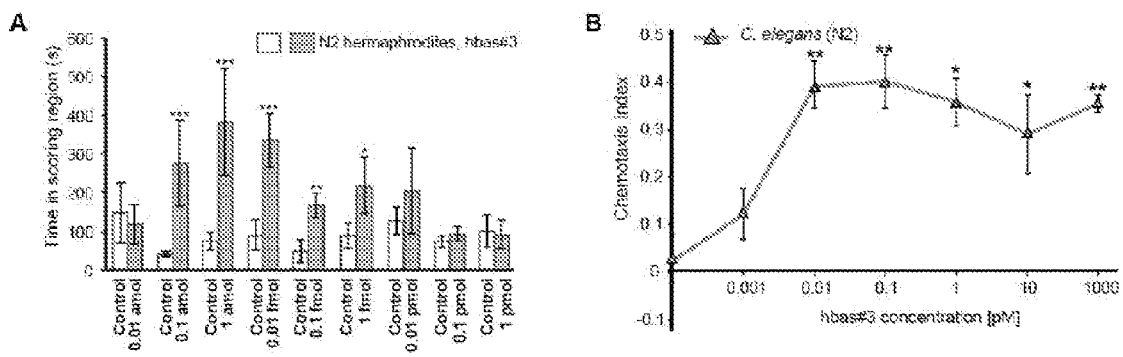
Figures 48A–B

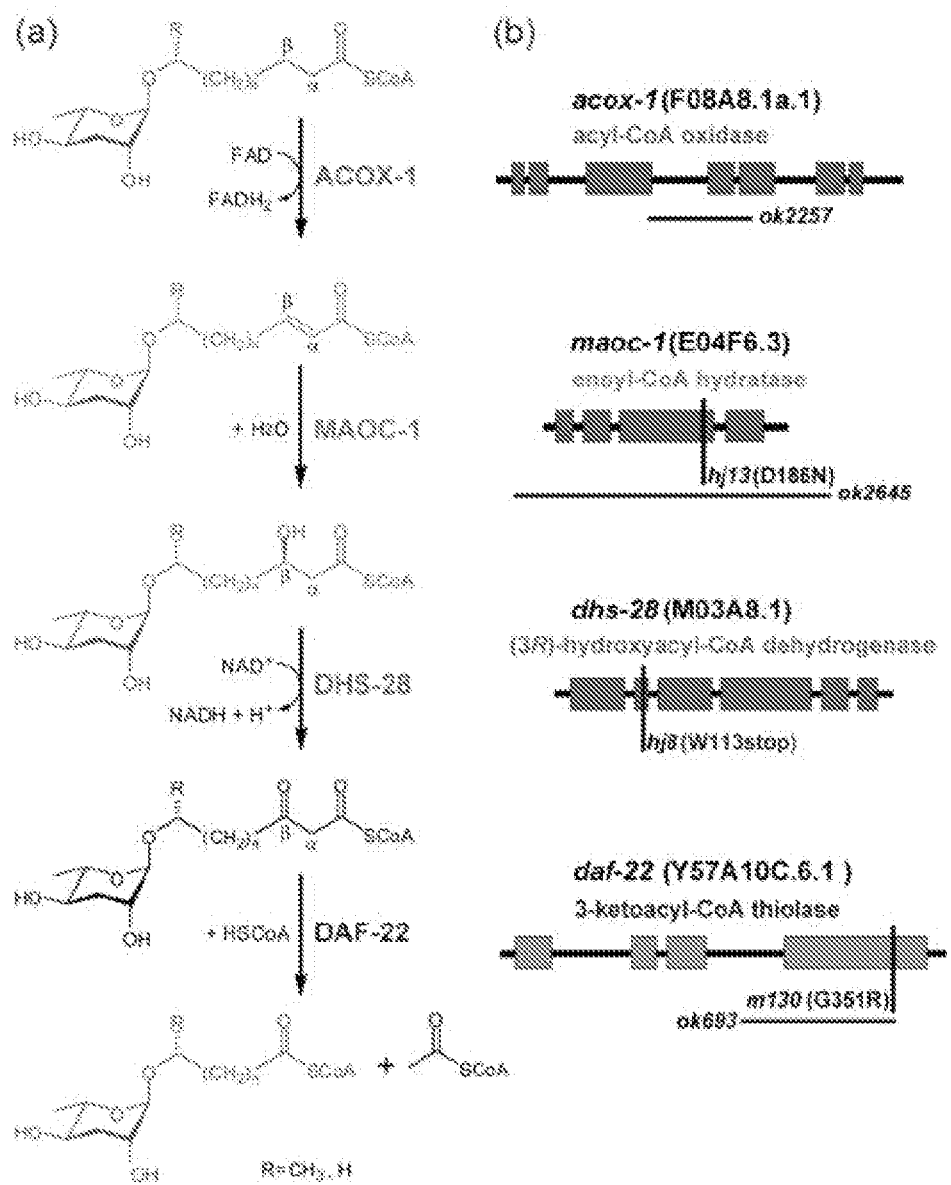
Figures 49A–B

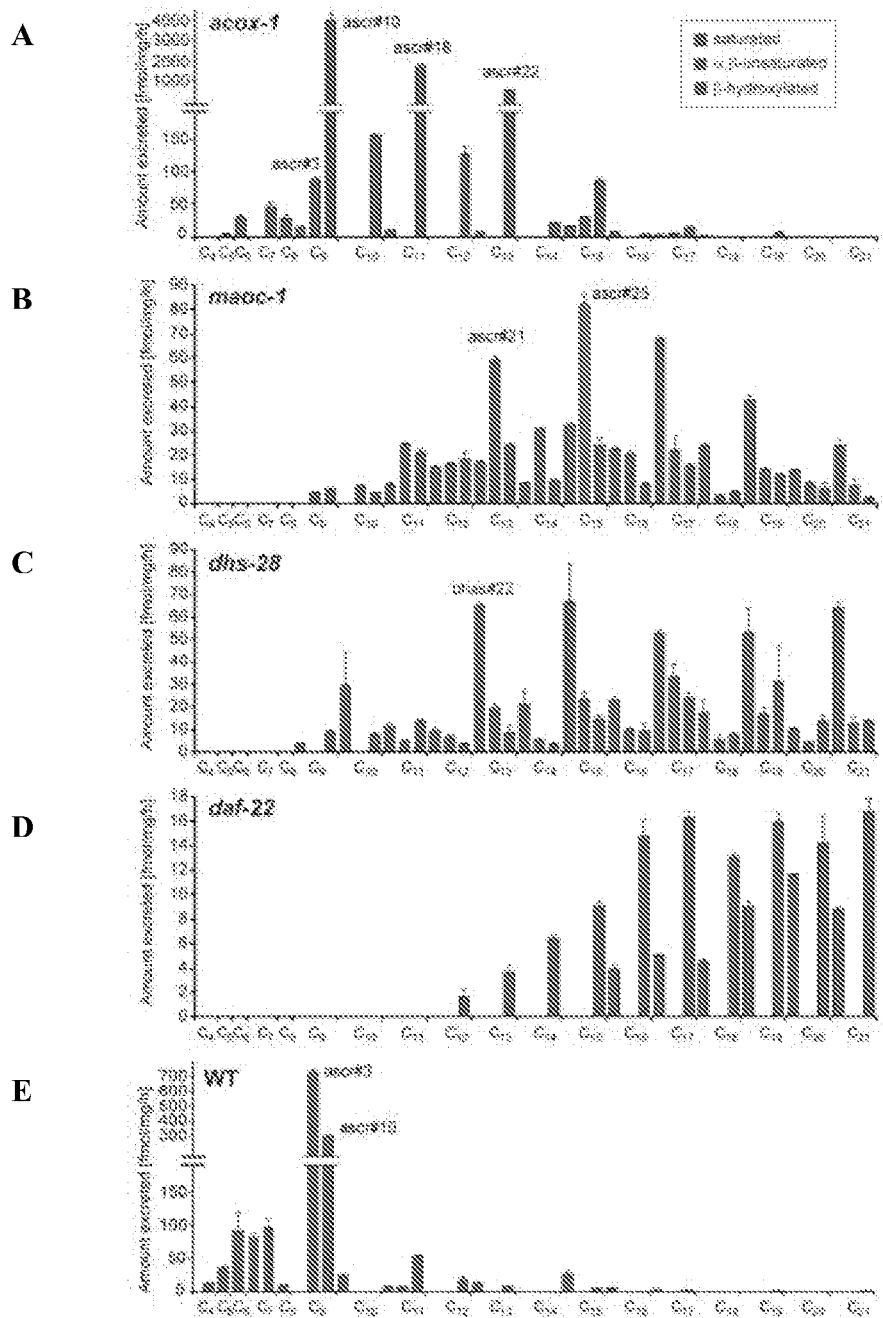
Figures 50A–E

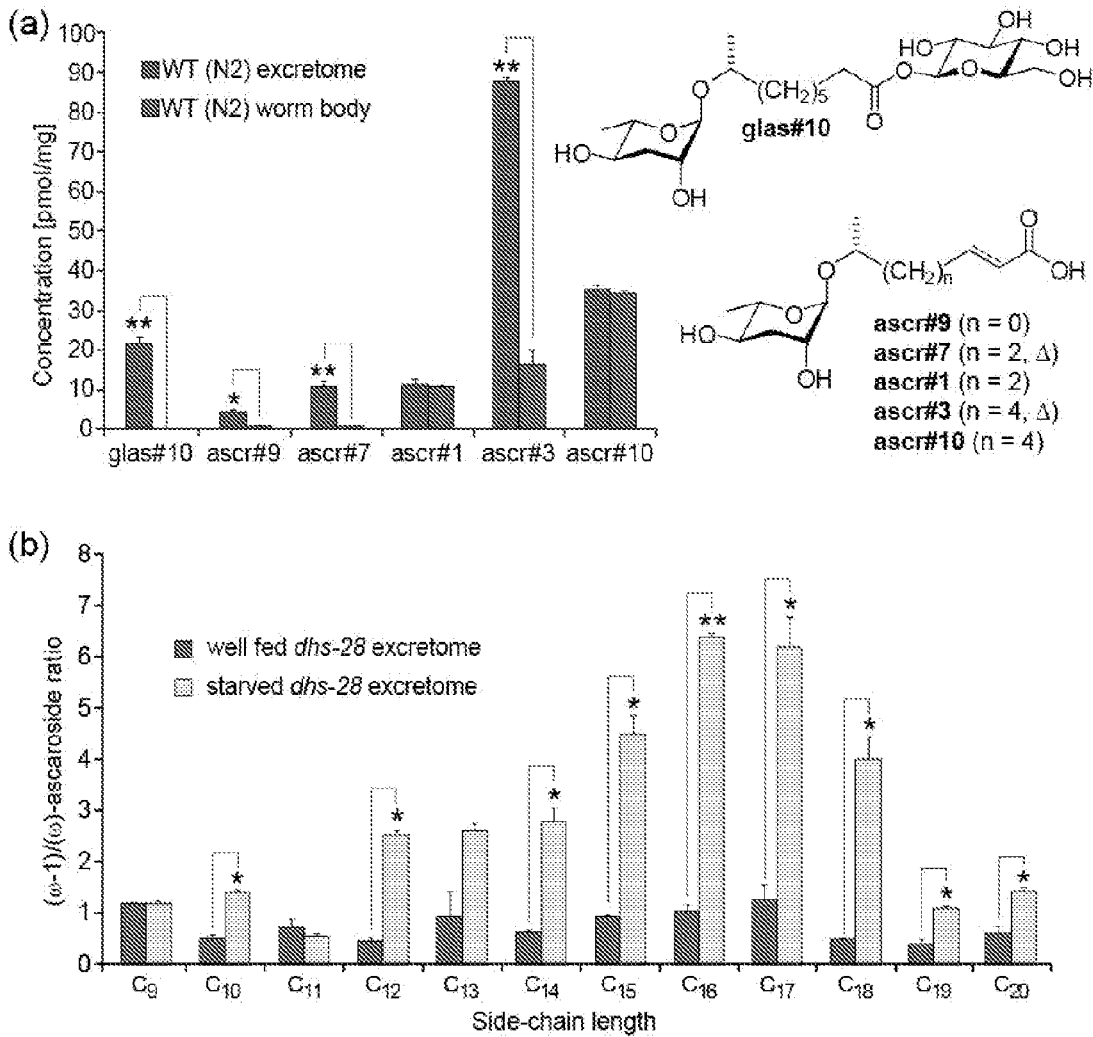
Figures 56A–B

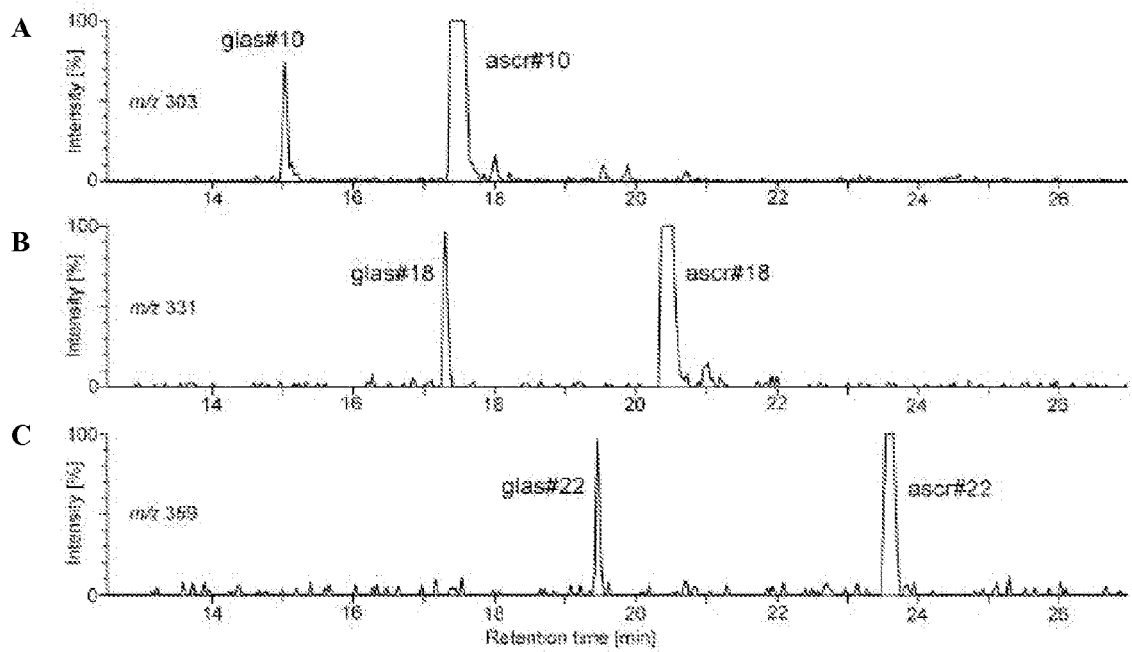
Figures 57A–C
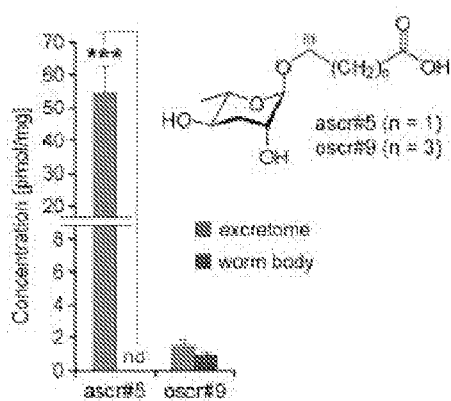
Figure 58

Figures 59A–C

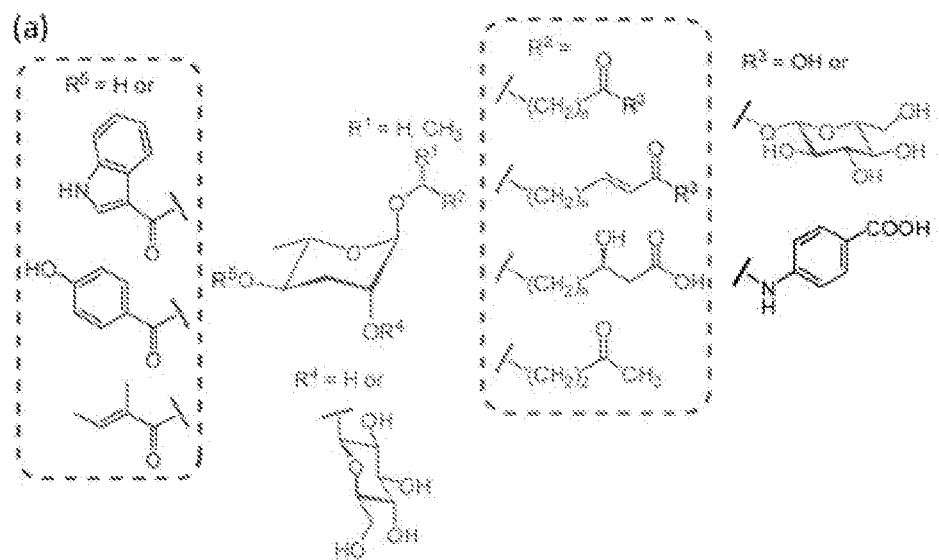
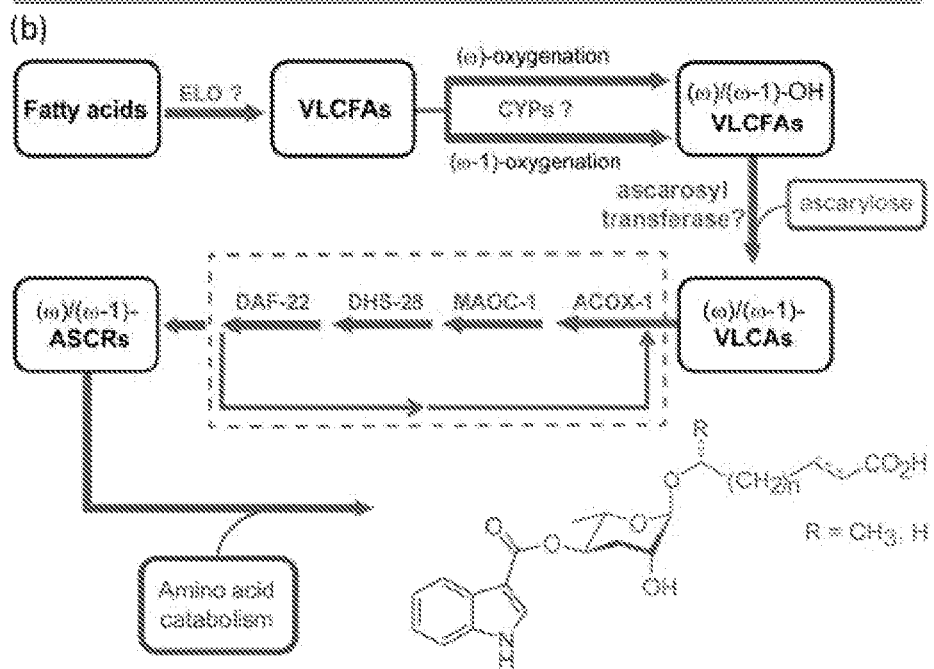
Figures 61A–B

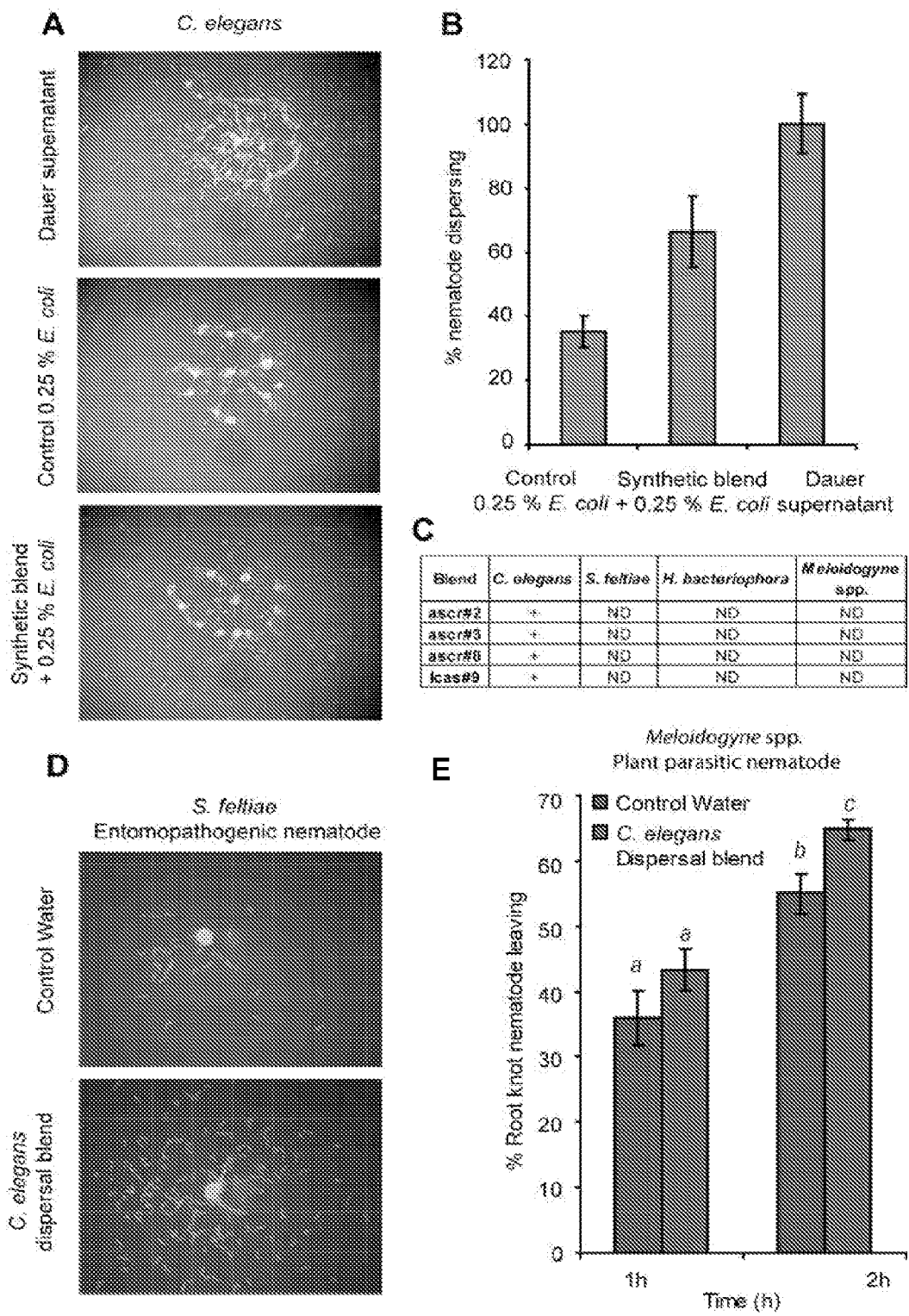
Figures 66A–E

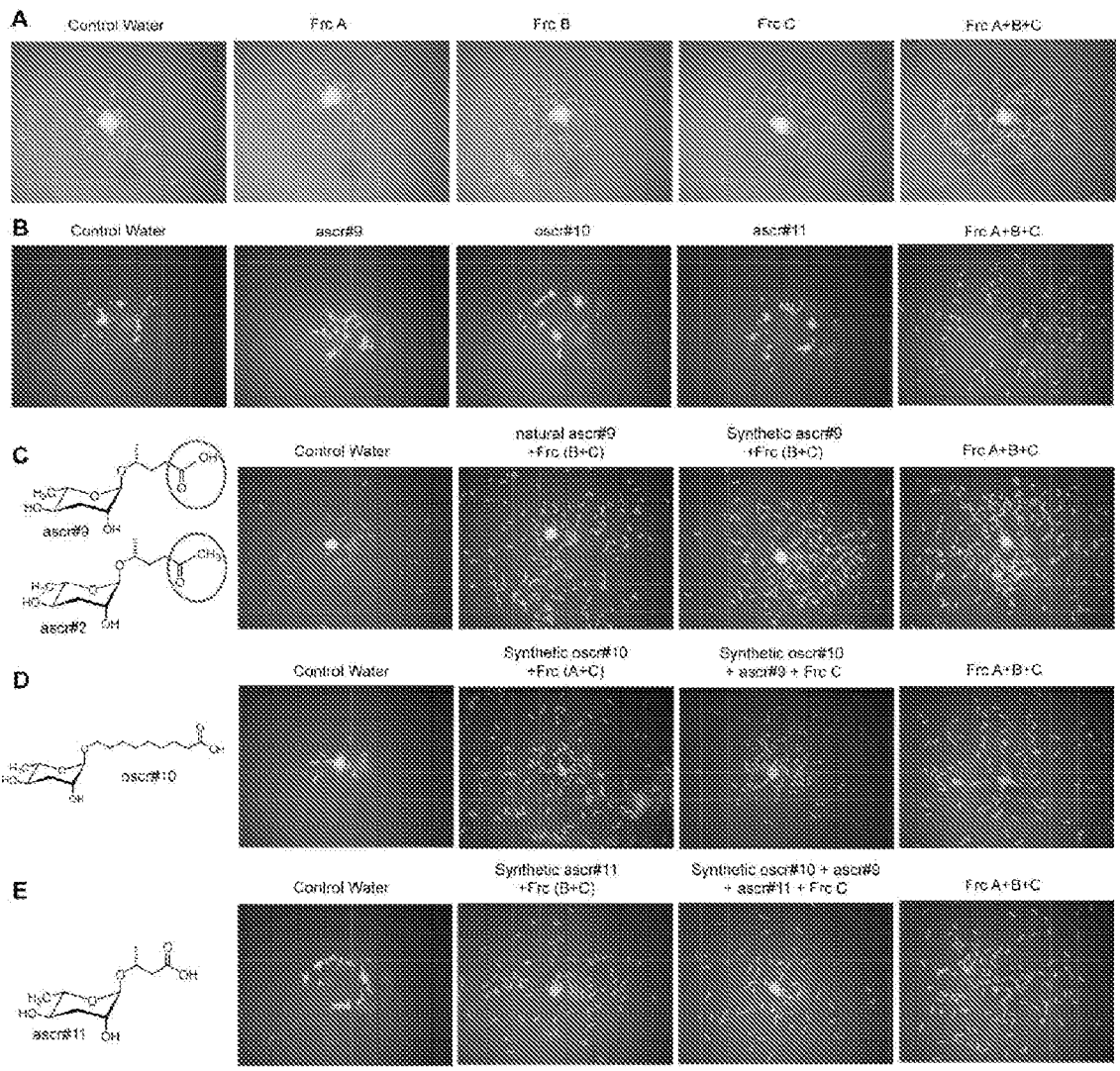
Figures 67A–E

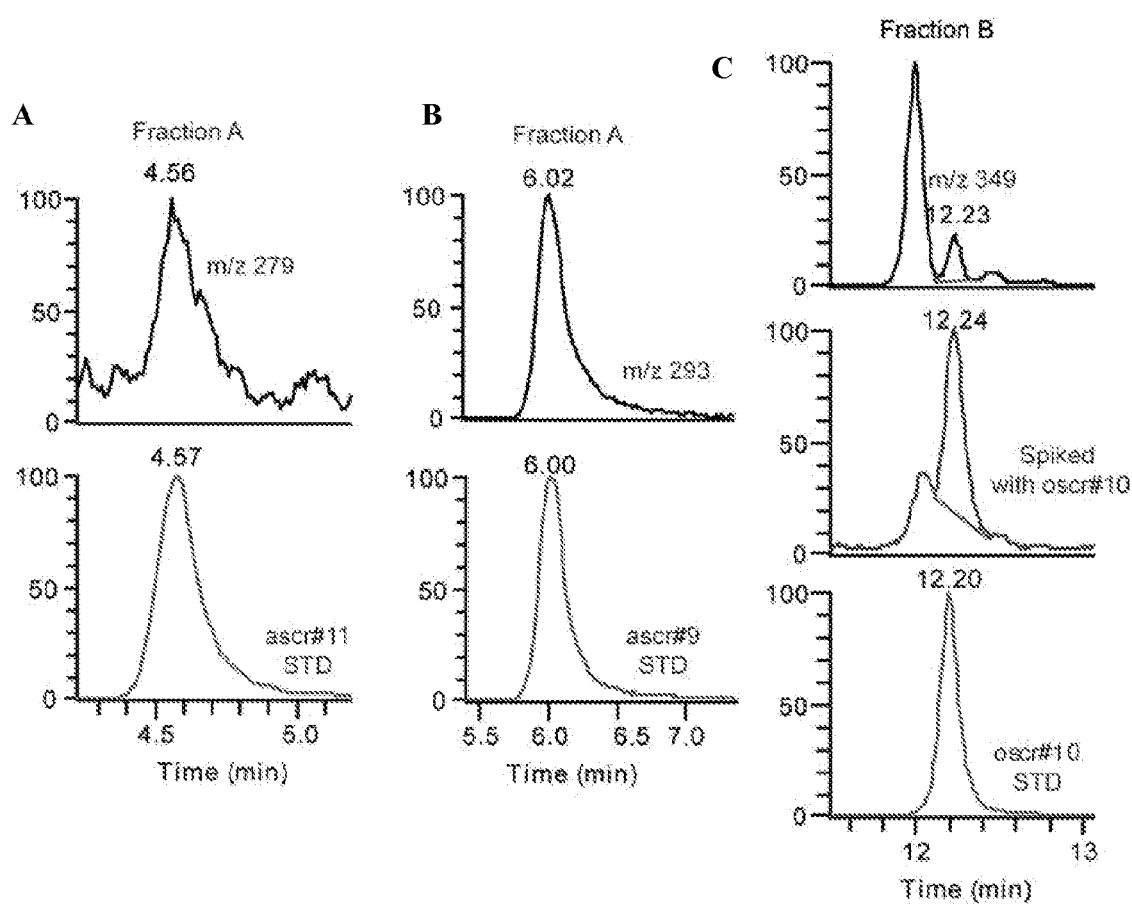
Figures 68A–C
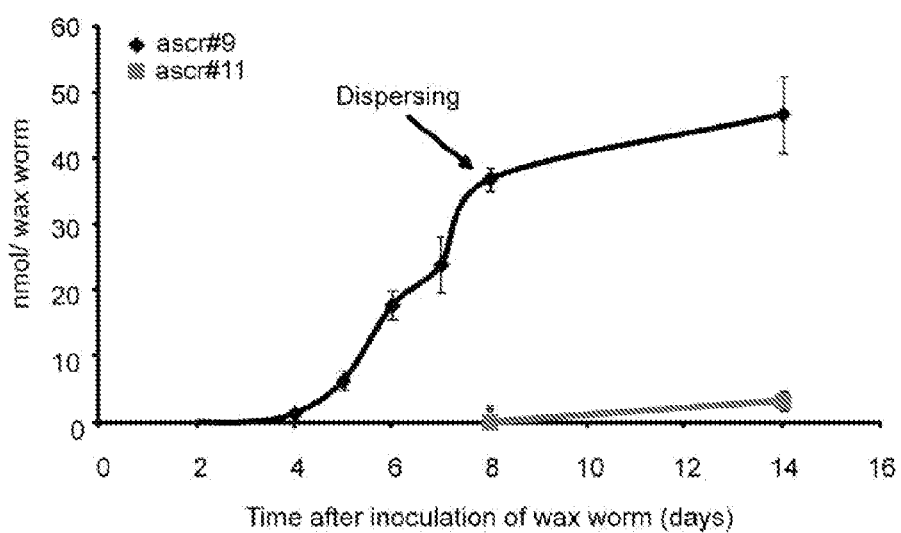
Figure 69

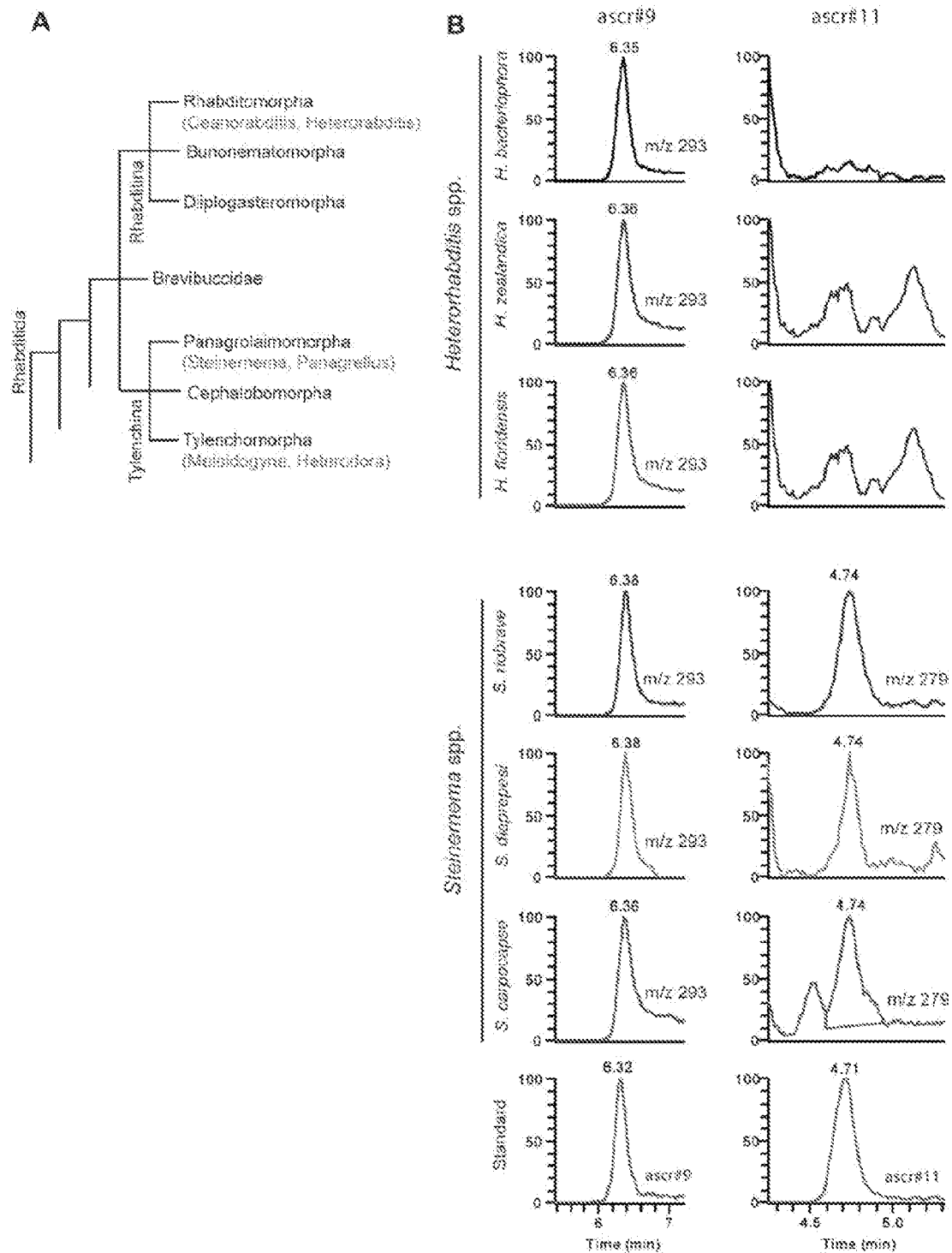
Figures 71A–B

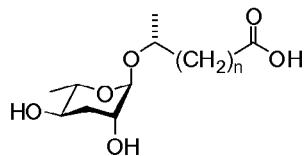

| Side chain (n) | SMID[1] | Molecular formula | Molecular mass g/mol | m/z M-H[-] |
|---|---|---|---|---|
| 1 | ascr#11 | $C_{10}H_{18}O_6$ | 234.11034 | 233.10 |
| 2 | ascr#9 | $C_{11}H_{20}O_6$ | 248.12599 | 247.12 |
| 3 | ascr#12 | $C_{12}H_{22}O_6$ | 262.14164 | 261.13 |
| 4 | ascr#1 | $C_{13}H_{24}O_6$ | 276.15729 | 275.15 |
| 5 | ascr#14 | $C_{14}H_{26}O_6$ | 290.17294 | 289.17 |
| 6 | ascr#10 | $C_{15}H_{28}O_6$ | 304.18859 | 303.18 |
| 7 | ascr#16 | $C_{16}H_{30}O_6$ | 318.20424 | 317.20 |
| 8 | ascr#18 | $C_{17}H_{32}O_6$ | 332.21989 | 331.21 |
| 9 | ascr#20 | $C_{18}H_{34}O_6$ | 346.23554 | 345.23 |
| 10 | ascr#22 | $C_{19}H_{36}O_6$ | 360.25119 | 359.24 |
| 11 | ascr#24 | $C_{20}H_{38}O_6$ | 374.26684 | 373.26 |
| 12 | ascr#26 | $C_{21}H_{40}O_6$ | 388.28249 | 387.28 |

Figure 72A

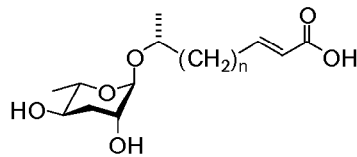

| Side chain (n) | SMID[1] | Molecular formula | Molecular mass g/mol | m/z M-H[-] |
|---|---|---|---|---|
| 2 | ascr#7 | $C_{13}H_{22}O_6$ | 274.14164 | 273.13 |
| 4 | ascr#3 | $C_{15}H_{26}O_6$ | 302.17294 | 301.17 |

Figure 72B

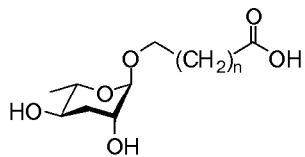

| Side chain (n) | SMID[1] | Molecular formula | Molecular mass g/mol | m/z M-H[-] |
|---|---|---|---|---|
| 1 | ascr#5 | $C_9H_{16}O_6$ | 220.09479 | 219.09 |
| 3 | oscr#9 | $C_{11}H_{20}O_6$ | 248.12599 | 247.12 |
| 7 | oscr#10 | $C_{15}H_{28}O_6$ | 304.18859 | 303.18 |

Figure 72C

| SMID[1] | Molecular formula | Molecular mass g/mol | m/z |
|---|---|---|---|
| icas#9 | $C_{20}H_{25}NO_7$ | 391.16310 | 390.16 M-H |
| ascr#2 | $C_{12}H_{22}O_5$ | 246.14672 | 269.14 M+Na |

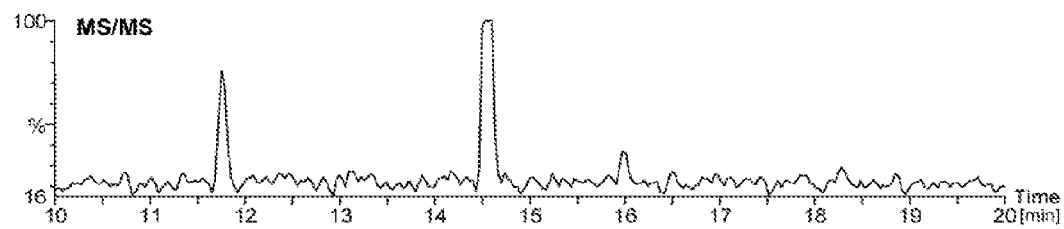
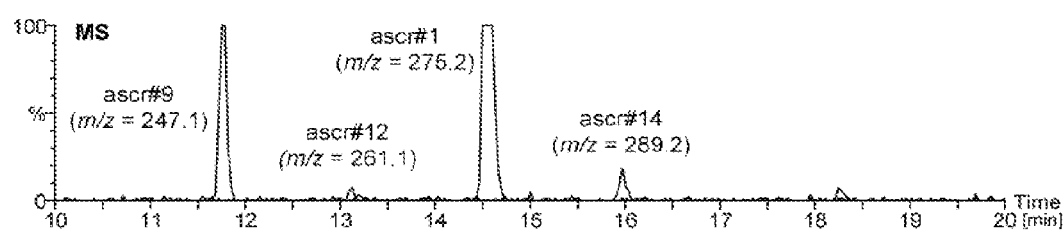
Figures 74A–B
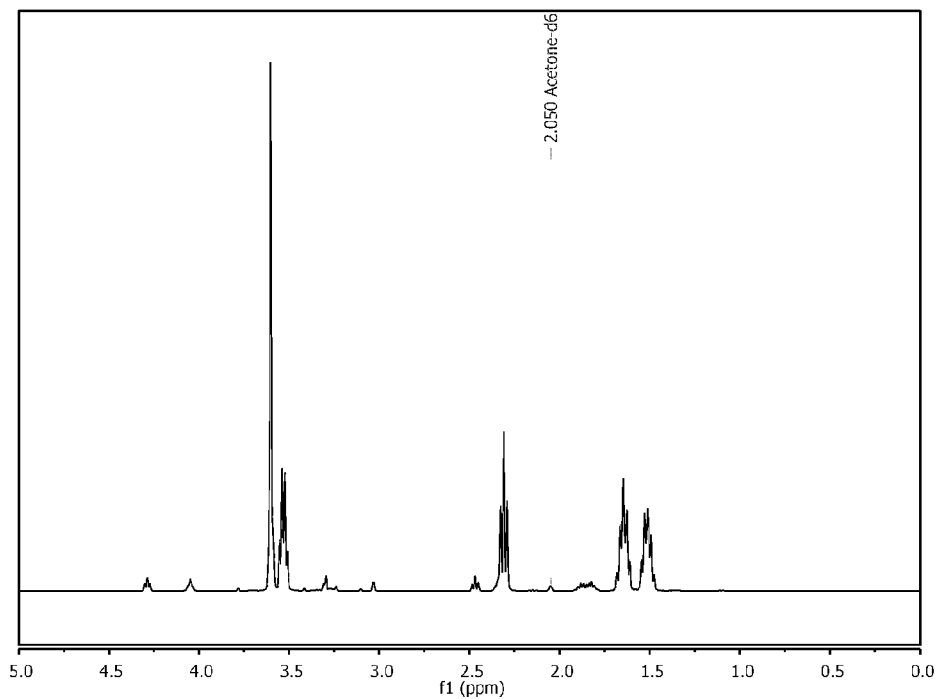
Figure 75A

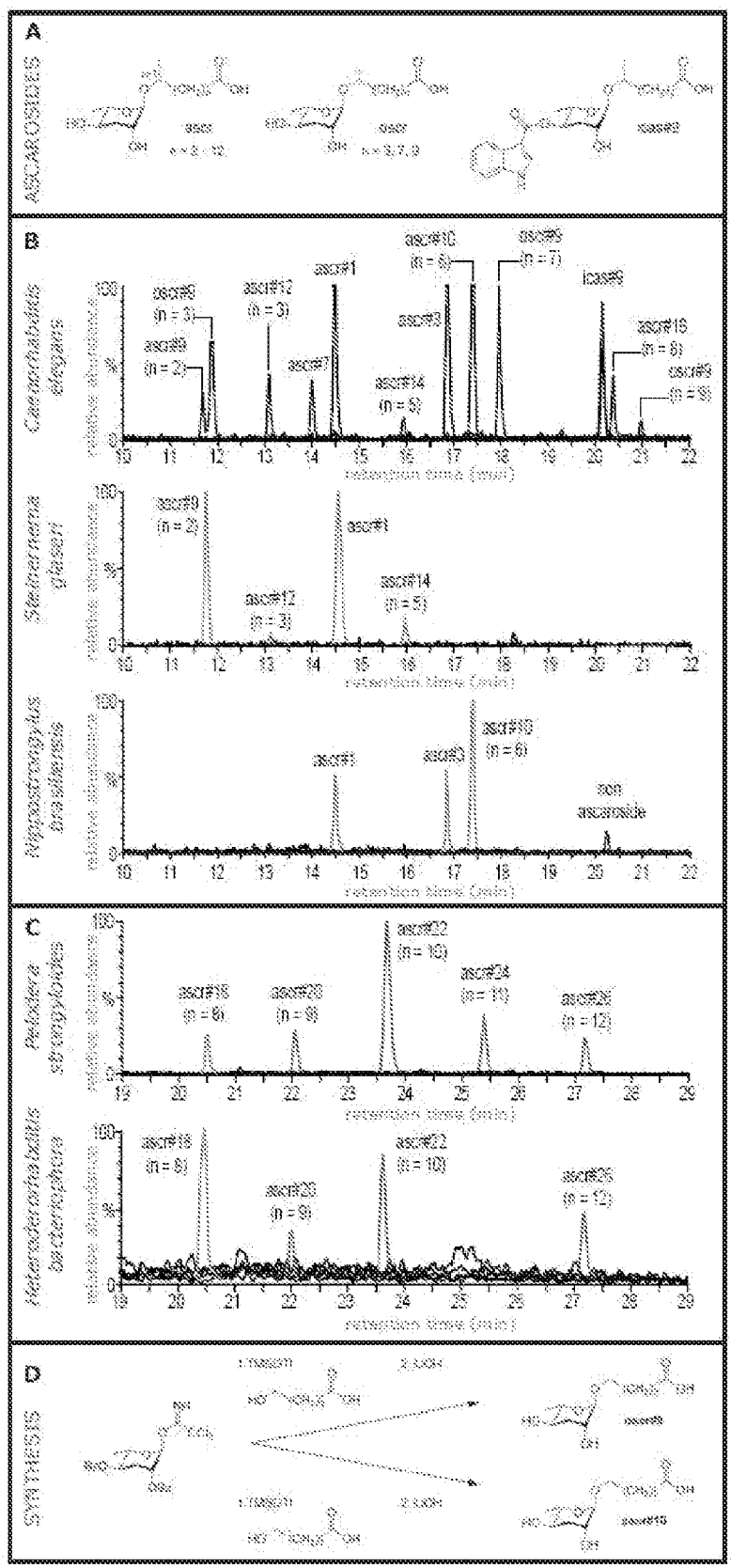
Figures 76A–D

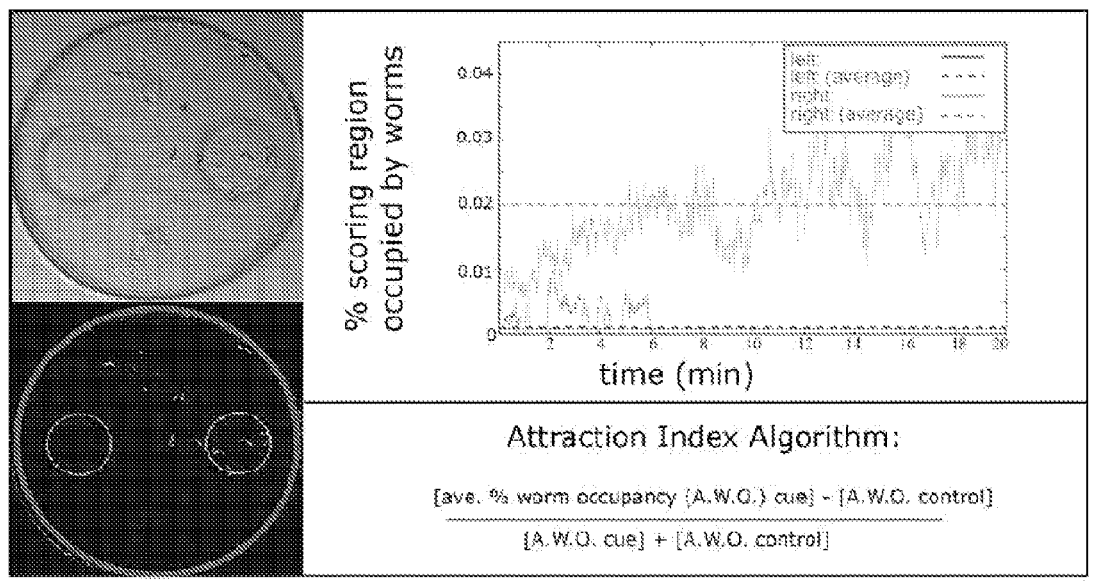
Figure 79
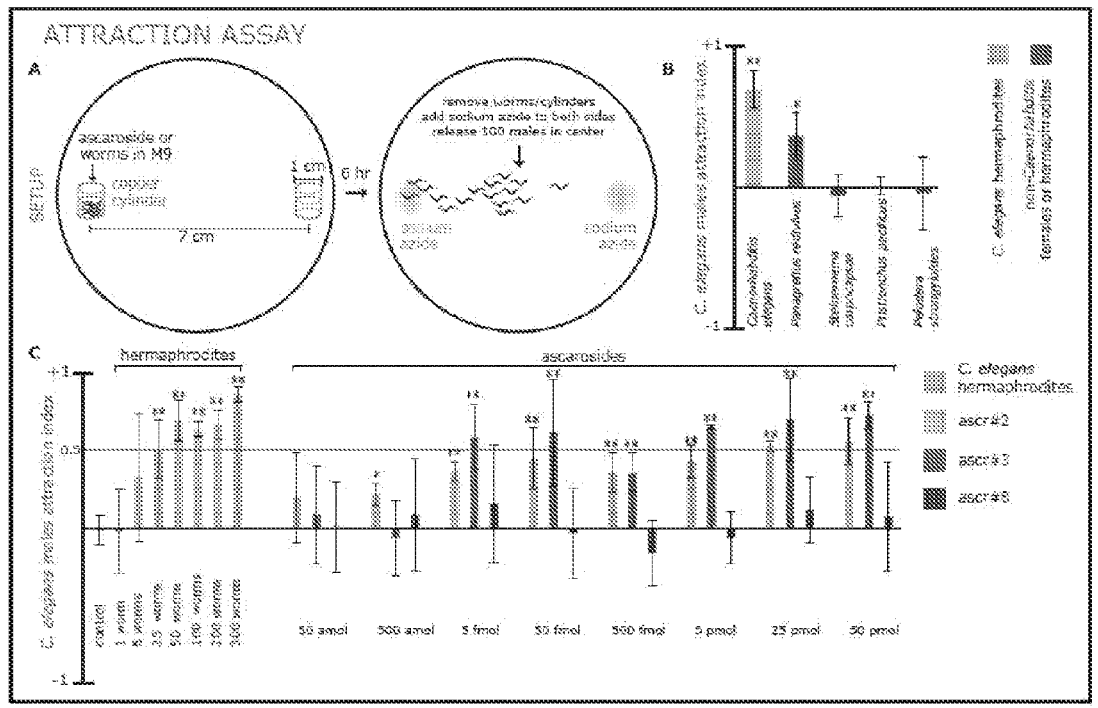
Figures 80A–C

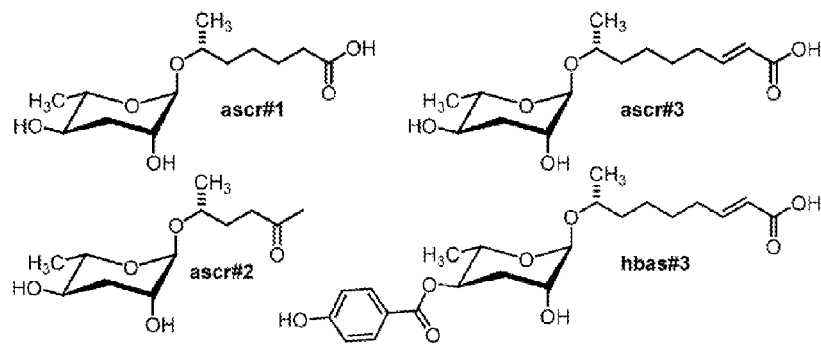
Figure 110A
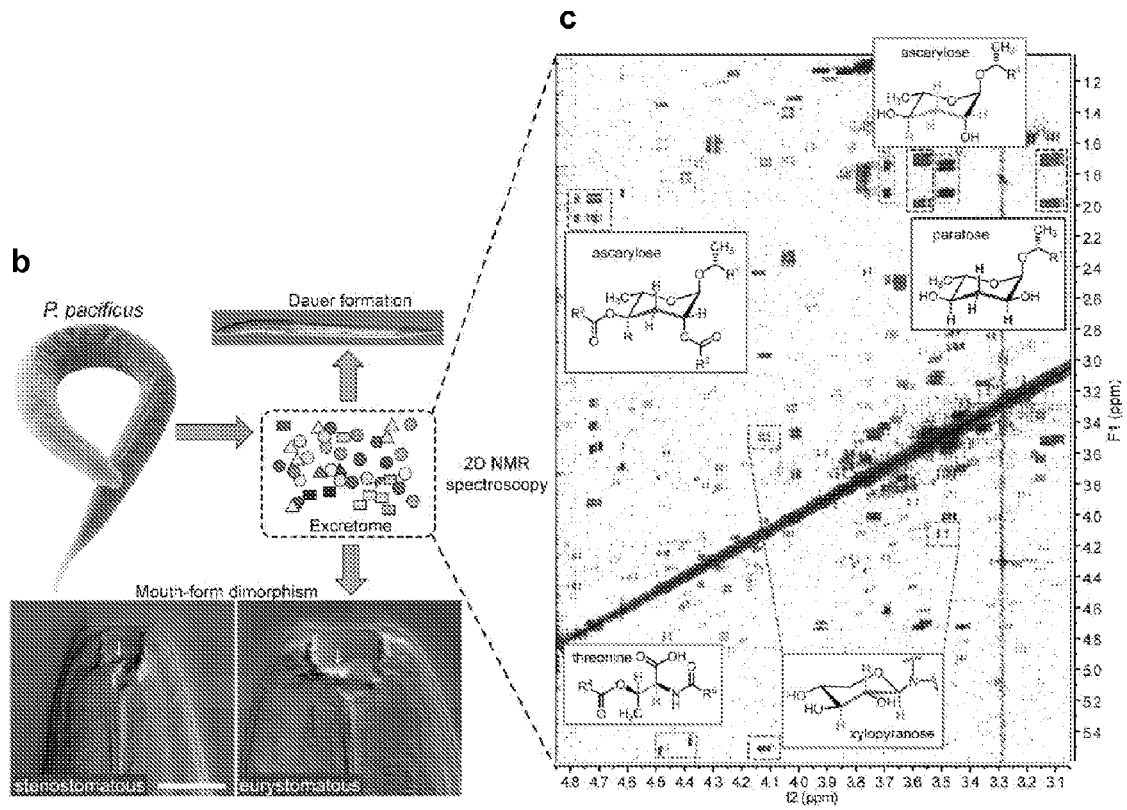
Figures 110B–C

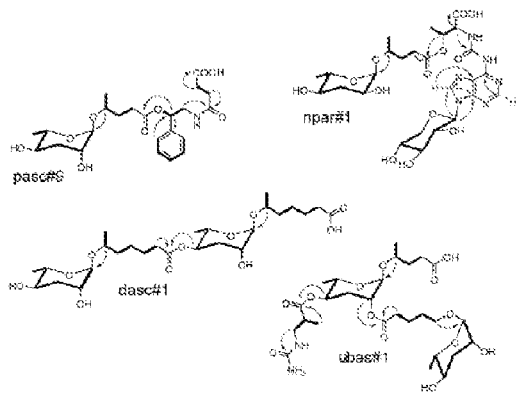

Figure 112

| SMID | Molecular formula | LC retention time [Min] ±SD | m/z [M-H]⁻ calculated | m/z [M-H]⁻ observed** | Estimated concentrations in culture supernatant (μM)*** |
|---|---|---|---|---|---|
| ascr#9* | $C_{11}H_{20}O_6$ | 11.68 ± 0.02 | 247.1187 | 247.1185 | 0.3-0.6 |
| ascr#12* | $C_{12}H_{22}O_6$ | 13.10 ± 0.01 | 261.1344 | 261.1305 | 0.1-0.3 |
| ascr#1* | $C_{13}H_{24}O_6$ | 14.51 ± 0.02 | 275.1500 | 275.1494 | 0.4-0.8 |
| pasc#9* | $C_{23}H_{33}NO_9$ | 17.10 ± 0.04 | 466.2083 | 466.2089 | 1.0-2.0 |
| pasc#12 | $C_{24}H_{35}NO_9$ | 17.81 ± 0.03 | 480.2239 | 480.2231 | 0.2-0.5 |
| pasc#1 | $C_{25}H_{37}NO_9$ | 18.59 ± 0.05 | 494.2396 | 494.2390 | 0.05-0.10 |
| ubas#1* | $C_{27}H_{46}N_2O_{13}$ | 17.51 ± 0.06 | 605.2927 | 605.2928 | 0.2-0.4 |
| ubas#2 | $C_{28}H_{48}N_2O_{13}$ | 18.11 ± 0.05 | 619.3084 | 619.3067 | 0.1-0.2 |
| dasc#1* | $C_{26}H_{46}O_{11}$ | 19.50 ± 0.01 | 533.2967 | 533.2951 | 0.2-0.5 |
| part#9* | $C_{11}H_{20}O_6$ | 11.99 ± 0.02 | 247.1187 | 247.1181 | 0.5-1.0 |
| npar#1* | $C_{26}H_{38}N_6O_{13}$ | 13.64 ± 0.05 | 641.2424 | 641.2443 | 0.5-1.0 |
| npar#2 | $C_{21}H_{30}N_6O_9$ | 14.34 ± 0.07 | 509.2002 | 509.1999 | 0.05-0.10 |

*Confirmed using synthetic standards.
**HRMS data was obtained from *P. pacificus* exo-metabolome extract analysis.
***Quantifications were based on integration of HPLC-MS signals from the corresponding ion-traces. Concentrations were calculated using response factors determined for synthetic standards. Concentrations for compounds that were not synthesized were based on extrapolation of available standards of closely related structures. A range of concentrations are reported as observed for multiple biological repeats.

Figure 113

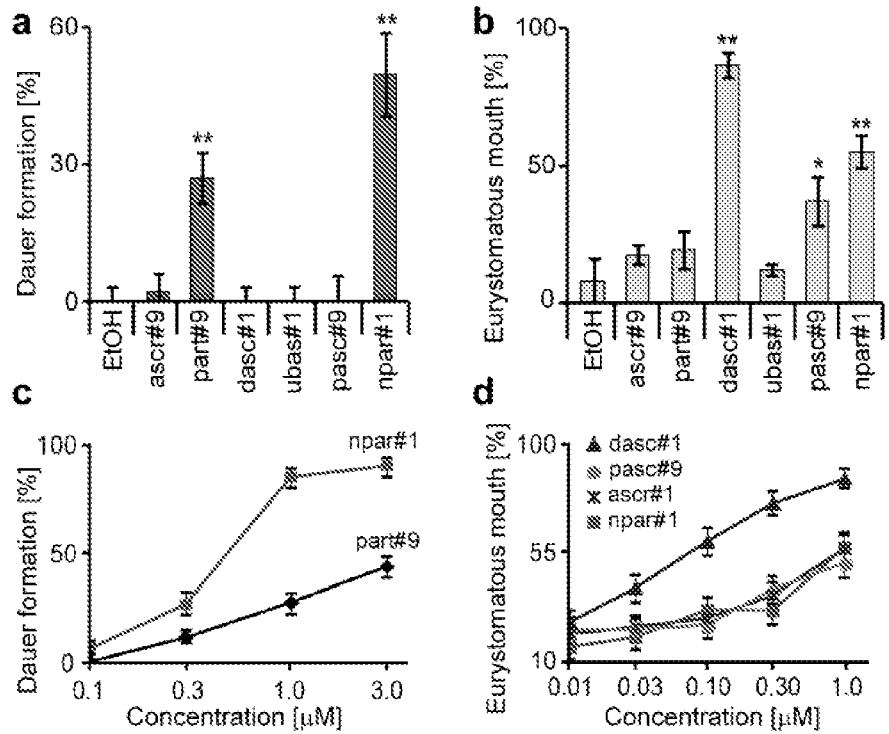
Figures 122A–D
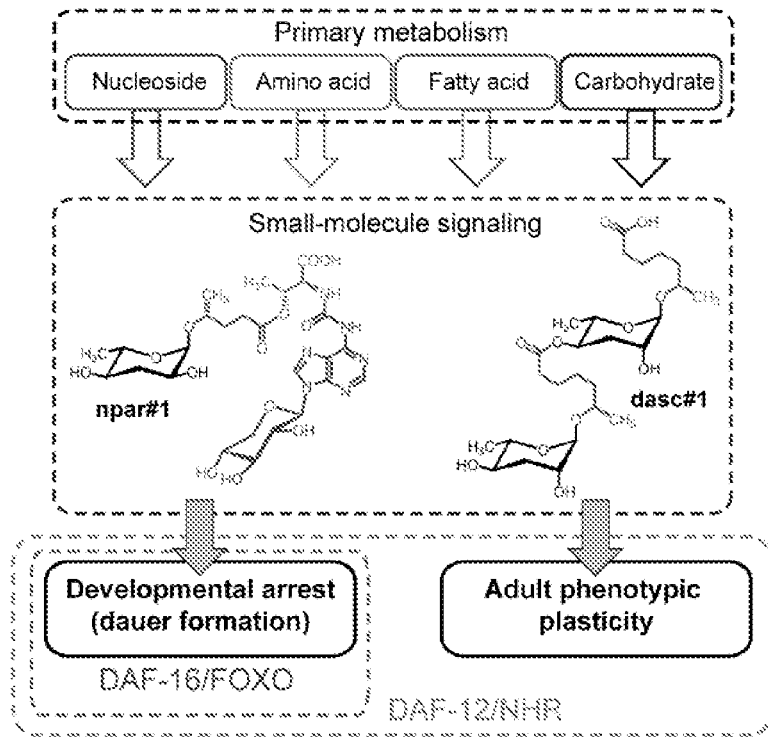
Figure 122E

Figures 125A–B

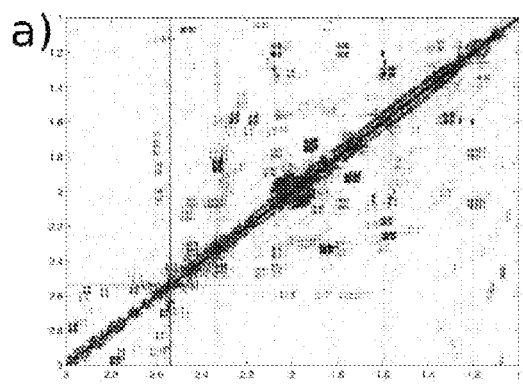 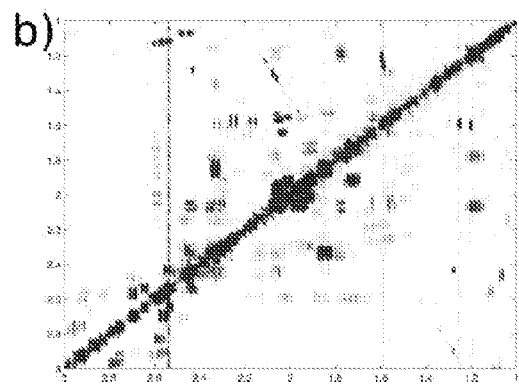
Figures 128A–B
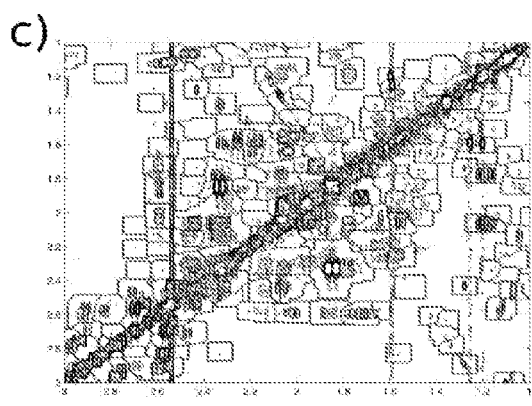 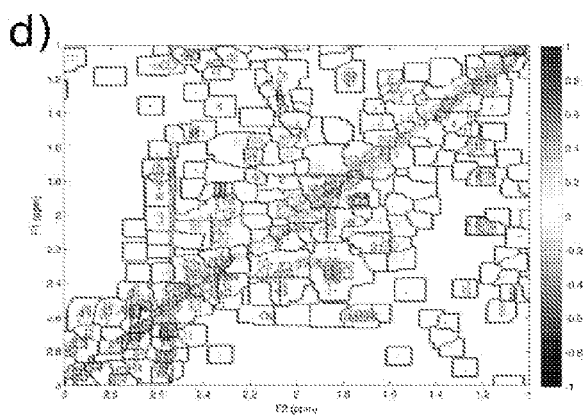
Figures 128C–D

Figures 130A–G

SMALL MOLECULE COMPOUNDS FOR THE CONTROL OF NEMATODES

This application is a §371 national-stage application based on Patent Cooperation Treaty Application serial number PCT/US2012/050016, filed Aug. 8, 2012, which claims the benefit of priority to U.S. Provisional Patent Application Ser. No. 61/521,295, filed Aug. 8, 2011 and U.S. Provisional Patent Application Ser. No. 61/620,348; each of which is hereby incorporated by reference in its entirety.

This invention was made with U.S. Government support under Grant Nos. GM088290, GM085285, and T32GM008500 awarded by the National Institutes of Health. The U.S. Government has certain rights in this invention.

FIELD OF THE INVENTION

The present invention relates to small molecule compounds involved in nematode signaling.

BACKGROUND OF THE INVENTION

Communication among individuals of a species relies on a number of different sensory inputs including chemical, mechanical, auditory, or visual cues (EDWARD O. WILSON, SOCIOBIOLOGY: THE NEW SYNTHESIS (25th anniv. ed. 2000)). Chemical signaling is perhaps the most ancient form of interorganismal communication (EDWARD O. WILSON, SOCIOBIOLOGY: THE NEW SYNTHESIS (25th anniv. ed. 2000); Wyatt, Nature 457:262-63 (2009)), and analysis of the chemical signals and the behaviors they mediate is of great significance for understanding the ecological and evolutionary dynamics of intra- and inter-specific interactions.

Nematodes are among the most abundant animals in the world, by individual count (SIEVERT LORENZEN: THE PHYLOGENETIC SYSTEMATICA OF FREELIVING NEMATODES (The Ray Society, London, 1994)). They inhabit sulfurous sediment, deep-sea trenches, mammals, insects, plants, arctic ice, and many other habitats, making them one of the most successful groups of animals on earth (Nussbaumer et al, Aquat. Microb. Ecol. 34:239-46 (2004); ISTVÁN ANDRASSY: EVOLUTION AS A BASIS FOR THE SYSTEMATIZATION OF NEMATODES (Budapest, 1976); Tietjen, Deep-Sea Res. 36:1579-94 (1989); Aben-Athar, Rev. Bras. Med. 2:89-94 (1951); Lutz, Weitere Mittheilungen 3:425-28 (1888); Blaxter, Science 282:2041-46 (1998)). Many nematode behaviors have been studied, such as mate finding in roots, bacteria, sand, agar, and intestines (DONALD L. LEE: THE BIOLOGY OF NEMATODES (CRC Press, London, 2002)). Little is known about nematode pheromone systems. Although there have been many attempts to identify nematode pheromones (DONALD L. LEE: THE BIOLOGY OF NEMATODES (CRC Press, London, 2002)), identification has only been successful in very few species (Jaffe et al, J. Chem. Ecol. 15:2031-43 (1989); Srinivasan et al, Nature 454:1115-18 (2008); Jeong, et al, Nature 433:541-45 (2005); Butcher et al, Nat. Chem. Biol. 7:420-22 (2007); Pungaliya et al, PNAS 19:7708-13 (2009)).

The free-living nematode C. elegans is used extensively as a model system for social behaviors such as foraging, population density sensing, mating, and aggregation (de Bono & Maricq, Annu. Rev. Neurosci. 28:451-501 (2005)). Entomopathogenic nematodes (EPN), such as Heterorhabditis spp. and Steinernema spp. are obligate insect parasites that kill and consume their hosts with the aid of symbiotic bacteria (Kaya & Gaugler, Annu. Rev. Entomol. 38:181-206 (1993)). C. elegans is typically found in decomposing plant material (Barriere & Felix, Curr. Biol. 15:1176-84 (2005)). It completes its life cycle within 3.5 days under standard laboratory conditions. When the conditions are not favorable for normal growth and development, such as high temperature, high density, or low food availability, it forms dauer larvae (alternative 3rd larvae). This specialized life stage, which does not feed and is resistant to stressful conditions (Golden & Riddle, Dev. Biol. 102:368-78 (1984); Golden & Riddle, Science 218:578-80 (1982); Golden & Riddle, PNAS 81:819-23 (1984)), is analogous to IJs of entomopathogenic nematodes and second stage juveniles (J2) of plant parasitic root-knot nematodes (PAUL DE LEY: A QUICK TOUR OF NEMATODE DIVERSITY AND THE BACKBONE OF NEMATODE PHYLOGENY (WormBook, ed. The C. elegans Research Community, 2006)) (Meloidogyne spp) that are equally adapted to survive conditions unfavorable for normal growth and development. Upon depletion of food resources or when overcrowded, infectious juveniles (IJs) of entomopathogenic nematodes and dauer larvae of the free living nematode Caenorhabditis elegans display a dispersal behavior (Golden & Riddle, Dev. Biol. 102:368-78 (1984); Rolston et al, J. Nematol. 38:221-28 (2006); Abebe et al, J. Exp. Biol. 213:3223-29 (2010)).

For C. elegans, entry of early larval stages (L1) into the dauer stage is regulated by a pheromone, called daumone (Jeong et al, Nature 433:541-45 (2005)). Subsequent to the identification of daumone, many related compounds have been found in C. elegans (Butcher et al, Nat. Chem. Biol. 3:420-22 (2007); Butcher et al, PNAS 105:14288-92 (2008); Srinivasan et al, Nature 454:1115-18 (2008); Butcher et al, Org. Lett. 11:3100-03 (2009); Pungaliya et al, PNAS 106:7708-13 (2009); von Reuss et al, J. Am. Chem. Soc. 134(3):1817-24 (2012)). All of these compounds have the unusual dideoxysugar ascarylose and are as a group called ascarosides.

Studies in C. elegans have shown that this family of small-molecule pheromones regulates gender specific attraction, repulsion, aggregation, olfactory plasticity, and entry into dauer (a stress-resistant life stage), collectively demonstrating that ascarosides mediate a wide range of C. elegans behaviors (Srinivasan et al, Nature 454:1115-18 (2008); Macosko et al, Nature 458:1171-75 (2009); Yamada et al, Science 329:1647-50 (2010); Butcher et al, Nat. Chem. Biol. 3:420-22 (2007)). Because ascarosides have not yet been found in any other animal phylum (Bartley et al., J. Nat. Prod. 59(10):921-26 (1996)), ascarosides may comprise a nematode-specific chemical code that may regulate important cues for multiple nematode species. Despite their importance for many aspects of C. elegans biology, however, knowledge of ascaroside structures, biosynthesis, and homeostatis, as well as the extent to which they may be produced and/or affect other nematodes, remained incomplete.

The present invention is directed to overcoming these and other deficiencies in the art.

SUMMARY OF THE INVENTION

One aspect of the present invention relates to an isolated compound of Formula I:

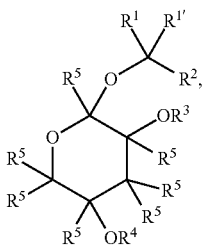

where:
R[1] is H, —C(R)$_3$, —OR, —N(R)$_2$, halogen, an alkyl, a haloalkyl, an alkenyl, or a haloalkenyl; where each R is independently H, halogen, an alkyl, or an alkenyl;

R[1'] is absent, H, —C(R)$_3$, —OR, —N(R)$_2$, halogen, an alkyl, a haloalkyl, an alkenyl, or a haloalkenyl; where each R is independently H, halogen, an alkyl, or an alkenyl;

R[2] is a moiety of formula

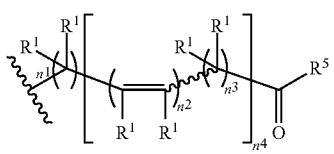

where:
each R[1] is independently H, —C(R)$_3$, —OR, —N(R)$_2$, halogen, an alkyl, a haloalkyl, an alkenyl, or a haloalkenyl; where each R is independently H, halogen, an alkyl, or an alkenyl;

R[5] is H, —OH, —OR[6], —OCR[6]R[7]R[8], —CR[6]R[7]R[8], —NH$_2$, —NHR[6], —NR[6]R[7], —CR[6]R[7]C(O)NHR[8], halogen, an alkyl, a haloalkyl, an alkenyl, a haloalkenyl, an aryl, a heteroaryl, an arylalkyl, a heterocyclyl, a cycloalkyl, a cycloalkenyl, an acyl, an amino acid, a nucleoside, a monosaccharide having 5 or 6 carbon atoms, or a bond connecting to R[3] or R[4] of another unit of Formula I;
where:
R[6] and R[7] are each independently H, —CR$_3$, —OR, —N(R)$_2$, halogen, an alkyl, a haloalkyl, an alkenyl, a haloalkenyl, an aryl, a heteroaryl, a heterocyclyl, a cycloalkyl, or a cycloalkenyl, where the alkyl, alkenyl, aryl, heteroaryl, heterocyclyl, cycloalkyl, or cycloalkenyl is optionally substituted with one or more substituents independently selected from the group consisting of —OR[8], —C(O)R[8], —NHC(O)R[8], an alkyl, a haloalkyl, an aryl, a heteroaryl, a heterocyclyl, and a cycloalkyl;
where:
each R is independently H, halogen, an alkyl, or an alkenyl; and
R[8] is H, —C(R)$_3$, —[C(R)$_2$]$_{n4}$NHC(O)R[9], —[C(R)$_2$]$_{n4}$C(O)(NH)R[9], —OR, —N(R)$_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —C(R)$_3$, —OR[9], —C(O)R[9], —NHC(O)R[9], halogen, an alkyl, a haloalkyl, an aryl, a heteroaryl, a heterocyclyl, a cycloalkyl, and a monosaccharide having 5 or 6 carbon atoms;
where:
each R is independently H, halogen, an alkyl, or an alkenyl;
R[9] is H, —C(R)$_3$, —OR, —N(R)$_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —C(R)$_3$, —OR, —C(O)R, halogen, an alkyl, a haloalkyl, an aryl, a heteroaryl, a heterocyclyl, and a cycloalkyl; where each R is independently H, halogen, an alkyl, or an alkenyl; and
n[4] is an integer of 1 to 30; and
R[8] is H, —C(R)$_3$, —[C(R)$_2$]$_{n4}$NHC(O)R[9], —[C(R)$_2$]$_{n4}$C(O)(NH)R[9], —OR, —N(R)$_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —C(R)$_3$, —OR[9], —C(O)R[9], —NHC(O)R[9], halogen, an alkyl, a haloalkyl, an aryl, a heteroaryl, a heterocyclyl, a cycloalkyl, and a monosaccharide having 5 or 6 carbon atoms;
where:
each R is independently H, halogen, an alkyl, or an alkenyl;
R[9] is H, —C(R)$_3$, —OR, —N(R)$_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —C(R)$_3$, —OR, —C(O)R, halogen, an alkyl, a haloalkyl, an aryl, a heteroaryl, a heterocyclyl, and a cycloalkyl; where each R is independently H, halogen, an alkyl, or an alkenyl; and
n[4] is an integer of 1 to 30;
n[1], n[2], and n[3] are each independently an integer of 0 to 30;
n[4] is an integer of 1 to 30; and
the sum of n[1], each n[2], and each n[3] is 1 to 30;
R[3] and R[4] are each independently H, —CR[6]R[7]R[8], —C(O)R[8], an alkyl, a haloalkyl, an alkenyl, a haloalkenyl, an aryl, a heteroaryl, a heterocyclyl, a cycloalkyl, a cycloalkenyl, an acyl, an amino acid, a nucleoside, a monosaccharide having 5 or 6 carbon atoms, or a bond connecting to R[5] of another unit of Formula I;
where:
R[6] and R[7] are each independently H, —CR$_3$, —OR, —N(R)$_2$, halogen, an alkyl, a haloalkyl, an alkenyl, a haloalkenyl, an aryl, a heteroaryl, a heterocyclyl, a cycloalkyl, or a cycloalkenyl, where the alkyl, alkenyl, aryl, heteroaryl, heterocyclyl, cycloalkyl, or cycloalkenyl is optionally substituted with one or more substituents independently selected from the group consisting of —$OR^8$, —$C(O)R^8$, —$NHC(O)R^8$, an alkyl, a haloalkyl, an aryl, a heteroaryl, a heterocyclyl, and a cycloalkyl;

where:

each R is independently H, halogen, an alkyl, or an alkenyl; and $R^8$ is H, —$C(R)_3$, —$[C(R)_2]_{n4}NHC(O)R^9$, —$[C(R)_2]_{n4}C(O)(NH)R^9$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —$OR^9$, —$C(O)R^9$, —$NHC(O)R^9$, halogen, an alkyl, a haloalkyl, an aryl, a heteroaryl, a heterocyclyl, a cycloalkyl, and a monosaccharide having 5 or 6 carbon atoms; where:

each R is independently H, halogen, an alkyl, or an alkenyl;

$R^9$ is H, —$C(R)_3$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —OR, —C(O)R, halogen, an alkyl, a haloalkyl, an aryl, a heteroaryl, a heterocyclyl, and a cycloalkyl; where each R is independently H, halogen, an alkyl, or an alkenyl; and $n^4$ is an integer of 1 to 30; and $R^8$ is H, —$C(R)_3$, —$[C(R)_2]_{n4}NHC(O)R^9$, —$[C(R)_2]_{n4}C(O)(NH)R^9$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —$OR^9$, —$C(O)R^9$, —$NHC(O)R^9$, halogen, an alkyl, a haloalkyl, an aryl, a heteroaryl, a heterocyclyl, a cycloalkyl, and a monosaccharide having 5 or 6 carbon atoms;

where:

each R is independently H, halogen, an alkyl, or an alkenyl;

$R^9$ is H, —$C(R)_3$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —OR, —C(O)R, halogen, an alkyl, a haloalkyl, an aryl, a heteroaryl, a heterocyclyl, and a cycloalkyl; where each R is independently H, halogen, an alkyl, or an alkenyl; and $n^4$ is an integer of 1 to 30; and each $R^5$ is independently H, —OH, —$OR^6$, —$OCR^6R^7R^8$, —$CR^6R^7R^8$, —$NH_2$, —$NHR^6$, —$NR^6R^7$, —$CR^6R^7C(O)NHR^8$, halogen, an alkyl, a haloalkyl, an alkenyl, a haloalkenyl, an aryl, a heteroaryl, an arylalkyl, a heterocyclyl, a cycloalkyl, a cycloalkenyl, an acyl, an amino acid, a nucleoside, a monosaccharide having 5 or 6 carbon atoms, or a bond connecting to $R^3$ or $R^4$ of another unit of Formula I; where:

$R^6$ and $R^7$ are each independently H, —$CR_3$, —OR, —$N(R)_2$, halogen, an alkyl, a haloalkyl, an alkenyl, a haloalkenyl, an aryl, a heteroaryl, a heterocyclyl, a cycloalkyl, or a cycloalkenyl, where the alkyl, alkenyl, aryl, heteroaryl, heterocyclyl, cycloalkyl, or cycloalkenyl is optionally substituted with one or more substituents independently selected from the group consisting of —$OR^8$, —$C(O)R^8$, —$NHC(O)R^8$, an alkyl, a haloalkyl, an aryl, a heteroaryl, a heterocyclyl, and a cycloalkyl;

where:

each R is independently H, halogen, an alkyl, or an alkenyl; and $R^8$ is H, —$C(R)_3$, —$[C(R)_2]_{n4}NHC(O)R^9$, —$[C(R)_2]_{n4}C(O)(NH)R^9$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —$OR^9$, —$C(O)R^9$, —$NHC(O)R^9$, halogen, an alkyl, a haloalkyl, an aryl, a heteroaryl, a heterocyclyl, a cycloalkyl, and a monosaccharide having 5 or 6 carbon atoms;

where:

each R is independently H, halogen, an alkyl, or an alkenyl;

$R^9$ is H, —$C(R)_3$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —OR, —C(O)R, halogen, an alkyl, a haloalkyl, an aryl, a heteroaryl, a heterocyclyl, and a cycloalkyl; where each R is independently H, halogen, an alkyl, or an alkenyl; and $n^4$ is an integer of 1 to 30; and $R^8$ is H, —$C(R)_3$, —$[C(R)_2]_{n4}NHC(O)R^9$, —$[C(R)_2]_{n4}C(O)(NH)R^9$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —C(R)$_3$, —OR$^9$, —C(O)R$^9$, —NHC(O)R$^9$, halogen, an alkyl, a haloalkyl, an aryl, a heteroaryl, a heterocyclyl, a cycloalkyl, and a monosaccharide having 5 or 6 carbon atoms;

where:

each R is independently H, halogen, an alkyl, or an alkenyl;

R$^9$ is H, —C(R)$_3$, —OR, —N(R)$_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —C(R)$_3$, —OR, —C(O)R, halogen, an alkyl, a haloalkyl, an aryl, a heteroaryl, a heterocyclyl, and a cycloalkyl; where each R is independently H, halogen, an alkyl, or an alkenyl; and n$^4$ is an integer of 1 to 30;

with the proviso that the compound is not ascr#1, ascr#2, ascr#3, ascr#4, ascr#5, ascr#6.1, ascr#6.2, ascr#7, ascr#8, ascr#12, ascr#19, ascr#21, ascr#23, ascr#25, bhas#24, bhas#26, bhas#28, bhas#30, or icas#9. These isolated compounds include those of Formula I' and Formula I":

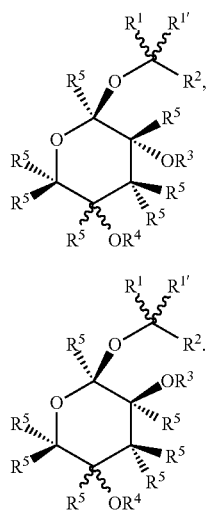

Another aspect of the present invention relates to an isolated compound comprising at least one nucleobase, at least one fatty acid, at least one amino acid, and at least one sugar. The at least one nucleobase, the at least one fatty acid, the at least one amino acid, and the at least one sugar are linked by covalent bonds. The compound has a molecular weight of less than about 2,000 g/mol.

BRIEF DESCRIPTION OF THE DRAWINGS

FIGS. 1A-E show that indole ascarosides attract *C. elegans* hermaphrodites and males. FIG. 1A is a schematic representation of the bioassay used to measure attraction behavior in worms. Zone A is the region where the sample or control solution is applied. The X denotes the initial position of the assayed worms. FIG. 1B is a schematic representation of a quadrant chemotaxis assay. An X denotes the spot where washed worms are placed at the beginning of the assay. The shaded regions of the quadrant plate indicate the agar containing the chemical, whereas the white regions denote control agar. The number of animals in each quadrant was counted after 30 minutes and a chemotaxis index was computed (see Example 9). The chemotaxis index for the schematic is 0.84. FIG. 1C shows that icas#1, icas#3, and icas#9 are attractive to both *C. elegans* sexes. All three compounds were assayed at 1 pmol using N2 hermaphrodites and him-5 males. Open bars: no compound (solvent vehicle) controls. FIG. 1D is a chart of the dose dependence of icas#3 response for N2 hermaphrodites and him-5 males in the spot attraction assay (*p<0.01, p<0.001, *p<0.0001, unpaired t test with Welch's correction). FIG. 1E is a graph of the dose dependence of icas#3 attraction for N2 hermaphrodites in the quadrant chemotaxis assay (one-factor ANOVA with Dunnett's post-test, **p<0.01).

FIGS. 2A-E demonstrate that the response to icas#3 in N2 hermaphrodites is mediated by ASK sensory neurons and the downstream AIA interneurons. FIG. 2A is a schematic representation of the connectivity of the ASK sensory neuron to other neurons. The primary synaptic output of ASK is the AIA interneuron. FIG. 2B shows that attraction of hermaphrodites to icas#3 is dependent on the ASK sensory neurons and the AIA interneurons. Ablation of the RMG interneuron does not affect attraction of N2 or ncs-1::gfp hermaphrodites to icas#3 (*p<0.01, *p<0.0001, unpaired Student's t test with Welch's correction). FIG. 2C is a graph of the aggregation of N2 and ASK-ablated hermaphrodites at low worm density (20 worms per plate). ASK-ablated worms do not aggregate in response to icas#3. icas#3 induces G-CaMP fluorescence signals in AIA interneurons (FIG. 2D). The colored traces represent fluorescence changes in the AIA neurons of individual animals upon exposure to 1 µM icas#3. The black traces represent fluorescent changes of individual animals upon exposure to buffer. The grey shading indicates presence of icas#3, n=10 animals. FIG. 2E is a graph of the average AIA fluorescence change in animals exposed to either buffer or icas#3 (p<0.01, unpaired Student's t test with Welch's correction). Error bars indicate standard error of mean (S.E.M).

FIGS. 3A-D show that social and solitary wild-type hermaphrodites are attracted to icas#3, but not to non-indole ascarosides. Solitary and social wild-type hermaphrodites are not attracted to a physiological ascr#2,3,5 mixture in the spot attraction assays, in contrast to npr-1(ad609) mutant worms (FIG. 3A) (***p<0.0001, unpaired t test with Welch's correction). In the quadrant chemotaxis assay, hermaphrodites from all tested strains are attracted to 1 pM icas#3 and repelled by a physiological mixture of non-indole ascarosides (10 nM ascr#2,3,5), except for npr-1(ad609) mutant worms, which are also attracted to the ascr#2,3,5 blend (FIG. 3B) (chemotaxis after 30 minutes (for chemotaxis indices at 15 minutes, see FIG. 5C). FIG. 3C is a graph of the dose-dependence of icas#3 attraction for social hermaphrodites in the quadrant chemotaxis assay. FIGS. 3B-C: *p<0.05, p<0.01, one-factor ANOVA with Dunnett's post-test. FIG. 3D shows that social wild-type hermaphrodites and npr-1(ad609) mutant worms are attracted to icas#3 in the spot attraction assay (p<0.001, ***p<0.0001, unpaired t test with Welch's correction).

FIGS. 4A-C relate to an emerging model for a modular language of signaling molecules. FIG. 4A shows that icas#3 and ascr#3 are competing signals for N2 hermaphrodites. Mixtures of 120 fmol ascr#3 and 10 fmol icas#3 (Condition 1) attract worms to zone A, whereas larger amounts of a mixture of the same ratio (Condition 2; 12 pmol ascr#3 and 1 pmol icas#3) deter worms from zone A and instead attract to the periphery (zones B and C). In experiments with Condition 2, only one worm entered the treated zone A, whereas 31 worms entered control zone A (***$p<0.0001$, unpaired Student's t test with Welch's correction). FIG. 4B shows that synergistic blends of non-indole ascarosides induce dauer at nanomolar to micromolar concentrations and function as a male attractant at picomolar to nanomolar concentrations, whereas indole ascarosides icas#3 and icas#9 act as hermaphrodite attractants and aggregation signals at femtomolar to picomolar concentrations. FIG. 4C shows the modular assembly of C. elegans signaling molecules, based on building blocks derived from tryptophan ("head group"), fatty acids ("lipid side chain"), p-aminobenzoic acid (PABA, "terminus"), and carbohydrate metabolism ("ascarylose").

FIGS. 5A-C show that indole ascarosides are strong hermaphrodite attractants. In the spot attraction assay, N2 hermaphrodites are strongly attracted to low concentrations of icas#9, whereas males are not attracted (***$p<0.0001$, unpaired Student's t test with Welch's correction) (FIG. 5A). FIG. 5B is a graph of quadrant chemotaxis indices of N2 and CB4856 hermaphrodites on plates containing 1 pM icas#3 with or without food. In the quadrant chemotaxis assay, hermaphrodites from all tested strains are attracted to 1 pM icas#3 and repelled by a physiological mixture of non-indole ascarosides (10 nM of each ascr#2,3,5), except for npr-1 (ad609) mutant worms, which are also attracted to the ascr#2,3,5 blend (FIG. 5C) (chemotaxis after 15 minutes (for chemotaxis indices at 30 minutes, see FIG. 3B), *$p<0.05$, **$p<0.01$, one-factor ANOVA with Dunnett's post-test).

FIGS. 6A-E relate to aggregation and locomotory changes in response to icas#3. FIG. 6A shows the aggregation behavior of solitary and social hermaphrodites on icas#9 plates at low worm density (20 worms per 5 cm plate) (*$p<0.05$, $p<0.01$, one-factor ANOVA with Dunnett's post-test). FIG. 6B shows the aggregation of him-5 males on plates containing 100 fM or 100 pM of icas#3 ($p<0.01$, one-factor ANOVA with Dunnett's post-test). FIG. 6C shows that daf-22 hermaphrodites are attracted to icas#3 in the spot attraction assay (*$p<0.01$, $p<0.01$, *$p<0.0001$, unpaired Student's t-test with Welch's correction). FIG. 6D shows the forward velocity (velocity of worms during the worm's forward movement) of N2 hermaphrodites at different icas#3 concentrations. FIG. 6E shows the number of reversals per minute of N2 hermaphrodites at different icas#3 concentrations. FIG. 6D-E: *$p<0.05$, **$p<0.01$, one-factor ANOVA with Dunnett's post-test.

FIGS. 7A-B show that ASK ablation affects icas#3-dependent locomotory behavior of hermaphrodites. ASK-ablated hermaphrodites do not display reduced forward velocity upon exposure to icas#3 (FIG. 7A). Reversal frequency of ASK ablated worms does not increase in response to icas#3 (FIG. 7B). **$p<0.001$, unpaired t test with Welch's correction).

FIGS. 8A-D show that indole ascarosides mediate aggregation behavior in C. elegans. FIG. 8A shows the aggregation behavior of solitary and social hermaphrodites at low worm densities (20 worms per plate) on different concentrations of icas#3. FIG. 8B shows the aggregation behavior of solitary and social hermaphrodites at high worm densities (~120 worms per plate) on different concentrations of icas#3. FIG. 8C shows the aggregation of daf-22 hermaphrodites at low worm density on two different concentrations of icas#3. FIG. 8D shows the mean stopped duration of N2 hermaphrodites at different icas#3 concentrations. FIGS. 8A-D: *$p<0.05$, **$p<0.01$ one-factor ANOVA with Dunnett's post-test.

FIGS. 9A-G relate to the identification of indole ascarosides as daf-22-dependent metabolites. FIG. 9A shows the chemical structures of important ascarosides (Srinivasan et al., Nature 454:1115-18 (2008), which is hereby incorporated by reference in its entirety). FIG. 9B is a schematic representation of Differential Analysis via 2D-NMR spectroscopy (DANS). Comparison of wild-type NMR spectra with daf-22 mutant NMR spectra enabled detection of spectroscopic signals that may represent daf-22-dependent signaling molecules. FIG. 9C is a small section of the actual wild-type and daf-22 NMR spectra used for DANS. Signals of indole carboxylic acid are present in both spectra (left box in each panel), whereas another indole-derived signal (right box in each panel) is only present in the wild-type, but not the daf-22 spectrum. (FIG. 9D is an HPLC-MS-based comparison of the wild-type and daf-22 metabolomes. Ion chromatograms obtained for wild-type show peaks for the molecular ions of five different indole ascarosides which are absent from the daf-22 chromatograms. FIG. 9E shows the structures of identified indole ascarosides. FIG. 9F shows the structures of additional non-indole ascarosides identified in this study. FIG. 9G is a graph of the relative amounts of indole ascarosides icas#3 and icas#9 and non-indole ascarosides ascr#3 and ascr#9 secreted by C. elegans N2 grown in liquid culture, as determined by HPLC-MS analyses of media extracts (normalized to concentration of ascr#3; n=5, ±SEM). For mass spectrometric quantification of indole and non-indole ascarosides, standard mixtures of authentic reference compounds were used.

FIGS. 11A-C are the $^1H$ NMR spectrum ($CD_3OD$, 600 MHz) (FIG. 11A), $^1H$, $^{13}C$-HSQC spectrum ($CD_3OD$, 600 MHz) (FIG. 11B), and $^1H$, $^{13}C$-HMBC spectrum ($CD_3OD$, 600 MHz) (FIG. 11C) of synthetic icas#3.

FIGS. 12A-E relate to HPLC-MS identification of indole ascarosides. They show the electrospray ionization MS spectra (negative ion mode) of icas#9, icas#7, icas#1, icas#3, and icas#10, respectively.

FIGS. 13 A-H relate to HPLC-MS analysis of the biosynthetic origin of indole ascarosides. They show the HPLC-MS ion chromatograms (acquired using negative-ion electrospray ionization and single-ion recording mode) of whole-body extracts of C. elegans cultivated in CeMM medium with a 1:1 mixture of L-[2,4,5,6,7-$D_5$]-tryptophan and L-tryptophan showing [$D_5$]- and [H]-isotopomers of icas#9 (FIGS. 13A-B), icas#1 (FIGS. 13E-F), icas#3 (FIGS. 13C-D), and icas#10 (FIGS. 13G-H), respectively.

FIGS. 14A-B also show that indole ascarosides mediate aggregation behavior in C. elegans. FIG. 14A shows the aggregation (arrow) of N2 hermaphrodites (20 worms per plate) on plates containing 10 pM of icas#3 compared to behavior on control plates. FIG. 14B shows the aggregation of N2 hermaphrodites (~120 worms per plate) on plates containing 1 pM of icas#3 compared to behavior on control plates.

FIGS. 15A-B are the $^1H$ NMR spectrum (FIG. 15A) and $^{13}C$ NMR spectrum (FIG. 15B) of Methyl 5-(3'R,5'R-dibenzoyloxy-6'S-methyl-(2H)-tetrahydropyran-2'-yloxy)pentanoate (3). $^1H$ NMR: 400 MHz, acetone-$d_6$; $^{13}C$ NMR: 100 MHz, acetone-$d_6$.

FIGS. 37A-K show the HPLC-ESI-MS data of: (ω-1)-oxygenated ascarosides (ascr) (FIG. 37A), (ω)-oxygenated ascarosides (oscr) (FIG. 37B), (ω-1)-oxygenated β-hydroxyascarosides (bhas) (FIG. 37C), (ω)-oygenated β-hydroxyascarosides (bhos) (FIG. 37D), (ω-1)-oxygenated indole ascarosides (icas) (FIG. 37E), (ω)-oxygenated indole ascarosides (icos) (FIG. 37F), (ω-1)-oxygenated indole β-hydroxy ascarosides (ibha) (FIG. 37G), (ω)-oxygenated indole β-hydroxy ascarosides (ibho) (FIG. 37H), glucosyl ascaroside esters (glas) (FIG. 37I), ascr#8 and 4-(4-hydroxybenzoyl)- and 4-(2-(E)-methyl-2-butenoyl)-ascarosides (hbas and mbas) (FIG. 37J), and ascr#2 and ascr#6.1 (FIG. 37K). *=confirmed using synthetic standards; $ SMID: Small Molecule IDentifier for small molecules identified from C. elegans and other nematodes. The SMID database (www.smid-db.org) is an electronic resource maintained by Frank C. Schroeder and Lukas Mueller at the Boyce Thompson Institute in collaboration with Wormbase (www.wormbase.org). The purpose of this database is to introduce searchable, gene-style identifiers, "SMIDs", for all small molecules newly identified from C. elegans and other nematodes.

FIGS. 43A-B are sections of dqfCOSY spectra (600 MHz, methanol-$d_4$) of glas#10-enriched fraction from acox-1 (ok2257) worm pellet extracts (FIG. 43A) and synthetic glas#10 (FIG. 43B), showing characteristic signals for methyl groups of the ascarylose ring and the side chain (blue), the anomeric hydrogen of the glucose unit (red), the glucose spin system (green), and the ascarylose spin system (black).

FIGS. 44A-P are MS/MS product ion spectra of ascaroside standards. ascr#5 shows m/z 147 [$C_6H_{11}O_4$] for ascarylose and m/z 73 for the $C_3$-sidechain and/or the ascarylose derived $C_3O_2H_5$ fragment of identical molecular composition (FIG. 44A). oscr#9 (FIG. 44B) and ascr#9 (FIG. 44C) show m/z 99 [$C_5H_7O_2$] for the $C_5$-sidechain, m/z 147 [$C_6H_{11}O_4$], and m/z 73 for the ascarylose derived $C_3O_2H_5$ fragment. ascr#7 shows m/z 125 [$C_7H_9O_2$] for the $C_7$-sidechain, m/z 111 [$C_6H_7O_2$] and m/z 73 for the ascarylose derived $C_3O_2H_5$ fragment (FIG. 44D). ascr#1 shows m/z 127 [$C_7H_{11}O_2$] for the $C_7$-sidechain and m/z 73 for the ascarylose derived $C_3O_2H_5$ fragment (FIG. 44E). ascr#3 shows m/z 111 [$C_6H_7O_2$] and m/z 73 for the ascarylose derived $C_3O_2H_5$ fragment (FIG. 44F). ascr#10 (FIG. 44G) and oscr#10 (FIG. 44H) show m/z 173 [$C_9H_{15}O_3$] and 155 [$C_9H_{13}O_2$] for the $C_9$-sidechain and m/z 73 for the ascarylose derived $C_3O_2H_5$ fragment. β-hydroxy ascarosides such as bhas#22 ($C_{13}$-sidechain) (FIG. 44I]) and bhos#26 ($C_{15}$-sidechain) (FIG. 44J]) show side chain specific fragment ions at m/z 185 [$C_{11}H_{21}O_2$] and m/z 213 [$C_{13}H_{25}O_2$], respectively, which originate from loss of ascarylose and acetic acid. Furthermore, bhas#22 and bhos#26 show an intensive product ion at m/z 59 [$C_2H_3O_2$] for acetate, as well as the diagnostic ion at m/z 73 for the ascarylose derived $C_3O_2H_5$ fragment. Indole ascarosides such as icas#9 (FIG. 44K]) and icas#1 (FIG. 44L]) show side chain specific fragment ions for the corresponding ascarosides at m/z 247 [$C_{11}H_{19}O_6$] and m/z 275 [$C_{13}H_{23}O_6$], respectively, which originate from loss of the indole carbonyl unit [$C_9H_5NO$]. Furthermore, icas#9 and icas#1 show m/z 160 [$C_9H_6NO_2$] for indole carboxylate ions. Ascaroside product ions of indole ascarosides show additional fragment ions corresponding to the fragmentation pattern of non-indole ascarosides, such as the diagnostic fragment ion at m/z 73 for the ascarylose derived $C_3O_2H_5$ fragment. icas#3 (FIG. 44M]) shows m/z 301 [$C_{15}H_{25}O_6$] from loss of indole carbonyl unit [$C_9H_5NO$], along with m/z 160 [$C_9H_6NO_2$] for indole carboxylate ions. mbas#3 (FIG. 44N]) shows m/z 301 [$C_{15}H_{25}O_6$] and m/z 283 [$C_{15}H_{23}O_5$], which originate from loss of tigloyl [$C_5H_6O$] and tiglate[$C_5H_8O_2$] units, respectively. Furthermore, mbas#3 shows m/z 99 [$C_5H_7O_2$] for tiglate ions. The diagnostic fragment ion at m/z 73 for the ascarylose derived $C_3O_2H_5$ fragment is of low intensity. hbas#3 (FIG. 44O]) shows m/z 301 [$C_{15}H_{25}O_6$] which originates from loss of a hydroxybenzoyl unit [$C_7H_4O$]. Furthermore, hbas#3 shows m/z 137 [$C_7H_5O_3$] and m/z 93 [$C_6H_5O$] for hydroxybenzoate and phenolate ions. The ascaroside diagnostic fragment ion at m/z 73 for the ascarylose derived $C_3O_2H_5$ fragment is of low intensity. PABA linked ascr#8 (FIG. 44P]) shows characteristic fragment ions at m/z 136 [$C_7H_6NO_2$] and m/z 92 [$C_6H_6N$] for PABA and anilid ions, respectively, along with the diagnostic fragment ion at m/z 73 for the ascarylose derived $C_3O_2H_5$ fragment.

FIGS. 46A-C relate to the identification of new ascarosides in *C. elegans*. FIG. 46A is the LC-MS total ion current (TIC) chromatogram of wild-type *C. elegans* excretome (ESI−). FIG. 46B illustrates the MS/MS fragmentation of ascarosides. FIG. 46C is the LC-MS/MS screen (precursors of m/z 73) of wild-type excretome, and reveals known ascarosides (black), new homologs (C4, C6, C8, C11, and C12), new (ω)-oxygenated isomers (C5$_\omega$, C9$_\omega$, and C11$_\omega$) and new 4'-acylated derivatives (hbas#3 and mbas#3) (* non-ascarosides). The highly polar ascr#5 elutes at 6.5 min, outside of the shown retention time range.

FIGS. 47A-C show ascarosides identified in wild-type, acox-1, maoc-1, dhs-28, and daf-22 worms via LC-MS/MS. FIG. 47A shows (ω-1)-oxygenated ascarosides, FIG. 47B shows (ω)-oxygenated ascarosides, and FIG. 47C shows examples for 4'-acylated derivatives. The stereochemistry of compounds that were not synthesized for syntheses and a complete list of the 146 characterized ascarosides) was proposed as shown based on analogy and HPLC-MS retention times (see FIG. 38).

FIGS. 48A-B relate to attraction to hbas#3. Wild-type (N2) hermaphrodites are attracted to hbas#3 in the spot attraction assay in a dose dependent manner (FIG. 48A). FIG. 48B shows the dose dependence of hbas#3 attraction for wild-type hermaphrodites in the quadrant chemotaxis assay.

FIGS. 49A-B relate to ascaroside biogenesis. FIG. 49A shows the proposed roles of peroxisomal β-oxidation enzymes ACOX-1, MAOC-1, DHS-28, and DAF-22 in ascaroside biosynthesis. FIG. 49B shows the gene structures of acox-1, maoc-1, dhs-28, and daf-22 mutant alleles, showing point mutations (vertical bars) and deletions (horizontal bars).

FIGS. 50A-E show the amount of (ω-1)-oxygenated ascarosides in wild-type (FIG. 50E) and β-oxidation mutants (acox-1 (FIG. 50A), maoc-1 (FIG. 50B), dhs-28 (FIG. 50C), and daf-22 (FIG. 50D) with saturated (blue), α,β-unsaturated (red), and β-hydroxylated (green) side chains.

Figure 51:
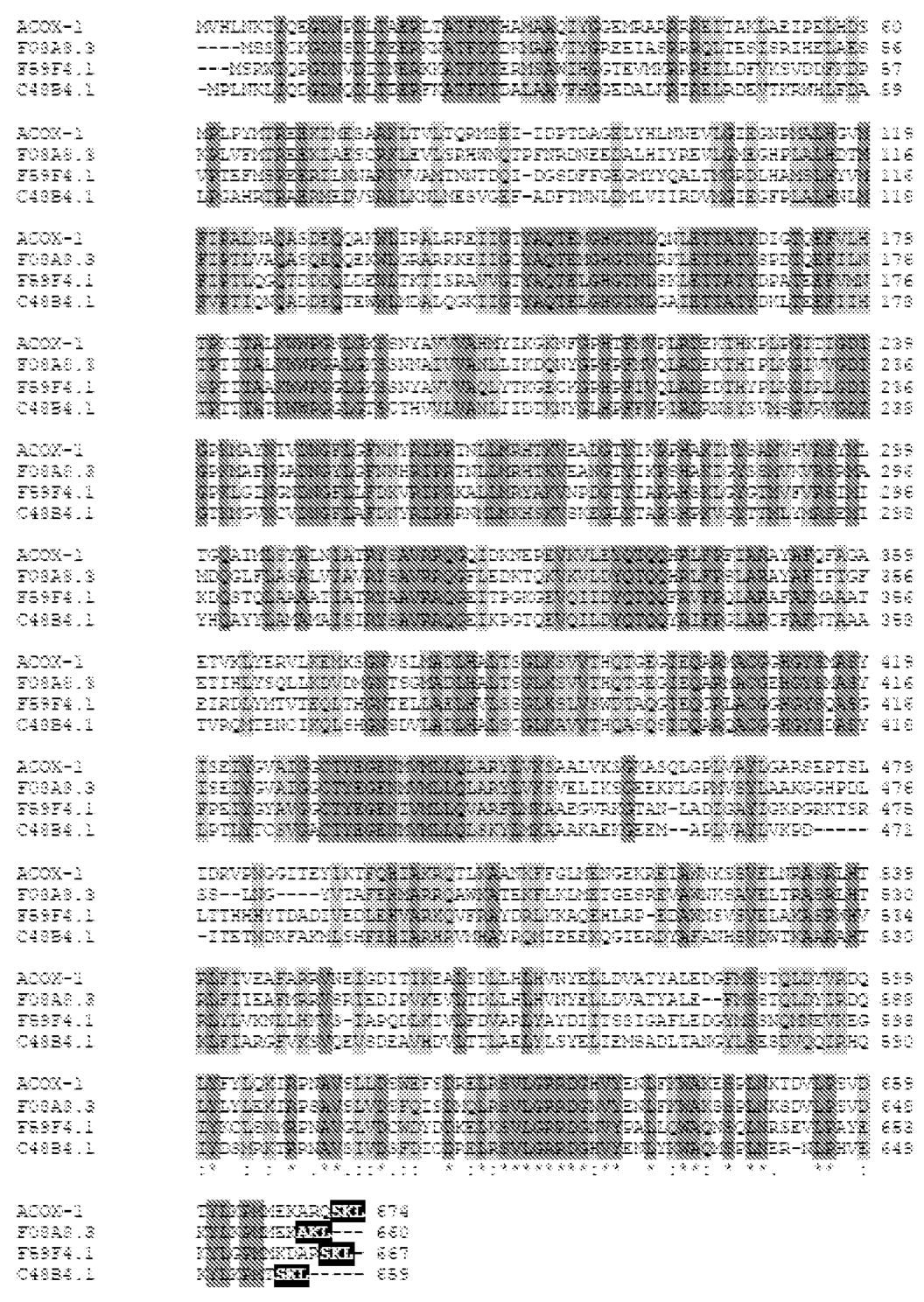

FIG. 51 shows the alignment of C. elegans ACOX-1 isoform a.1 with other peroxisomal acyl-CoA oxidases performed using ClustalW. Identical amino acids are marked in grey, similar amino acids are marked in light grey, and the peroxisomal targeting signal is marked in black.

FIG. 54B includes the LC-MS ion traces of daf-22(m130) excretome following incubation with a 1:1 mixture of ascr#10 and oscr#10, showing a preference for indole-3-carbonyl attachment to the (ω-1)-oxygenated ascr#10.

FIGS. 56A-B relate to the ascaroside profiles. Analysis of worm body ascaroside profiles (FIG. 56A) reveals ascaroside glucosides (e.g. glas#10) and indicates preferential excretion of unsaturated ascarosides. Ratio of (ω-1) to (ω)-linked saturated ascarosides in dhs-28 mutant excretome (FIG. 56B) shows strong dependence on nutritional conditions (for β-hydroxy ascarosides see FIGS. 59A-C), reflecting starvation dependence of ascr#3/ascr#5 ratio in wild-type C. elegans (see FIG. 60) (Welch's t-test, *: P<0.05; **P<0.001).

FIGS. 57A-C are LC-MS/MS chromatograms (precursor ions of m/z=73) of acox-1 (ok2257) worm body extracts showing glucosyl esters glas#10, glas#18, and glas#22 and the corresponding non-glycosylated ascarosides ascr#10, ascr#18, and ascr#22.

FIG. 58 shows the differential excretion of (ω)-oxygenated ascarosides by wild type C. elegans (For (ω-1)-oxygenated ascarosides see FIG. 56A).

FIG. 59A is the ratio of β-hydroxy ascarosides in dhs-28(hj8) excretome extracts. FIG. 59B is the ratio of β-hydroxy ascarosides in dhs-28 (hj8) worm body extracts. FIG. 59C is the ratio of saturated ascarosides in dhs-28(hj8) worm body extracts (saturated ascarosides in dhs-28(hj8) excretome extracts are shown in FIG. 56B).

FIGS. 61A-B relate to ascaroside biogenesis. FIG. 61A shows the modular assembly of ascarosides from amino acid (green), fatty acid (blue), and carbohydrate (red) building blocks. FIG. 61B shows a model for ascaroside biogenesis. Chain elongation of fatty acids (by putative elongase homologs elo-1-9[25]) (Agbaga et al., PNAS 105:12843-48 (2008), which is hereby incorporated by reference in its entirety) is followed by (ω-1)- or (ω)-oxygenation of VLC-FAs and ascarylose attachment. The resulting VLCAs enter peroxisomal β-oxidation via ACOX-1, MAOC-1, DHS-28, and DAF-22 producing short chain ascarosides, which are linked to amino acid-derived moieties and other building blocks.

Figure 62:
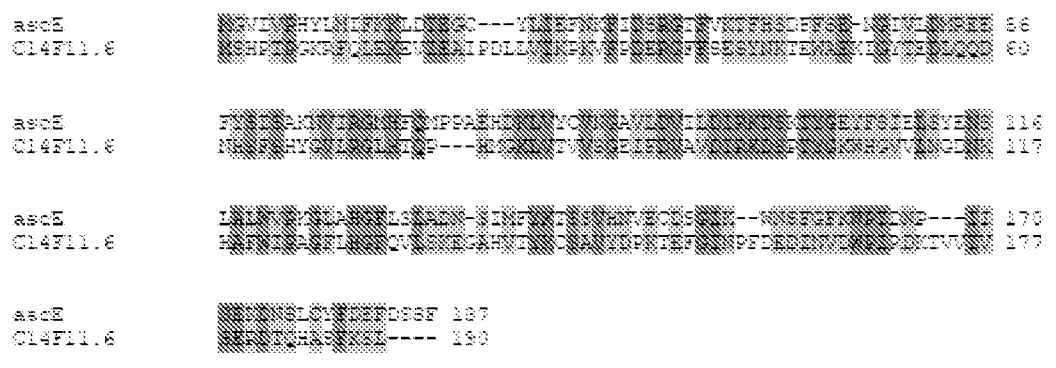

FIG. 62 is the alignment of Yersinia pseudotuberculosis CDP-3,6-dideoxy-D-glycero-D-glycero-4-hexylose-5-epimerase or ascE (AAA88702.1) with C. elegans homolog C14F11.6 (CCD64543.1) performed using ClustalW. Identical amino acids are marked in grey and similar amino acids are marked in light grey.

FIG. 63A shows the structures of the ascarosides for the dispersal blend. FIG. 63B shows the quantification of dispersing C. elegans using Image J. (the second column shows inverted pictures and the third column shows the counted nematodes). FIG. 63C shows the contribution of individual ascarosides to the activity of the synthetic blend. ascr#2 (3.68 pmol/ul), ascr#3 (0.165 pmol/ul), ascr#8 (0.25 pmol/ul), and icas#9 (0.005 pmol/ul). Seven experiments were done for each treatment. +, present and −, absent. Student's t-test, unpaired (p<0.05). FIG. 63D shows the S. feltiae response to the C. elegans dispersal blend visualized within an entire plate.

FIG. 64A shows naturally dispersing infective juveniles (IJ) of S. feltiae from an insect cadaver. FIG. 64B shows approximately 300 IJs placed on an agar plate in water. FIG. 64C shows IJs treated with either water (control) or insect cadaver extract. Images are representative of six experiments for each treatment. FIG. 64D shows the dispersal assay on the same plate. The illustration represents two experiments. Behavior is temperature and season dependent. Assays were conducted at RT (22±0.5° C.) or under temperature controlled conditions.

FIGS. 66A-E show that an ascaroside blend regulates C. elegans dispersal behavior, and the dispersal blend is recognized by other nematodes. FIG. 66A shows the identification of the dispersal blend. Images (~250 nematodes) are representative of 9, 10, and 11 experiments of control (0.25% E. coli (HB101)), synthetic blend with 0.25% E. coli (HB101), and dauer supernatant, respectively. FIG. 66B shows quantification using Image J (http://rsbweb.nih.gov/ij/download.html). Control vs synthetic blend student's t-test unpaired (p<0.02). FIG. 66C shows the analysis of host cadavers infected by entomopathogenic nematodes or root knot nematodes for components of the C. elegans dispersal blend. FIG. 66D shows the S. feltiae IJs' (~250) response to the dispersal blend; four experiments for each treatment. FIG. 66E shows the response of root-knot J2s (Meloidogyne spp., mixture of M. incognita, M. javanica, and M. floridensis) to the C. elegans dispersal blend. The data represent 19 and 20 experiments from control water and C. elegans dispersal blend, respectively. At 2 h, using a student's t-test, unpaired, p<0.007.

FIGS. 67A-E show the activity guided fractionation of the S. feltiae dispersal pheromone. FIG. 67A shows the response to reverse phase (C18) chromatography fractions of insect cadaver extract. The image represents two independent experiments. The estimated physiologically relevant concentration was used in the assays; Frc, fraction. FIG. 67B relates to the testing of physiologically relevant concentration of ascarosides found in Frc A (ascr#9, 40.3 pmol/μl and ascr#11, 1.3 pmol/μl). Image represents three experiments. FIG. 67C shows that ascr#2 and ascr#9 are structural analogs. Natural and synthetic ascr#9 were tested in combination with fraction B and C. Image represents four experiments. FIG. 67D shows the structure of oscr#10, and its testing in combination with fraction A and C, FIG. 67E shows the structure of ascr#11. It (1.3 pmol/μl) is also sufficient to cause dispersal in combination with fractions B and C. Image represents three experiments.

FIGS. 68A-C are LC-MS ion chromatograms of fraction A (FIGS. 68A-B) and fraction B (FIG. 68C). First panel shows ascr#11 at m/z 279, second panel shows ascr#9 at m/z 293.

FIG. 69 shows the ascr#9 and ascr#11 profile during *S. feltiae* development. For each time point, six insect cadavers were analyzed by LC-MS. For the 0 time point, 4 uninfected larvae were analyzed. * detected but not quantifiable.

FIGS. 74A-B show the identification of ascarosides in worm water extract of adult *S. glaseri*. FIG. 74A is the total ion current (TIC) chromatogram from LC-MS/MS; screen for precursor ions of m/z 73.0 reveals ascaroside signals. FIG. 74B is the corresponding ion traces for ascr#9, ascr#12, ascr#1, and ascr#14 from LC-MS measurement.

FIGS. 75A-K are NMR spectra of components in ascaroside synthesis, as follows.

Figure 75B:
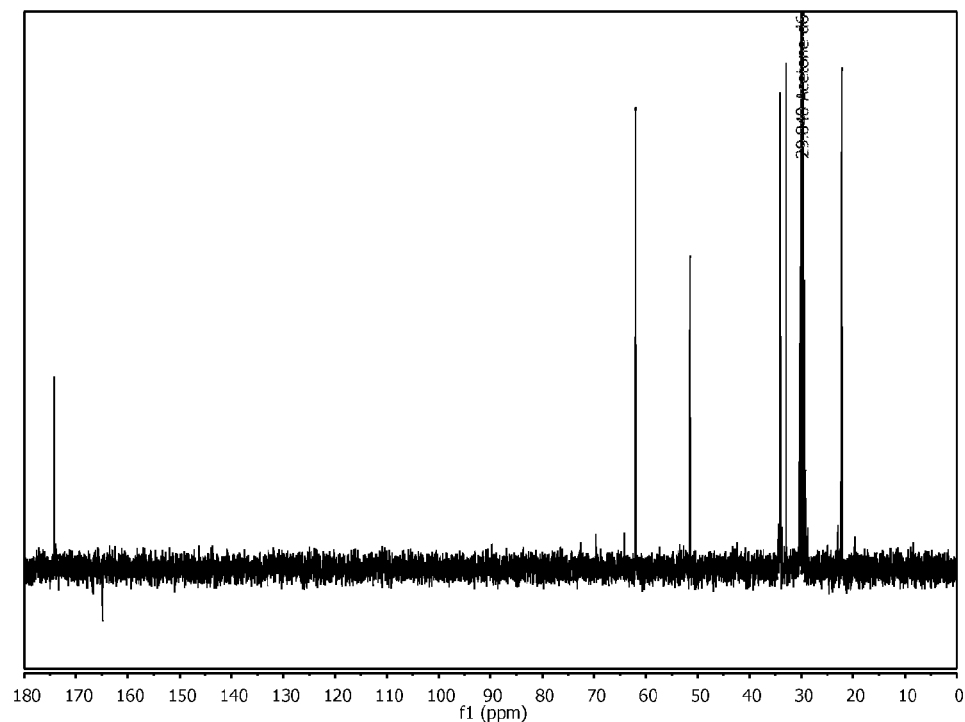
Figure 75C:
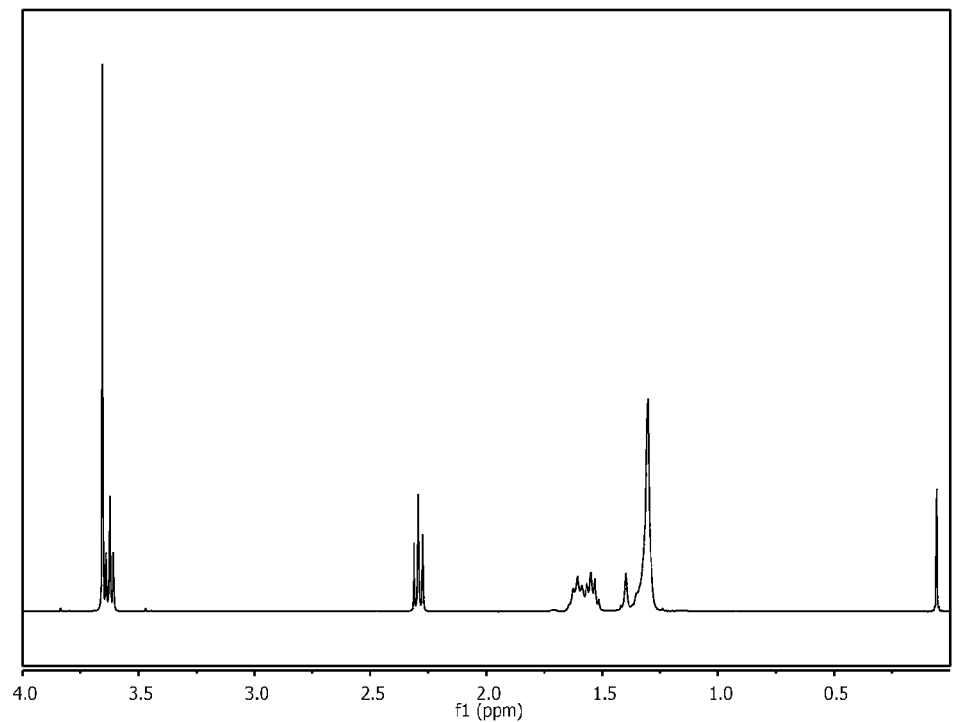
Figure 75D:
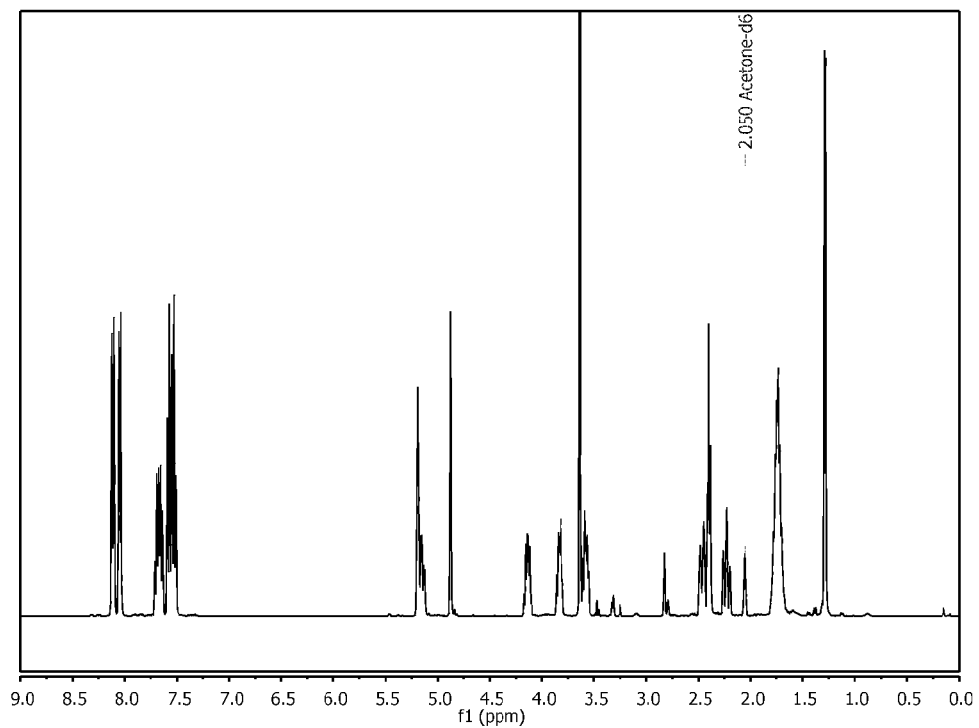
Figure 75E:
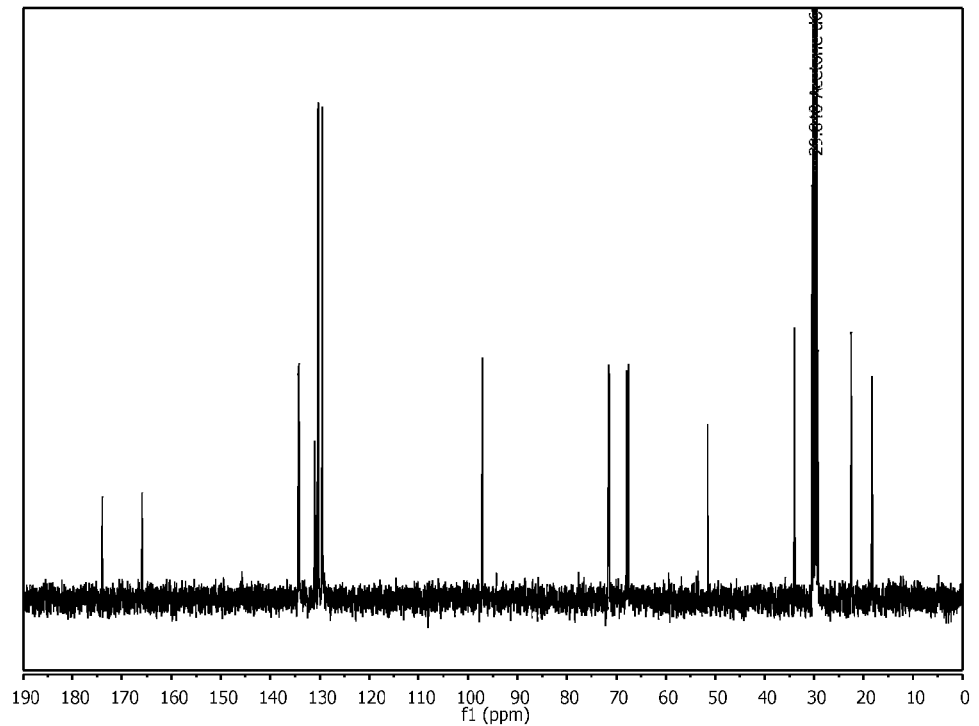
Figure 75F:
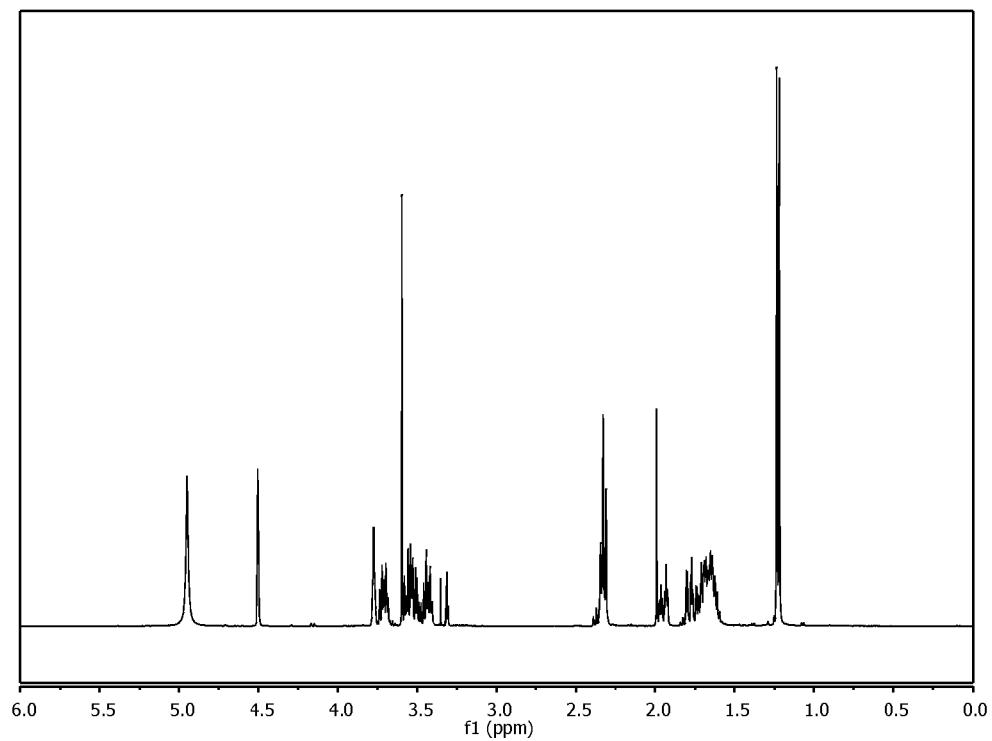
Figure 75G:
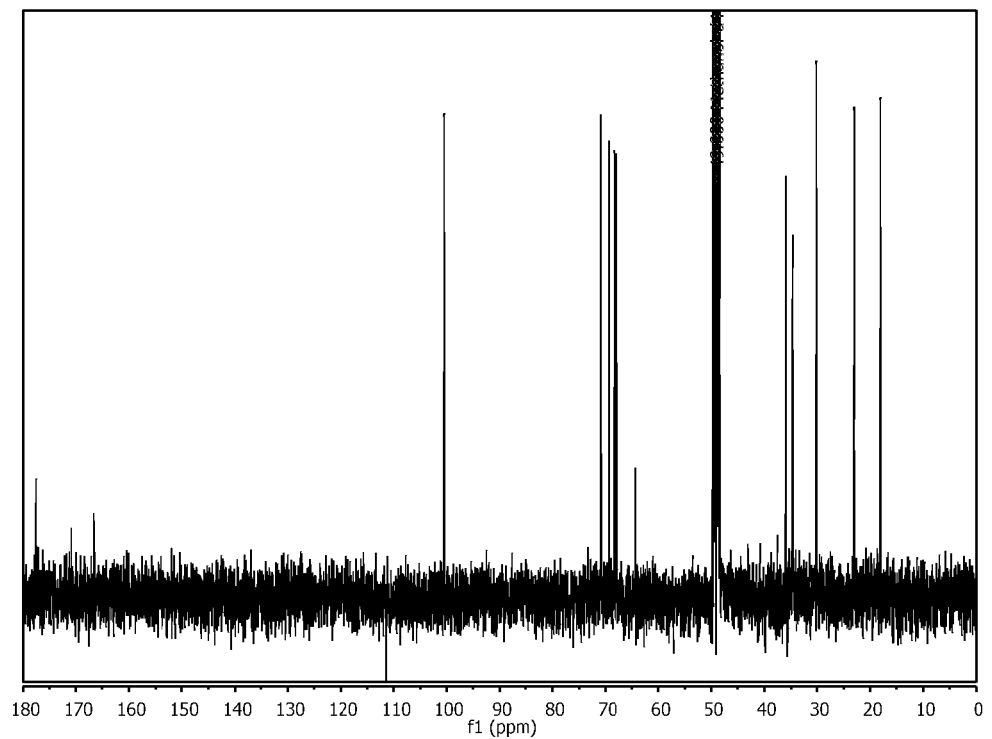
Figure 75H:
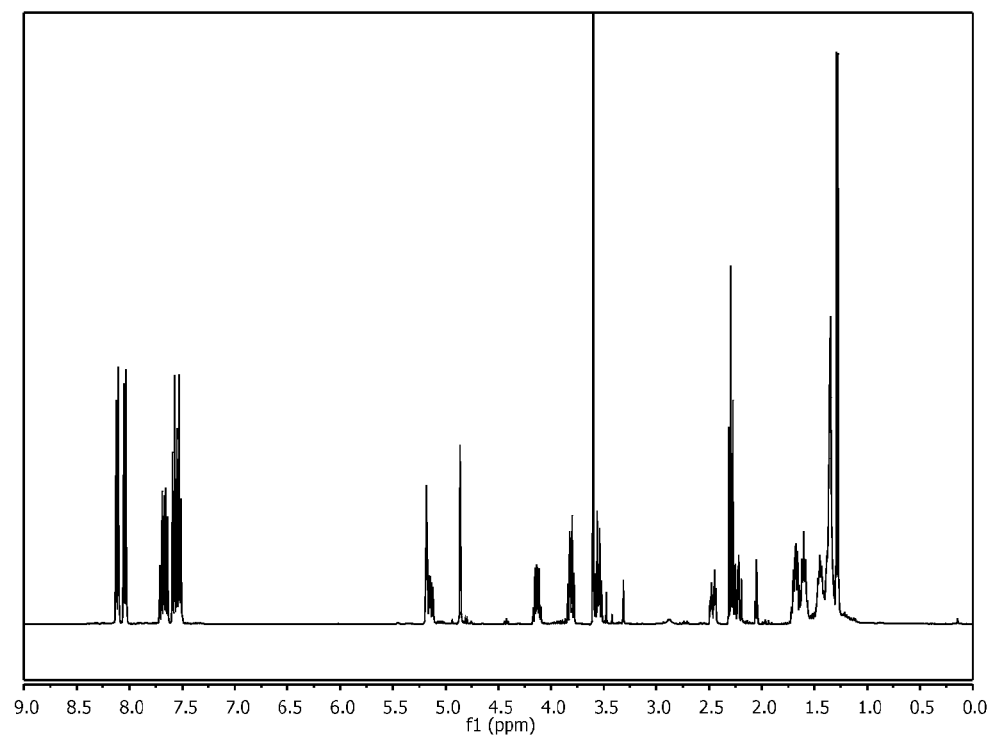
Figure 75I:
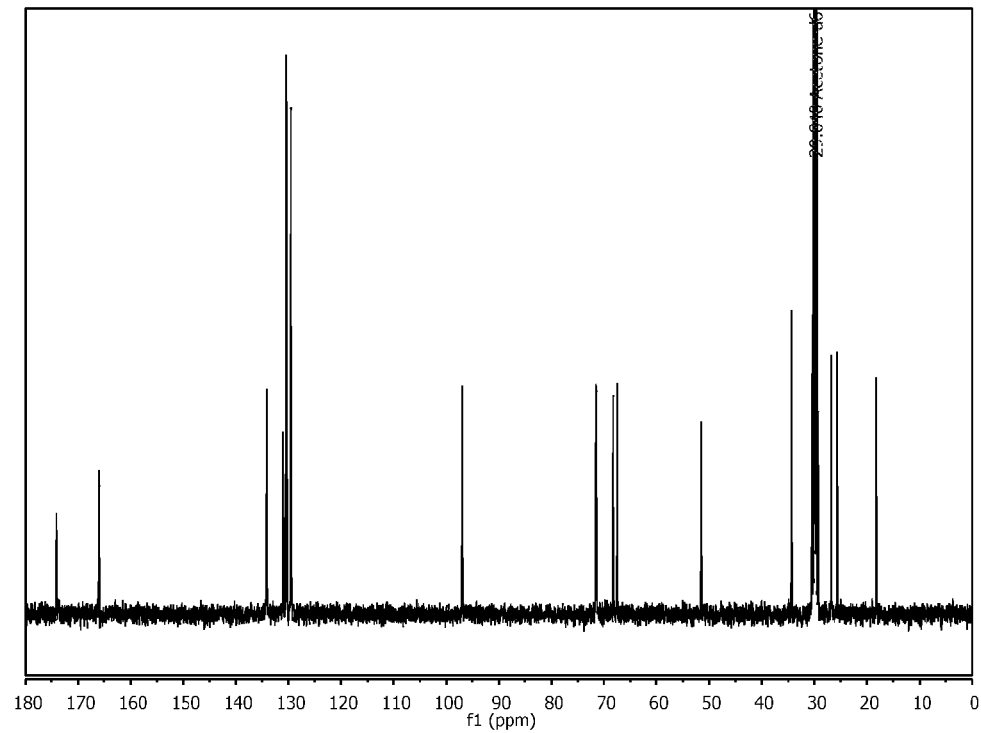
Figure 75J:
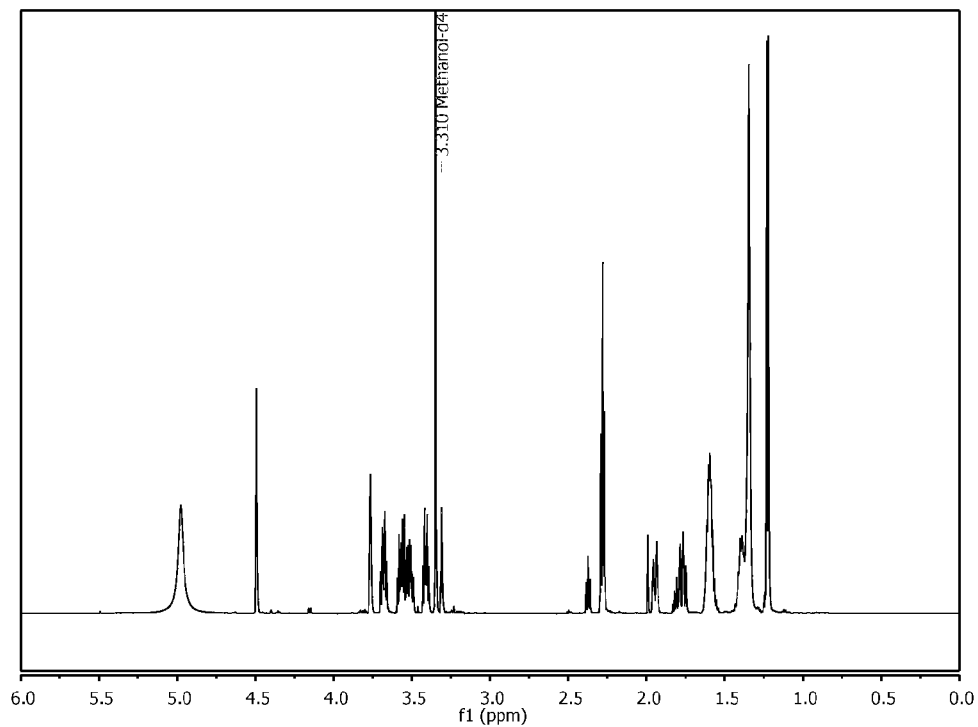
Figure 75K:
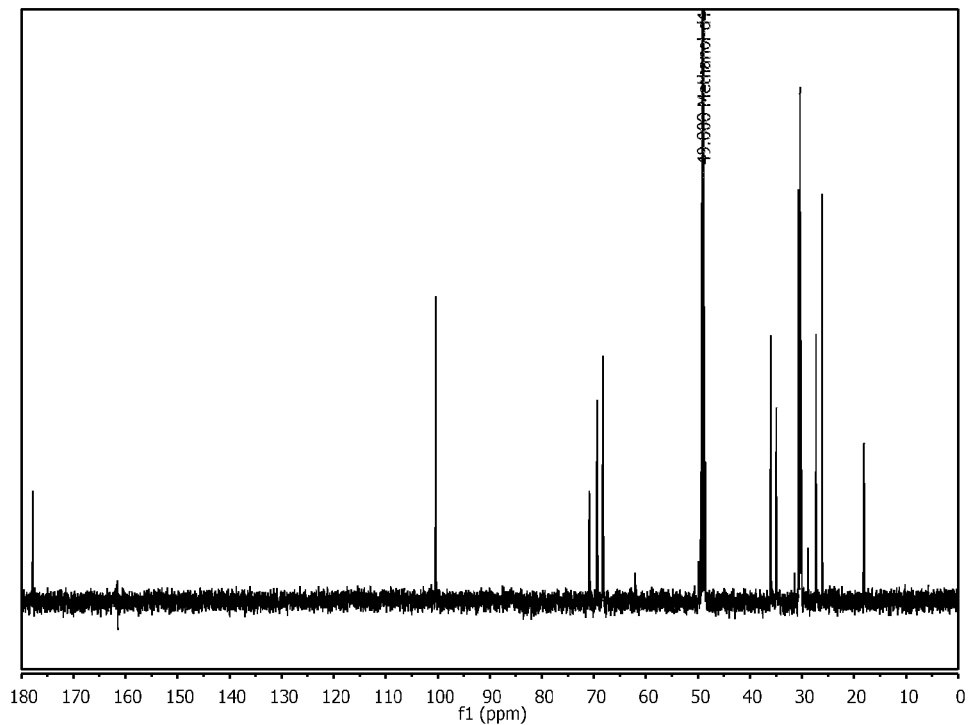

| NMR Conditions | Component | Figure |
| --- | --- | --- |
| $^1$H NMR (400 MHz, acetone-$d_6$) | methyl 5-hydroxypentanoate | FIG. 75A |
| $^{13}$C NMR (100 MHz, acetone-$d_6$) | methyl 5-hydroxypentanoate | FIG. 75B |
| $^1$H NMR (400 MHz, chloroform-$d_1$) | methyl 9-hydroxynonanoate | FIG. 75C |
| $^1$H NMR (400 MHz, acetone-$d_6$) | 5-(3'R,5'R-dibenzoyloxy-6'S-methyl-(2H)-tetrahydropyran-2-yloxy)-pentanoic acid methyl ester | FIG. 75D |
| $^{13}$C NMR (100 MHz, acetone-$d_6$) | 5-(3'R,5'R-dibenzoyloxy-6'S-methyl-(2H)-tetrahydropyran-2-yloxy)-pentanoic acid methyl ester | FIG. 75E |
| $^1$H NMR (400 MHz, methanol-$d_4$) | 5-(3'R,5'R-dihydroxy-6'S-methyl-(2H)-tetrahydropyran-2-yloxy)-pentanoic acid | FIG. 75F |
| $^{13}$C NMR (100 MHz, methanol-$d_4$) | 5-(3'R,5'R-dihydroxy-6'S-methyl-(2H)-tetrahydropyran-2-yloxy)-pentanoic acid | FIG. 75G |
| $^1$H NMR (400 MHz, acetone-$d_6$) | 9-(3'R,5'R-dibenzoyloxy-6'S-methyl-(2H)-tetrahydropyran-2-yloxy)-nonanoic acid methyl ester | FIG. 75H |
| $^{13}$C NMR (100 MHz, acetone-$d_6$) | 9-(3'R,5'R-dibenzoyloxy-6'S-methyl-(2H)-tetrahydropyran-2-yloxy)-nonanoic acid methyl ester | FIG. 75I |
| $^1$H NMR (600 MHz, methanol-$d_4$) | 9-(3'R,5'R-dihydroxy-6'S-methyl-(2H)-tetrahydropyran-2-yloxy)-nonanoic acid | FIG. 75J |
| $^{13}$C NMR (100 MHz, methanol-$d_4$) | 9-(3'R,5'R-dihydroxy-6'S-methyl-(2H)-tetrahydropyran-2-yloxy)-nonanoic acid | FIG. 75K |

Figure 70:
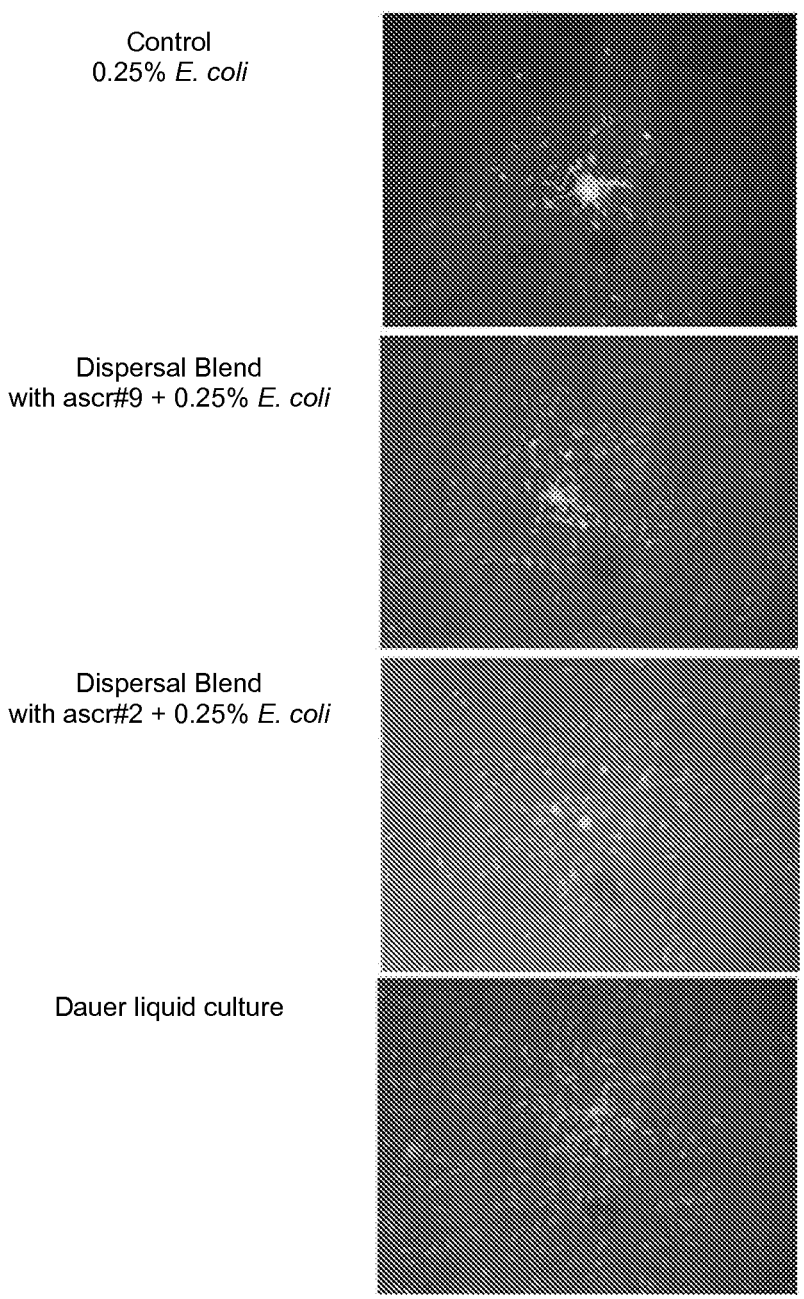

FIG. 70 shows that ascr#9 can replace the function of ascr#2 in the *C. elegans* dispersal blend. Representative pictures are presented. Negative control using 0.25% *E. coli* HB101 (3 experiments), ascr#9 substitution in the *C. elegans* dispersal blend (6 experiments), and positive controls: the synthetic blend dispersal blend (7 experiments) and positive control dauer liquid culture (3 experiments).

FIGS. 71A-B relate to the dispersal blend of the phylogenetically related nematodes species. FIG. 71A is the phylogenetic tree for entomopathogenic nematodes, plant parasitic nematodes, and *C. elegans*. The figure is adapted from *C. elegans* and the biology of nematodes (PAUL DE LEY: A QUICK TOUR OF NEMATODE DIVERSITY AND THE BACKBONE OF NEMATODE PHYLOGENY (WormBook, ed. The *C. elegans* Research Community, 2006), which is hereby incorporated by reference in its entirety). Red color indicates the example of genera. FIG. 71B shows the presence of ascr#9 and ascr#11 in host insect cadaver of *Steinernema* spp. and *Heterorhabditis* spp. For each species, four insect (*G. mellonella*) cadavers infected with both *Steinernema* spp. or *Heterorhabitis* spp. were analyzed by LC-MS for ascr#9 and ascr#11 profiles.

Figure 72D:
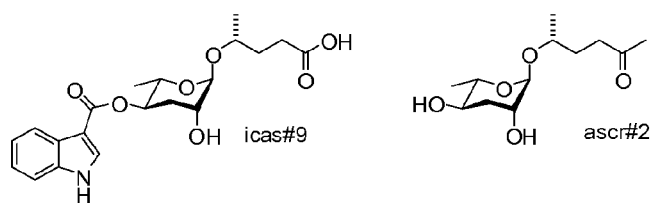

FIGS. 72A-D show the structure and HPLC-ESI-MS data of (ω-1)-oxygenated saturated ascarosides (FIG. 72A), (ω-1)-oxygenated unsaturated ascarosides (FIG. 72B), (ω)-oxygenated saturated ascarosides (FIG. 72C), and indole ascaroside icas#9 and ascr#2 (FIG. 72D). $^1$SMID: Small Molecule IDentifier for small molecules identified from *C. elegans* and other nematodes.

FIGS. 76A-D relate to the structure (FIG. 76A), detection (FIGS. 76B-C), and synthesis (FIG. 76D) of ascarosides. Both ascarosides (ascr) and indole ascarosides (icas) have been previously described ascarosides in *C. elegans*. In addition to (ω-1)-oxygenated ascr, their (ω)-oxygenation isomers (oscr) were identified in this HPLC-MS screen. FIG. 76B shows the HPLC-MS identification of short and medium chain ascarosides in conditioned worm water obtained from free-living *C. elegans* (mixed-stage), insect parasitic *S. glaseri* (adult), and rat parasitic *N. brasiliensis* (adult). HPLC-MS analysis of *C. elegans* exudate shows known ascarosides (ascr#1, #3, #7, and icas#9), along with the corresponding homologs (ascr#9, #10, #12, #14, and #18), and (ω)-oxygenated isomers (oscr#9, #10, #18). The highly polar ascr#5 elutes at 6.5 minutes, outside of the shown retention time range. Cross species comparison of molecular ion signals and their HPLC-retention times indicated that ascarosides abundantly produced by *C. elegans* are also found in many other nematode species, including *S. glaseri* and *N. brasiliensis* (peaks representing compounds also abundant in *C. elegans* shown in blue). FIG. 76C shows the HPLC-MS identification of medium and long chain ascarosides in *P. strongyloides* (mixed-stage) and *H. bacteriophora* (adult). ascr#18 (blue) is produced in significant amounts by *C. elegans*, whereas longer chain homologs (red peaks) are abundantly produced by *P. strongyloides* and *H. bacteriophora*, but not *C. elegans*. FIG. 76D shows the synthesis of (ω)-oxygenated ascarosides, oscr#9 and oscr#10.

Figure 77:
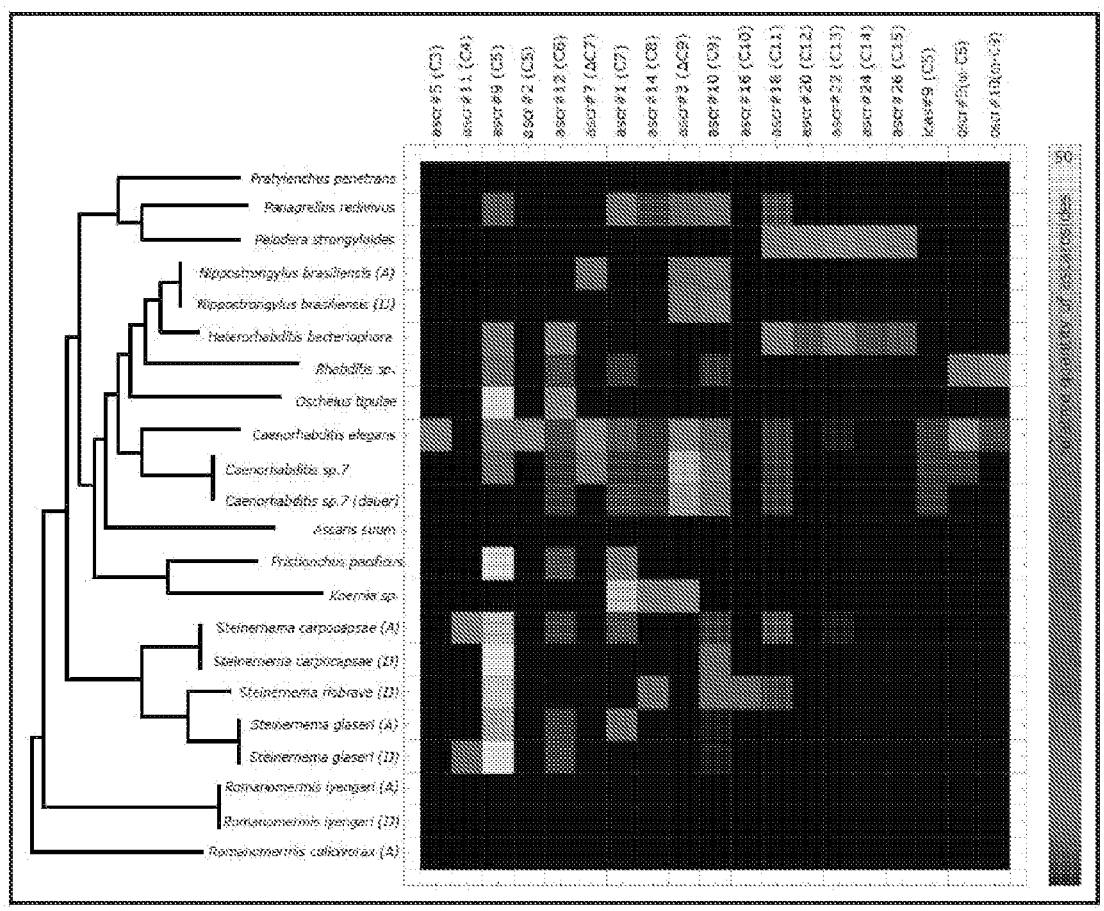

FIG. 77 is a heat map showing that ascarosides are produced by a wide range of nematode species. It is based on results from the HPLC-MS analysis of worm media samples obtained from incubating worms for several hours in S Basal, ddH$_2$0, or DMEM. Parasitic species indicated as infective juveniles (IJ) and adults (A) were collected separately; all other samples were obtained from mixed stage cultures. Colors in this heat map represent relative abundance of ascarosides detected by HPLC-MS, as indicated in the bar diagram on the right. For example, of the ascarosides detected in *S. glaseri* infective juveniles, the total was composed of 5.7% ascr#11, 92.2% ascr#9, 2.1% ascr#12, and 0.1% ascr#10.

Figure 78:
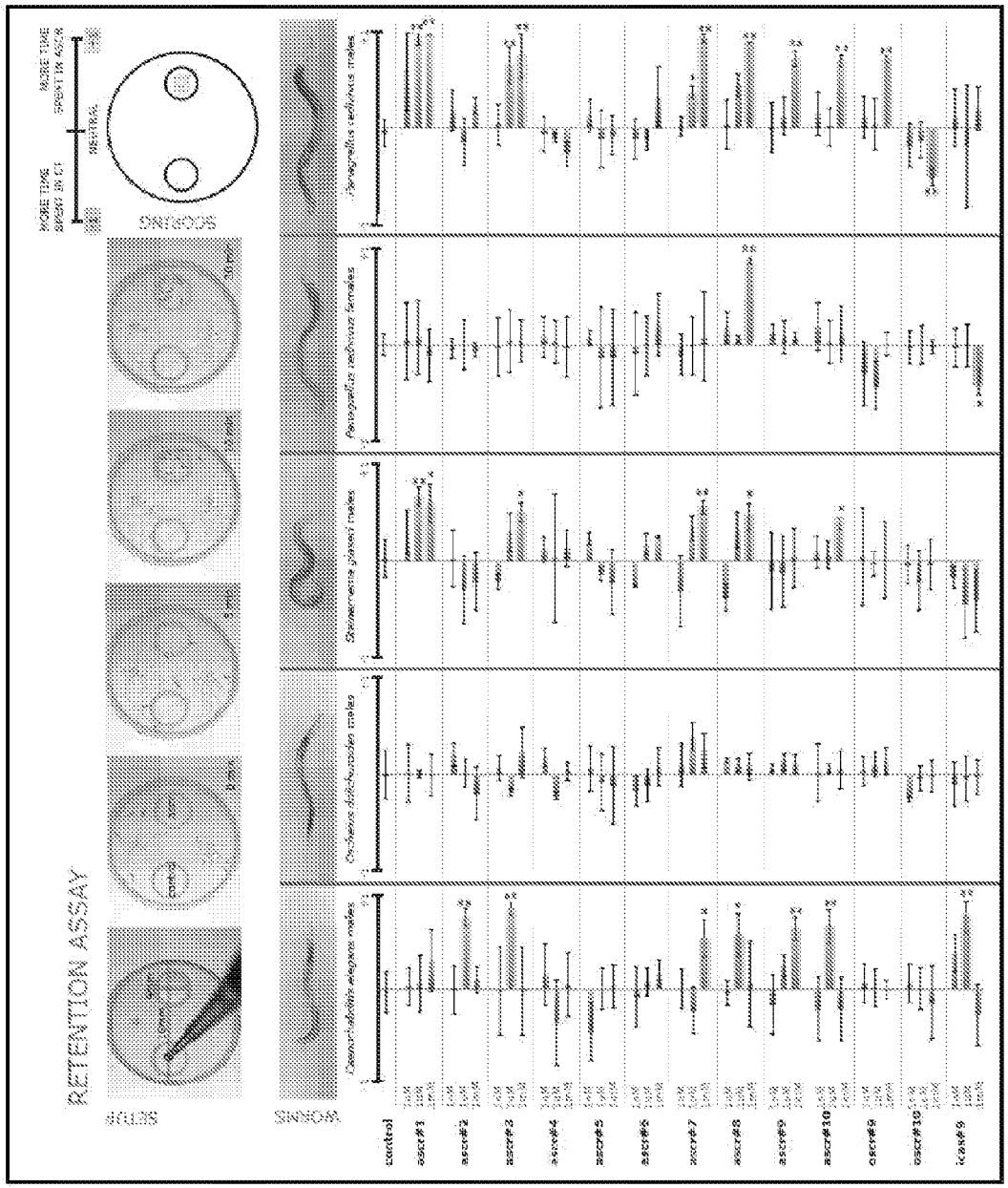

FIG. 78 shows that nematodes respond uniquely to areas conditioned by ascarosides. Several nematode species were scored for their response to areas conditioned with three concentrations of synthesized ascarosides (0.6 µL of 1 nM, 1 µM, and 1 mM, corresponding to 0.6 fmol, 0.6 pmol, and 0.6 nmol, respectively, per scoring area). Their occupancy in the conditioned region was compared to their occupancy in the control region for 20 minutes; 10 individuals per trial. Experiments in which nematodes that spent significantly more time in regions conditioned with ascaroside are highlighted in green. Experiments in which nematodes that spent significantly more time in control regions are highlighted in red, indicating avoidance of the ascaroside. Error bars, S.D. Statistical significance for each value was calculated in comparison to the response to water, shown first in each set. P-values were determined using an unpaired Student's t-test. **$P<0.01$, *$P<0.05$.

FIG. 79 relates to the retention assay using software that detects the presence of worms in both regions and provides an output of the percentage of each scoring region occupied by worms, which is calculated once per second during the entire trial. The output is a plot of worm occupancy ratio vs. time for both scoring regions (right panel). The scoring index described by Bargmann et al., *Cell* 74:515-27 (1993), which is hereby incorporated by reference in its entirety, was adopted.

FIGS. 80A-C relate to the attraction assay. *C. elegans* males demonstrate differential long-range attraction to different nematode species and ascarosides. Long-range attraction of *C. elegans* males to conspecific hermaphrodites was established by scoring chemotaxis to a hermaphrodite or ascaroside-conditioned point source on a 10 cm agar plate (FIG. 80A). Hermaphrodites were suspended in M9 buffer and placed within a copper cylinder on the agar plate for 6 hours before they were removed and the paralyzing agent sodium azide was added. The same was done with an M9 buffer control in a copper cylinder, on the opposite side. *C. elegans* males were placed in the center of the plate and allowed to wander until they became paralyzed in either spot. An Attraction Index adapted from Bargmann et al., *Cell*. 74:515-27 (1993), which is hereby incorporated by reference in its entirety, was then calculated, comparing worms that became paralyzed in the control vs. cue region. FIG. 80B shows that *C. elegans* males are attracted to a point source conditioned by 50 conspecific hermaphrodites. They demonstrate partial attraction to equal numbers of *P. redivivus* females, but not to *S. carpocapsae, P. pacificus,* or *P. strongyloides* females/hermaphrodites. FIG. 80C shows that *C. elegans* males can detect and chemotax towards a point source conditioned by 25 hermaphrodites over 6 hours. They chemotax towards a point source of ascr#2 and ascr#3, but not ascr#8. Error bars, S.D. Statistical significance for each value was calculated in comparison to the control, shown in FIG. 80C. P-values were determined using an unpaired Student's t-test. **$P<0.01$, *$P<0.05$.

Figure 81:
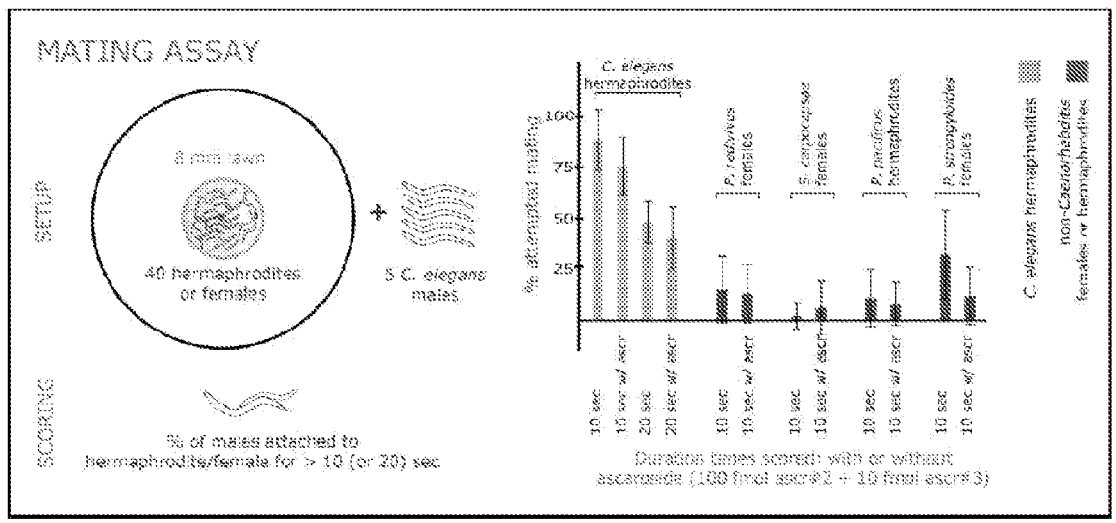

FIG. 81 shows that ascarosides do not increase mating to conspecific hermaphrodites, nor do they induce mating to different nematode species. A mating response assay (Peden et al., *Curr. Biol.* 15:394-404 (2005), which is hereby incorporated by reference in its entirety) was adapted, quantifying the percentage of males that successfully placed their ventral tail on hermaphrodites for 10 consecutive seconds, within the span of a 3-minute trial. Error bars, S.D.

Figure 82:
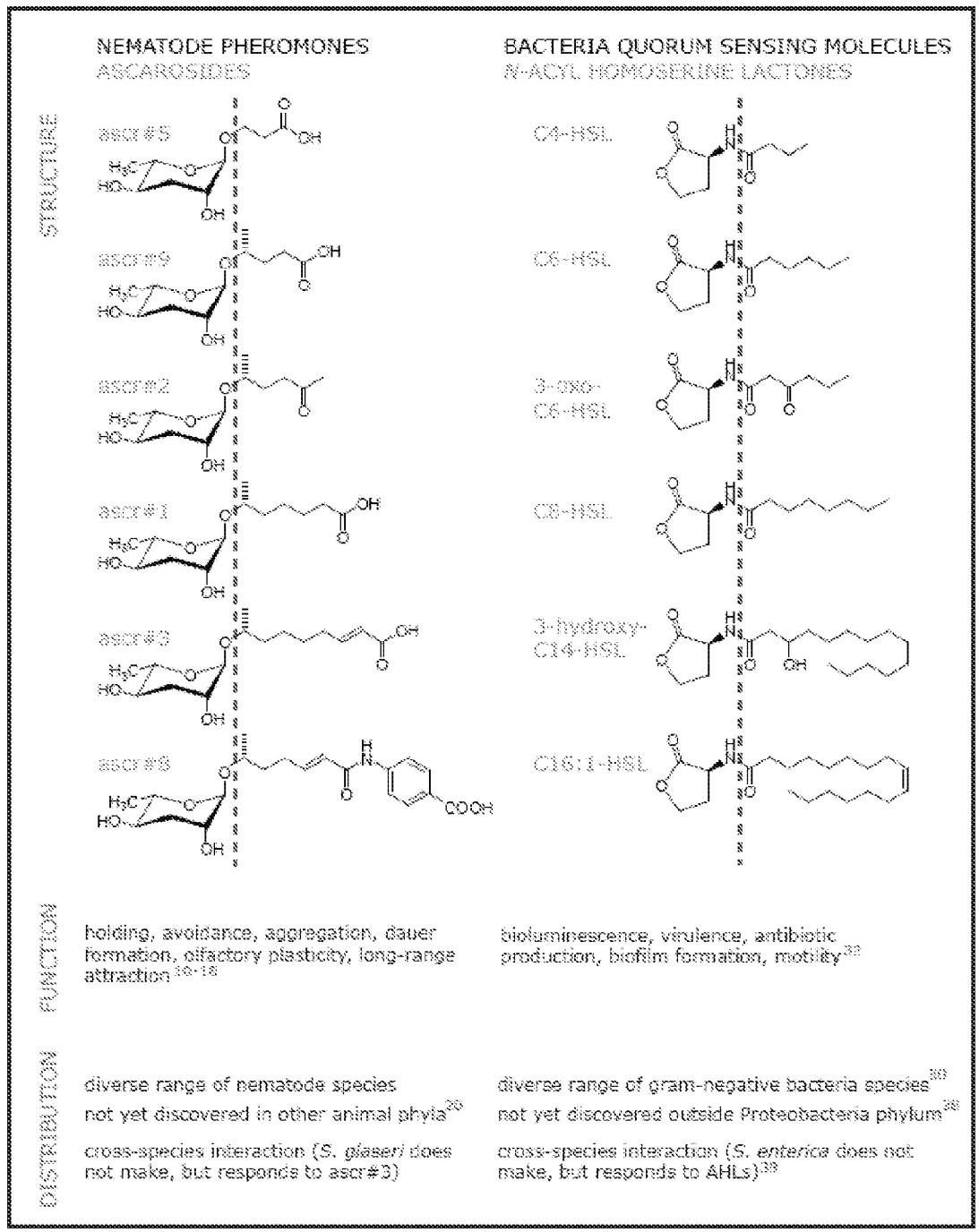

FIG. 82 shows the similar assembly of signaling molecules in nematodes and bacteria. N-acyl homoserine lactones (AHLs) are a family of small-molecules that mediate bacterial quorum sensing. AHLs are based on a homoserine lactone and feature species-specific variations in the N-acyl chain (Dickschat, *Nat. Prod. Rep.* 27:343-69 (2010), which is hereby incorporated by reference in its entirety). Ascarosides are assembled in a very similar fashion, based on the dideoxysugar ascarylose scaffold to which a variable lipid chain is attached (Edison, *Curr. Opin. Neurobiol.* 4:378-88 (2009), which is hereby incorporated by reference in its entirety). They both play significant roles in mediating important survival strategies.

Figures 83, 84:
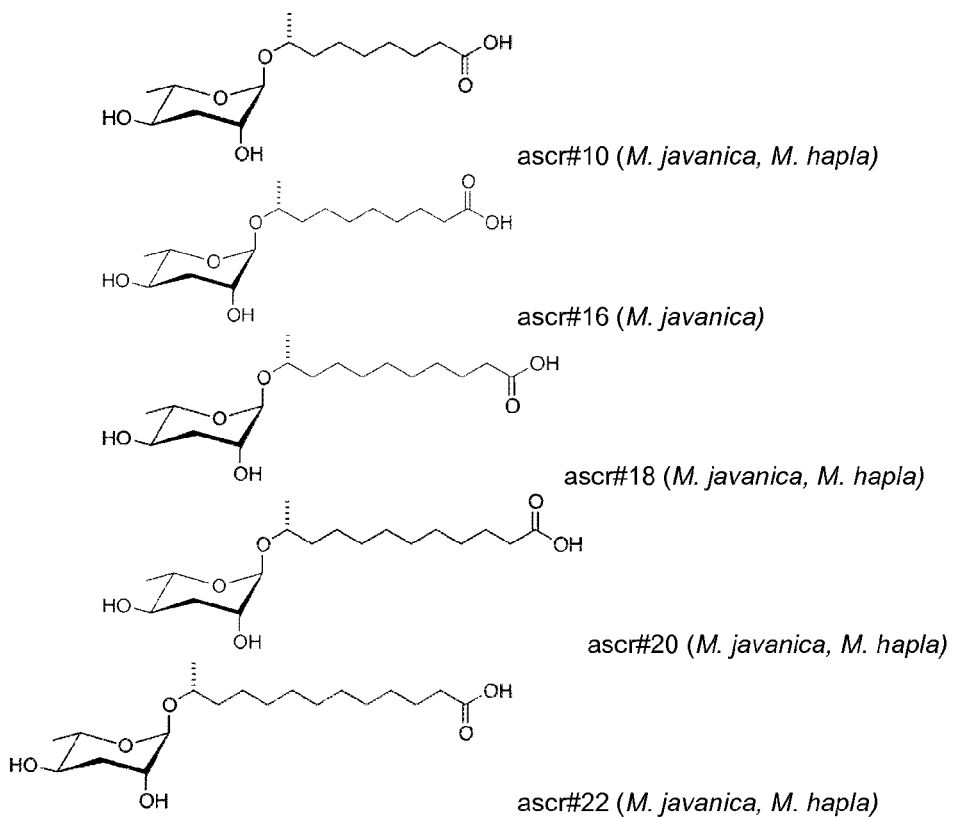

FIG. 83 is a list of ascaroside compounds detected in *M. javanica* and/or *M. hapla*.

FIG. 84 shows the high-resolution mass spectrometry data of ascaroside signaling molecules identified from root knot nematodes.

Figure 85:
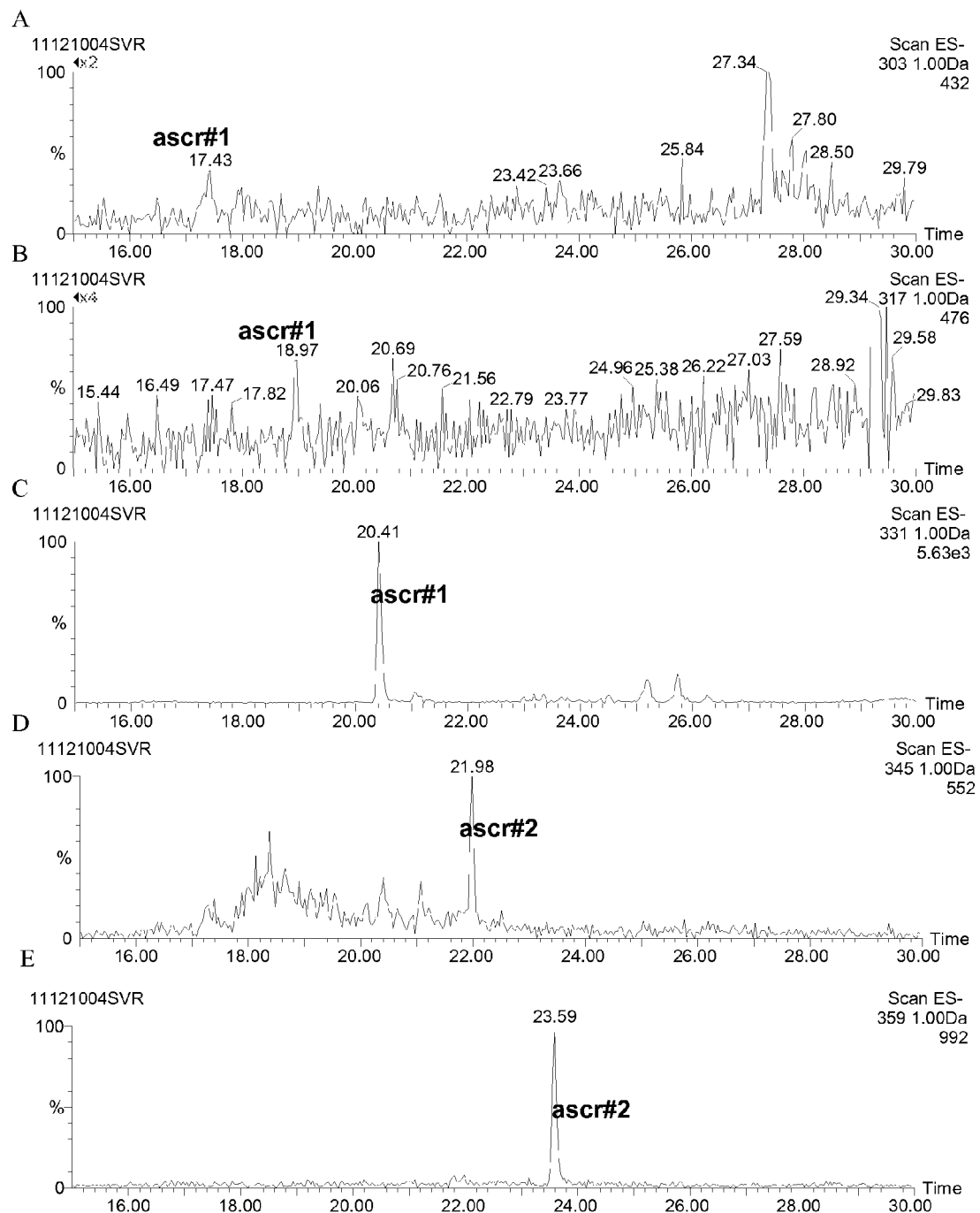

FIGS. 85A-E are HPLC-MS chromatograms of extracts from root knot nematodes (*M. javanica, M. floridensis, M. incognita*) demonstrating the presence of ascarosides ascr#10 (FIG. 85A), ascr#16 (FIG. 85B), ascr#18 (FIG. 85C), ascr#20 (FIG. 85D), and ascr#22 (FIG. 85E).

Figure 86:
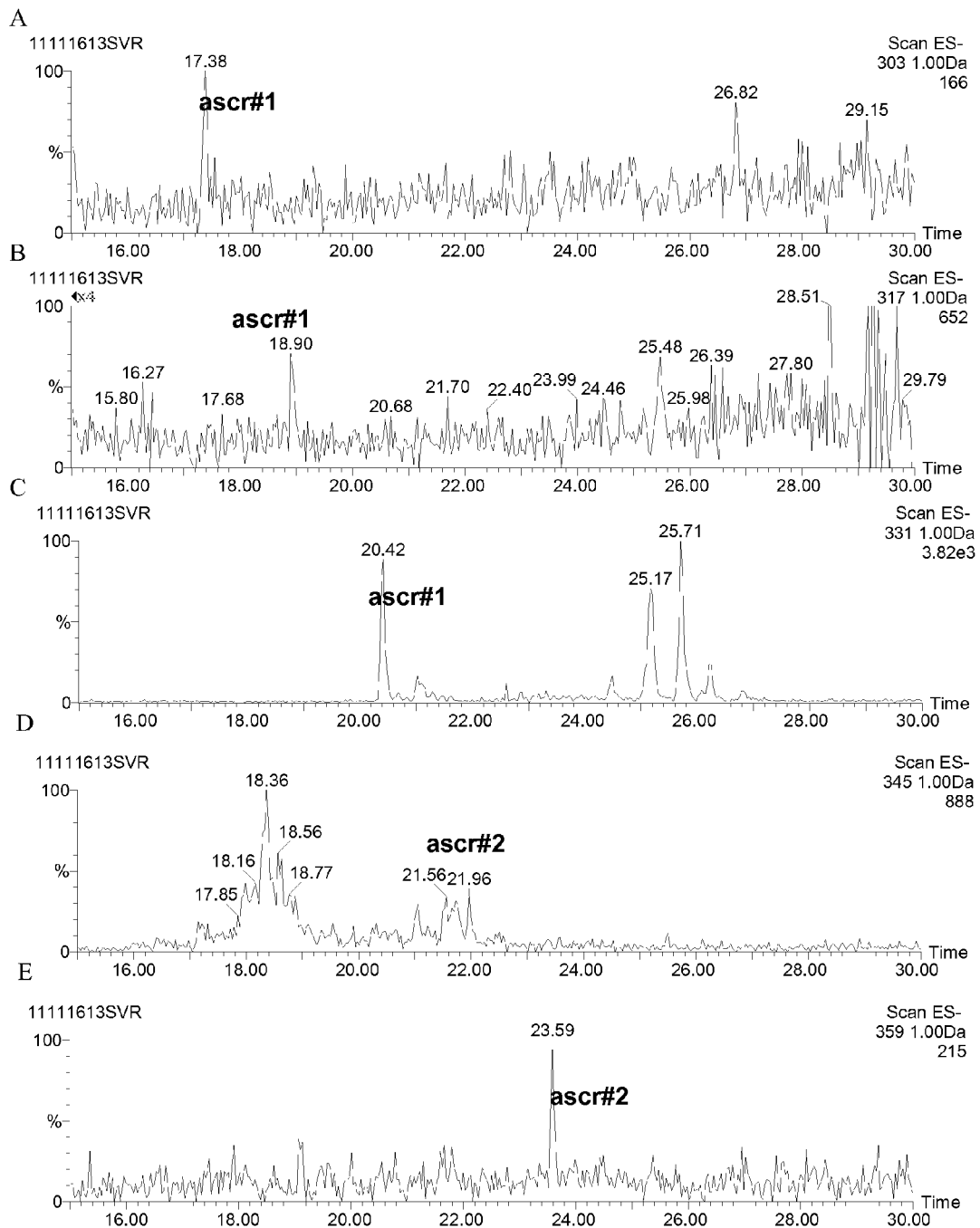

FIGS. 86A-E are HPLC-MS chromatograms of extracts from *M. javanica* (J2 larvae) demonstrating the presence of ascarosides ascr#10 (FIG. 86A), ascr#16 (FIG. 86B), ascr#18 (FIG. 86C), ascr#20 (FIG. 86D), and ascr#22 (FIG. 86E).

Figure 87:
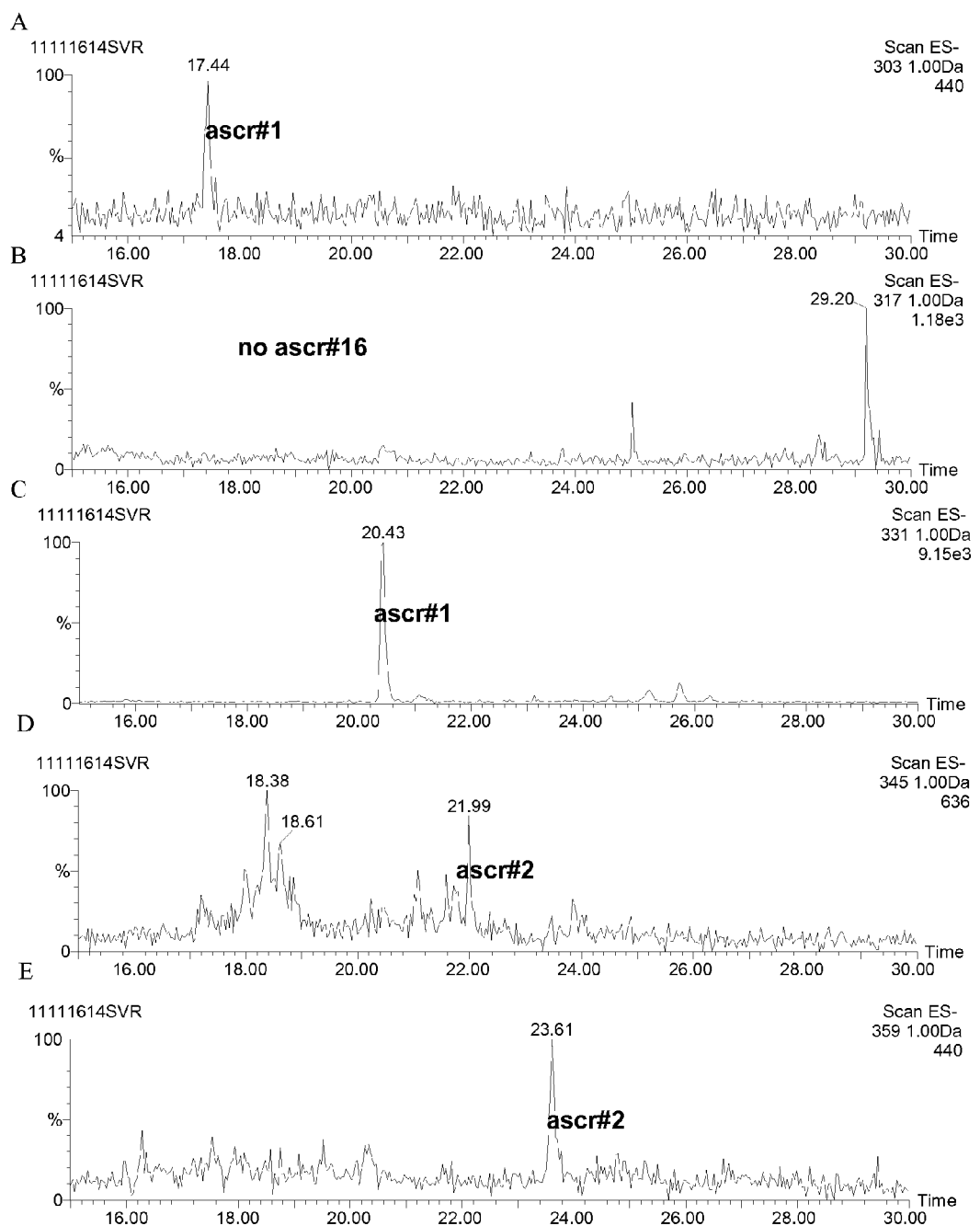
Figure 88:
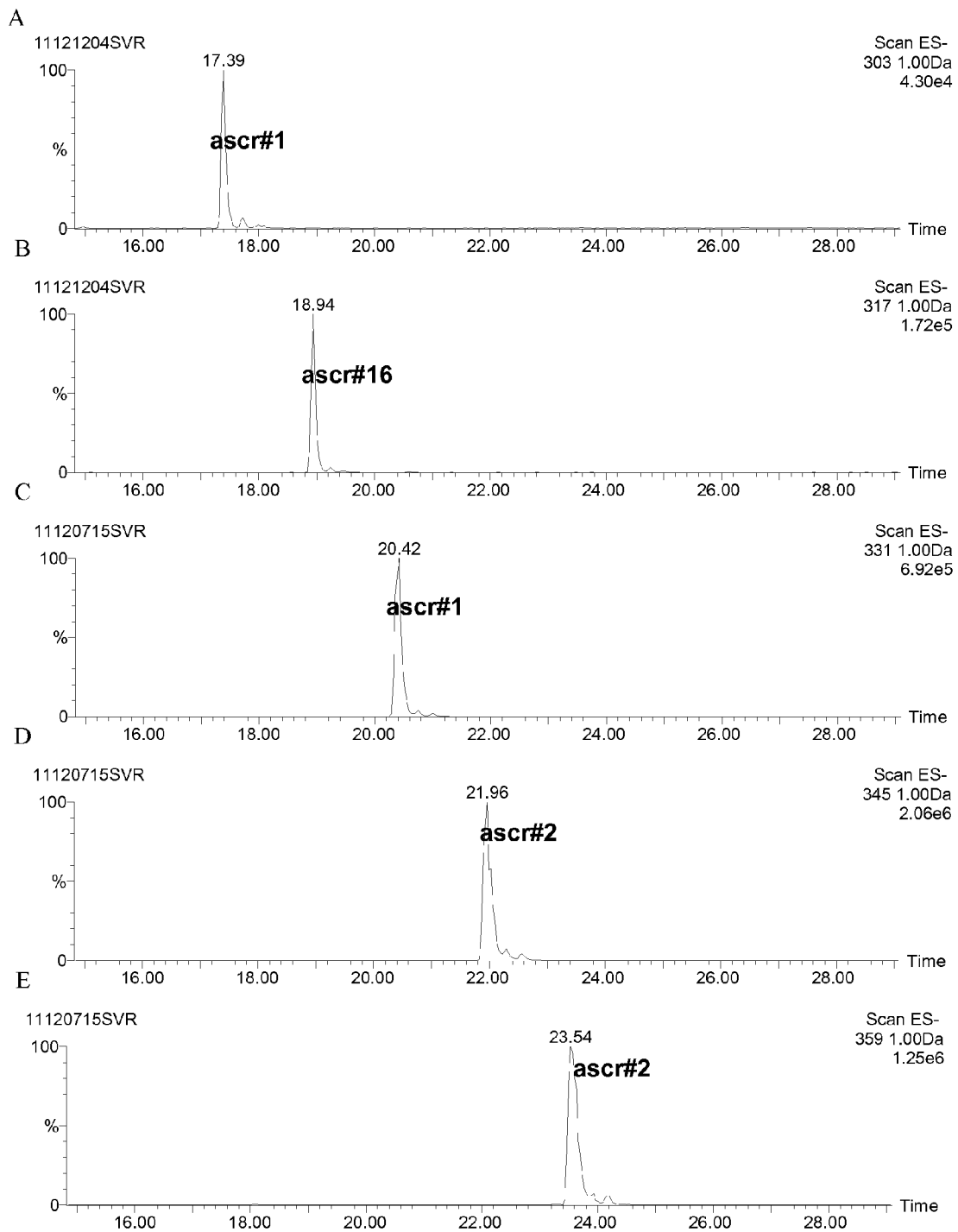

FIGS. 87A-E are HPLC-MS chromatograms of extracts from Northern Root-Knot Nematode *M. hapla* (J2 larvae) demonstrating the presence of ascarosides ascr#10 (FIG. 87A), ascr#16 (FIG. 87B), ascr#18 (FIG. 87C), ascr#20 (FIG. 87D), and ascr#22 (FIG. 87E).

FIGS. 88A-E are HPLC-MS chromatograms of synthetic ascaroside standards (ascr#10 (FIG. 88A), ascr#16 (FIG. 88B), ascr#18 (FIG. 88C), ascr#20 (FIG. 88D), and ascr#22 (FIG. 88E)).

Figure 89:
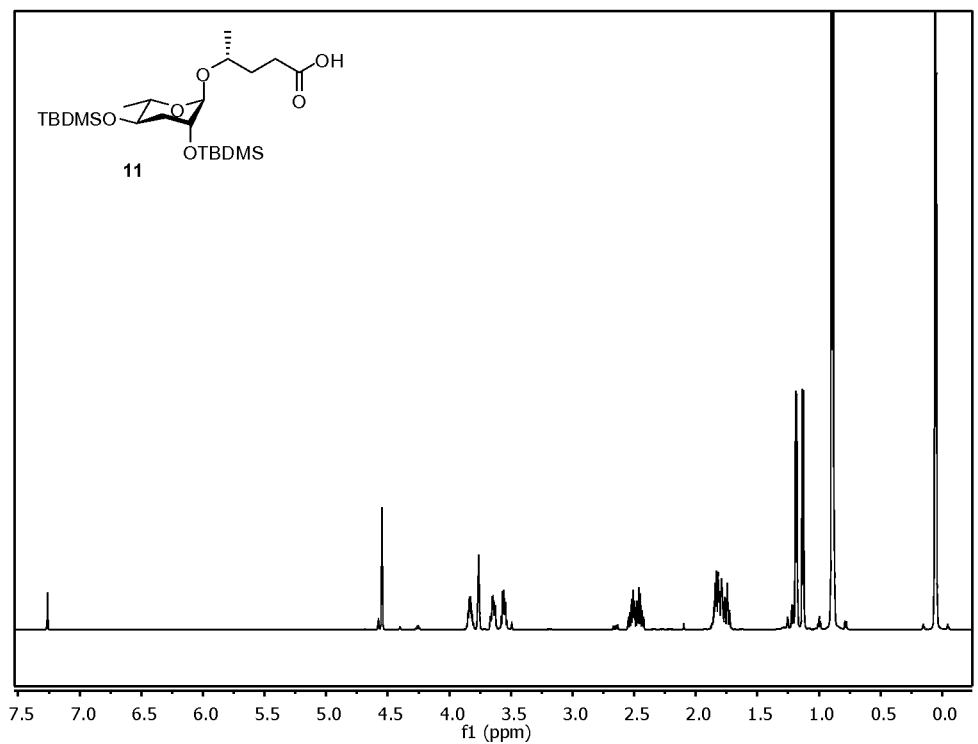

FIG. 89 is the $^1$H NMR spectrum (600 MHz, chloroform-d) of (R)-4-(((2R,3R,5R,6S)-3,5-bis((tert-butyldimethylsilyl)oxy)-6-methyltetrahydro-2H-pyran-2-yl)oxy)pentanoic acid (11).

Figure 90A:
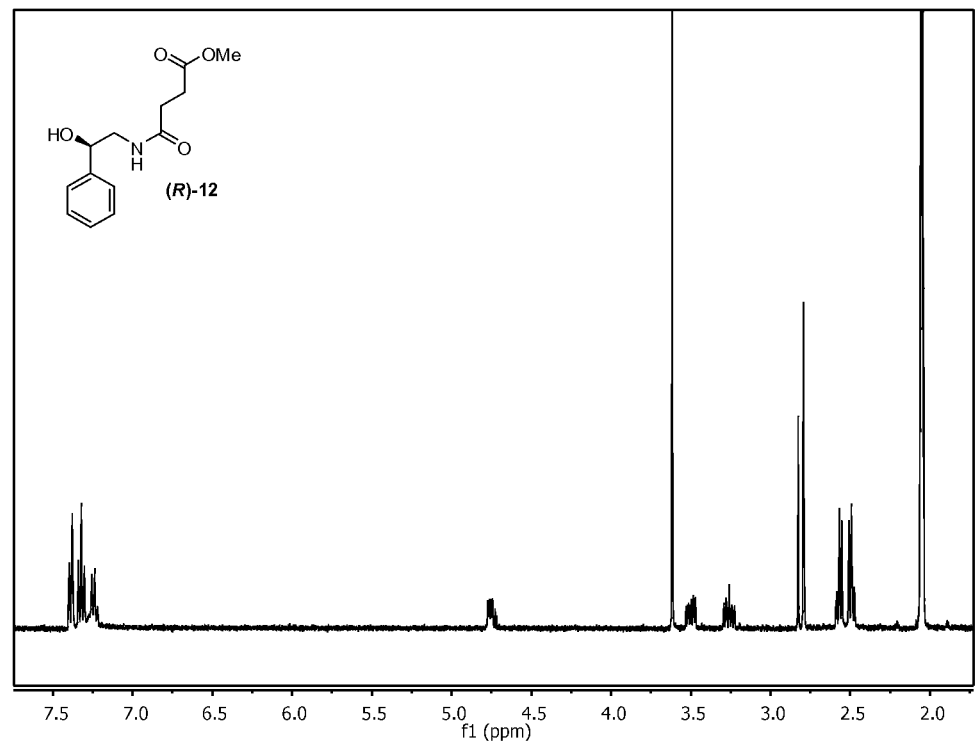
Figure 90B:
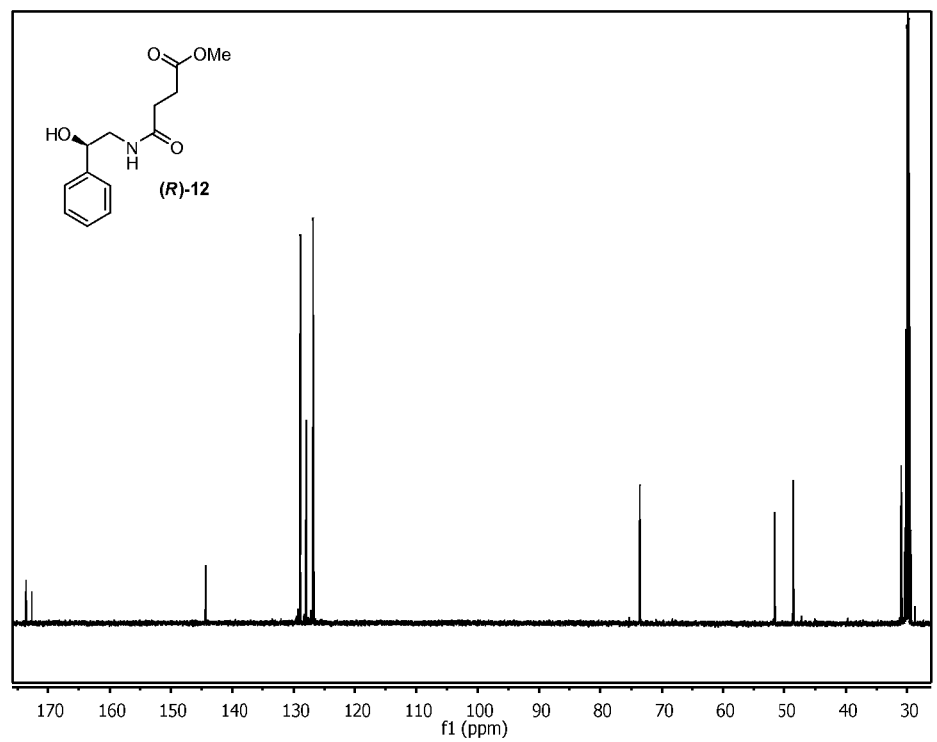

FIGS. 90A-B are the $^1$H NMR (400 MHz, acetone-d$_6$) (FIG. 90A) and $^{13}$C NMR (100 MHz, acetone-d$_6$) (FIG. 90B) spectra of (R)-methyl 4-((2-hydroxy-2-phenylethyl) amino)-4-oxobutanoate ((R)-12).

Figure 91A:
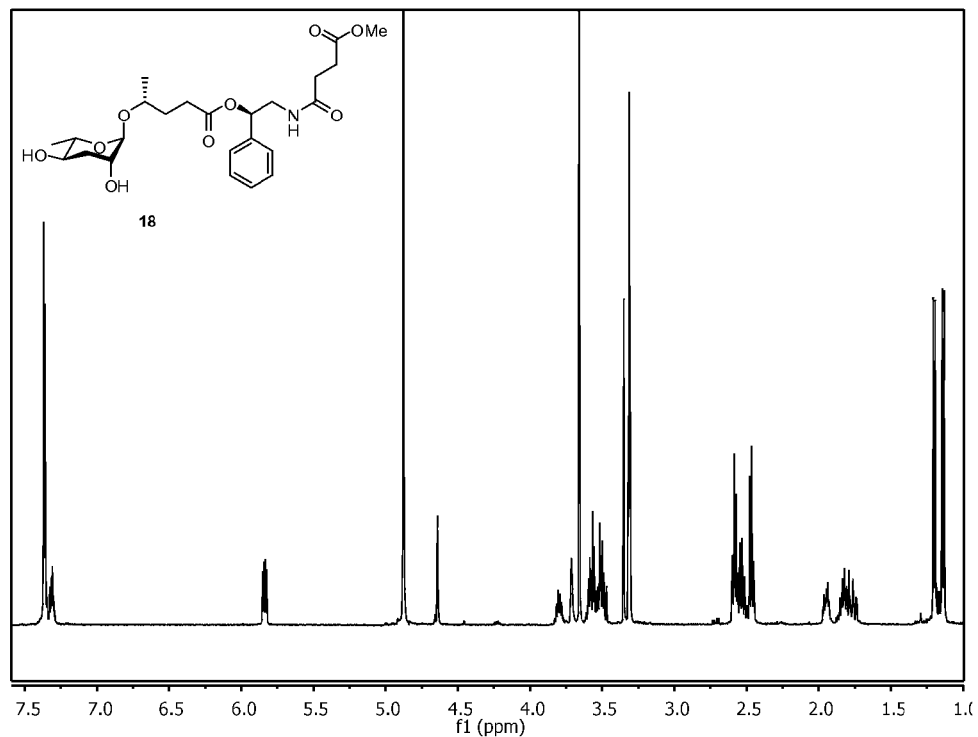
Figure 91B:
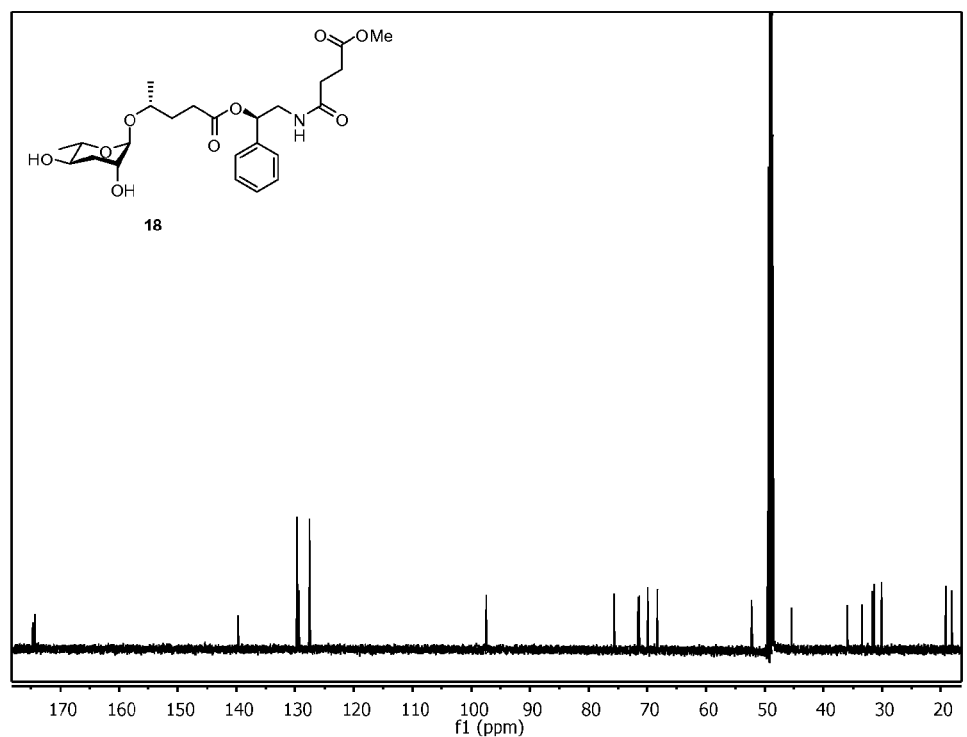
Figure 92A:
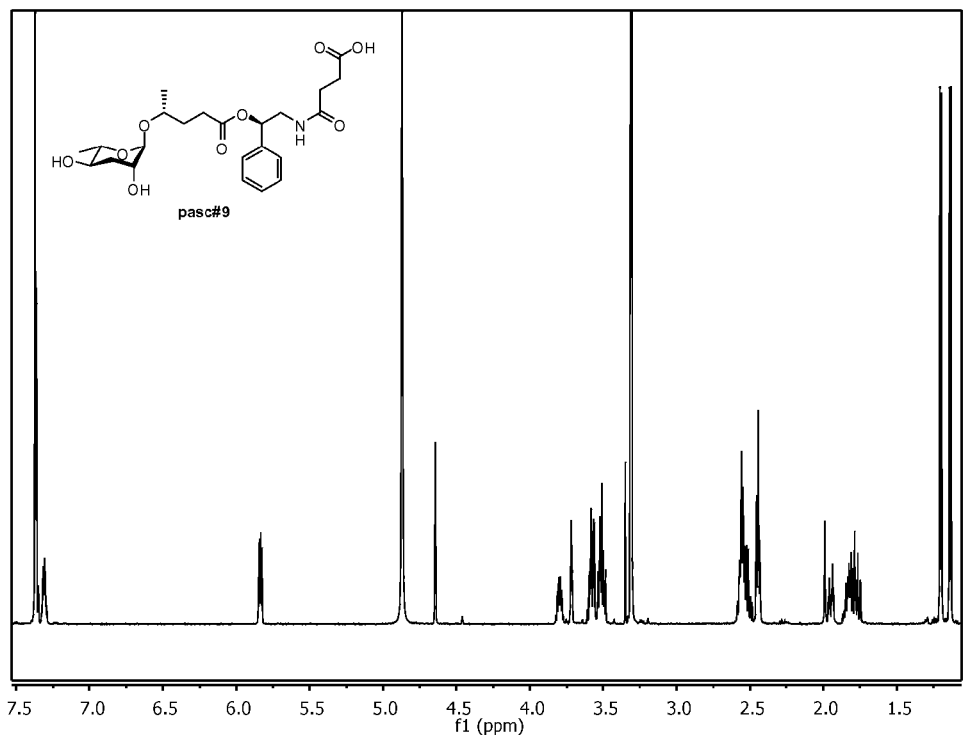
Figure 92B:
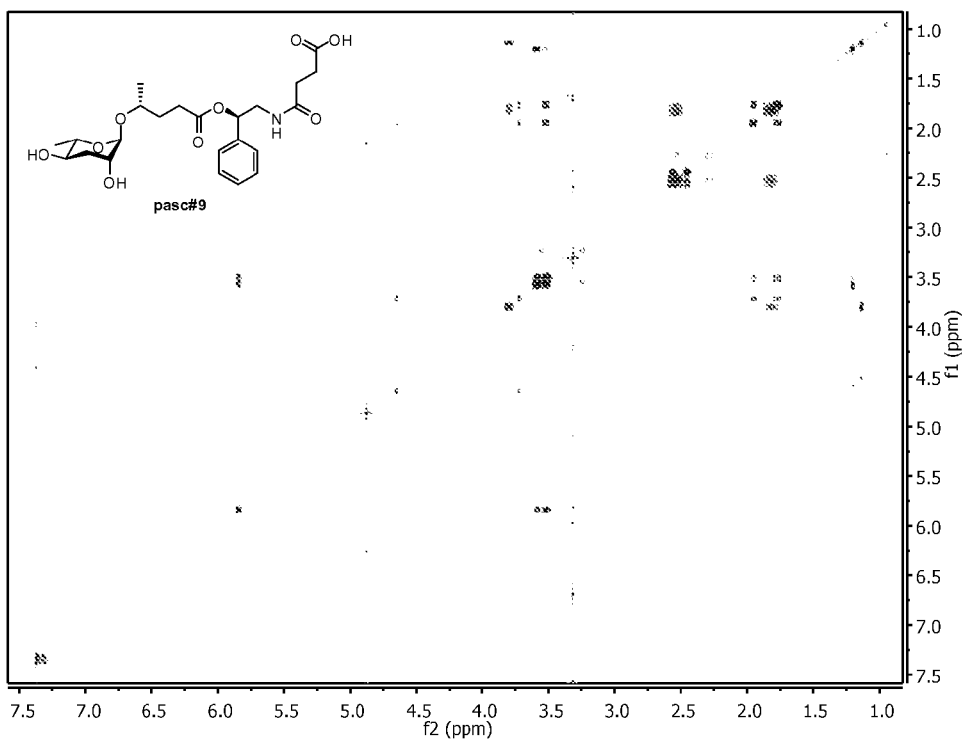
Figure 92C:
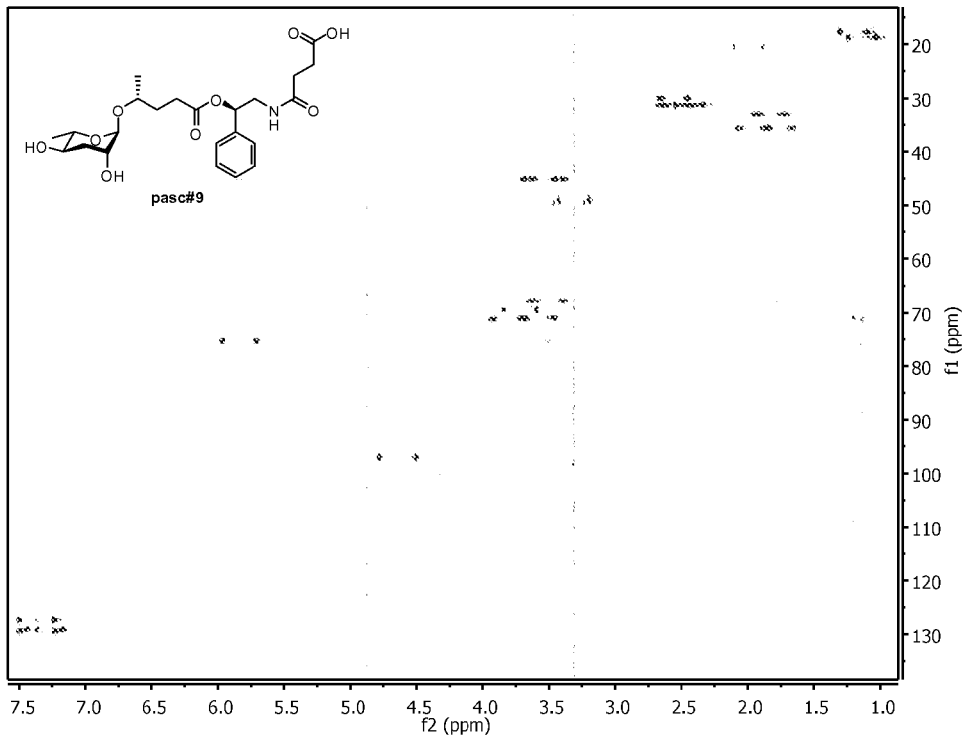
Figure 92D:
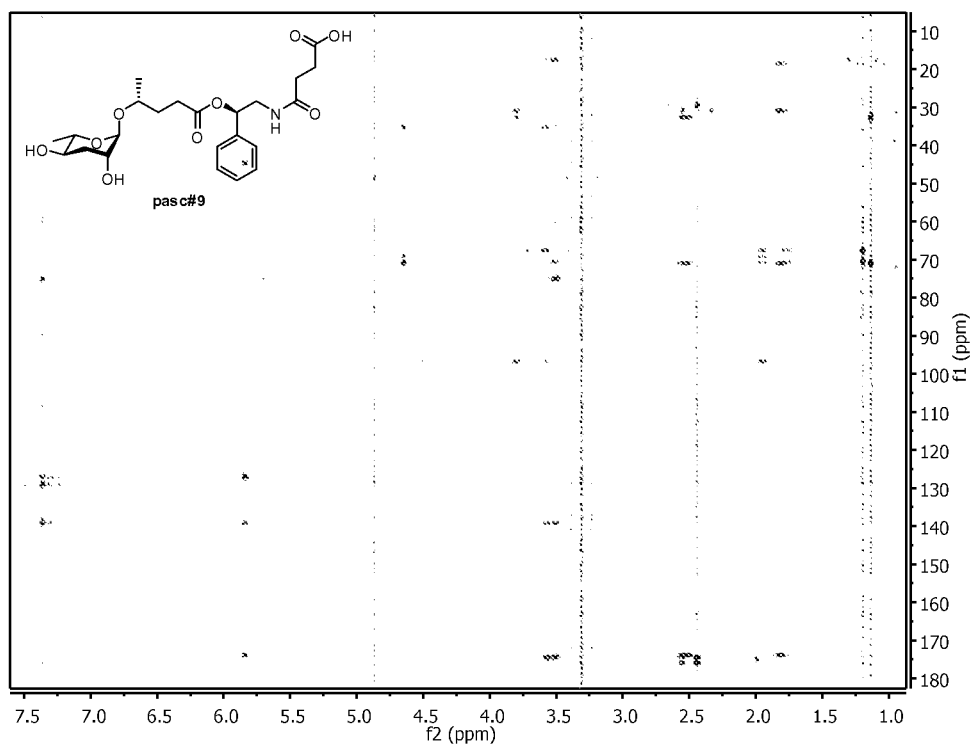

FIGS. 91A-B are the $^1$H NMR (500 MHz, methanol-d$_4$) (FIG. 91A) and $^{13}$C NMR (125 MHz, methanol-d$_4$) (FIG. 91B) spectra of (R)—(R)-2-(4-methoxy-4-oxobutanamido)-1-phenylethyl 4-(((2R,3R,5R,6S)-3,5-dihydroxy-6-methyltetrahydro-2H-pyran-2-yl)oxy)pentanoate (18).

FIGS. 92A-D are the $^1$H NMR (600 MHz, methanol-d$_4$) (FIG. 92A), dqfCOSY (600 MHz, methanol-d$_4$) (FIG. 92B), HMQC (600 MHz for $^1$H, 151 MHz) (FIG. 92C), and HMBC (600 MHz for $^1$H, 151 MHz) (FIG. 92D) spectra of 4-(((R)-2-(((R)-4-(((2R,3R,5R,6S)-3,5-dihydroxy-6-methyltetrahydro-2H-pyran-2-yl)oxy)pentanoyl)oxy)-2-phenylethyl)amino)-4-oxobutanoic acid (pasc#9).

Figure 93A:
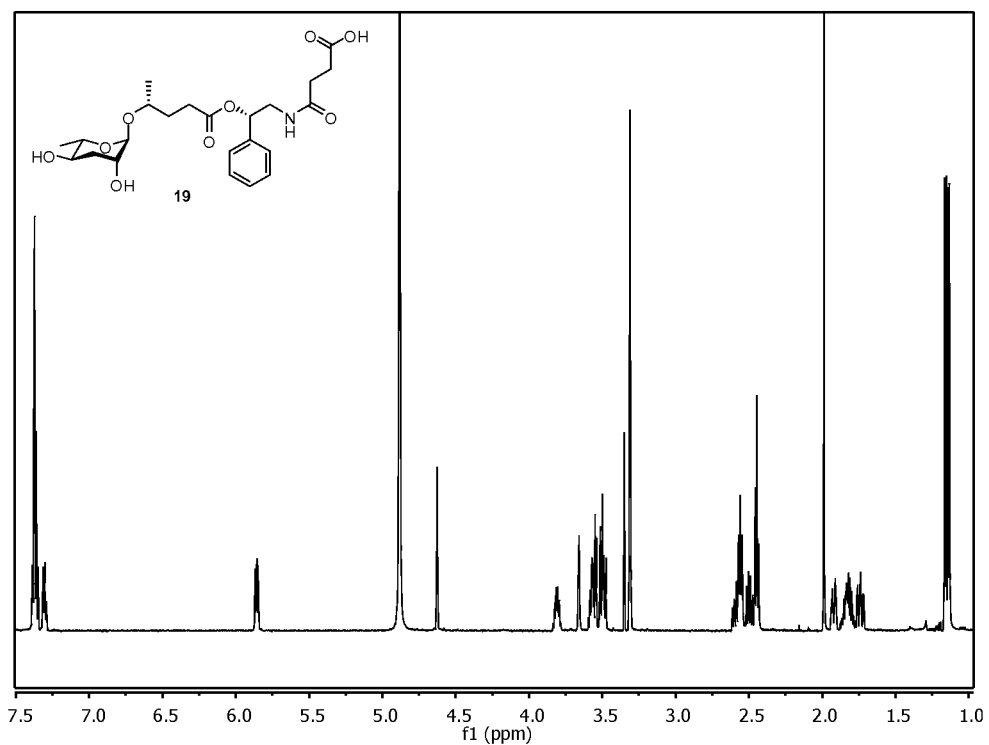
Figure 93B:
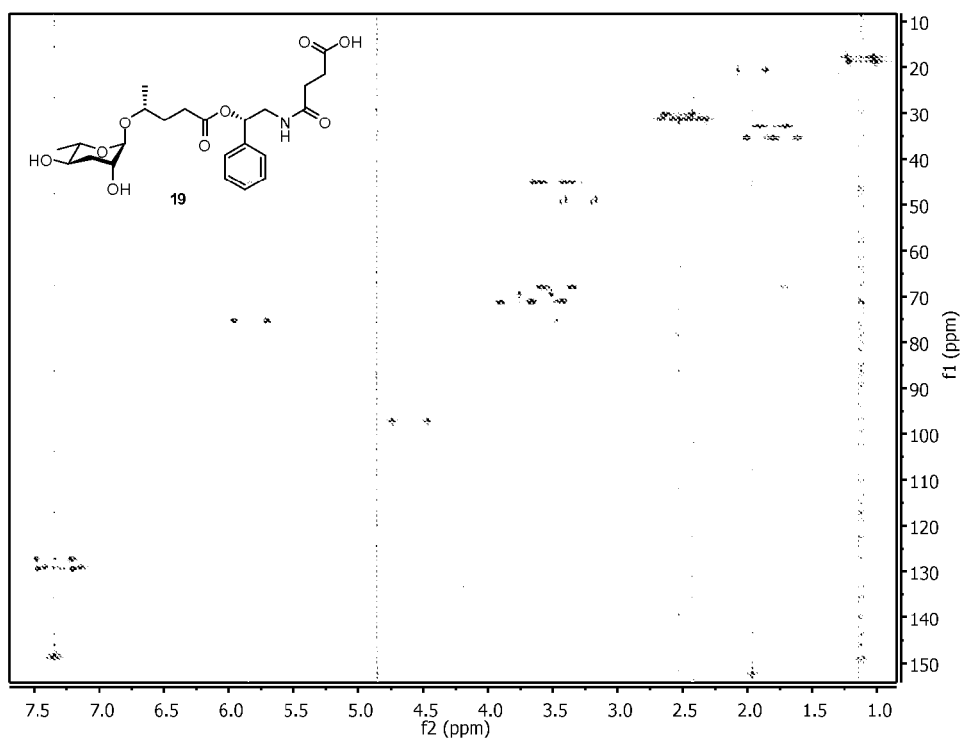
Figure 93C:
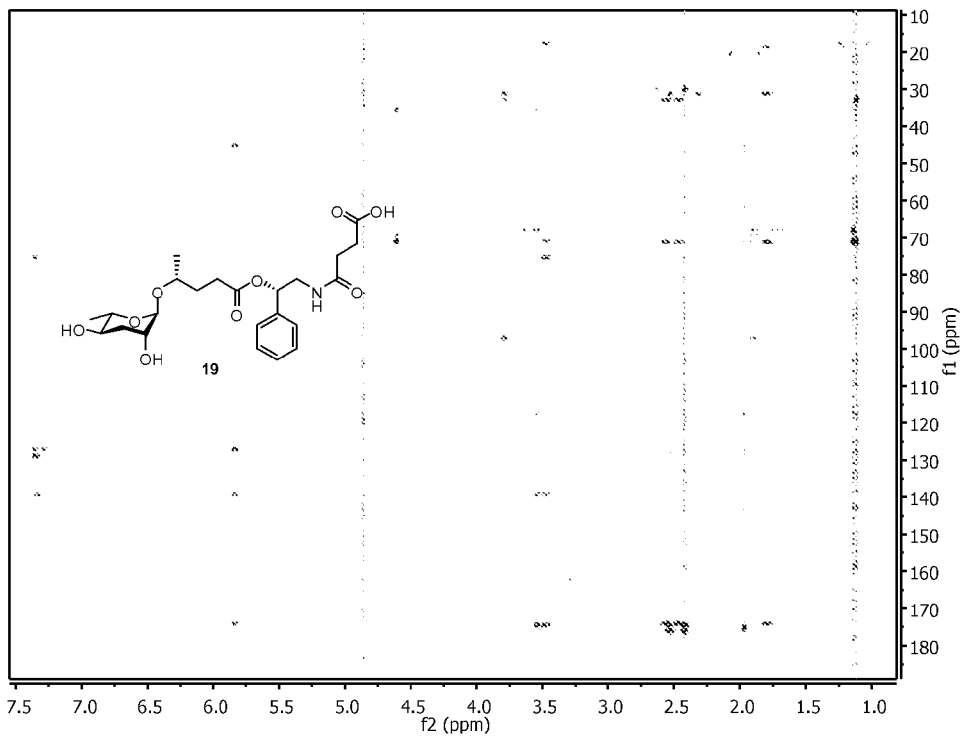

FIGS. 93A-C are the ¹H NMR (600 MHz, methanol-d₄) (FIG. 93A), HMQC (600 MHz for ¹H, 151 MHz) (FIG. 93B), and HMBC (600 MHz for ¹H, 151 MHz) (FIG. 93C) spectra of 4-(((S)-2-(((R)-4-(((2R,3R,5R,6S)-3,5-dihydroxy-6-methyltetrahydro-2H-pyran-2-yl)oxy)pentanoyl) oxy)-2-phenylethyl)amino)-4-oxobutanoic acid (19).

Figure 94A:
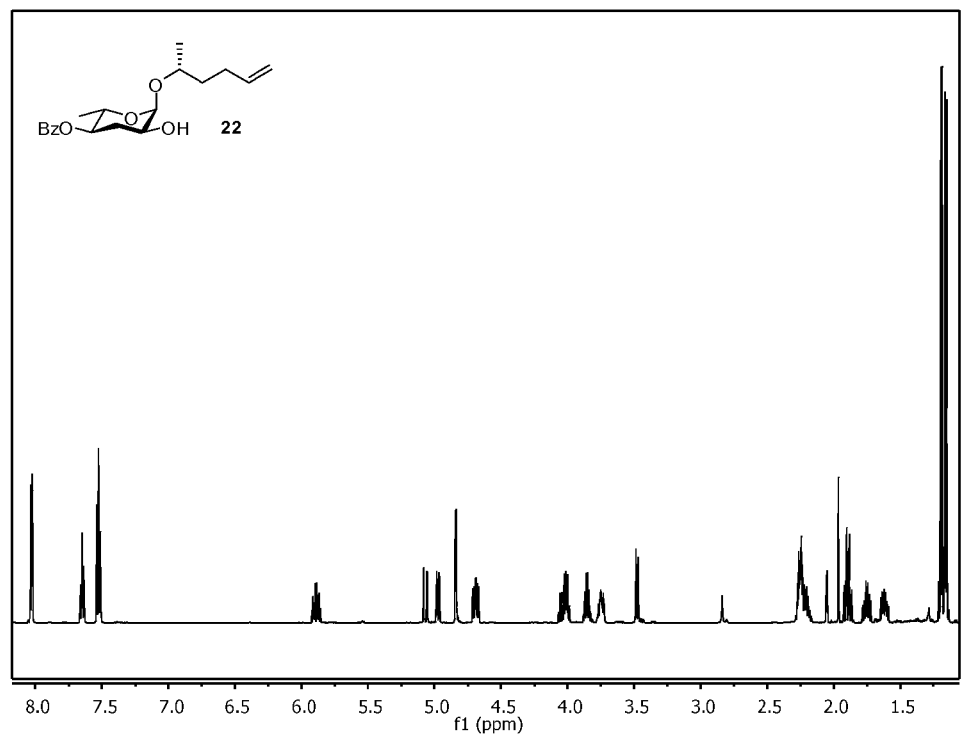
Figure 94B:
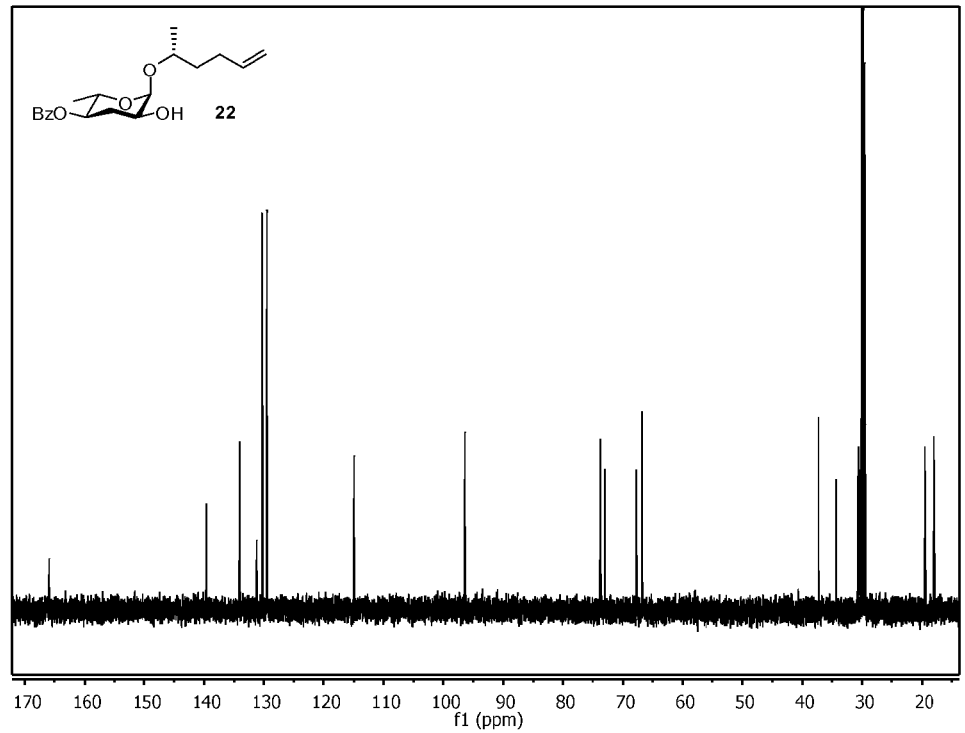

FIGS. 94A-B are the ¹H NMR (600 MHz, acetone-d) (FIG. 94A) and ¹³C NMR (151 MHz, acetone-d₆) (FIG. 94B) spectra of (2S,3R,5S,6R)-6-((R)-hex-5-en-2-yloxy)-5-hydroxy-2-methyltetrahydro-2H-pyran-3-yl benzoate (22).

Figure 95A:
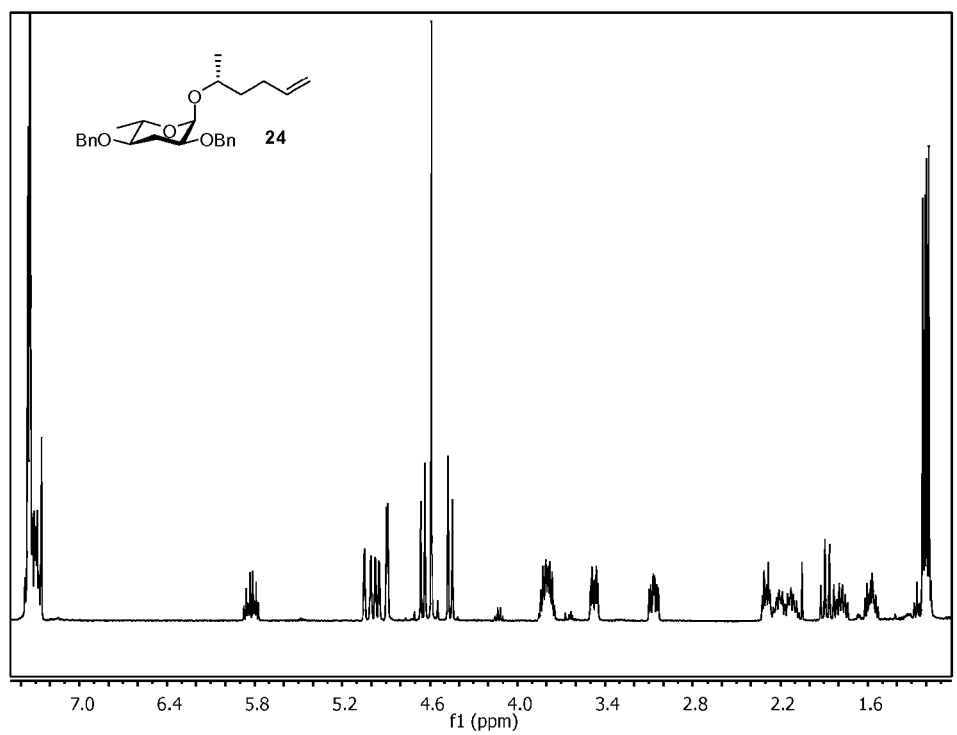
Figure 95B:
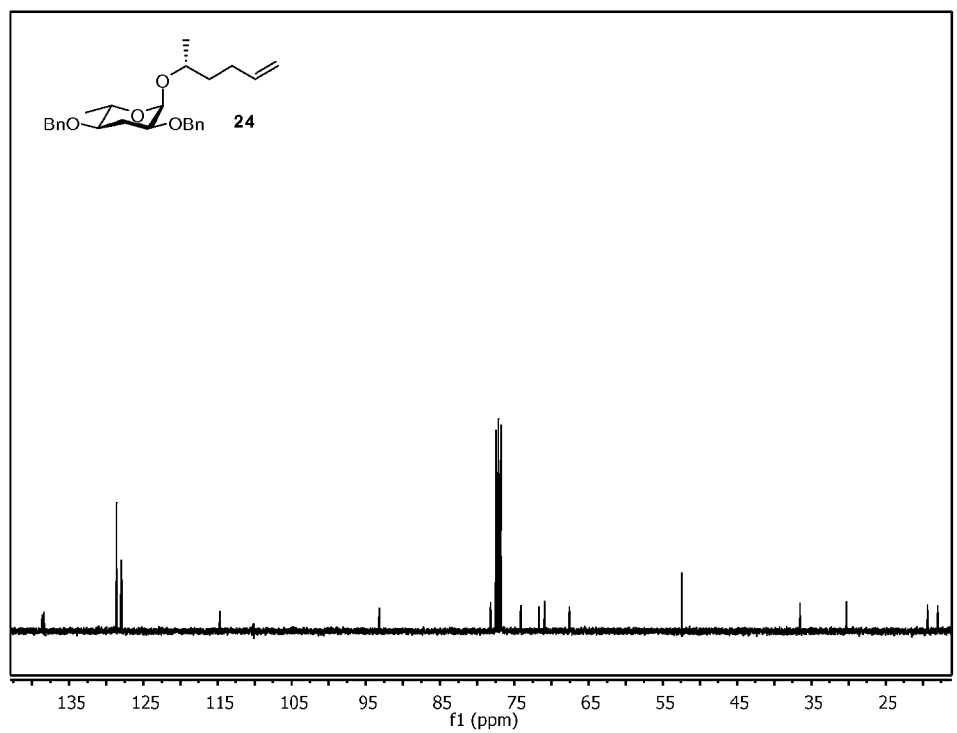
Figure 96A:
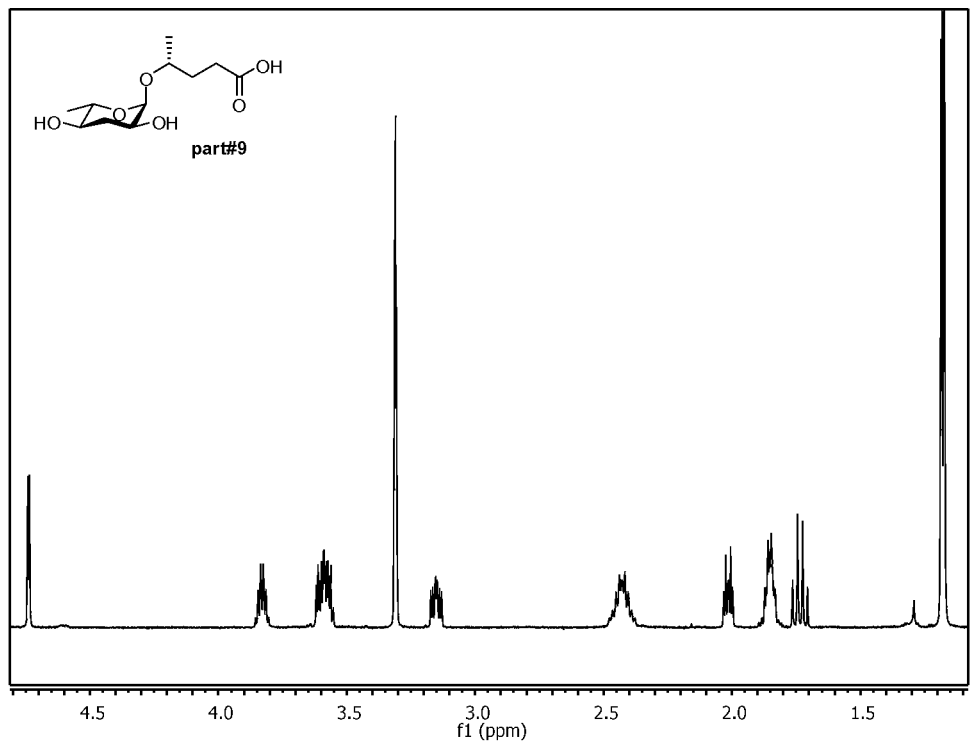
Figure 96B:
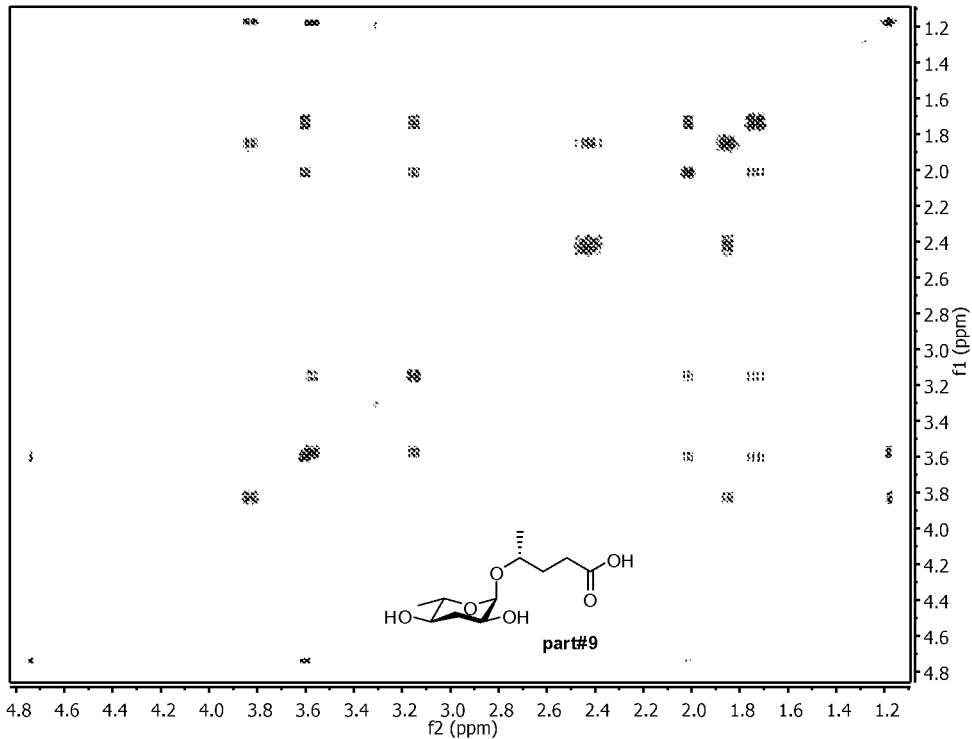
Figure 96C:
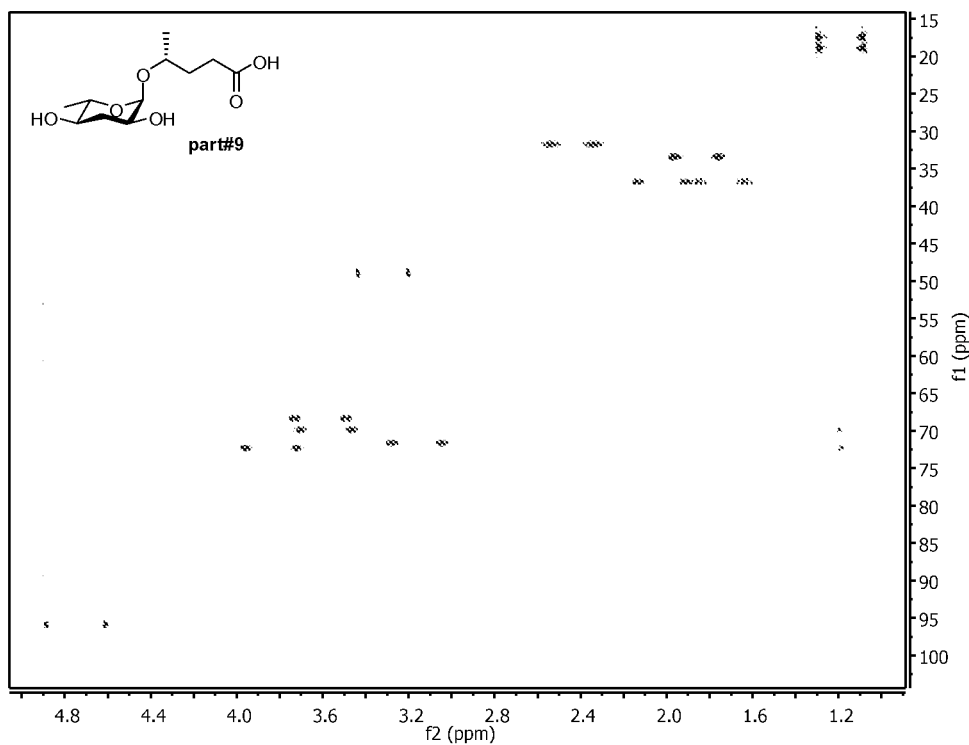
Figure 96D:
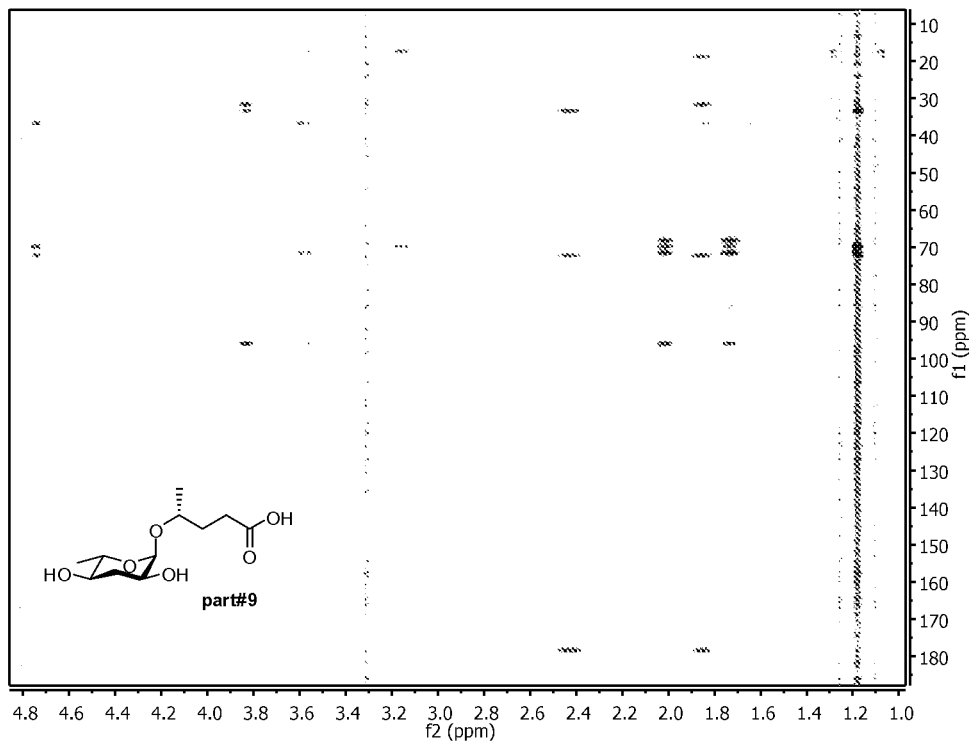

FIGS. 95A-B are the ¹H NMR (400 MHz, chloroform-d) (FIG. 95A) and ¹³C NMR (100 MHz, chloroform-d) (FIG. 95B) spectra of (2R,3S,5R,6S)-3,5-bis(benzyloxy)-2-((R)-hex-5-en-2-yloxy)-6-methyltetrahydro-2H-pyran (24).

FIGS. 96A-D are the ¹H NMR (600 MHz, methanol-d₄) (FIG. 96A), dqfCOSY (600 MHz, methanol-d₄) (FIG. 96B), HMQC (600 MHz for ¹H, 151 MHz) (FIG. 96C), and HMBC (600 MHz for ¹H, 151 MHz) (FIG. 96D) spectra of (R)-4-(((2R,3S,5R,6S)-3,5-dihydroxy-6-methyltetrahydro-2H-pyran-2-yl)oxy)pentanoic acid (part#9).

Figure 97A:
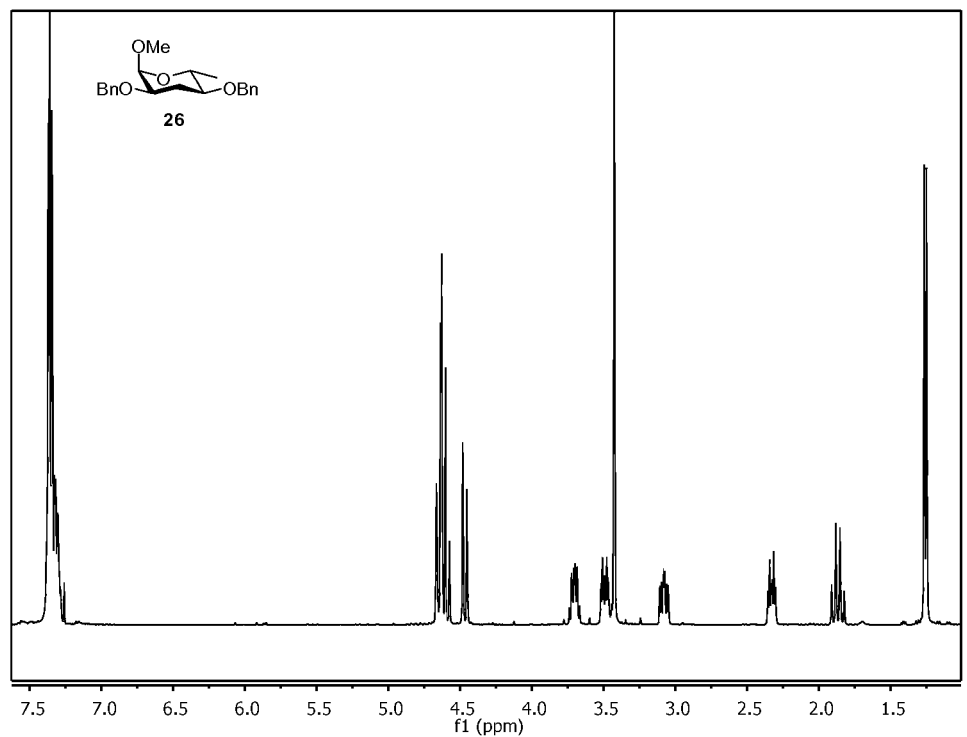
Figure 97B:
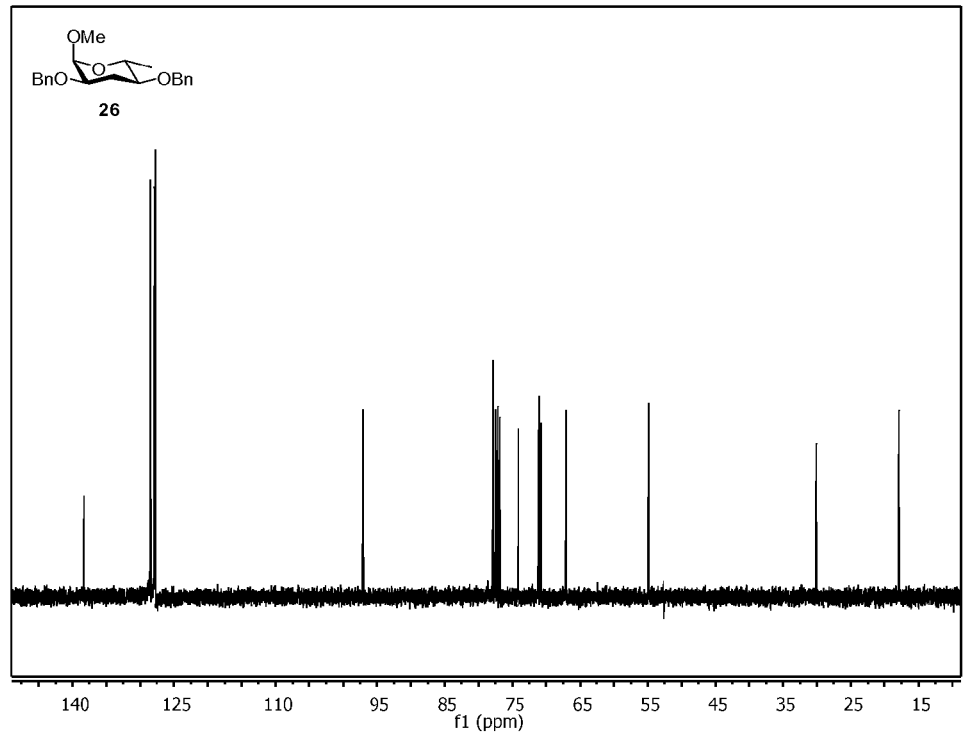

FIGS. 97A-B are the ¹H NMR (400 MHz, chloroform-d) (FIG. 97A) and ¹³C NMR (100 MHz, chloroform-d) (FIG. 97B) spectra of (2S,3R,5S,6R)-3,5-bis(benzyloxy)-2-methoxy-6-methyltetrahydro-2H-pyran (26).

Figure 98A:
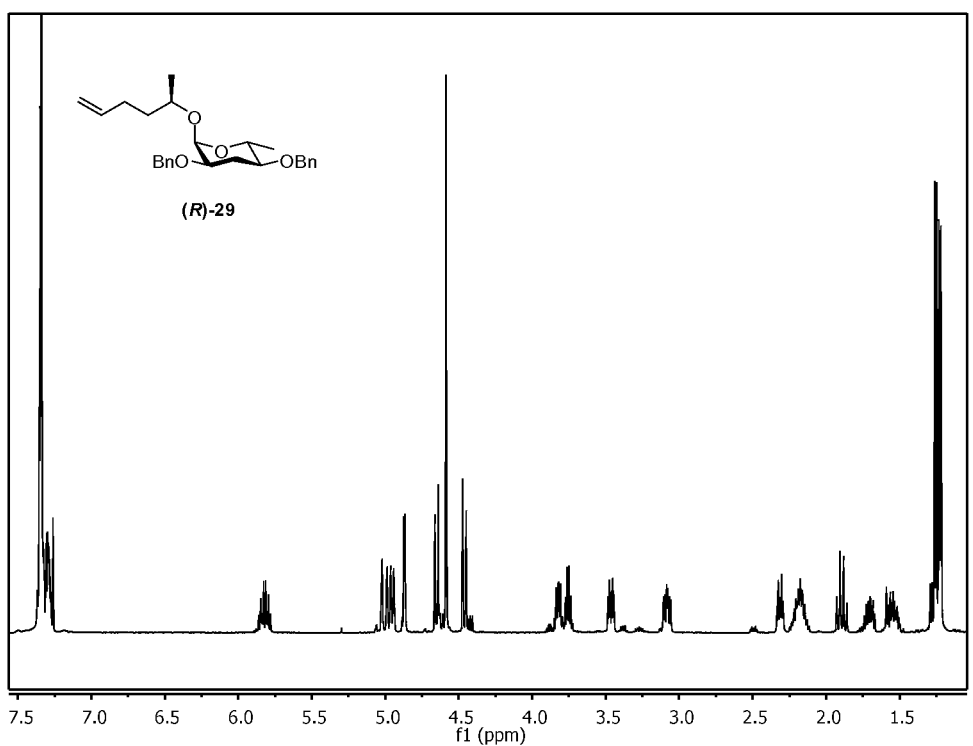
Figure 98B:
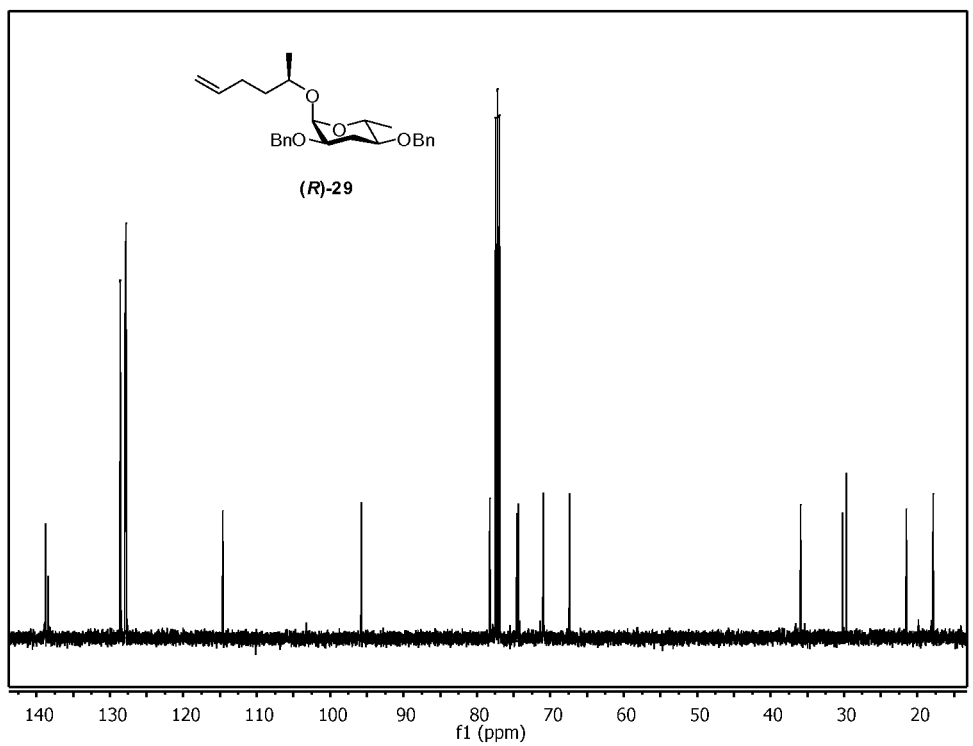

FIGS. 98A-B are the ¹H NMR (500 MHz, chloroform-d₄) (FIG. 98A) and ¹³C NMR (125 MHz, chloroform-d₄) (FIG. 98B) spectra of (3R,5S,6R)-3,5-bis(benzyloxy)-2-((R)-hex-5-en-2-yloxy)-6-methyltetrahydro-2H-pyran ((R)-29, α-anomer).

Figure 99A:
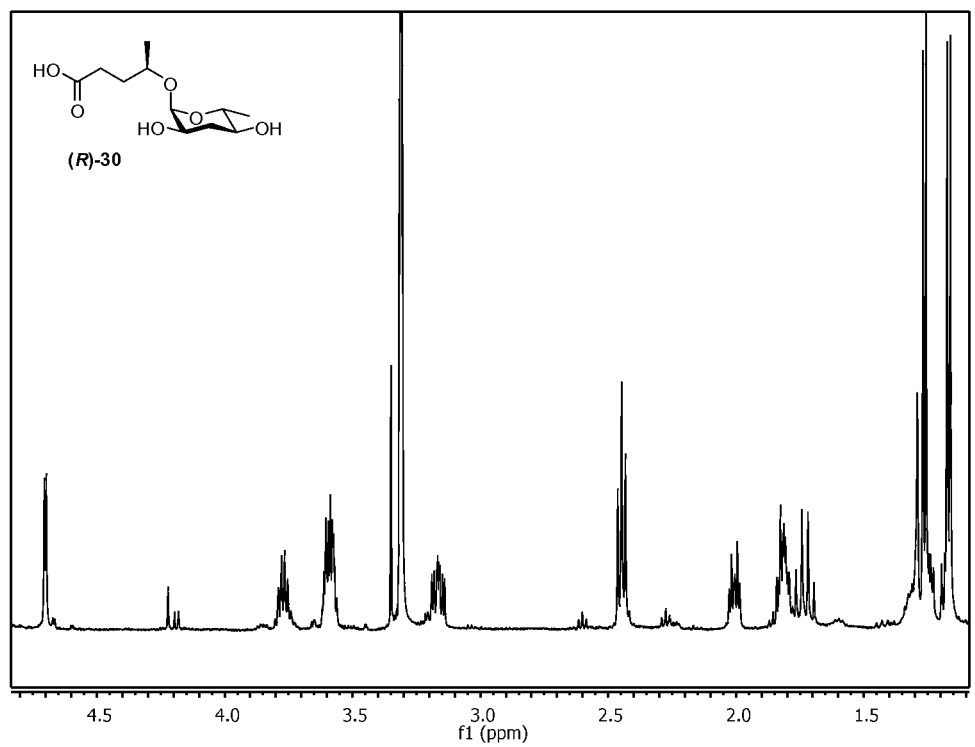
Figure 99B:
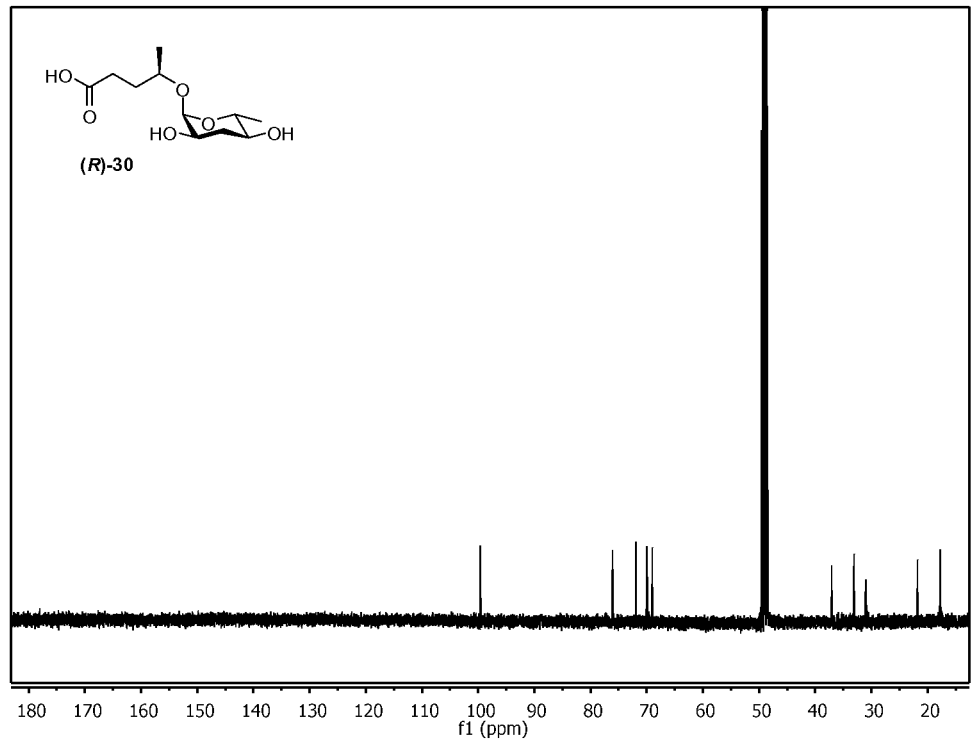

FIGS. 99A-B are the ¹H NMR (500 MHz, methanol-d₄) (FIG. 99A) and ¹³C NMR (125 MHz, methanol-d₄) (FIG. 99B) spectra of (R)-4-(((2S,3R,5S,6R)-3,5-dihydroxy-6-methyltetrahydro-2H-pyran-2-yl)oxy)pentanoic acid ((R)-30).

Figure 100A:
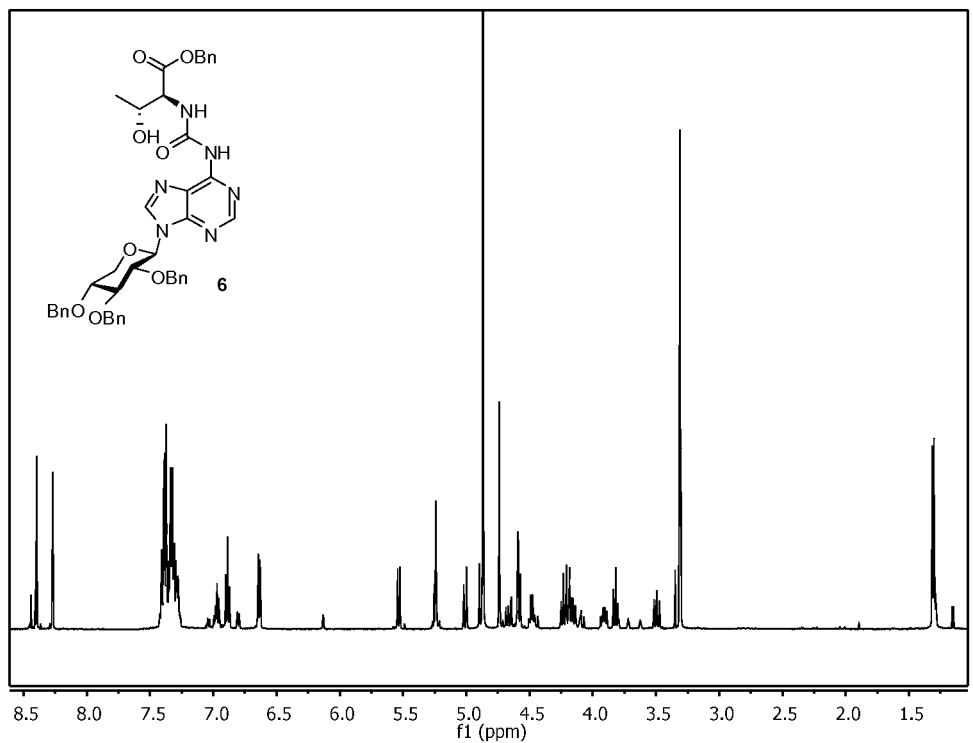
Figure 100B:
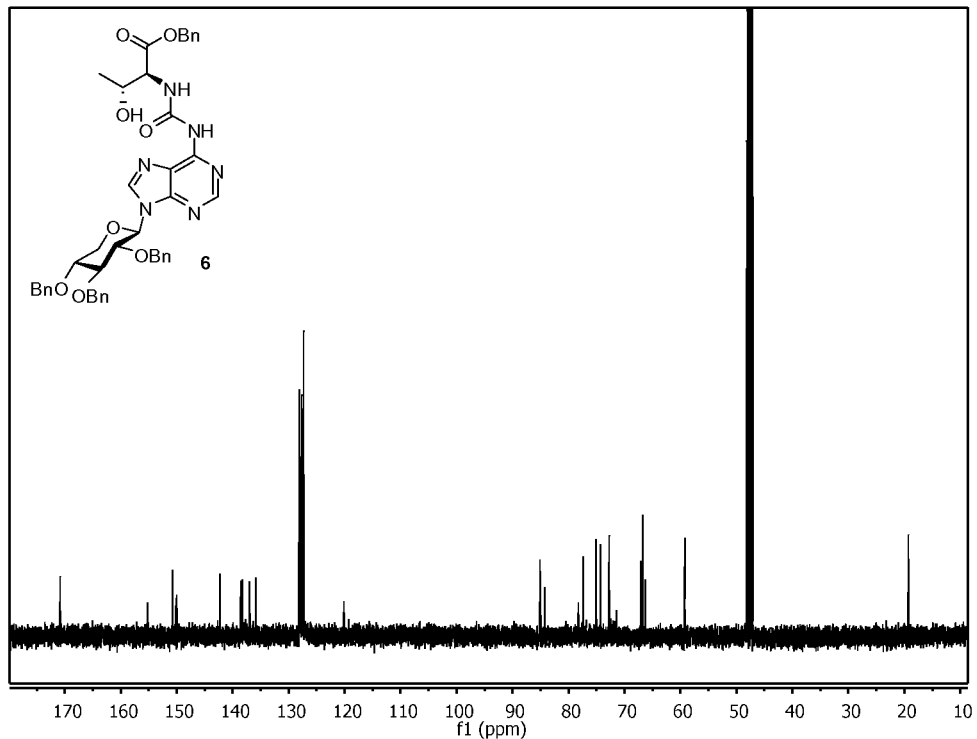
Figure 101A:
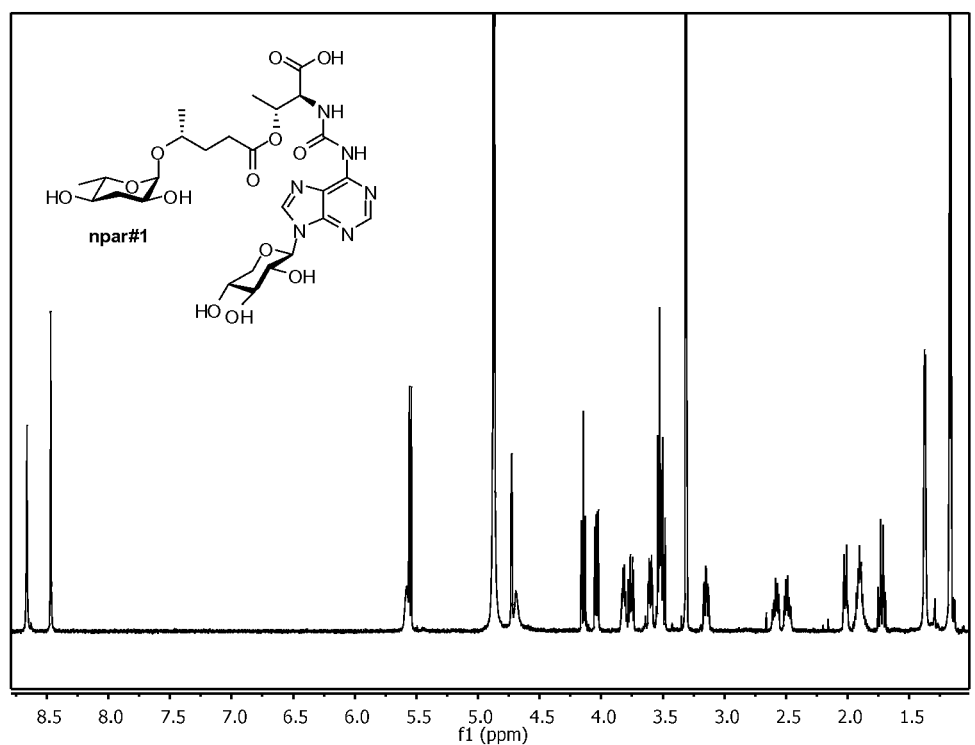
Figure 101B:
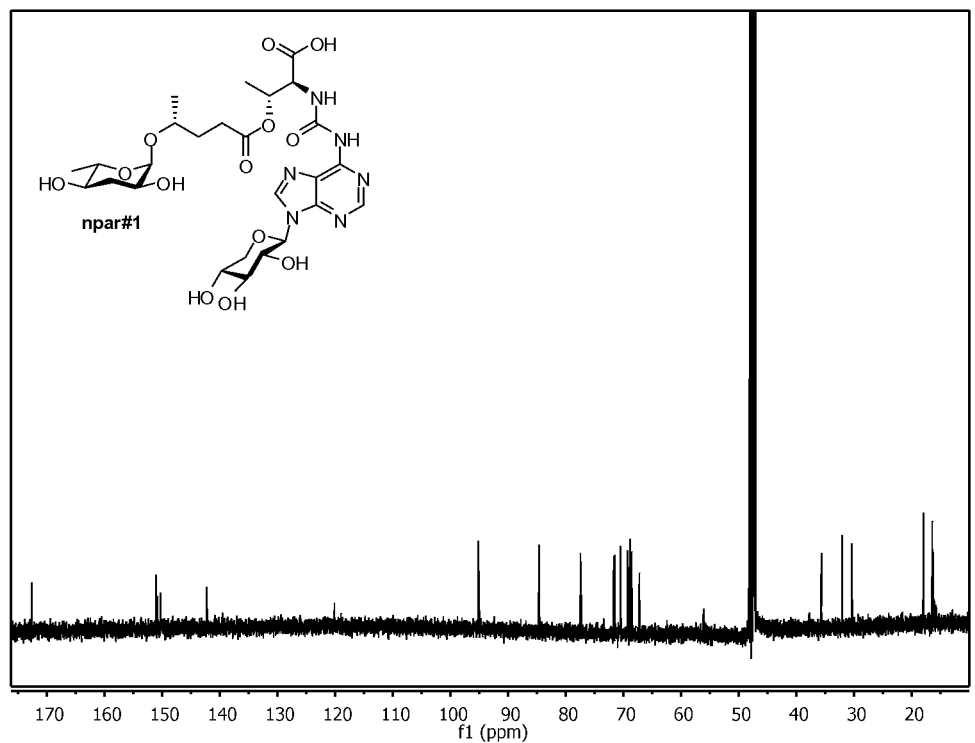
Figure 101C:
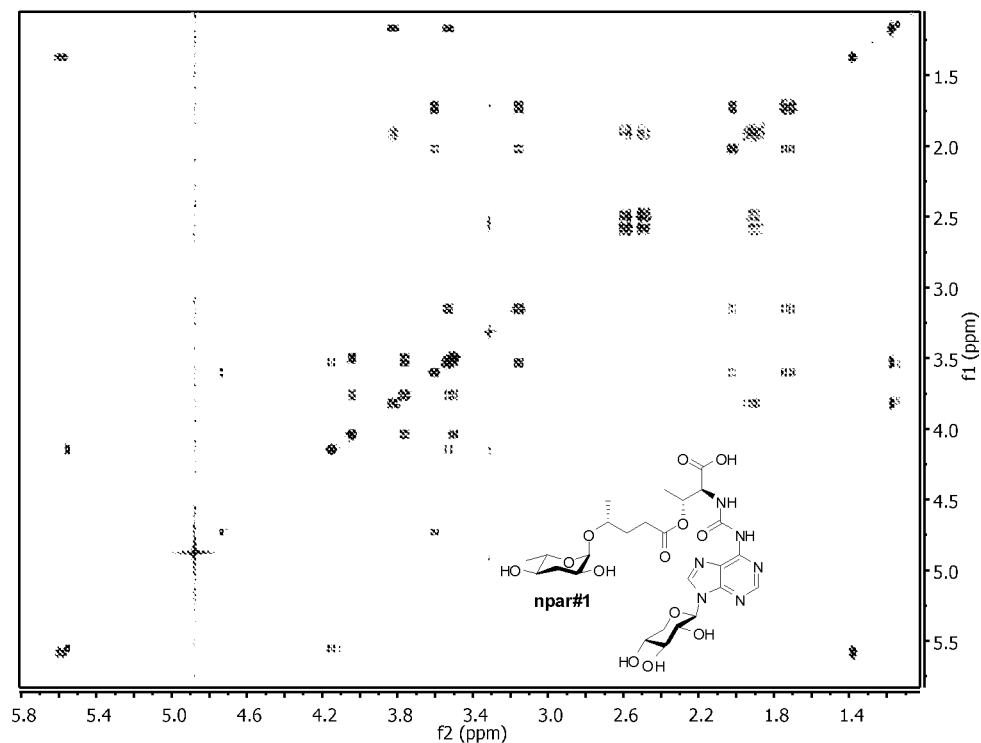
Figure 101D:
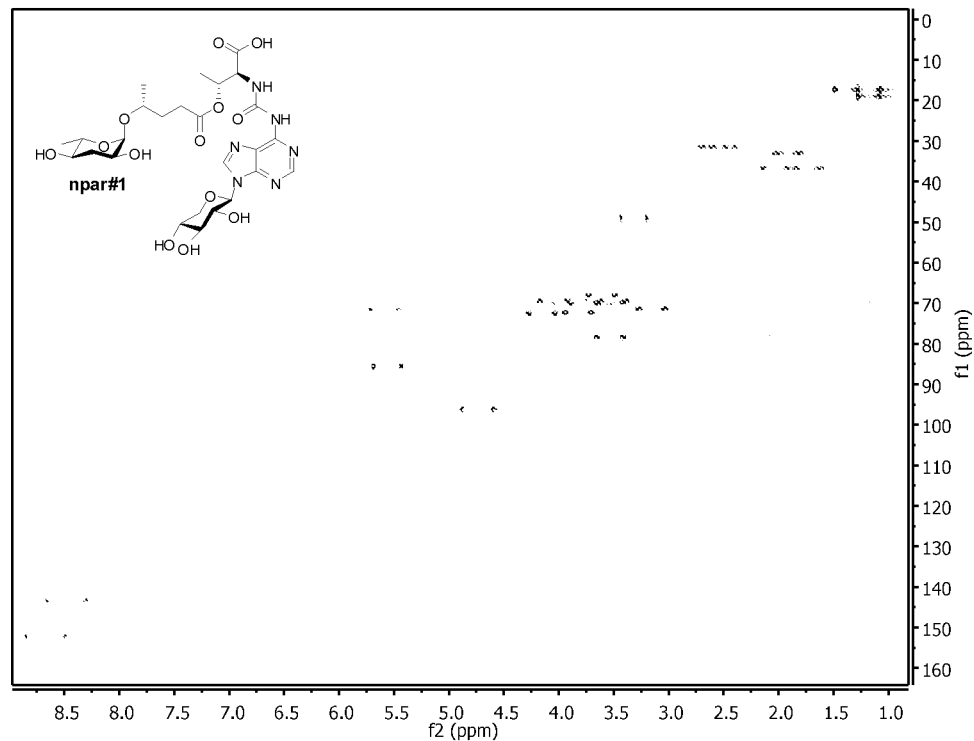
Figure 101E:
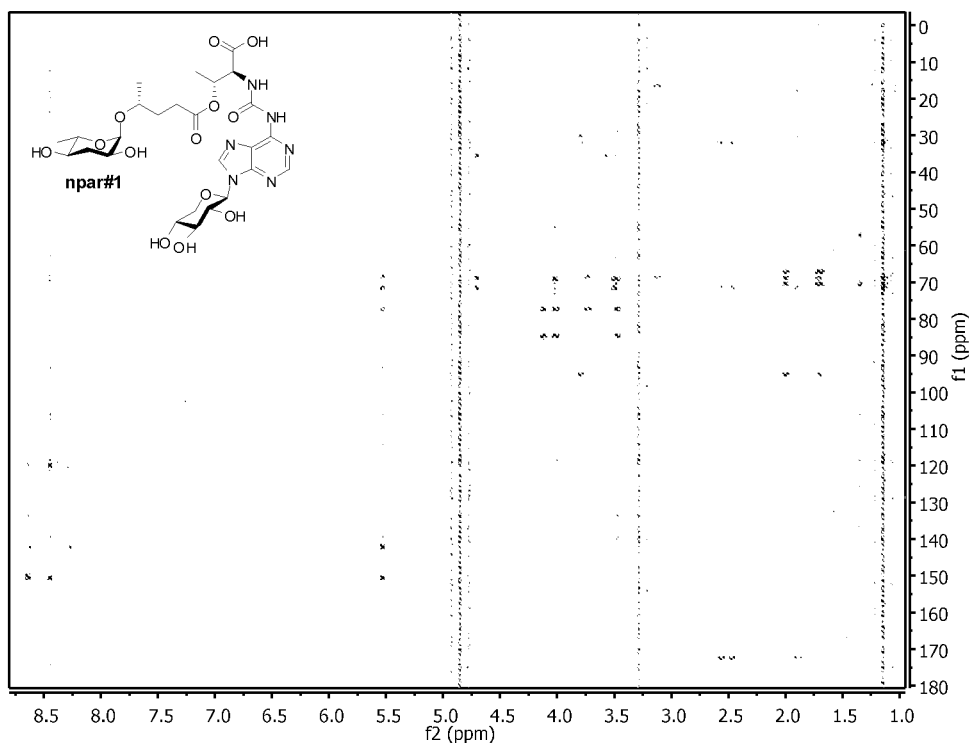

FIGS. 100A-B are the ¹H NMR (500 MHz, methanol-d₄) (FIG. 100A) and ¹³C NMR (125 MHz, methanol-d₄) (FIG. 100B) spectra of (2S,3R)-benzyl 3-hydroxy-2-(3-(9-((3R,4S,5R)-3,4,5-tris(benzyloxy)tetrahydro-2H-pyran-2-yl)-9H-purin-6-yl)ureido)butanoate (6).

FIGS. 101A-E are the ¹H NMR (600 MHz, methanol-d₄) (FIG. 101A), ¹³C NMR (600 MHz, methanol-d₄) (FIG. 101B), dqfCOSY (600 MHz, methanol-d₄) (FIG. 101C), HSQCAD (600 MHz for ¹H, 151 MHz) (FIG. 101D), and HMBC (600 MHz for ¹H, 151 MHz) (FIG. 101E) spectra of (2S,3R)-3-(((R)-4-(((2R,3S,5R,6S)-3,5-dihydroxy-6-methyltetrahydro-2H-pyran-2-yl)oxy)pentanoyl)oxy)-2-(3-(9-((2R,3R,4S,5R)-3,4,5-trihydroxytetrahydro-2H-pyran-2-yl)-9H-purin-6-yl)ureido)butanoic acid (npar#1).

Figure 102A:
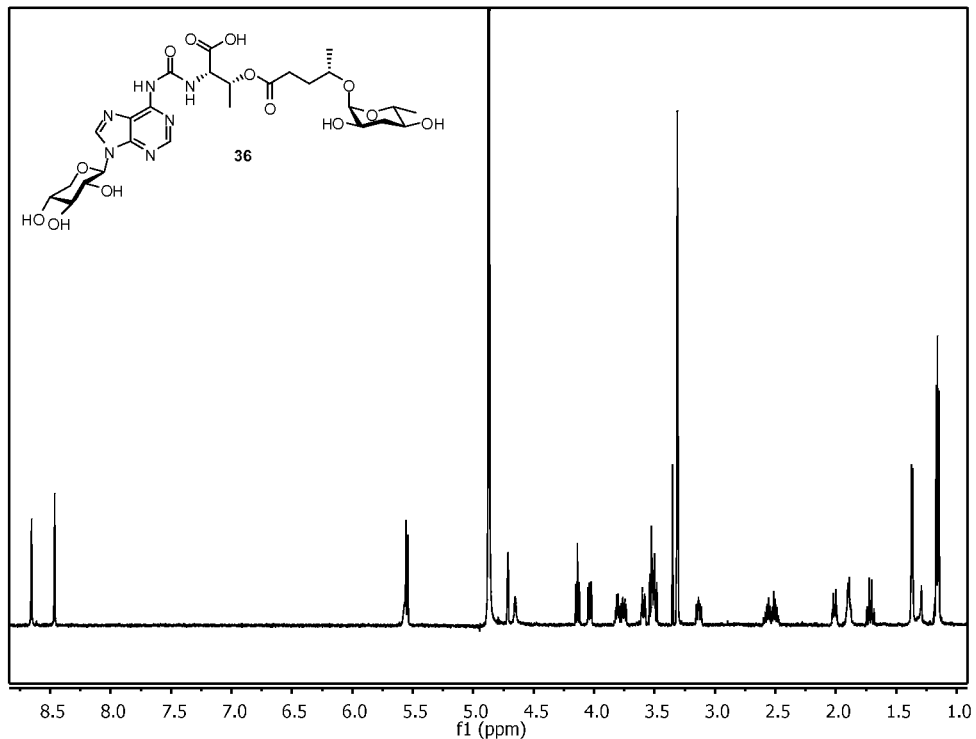
Figure 102B:
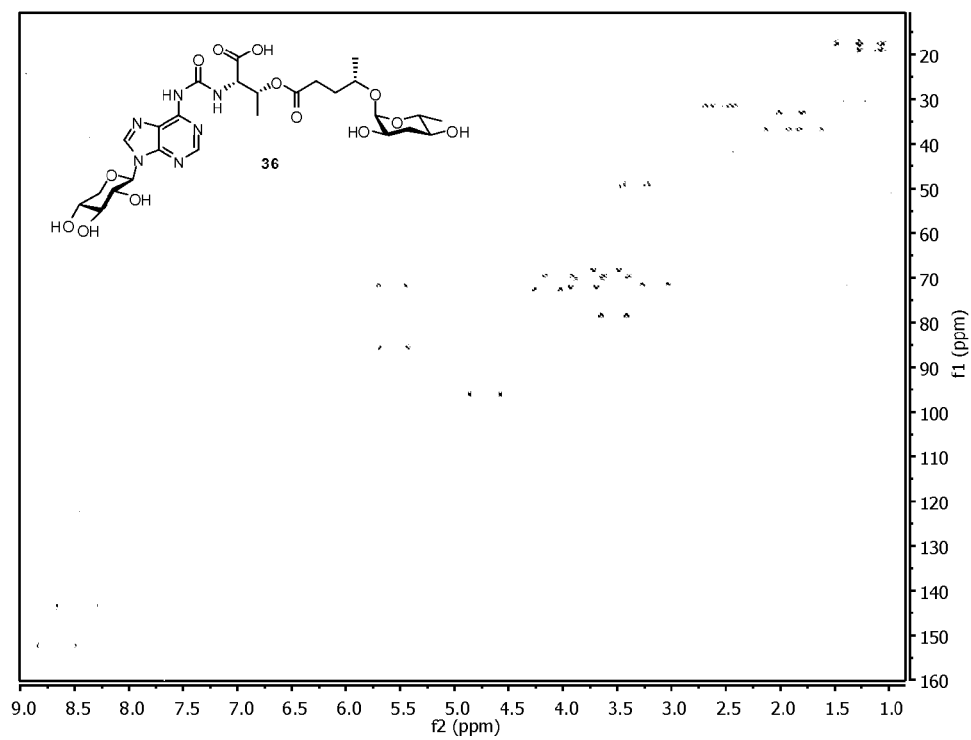
Figure 102C:
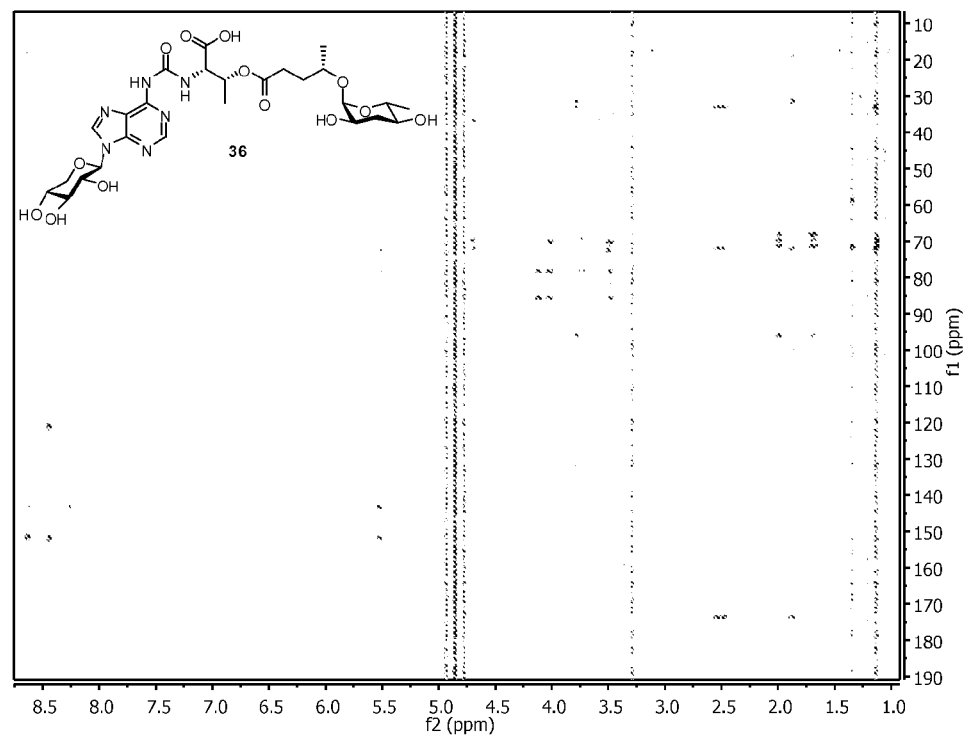
Figure 103A:
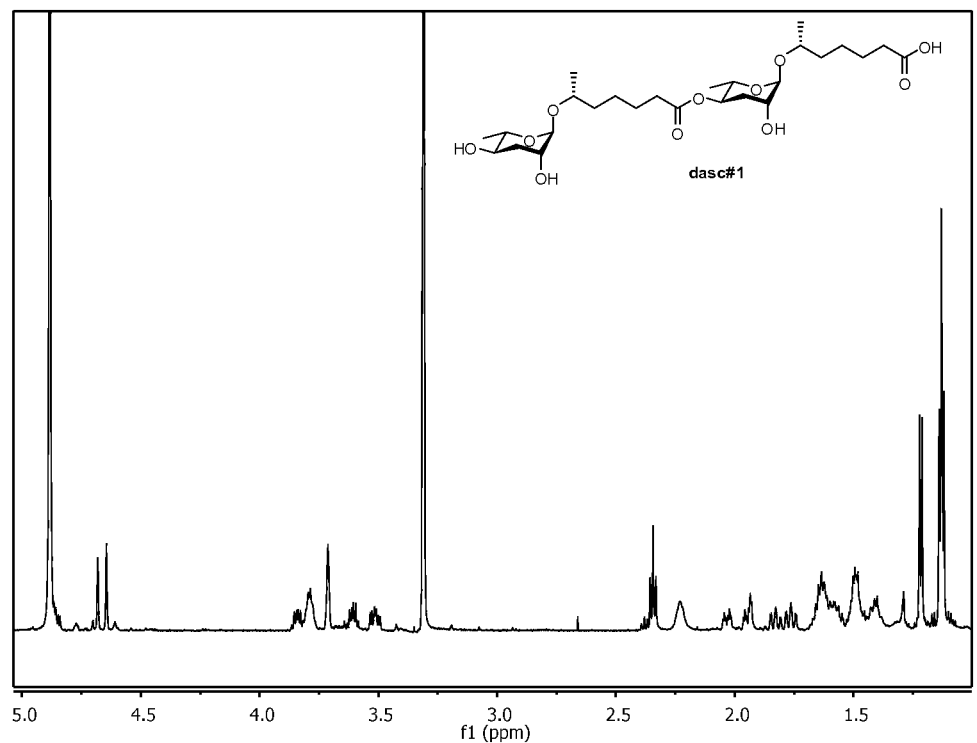
Figure 103B:
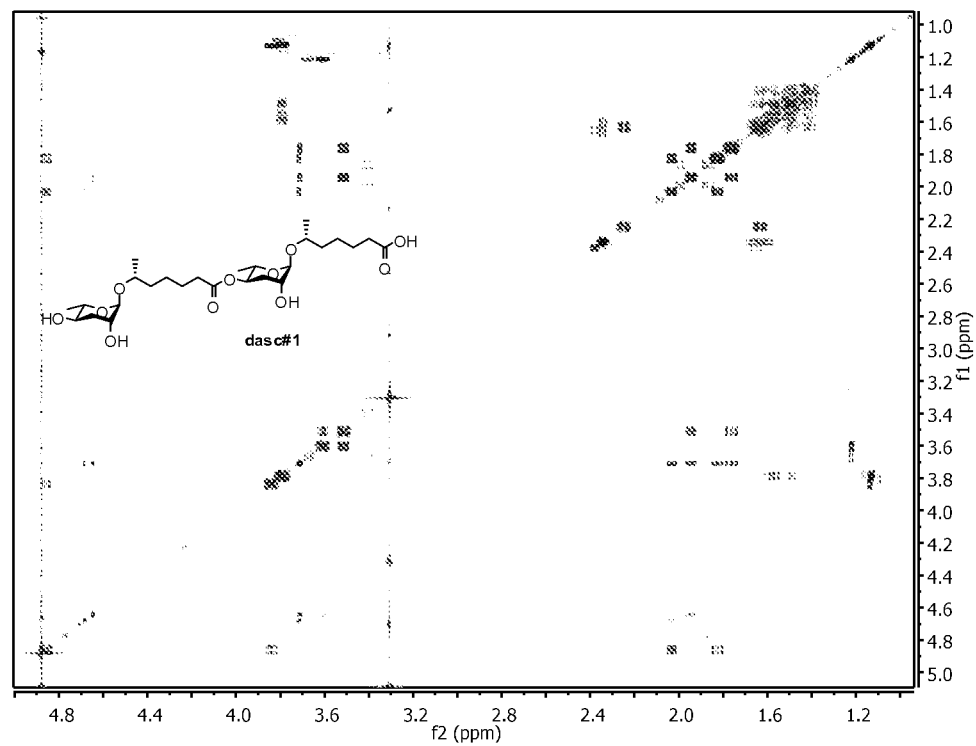
Figure 103C:
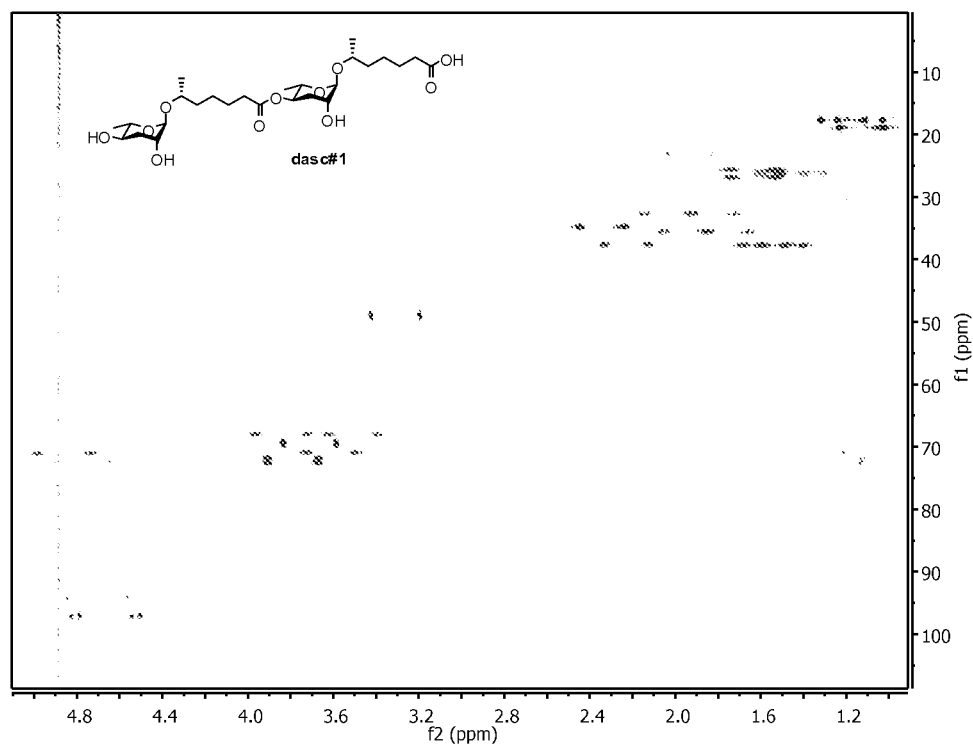
Figure 103D:
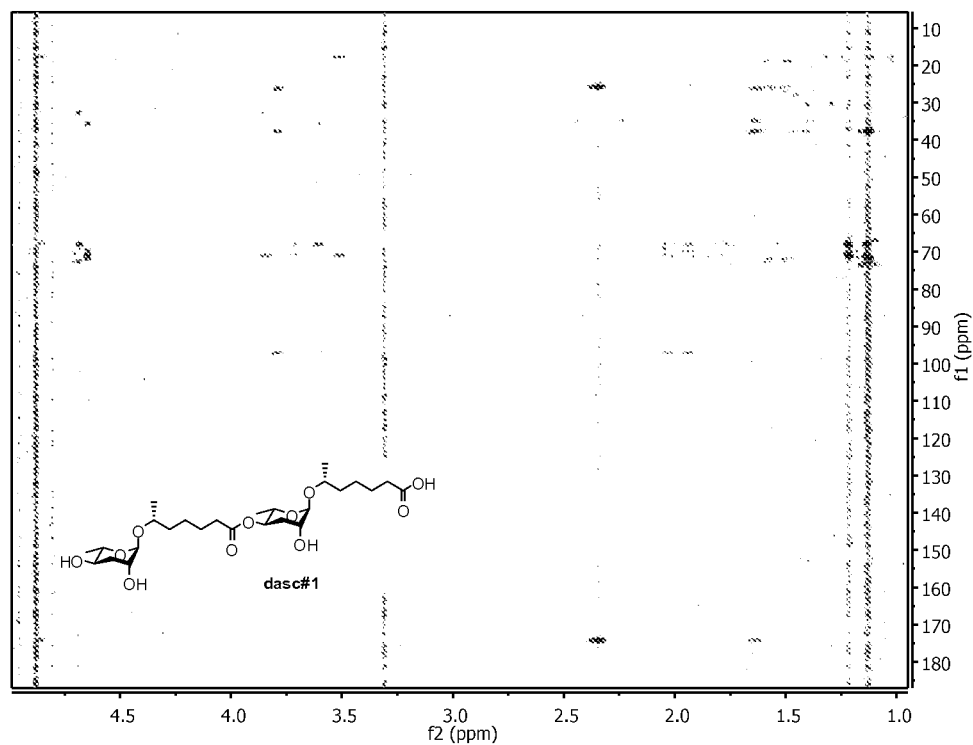

FIGS. 102A-C are the ¹H NMR (600 MHz, methanol-d₄) (FIG. 102A), HSQCAD (600 MHz for ¹H, 151 MHz) (FIG. 102B), and HMBC (600 MHz for ¹H, 151 MHz) (FIG. 102C) spectra of (2S,3R)-3-(((S)-4-(((2S,3R,5S,6R)-3,5-dihydroxy-6-methyltetrahydro-2H-pyran-2-yl)oxy)pentanoyl) oxy)-2-(3-(9-((2R,3R,4S,5R)-3,4,5-trihydroxytetrahydro-2H-pyran-2-yl)-9H-purin-6-yl)ureido)butanoic acid (36).

FIGS. 103A-D are the ¹H NMR (600 MHz, methanol-d₄) (FIG. 103A), dqfCOSY (600 MHz, methanol-d₄) (FIG. 103B), HMQC (600 MHz for ¹H, 151 MHz) (FIG. 103C), and HMBC (600 MHz for ¹H, 151 MHz) (FIG. 103D) spectra of (R)-6-(((2R,3R,5R,6S)-5-(((R)-6-(((2R,3R,5R,6S)-3,5-dihydroxy-6-methyltetrahydro-2H-pyran-2-yl)oxy) heptanoyl)oxy)-3-hydroxy-6-methyltetrahydro-2H-pyran-2-yl)oxy)heptanoic acid (dasc#1).

Figure 104A:
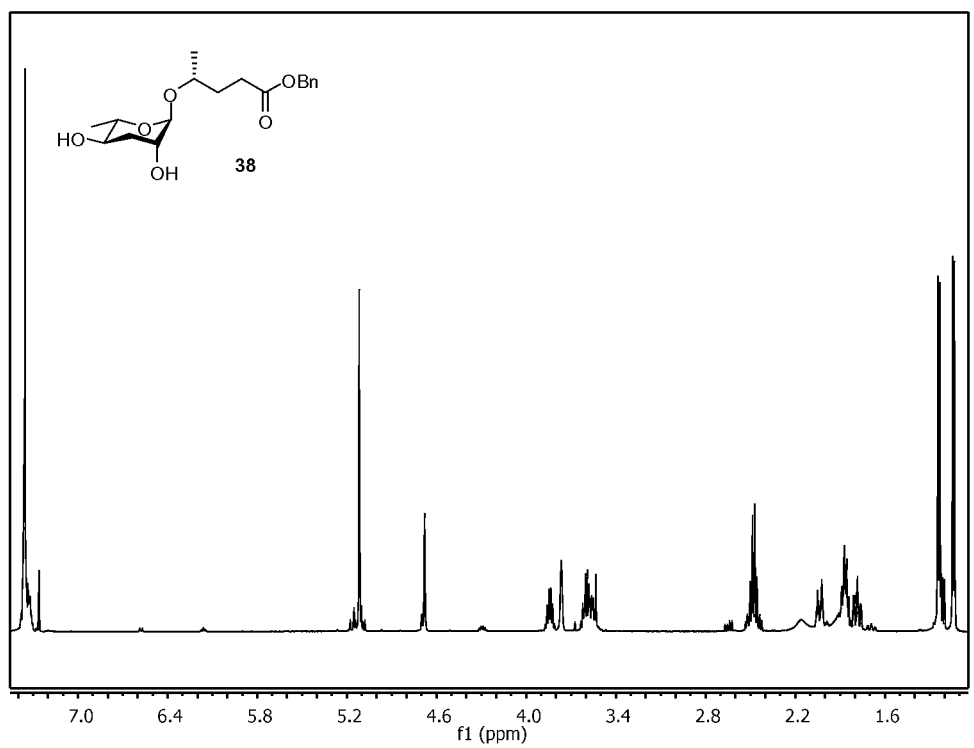
Figure 104B:
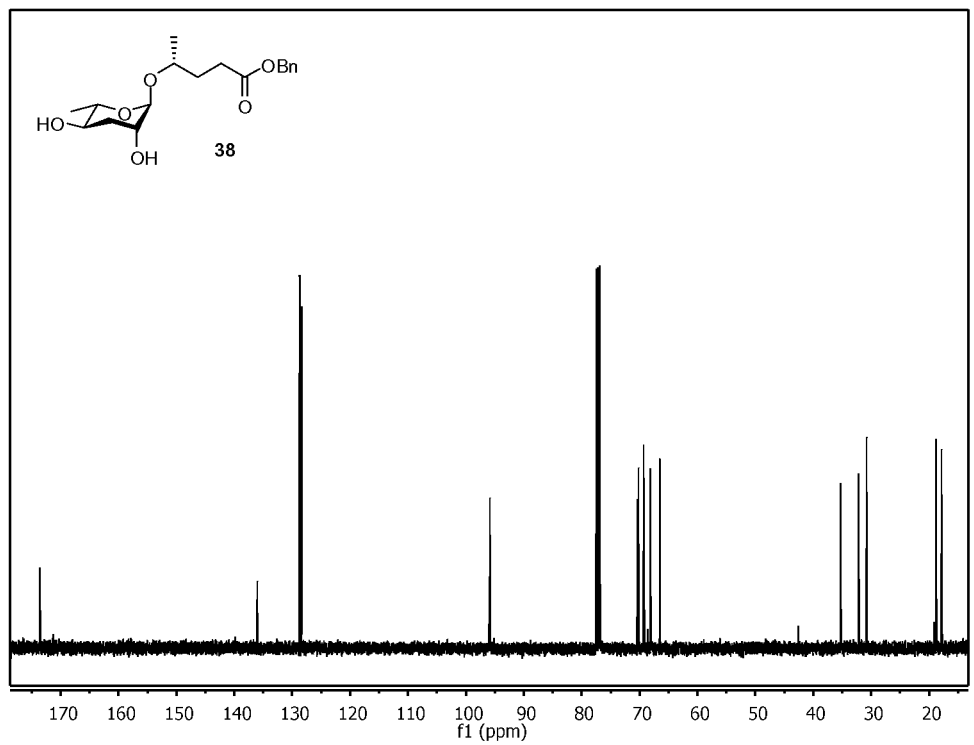

FIGS. 104A-B are the ¹H NMR (500 MHz, chloroform-d) (FIG. 104A) and ¹³C NMR (125 MHz, chloroform-d) (FIG. 104B) spectra of (R)-benzyl 4-(((2R,3R,5R,6S)-3,5-dihydroxy-6-methyltetrahydro-2H-pyran-2-yl)oxy)pentanoate (38).

Figure 105:
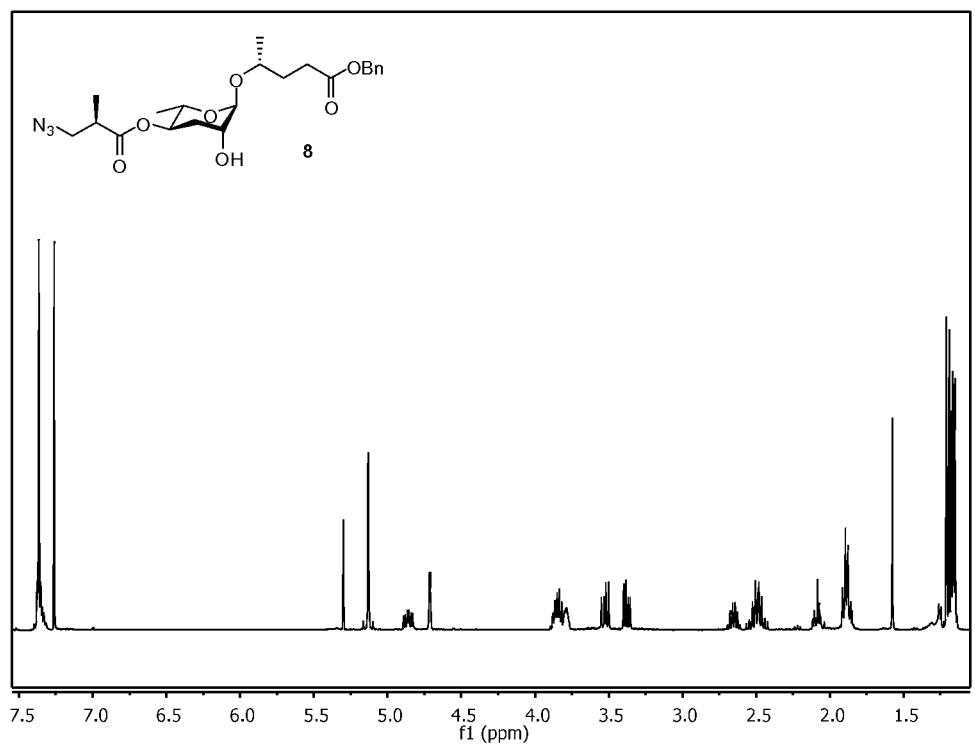

FIG. 105 is the ¹H NMR spectrum (400 MHz, chloroform-d) of (R)-benzyl 4-(((2R,3R,5R,6S)-5-(((R)-3-azido-2-methylpropanoyl)oxy)-3-hydroxy-6-methyltetrahydro-2H-pyran-2-yl)oxy)pentanoate (8).

Figure 106A:
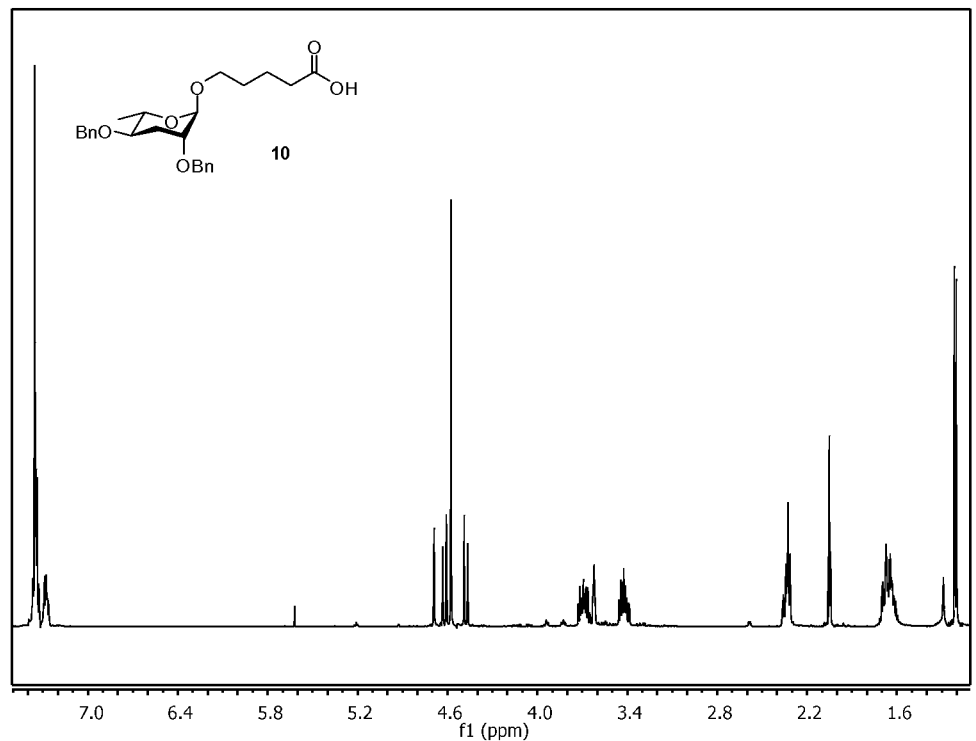
Figure 106B:
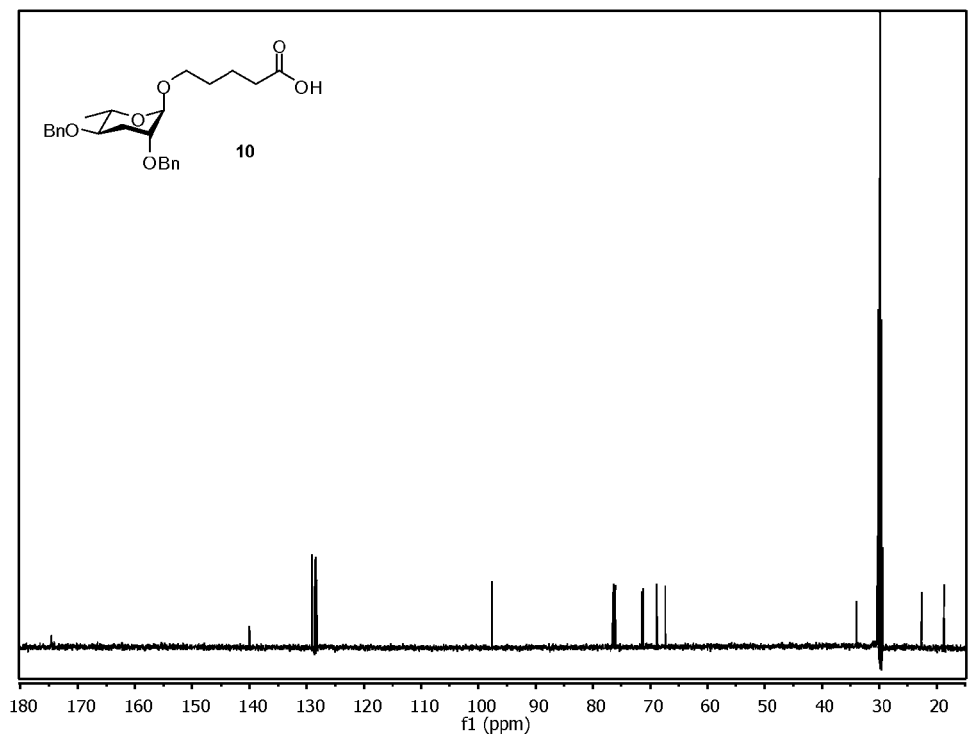

FIGS. 106A-B are the ¹H NMR (500 MHz, acetone-d₆) (FIG. 106A) and ¹³C NMR (125 MHz, acetone-d₆) (FIG. 106B) spectra of 5-(((2R,3R,5R,6S)-3,5-bis(benzyloxy)-6-methyltetrahydro-2H-pyran-2-yl)oxy)pentanoic acid (10).

Figure 107A:
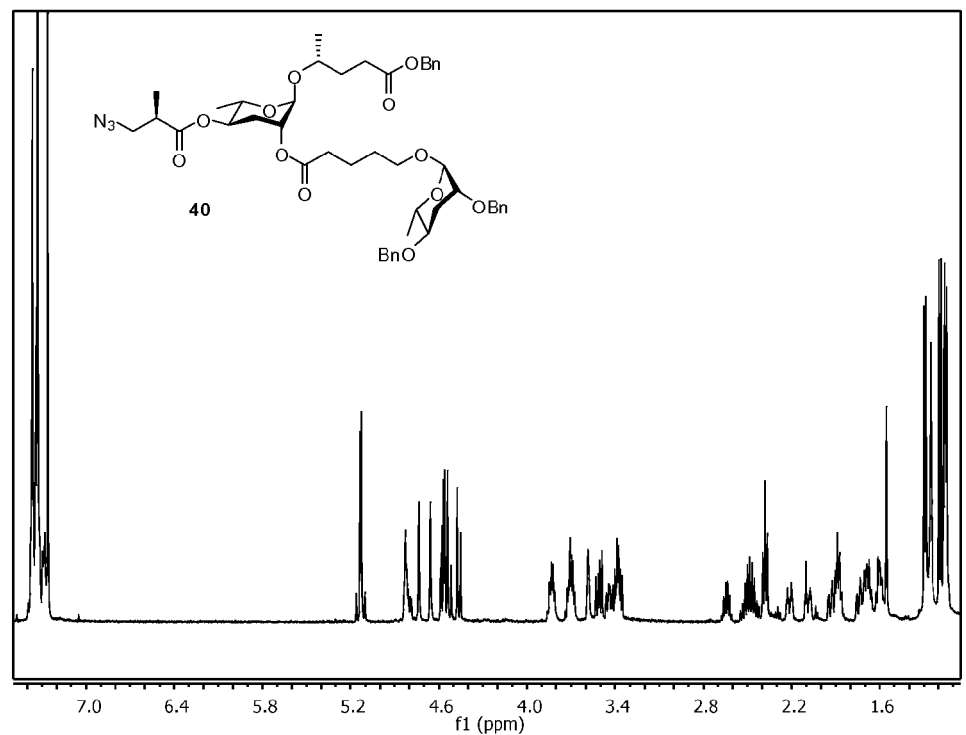
Figure 107B:
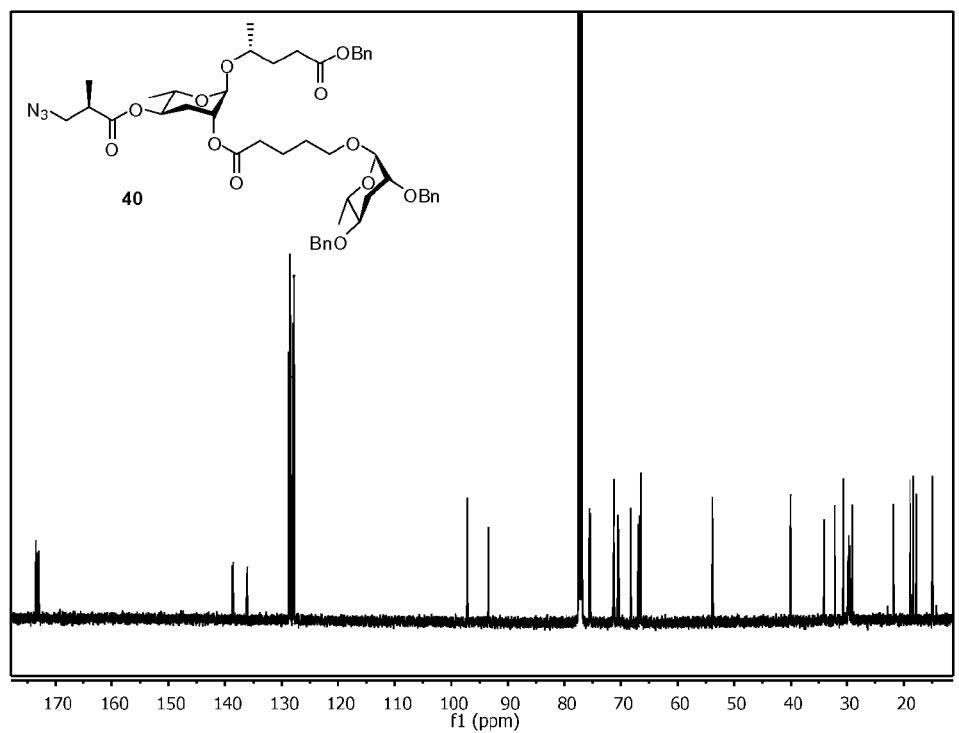
Figure 108A:
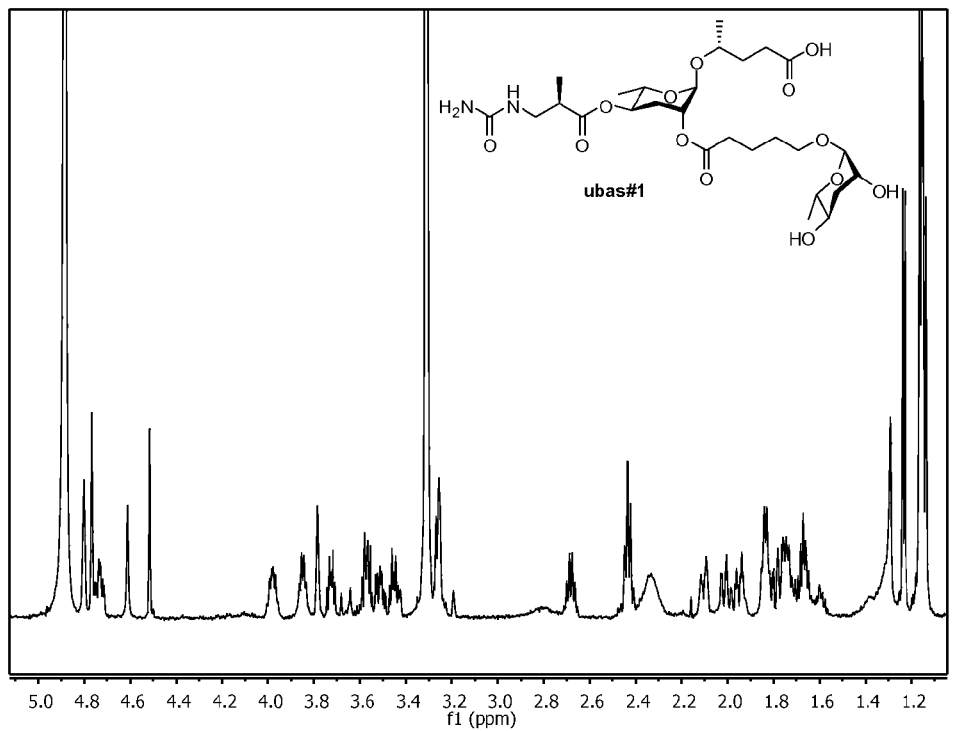
Figure 108B:
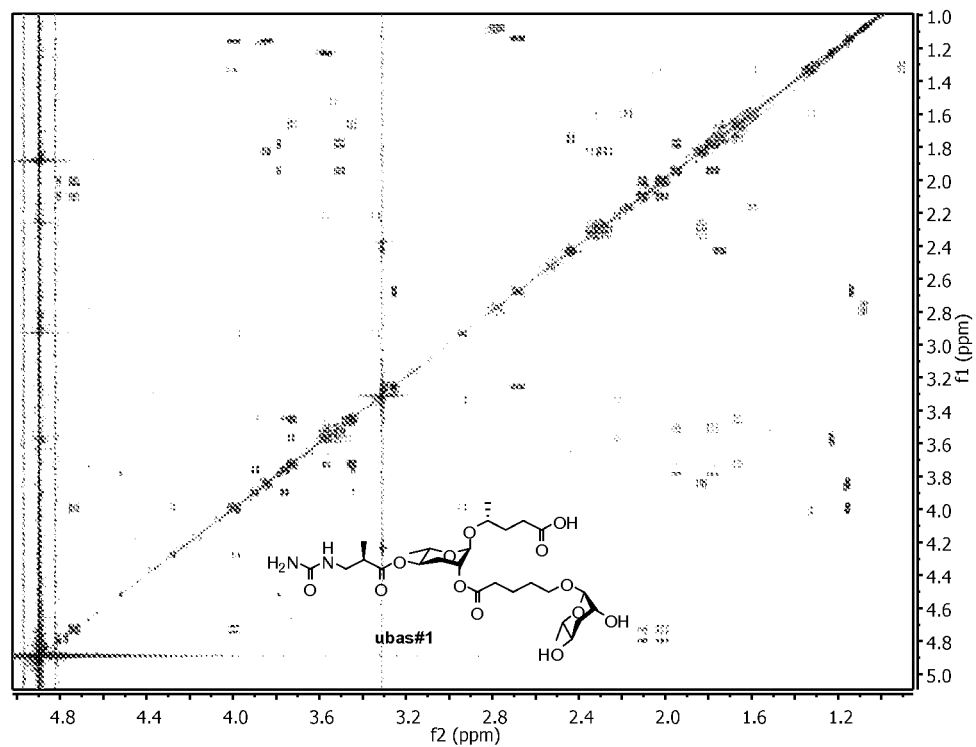
Figure 108C:
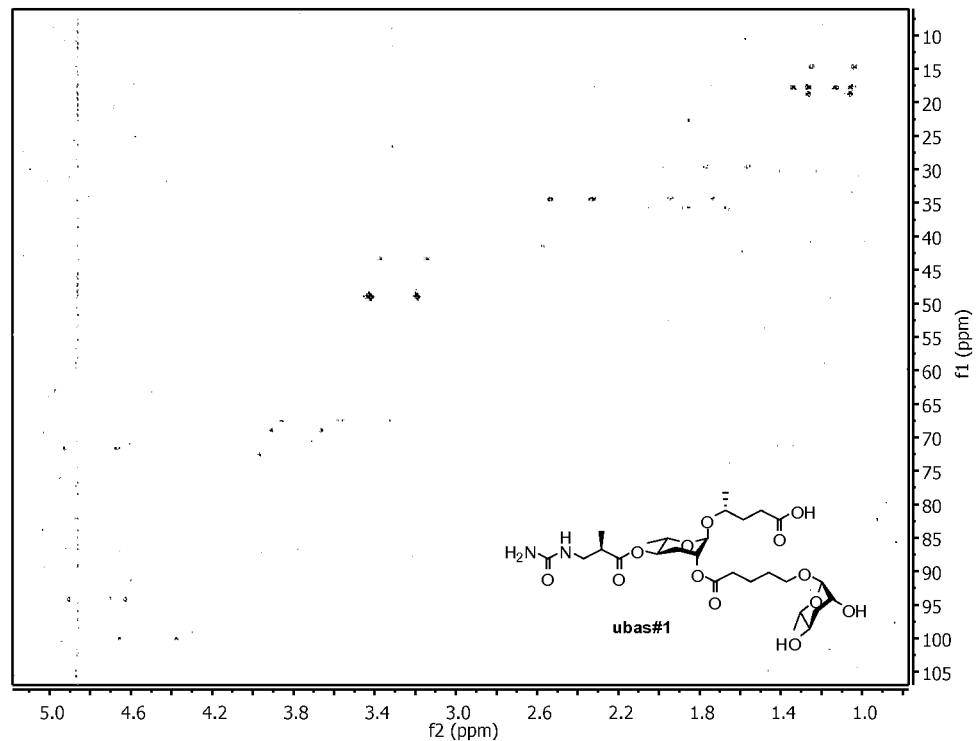
Figure 108D:
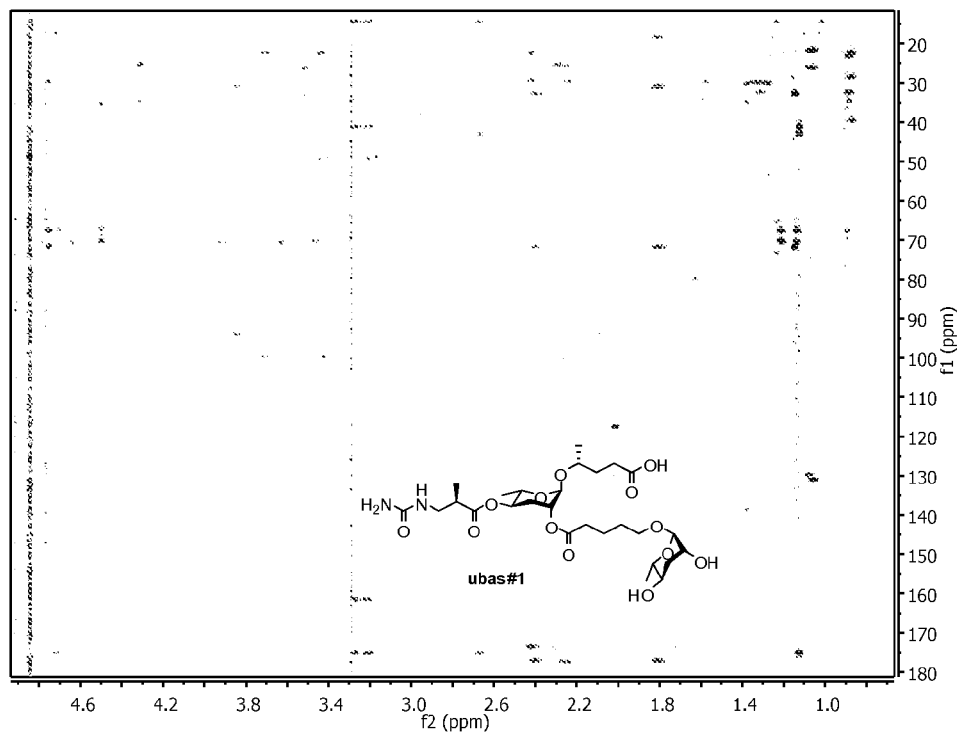

FIGS. 107A-B are the ¹H NMR (500 MHz, acetone-d₆) (FIG. 107A) and ¹³C NMR (125 MHz, acetone-d₆) (FIG. 107B) spectra of (2R,3R,5R,6S)-5-(((R)-3-azido-2-methylpropanoyl)oxy)-2-(((R)-5-(benzyloxy)-5-oxopentan-2-yl) oxy)-6-methyltetrahydro-2H-pyran-3-yl 5-(((2R,3R,5R,6S)-3,5-bis(benzyloxy)-6-methyltetrahydro-2H-pyran-2-yl)oxy) pentanoate (40).

FIGS. 108A-D are the ¹H NMR (600 MHz, methanol-d₄) (FIG. 108A), dqfCOSY (600 MHz, methanol-d₄) (FIG. 108B), HMQC (600 MHz for ¹H, 151 MHz) (FIG. 108C), and HMBC (600 MHz for ¹H, 151 MHz) (FIG. 108D) spectra of (R)-4-(((2R,3R,5R,6S)-3-((5-(((2R,3R,5R,6S)-3,5-dihydroxy-6-methyltetrahydro-2H-pyran-2-yl)oxy)pentanoyl)oxy)-6-methyl-5-(((R)-2-methyl-3-ureidopropanoyl) oxy)tetrahydro-2H-pyran-2-yl)oxy)pentanoic acid (ubas#1).

Figure 109:
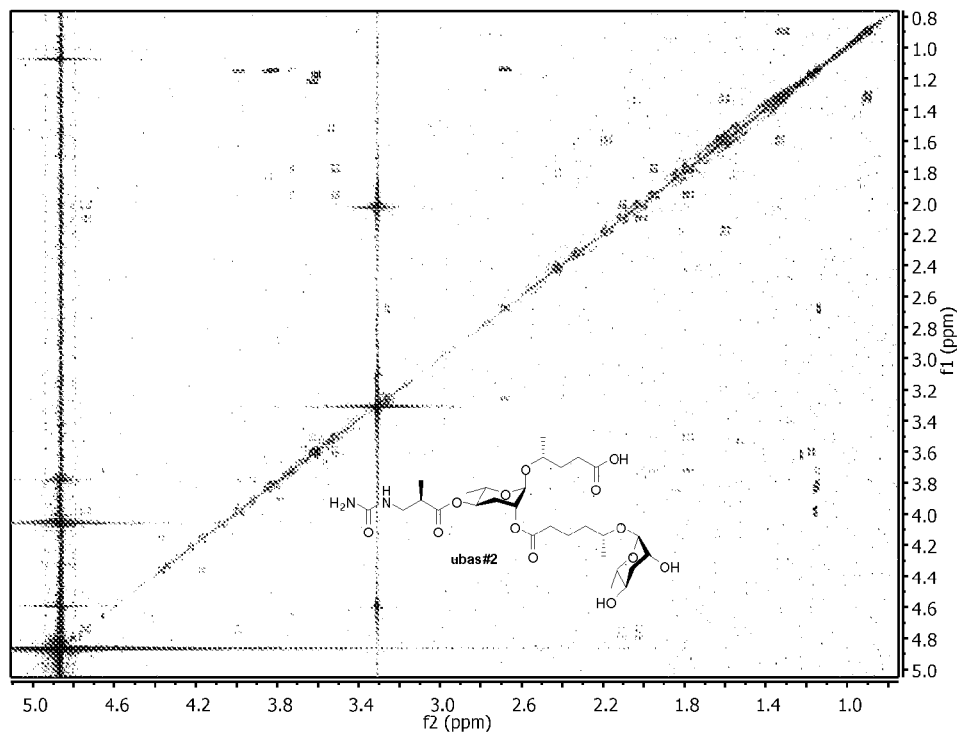

FIG. 109 is the dqfCOSY spectrum (600 MHz, methanol-d₄) of natural sample containing (R)-4-(((2R,3R,5R,6S)-3-(((R)-5-(((2R,3R,5R,6S)-3,5-dihydroxy-6-methyltetrahydro-2H-pyran-2-yl)oxy)hexanoyl)oxy)-6-methyl-5-(((R)-2-methyl-3-ureidopropanoyl)oxy)tetrahydro-2H-pyran-2-yl)oxy)pentanoic acid (ubas#2).

FIGS. 110A-C relate to the analysis of *P. pacificus* exo-metabolome and previously identified signaling molecules from *C. elegans*. FIG. 110A shows the structures of ascaroside-based small molecule signals regulating development and behavior in *C. elegans*. FIG. 110B shows that metabolites excreted by *P. pacificus* induce dauer arrest and affect mouth-form dimorphism, promoting eurystomatous mouth development. FIG. 110C is an example section of the 2D NMR (dqfCOSY) spectrum of *P. pacificus* exo-metabolome fraction, revealing a complex metabolite mixture, including known primary metabolites as well as unknown components. Detailed analysis of crosspeak fine structure and additional HMBC spectra led to detection of a series of unusual chemical structures based on combinations of ascarylose, paratose, threonine, xylose, and other building blocks.

Figure 111A:
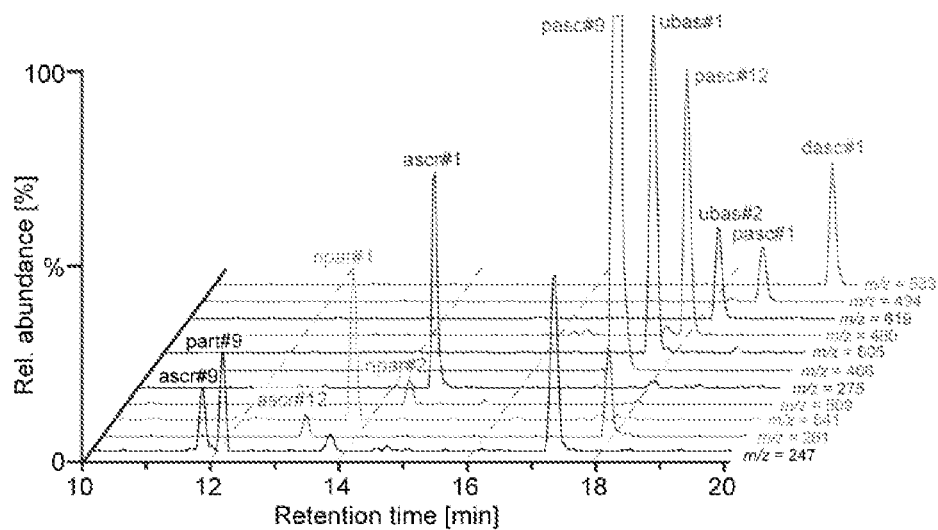
Figure 111B:
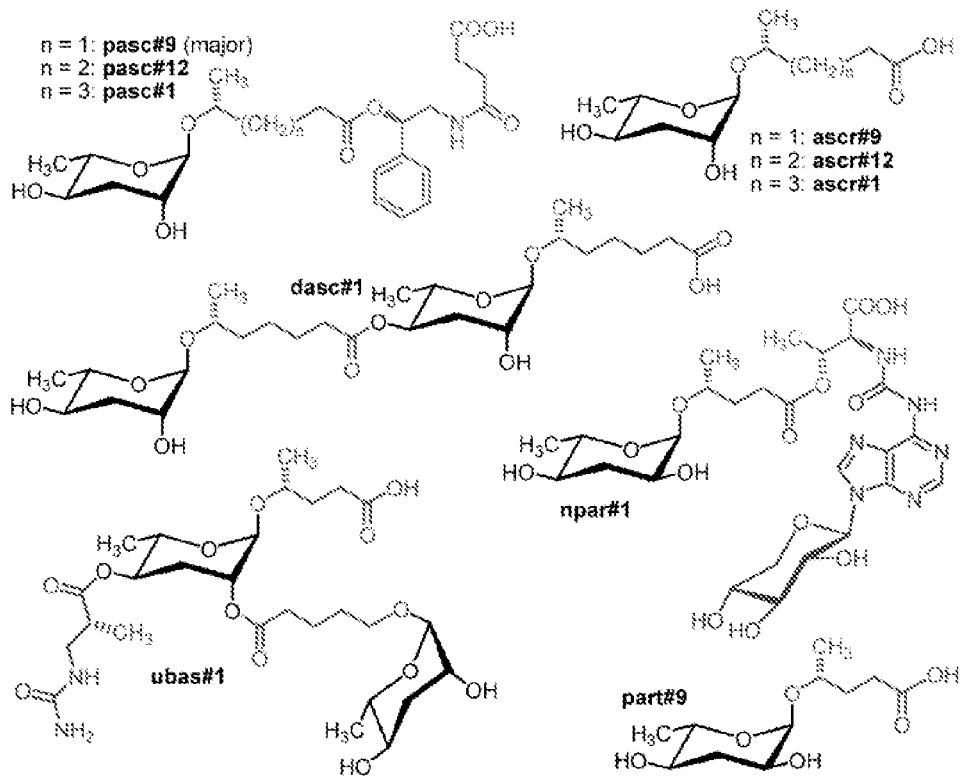
Figure 111C:
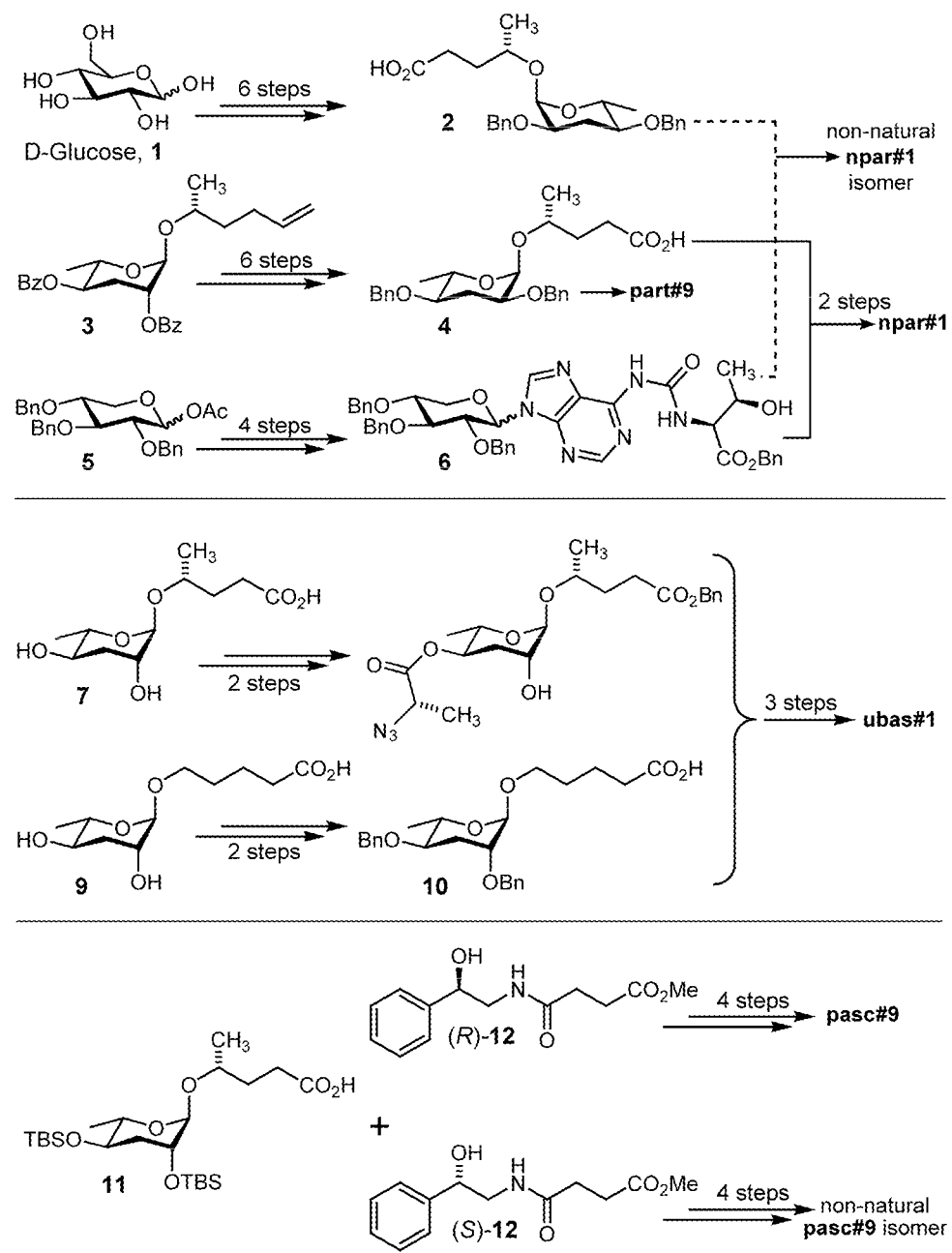

FIGS. 111A-C relate to the HPLC-MS/MS analysis, modular architectures, and chemical synthesis of *P. pacificus* metabolites. As shown in FIG. 111A, high-resolution HPLC-MS analysis reveals species whose molecular formulae provide additional constraints for structures proposed based on NMR-spectroscopic analysis of the *P. pacificus* exo-metabolome. Major components of the *P. pacificus* exo-metabolome derived from assembly of building blocks from carbohydrate (black), amino acid (green), and nucleoside (red) metabolism, as well as likely TCA cycle-derived succinate (magenta), are shown in FIG. 111B. FIG. 111C shows an abbreviated synthesis scheme for identified *P. pacificus* metabolites and several non-natural stereoisomers.

FIG. 112 shows the major *P. pacificus* small molecules pasc#9, npar#1, dasc#1, and ubas#1. The structures were elucidated using NMR spectroscopy. The bold lines indicate spin systems in dqfCOSY spectra. Curved arrows indicate key HMBC correlations used to assign the structures.

Marked protons (—H) in npar#1 are characteristic of N⁶-carbamoyl adenosine and observed in ¹H, HSQCAD, and HMBC spectra.

FIG. 113 is a table identifying the molecular formula, LC retention time, spectroscopic data, and estimated concentrations in culture supernatant of ascarosides ascr#1, ascr#9, ascr#12, pasc#1, pasc#9, pasc#12, ubas#1, ubas#2, dasc#1, part#9, npar#1, and npar#2.

Figure 114:
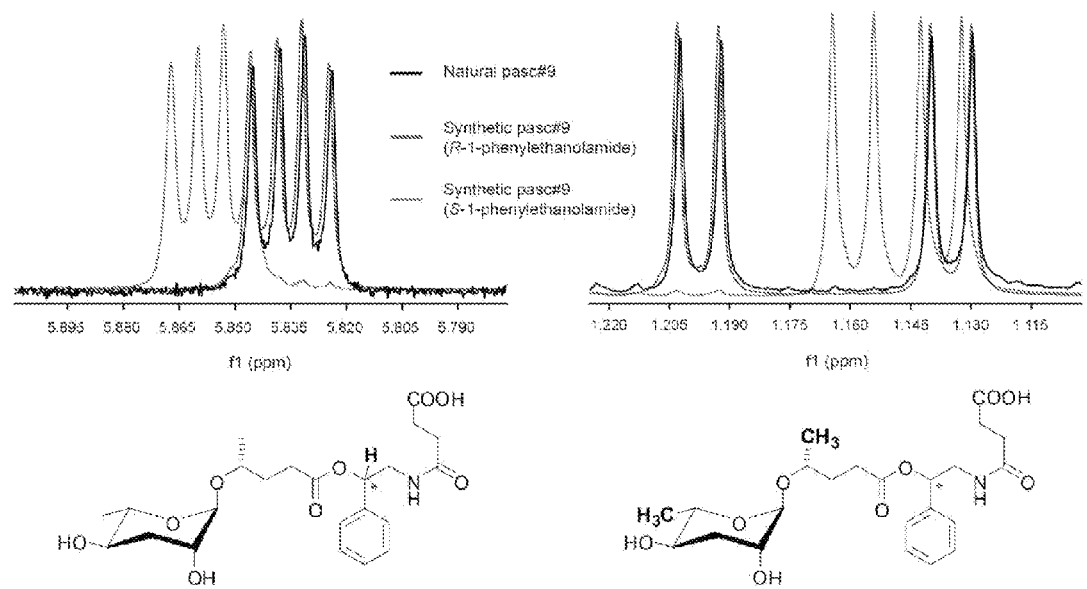

FIG. 114 shows sections of ¹H-NMR spectra of natural pasc#9 (black), synthetic pasc#9 including a (R)—N-succinyl-1-phenylethanolamide moiety (red), and synthetic pasc#9 including a (S)—N-succinyl-1-phenylethanolamide moiety (blue). The ¹H NMR for the natural sample matches that of the (R)—N-succinyl-1-phenylethanolamide diastereomer, indicating that natural pasc#9 contains (R)—N-succinyl-1-phenylethanolamide.

Figure 115A:
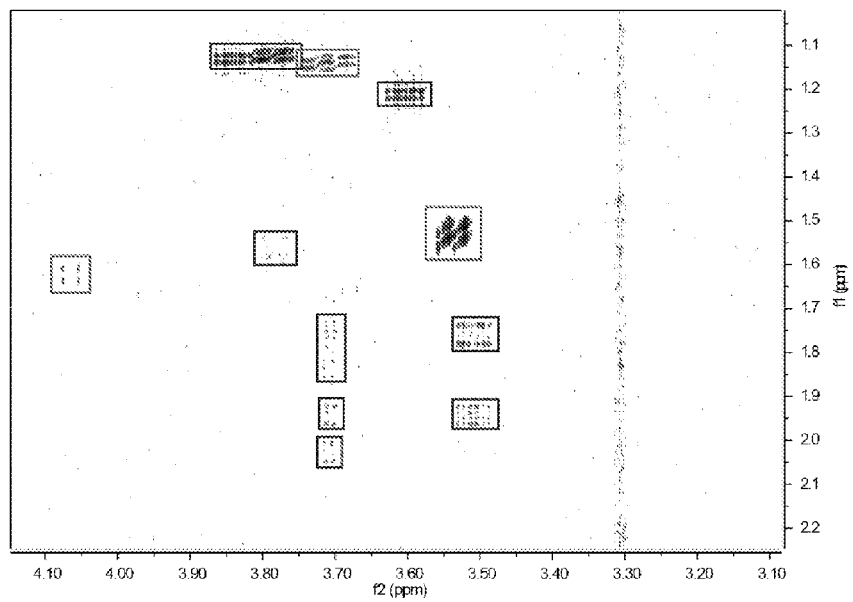
Figure 115B:
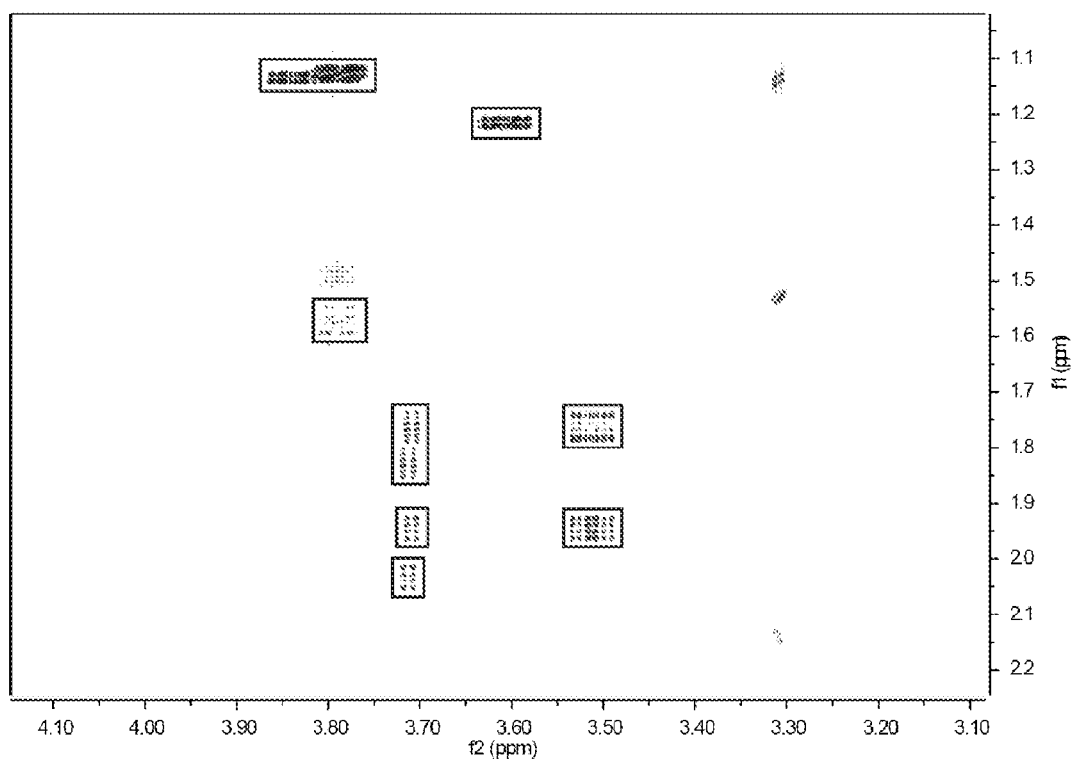

FIGS. 115A-B are sections of dqfCOSY spectra (600 MHz, methanol-d₄) of an HPLC-enriched *P. pacificus* exo-metabolome extract fraction containing dasc#1 (FIG. 115A) and a synthetic sample of dasc#1 (FIG. 115B). Characteristic crosspeaks for dasc#1 are boxed blue whereas unrelated crosspeaks from other metabolites present in the natural sample are boxed red. The precise match of crosspeaks between the natural and synthetic sample proves dasc#1 structural and stereochemical assignments and confirms the presence of dasc#1 in *P. pacificus* exo-metabolome.

Figure 116A:
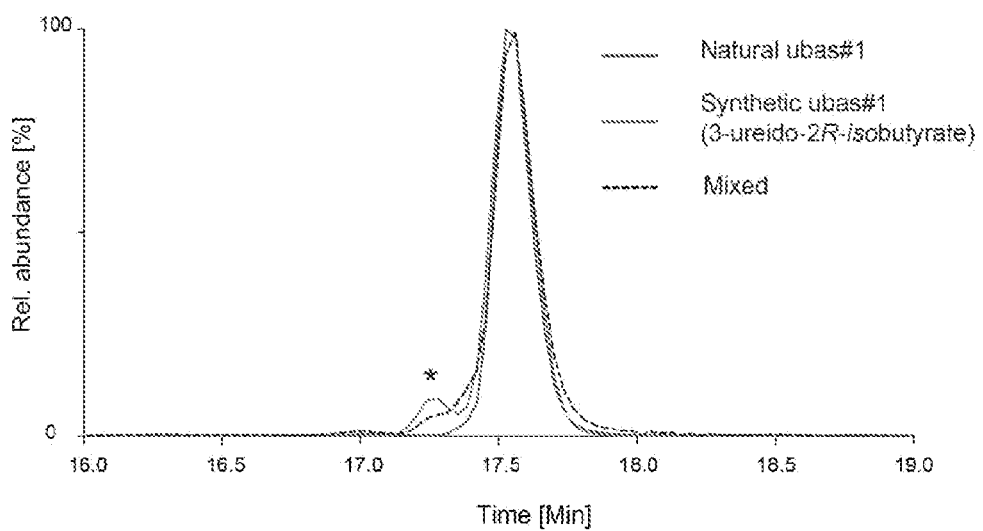
Figure 116B:
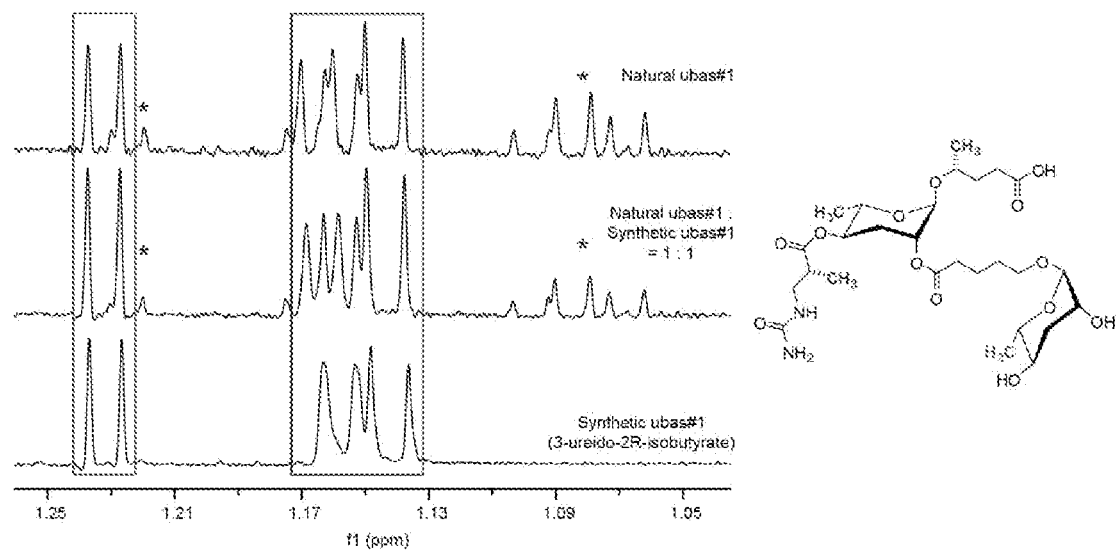

FIGS. 116A-B are HPLC-MS traces (FIG. 116A) and ¹H-NMR spectra (FIG. 116B) that relate to the determination of the stereochemistry of ubas#1. A comparison of the HPLC-MS retention times (ESI, ion chromatogram for m/z=605) of natural ubas#1 (red), a synthetic mixture of ubas#1 diastereomers containing the 3-ureido-2R-isobutyrate and 3-ureido-2S-isobutyrate in a ~95:5 ratio (blue), and a mixture of the natural and synthetic samples (dotted black) is shown in FIG. 116A. The HPLC-retention time of synthetic (3-ureido-2R-isobutyrate)-derived ubas#1 matches that of natural ubas#1 and is distinctly different from the (3-ureido-2S-isobutyrate)-derived ubas#1 diastereomer (marked *) indicating that natural ubas#1 includes a 3-ureido-2R-isobutyrate moiety. As shown in FIG. 116B, comparison of sections of ¹H-NMR spectra of synthetic (3-ureido-2R-isobutyrate)-derived ubas#1 (bottom), a natural sample containing ubas#1 (top), and a 1:1 mixture of these two samples (middle) shows that the relative intensity of the four characteristic methyl doublets (indicated by the red and blue boxes in the accompanying structure) increases upon adding synthetic ubas#1 to the natural sample (unrelated peaks in the natural sample are marked *). This confirms that natural ubas#1 contains 3-ureido-2R-isobutyrate, and not 3-ureido-2S-isobutyrate. Differences in pH and concentrations between the natural and synthetic samples slightly affect chemical shifts of the methyl doublets, resulting in small changes of chemical shift values upon mixing of natural and synthetic samples.

Figure 117A:
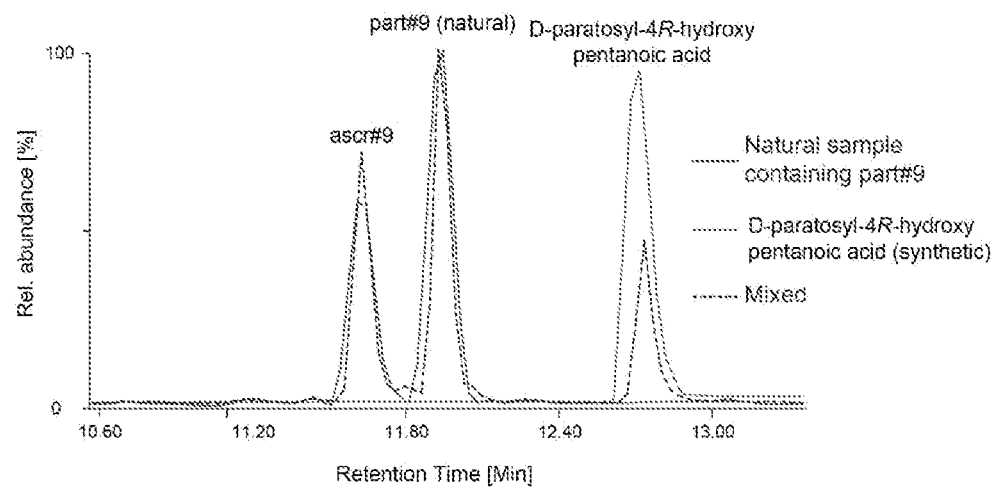
Figure 117B:
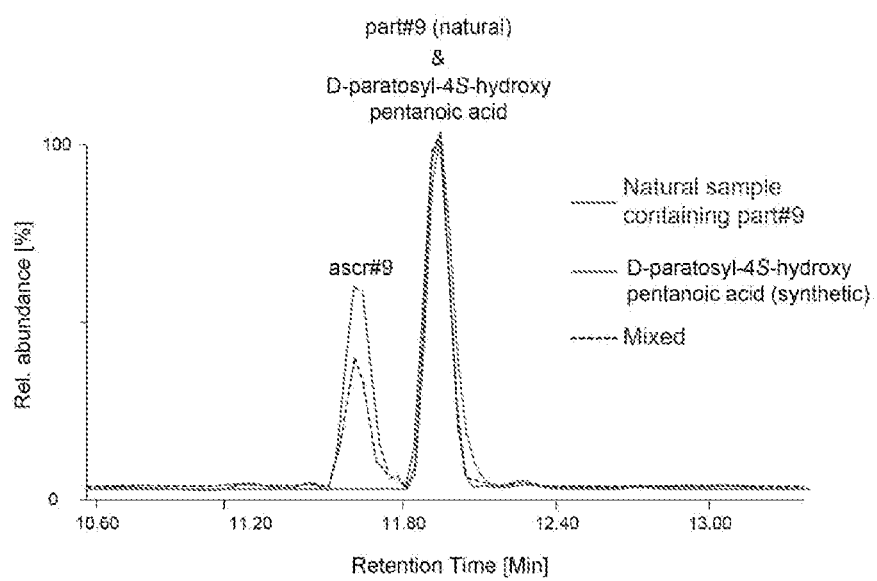

FIGS. 117A-B are HPLC-MS traces that relate to the determination of the stereochemistry of part#9. Both show a comparison of HPLC-MS retention times (ESI, ion chromatogram for m/z=247) of a natural mixture of ascr#9 and part#9 (red), synthetic samples of part#9 (blue), and a 1:1 mixture of the natural and synthetic samples (dotted black). Synthetic D-paratosyl-4R-hydroxypentanoic acid was used in FIG. 117A. Its HPLC-retention times do not match natural part#9, indicating that neither D-paratosyl-4R-hydroxypentanoic acid nor its enantiomer could be natural part#9. Synthetic D-paratosyl-4S-hydroxypentanoic acid was used in FIG. 117B. HPLC-retention times of D-paratosyl-4S-hydroxypentanoic acid match that of natural part#9. This indicates that natural part#9 is either D-paratosyl-4S-hydroxypentanoic acid or its enantiomer L-paratosyl-4R-hydroxypentanoic acid. Comparison of NMR spectra and HPLC-retention times of natural npar#1 with the two synthetic npar#1 diastereomers derived from either D-paratosyl-4S-hydroxypentanoic acid or L-paratosyl-4R-hydroxypentanoic acid (see FIGS. 118A-C) reveal that natural part#9 and npar#1 are based on L-paratosyl-4R-hydroxypentanoic acid.

Figure 118A:
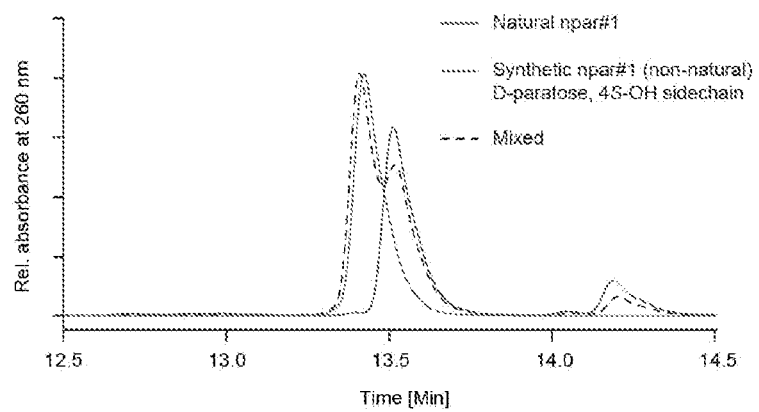
Figure 118B:
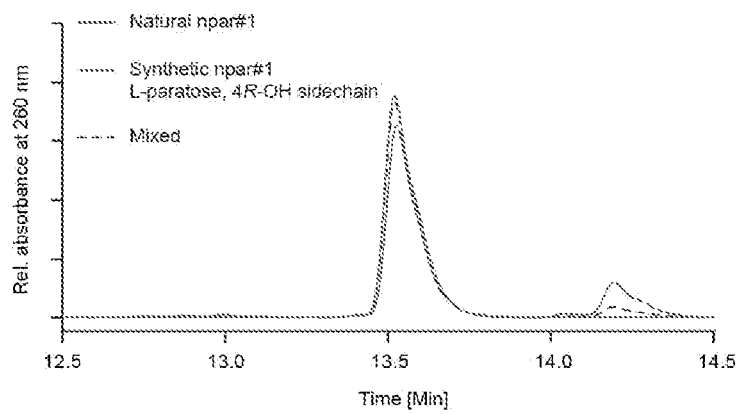
Figure 118C:
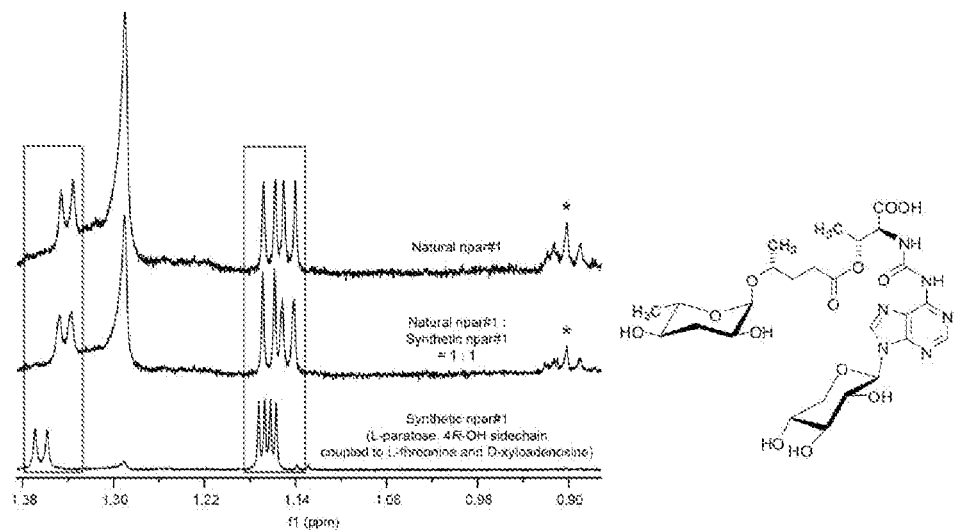

FIGS. 118A-C are HPLC-UV traces (FIGS. 118A-B) and ¹H-NMR spectra (FIG. 118C) that relate to the determination of the stereochemistry of npar#1. FIGS. 118A-B show a comparison of HPLC-UV retention times (260 nm) of a natural sample containing npar#1 (red), synthetic samples of npar#1 (blue), and mixtures of the natural and synthetic samples (dotted black). A synthetic npar#1 diastereomer derived from D-paratosyl-4S-hydroxypentanoic acid coupled to L-threonine and D-xyloadenosine was used in FIG. 118A. HPLC-retention times do not match that of natural npar#1. A synthetic npar#1 diastereomer derived from L-paratosyl-4R-hydroxypentanoic acid coupled to L-threonine and D-xyloadenosine was used in FIG. 118B. HPLC-retention times match that of natural npar#1. As shown in FIG. 118C, comparison of sections of ¹H-NMR spectra of synthetic npar#1 derived from L-paratosyl-4R-hydroxypentanoic acid coupled to L-threonine and D-xyloadenosine (bottom), natural npar#1 (top), and a 1:1 mixture of the two (middle) shows that changes in pH and concentrations affect the shifts of the three characteristic methyl doublets (indicated by the red and blue boxes in the accompanying structure). In the mixed sample however, no new peaks show up and the relative intensity of the methyl doublets increases in comparison to unrelated peaks in the natural sample (marked with *). In combination with the HPLC-UV results shown in FIGS. 118A-B, these findings show that natural npar#1 consists of L-paratosyl-4R-hydroxypentanoic acid coupled to L-threonine and D-xyloadenosine.

Figure 119:
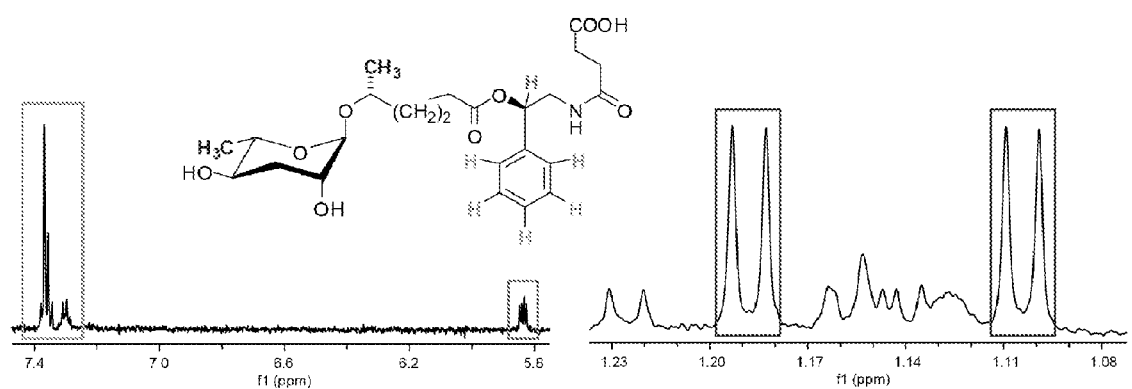

FIG. 119 is a pair of spectra showing characteristic ¹H NMR signals for pasc#12 in HPLC-enriched *P. pacificus* exo-metabolome extract fraction.

Figure 120A:
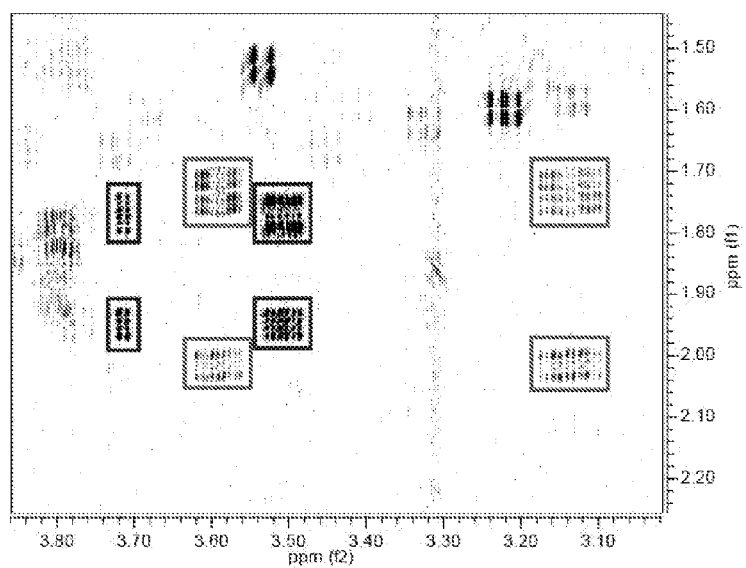
Figure 120B:
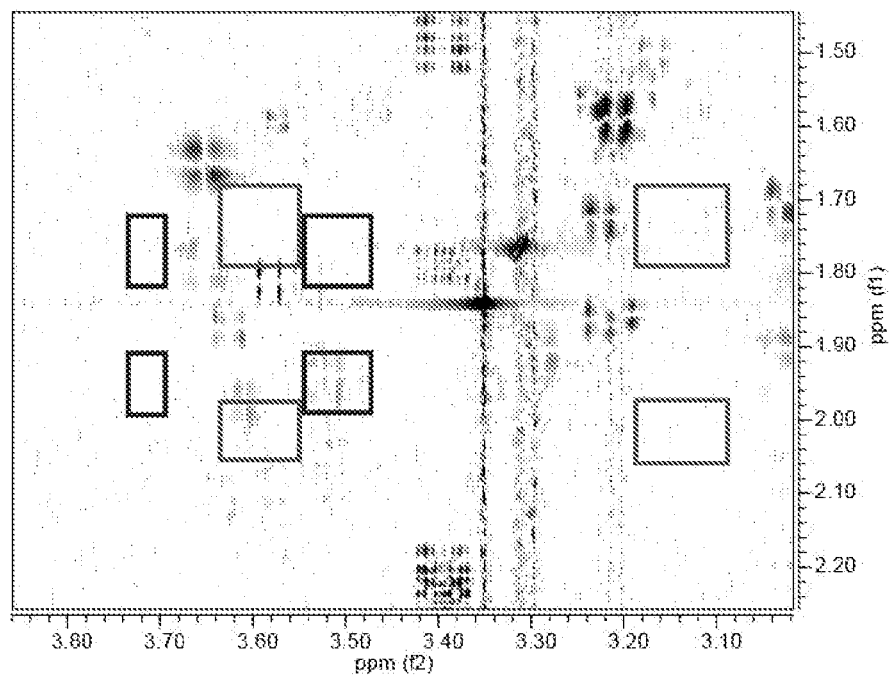

FIGS. 120A-B are sections of dqfCOSY spectra (600 MHz, methanol-d₄) of *P. pacificus* exo-metabolome extract (FIG. 120A) and *E. coli* OP50 metabolome extract (FIG. 120B). Characteristic crosspeaks for ascarosides are boxed blue and that of paratosides are boxed red. Comparison of the two spectra indicates that the complex small molecules identified from *P. pacificus* exo-metabolome are not of bacterial origin. Correspondingly, HPLC-MS analyses of bacterial extracts did not show any of the peaks detected in *P. pacificus* exo-metabolome samples.

Figure 121:
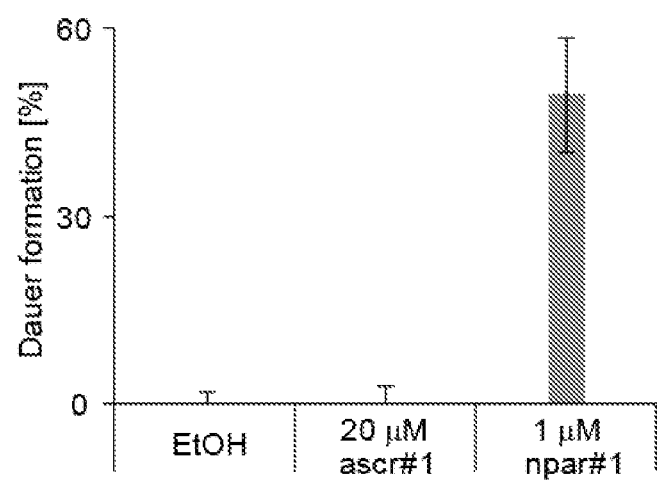

FIG. 121 is a graph of dauer formation in *P. pacificus* administered with ethanol, ascr#1, or npar#1, and demonstrates that ascr#1 does not induce dauer formation in *P. pacificus*, even at very high concentrations (20 μM). npar#1 (1 μM) was used as a positive control for *P. pacificus* dauer formation.

FIGS. 122A-E relate to functional assays with identified metabolites and the relation of small molecule signaling in *P. pacificus* to evolutionarily conserved pathways. FIGS. 122A-D are graphs showing the regulation of adult phenotypic plasticity (mouth form). FIGS. 122A and 122C and dauer induction (FIGS. 122B and 122D) by synthetic samples of major components of active *P. pacificus* exo-metabolome fractions. All experiments were performed in triplicate for each treatment. Compounds were first assayed at 1 μM concentration (*P<0.01 and **P<0.001) (FIGS.

122A-B). Compounds with significant activity at 1 μM concentration (P<0.01) were subsequently tested at a range of concentrations (FIGS. 122C-D). As illustrated in FIG. 122E, small molecule signaling in nematodes occupies a central position connecting primary metabolism to evolutionarily conserved transcription factors, including DAF-16/FOXO and the nuclear hormone receptor (NHR) DAF-12, a vitamin D and liver X receptor homolog. Whereas npar#1 induces dauer arrest, which requires both signaling via DAF-12 and DAF-16, dasc#1 regulates adult morphology, which also requires DAF-12 but is DAF-16 independent.

Figure 123A:
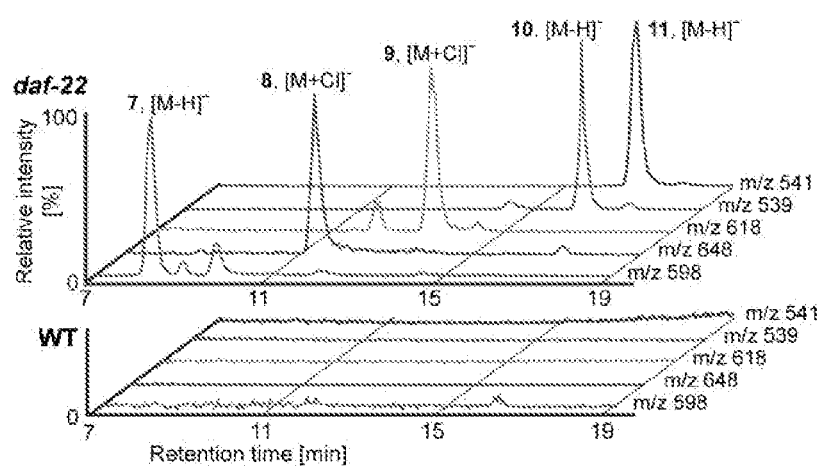
Figure 123B:
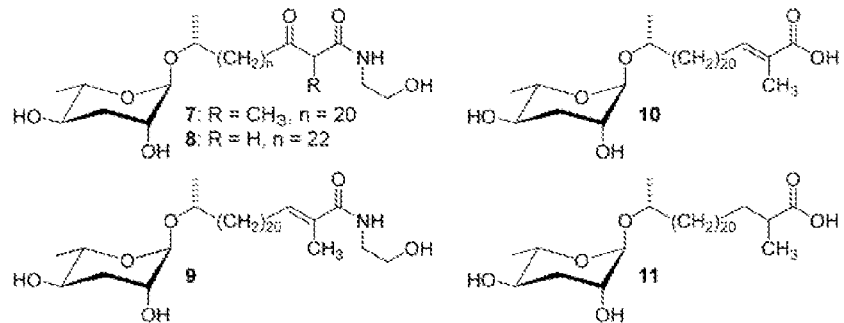
Figure 123C:
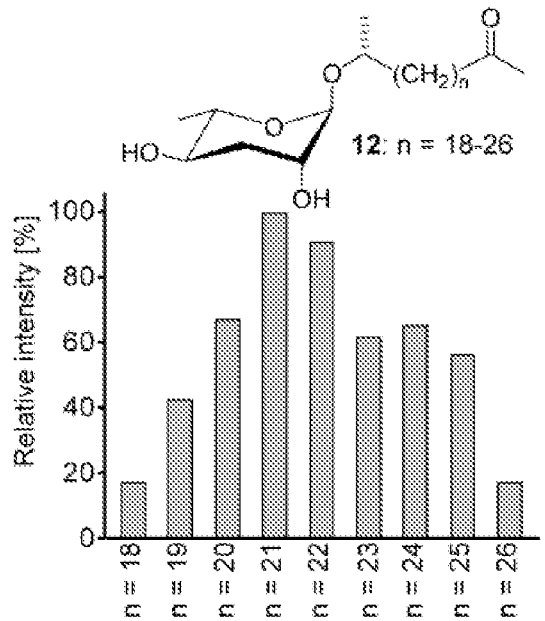
Figure 123D:
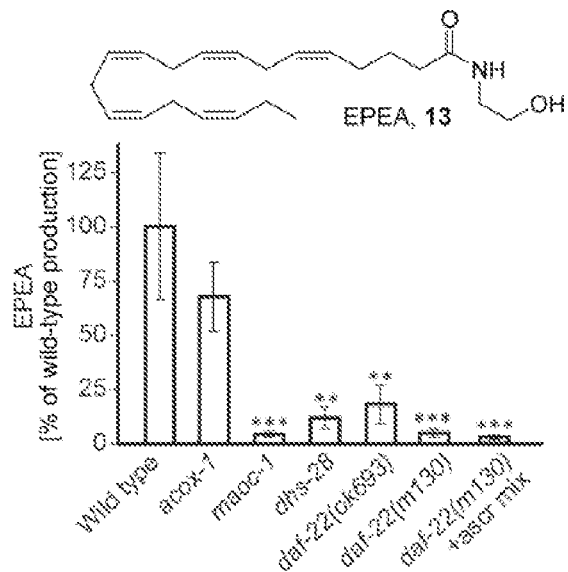
Figure 123E:
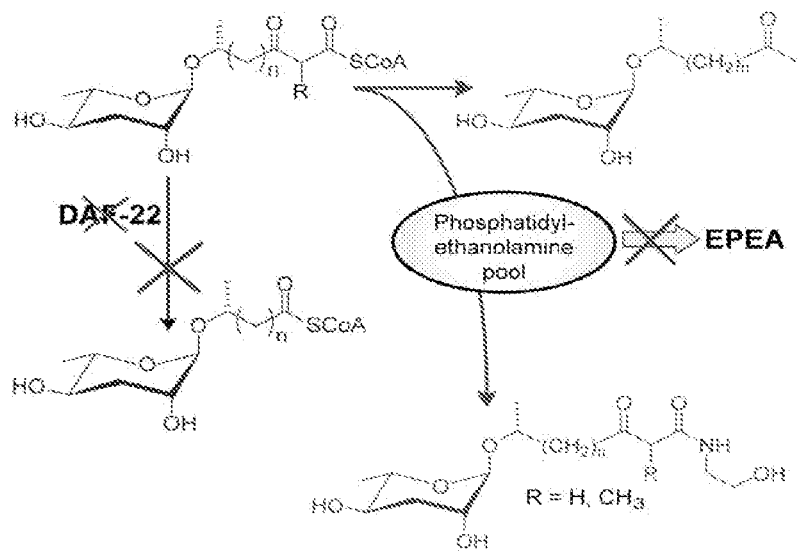

FIGS. 123A-E relate to the identification of daf-22 mutant-specific VLCAs 7-11, which were identified via mvaDANS and subsequent HPLC-MS analysis. FIG. 123A shows the HPLC-MS spectra for daf-22 mutant and wild-type metabolome. HPLC-MS analysis confirms long-chain ascarosides and ethanolamides in the daf-22 metabolome that are absent in wild-type. The structure of the metabolites is shown in FIG. 123B. FIG. 123C is a graph showing the quantitative distribution of daf-22-upregulated ascarosylmethylketones. FIG. 123D is a graph of EPEA production in the metabolomes of wild type and various mutants. Mutation of maoc-1, dhs-28, and daf-22 greatly reduces EPEA production and addition of ascarosides (2.5 μMascr#3 and ascr#9) to daf-22(m130) cultures does not rescue EPEA production. *P<0.05, P<0.01, *P<0.001. FIG. 123E is a schematic diagram illustrating the interactions of peroxisomal β-oxidation and endocannabinoid biosynthesis. Mutation of daf-22 abolishes processing of long-chain ascaroside CoA esters, whose conversion into ethanolamides is associated with reduced EPEA production (13), likely due to depletion of phosphatidylethanolamine pools.

Figure 124:
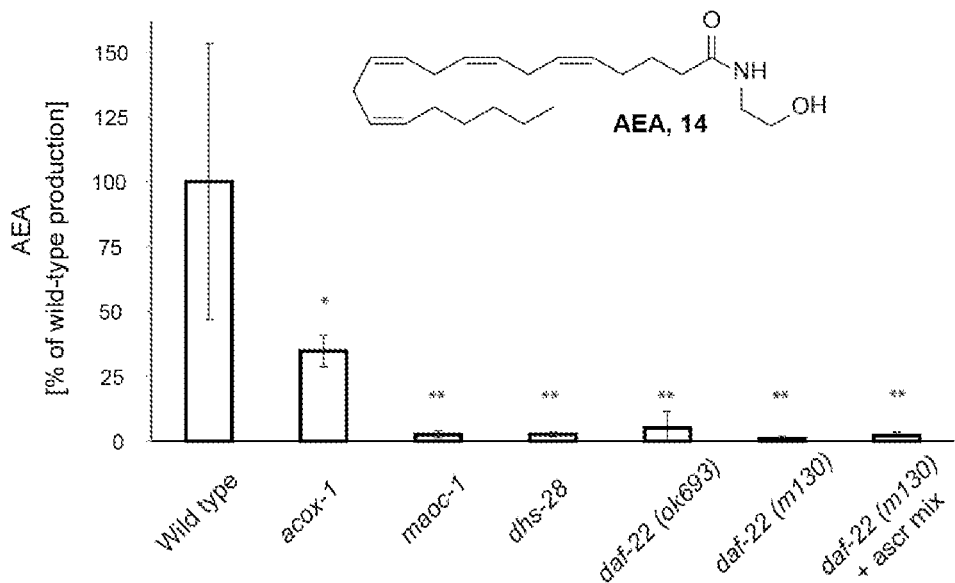

FIG. 124 is a graph of AEA production in wild type and various mutants. Mutation of maoc-1, dhs-28, and daf-22 greatly reduces AEA production, while mutation of acox-1 slightly decreases AEA production. *P<0.05, P<0.01, *P<0.001.

FIGS. 125A-B relate to the identification of up- and down-regulated metabolites in daf-22 mutants. A schematic overview of mvaDANS is shown in FIG. 125A. In the Principal Component Analysis (PCA), PC 1 separates the four wild-type data sets (blue dots) from both daf-22 mutant data sets (red and brown dots), whereas PC2 separates the two daf-22 alleles. In the back projection (lower left), the coloring of crosspeaks corresponds to the PC 1 loading coefficients; blue peaks represent signals downregulated and red peaks represent signals upregulated in the two daf-22 mutant strains. See FIG. 130 for actual spectra. FIG. 125B shows partial structures inferred from manual analysis of daf-22-specific crosspeaks suggesting α-methyl branched fatty acids, methyl ketones, and β-keto fatty acid derivatives.

Figure 126:
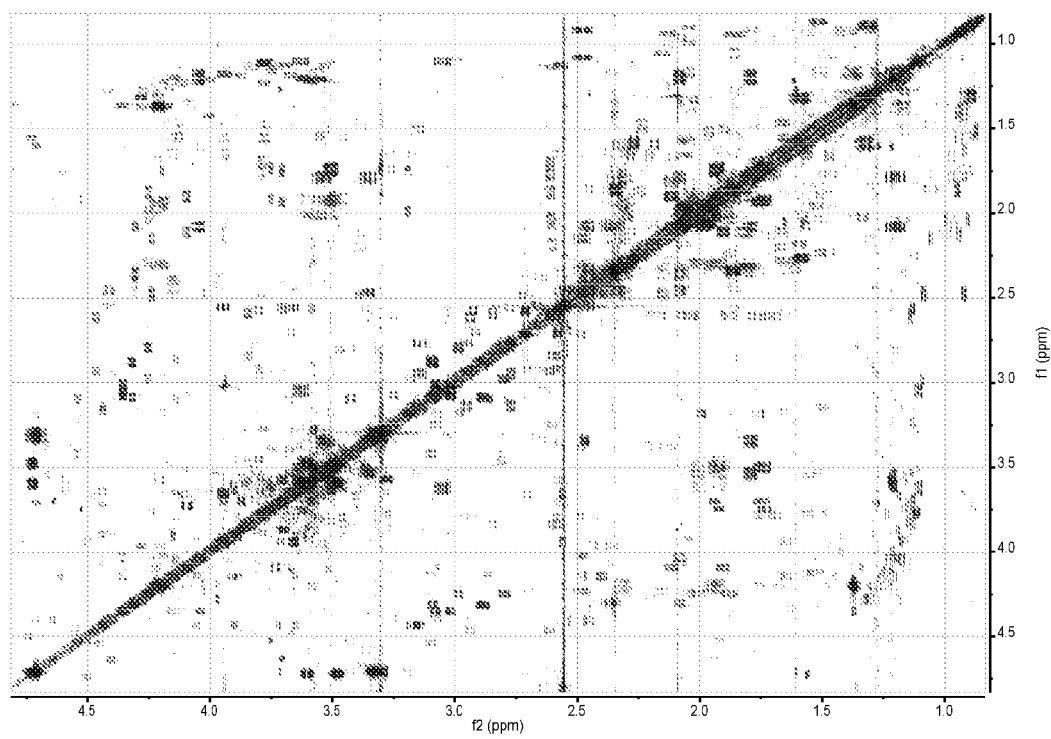

FIG. 126 is a section (0.85-4.80 ppm) of the dqfCOSY spectrum of one of four C. elegans wild-type exo-metabolome extracts.

Figure 127:
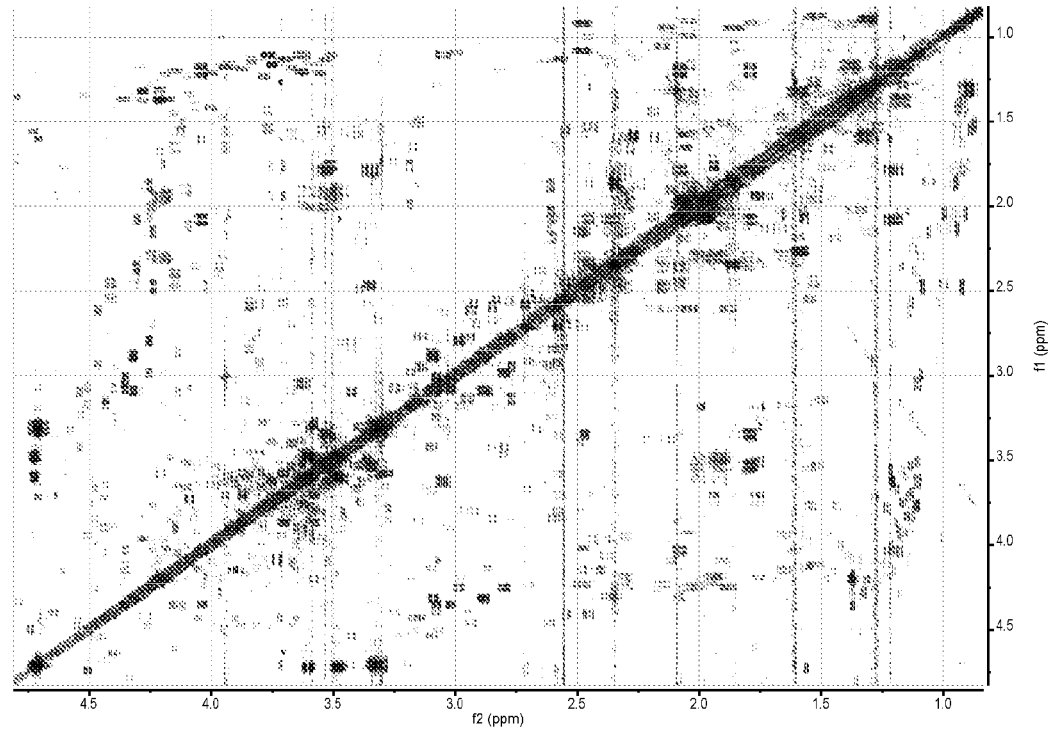

FIG. 127 is a section (0.85-4.80 ppm) of the dqfCOSY spectrum of one of four daf-22(m130) exo-metabolome extracts.

FIGS. 128A-D are a series of spectra showing how mvaDANS automatically identifies spectral crosspeaks and creates statistically derived pseudo-spectra. FIG. 128A is a 1-3 ppm region of the phase-sensitive dqfCOSY spectrum of C. elegans wild-type metabolome. FIG. 128B is the same NMR spectrum as that shown in FIG. 128A, but processed in magnitude mode prior to automatic binning. FIG. 128C is a contour plot of the NMR spectra from FIGS. 128A-B plotted with boundaries of bin regions identified by mvaDANS. FIG. 128D is the back-projected pseudo-spectrum derived from Principal Component 1 of the C. elegans wild-type/daf-22 comparison NMR dataset. Crosspeak colors indicate the normalized PC 1 loading coefficient of the region bin.

Figure 129:
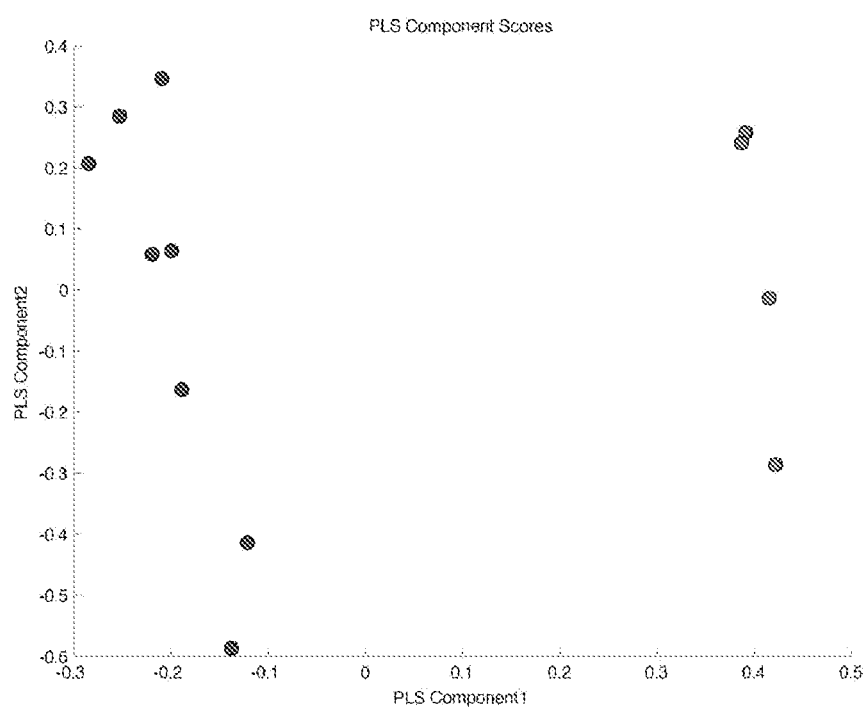

FIG. 129 is a graph of PLS component scores. PLS component scores separate 4 wildtype cultures (red dots) from 8 daf-22 cultures (blue dots).

FIGS. 130A-G show how PCA identifies crosspeaks distinguishing wild-type and two daf-22 mutant alleles. As shown in FIG. 130A back-projection of PC 1 loadings onto magnitude mode dqfCOSY spectrum identify crosspeaks increased (red) or decreased (blue) in wild-type spectra relative to mutant spectra. FIGS. 130B-C provide an example for mvaDANS work flow and method validation via identification of a known compound. Analysis of crosspeaks in the phase sensitive dqfCOSY-spectrum shown in FIG. 130C corresponding to the wild-type specific red crosspeaks in FIG. 130B reveals the known ascaroside ascr#5, whose biosynthesis has previously been shown to be daf-22 dependent. Similarly, most of the other wild-type specific (red) signals in FIG. 130A can be assigned to one of the known ascaroside pheromones. See FIG. 129 as well. FIGS. 130D-F show partial structures inferred from analysis of daf-22-specific crosspeaks that suggest α-methyl branched fatty acids, methyl ketones, and 3-keto fatty acid derivatives. FIG. 130G provides an example for a metabolite (a putative methionine derivative) not strictly for specific daf-22. This compound is upregulated in daf-22 mutants but also present in wild-type.

Figure 131:
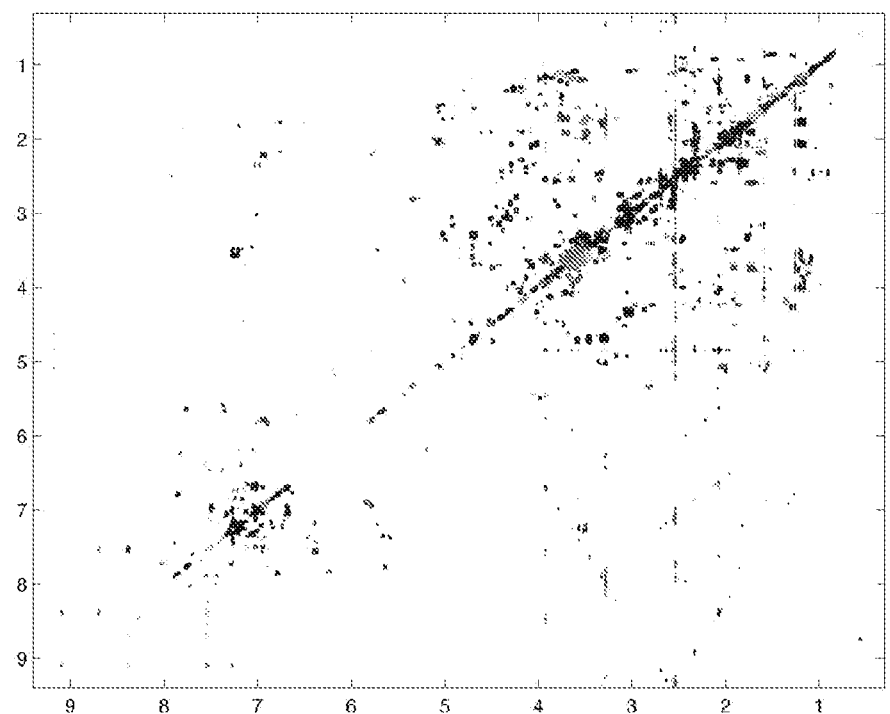

FIG. 131 is an NMR spectrum. Back projection of PLS-DA predictors from 1 component model with 4× cross validation, largely matching the result from PCA (FIG. 123). More significant PLS-DA results would be achieved using a larger number of replicates for wild-type.

Figure 132:
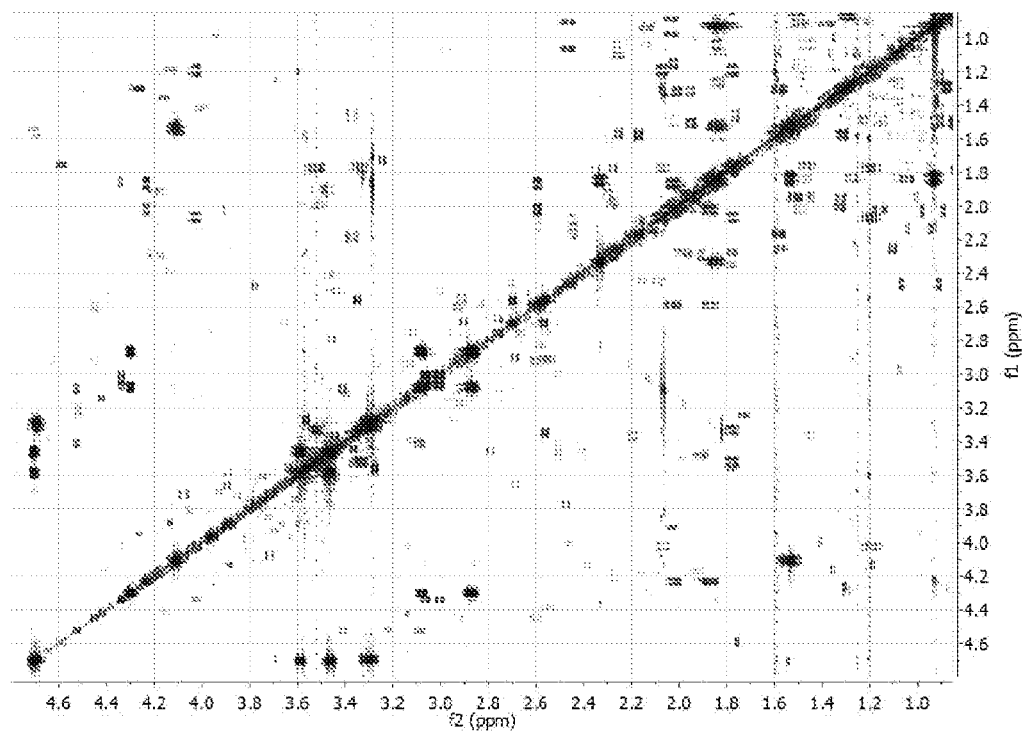

FIG. 132 is a section (0.85-4.80 ppm) of the dqfCOSY of E. coli OP50 for exo-metabolome extracts.

Figure 133:
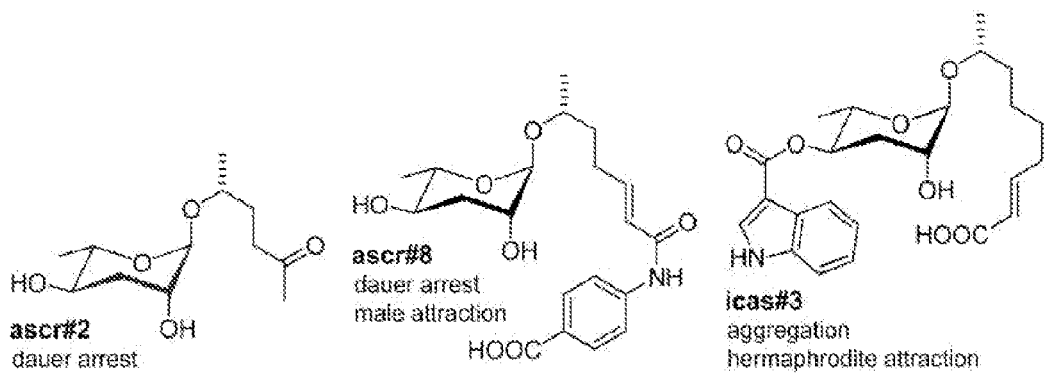

FIG. 133 shows example structures and lists the biological functions of ascaroside-based signaling molecules in C. elegans.

Figure 134:
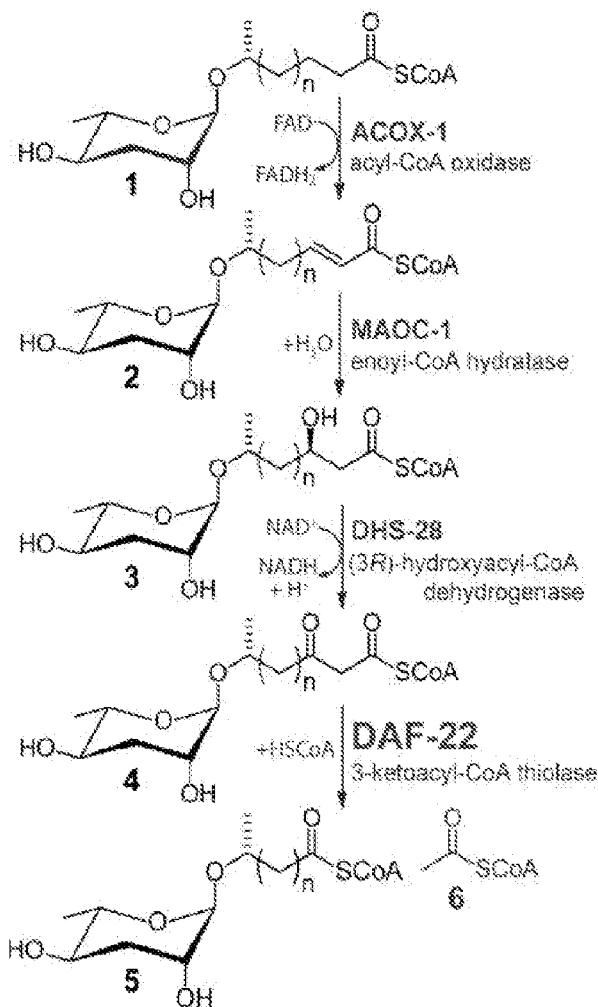

FIG. 134 is a schematic diagram of a model for peroxisomal biosynthesis of ascaroside sidechains showing the roles of the peroxisomal β-oxidation enzymes ACOX-1, MAOC-1, DHS-28, and the putative 3-ketoacyl-CoA thiolase DAF-22.

Figure 135A:
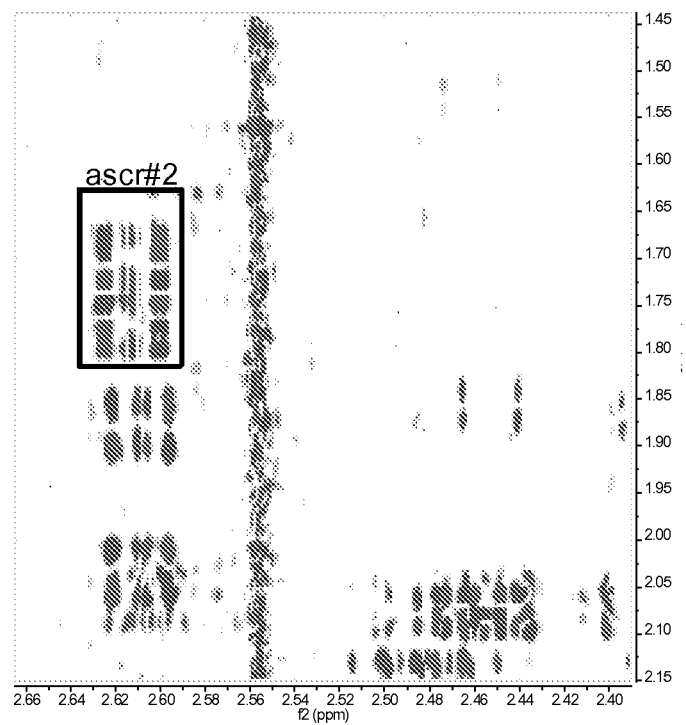
Figure 135B:
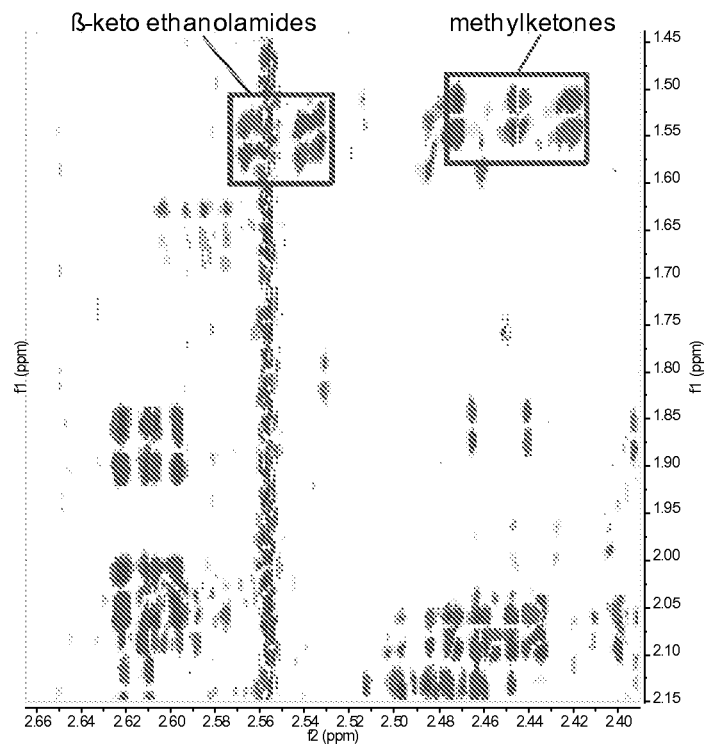

FIGS. 135A-B are spectra showing examples for differential crosspeaks identified by mvaDANS. FIG. 135A shows ascr#2-crosspeaks detected in wild-type spectrum. FIG. 135B shows β-keto ethanolamide and methylketone crosspeaks detected in the daf-22(m130) spectrum from FIG. 128.

DETAILED DESCRIPTION OF THE INVENTION

Disclosed herein are classes of compounds that act as signaling molecules in nematodes, to regulate nematode behaviors including reproduction, development, dauer formation, aggregation, attraction, repulsion, dispersal, deterrence, feeding, host finding, and/or host invasion.

DEFINITIONS

As used herein, the following terms, unless otherwise indicated, shall be understood to have the following meanings. If not defined otherwise herein, all technical and scientific terms used herein have the same meaning as is commonly understood by one of ordinary skill in the art to which this invention belongs. In the event that there is a plurality of definitions for a term herein, those in this section prevail unless stated otherwise.

The term "alkyl" refers to an aliphatic hydrocarbon group which may be a linear, branched, or cyclic hydrocarbon structure or combination thereof. Representative alkyl groups are those having 24 or fewer carbon atoms, for instance, methyl, ethyl, n-propyl, i-propyl, n-butyl, s-butyl, t-butyl, n-pentyl, i-pentyl, n-hexyl, and the like. Lower alkyl refers to alkyl groups having about 1 to about 6 carbon atoms in the chain. Branched alkyl means that one or more lower alkyl groups such as methyl, ethyl, or propyl are attached to a linear alkyl chain.

The statement that alkyl is intended to include linear, branched, or cyclic hydrocarbon structures and combinations thereof means that an "alkyl" group also includes the following combination of linear and cyclic structural elements

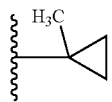

(and similar combinations).

"Alkenyl" means an alkyl, as defined above, containing at least one double bond between adjacent carbon atoms. Alkenyls include both cis and trans isomers. Branched alkenyl means that one or more lower alkyl groups such as methyl, ethyl, or propyl are attached to a linear alkenyl chain. Representative straight chain and branched alkenyls are those having about 2 to about 6 carbon atoms in the chain, for instance, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

The term "halogen" refers to fluoro, chloro, bromo, and iodo.

The term "haloalkyl" refers to a branched or straight-chain alkyl as described above, substituted with one or more halogens.

The term "haloalkenyl" refers to a branched or straight-chain alkenyl as described above, substituted with one or more halogens.

The term "aryl" means an aromatic monocyclic or multi-cyclic (polycyclic) ring system of 6 to about 19 carbon atoms, for instance, about 6 to about 10 carbon atoms, and includes arylalkyl groups. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl.

The term "arylalkyl" means an alkyl residue attached to an aryl ring. Examples are benzyl, phenethyl, and the like.

The term "heteroaryl" means an aromatic monocyclic or multi-cyclic ring system of about 5 to about 19 ring atoms, for instance, about 5 to about 10 ring atoms, in which one or more of the atoms in the ring system is/are element(s) other than carbon, for example, nitrogen, oxygen, and/or sulfur. As is well known to those skilled in the art, heteroaryl rings have less aromatic character than their all-carbon counter parts. Thus, for the purposes of the invention, a "heteroaryl" group need only have some degree of aromatic character. For instance, in the case of multi-cyclic ring systems, only one of the rings needs to be aromatic for the ring system to be defined as "heteroaryl". Exemplary heteroaryls contain about 5 to 6 ring atoms. The prefix aza, oxa, thia, or thio before heteroaryl means that at least a nitrogen, oxygen, or sulfur atom, respectively, is present as a ring atom. A nitrogen, carbon, or sulfur atom in the heteroaryl ring may be optionally oxidized; the nitrogen may optionally be quaternized. Representative heteroaryls include, but are not limited to, purinyl, pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, quinolinyl, isoquinolinyl, quinazolinyl, cinnolinyl, pthalazinyl, quinoxalinyl, and the like.

The terms "cycloalkyl" and "cycloalkenyl" refer to a non-aromatic, saturated (cycloalkyl) or unsaturated (cycloalkenyl), mono- or multi-cyclic ring system of about 3 to about 8 carbon atoms, for instance, about 5 to about 7 carbon atoms. Exemplary cycloalkyl and cycloalkenyl groups include, without limitation, cyclopropyl, cyclobutyl, cyclopentyl, cyclohexyl, cycloheptyl, norbornyl, cyclopropenyl, cyclobutenyl, cyclopentenyl, cyclohexenyl, cyclophenyl, anti-bicyclopropane, syn-tricyclopropane, and the like.

As used herein, "heterocycle" or "heterocyclyl" refers to a stable 3- to 18-membered ring (radical) which is saturated, unsaturated, or aromatic, and which consists of carbon atoms and from one to five heteroatoms selected from the group consisting of nitrogen, oxygen and sulfur. For purposes of this invention, the heterocycle may be a monocyclic, bicyclic, or a polycyclic ring system, which may include fused, bridged, or spiro ring systems, including bicyclic rings in which any of the above heterocycles are fused to a benzene ring. The nitrogen, carbon, or sulfur atoms in the heterocycle may be optionally oxidized; the nitrogen atom may be optionally quaternized; and the ring may be partially or fully saturated. The heterocycle may be attached via any heteroatom or carbon atom. Heterocycles include heteroaryls as defined below. Examples of such heterocycles include, without limitation, morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like. Further heterocycles and heteroaryls are described in Katritzky et al., eds., Comprehensive Heterocyclic Chemistry: The Structure, Reactions, Synthesis and Use of Heterocyclic Compounds, Vol. 1-8, Pergamon Press, N.Y. (1984), which is hereby incorporated by reference in its entirety.

The term "acyl" refers to groups of from 1 to 8 carbon atoms of a straight, branched, or cyclic configuration, saturated, unsaturated, or aromatic, and combinations thereof, attached to the parent structure through a carbonyl functionality. One or more carbons in the acyl residue may be replaced by nitrogen, oxygen, or sulfur as long as the point of attachment to the parent remains at the carbonyl. Examples include acetyl (Ac), benzoyl, propionyl, isobutyryl, t-butoxycarbonyl, benzyloxycarbonyl, and the like.

The term "amino acid" refers to the fragment of an amino acid that remains following amide bond formation via reaction of the amino acid carboxyl group with an amino group of another molecule. The amino acid can be in D- or L-configuration. Suitable amino acids include α-amino acids, β-amino acids, γ-amino acids, δ-amino acids, and ε-amino acids, and include not only natural amino acids (i.e., those found in biological systems, including the twenty amino acids found in natural proteins), but also naturally-occurring variants of such amino acids, as well as synthetic amino acids and their analogues known to those skilled in the art. Exemplary amino acids include the twenty natural amino acids, 4-hydroxyproline, hydroxyysine, demosine, isodemosine, 3-methylhistidine, norvalin, beta-alanine, gamma-aminobutyric acid, citrulline, homocysteine, homoserine, ornithine, and methionine sulfone.

The term "pyrimidine" refers to a heteroaromatic compound containing a benzene ring with two carbon atoms replaced by two nitrogen atoms (diazine). For instance, the following moiety having the carbon atoms at positions 1 and 3 replaced by nitrogen atoms is considered a pyrimidine:

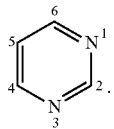

This term, as it is defined herein, also includes its isomeric forms of diazine, such as pyridazine, with the nitrogen atoms in positions 1 and 2; and pyrazine, with the nitrogen atoms in positions 1 and 4. The term "pyrimidine" also generally includes its analogues and derivatives. For instance, the natural nucleobases, cytosine (C), thymine (T), and uracil (U), are pyrimidine derivatives. The term "purine" refers to a heteroaromatic compound containing a pyrimidine ring fused to an imidazole ring. The term "purine" also generally includes its analogues and derivatives. For instance, the natural nucleobases, adenine (A) and guanine (G). Other examples of naturally occurring purine derivatives are hypoxanthine, xanthine, theobromine, caffeine, uric acid, and isoguanine. Exemplary purines and pyrimidines include those disclosed in U.S. Pat. No. 3,687,808; Concise Encyclopedia Of Polymer Science And Engineering, pages 858-859; Kroschwitz, J. I., ed. John Wiley & Sons, 1990; and Englisch et al., Angewandte Chemie, International Edition, 1991, 30, 613, each of which is hereby incorporated by reference in its entirety.

The term "nucleobase" includes all natural and synthetic nucleobases as well as universal nucleobases. Typical natural nucleobases include adenine, guanine, cytosine, uracil, and thymine. Synthetic nucleobases typically include inosine, xanthine, hypoxanthine, nubularine, isoguanisine, or tubercidine. As used herein, a universal nucleobase is any modified, unmodified, naturally occurring or non-naturally occurring nucleobase that can substitute for more than one of the natural nucleobases. Universal bases typically contain an aromatic ring moiety that may or may not contain nitrogen atoms and generally use aromatic ring stacking to stabilize an oligonucleotide duplex. Some universal bases can be covalently attached to the C-1' carbon of a pentose sugar to make a universal nucleotide. Some universal bases do not hydrogen bond specifically with another nucleobase. Some universal bases base pair with all of the naturally occurring nucleobases. Some universal bases may interact with adjacent nucleotide bases on the same nucleic acid strand by hydrophobic stacking. Exemplary universal nucleobases include, but are not limited to, 2,4-difluorotoluene, nitropyrrolyl, nitroindolyl, 8-aza-7-deazaadenine, 4-fluoro-6-methylbenzimidazle, 4-methylbenzimidazle, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylinolyl, 4,6-dimethylindolyl, phenyl, napthalenyl, anthracenyl, phenanthracenyl, pyrenyl, stilbenzyl, tetracenyl, pentacenyl, and structural derivatives thereof.

Suitable nucleobases include, but are not limited to, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, N4-acetyl cytosine, 2-thiocytosine, N6-methyladenine, N6-isopentyladenine, 2-methylthio-N-6-isopentenyladenine, N-methylguanines, and O-alkylated bases. Further purines and pyrimidines include those disclosed in U.S. Pat. No. 3,687,808; Concise Encyclopedia Of Polymer Science And Engineering, pages 858-859; Kroschwitz, J. I., ed. John Wiley & Sons, 1990; and Englisch et al., Angewandte Chemie, International Edition, 1991, 30, 613, each of which is hereby incorporated by reference in its entirety.

The term "nucleoside" refers to a compound comprising a nucleobase, as defined herein, linked to a pentose at the 1'-position. When the nucleobase is a purine derivative or anologue, the pentose is typically attached to the nucleobase at the 9-position of the purine derivative or anologue. When the nucleobase is a pyrimidine derivative or anologue, the pentose is typically attached to the nucleobase at the 1-position of the pyrimidine (e.g., Kornberg and Baker, DNA Replication, 2nd Ed., Freeman, San Francisco, 1992, which is hereby incorporated by reference in its entirety). When a nucleoside is present in $R^3$, $R^4$, or $R^5$ herein, the nucleoside may be connected to the neighboring atom(s) through any atom on the nucleobase or pentose.

The term "fatty acid" generally refers to a carboxylic acid with an aliphatic tail (chain). The aliphatic chain can be between about 2 and about 36 carbon atoms in length. Fatty acids can be saturated, unsaturated, or polyunsaturated. The aliphatic chain can be a linear or a branched chain. The term "fatty acid" may be used herein to refer to a "fatty acid derivative" which can include one or more different fatty acid derivatives, or mixtures of fatty acids derivatives. Exemplary fatty acids include unsaturated fatty acids, saturated fatty acids, and diacids; mono-, di-, and tri-glycerides of ascarosides that have a carboxylic acid functionality; hydroxy acids, ω hydroxy acids, ω-1 hydroxy acids, dihydroxy fatty acids (e.g., dihydroxy fatty acids that are omega- or omega-1 hydroxylated, as well as alpha- or beta-hydroxylated fatty acids).

The term "sugar" refers to a compound which is either a carbohydrate per se made up of one or more monosaccharide units having at least 5 carbon atoms (which may be linear, branched, or cyclic) with an oxygen, nitrogen, or sulfur atom bonded to each carbon atom; or a compound having as a part thereof a carbohydrate moiety made up of one or more monosaccharide units each having at least 5 carbon atoms (which may be linear, branched or cyclic), with an oxygen, nitrogen or sulfur atom bonded to each carbon atom. Representative sugars include the mono-, di-, tri-, and oligosaccharides containing from about 4-9 monosaccharide units, and polysaccharides such as starches, glycogen, cellulose, and polysaccharide gums. Exemplary monosaccharides include $C_5$ and above (e.g., $C_5$-$C_8$ or $C_5$-$C_6$) sugars; di- and trisaccharides include sugars having two or three monosaccharide units (e.g., $C_5$-$C_8$ or $C_5$-$C_8$).

The term "monosaccharide" means a sugar molecule having a chain of 3-10 carbon atoms in the form of an aldehyde (aldose) or ketone (ketose). Suitable monosaccharides include both naturally occurring and synthetic monosaccharides. Suitable monosaccharides include trioses, such as glycerose and dihydroxyacetone; textroses such as erythrose and erythrulose; pentoses, such as xylose, arabinose, ribose, xylulose ribulose; methyl pentoses (6-deoxyhexoses), such as rhamnose and fucose; hexoses, such as ascarylose, glucose, mannose, galactose, fructose, and sorbose; and heptoses, such as glucoheptose, galamannoheptose, sedoheptulose, and mannoheptulose. Exemplary monosaccharides embrace radicals of allose, altrose, arabinose, cladinose, erythrose, erythrulose, fructose, D-fucitol, L-fucitol, fucosamine, fucose, fuculose, galactosamine, D-galactosaminitol, N-acetyl-galactosamine, galactose, glucosamine, N-acetyl-glucosamine, glucosaminitol, glucose, glucose-6-phosphate, gulose glyceraldehyde, L-glycero-D-mannos-heptose, glycerol, glycerone, gulose, idose, lyxose, mannosamine, mannose, mannose-6-phosphate, psicose, quinovose, quinovasamine, rhamnitol, rhamnosamine, rhamnose, ribose, ribulose, sedoheptulose, sorbose, tagatose, talose, tartaric acid, threose, xylose, and xylulose. The monosaccharide can be in D- or L-configuration. A typical monosaccharide used herein is hexose.

The monosaccharide may further be a deoxy sugar (alcoholic hydroxy group replaced by hydrogen), amino sugar (alcoholic hydroxy group replaced by amino group), a thio sugar (alcoholic hydroxy group replaced by thiol, or C=O replaced by C=S, or a ring oxygen of cyclic form replaced by sulfur), a seleno sugar, a telluro sugar, an aza sugar (ring carbon replaced by nitrogen), an imino sugar (ring oxygen replaced by nitrogen), a phosphano sugar (ring oxygen replaced with phosphorus), a phospha sugar (ring carbon replaced with phosphorus), a C-substituted monosaccharide (hydrogen at a non-terminal carbon atom replaced with carbon), an unsaturated monosaccharide, an alditol (carbonyl group replaced with CHOH group), aldonic acid (aldehydic group replaced by carboxy group), a ketoaldonic acid, a uronic acid, an aldaric acid, and so forth. Amino sugars include amino monosaccharides, such as galactosamine, glucosamine, mannosamine, fucosamine, quinovasamine, neuraminic acid, muramic acid, lactosediamine, acosamine, bacillosamine, daunosamine, desosamine, forosamine, garosamine, kanosamine, kansosamine, mycaminose, mycosamine, perosamine, pneumosamine, purpurosamine, rhodosamine. It is understood that the monosaccharide and the like can be further substituted.

The terms "disaccharide", "trisaccharide", and "polysaccharide" embrace radicals of abequose, acrabose, amicetose, amylopectin, amylose, apiose, arcanose, ascarylose, ascor-bic acid, boivinose, cellobiose, cellotriose, cellulose, chacotriose, chalcose, chitin, colitose, cyclodextrin, cymarose, dextrin, 2-deoxyribose, 2-deoxyglucose, diginose, digitalose, digitoxose, evalose, evemitrose, fructoologosachharide, galto-oligosaccharide, gentianose, gentiobiose, glucan, glucogen, glycogen, hamamelose, heparin, inulin, isolevoglucosenone, isomaltose, isomaltotriose, isopanose, kojibiose, lactose, lactosamine, lactosediamine, laminarabiose, levoglucosan, levoglucosenone, β-maltose, maltriose, mannan-oligosaccharide, manninotriose, melezitose, melibiose, muramic acid, mycarose, mycinose, neuraminic acid, nigerose, nojirimycin, moviose, oleandrose, panose, paratose, planteose, primeverose, raffinose, rhodinose, rutinose, sarmentose, sedoheptulose, solatriose, sophorose, stachyose, streptose, sucrose, α, α-trehalose, trehalosamine, turanose, tyvelose, xylobiose, umbelliferose, and the like. Further, it is understood that the "disaccharide", "trisaccharide", and "polysaccharide" and the like can be further substituted. Disaccharide also includes amino sugars and their derivatives, particularly, a mycaminose derivatized at the C-4' position or a 4 deoxy-3-amino-glucose derivatized at the C-6' position.

The term "polycyclic" or "multi-cyclic" used herein indicates a molecular structure having two or more rings, including, but not limited to, fused, bridged, or spiro rings.

The above "alkyl", "alkenyl", "cycloalkyl", and "cycloalkenyl" radicals, as well as the ring system of the above aryl, heterocyclyl, or heteroaryl groups, may be optionally substituted.

The term "substituted" or "optionally substituted" is used to indicate that a group may have a substituent at each substitutable atom of the group (including more than one substituent on a single atom), provided that the designated atom's normal valency is not exceeded and the identity of each substituent is independent of the others. In accordance with the present invention, up to three H atoms in each residue can be replaced with alkyl, halogen, haloalkyl, alkenyl, haloalkenyl, cycloalkyl, cycloalkenyl, hydroxy, alkoxy, acyl, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, aryl, heteroaryl, heterocyclyl, aryloxy, heteroaryloxy, a purine or pyridimine or an analogue or derivative thereof (as defined in "nucleobase"), or a sugar such as a monosaccharide having 5 or 6 carbon atoms (as defined in "monosaccharide"). "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious agent.

In the characterization of some of the substituents, certain substituents may combine to form rings. Unless stated otherwise, it is intended that such rings may exhibit various degrees of unsaturation (from fully saturated to fully unsaturated), may include heteroatoms, and may be substituted with other substituent groups as described above.

The compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration; thus a carbon-carbon double bond depicted arbitrarily herein as trans may be Z, E, or a mixture of the two in any proportion.

The term "compounds of the invention," and equivalent expressions, are meant to embrace the prodrugs, the pharmaceutically acceptable salts, the oxides, the solvates, e.g. hydrates, and inclusion complexes of that compound, where the context so permits, as well as any stereoisomeric form, or a mixture of any such forms of that compound in any ratio, unless otherwise specified. Inclusion complexes are described in Remington, The Science and Practice of Pharmacy, 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed within the claims. Thus, in accordance with some embodiments of the invention, a compound as described herein, including in the contexts of pharmaceutical compositions, methods of treatment, and compounds per se, is provided as the salt form. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The "quaternization" of any basic nitrogen-containing groups of the compounds disclosed herein is also contemplated. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

One aspect of the present invention relates to an isolated compound of Formula I:

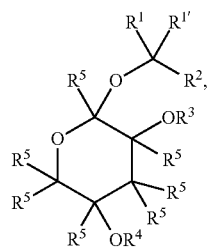

I where:
$R^1$ is H, —C(R)$_3$, —OR, —N(R)$_2$, halogen, an alkyl, a haloalkyl, an alkenyl, or a haloalkenyl; where each R is independently H, halogen, an alkyl, or an alkenyl;
$R^{1'}$ is absent, H, —C(R)$_3$, —OR, —N(R)$_2$, halogen, an alkyl, a haloalkyl, an alkenyl, or a haloalkenyl; where each R is independently H, halogen, an alkyl, or an alkenyl;
$R^2$ is a moiety of formula

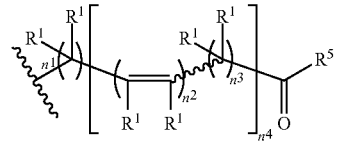

where:
each $R^1$ is independently H, —C(R)$_3$, —OR, —N(R)$_2$, halogen, an alkyl, a haloalkyl, an alkenyl, or a haloalkenyl; where each R is independently H, halogen, an alkyl, or an alkenyl;
$R^5$ is H, —OH, —OR$^6$, —OCR$^6$R$^7$R$^8$, —CR$^6$R$^7$R$^8$, —NH$_2$, —NHR$^6$, —NR$^6$R$^7$, —CR$^6$R$^7$C(O)NHR$^8$, halogen, an alkyl, a haloalkyl, an alkenyl, a haloalkenyl, an aryl, a heteroaryl, an arylalkyl, a heterocyclyl, a cycloalkyl, a cycloalkenyl, an acyl, an amino acid, a nucleoside, a monosaccharide having 5 or 6 carbon atoms, or a bond connecting to $R^3$ or $R^4$ of another unit of Formula I;
where:
$R^6$ and $R^7$ are each independently H, —CR$_3$, —OR, —N(R)$_2$, halogen, an alkyl, a haloalkyl, an alkenyl, a haloalkenyl, an aryl, a heteroaryl, a heterocyclyl, a cycloalkyl, or a cycloalkenyl, where the alkyl, alkenyl, aryl, heteroaryl, heterocyclyl, cycloalkyl, or cycloalkenyl is optionally substituted with one or more substituents independently selected from the group consisting of —OR$^8$, —C(O)R$^8$, —NHC(O)R$^8$, an alkyl, a haloalkyl, an aryl, a heteroaryl, a heterocyclyl, and a cycloalkyl;
where:
each R is independently H, halogen, an alkyl, or an alkenyl; and
$R^8$ is H, —C(R)$_3$, —[C(R)$_2$]$_{n4}$NHC(O)R$^9$, —[C(R)$_2$]$_{n4}$C(O)(NH)R$^9$, —OR, —N(R)$_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —C(R)$_3$, —OR$^9$, —C(O)R$^9$, —NHC(O)R$^9$, halogen, an alkyl, a haloalkyl, an aryl, a heteroaryl, a heterocyclyl, a cycloalkyl, and a monosaccharide having 5 or 6 carbon atoms;
where:
each R is independently H, halogen, an alkyl, or an alkenyl;
$R^9$ is H, —C(R)$_3$, —OR, —N(R)$_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —C(R)$_3$, —OR, —C(O)R, halogen, an alkyl, a haloalkyl, an aryl, a heteroaryl, a heterocyclyl, and a cycloalkyl; where each R is independently H, halogen, an alkyl, or an alkenyl; and n$^4$ is an integer of 1 to 30; and R$^8$ is H, —C(R)$_3$, —[C(R)$_2$]$_{n4}$NHC(O)R$^9$, —[C(R)$_2$]$_{n4}$C(O)(NH)R$^9$, —OR, —N(R)$_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —C(R)$_3$, —OR$^9$, —C(O)R$^9$, —NHC(O)R$^9$, halogen, an alkyl, a haloalkyl, an aryl, a heteroaryl, a heterocyclyl, a cycloalkyl, and a monosaccharide having 5 or 6 carbon atoms;

where:

each R is independently H, halogen, an alkyl, or an alkenyl;

R$^9$ is H, —C(R)$_3$, —OR, —N(R)$_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —C(R)$_3$, —OR, —C(O)R, halogen, an alkyl, a haloalkyl, an aryl, a heteroaryl, a heterocyclyl, and a cycloalkyl; where each R is independently H, halogen, an alkyl, or an alkenyl; and n$^4$ is an integer of 1 to 30;

n$^1$, n$^2$, and n$^3$ are each independently an integer of 0 to 30;

n$^4$ is an integer of 1 to 30; and the sum of n$^1$, each n$^2$, and each n$^3$ is 1 to 30;

R$^3$ and R$^4$ are each independently H, —CR$^6$R$^7$R$^8$, —C(O)R$^8$, an alkyl, a haloalkyl, an alkenyl, a haloalkenyl, an aryl, a heteroaryl, a heterocyclyl, a cycloalkyl, a cycloalkenyl, an acyl, an amino acid, a nucleoside, a monosaccharide having 5 or 6 carbon atoms, or a bond connecting to R$^5$ of another unit of Formula I;

where:

R$^6$ and R$^7$ are each independently H, —CR$_3$, —OR, —N(R)$_2$, halogen, an alkyl, a haloalkyl, an alkenyl, a haloalkenyl, an aryl, a heteroaryl, a heterocyclyl, a cycloalkyl, or a cycloalkenyl, where the alkyl, alkenyl, aryl, heteroaryl, heterocyclyl, cycloalkyl, or cycloalkenyl is optionally substituted with one or more substituents independently selected from the group consisting of —OR$^8$, —C(O)R$^8$, —NHC(O)R$^8$, an alkyl, a haloalkyl, an aryl, a heteroaryl, a heterocyclyl, and a cycloalkyl;

where:

each R is independently H, halogen, an alkyl, or an alkenyl; and

R$^8$ is H, —C(R)$_3$, —[C(R)$_2$]$_{n4}$NHC(O)R$^9$, —[C(R)$_2$]$_{n4}$C(O)(NH)R$^9$, —OR, —N(R)$_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —C(R)$_3$, —OR$^9$, —C(O)R$^9$, —NHC(O)R$^9$, halogen, an alkyl, a haloalkyl, an aryl, a heteroaryl, a heterocyclyl, a cycloalkyl, and a monosaccharide having 5 or 6 carbon atoms;

where:

each R is independently H, halogen, an alkyl, or an alkenyl;

R$^9$ is H, —C(R)$_3$, —OR, —N(R)$_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —C(R)$_3$, —OR, —C(O)R, halogen, an alkyl, a haloalkyl, an aryl, a heteroaryl, a heterocyclyl, and a cycloalkyl; where each R is independently H, halogen, an alkyl, or an alkenyl; and n$^4$ is an integer of 1 to 30; and R$^8$ is H, —C(R)$_3$, —[C(R)$_2$]$_{n4}$NHC(O)R$^9$, —[C(R)$_2$]$_{n4}$C(O)(NH)R$^9$, —OR, —N(R)$_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —C(R)$_3$, —OR$^9$, —C(O)R$^9$, —NHC(O)R$^9$, halogen, an alkyl, a haloalkyl, an aryl, a heteroaryl, a heterocyclyl, a cycloalkyl, and a monosaccharide having 5 or 6 carbon atoms;

where:

each R is independently H, halogen, an alkyl, or an alkenyl;

R$^9$ is H, —C(R)$_3$, —OR, —N(R)$_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —C(R)$_3$, —OR, —C(O)R, halogen, an alkyl, a haloalkyl, an aryl, a heteroaryl, a heterocyclyl, and a cycloalkyl; where each R is independently H, halogen, an alkyl, or an alkenyl; and n$^4$ is an integer of 1 to 30; and each R$^5$ is independently H, —OH, —OR$^6$, —OCR$^6$R$^7$R$^8$, —CR$^6$R$^7$R$^8$, —NH$_2$, —NHR$^6$, —NR$^6$R$^7$, —CR$^6$R$^7$C(O)NHR$^8$, halogen, an alkyl, a haloalkyl, an alkenyl, a haloalkenyl, an aryl, a heteroaryl, an arylalkyl, a heterocyclyl, a cycloalkyl, a cycloalkenyl, an acyl, an amino acid, a nucleoside, a monosaccharide having 5 or 6 carbon atoms, or a bond connecting to $R^3$ or $R^4$ of another unit of Formula I;

where:

$R^6$ and $R^7$ are each independently H, —$CR_3$, —OR, —$N(R)_2$, halogen, an alkyl, a haloalkyl, an alkenyl, a haloalkenyl, an aryl, a heteroaryl, a heterocyclyl, a cycloalkyl, or a cycloalkenyl, where the alkyl, alkenyl, aryl, heteroaryl, heterocyclyl, cycloalkyl, or cycloalkenyl is optionally substituted with one or more substituents independently selected from the group consisting of —$OR^8$, —$C(O)R^8$, —$NHC(O)R^8$, an alkyl, a haloalkyl, an aryl, a heteroaryl, a heterocyclyl, and a cycloalkyl;

where:

each R is independently H, halogen, an alkyl, or an alkenyl; and $R^8$ is H, —$C(R)_3$, —$[C(R)_2]_{n4}NHC(O)R^9$, —$[C(R)_2]_{n4}C(O)(NH)R^9$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —$OR^9$, —$C(O)R^9$, —$NHC(O)R^9$, halogen, an alkyl, a haloalkyl, an aryl, a heteroaryl, a heterocyclyl, a cycloalkyl, and a monosaccharide having 5 or 6 carbon atoms;

where:

each R is independently H, halogen, an alkyl, or an alkenyl;

$R^9$ is H, —$C(R)_3$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —OR, —$C(O)R$, halogen, an alkyl, a haloalkyl, an aryl, a heteroaryl, a heterocyclyl, and a cycloalkyl; where each R is independently H, halogen, an alkyl, or an alkenyl; and $n^4$ is an integer of 1 to 30; and $R^8$ is H, —$C(R)_3$, —$[C(R)_2]_{n4}NHC(O)R^9$, —$[C(R)_2]_{n4}C(O)(NH)R^9$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —$OR^9$, —$C(O)R^9$, —$NHC(O)R^9$, halogen, an alkyl, a haloalkyl, an aryl, a heteroaryl, a heterocyclyl, a cycloalkyl, and a monosaccharide having 5 or 6 carbon atoms;

where:

each R is independently H, halogen, an alkyl, or an alkenyl;

$R^9$ is H, —$C(R)_3$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, where the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —OR, —$C(O)R$, halogen, an alkyl, a haloalkyl, an aryl, a heteroaryl, a heterocyclyl, and a cycloalkyl; where each R is independently H, halogen, an alkyl, or an alkenyl; and $n^4$ is an integer of 1 to 30;

with the proviso that the compound is not ascr#1, ascr#2, ascr#3, ascr#4, ascr#5, ascr#6.1, ascr#6.2, ascr#7, ascr#8, ascr#12, ascr#19, ascr#21, ascr#23, ascr#25, bhas#24, bhas#26, bhas#28, bhas#30, or icas#9.

One embodiment of this aspect of the present invention is a compound of Formula I in which $R^1$ is H, an alkyl (e.g., —$CH_3$), or an alkenyl; and R' is absent or H. The alkyl or alkenyl can be optionally substituted with one or more of the substituents defined herein.

Another embodiment of this aspect of the present invention is a compound of Formula I in which $R^3$ and $R^4$ are each independently H, —$C(O)R^8$, or a carbohydrate, such as a monosaccharide having 5 or 6 carbon atoms (e.g., a hexose, such as a glycosyl). Suitable compounds according to this embodiment include, e.g., compounds of Formula I':

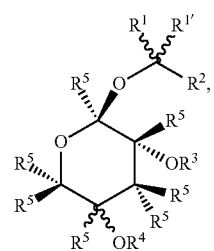

I' including, e.g., those in which $R^3$ is H or a monosaccharide having 5 or 6 carbon atoms; and those in which $R^4$ is H or —$C(O)R^8$.

Another embodiment of this aspect of the present invention is a compound of Formula I in which $R^5$ is —OH, —$NHR^6$, —$OCHR^6R^7$, —$CR^6R^7C(O)NHR^8$, an alkyl, or a carbohydrate, such as a monosaccharide having 5 or 6 carbon atoms. The alkyl or carbohydrate can be optionally substituted with one or more of the substituents defined herein. Exemplary compounds according to this embodiment include those in which $R^5$ is —OH, —$NHR^6$, an alkyl, or a monosaccharide having 5 or 6 carbon atoms (e.g., hexose, such as a glycosyl).

Another embodiment of this aspect of the present invention is a compound of Formula I in which at least one of $R^6$ and $R^7$ is present. In this embodiment, $R^6$ and $R^7$ typically are each independently an alkyl or an aryl. The alkyl or aryl group can be optionally substituted with one or more of the substituents defined herein. For instance, these groups can be optionally substituted with one or more substituents independently selected from the group consisting of —$C(O)R^8$ and —$NHC(O)R^8$. Exemplary compounds according to this embodiment include those in which $R^6$ is present and is an aryl optionally substituted with one or more substituents of —$C(O)R^8$.

Another embodiment of this aspect of the present invention is a compound of Formula I in which $R^8$ is present. In this embodiment, $R^8$ is typically —OH, —$NH_2$, an alkyl, an alkenyl, an aryl, a heteroaryl, a purine, or a pyrimidine. The alkyl, alkenyl, aryl, heteroaryl, purine, or pyrimidine can be optionally substituted with one or more of the substituents defined herein. For instance, these groups can be optionally substituted with one or more substituents independently selected from the group consisting of —$OR^9$, —$NHC(O)R^9$, an alkyl, and a carbohydrate such as a monosaccharide having 5 or 6 carbon atoms. Exemplary compounds according to this embodiment include those in which $R^8$ is —OH, —$NH_2$, or a purine or pyrimidine optionally substituted with one or more monosaccharides having 5 or 6 carbon atoms (e.g., hexose, such as a glycosyl). Exemplary $R^8$ moieties according to this embodiment include indolyl, hydroxyphenyl, carboxyphenyl, and butenyl.

Another embodiment of this aspect of the present invention is a compound of Formula I in which $R^9$ is present. In this embodiment, $R^9$ is typically H, —$NH_2$, or an alkyl, preferably H or an alkyl.

The compounds of Formula I' include the stereoisomer of Formula I'a:

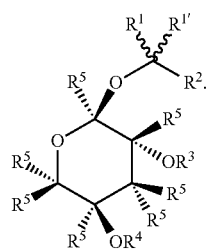

Another embodiment of this aspect of the present invention is a compound of Formula I or Formula I'a in which $R^1$ is —$CH_3$ and $R^{1'}$ is absent or H. Exemplary compounds according to this embodiment include ascarosides (e.g., compounds labeled "ascr" herein), (ω-1)-oxygenated indole ascarosides (e.g., compounds labeled "icas" herein), (ω-1)-oxygenated β-hydroxyascarosides (e.g., compounds labeled "bhas" herein), (ω-1)-oxygenated indole β-hydroxyascarosides (e.g., compounds labeled "ibha" herein), 4-(2-(E)-methyl-2-butenoyl)-ascarosides (e.g., compounds labeled "mhas" herein), glycosyl ascaroside esters (e.g., compounds labeled "glas" herein), and 4-(4-hydroxybenzoyl)-ascarosides (e.g., compounds labeled "hbas" herein).

Another embodiment of this aspect of the present invention is a compound of Formula I or Formula I'a in which $R^1$ is H and $R^{1'}$ is absent or H. Exemplary compounds according to this embodiment include (ω)-oxygenated ascarosides (e.g., compounds labeled "oscr" herein), (ω)-oxygenated indole ascarosides (e.g., compounds labeled "icos" herein), (ω)-oxygenated β-hydroxyascarosides (e.g., compounds labeled "bhos" herein), and (ω)-oxygenated indole β-hydroxyascarosides (e.g., compounds labeled "ibho" herein).

Another embodiment of this aspect of the present invention is a compound of Formula I or Formula I'a in which $R^4$ is —$C(O)R^8$ and $R^8$ is indolyl (e.g., 3-indolyl). Exemplary compounds according to this embodiment include those in which $R^1$ is —$CH_3$ and $R^{1'}$ is absent or H. Such compounds include (ω-1)-oxygenated indole ascarosides. Exemplary compounds according to this embodiment also include those in which $R^1$ is H and $R^{1'}$ is absent or H. Such compounds include (ω)-oxygenated ascarosides.

Another embodiment of this aspect of the present invention is a compound of Formula I or Formula I'a in which $R^4$ is 4-hydroxybenzoyl. Exemplary compounds according to this embodiment include those in which $R^1$ is —$CH_3$ and $R^{1'}$ is absent or H. Such compounds include (ω)-oxygenated 4-(4-hydroxybenzoyl)-ascarosides (e.g., compounds labeled "hbos" herein). Exemplary compounds according to this embodiment also include those in which $R^1$ is H and $R^{1'}$ is absent or H. Such compounds include (ω-1)-oxygenated 4-(4-hydroxybenzoyl)-ascarosides (e.g., compounds labeled "hbas" herein).

Another embodiment of this aspect of the present invention is a compound of Formula I or Formula I'a in which $R^4$ is 2-methyl-2-butenoyl. Exemplary compounds according to this embodiment include those in which $R^1$ is —$CH_3$ and $R^{1'}$ is absent or H. Such compounds include (ω)-oxygenated 4-(2-(E)-methyl-2-butenoyl)-ascarosides (e.g., compounds labeled "mbos" herein). Exemplary compounds according to this embodiment also include those in which $R^1$ is H and $R^{1'}$ is absent or H. Such compounds include (ω-1)-oxygenated 4-(2-(E)-methyl-2-butenoyl)-ascarosides (e.g., compounds labeled "mbas" herein).

Another embodiment of this aspect of the present invention is a compound of Formula I or Formula I'a in which $R^5$ is α-D-glucosyl. Exemplary compounds according to this embodiment include those in which $R^1$ is —$CH_3$ and $R^{1'}$ is absent or H. Such compounds include (ω)-oxygenated glycosyl ascaroside esters (e.g., compounds labeled "glos" herein). Exemplary compounds according to this embodiment also include those in which $R^1$ is H and $R^{1'}$ is absent or H. Such compounds include (ω-1)-oxygenated glycosyl ascaroside esters (e.g., compounds labeled "glas" herein).

Another embodiment of this aspect of the present invention is a compound of Formula I or Formula I'a in which $R^5$ is —$OCHR^6R^7$. Exemplary compounds according to this embodiment include those in which $R^1$ is —$CH_3$ and $R^{1'}$ is absent or H. Exemplary compounds according to this embodiment also include those in which $R^1$ is H and $R^{1'}$ is absent or H.

Another embodiment of this aspect of the present invention is a compound of Formula I or Formula I'a in which $R^5$ is —$CR^6R^7C(O)NHR^8$.

Another embodiment of this aspect of the present invention is a compound of Formula IA:

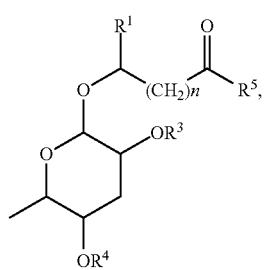

wherein n is an integer of 1 to 30. Exemplary compounds according to this embodiment include those of Formula IA':

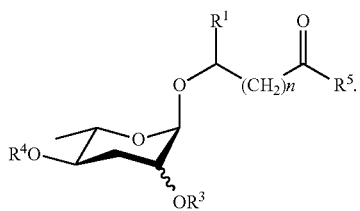

Exemplary compounds of Formula IA and IA' include compounds labeled with SMIDs "ascr", "oscr", "icas", "icos", "glas", "hbas", and "mbas", including, e.g., ascr#1, 2, 4-5, 9-12, 14, 16, 18, 20, 22, 24, 26, 28, 30, 32, 34, 36, and 38; oscr#1, 3, 9, 10, 12, 14, 16, 18, 20, 22, 24, 26, 28, 30, 32, 34, 36, and 38; icas#1, 9, 10, 12, 14, 16, 18, 20, and 22; icos#1, 9, 10, 16, and 18; glas#1, 10, 16, 18, 20, 22, 24, and 26; hbas#10; and mbas#10.

Another embodiment of this aspect of the present invention is a compound of Formula IB:

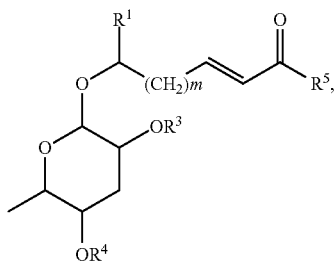

wherein m is an integer of 1 to 28. Exemplary compounds according to this embodiment include those of Formula IB':

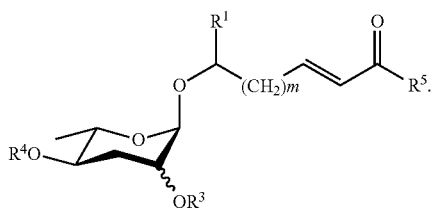

Exemplary compounds of Formula IB and IB' include compounds labeled with SMIDs "ascr", "oscr", "icas", "icos", "glas", "hbas", and "mbas", including, e.g., ascr#3, 7-8, 13, 15, 17, 19, 21, 23, 25, 27, 29, 31, 33, 35, and 37; oscr#7, 15, 17, 19, 21, 23, 25, 27, 29, 31, 33, 35, and 37; icas#3, 7, 15, 17, 19, and 21; icos#3, 15, and 17; glas#3; hbas#3; and mbas#3.

Another embodiment of this aspect of the present invention is a compound of Formula IC:

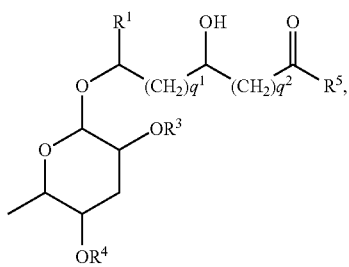

wherein $q^1$ and $q^2$ are each independently an integer of 1 to 28 and the sum of $q^1$ and $q^2$ is less than or equal to 29. Exemplary compounds according to this embodiment include those of Formula IC':

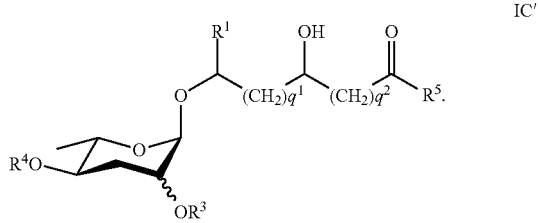

Exemplary compounds of Formula IC and Formula IC' include those in which $R^1$ is —$CH_3$ and $R^{1'}$ is absent or H. Such compounds include compounds labeled with SMIDs "bhas" and "ibha", e.g., bhas#10, 16, 18, 20, 22, 24, 26, 28, 30, 32, 34, 36, 38, 40, and 42; and ibha#10, 16, 18, 20, 22, 24, 26, 28, and 30. Exemplary compounds of Formula IC and Formula IC' also include those in which $R^1$ is H and $R^{1'}$ is absent or H. Such compounds include compounds labeled with SMIDs "bhos" and "ibho", e.g., bhos#10, 16, 18, 20, 22, 24, 26, 28, 30, 32, 34, 36, 38, 40, and 42; and ibho#10, 16, 18, 20, 22, 24, and 26. Exemplary compounds of Formula IC and Formula IC' also include those in which $R^1$ is H or —$CH_3$, $R^{1'}$ is absent or H, and $R^4$ is —$C(O)R^8$ and $R^8$ is 3-indolyl. Such compounds include compounds labeled with SMIDs "ibha" ($R^1$ is —$CH_3$) and "ibho" ($R^1$ is H).

Another embodiment of this aspect of the present invention is a compound of Formula ID:

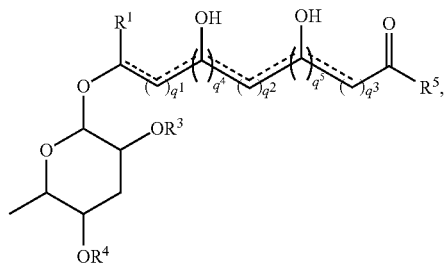

where each ═ is independently a single or double bond; $q^1$, $q^2$, and $q^3$ are each independently an integer of 1 to 26; $q^4$ and $q^5$ are each independently an integer of 0 to 26; the sum of $q^1$, $q^2$, $q^3$, $q^4$, and $q^5$ is less than or equal to 28; and the sum of $q^4$ and $q^5$ is greater than or equal to 1. Exemplary compounds according to this embodiment include those of Formula ID':

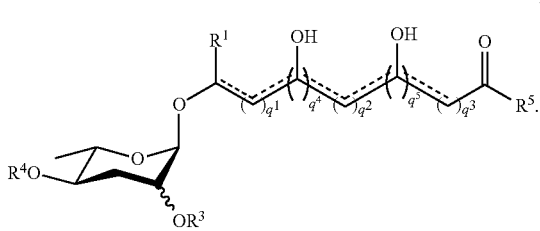

The compounds of this aspect of the present invention may also contain two or more units of Formula I. These units can be connected to each other through any of the substituents extended from the 6-member ring of the unit. For instance, one unit of general Formula I may be connected to any substituent at the 1', 2', 3', 4', or 5' position shown below of another unit of Formula I through a same or different position.

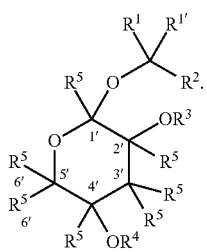

I

Another embodiment of this aspect of the present invention is a compound in which $R^5$ in one unit of Formula I is a bond connecting to $R^3$ or $R^4$ of another unit of Formula I, forming a compound containing at least two units (including only two units) of Formula I. Exemplary compounds according to this embodiment include, e.g., compounds of Formula IE and Formula IF:

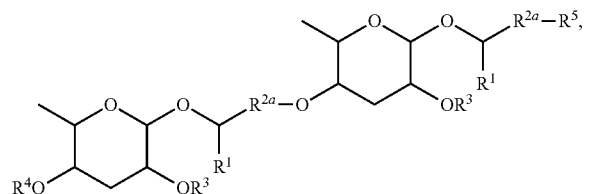

IE

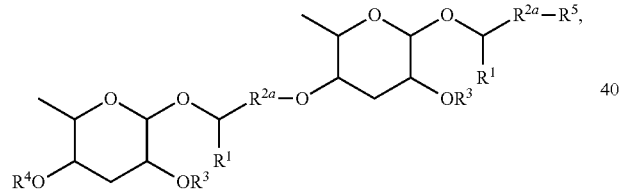

IF wherein $R^{2a}$ and $R^{2b}$ are each independently a moiety of formula

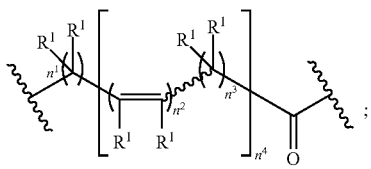

each $R^3$ and $R^4$ is independently H, —$CR^6R^7R^8$, —$C(O)R^8$, an alkyl, a haloalkyl, an alkenyl, a haloalkenyl, an aryl, a heteroaryl, a heterocyclyl, a cycloalkyl, a cycloalkenyl, an acyl, an amino acid, a nucleoside, or a monosaccharide having 5 or 6 carbon atoms; and $R^5$ is H, —OH, —$OR^6$, —$OCR^6R^7R^8$, —$CR^6R^7R^8$, —$NH_2$, —$NHR^6$, —$NR^6R^7$, —$CR^6R^7C(O)NHR^8$, halogen, an alkyl, a haloalkyl, an alkenyl, a haloalkenyl, an aryl, a heteroaryl, an arylalkyl, a heterocyclyl, a cycloalkyl, a cycloalkenyl, an acyl, an amino acid, a nucleoside, or a monosaccharide having 5 or 6 carbon atoms. Suitable compounds include, e.g., compounds of Formula IE' and Formula IF':

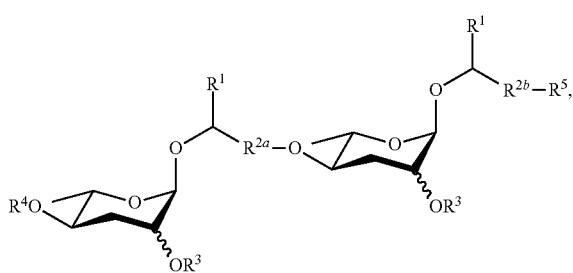

IE'

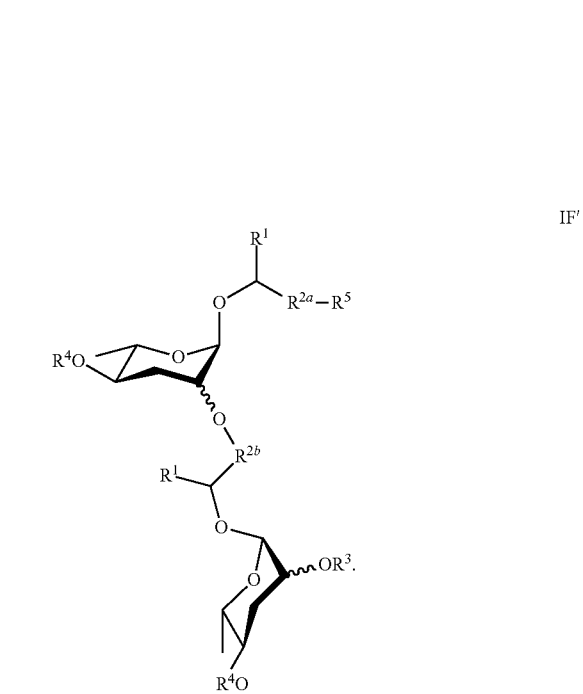

IF'

Compounds of IE, IE', IF and IF' include dimeric ascarosides (e.g., compounds labeled "dasc" herein), for example dasc#1, dascs#2, and dasc#3:

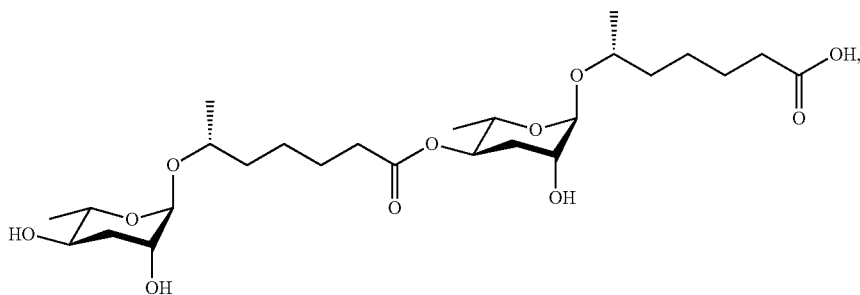

dasc#1

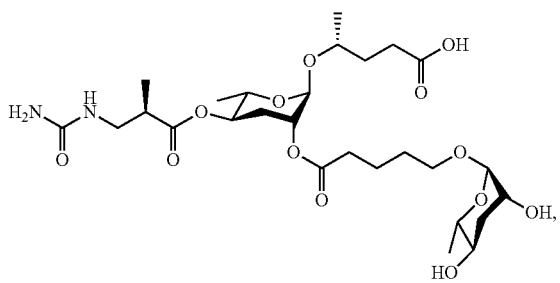

dasc#2

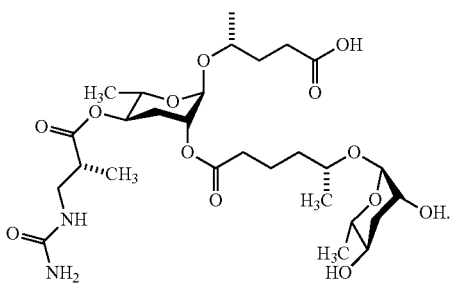

dasc#3

Another embodiment of this aspect of the present invention is a compound of Formula I":

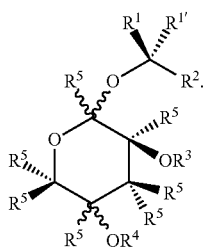

I"

Formula I" is a stereoisomer of Formula I'. All the preferred and exemplary definitions of $R^1$, $R^{1'}$, $R^2$, $R^3$, $R^5$, $R^6$, $R^7$, $R^8$, and $R^9$ described above for compounds of Formula I' are also suitable examples for compounds of Formula I". Suitable compounds according to this embodiment include those in which $R^5$ is —OCHR$^6$R$^7$ and at least one of $R^6$ and $R^7$ is an alkyl substituted with —NHC(O)R$^8$.

Another embodiment of this aspect of the present invention is a compound of Formula I in which at least one of the following conditions is met:

(i) $R^1$ is independently —C(R')$_3$, —OR, —N(R)$_2$, halogen, a haloalkyl, an alkenyl, or a haloalkenyl; wherein each R is independently H, halogen, an alkyl, or an alkenyl, and each R' is independently halogen or an alkenyl; and $R^{1'}$ is independently absent, H, —C(R)$_3$, —OR, —N(R)$_2$, halogen, an alkyl, a haloalkyl, an alkenyl, or a haloalkenyl;

(ii) $R^2$ is

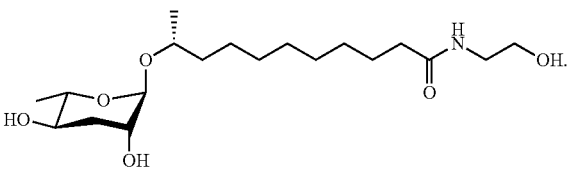

wherein:
each ═ is independently a single or double bond;
$q^1$, $q^2$, and $q^3$ are each independently an integer of 1 to 26;
$q^4$ and $q^5$ are each independently an integer of 0 to 26;
the sum of $q^1$, $q^2$, $q^3$, $q^4$, and $q^5$ is less than or equal to 28; and
the sum of $q^4$ and $q^5$ is greater than or equal to 2;

(iii) $R^5$ is H, —OR$^6$, —OCR$^6$R$^7$R$^8$, —CR$^6$R$^7$R$^8$, —NH$_2$, —NR$^6$R$^7$, —CR$^6$R$^7$C(O)NHR$^8$, halogen, a haloalkyl, an alkenyl, a haloalkenyl, an aryl, a heteroaryl, an arylalkyl, a heterocyclyl, a cycloalkyl, a cycloalkenyl, an acyl, an amino acid, or a nucleoside;

(iv) $R^5$ is a bond connecting to $R^3$ or $R^4$ of another unit of Formula I, forming a compound containing at least two units of Formula I;

(v) $R^3$ and $R^4$ are each independently —CR$^6$R$^7$R$^8$, a haloalkyl, an alkenyl, a haloalkenyl, an aryl, a heteroaryl, a heterocyclyl, a cycloalkyl, a cycloalkenyl, an acyl, an amino acid, a nucleoside, or —(CO)R$^8$ wherein R$^8$ is H, —C(R)$_3$, —[C(R)$_2$]$_{n4}$NHC(O)R$^9$, —[C(R)$_2$]$_{n4}$C(O)(NH)R$^9$, —OR, —N(R)$_2$, halogen, an alkyl, a haloalkyl, a cycloalkyl, a cycloalkenyl, a purine, a pyrimidine, or a monosaccharide having 5 or 6 carbon atoms, wherein the alkyl, cycloalkyl, cycloalkenyl, purine, pyrimidine, or monosaccharide is optionally substituted with one or more substituents independently selected from the group consisting of —C(R)$_3$, —OR$^9$, —C(O)R$^9$, —NHC(O)R$^9$, halogen, an alkyl, a haloalkyl, an aryl, a heteroaryl, a heterocyclyl, a cycloalkyl, and a monosaccharide having 5 or 6 carbon atoms;

(vi) the compound is a compound of Formula I";
with the proviso that the compound is not One example of this embodiment is a compound in which condition (i) is met. The alkyl or alkenyl groups can be optionally substituted with one or more of the substituents defined herein. This example includes compounds in which $R^1$ is an alkenyl and $R^{1'}$ is absent or H.

Another example of this embodiment is a compound in which condition (ii) is met. Such compounds include, e.g., compounds of Formula ID and ID', for example

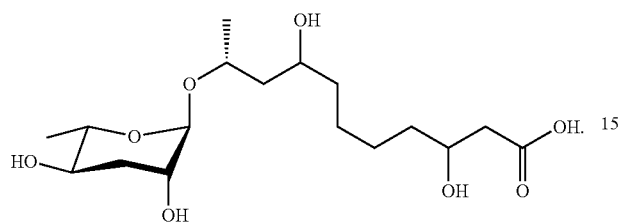

Another example of this embodiment is a compound in which condition (iii) is met. The alkenyl, aryl, heteroaryl, arylalkyl, heterocyclyl, cycloalkyl, cycloalkenyl, acyl, amino acid, or nucleoside group is optionally substituted with one or more of the substituents defined herein. Preferably, $R^5$ in this example is —$OR^6$, —$OCR^6R^7R^8$, —$CR^6R^7R^8$, —$NR^6R^7$, or —$CR^6R^7C(O)NHR^8$. —$OCHR^6R^7$ is particularly preferred. In these preferred examples, $R^6$ and $R^7$ are typically each independently an alkyl or an aryl. The alkyl or aryl group can be optionally substituted with one or more of the substituents defined herein. For instance, these groups can be optionally substituted with one or more substituents independently selected from the group consisting of —$OR^8$, —$C(O)R^8$, and —NHC(O)$R^8$. Preferably, $R^8$ is H, —OH, —$NH_2$, an alkyl, a purine, or a pyrimidine. The alkyl, purine, or pyrimidine group can be optionally substituted with one or more substituents independently selected from the group consisting of —COOH and a monosaccharide having 5 or 6 carbon atoms.

Suitable compounds according to this example include those in which $R^5$ is:

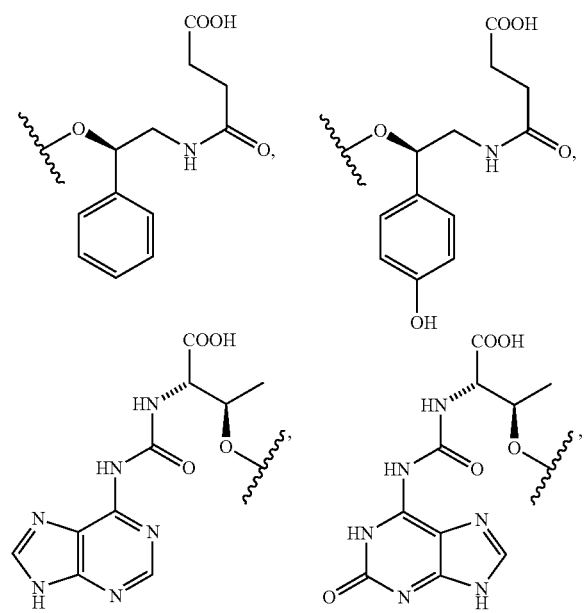

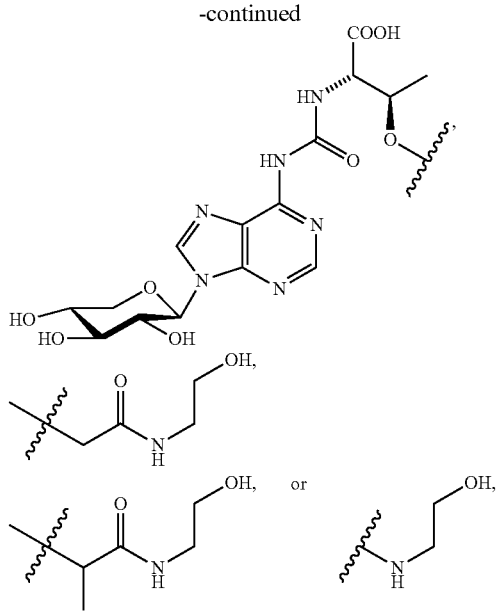

Such compounds include phenylethanolamine ascarosides (e.g., compounds labeled "pasc" herein), and ascaroside ethanolamides. Exemplary compounds according to this example include:

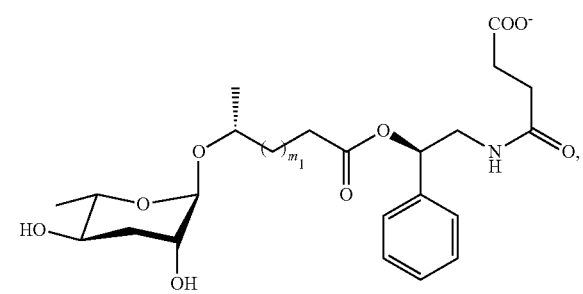

where $m_1$ is 1 (i.e., pasc#9), 2 (i.e., pasc#12), or 3 (i.e., pasc#1). Additional exemplary compounds according to this example also include the compounds as shown below:

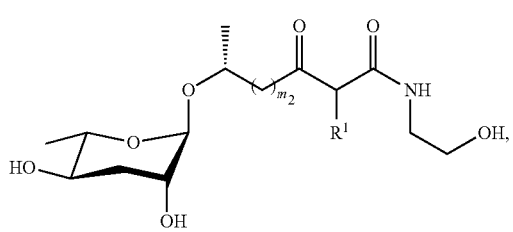

where $R^I$ is —$NH_3$ and $m_2$ is 20; or $R^I$ is H and $m_2$ is 22.

Another example of this embodiment is a compound in which condition (iv) is met. The at least two units of Formula I can be connected as described above. Suitable compounds according to this example include, e.g., compounds of Formula IE, Formula IF, Formula IE', Formula IF', and compounds that contain only two units of general Formula I. In some examples, $R^1$ is independently H or alkyl (e.g., —$CH_3$). Exemplary compounds include: compounds of Formula IE and IE' in which $R^{2a}$ is —$(CH_2)_nC(O)$—, $R^{2b}$ is —$(CH_2)_nC(O)$—, and both $R^{2a}$ and $R^{2b}$ are —$(CH_2)_nC(O)$—; compounds of Formula IF and IF' in which $R^{2a}$ is —$(CH_2)_nC(O)$—, $R^{2b}$ is —$(CH_2)_nC(O)$—, and both $R^{2b}$ and $R^{2b}$ are —$(CH_2)_nC(O)$—; compounds in which $R^3$ is H; compounds of Formula IE, IE', IF, and IF' in which each $R^1$ is independently H or alkyl (e.g., —$CH_3$); compounds of Formula IE, IE', IF, and IF' in which $R^3$ is H; compounds of IE, IE', IF, and IF' in which $R^4$ is independently H or —$C(O)R^8$, $R^8$ is an alkyl optionally substituted with —NHC(O)$R^9$, and $R^9$ is H or —$NH_2$. Compounds of IE, IE', IF, and IF include dimeric ascarosides (e.g., compounds labeled "dasc" or "ubas" (for "3-ureido isobutyrate ascaroside") herein), for example dasc#1, dasc#2 (also called ubas#1), and dasc#3 (also called ubas#2):

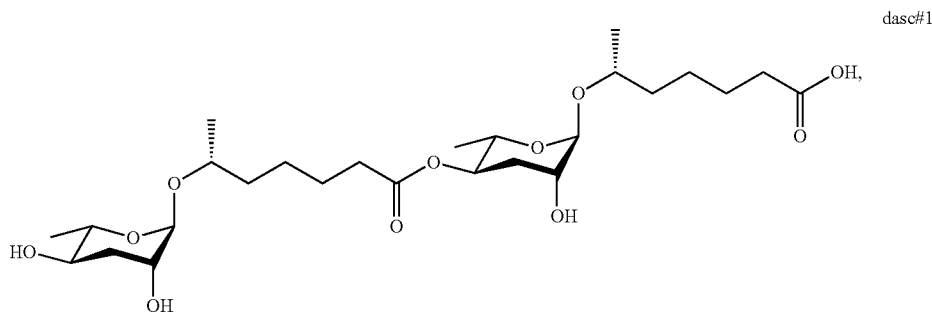

dasc#1

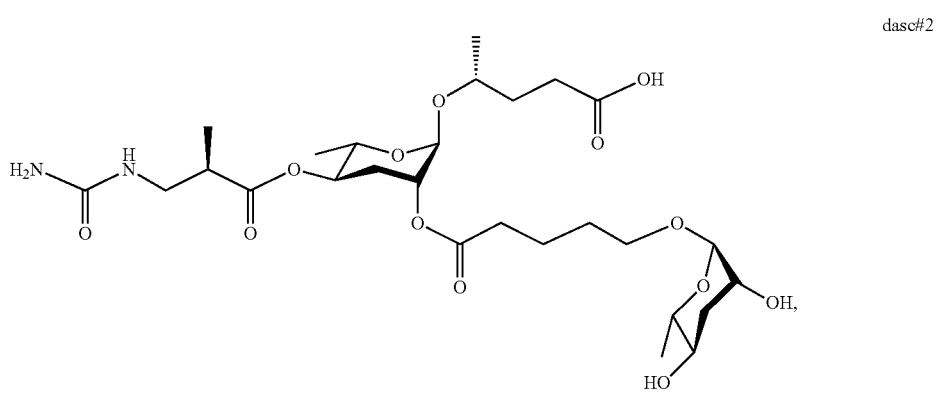

dasc#2

(ubas#1)

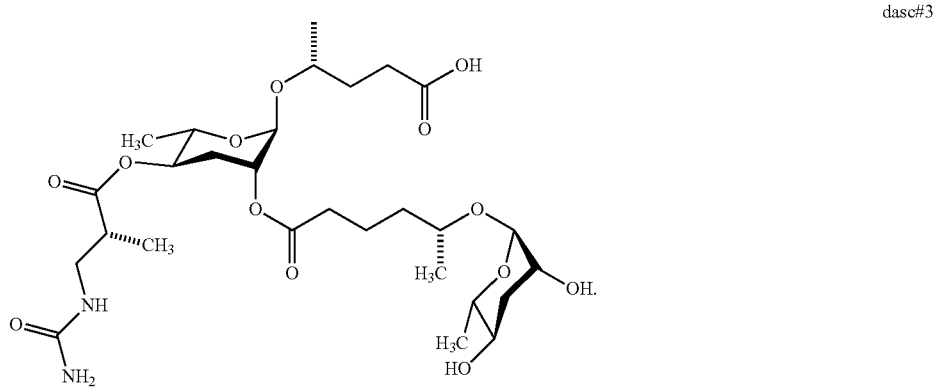

dasc#3

(ubas#2)

Another example of this embodiment is a compound in which condition (v) is met. The alkyl, alkenyl, aryl, heteroaryl, heterocyclyl, cycloalkyl, cycloalkenyl, acyl, amino acid, or nucleoside can be optionally substituted with one or more of the substituents defined herein. Suitable compounds according to this example include those in which $R^3$ and $R^4$ are each —C(O)$R^8$; $R^8$ is preferably an alkyl substituted with either —NHC(O)NH$_2$ or a monosaccharide having 5 or 6 carbon atoms (e.g., a hexose, such as a glycosyl). Suitable compounds according to this example also include those in which $R^8$ is —[CH$_2$]$_{n4}$NHC(O)$R^9$ or —[CH$_2$]$_{n4}$C(O)(NH)$R^9$; $R^9$ is preferably an alkyl or aryl substituted with one or more substituents selected from the group consisting of —OH, phenyl, phenol, and carboxyphenyl. Example compounds according to this example also include those in which $R^3$ and/or $R^4$ is:

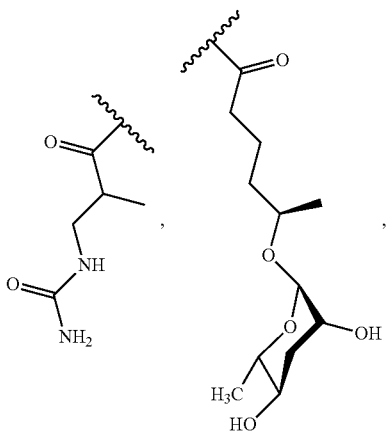

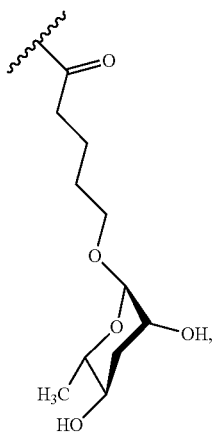

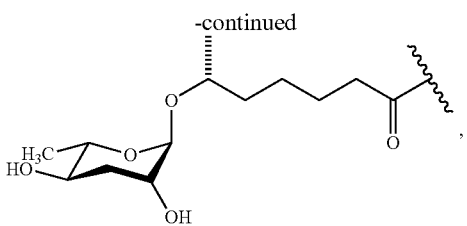

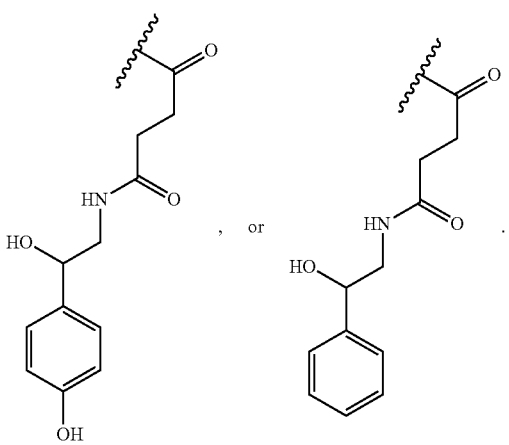

Another example of this embodiment is a compound in which condition (vi) is met. Exemplary compounds according to this example include, e.g., compounds of Formula I″a:

I″a

All the preferred and exemplary definitions of $R^1$, $R^{1'}$, $R^2$, $R^3$, $R^5$, $R^6$, $R^7$, $R^8$, and $R^9$ described above for conditions (i)-(iv) are also suitable in this example. Suitable compounds according to this example include, e.g., compounds of Formula I″ and I″a in which: $R^1$ is H or an alkyl (e.g., —CH$_3$) and R' is absent or H, the alkyl or alkenyl groups being optionally substituted with one or more of the substituents defined herein; $R^2$ is —(CH$_2$)$_n$C(O)$R^5$; $R^3$ is H; $R^4$ is H; $R^5$ is —OH or —OCHR$^6$R$^7$, with $R^6$, $R^7$, $R^8$, and $R^9$ being optionally defined as noted above for examples in which condition (iii) is met. Compounds according to this example also include paratosides (e.g., compounds labeled "part" herein) and nucleoside-containing paratosides (e.g., compounds labeled "npar" herein), for example part#9, npar#1, npar#2, and npar#3:

part#9

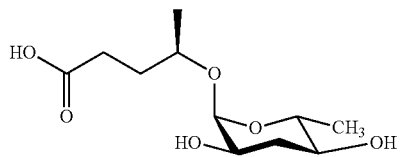

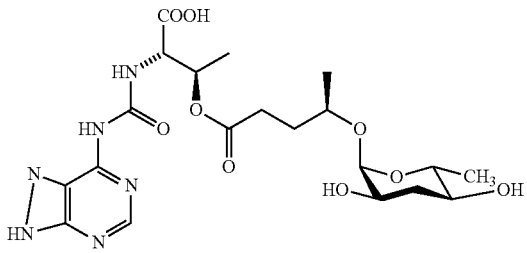

npar#1

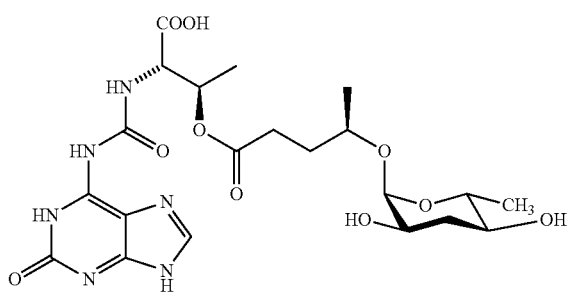

npar#2

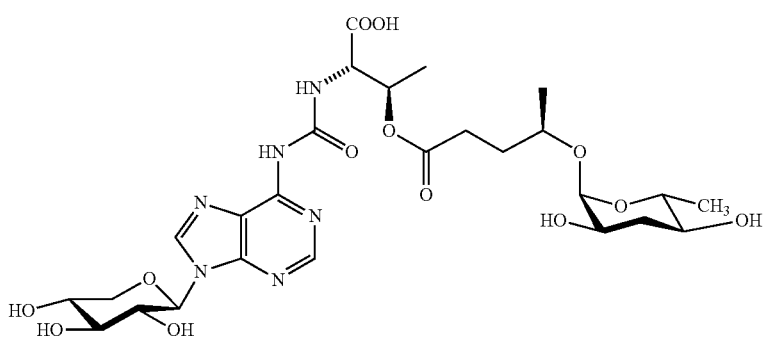

npar#3

Another aspect of the present invention relates to an isolated compound comprising at least one nucleobase, at least one fatty acid, at least one amino acid, and at least one sugar. The at least one nucleobase, the at least one fatty acid, the at least one amino acid, and the at least one sugar are linked by covalent bonds. The compound preferably has a molecular weight of less than about 2,000 g/mol.

Suitable nucleobases according to this aspect of the present invention include natural or synthetic nucleobases, and universal bases, as described above. In at least one embodiment, the at least one nucleobase is selected from the group consisting of purines, pyrimidines, adenine, guanine, thymine, uracil, cytosine, inosine, xanthine, hypoxanthine, nubularine, isoguanisine, tubercidine, and derivatives and analogues thereof. In at least one embodiment, the nucleobase is an optionally substituted purine, e.g., a purine having a substituent (e.g., an at least one sugar (e.g., pyranose, 3,6-dideoxy sugar)) linked to the 9 position. The at least one nucleobase may be connected to an at least one sugar, at least one amino acid, and/or at least one fatty acid through any atom on the nucleobase or, in the case of a nucleoside, the ribose sugar. For example, the nucleobase may be linked to an at least one amino acid via, e.g., a linkage to an exocyclic amino group on the nucleobase.

Suitable fatty acids according to this aspect of the present invention include saturated, unsaturated, and polyunsaturated fatty acids, as described above. In at least one embodiment, the at least one fatty acid comprises a hydroxy acid (e.g., a $C_{4-32}$ hydroxy acid). There may be multiple hydroxyl substituents on the aliphatic chain of the fatty acid. At least one hydroxy group is at the β position, as shown in Scheme 1 below.

Scheme 1

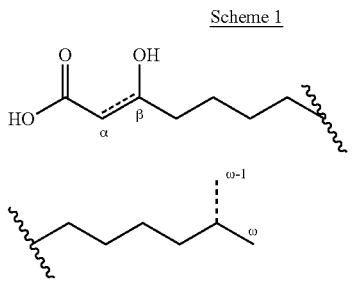

In at least one embodiment, the at least one fatty acid is the product of β-oxygenation. In such embodiments, at least one double bond occurs between the α and β positions of the fatty acid. In at least one embodiment, an at least one fatty acid is a $C_{4-32}$ hydroxy acid linked to an at least one sugar via, e.g., an ether linkage to a hydroxyl group of the hydroxy acid. This includes, e.g., linked via an ether linkage to its anomeric hydroxyl group, linked via a beta pyranosidic linkage, etc.

Suitable amino acids according to this aspect of the present invention include natural or synthetic amino acids, as described above. In at least one embodiment, the at least one amino acid is selected from the group consisting of alpha amino acids, beta amino acids, gamma amino acids, L-amino acids, and D-amino acids. A sidechain of the at least one amino acid may include, e.g., a substituent selected from the group consisting of: *—OR, *—NRR', *—SR, *—C(O)NRR', and *-Im-R, where *- represents the site of attachment of the substituent to a carbon atom of the amino acid, R is an acyl group arising from linkage to the carboxy group of an at least one fatty acid, Im is an imidazole ring, and R' is —H, an optionally substituted $C_{1-12}$ aliphatic, or an optionally substituted aryl.

Suitable sugars according to this aspect of the present invention include any carbohydrate known to those skilled in the art, including, e.g., monosaccharides. In at least one embodiment, the at least one sugar is selected from the group consisting of deoxy sugars, dideoxy sugars, and 3',6'-dideoxy sugars, including, e.g., ascarylose, mannose, pentose, hexose, ribose, and deoxyribose.

The at least one nucleobase, the at least one fatty acid, the at least one amino acid, and the at least one sugar can be connected to each other in any order through various connection atoms as long as such connection is valid and the resulting compound is stable.

Suitable embodiments according to this aspect of the present invention include, e.g., those in which an at least one fatty acid is linked to an at least one sugar (e.g., ascarylose) through ω-linking or through ω-1 linking, as shown in Scheme 1 above.

In at least one embodiment of this aspect of the present invention, the compound further comprises at least one second sugar. Suitable sugars include those identified above. In a preferred embodiment, the at least one second sugar is a pentose such as a ribose sugar or modified ribose sugar. Preferably, the at least one second sugar can form at least one nucleoside with an at least one nucleobase through a beta-glycosidic linkage.

Embodiments of this aspect of the present invention include compounds having the formula [NB]-[AA]-[FA]-[S], compounds having the formula [$S^1$]-[NB]-[AA]-[FA]-[$S^2$], and compounds having the formula [$S^1$]-[$S^2$]-[NB]-[AA]-[FA]-[$S^3$], where NB is a nucleobase, AA is an amino acid, FA is a fatty acid, and S, $S^1$, $S^2$, and $S^3$ are each independently a sugar. $S^1$ and NB in the second formula, and $S^2$ and NB in the third formula, can optionally form a nucleoside. The nucleoside may be linked, for example, via a urea linkage to the α amino group of the amino acid. The amino acid may comprise a sidechain having one or more heteroatoms. The fatty acid may be linked to the amino acid via, e.g., a covalent bond between a heteroatom present on the sidechain of the amino acid and the carboxy moiety of the fatty acid. For example, the amino acid may be linked to the carboxy group of the fatty acid by a an ester linkage, an amide linkage, a thioester linkage, an imide linkage, an acyl amidine linkage, an acyl guanidine linkage, etc. Alternatively, the amino acid may be linked to the fatty acid via, e.g., an ester linkage between the fatty acid carboxy group and a hydroxy group present on the amino acid sidechain.

The isolated compounds according to all aspects of the present invention may be prepared by the application or adaption of known methods. Suitable methods include the isolation of naturally-produced compounds, as well as synthesis using methods used heretofore or described in the literature, for example, those described by LAROCK: COMPREHENSIVE ORGANIC TRANSFORMATIONS (Wiley-VCH publishers, New York (1989)), which is hereby incorporated by reference in its entirety. Suitable methods for synthesizing compounds include those described in Examples 15-21, 35-43, and 80-81.

The present invention may be further illustrated by reference to the following examples.

EXAMPLES

The following Examples are intended to illustrate, but by no means are intended to limit, the scope of the present invention as set forth in the appended claims.

Example 1

Analytical Instrumentation and Procedures

Nuclear magnetic resonance (NMR) spectra were recorded on a Varian INOVA 600 NMR (600 MHz for $^1$H, 151 MHz for $^{13}$C). NMR-spectra were processed using Varian VNMR and MestreLabs MestReC software packages. Additional processing of bitmaps derived from NMR spectra was performed using Adobe Photoshop CS3 as described in Pungaliya et al., *PNAS* 106:7708-13 (2009), which is hereby incorporated by reference in its entirety. High-performance liquid chromatography-mass spectrometry (HPLC-MS) was performed using an Agilent 1100 Series HPLC system equipped with a diode array detector and connected to a Quattro II spectrometer (Micromass/Waters). Data acquisition and processing were controlled by MassLynx software. Flash chromatography was performed using a Teledyne ISCO CombiFlash system.

Example 2

*C. elegans* Strains and General Culture Methods

All strains were maintained at 20° C., unless mentioned otherwise, on NGM agar plates, made with Bacto agar (BD Biosciences) and seeded with OP50 bacteria grown overnight. *C. elegans* variety N2 Bristol and males from the him-5(e1490) strain CB1490 were used for the attraction bioassays and the automated tracker experiments. The him-5(e1490) mutant segregates XO male progeny by X chromosome nondisjunction during meiosis (Hodgkin et al., *Genetics* 91:67-94 (1979), which is hereby incorporated by reference in its entirety). The transgenic strain PS6025 qrIs2-[sra-9::mCasp1], which expresses mammalian caspase in the ASK neuron under the influence of the sra-9 promoter (gift of Tokumitsu Wakabayashi, Iwate University), was used for genetic ablation of the ASK neuron. Other strains used are as follows: CB4856, *C. elegans* Hawaii isolate (Hodgkin & Doniach, *Genetics* 146:149-64 (1997), which is hereby incorporated by reference in its entirety); RC301, *C. elegans* Freiburg isolate (de Bono & Bargmann, *Cell* 94:679-89 (1998); Hodgkin & Doniach, *Genetics* 146:149-64 (1997), which are hereby incorporated by reference in their entirety); DA609 npr-1(ad609); CX4148 npr-1(ky13) (de Bono & Bargmann, *Cell* 94:679-89 (1998), which is hereby incorporated by reference in its entirety); CX9740 *C. elegans* (N2); kyEx2144 [ncs-1::GFP] (Macosko et al., *Nature* 458:1171-75 (2009), which is hereby incorporated by reference in its entirety); N2; Ex(gcy-28::dp::mec-4D) (Shinkai et al., *J. Neurosci.* 31:3007-15 (2011), which is hereby incorporated by reference in its entirety); CX10981 kyEx2866 ["ASK::GCaMP2.2b" sra-9::GCaMP2.2b SL2 GFP, ofm-1::GFP] (ASK imaging line); CX11073 kyEx2916 ["AIA::GCaMP2.2b" T01A4.1::GCaMP2.2b SL2 GFP, ofm-1::GFP] (AIA imaging line) (Macosko et al., *Nature* 458:1171-75 (2009), which is hereby incorporated by reference in its entirety); DR476 daf-22 (m130) (Golden & Riddle, *Mol. Gen. Genet.* 198:534-36 (1985), which is hereby incorporated by reference in its entirety); and daf-22 (ok693) (Butcher et al., *PNAS* 106:1875-79 (2009), which is hereby incorporated by reference in its entirety).

Example 3

*C. elegans* Metabolite Naming

All newly identified ascarosides are named with four letter "SMID"s (SMID: Small Molecule IDentifiers), for instance, "icas#3" or "ascr#10." The SMID database, which is hereby incorporated by reference in its entirety, is an electronic resource maintained by Frank Schroeder and Lukas Mueller at the Boyce Thompson Institute in collaboration with Paul Sternberg and WormBase. This database catalogues newly identified *C. elegans* small molecules from *C. elegans* and other nematodes, assigns a unique four-letter SMID (a searchable, gene-style Small Molecule IDentifier) to the small molecule identified, and includes a list of other names and abbreviations used in the literature for each compound.

Example 4

Preparation of Metabolite Extracts

Metabolite extracts were prepared according to a method previously described in Pungaliya et al., *PNAS* 106:7708-13 (2009), which is hereby incorporated by reference in its entirety, which was modified as follows.

Worms (N2 or daf-22) from three 10 cm NGM plates were washed using M9-medium into a 100 mL S-medium pre-culture, where they were grown for 5 days at 22° C. on a rotary shaker. Concentrated *E. coli* OP50 derived from 1 L of bacterial culture (grown for 16 hours in LB media) was added as food at days 1 and 3. Subsequently, the pre-culture was divided equally into four 1 L Erlenmeyer flask containing 400 mL of S-medium for a combined volume of 425 mL of S-medium, which was then grown for an additional 10-day period at 22° C. on a rotary shaker. Concentrated OP50 derived from 1 L of bacterial culture was added as food every day from days 1 to 9. Subsequently, the cultures were centrifuged and the supernatant media and worm pellet were lyophilized separately. The lyophilized materials were extracted with 95% ethanol (250 mL, 2 times) at room temperature for 12 hours. The resulting yellow suspensions were filtered. The filtrate was then evaporated in vacuo at room temperature, producing media and worm pellet metabolite extracts.

Example 5

Chromatographic Fractionation

The media metabolite extract from two cultures was adsorbed on 6 g of octadecyl-functionalized silica gel and dry-loaded into an empty 25 g RediSep Rf sample loading cartridge. The adsorbed material was then fractionated via a reversed-phase RediSep Rf GOLD 30 g HPLC 18 column using a water-methanol solvent system. The solvent starts with 100% water for 4 minutes, followed by a linear increase of methanol content up to 100% methanol at 42 minutes, which was continued up until 55 minutes. The eight fractions generated from this fractionation were evaporated in vacuo. The residue was analyzed by HPLC-MS and two-dimensional nuclear magnetic resonance (2D-NMR) spectroscopy.

Example 6

Mass Spectrometric Analysis

Worm media extracts or metabolite fractions derived from the chromatographic fractionation were resuspended in 1.5 ml methanol and centrifuged at 2,000 g for 5 minutes. The supernatant was submitted to HPLC-MS analyses. HPLC was performed with an Agilent Eclipse XDB-C18 column (9.4×250 mm, 5 μm particle diameter). A 0.1% acetic acid-acetonitrile solvent gradient was used, starting with an acetonitrile content of 5% for 5 minutes, which was increased to 100% over a period of 40 minutes. Mass spectrometry was performed using electrospray ionization in either negative or positive ion mode.

Example 7

*C. elegans* Axenic Cultures and Biosynthetic Studies

Axenic in vitro cultures of *C. elegans* (N2, Bristol) were established as described by Nass & Hamza, *Curr. Protoc. Toxicol.* 31:1.9.1-1.9.18 (2007), which is hereby incorporated by reference in its entirety, using the *C. elegans* Maintenance Medium (CeMM, Lu & Goetsch, *Nematologica* 39:303-11 (1993), which is hereby incorporated by reference in its entirety) with cholesterol (5 mg/l) instead of sitosterol and nucleoside-5-phosphates. After 21 days, the cultures were centrifuged. The resulting supernatant media and worm pellet were lyophilized separately. The lyophilized worm pellets (1.2-2.0 mg) were extracted with 2 ml methanol, filtered, and then concentrated in vacuo. The lyophilized worm media were extracted with ethyl acetate-methanol (95:5, 100 mL, two times), filtered, and then concentrated in vacuo. Residues were taken up in 150 μl methanol and investigated by high-performance liquid chromatography-electrospray ionization tandem-mass spectrometry (HPLC-ESI-MS). For the application experiment, 50 ml CeMM medium was supplemented with 9.2 mg L-[2,4,5,6, 7-$D_5$]-tryptophan from Cambridge Isotope Laboratories.

Example 8

Spot Attraction Assays

The spot attraction assays were conducted according to a previously reported method (Pungaliya et al., *PNAS* 106: 7708-13 (2009); Srinivasan et al., *Nature* 454:1115-18 (2008), which are hereby incorporated by reference in their entirety). For both *C. elegans* hermaphrodites and males, 50-60 worms were harvested daily at the fourth larval stage (L4) and stored segregatedly by sex at 20° C. overnight, to be used as young adults the following day. For the competition experiments, two conditions were used: 120 nM ascr#3 and 10 nM icas#3 (Condition 1), or 12 μM ascr#3 and 1 µM icas#3 (Condition 2) in water containing 10% ethanol. Aliquots were stored at −20° C. in 20 µL tubes. 10% ethanol in water was used as control.

Example 9

Quadrant Chemotaxis Assays

Chemotaxis to both non-indole and indole ascarosides was assessed on 10 cm four-quadrant petri plates (Wicks et al., *Dev. Biol.* 221:295-307 (2000), which is hereby incorporated by reference in its entirety). Each quadrant was separated from adjacent ones by plastic spacers (FIG. 1B). Pairs of opposite quadrants were filled with nematode growth medium (NGM) agar containing either indole ascarosides or non-indole ascarosides at different concentrations. Animals were washed gently in a S-basal buffer, placed in the center of a four-quadrant plate with ascarosides in alternating quadrants, and scored after 15 minutes and 30 minutes. A chemotaxis index was calculated as: (the number of animals on ascaroside quadrants minus the number of animals on buffer quadrants)/(total number of animals).

Example 10

Measurement of Locomotory Parameters

Reversal frequency and velocity were measured using an automated worm-tracking system (Pungaliya et al., *PNAS* 106:7708-13 (2009); Srinivasan et al., *Nature* 454:1115-18 (2008), which are hereby incorporated by reference in their entirety).

Example 11

Aggregation Assays

Aggregation behavior of worms was measured using assays reported in de Bono & Bargmann, *Cell* 94:679-89 (1998), which is hereby incorporated by reference in its entirety. Aggregation assays were conducted on standard NGM plates. Plates containing indole ascarosides were made by adding the indole ascaroside stock solution to the NGM media before they were poured onto the plates. These plates were dried at room temperature for 2 to 3 days. Control plates were treated similarly, except that ethanol solutions instead of icas solutions were added to the plates, corresponding to the amount of ethanol introduced via the icas solutions. Final ethanol concentrations of the plates were below 0.1% for all conditions. After drying, both control plates and plates containing indole ascarosides were seeded with 150 µl of an overnight culture of *E. coli* OP50 using a micropipette, and were allowed to dry for 2 days at room temperature.

For "low worm density" experiments, 20 worms were placed onto the lawn and left at 20° C. for 3 hours. For "high worm density" experiments, approximately 120 worms were placed onto the bacterial lawn and left at 20° C. for 3 hours. Aggregation behavior was quantified as the number of animals that were in touch with two or more animals at greater than 50% of their body length.

Example 12

Calcium Imaging and Analysis

Transgenic lines that express the genetically encoded $Ca^{2+}$ sensor in ASK (kyEx2866) and AIA (kyEx2916) (Macosko et al., *Nature* 458:1171-75 (2009), which is hereby incorporated by reference in its entirety) were used for calcium imaging. Young adults or adult worms were inserted into an "Olfactory chip" microfluidic device (Chronis et al., *Nat. Methods* 4:727-31 (2007), which is hereby incorporated by reference in its entirety). Dilutions of icas#3 were done with S-basal buffer (with no cholesterol). As stock solutions of icas#3 contained small amounts of ethanol, equivalent amounts of ethanol were added to the S-basal control flow.

Imaging was conducted using an inverted Zeiss microscope equipped with an Andor camera. Exposure time for image acquisition was 300 milliseconds. Before imaging the ASK neuron, the worm was exposed to blue light for 3 minutes as ASK responds to the blue light itself. This step is necessary for the neuron to adapt to the blue light that is used for $Ca^{2+}$ measurements. Movies were analyzed using custom-made Matlab scripts. The first peak of fluorescence immediately after exposure to buffer or icas#3 was chosen for calculating the average change in fluorescence upon exposure to either buffer or icas#3. The value for this maximum was then subtracted from the mean fluorescence during the 5 seconds before the delivery of icas#3/buffer (corresponding to the region between 5 to 10 seconds in FIG. 2D).

Example 13

Statistical Analysis

Unpaired Student's t tests with Welch's correction was used: (i) for comparing attraction of hermaphrodites and males on indole ascarosides (*: $p<0.01$, : $p<0.001$, *: $p<0.0001$) (FIGS. 1C-1D, 3A, 3D, 4A, 5A, and 6C); (ii) to compare reversals between unablated and ASK ablated lines (*: $p<0.01$, : $p<0.001$) (FIGS. 7A-B); (iii) to compare the attraction of wild-type worms to the genetically ablated lines for ASK and AIA as well as the ASI and RMG neuron ablations (*: $p<0.0001$) (FIG. 2B); and (iv) for comparing G-CaMP fluorescence changes to buffer and icas#3 (**: $p<0.001$) (FIG. 2E). One-factor ANOVA followed by Dunnett's post-test was used: (i) for comparing the quadrant chemotaxis indices of the various strains (*: $p<0.05$, **: $p<0.01$) (FIGS. 1E and 3B-C); (ii) for comparing aggregation of solitary, social worms and Cel-daf-22 on plates containing indole ascarosides (*: $p<0.05$, **: $p<0.01$) (FIGS. 5C, 6A-B, and 8A-C); (iii) to compare stopped duration of worms on plates with indole ascarosides (*: $p<0.05$, **: $p<0.01$) (FIG. 8D); and (iv) to compare velocities and reversal frequencies on plates with indole ascarosides (*: $p<0.05$, **: $p<0.01$) (FIGS. 6D-E). All error bars indicate standard error of mean (S.E.M).

Example 14

Calculation of Number of Molecules of icas#3 in One L4 Worm Volume at 100 fM The number of molecules (n) of icas#3 in one L4 worm volume at 100 fM (femtomolar) was calculated using equation (1):

$$n = V_{YA} * c * N_A \qquad (1)$$

where:
$V_{YA}$=volume of *C. elegans* young adult (Knight et al., *Evol. Dev.* 4:16-27 (2002), which is hereby incorporated by reference in its entirety)
c=concentration (100 fM)
$N_A$=Avogadro's number In this case, $V_{YA}=3*10^6$ μm³$=3*10^{-9}$ L and c=10 fM= $10^{-14}$ M. Solving for n, $n=V_{YA}*c*NA=3*10^{-9}$ L*$10^{-14}$ mol*L$^{-1}$*$6.022*10^{23}$ mol$^{-1}$=18 molecules. Therefore, there are 18 icas#3 molecules contained in one worm volume of agar at an icas#3 concentration of 10 fM.

Example 15

Chemical Syntheses

Samples of indole ascarosides icas#1, icas#7, icas#3, and icas#9 for use in biological assays and as standards for HPLC-MS were prepared via chemical synthesis. Detailed synthetic procedures and NMR-spectroscopic data are set forth in Examples 16-21.

Example 16

Synthesis of Ascaroside ascr#9

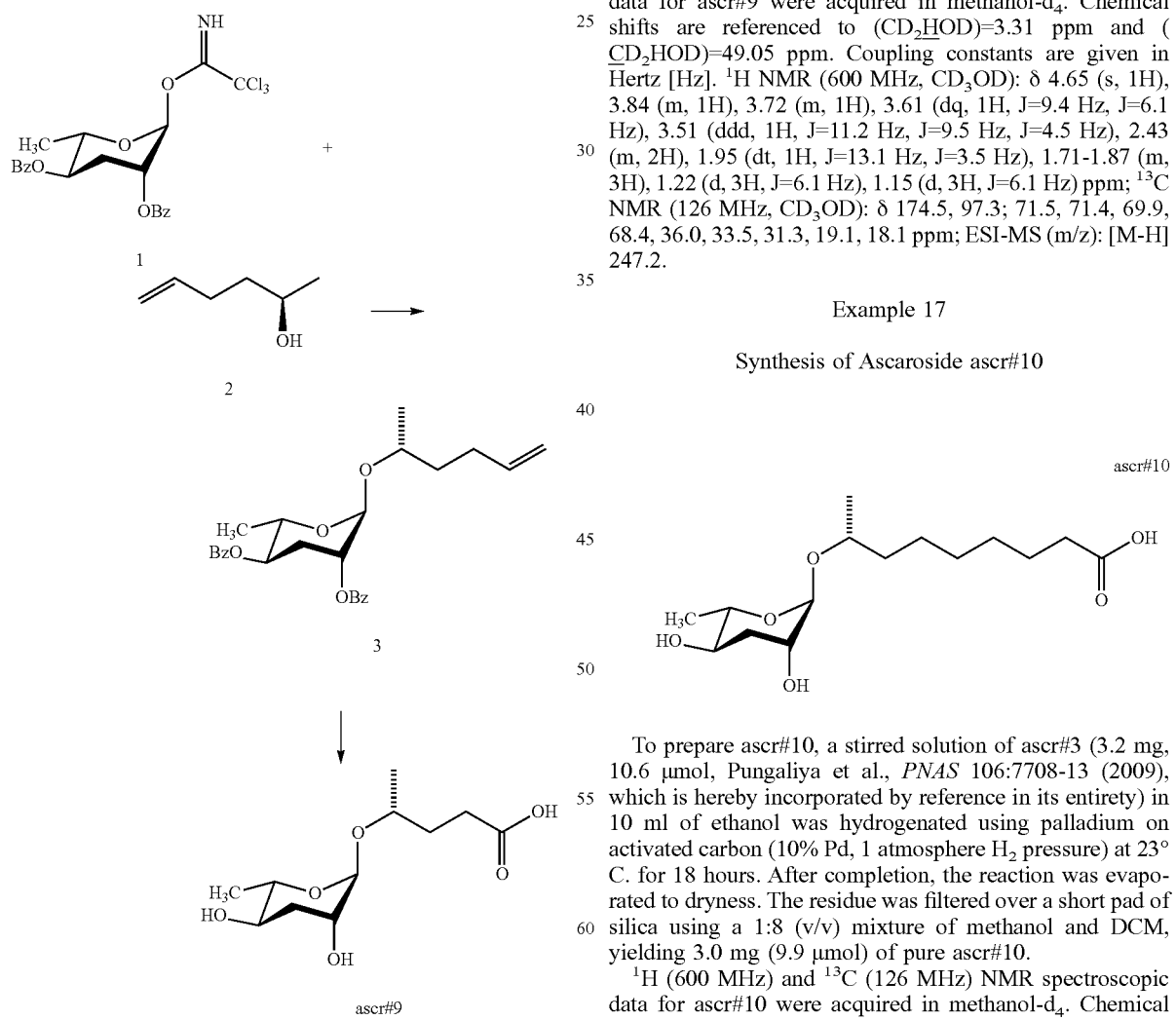

To prepare ascr#9, (R)-hex-5-en-2-ol 2 (32 mg, 0.32 mmol) (prepared as described in Pungaliya et al., *PNAS* 106:7708-13 (2009), which is hereby incorporated by reference in its entirety, using the conditions described for the synthesis of ascr#6) was coupled to trichloroacetimide 1 (150 mg, 0.3 mmol, Pungaliya et al., *PNAS* 106:7708-13 (2009), which is hereby incorporated by reference in its entirety). The resulting glycoside 3 (92 mg, 0.21 mmol) was dissolved in acetone (2 ml) and treated with 2 ml of a 1 M solution of potassium permanganate. After 30 minutes, the reaction mixture was poured into a mixture of ice-cold saturated aqueous sodium chloride solution (5 ml), acetic acid (0.1 ml), and dichloromethane (DCM) (5 ml). The organic phase was separated and the aqueous phase was extracted with two 5 ml-portions of DCM. The combined organic extracts were dried over sodium sulfate, evaporated to dryness, and re-dissolved in a mixture of 0.5 M aqueous lithium hydroxide (2 ml) and dioxane (6 ml). The mixture was stirred for 3 hours at 70° C., then cooled to 23° C. and acidified with 0.2 M aqueous hydrochloric acid. The mixture was evaporated to dryness and purified via Combiflash column chromatography using a methanol-DCM solvent gradient, yielding 15.6 mg (0.063 mmol) of pure ascr#9 as a viscous oil.

$^1$H (600 MHz) and $^{13}$C (126 MHz) NMR spectroscopic data for ascr#9 were acquired in methanol-d$_4$. Chemical shifts are referenced to (CD$_2$HOD)=3.31 ppm and (CD$_2$HOD)=49.05 ppm. Coupling constants are given in Hertz [Hz]. $^1$H NMR (600 MHz, CD$_3$OD): δ 4.65 (s, 1H), 3.84 (m, 1H), 3.72 (m, 1H), 3.61 (dq, 1H, J=9.4 Hz, J=6.1 Hz), 3.51 (ddd, 1H, J=11.2 Hz, J=9.5 Hz, J=4.5 Hz), 2.43 (m, 2H), 1.95 (dt, 1H, J=13.1 Hz, J=3.5 Hz), 1.71-1.87 (m, 3H), 1.22 (d, 3H, J=6.1 Hz), 1.15 (d, 3H, J=6.1 Hz) ppm; $^{13}$C NMR (126 MHz, CD$_3$OD): δ 174.5, 97.3; 71.5, 71.4, 69.9, 68.4, 36.0, 33.5, 31.3, 19.1, 18.1 ppm; ESI-MS (m/z): [M-H] 247.2.

Example 17

Synthesis of Ascaroside ascr#10

To prepare ascr#10, a stirred solution of ascr#3 (3.2 mg, 10.6 μmol, Pungaliya et al., *PNAS* 106:7708-13 (2009), which is hereby incorporated by reference in its entirety) in 10 ml of ethanol was hydrogenated using palladium on activated carbon (10% Pd, 1 atmosphere H$_2$ pressure) at 23° C. for 18 hours. After completion, the reaction was evaporated to dryness. The residue was filtered over a short pad of silica using a 1:8 (v/v) mixture of methanol and DCM, yielding 3.0 mg (9.9 μmol) of pure ascr#10.

$^1$H (600 MHz) and $^{13}$C (126 MHz) NMR spectroscopic data for ascr#10 were acquired in methanol-d$_4$. Chemical shifts were referenced to (CD$_2$HOD)=3.31 ppm and (CD$_2$HOD)=49.05 ppm. Coupling constants were given in Hertz [Hz]. $^1$H NMR (600 MHz, CD$_3$OD): δ 4.64 (s, 1H), 3.78 (m, 1H), 3.71 (m, 1H), 3.63 (dq, 1H, J=9.3 Hz, J=6.2

Hz), 3.51 (ddd, 1H, J=11.2 Hz, J=9.3 Hz, J=4.6 Hz), 2.27 (t, 2H, J=7.4 Hz), 1.94 (dt, 1H, J=13.0 Hz, J=3.7 Hz), 1.77 (ddd, 1H, J=13.3 Hz, J=11.5 Hz, J=3.0 Hz), 1.61 (m, 2H), 1.56 (m, 1H), 1.46 (m, 1H), 1.32-1.38 (m, 6H), 1.21 (d, 3H, J=6.2 Hz), 1.12 (d, 3H, J=6.1 Hz) ppm; $^{13}$C NMR (126 MHz, CD$_3$OD): δ 177.7, 97.3, 72.3, 71.0, 69.8, 68.1, 38.1, 38.2, 35.7, 34.9, 30.0, 26.5, 26.0, 19.0, 18.0 ppm; ESI-MS (m/z): [M-H] 303.2.

Example 18

Synthesis of Indole Carboxy Ascaroside icas#1

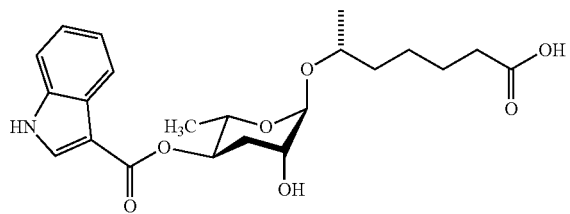

icas#1

To prepare icas#1, ascr#1 was first converted into the corresponding methyl ester. Ascr#1 (10 mg, 0.036 mmol), prepared as reported in Pungaliya et al., *PNAS* 106:7708-13 (2009), which is hereby incorporated by reference in its entirety, was dissolved in a mixture of toluene (1 mL) and methanol (1 mL). To this mixture, a solution of trimethylsilyldiazomethane (TMS-diazomethane) (2 M solution in hexane, 50 µL, 0.1 mmol) was added. After stirring for 20 minutes at 23° C., excess TMS-diazomethane was destroyed by addition of acetic acid (40 µL) and the solvents were removed in vacuo, yielding the methyl ester of ascr#1 (10.3 mg, 0.035 mmol) as a viscous oil.

Next, a solution of indole-3-carbonyl chloride was prepared. A well-stirred suspension of indole-3-carboxylic acid (67.7 mg, 0.42 mmol) in dry DCM (2 ml) containing a small amount of dimethylformamide (DMF) (20 µL) was treated with oxalyl chloride (0.84 mmol, 107 mg, 72 µL) at 0° C. Following addition of the oxalyl chloride, the mixture was stirred for 20 minutes at 23° C., producing a clear, slightly yellow solution. This solution was evaporated to dryness in vacuo at 0.1 Torr to ensure removal of excess oxalyl chloride, and was subsequently re-dissolved in 2 ml of dry DCM.

The sample of ascr#1 methyl ester (10.3 mg, 0.035 mmol) was dissolved in 1 ml of dry DCM, to which diisopropylethylamine was added (129 mg, 1 mmol). The resulting solution was equipped with an effective stir bar and cooled to −20° C. Subsequently, the solution of indole-3-carboxylic acid chloride was added drop-wise over a period of 10 minutes with vigorous stirring. The well-stirred reaction was gradually warmed to −7° C., at which temperature ice cold saturated aqueous sodium bicarbonate solution (2 ml) was added. The biphasic mixture was allowed to warm to 20° C., and was extracted three times with ethyl acetate. The combined ethyl acetate extracts were evaporated in vacuo and subjected to column chromatography on silica gel using 0-10% methanol in DCM.

Fractions containing the bis-2,4-O-(-indole-3-carbonyl)-derivative of the ascr#1 methyl ester were combined, evaporated to dryness, and treated with a mixture of 3 ml aqueous 0.5 M lithium hydroxide solution and 7 ml dioxane at 67° C. for 3 hours. Subsequently, the reaction mixture was cooled to 23° C., neutralized by addition of 0.2 M aqueous hydrochloric acid, and evaporated in vacuo. The residue was purified by HPLC with an Agilent Eclipse XDB C-18 column (25 cm×9.4 mm, 5 µm particle diameter). Acetonitrile and 0.1% aqueous acetic acid were used as solvents, increasing the percentage of acetonitrile from 15% at 0 minute to 85% at 30 minutes. Icas#1-containing fractions were evaporated, yielding 5.8 mg (0.014 mmol) of the target compound as a wax-like white solid.

$^1$H (600 MHz), $^{13}$C (126 MHz), and HMBC NMR spectroscopic data for icas#1 were obtained using methanol-d$_4$ and are shown in Table 1 below. Chemical shifts are referenced to (CD$_2$HOD)=3.31 ppm and (CD$_2$HOD)=49.05 ppm. Coupling constants are given in Hertz [Hz]; *: interchangeable.

TABLE 1

NMR spectroscopic data of icas#1

| Position | δ $^{13}$C [ppm] | δ $^1$H [ppm] | $^1$H—$^1$H-coupling constants |
|---|---|---|---|
| 1 | 177.6 | | |
| 2 | 35.1 | 2.35 | $J_{2,3}$ = 7.4 |
| 3 | 26.6* | 1.45-1.70 | |
| 4 | 26.2* | 1.45-1.70 | |
| 5 | 38.1 | 1.45-1.70 | |
| 6 | 72.7 | 3.86 | |
| 7 | 19.4 | 1.17 | $J_{6,7}$ = 6.1 |
| 1' | 97.7 | 4.75 | |
| 2' | 69.6 | 3.79 | |
| 3' | 33.5 | 2.01 (ax) | $J_{3'ax, 3'eq}$ = 13.0, $J_{3'ax, 4'}$ = 11.4, $J_{2', 3'ax}$ = 2.9 |
| | | 2.21 (eq) | $J_{2', 3'eq}$ = 3.2, $J_{3'eq, 4'}$ = 4.7 |
| 4' | 70.6 | 5.12 | $J_{4', 5'}$ = 9.6 |
| 5' | 68.8 | 4.05 | $J_{5', 6'}$ = 6.3 |
| 6' | 18.3 | 1.24 | |
| 2" | 133.5 | 7.97 | |
| 3" | 108.4 | | |
| 3"-COO | 166.5 | | |
| 3a" | 127.3 | | |
| 4" | 121.9 | 8.02 | $J_{4", 5"}$ = 7.2 |
| 5" | 122.7 | 7.16 | |
| 6" | 123.8 | 7.29 | |
| 7" | 113.1 | 7.44 | $J_{6", 7"}$ = 7.9 |
| 7a" | 138.2 | | |

Example 19

Synthesis of Indole Carboxy Ascaroside icas#3

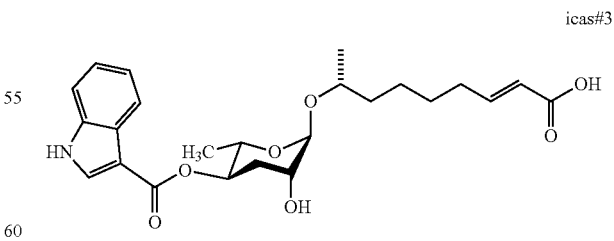

icas#3

To prepare icas#3, ascr#3 was first converted into the corresponding methyl ester. Ascr#3 (5.2 mg, 0.017 mmol), prepared as reported in Pungaliya et al., *PNAS* 106:7708-13 (2009), which is hereby incorporated by reference in its entirety, was dissolved in a mixture of toluene (1 mL) and methanol (1 mL). To this mixture, a solution of TMS-diazomethane (2 M solution in hexane, 25 μL, 0.05 mmol) was added. After stirring for 20 minutes at 23° C., excess TMS-diazomethane was destroyed by addition of acetic acid (30 μL) and the solvents were removed in vacuo, yielding the methyl ester of ascr#3 (5.3 mg, 0.017 mmol) as a viscous oil.

The sample of ascr#3 methyl ester (10.3 mg, 0.035 mmol) was reacted with indole carbonyl chloride as described in Example 18 for the preparation of icas#1, using proportionally smaller amounts of all reagents. Purification of the crude reaction products via HPLC using the conditions described in Example 18 yielded icas#3 (2.3 mg, 5.2 μmol) as a colorless oil.

$^1$H (600 MHz), $^{13}$C (126 MHz), and HMBC NMR spectroscopic data for icas#3 were obtained using methanol-d$_4$ and are shown in Table 2 below. Chemical shifts are referenced to (CD$_2$HOD)=3.31 ppm and (CD$_2$HOD)=49.05 ppm. Coupling constants are given in Hertz [Hz].

TABLE 2

NMR spectroscopic data of icas#3

| Position | $^{13}$C [ppm] | $^1$H [ppm] | $^1$H—$^1$H-coupling constants | Relevant HMBC correlations |
|---|---|---|---|---|
| 1 | 173.7 | | | |
| 2 | 126.7 | 5.82 | $J_{2,3}$ = 15.1 | |
| 3 | 147.8 | 6.79 | $J_{3,4}$ = 6.9 | C-1, C-4, C-5 |
| 4 | 33.6 | 2.23 | | C-2, C-3, C5, C-6 |
| 5 | 29.9 | 1.54 | | C-4, C-6 |
| 6 | 27.2 | 1.51 | | |
| 7 | 38.7 | 1.53 | | C-5, C-6, C-8 |
| 8 | 73.1 | 3.83 | | C-6, C-7, C-9 |
| 9 | 19.9 | 1.15 | $J_{8,9}$ = 6.1 | C-7, C-8 |
| 1' | 98.0 | 4.73 | | C-3', C-5', C-8 |
| 2' | 70.1 | 3.77 | | C-4' |
| 3' | 33.8 | 1.98 (ax) | $J_{3'ax, 3'eq}$ = 13.0, $J_{3'ax, 4'}$ = 11.4, $J_{2',3'ax}$ = 2.9 | |
| | | 2.19 (eq) | $J_{2', 3'eq}$ = 3.2, $J_{3'eq, 4'}$ = 4.7 | C-4' |
| 4' | 70.9 | 5.09 | $J_{4', 5'}$ = 9.6 | C-6' |
| 5' | 69.1 | 4.02 | $J_{5', 6'}$ = 6.3 | C-4' |
| 6' | 18.8 | 1.21 | | C4', C-5' |
| 2" | 133.9 | 7.94 | | C-3", C-3a", C-7a" |
| 3" | 108.8 | | | |
| 3"-COO | 167.0 | | | |
| 3a" | 127.9 | | | |
| 4" | 122.3 | 7.99 | $J_{4", 5"}$ = 7.4 | C-6", C-7a", 3"-COO |
| 5" | 123.0 | 7.15 | | C-3a", C-7" |
| 6" | 124.2 | 7.18 | | C-4", C-7a" |
| 7" | 113.5 | 7.42 | $J_{6", 7"}$ = 7.9 | C-3a", C-5" |
| 7a" | 138.8 | | | |

Example 20

Synthesis of Indole Carboxy Ascaroside icas#7

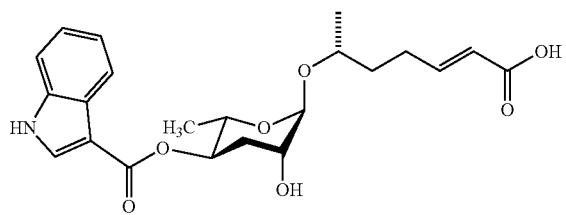

icas#7

A standard sample of icas#7 (120 μg) was obtained from ascr#7 (0.5 mg, Pungaliya et al., *PNAS* 106:7708-13 (2009), which is hereby incorporated by reference in its entirety) as described in Example 18 for the preparation of icas#1 from ascr#1.

$^1$H (600 MHz) NMR spectroscopic data for icas#7 were obtained using methanol-d$_4$ and are shown in Table 3 below. Chemical shifts are referenced to (CD$_2$HOD)=3.31 ppm. Coupling constants are given in Hertz [Hz].

TABLE 3

NMR spectroscopic data of icas#7

| Position | $^1$H [ppm] | $^1$H—$^1$H-coupling constants |
|---|---|---|
| 2 | 5.84 | $J_{2,3}$ = 15.3 |
| 3 | 6.99 | $J_{3,4}$ = 6.8 |
| 4 | 2.40 | |
| | 2.33 | |
| 5 | 1.70 | |
| | 1.65 | |
| 6 | 3.91 | |
| 7 | 1.18 | $J_{6,7}$ = 6.1 |
| 1' | 4.75 | |
| 2' | 3.80 | |
| 3' | 2.03 (ax) | $J_{3'ax, 3'eq}$ = 13.0, $J_{3'ax, 4'}$ = 11.4, $J_{2', 3'ax}$ = 2.9 |
| | 2.21 (eq) | $J_{2', 3'eq}$ = 3.2, $J_{3'eq, 4'}$ = 4.7 |
| 4' | 5.12 | $J_{4', 5'}$ = 9.6 |
| 5' | 4.07 | $J_{5', 6'}$ = 6.3 |
| 6' | 1.24 | |
| 2" | 7.97 | |
| 4" | 8.04 | $J_{4", 5"}$ = 7.5 |
| 5" | 7.15 | |
| 6" | 7.16 | |
| 7" | 7.43 | $J_{6", 7"}$ = 7.9 |

Example 21

Synthesis of Indole Carboxy Ascaroside icas#9

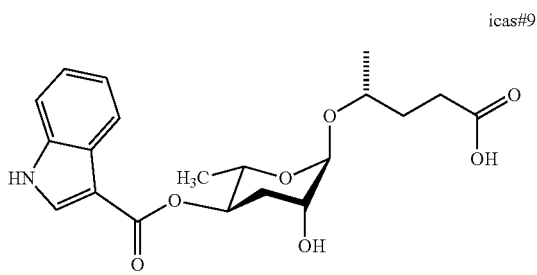

icas#9

Icas#9 was obtained from ascr#9 as described in Example 18 for the preparation of icas#1 from ascr#1. NMR-spectroscopic data are in agreement with published data (Butcher et al., *Org. Lett.* 11:3100-03 (2009), which is hereby incorporated by reference in its entirety).

Example 22

Identification of the Indole Ascaroside icas#3 Via Comparative Metabolomics

All currently known small-molecule pheromones in *C. elegans* are derived from peroxisomal β-oxidation of long-chained fatty acids via DAF-22, a protein with strong homology to human sterol carrier protein SCPx (Pungaliya et al., *PNAS* 106:7708-13 (2009); Butcher et al., *PNAS* 106:1875-79 (2009), which are hereby incorporated by reference in their entirety). It was suspected that putative aggregation pheromones may be derived from the same pathway, suggesting that daf-22 mutants would not produce them. In that case, a spectroscopic comparison of the wild-type metabolome with that obtained from daf-22 mutant worms should reveal candidate compounds for attraction or aggregation signals.

In a previous study, an NMR spectroscopy-based technique termed Differential Analysis of NMR spectra ("DANS") was used to compare the wild-type metabolome with that of daf-22 mutant worms (Pungaliya et al., *PNAS* 106:7708-13 (2009), which is hereby incorporated by reference in its entirety). This comparison had led to the identification of ascr#6-8, of which ascr#8 is a major component of the male-attracting signal (Pungaliya et al., *PNAS* 106:7708-13 (2009), which is hereby incorporated by reference in its entirety). Based on NMR spectra with improved signal-to-noise ratio, a more detailed comparison of wild type and daf-22-mutant metabolomes was conducted, revealing several indole-containing compounds in the wild-type metabolome that were not produced by daf-22 worms (FIGS. 9B-C). The established role of DAF-22 in pheromone biosynthesis (Pungaliya et al., *PNAS* 106:7708-13 (2009); Butcher et al., *PNAS* 106:1875-79 (2009); Golden & Riddle, *Mol. Gen. Genet.* 198:534-36 (1985), which are hereby incorporated by reference in their entirety) suggests that these indole derivatives may represent a previously unrecognized family of signaling molecules.

To clarify the structures and biological roles of the daf-22-dependent indole derivatives, complete identification of these indole derivatives was pursued via NMR spectroscopy-guided fractionation of the wild-type metabolome. Reverse-phase chromatography produced eight metabolite fractions, which were analyzed by two-dimensional NMR spectroscopy. The NMR spectra revealed the presence of daf-22-dependent indole derivatives in two fractions, which were selected for additional NMR-spectroscopic and mass spectrometric studies. These analyses indicate that the most abundant daf-22-dependent indole derivative consists of an indole-carboxy unit linked to ascarylose bearing a 9-carbon unsaturated side-chain identical to that found in the known ascr#3 (Srinivasan et al., *Nature* 454:1115-18 (2008), which is hereby incorporated by reference in its entirety) (see NMR and MS data in Examples 18-19, FIGS. 10-13). Based on its structural relationship to the known ascr#3, this newly identified metabolite was named indole carboxy ascaroside "icas#3" (FIG. 9E).

Example 23

Icas#3 is Part of a Larger Family of Tryptophan-Derived Small Molecules

Some other daf-22-dependent indole compounds detected by DANS were investigated to determine whether they also represent indole ascarosides. A mass spectrometric (MS) approach was employed for this investigation, as analysis of the mass spectra of icas#3 had revealed a characteristic MS fragmentation pattern (loss of the indole-3-carboxy moiety, FIG. 12) that enabled a screen for related compounds.

MS screening for compounds with similar fragmentation profiles indicates that icas#3 is a member of a larger series of indole ascarosides featuring side chains with five to nine carbons (FIGS. 9D-E). The most abundant components of this family of indole ascarosides are icas#3, icas#9, and icas#10, which are accompanied by smaller amounts of icas#1 and icas#7 (FIG. 9E). All of these compounds represent new metabolites, except for icas#9, which has been reported to possess moderate dauer-inducing activity and is unique among known dauer pheromones in producing a bell-shaped response curve (Butcher et al., *Org. Lett.* 11:3100-03 (2009), which is hereby incorporated by reference in its entirety).

Two new non-indole ascarosides were also detected: ascr#9, which features a saturated 5-carbon side chain, and ascr#10, which features a saturated 9-carbon side chain, representing the saturated analog of the known ascr#3 (FIG. 9F).

The MS analyses further revealed that the indole ascarosides' quantitative distribution is distinctly different from that of the corresponding non-indole ascarosides, suggesting that incorporation of the indole unit is strongly regulated. The most abundant indole ascaroside, icas#3, is accompanied by 10- to 40-fold larger amounts of the corresponding non-indole ascaroside, ascr#3; whereas icas#9 is more abundant than the corresponding ascr#9 (FIG. 9G).

To determine the biosynthetic origin of the indole ascarosides and to exclude the possibility that they are produced by the *E. coli* food source, axenic (bacteria-free) in vitro cultures of *C. elegans* (N2) were established using the chemically defined CeMM medium (Lu & Goetsch, *Nematologica* 39:303-11 (1993); Nass & Hamza, *Curr. Protoc. Toxicol.* 31:1.9.1-1.9.18 (2007), which are hereby incorporated by reference in their entirety). HPLC-MS analysis of the axenic cultures revealed the presence of icas#1, icas#3, icas#9, and icas#10, thus indicating that indole ascarosides are produced by *C. elegans* without participation of dietary bacteria. Use of a 1:1 mixture of L-[2,4,5,6,7-$D_5$]-tryptophan and L-tryptophan in the axenic medium resulted in production of [$D_5$]-icas#1, [$D_5$]-icas#3, [$D_5$]-icas#9, and [$D_5$]-icas#10, along with equivalent amounts of the unlabelled compounds (FIG. 13). In conclusion, these biochemical studies established the tryptophan origin of the indole-3-carboxy moiety in the indole ascarosides and indicate that these compounds are products of a strongly regulated biosynthetic pathway.

Example 24

Indole Ascarosides Strongly Attract Hermaphrodites

The addition of an indole-3-carboxy moiety to the ascarosides represents a significant structural change. This chemical difference may indicate signaling functions for these compounds distinct from those of their non-indole cognates.

Three synthetic indole ascarosides of varying side-chain lengths, icas#1, icas#3, and icas#9, were tested in the spot attraction assay to demonstrate social functions of small molecules (Pungaliya et al., *PNAS* 106:7708-13 (2009); Srinivasan et al., *Nature* 454:1115-18 (2008), which are hereby incorporated by reference in their entirety) (FIG. 1A). All three tested indole ascarosides, icas#1, icas#3, and icas#9, attracted both males and hermaphrodites at high concentrations (FIG. 1C). Testing the most abundant indole ascaroside, icas#3, over a broader range of concentrations revealed that, at low concentrations, icas#3 was strongly attractive to hermaphrodites, whereas males were no longer attracted (FIG. 1D). Similarly, hermaphrodites, but not males, were strongly attracted to low concentrations of icas#9 (FIG. 5A).

Hermaphrodite attraction to icas#3 was further investigated using a quadrant chemotaxis bioassay as reported in Macosko et al., *Nature* 458:1171-75 (2009); Wicks et al., *Dev. Biol.* 221:295-307 (2000), which are hereby incorporated by reference in their entirety (FIG. 1B). In contrast to the spot attraction assay, which measures attraction to a point source of compounds, the quadrant chemotaxis assay measures aggregation of hermaphrodites on plate sections with well-defined compound concentration (Macosko et al., *Nature* 458:1171-75 (2009); Wicks et al., *Dev. Biol.* 221: 295-307 (2000), which are hereby incorporated by reference in their entirety). It was found that concentrations as low as 1 pM icas#3 resulted in a strong attraction of hermaphrodites (FIG. 1E), both in the presence and absence of food (FIG. 5B).

The biological role of icas#3 thus starkly differs from that of the corresponding non-indole ascaroside ascr#3, which strongly attracts males but repels hermaphrodites (Pungaliya et al., *PNAS* 106:7708-13 (2009); Srinivasan et al., *Nature* 454:1115-18 (2008), which are hereby incorporated by reference in their entirety). The results herein show that by simply attaching an indole-3-carboxy group to the 4-position of the ascarylose, the strongly male-attracting ascr#3 is converted into a signal that primarily attracts hermaphrodites. The difference in the amounts at which ascr#3 and icas#3 are produced by the worms corresponds to their relative potency: the male-attracting ascr#3, which is of much lower potency than icas#3, is produced in much higher concentrations than the highly potent hermaphrodite attractant icas#3 (FIG. 9G).

Example 25

Solitary and Social Wild-Type Hermaphrodites are Attracted to icas#3, but not to Non-Indole Ascarosides The results from the spot attraction and quadrant chemotaxis assays indicate that hermaphrodites are strongly attracted to indole ascarosides, suggesting that these compounds regulate *C. elegans* aggregation behavior. *C. elegans* exhibits natural variation in its foraging behavior, with some strains (e.g., the common laboratory strain N2) dispersing individually on a bacterial lawn, whereas most wild-type strains (e.g., RC301 and CB4856 (Hawaii)) accumulate and aggregate where bacteria are the most abundant (de Bono & Bargmann, *Cell* 94:679-89 (1998); Hodgkin & Doniach, *Genetics* 146:149-64 (1997), which are hereby incorporated by reference in their entirety). These variants are referred to as "solitary" and "social," respectively (de Bono & Bargmann, *Cell* 94:679-89 (1998); Rogers et al., *Nat. Neurosci.* 6:1178-85 (2003), which are hereby incorporated by reference in their entirety). These differences in foraging and aggregation behavior are associated with two different alleles of the neuropeptide Y-like receptor NPR-1 (de Bono & Bargmann, *Cell* 94:679-89 (1998); Rogers et al., *Nat. Neurosci.* 6:1178-85 (2003), which are hereby incorporated by reference in their entirety), which differ at a single amino acid position: solitary strains such as N2 express a high-activity variant of NPR-1 (215-valine), whereas aggregating strains such as CB4856 express a low-activity variant of NPR-1 (215-phenylalanine) (de Bono & Bargmann, *Cell* 94:679-89 (1998); Rogers et al., *Nat. Neurosci.* 6:1178-85 (2003), which are hereby incorporated by reference in their entirety). The strong loss-of-function mutants npr-1(ad609) and npr-1(ky13), which were generated in the N2 background, also show a high tendency to aggregate (de Bono & Bargmann, *Cell* 94:679-89 (1998); Hodgkin & Doniach, *Genetics* 146:149-64 (1997), which are hereby incorporated by reference in their entirety).

A previous study showed that loss of function of npr-1 affects the hermaphrodite's response to non-indole ascarosides (Macosko et al., *Nature* 458:1171-75 (2009), which is hereby incorporated by reference in its entirety). While wild-type (N2) worms expressing the high-activity variant of NPR-1 are repulsed by non-indole ascarosides, npr-1 (ad609) mutants showed attraction to a near-physiological mixture of the most abundant non-indole ascarosides, ascr#2, ascr#3, and ascr#5 (Macosko et al., *Nature* 458: 1171-75 (2009), which is hereby incorporated by reference in its entirety).

Both the quadrant chemotaxis and spot attraction assays confirmed the attraction of npr-1(ad609) hermaphrodites to ascr#2/3/5 mixtures; however, hermaphrodites of the two tested social wild-type strains (RC301 and CB4856) showed no attraction in either assay (FIGS. 3A-B). In contrast, both social wild-type strains (RC301 and CB4856) as well as npr-1(ad609) hermaphrodites were strongly attracted to icas#3, in both the quadrant chemotaxis and spot-attraction assays (FIGS. 3B-D and 5B-C). These results indicate that icas#3 functions as a hermaphrodite attractant in both solitary and social *C. elegans* strains.

Example 26

Femtomolar Concentrations of Indole Ascarosides Promote *C. elegans* Aggregation How a constant background concentration of indole ascarosides affects hermaphrodite behavior was tested. Aggregation of solitary N2 worms and several social strains (including the social wild-type strain CB4856 and two npr-1 loss-of-function mutants) were measured in response to icas#3 using two different conditions: "high worm density," with 120 worms per 5 cm plate; and "low worm density," with 20 worms per 5 cm plate.

At low worm density, a very strong increase in aggregation was observed at concentrations as low as 10 fM (femtomolar) icas#3 for both solitary and social hermaphrodites (FIGS. 8A and 14E). Aggregation of N2 hermaphrodites increased as much as 4-fold at 1 pM icas#3, with higher icas#3 concentrations producing less aggregation. Similarly, the naturally occurring social strain CB4856 displayed a bell-shaped response curve with maximal aggregation at 1 pM of icas#3 and lower aggregation not significantly different from the control at 1 nM of icas#3 (FIG. 8A). In contrast, icas#3 increased aggregation of npr-1 (ad609) hermaphrodites over the entire tested concentration range, without a drop off at higher concentrations (FIG. 8A). At high worm density, up to a 3-fold increase in aggregation of N2 hermaphrodites was observed on icas#3 plates (FIGS. 8B and 14F), whereas hermaphrodites from all three tested social strains showed nearly complete aggregation even in the absence of icas#3, which precluded detection of any additional aggregation-promoting effect of icas#3 (FIG. 8B). These results show that icas#3 increases hermaphrodite aggregation even in the absence of a concentration gradient of this compound, and that solitary and social strains are similarly affected. Similarly, the second-most abundant indole ascaroside, icas#9, increased aggregation of both solitary and social hermaphrodites (FIG. 6A).

The effect of icas#3 on aggregation of males, which generally tend to aggregate in the absence of hermaphrodites (Gems & Riddle, *Genetics* 154:1597-610 (2000), which is hereby incorporated by reference in its entirety), was also investigated. The aggregation of him-5 males on icas#3 plates was found to be significantly increased (FIG. 6B).

These results show that indole ascarosides promote aggregation behavior even in the absence of a concentration gradient, suggesting that sensing of icas#3 and icas#9 affects the response to other aggregation-promoting (chemical or other) signals or conditions. For example, secretion of additional indole ascarosides by the worms on plates containing exogenous icas#3 could contribute to the observed increase in aggregation. To investigate this possibility, daf-22 hermaphrodites in the aggregation assay were tested. daf-22 hermaphrodites did not produce indole ascarosides but responded to icas#3 in both the spot attraction and quadrant chemotaxis assay as strongly as N2 worms (FIGS. 3B and 5C). daf-22 hermaphrodites were found to show less aggregation than N2 worms at 1 pM icas#3 but not at 10 pM icas#3 (FIG. 8C). These results suggest that secretion of additional indole ascarosides or other daf-22-dependent compounds by the worms may contribute to aggregation on icas#3 plates; however, other factors, such as low oxygen levels or contact with other worms (Rogers et al., Curr. Biol. 16:649-59 (2006); Chang et al., Publ. Lib. Sci. Biol. 4(9): e274 (2006); Chang & Bargmann, PNAS 105:7321-26 (2008), which are hereby incorporated by reference in their entirety), may be more important. Furthermore, changes in locomotory behavior on icas#3 plates could affect the level of aggregation (Rogers et al., Curr. Biol. 16:649-59 (2006), which is hereby incorporated by reference in its entirety). Using an automated machine-vision system to track worm movement (Cronin et al., BMC Genet. 6:5 (2005), which is hereby incorporated by reference in its entirety), aggregation-inducing concentrations of icas#3 were found to strongly increase mean stopped duration and affect other locomotory parameters (FIGS. 6D-E and 8D). These changes in worm locomotion, in conjunction with other aggregation-mediating factors, may contribute to the observed increase in aggregation on icas plates.

Example 27

Response to icas#3 Requires the Sensory Neuron ASK and the Interneuron AIA

The amphid single-ciliated sensory neurons type K (ASK) play an important role in mediating C. elegans behaviors. Previous work has shown that the ASK neurons are required for behavioral responses of males and hermaphrodites to non-indole ascarosides (Srinivasan et al., Nature 454:1115-18 (2008); Macosko et al., Nature 458:1171-75 (2009), which are hereby incorporated by reference in their entirety). ASK sensory neurons are connected via anatomical gap-junctions to the RMG interneuron, which has been shown to act as a central hub regulating aggregation and related behaviors based on input from ASK and other sensory neurons (Macosko et al., Nature 458:1171-75 (2009); White et al., Philos. Trans. R. Soc. London [Biol] 314:1-340 (1986), which are hereby incorporated by reference in their entirety) (FIG. 2A).

To investigate the neural circuitry required for icas#3-mediated hermaphrodite attraction and aggregation, tests were conducted to determine whether the ASK neurons are required for these behaviors. Worms lacking the ASK neurons due to cell-specific expression of mammalian caspase in the developing neurons (Tokumitsu Wakabayashi, Iwate University Japan) were used for these tests. Ablation of ASK sensory neurons resulted in a near complete loss of attraction to icas#3 (FIG. 2B). In contrast, ablation of the ASI neurons, which, like the ASK neurons partake in dauer pheromone sensing, had no significant effect on icas#3-mediated attraction in hermaphrodites (FIG. 2B). Further, ablation of both ASI and ASK neurons did not result in a more significant loss of attraction compared to ASK ablation alone, suggesting that the ASK sensory neurons are required for sensing icas#3 (FIG. 2B).

Tests were also conducted to determine whether the ASK neurons are required for icas#3-mediated aggregation. The results show that hermaphrodites lacking the ASK neurons did not aggregate in response to icas#3 at any of the tested concentrations (FIG. 2C). Locomotory analysis of ASK-ablated hermaphrodites on icas#3 plates showed neither increased reversal frequency nor decreased velocity, as observed for wild-type worms (FIGS. 7A-B).

Tests were then conducted to determine whether the RMG interneuron is required for icas#3-mediated behaviors. The cell position of the RMG interneuron in wild-type worms and in a transgenic strain expressing ncs-1::gfp (a gift from the Bargmann lab) was identified using differential interference contrast (DIC) microscopy (Sulston et al., Dev. Biol. 100:64-119 (1983), which is hereby incorporated by reference in its entirety). This transgene expresses GFP in the RMG interneuron and a few other sensory neurons (Macosko et al., Nature 458:1171-75 (2009), which is hereby incorporated by reference in its entirety). It was found that ablation of the RMG interneuron in both wild-type and ncs-1::gfp worms did not affect icas#3 response in the spot attraction assay (FIG. 2B). These results indicate that the RMG interneuron is not required for transduction of icas#3-derived attraction signals from the ASK sensory neurons, contrary to the behavioral effects of non-indole ascarosides, which require both the ASK sensory neurons and the RMG interneuron (Macosko et al., Nature 458:1171-75 (2009), which is hereby incorporated by reference in its entirety).

Given this observation, tests were also conducted to determine which interneuron downstream of ASK is required for response to icas#3. According to the wiring diagram of C. elegans, the primary synaptic output of the ASK neuron is the AIA interneuron (White et al., Philos. Trans. R. Soc. London [Biol] 314:1-340 (1986), which is hereby incorporated by reference in its entirety). A transgenic line expressing a hyperactive form of MEC-4 in the AIA interneuron (a gift from the Ishihara lab, Japan) (Shinkai et al., J. Neurosci. 31:3007-15 (2011), which is hereby incorporated by reference in its entirety) was used to test whether the AIA interneuron is required for sensing icas#3. Expression of MEC-4, a DEG/ENaC sodium channel, causes neuronal toxicity in C. elegans, thereby resulting in the loss of the AIA neuron (Harbinder et al., PNAS 94:13128-33 (1997), which is hereby incorporated by reference in its entirety). The AIA-deficient worms did not show any attraction to icas#3, suggesting that the AIA interneurons are required for the icas#3 response. Hence the neural circuitry required for attraction to icas#3 is different from that of the non-indole ascarosides.

Because behavioral assays showed that the ASK and AIA neurons participate in sensing icas#3, tests were conducted to determine whether icas#3 elicits calcium flux in these neurons. To measure $Ca^{2+}$ flux, transgenic lines expressing the genetically encoded calcium sensors (GCaMP) in these neurons (Macosko et al., Nature 458:1171-75 (2009), which is hereby incorporated by reference in its entirety) were used. The "Olfactory chip" was used to restrain the worms and apply ON and OFF steps of icas#3 while imaging from these neurons (Chronis et al., Nat. Methods 4:727-31 (2007), which is hereby incorporated by reference in its entirety). There was no detection of $Ca^{2+}$ transients in ASK neurons even when a wide range of concentration ranging from 1 pM to 1 µM was applied. Calcium responses in the AIA interneuron, which is the primary synaptic target of the ASK neuron (White et al., *Philos. Trans. R. Soc. London [Biol]* 314:1-340 (1986), which is hereby incorporated by reference in its entirety), was then monitored. The results showed that icas#3 elicited significantly increased G-CaMP fluorescence in the AIA neurons (FIGS. 2D-E), similar to the results reported for stimulation of AIA interneurons with a mixture of three non-indole ascarosides (Macosko et al., *Nature* 458:1171-75 (2009), which is hereby incorporated by reference in its entirety). These results show that the ASK sensory neurons are required for the response to icas and that this response is transduced via the AIA interneuron.

Example 28

Icas#3 and ascr#3 are Competing Signals

Previous studies have shown that high dauer-inducing concentrations of ascr#3 strongly deter both social and solitary hermaphrodites (Srinivasan et al., *Nature* 454:1115-18 (2008); Macosko et al., *Nature* 458:1171-75 (2009), which are hereby incorporated by reference in their entirety). To investigate whether addition of ascr#3 would affect icas#3-mediated attraction of hermaphrodites, mixtures containing these two compounds in a near-physiological ratio of 12:1 (ascr#3:icas#3) were tested in a modified spot attraction assay, in which N2 hermaphrodite attraction was scored to three concentric zones A-C (FIG. 1A). The results show that at the lower of the two concentrations tested (120 fmol ascr#3 and 10 fmol icas#3), the presence of ascr#3 did not interfere with icas#3-mediated attraction, whereas higher concentrations of ascr#3 resulted in strong repulsion, even in the presence of proportionally increased icas#3 concentrations (12 pmol ascr#3 and 1 pmol icas#3, FIG. 4A). Following retreat from the outer edge of zone A, many worms remained "trapped" in a circular zone B surrounding central zone A, repulsed by the high concentration of the icas#3/ascr#3 blend inside zone A, but attracted by the lower concentrations of the icas#3/ascr#3 blend that diffused into zone B. These results show that the repulsive effect of ascr#3 prevails at high concentrations of physiological icas#3/ascr#3 mixtures, whereas attraction by icas#3 dominates at lower concentrations.

Discussion of Examples 1-28

Indole ascarosides are the first *C. elegans* pheromones shown to strongly attract wild-type hermaphrodites and promote aggregation. The indole ascarosides fit the broad definition of aggregation pheromones in that they attract and/or arrest conspecifics to the region of release irrespective of sex (EDWARD O. WILSON, SOCIOBIOLOGY: THE NEW SYNTHESIS (The Belknap Press of Harvard University, Cambridge, Mass., 25th Anniv. ed. 2000); Shorey, *Annu. Rev. Entomol.* 18:349-80 (1973); Wertheim et al., *Annu. Rev. Entomol.* 50:321-46 (2005), which are hereby incorporated by reference in their entirety). In promoting these behaviors, the indole ascarosides are active at such low (femtomolar) concentrations that the worm's behavioral response must result from sensing of only a few molecules. For example, at an icas#3 concentration of 10 fM, there are only about 20 icas#3 molecules contained in a cylinder corresponding to the length and diameter of an adult hermaphrodite. Given their high specific activity, it is reasonable that indole ascarosides are of much lower abundance than non-indole ascarosides.

The indole ascarosides' strongly attractive properties suggest that these compounds serve to attract conspecifics to desirable environments such as food sources. However, the results from the competition experiments indicate that attraction of hermaphrodites by icas#3 can be counteracted by high concentrations of ascr#3, which are repulsive to hermaphrodites (Srinivasan et al., *Nature* 454:1115-18 (2008), which is hereby incorporated by reference in its entirety). The competition experiments further show that at low concentrations of a physiological blend of icas#3 and ascr#3, the attractive properties of icas#3 dominate, whereas at high concentrations of the same blend, the repulsion by ascr#3 becomes dominant (FIG. 4A). These findings suggest that under dauer-inducing conditions with high population density, the associated high concentrations of ascr#3 promote dispersal (Srinivasan et al., *Nature* 454:1115-18 (2008), which is hereby incorporated by reference in its entirety), whereas low population density and correspondingly lower concentrations of ascr#3 result in attraction mediated by icas#3. Therefore, icas' and ascr's can represent opposing stimuli regulating population density and level of aggregation. In turn, population density, food availability, and other environmental factors may affect relative rates of the biosyntheses of ascr's and icas' as part of a regulatory circuit.

Indole ascarosides affect aggregation behavior even in the absence of a concentration gradient: very low background concentrations (fM-pM) of icas#3 and icas#9 strongly increased the propensity of hermaphrodites (and males) to aggregate. This finding suggests that sensing of icas#3 and icas#9 increases susceptibility for aggregation-promoting (chemical or other) signals or conditions, such as additional quantities of icas secreted by the worms on the plate.

Aggregation in *C. elegans* is known to depend on a diverse set of genetic factors and environmental conditions, including food availability and oxygen concentration, suggesting the existence of neuronal circuitry that integrates inputs from different sources (de Bono & Bargmann, *Cell* 94:679-89 (1998); Cheung et al., *Curr. Biol.* 15:905-17 (2005); Coates & de Bono, *Nature* 419:925-29 (2002); de Bono et al., *Nature* 419:899-903 (2002); Gray et al., *Nature* 430:317-22 (2004), which are hereby incorporated by reference in their entirety). Aggregation and attraction signals originating from several different sensory neurons, including the oxygen-sensing URX-neurons and the ascr-sensing ASK neurons, have recently been shown to converge on the RMG interneuron, which is proposed to act as a central hub coordinating these behaviors (Macosko et al., *Nature* 458:1171-75 (2009), which is hereby incorporated by reference in its entirety). The RMG interneuron is the central site of action of the neuropeptide-Y receptor homolog NPR-1, which distinguishes solitary strains (high NPR-1 activity) from social strains (low NPR-1 activity) (de Bono & Bargmann, *Cell* 94:679-89 (1998); Rogers et al., *Nat. Neurosci.* 6:1178-85 (2003), which are hereby incorporated by reference in their entirety). In social npr-1(lf) mutant hermaphrodites, oxygen-sensing URX neurons promote aggregation at the edges of the bacterial lawn, whereas solitary N2 hermaphrodites do not respond to oxygen gradients. Similarly, repulsion by ascr depends on NPR-1, as solitary hermaphrodites are repelled by ascr, whereas social npr-1(lf) hermaphrodites display either greatly diminished repulsion or weak attraction (Macosko et al., *Nature* 458:1171-75 (2009), which is hereby incorporated by reference in its entirety).

In contrast, icas#3 was shown to promote hermaphrodite attraction and aggregation in both social and solitary strains. Icas#3 attracted solitary N2 as well as social npr-1(lf) hermaphrodites and increased hermaphrodite aggregation in the solitary strain N2, the social wild-type strains RC301 and CB4856 (Hawaii) carrying a low-activity variant of NPR-1, and the two tested npr-1 null alleles. The finding that icas#3-mediated attraction and aggregation were not reduced by high NPR-1 activity suggests that these icas#3-mediated behaviors rely on signaling pathways distinct from those controlling aggregation responses to other types of stimuli, such as low oxygen levels. This is supported by the observation that hermaphrodites lacking the RMG interneuron, which coordinates other aggregation responses via NPR-1, were still attracted to icas#3. Furthermore, icas#3-mediated aggregation differed from NPR-1-dependent aggregation behavior in that aggregation of worms on icas#3 plates was more dynamic and not restricted to the edge of the bacterial lawn where oxygen is limited. Worm velocity was not significantly reduced at the icas#3 concentrations that induce maximal aggregation (1-10 pM, FIG. 6D), and icas#3-mediated aggregation was associated with less clumping (average clump size 3-5 worms) than that found for aggregating NPR-1 mutant worms (average clump size 6-16 worms) (Rogers et al., *Curr. Biol.* 16:649-59 (2006), which is hereby incorporated by reference in its entirety). These observations show that icas#3-mediated aggregation is phenotypically distinct from aggregation behaviors controlled by NPR-1 and the RMG interneuron.

Icas#3-mediated attraction and aggregation were shown to depend on the ASK neurons, similar to hermaphrodite repulsion and male attraction by ascr (Srinivasan et al., *Nature* 454:1115-18 (2008), which is hereby incorporated by reference in its entirety), confirming the central role of this pair of sensory neurons for perception of different types of pheromones in *C. elegans* (FIGS. 2A-E). Further, icas#3 responses were shown to depend on the AIA interneurons and did not require the RMG interneuron. Therefore, it appears that the sensory neuron ASK participates in perception of two different types of pheromones, ascr's and icas', and that these signals are transduced via two different neurophysiological pathways as part of a complex neural and genetic circuitry integrating a structurally diverse array of pheromone signals.

Calcium transients have been recorded from amphid sensory neurons in response to non-indole ascarosides; however, the reported changes in G-CaMP fluorescence are relatively small (on the order of about 20%) (Macosko et al., *Nature* 458:1171-75 (2009); Kim et al., *Science* 326:994-98 (2009), which are hereby incorporated by reference in their entirety). It has been recently reported that the non-indole ascaroside ascr#5 does not elicit calcium transients in the ASI sensory neurons, although the ASI neurons function as sensors of ascr#5 and express the ascr#5-receptors srg-36 and srg-37 (McGrath et al., *Nature* 477:321-25 (2011), which is hereby incorporated by reference in its entirety). Similarly, there was no detection of significant $Ca^{2+}$ transients in the ASK neurons in response to a wide range of concentrations of icas#3. Perhaps any icas#3-elicited $Ca^{2+}$ signals in this neuron are even weaker than those of non-indole ascarosides, as icas#3 is active at extremely low concentrations (femtomolar to low picomolar). Further, there may be involvement of additional neurons in icas#3 signaling, given that the ASK neurons are postsynaptic to a number of other sensory neurons (White et al., *Philos. Trans. R. Soc. London [Biol]* 314:1-340 (1986), which is hereby incorporated by reference in its entirety). In particular, as shown herein, icas#3 elicited significant changes in G-CaMP fluorescence in the AIA interneurons, which are the primary postsynaptic targets of the ASK sensory neurons (FIGS. 2D-E).

The identification of indole ascarosides as aggregation signals reveals an unexpected complexity of social signaling in *C. elegans*. The results herein indicate that ascarylose-derived small molecules (icas' and ascr's) serve at least three distinct functions in *C. elegans*: dauer induction, male attraction, and hermaphrodite social signaling (FIG. 4B). Previous studies have shown that ascr's often have more than one function. For example, ascr#3 plays significant roles for both dauer signaling and male attraction (Butcher et al., *Nat. Chem. Biol.* 3:420-22 (2007); Srinivasan et al., *Nature* 454:1115-18 (2008), which are hereby incorporated by reference in their entirety). The results herein demonstrate that specific structural variants of ascarylose-derived small molecules are associated with specific functions (FIG. 4C). Addition of an indole carboxy group to ascr's changes the signaling properties such that the indole-modified compounds can have signaling effects very different from those of the unmodified compounds: icas#3 strongly attracts hermaphrodites and promotes aggregation, whereas ascr#3 repulses hermaphrodites and attracts males. It has also been shown herein that, in addition to structural variation, distinct signaling functions are associated with different concentration windows: while high nanomolar concentrations of ascr's are required for dauer formation, low nanomolar to high picomolar concentrations of ascr's promote male attraction; and picomolar to femtomolar concentrations of icas' promote hermaphrodite attraction and aggregation (FIG. 4B).

Social signaling in *C. elegans* thus appears to be based on a modular language of small molecules, derived from combinatorial assembly of several structurally distinct building blocks (FIG. 4C). Different combinations of these building blocks serve different, occasionally overlapping, signaling functions. The results for the relative abundance of ascr's and icas' with identical side chains (FIG. 9G) indicate that integration of the different building blocks is carefully controlled. Biochemically, the building blocks are derived from three basic metabolic pathways: carbohydrate metabolism, peroxisomal fatty-acid β-oxidation, and amino acid metabolism. These structural observations raise the possibility that social signaling via small molecules transduces input from the overall metabolic state of the organism. Food availability and nutrient content in conjunction with other environmental factors may control ascr and icas biosynthesis pathways to generate specific pheromone blends that differentially regulate aggregation, mate attraction, and developmental timing. The expansive vocabulary of a modular chemical language would make it possible for different nematodes to signal conspecifically as well as interspecifically, but it was not known whether nematode species other than *C. elegans* rely on ascarylose-based small molecules for chemical communication. Lipid-derived glycosides of ascarylose have been identified from several other nematode species (Bartley et al., *J. Nat. Prod.* 59:921-26 (1996), which is hereby incorporated by reference in its entirety), which may indicate that nematodes may have the ability to produce ascr- or icas-like compounds.

The identification of indole ascarosides as attraction and aggregation signals has demonstrated that *C. elegans* aggregation behavior depends on dedicated chemical signals produced by conspecifics and not just shared preference for specific environmental conditions. *C. elegans* social signaling thus appears to be significantly more highly evolved than previously suspected.

Example 29

Analytical Instrumentation

NMR spectra were recorded on a Varian INOVA 600 (600 MHz for $^1$H, 151 MHz for $^{13}$C), INOVA 500 (500 MHz for $^1$H, 125 MHz for $^{13}$C), or INOVA 400 (400 MHz for $^1$H, 100 MHz for $^{13}$C) spectrometer. NMR spectra were processed using Varian VNMR, MestreLabs MestReC and Mnova software packages.

Low-resolution HPLC-MS and HPLC-MS/MS were performed using an Agilent 1100 Series HPLC system equipped with a diode array detector and connected to a Quattro II mass spectrometer (Micromass/Waters). High-resolution MS/MS was performed using an LTQ Orbitrap Velos Hybrid Fourier transform (FT) mass spectrometer (Thermo Scientific, Cornell University Life Sciences Core Laboratories Center). High-resolution HPLC-MS was performed using a Waters nanoACQUITY UPLC System equipped with a Waters Acquity UPLC HSS C-18 column (2.1×100 mm, 1.8 μm particle diameter) connected to a Xevo G2 QT of Mass Spectrometer. MassLynx software was used for MS data acquisition and processing.

Flash column chromatography was performed using a Teledyne ISCO CombiFlash system. HPLC fractionation was performed using the Agilent 1100 Series HPLC system equipped with an Agilent Eclipse XDB-C18 column (9.4×250 mm, 5 μm particle diameter) coupled to a Teledyne ISCO Foxy 200 fraction collector.

Example 30

*C. elegans* Strains and General Culture Methods

*C. elegans* variety Bristol, strain N2 (wild type), acox-1 (ok2257), dhs-28(hj8), maoc-1(hj13), maoc-1(ok2645), daf-22(m130), daf-22(ok693), F58F9.7(tm4033), C48B4.1 (ok2619), F59F4.1(ok2119), and F08A8.3(tm5192) were maintained at 20° C. on NGM agar plates, made with Bacto agar (BD Biosciences) and seeded with *E. coli* OP50 grown overnight.

Example 31

Preparation of Metabolite Extracts

Wild-type (N2, Bristol) or acox-1(ok2257), maoc-1 (hj13), dhs-28(hj8), and daf-22(ok693) mutant worms from four 10 cm NGM plates were washed using M9-medium into a 100 mL S-medium pre-culture where they were grown for four days at 22° C. on a rotary shaker at 220 evolutions per minute (rpm). Concentrated *E. coli* OP50 derived from 1 L of bacterial culture was added as food at days 1 and 3. Subsequently, each pre-culture was divided equally into four 500 mL Erlenmeyer flasks containing 100 mL of S-medium on day 4. Two of these cultures, labeled non-starved (NS), were grown for 5 days at 22° C. on a rotary shaker, and fed with concentrated OP50 derived from 500 mL of bacterial culture every day from day 1 to day 4. The remaining two cultures of each set, labeled starved (S), were fed once with concentrated OP50 derived from 500 mL of bacterial culture on day 1, and grown for an additional 9 days at 22° C. on a rotary shaker without food. Subsequently, the cultures were harvested on day 5 for NS and day 10 for S, and centrifuged. The resulting supernatant media and worm pellets were frozen over dry ice-acetone slush and lyophilized separately. The lyophilized materials from the supernatant were extracted with 150 mL of 95% ethanol at room temperature for 16 hours. The worm pellets were crushed with ~2 g of granular NaCl using a mortar and pestle, and extracted with 100 mL of 100% ethanol at room temperature for 16 hours. The resulting suspensions were filtered. The filtrate was evaporated in vacuum at room temperature, producing media metabolite (the worm "excretome") extracts and worm pellet metabolite extracts.

Example 32

Ascaroside Feeding Experiment with daf-22(m130)

Ascaroside feeding experiments were performed with the daf-22(m130) mutant, which is less sensitive to growth defects due to added ascarosides than the daf-22(ok693) mutant. HPLC-MS analysis of daf-22(m130) showed similar ascaroside profiles as daf-22(ok693), notably a total lack of short chain ascarosides with chain length less than 12 carbons. Non-starved cultures of daf-22 (m130) were grown as described in Example 31, but with the addition of 5 μM per culture of either ascr#3 or a 1:1 mixture of ascr#10 and oscr#10, added on day 1 after pre-culture splitting.

Example 33

Sample Preparation

Media or worm pellet metabolite extracts were resuspended in ~15 mL methanol and centrifuged. The supernatants were then collected, concentrated in vacuum at room temperature, resuspended in 1 mL methanol, and centrifuged. 30 μL of the resulting extract was directly injected for LC-MS/MS analysis.

Example 34

Mass Spectrometric Analysis

Low resolution HPLC-MS/MS profiling was performed using the Agilent 1100 Series HPLC system equipped with an Agilent Eclipse XDB-C18 column (9.4×250 mm, 5 μm particle diameter) connected to the Quattro II mass spectrometer using a 10:1 split. A 0.1% acetic acid-acetonitrile solvent gradient was used at a flow rate of 3.6 ml/min, starting with an acetonitrile content of 5% for 5 minutes, which was increased to 100% over a period of 40 minutes. Metabolite extracts were analyzed by HPLC-ESI-MS in negative and positive ion modes, using a capillary voltage of 3.5 kV and a cone voltage of −40 V and +20 V, respectively. HPLC-MS/MS screening for precursor ions of m/z=73.0 (negative mode) and neutral loss of 130.0 (positive mode) was performed using argon as collision gas at 2.1 mtorr and 30 eV. Ascaroside fragmentation was further analyzed by high-resolution MS/MS using the LTQ Orbitrap. To confirm the elemental composition of new compounds, mutant metabolome samples and fractions were additionally analyzed by high-resolution HPLC-MS using the Xevo G2 QTof.

Example 35

Synthesis of Ascaroside oscr#9

Ascaroside oscr#9 was prepared as shown in Scheme 2 below.

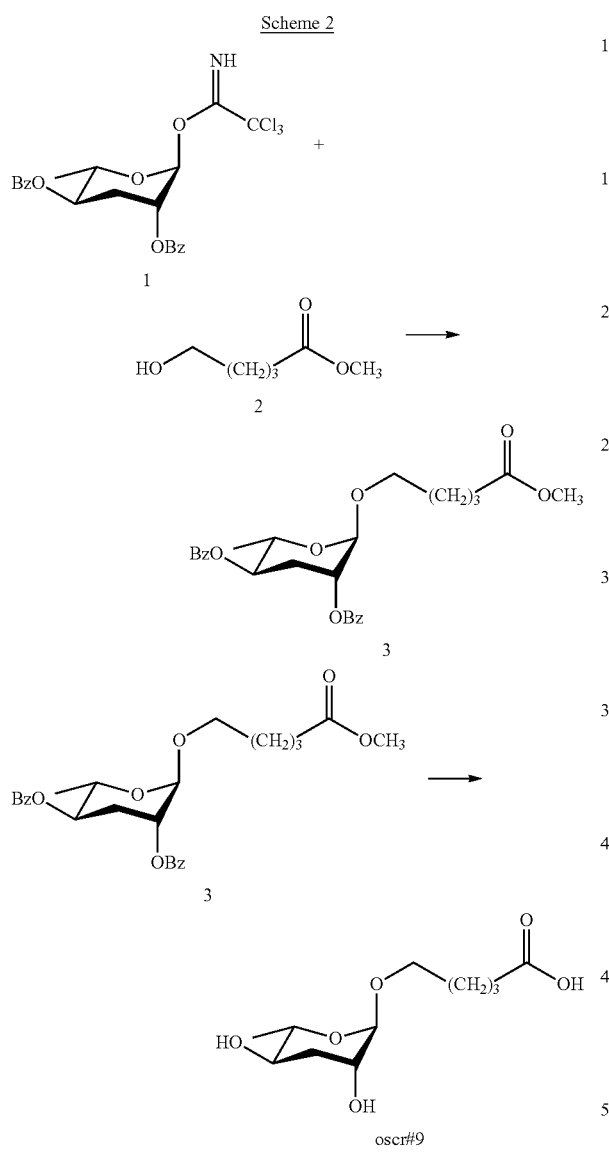

Figure 10:
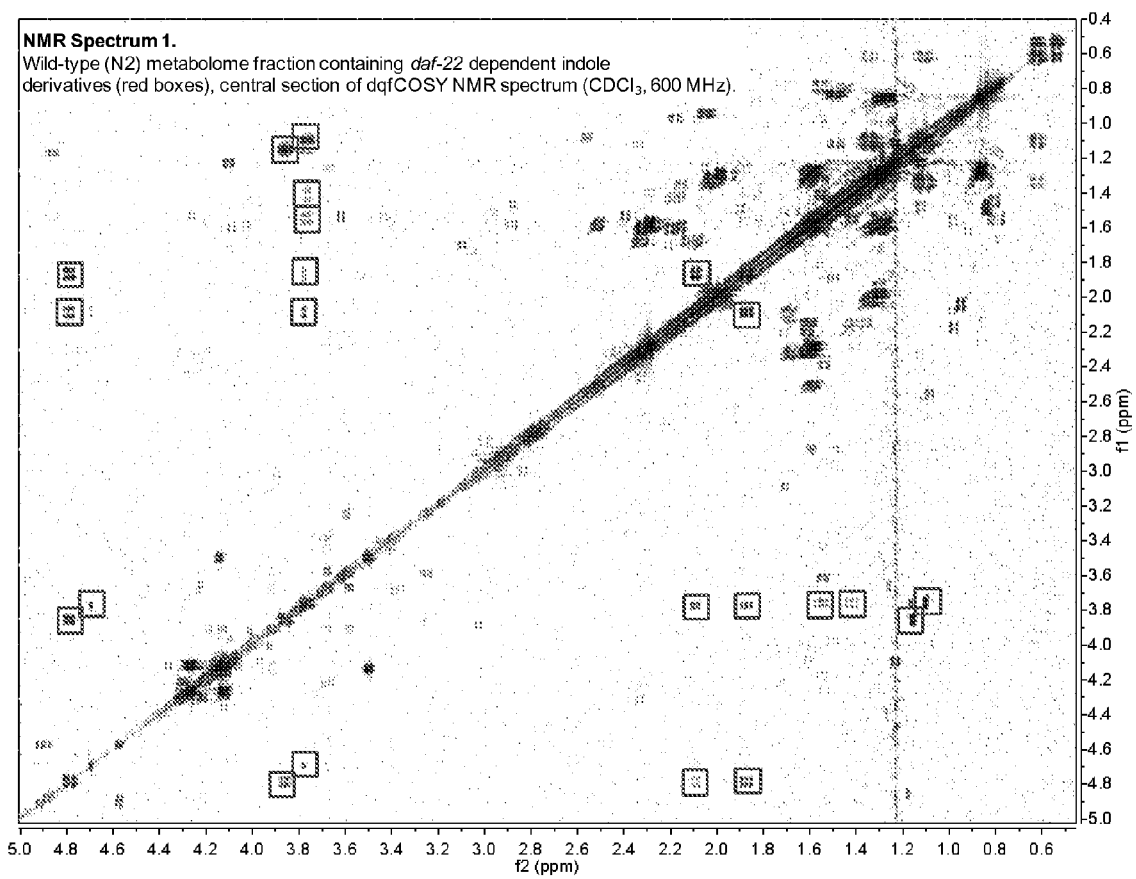
FIG. 10 is the central section of the dqfCOSY NMR spectrum ($CDCl_3$, 600 MHz) of the wild-type (N2) metabolome fraction containing daf-22 dependent indole derivatives (boxes).
Figure 11C:
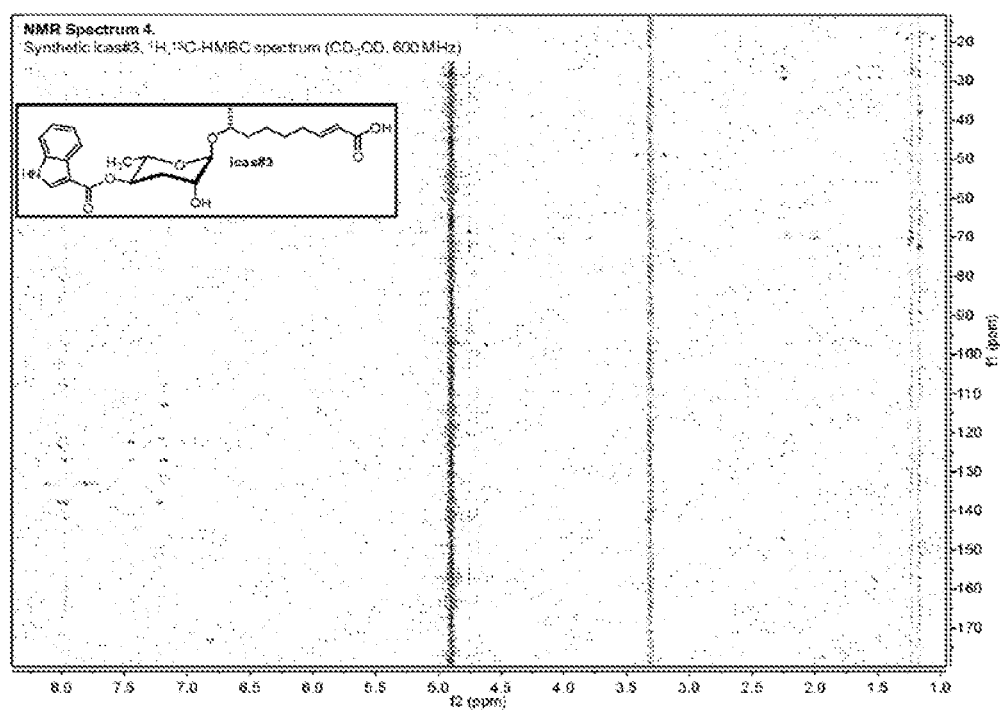
Figure 15B:
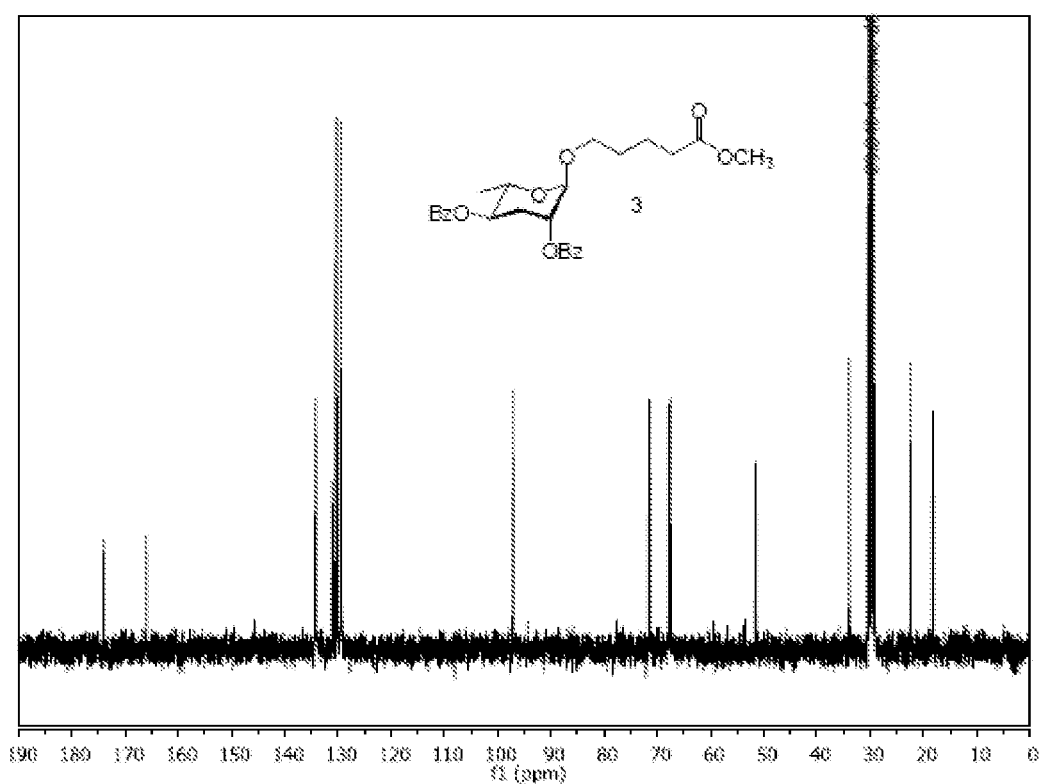

To prepare 3, a solution of 2,4-di-O-benzoyl-ascarylose-1-(2,2,2-trichloroacetimide) (1, 132 mg, 263 µmol, Butcher et al., *Nat. Chem. Biol.* 3:420-22 (2007), which is hereby incorporated by reference in its entirety) and methyl 5-hydroxypentanoate (2, 125 mg, 950 µmol, Huckstep et al., *Synthesis* 10:881-82 (1982), which is hereby incorporated by reference in its entirety) in dry DCM (3 ml) at 0° C. was treated with trimethylsilyloxy triflate (5 µl). After 3 hours, the solution was washed with saturated aqueous NaHCO₃ solution (0.5 ml), dried over Na₂SO₄, and concentrated in vacuum. Flash column chromatography on silica using a gradient of 20-40% ethyl acetate in hexanes afforded Methyl 5-(3'R,5'R-dibenzoyloxy-6'S-methyl-(2H)-tetrahydropyran-2'-yloxy)pentanoate (3) (66.8 mg, 142 µmol, 47%) as a colorless oil. ¹H NMR (400 MHz, acetone-d₆): δ (ppm) 1.28 (d, J=6.2 Hz, 3H), 1.67-1.80 (m, 4H), 2.23 (m, 1H), 2.40 (t, J=6.9 Hz, 2H), 2.48 (m, 1H), 3.58 (m, 1H), 3.64 (s, 3H), 3.83 (m, 1H), 4.13 (dq, J=9.8 Hz, J=6.0 Hz, 1H), 4.87 (s.br, 1H), 5.15 (ddd, J=11.0 Hz, J=10.4 Hz, J=4.5 Hz, 1H), 5.18 (s.br, 1H), 7.50-7.60 (m, 4H), 7.62-7.72 (m, 2H), 8.05 (d, J=7.5 Hz, 2H), 8.11 (d, J=7.5 Hz, 2H); ¹³C NMR (100 MHz, acetone-d₆): δ (ppm) 18.3, 22.5, 29.6, 30.4, 34.0, 51.5, 67.5, 67.9, 71.4, 71.5, 97.0, 129.4, 129.5, 130.3, 130.4, 131.0, 131.0, 134.1, 134.2, 165.9, 166.0, 174.0. See FIGS. 15A-B.

Figure 16A:
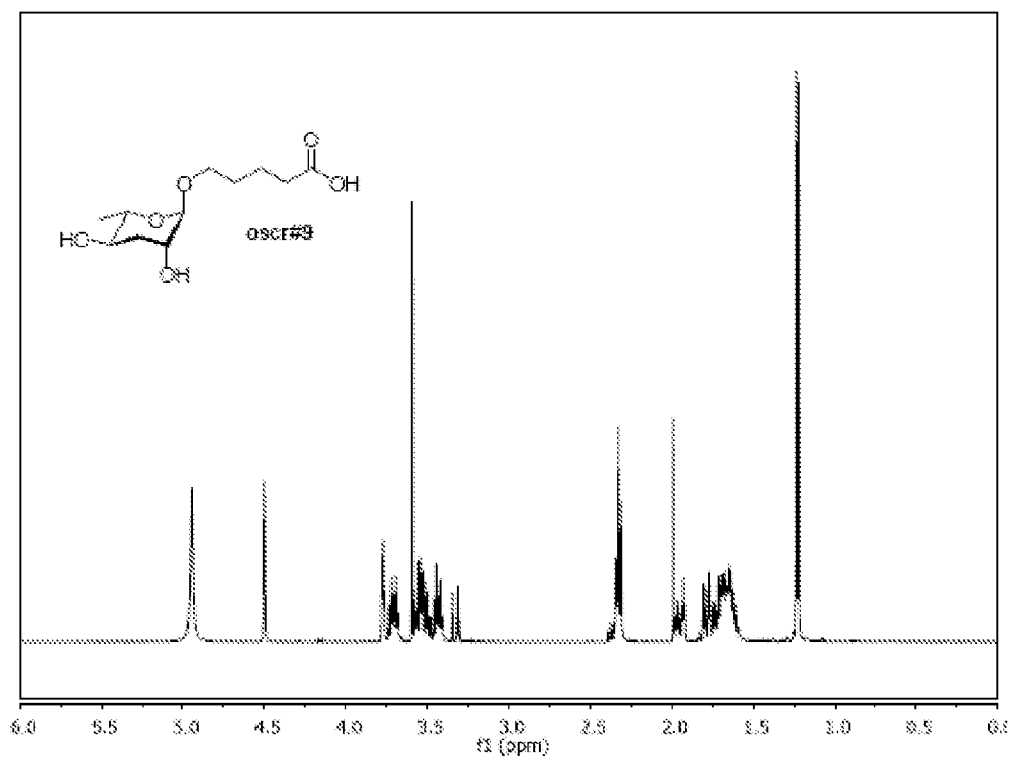
FIGS. 16A-B are the $^1$H NMR spectrum (FIG. 16A) and $^{13}$C NMR spectrum (FIG. 16B) of 5-(3'R,5'R-dihydroxy-6'S-methyl-(2H)-tetrahydropyran-2'-yloxy)pentanoic acid (oscr#9). $^1$H NMR: 400 MHz, methanol-d$_4$); $^{13}$C NMR: 100 MHz, methanol-d$_4$.
Figure 16B:
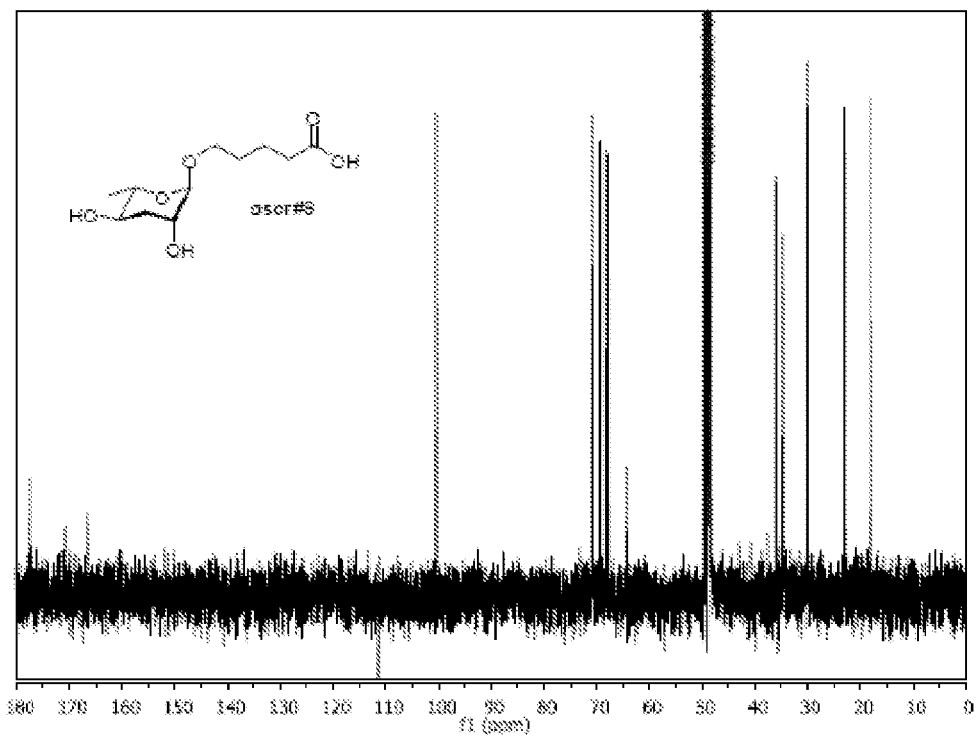

To prepare oscr#9, a solution of 3 (66.8 mg, 142 µmol) in dry THF (0.5 ml) was added to a mixture of LiOH (28 mg, 1.4 mmol) and water (0.6 ml) in 1,4-dioxane (4 ml). After stirring at 66° C. for 2 hours, the solution was acidified with glacial acetic acid and concentrated in vacuum. Flash column chromatography on silica using a gradient of 5-30% methanol in DCM containing 1% acetic acid afforded 5-(3'R,5'R-Dihydroxy-6'S-methyl-(2H)-tetrahydropyran-2'-yloxy)pentanoic acid (oscr#9) (26 mg, 105 µmol, 74%) as a colorless oil. ¹H NMR (400 MHz, methanol-d₄): δ (ppm) 1.22 (d, J=6.0 Hz, 3H), 1.58-1.72 (m, 4H), 1.77 (ddd, J=13.1 Hz, J=11.1 Hz, J=3.2 Hz, 1H), 1.95 (ddt, J=13.1 Hz, J=3.7 Hz, J=0.9 Hz, 1H), 2.33 (t, J=7.2 Hz, 2H), 3.43 (dt, J=9.6 Hz, J=6.0 Hz, 1H) 3.47-3.59 (m, 2H), 3.71 (dt, J=9.8 Hz, J=6.2 Hz, 1H), 3.77 (m, 1H), 4.50 (s, 1H); ¹³C NMR (100 MHz, methanol-d₄): δ (ppm) 18.1, 23.0, 30.1, 34.7, 36.0, 67.9, 68.3, 69.4, 70.9, 100.4, 177.5. See FIGS. 16A-B.

Example 36

Synthesis of Ascaroside oscr#10

Ascaroside oscr#10 was prepared as shown in Scheme 3 below.

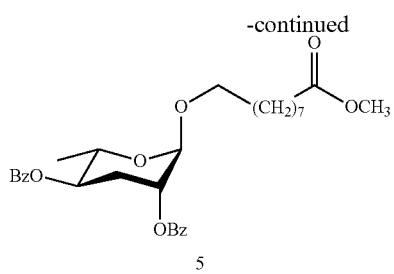

5

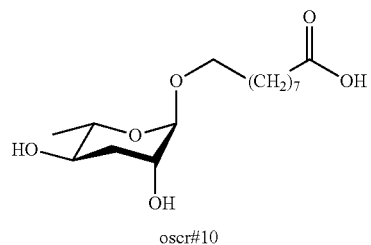

oscr#10

Figure 17A:
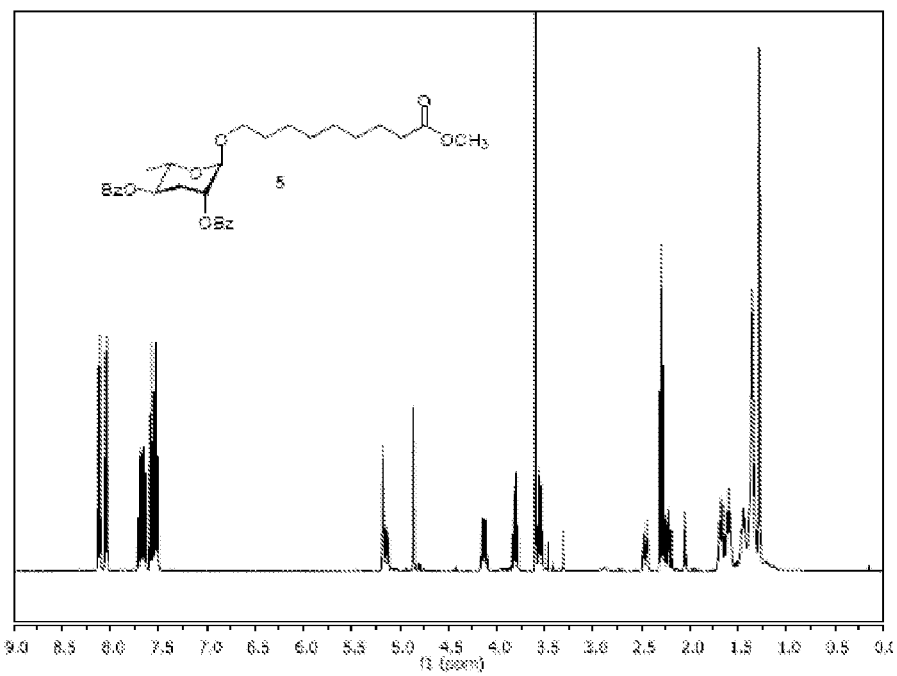
FIGS. 17A-B are the $^1$H NMR spectrum (FIG. 17A) and $^{13}$C NMR spectrum (FIG. 17B) of Methyl 9-(3'R,5'R-dibenzoyloxy-6'S-methyl-(2H)-tetrahydropyran-2'-yloxy) nonanoate (5). $^1$H NMR: 400 MHz, acetone-d$_6$; $^{13}$C NMR: 100 MHz, acetone-d$_6$.
Figure 17B:
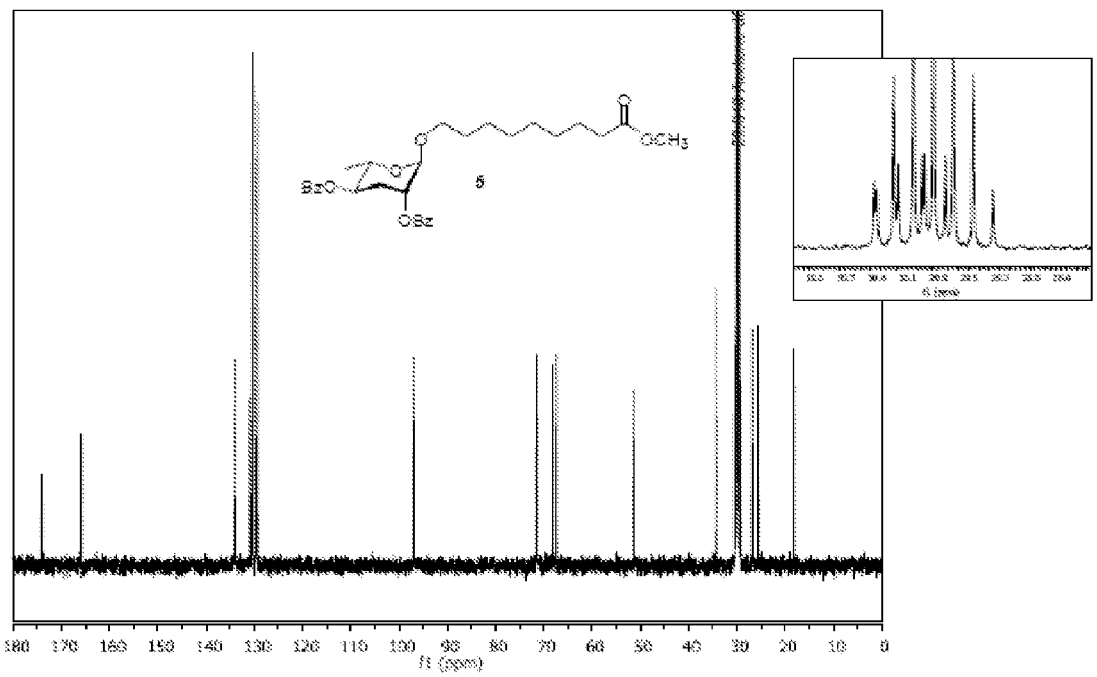

To prepare 5, a solution of 2,4-di-O-benzoyl-ascarylose-1-(2,2,2-trichloroacetimide) (1, 132 mg, 263 μmol, Butcher et al., *Nat. Chem. Biol.* 3:420-22 (2007), which is hereby incorporated by reference in its entirety) and methyl 9-hydroxynonanoate (4, 112.8 mg, 600 μmol, Kai et al., *Tetrahedron* 64:6760-69 (2008), which is hereby incorporated by reference in its entirety) in dry DCM (3 ml) at 0° C. was treated with trimethylsilyloxy triflate (5 μl). After 3 hours, the solution was washed with saturated aqueous NaHCO$_3$ solution (0.5 ml), dried over Na$_2$SO$_4$, and concentrated in vacuum. Flash column chromatography on silica using a gradient of 20-40% ethyl acetate in hexanes afforded Methyl 9-(3'R,5'R-dibenzoyloxy-6'S-methyl-(2H)-tetrahydropyran-2'-yloxy)nonanoate (5) (99.3 mg, 190 μmol, 72%) as a colorless oil. $^1$H NMR (400 MHz, acetone-d$_6$): δ (ppm) 1.28 (d, J=6.2 Hz, 3H), 1.30-1.40 (m, 6H), 1.40-1.49 (m, 2H), 1.56-1.72 (m, 2H), 2.22 (ddd, J=13.6 Hz, J=11.5 Hz, J=3.2 Hz, 1H), 2.30 (t, J=7.5 Hz, 2H), 2.46 (m, 1H), 3.55 (dt, J=9.8 Hz, J=6.5 Hz, 1H), 3.60 (s, 3H), 3.81 (dt, J=9.6 Hz, J=6.6 Hz, 1H), 4.13 (dq, J=9.7 Hz, J=6.2 Hz, 1H), 4.86 (s.br, 1H), 5.15 (ddd, J=11.4 Hz, J=9.8 Hz, J=4.6 Hz, 1H), 5.18 (m, 1H), 7.50-7.60 (m, 4H), 7.63-7.71 (m, 2H), 8.04 (m, 2H), 8.11 (m, 2H); $^{13}$C NMR (100 MHz, acetone-d$_6$): δ (ppm) 18.3, 25.6, 26.8, 29.7, 29.9, 30.0, 30.2, 30.4, 34.4, 51.4, 67.4, 68.2, 71.4, 71.5, 97.0, 129.4, 129.5, 130.2, 130.3, 130.9, 131.0, 134.1, 134.2, 165.9, 165.9, 174.3. See FIGS. 17A-B.

Figure 18A:
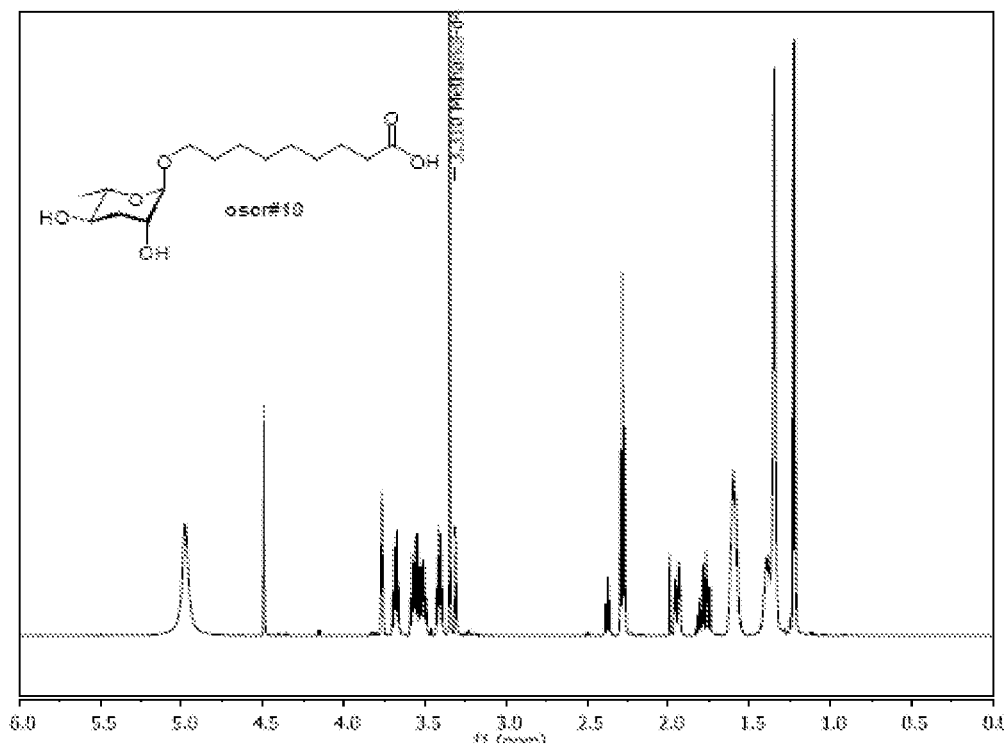
FIGS. 18A-B are the $^1$H NMR spectrum (FIG. 18A) and $^{13}$C NMR spectrum (FIG. 18B) of 9-(3'R,5'R-dihydroxy-6'S-methyl-(2H)-tetrahydropyran-2'-yloxy)nonanoic acid (oscr#10). $^1$H NMR: 600 MHz, methanol-d$_4$; $^{13}$C NMR: 100 MHz, methanol-d$_4$.
Figure 18B:
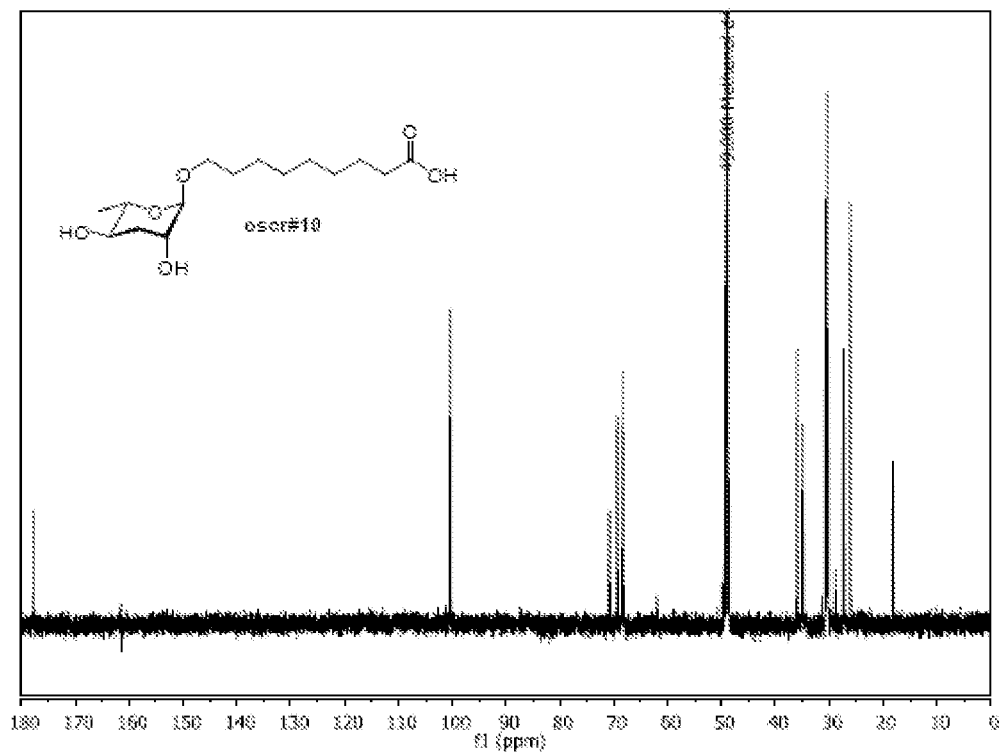

To prepare ascr#10, a solution of 5 (99.3 mg, 190 μmol) in THF (500 μl) was added to a mixture of LiOH (38 mg, 1.9 mmol) and water (800 μl) in 5 ml 1,4-dioxane (5 ml). After stirring at 66° C. for 3 hours, the solution was acidified with acetic acid and concentrated in vacuum. Flash column chromatography on silica gel using a gradient of 5-30% methanol in DCM containing 1% glacial acetic acid afforded 9-(3'R,5'R-Dihydroxy-6'S-methyl-(2H)-tetrahydropyran-2'-yloxy)nonanoic acid (oscr#10) (49 mg, 161 μmol, 85%) as a colorless oil. $^1$H NMR (400 MHz, methanol-d$_4$): δ (ppm) 1.22 (d, J=6.1 Hz, 3H), 1.32-1.43 (m, 8H), 1.56-1.63 (m, 4H), 1.77 (ddd, J=13.1 Hz, J=11.1 Hz, J=3.2 Hz, 1H), 1.96 (ddt, J=13.1 Hz, J=3.7 Hz, J=0.9 Hz, 1H), 2.28 (t, J=7.4 Hz, 2H), 3.41 (dt, J=9.6 Hz, J=6.2 Hz, 1H) 3.49-3.59 (m, 2H), 3.68 (dt, J=9.8 Hz, J=5.5 Hz, 1H), 3.76 (m, 1H), 4.49 (s, 1H); $^{13}$C NMR (100 MHz, methanol-d$_4$): δ (ppm) 17.3, 25.2, 26.4, 28.0, 29.3, 29.5, 29.6, 30.5, 34.1, 61.1, 67.4, 68.5, 69.9, 99.4, 176.8. See FIGS. 18A-B.

Example 37

Synthesis of Ascaroside bhas#10

Ascaroside bhas#10 was prepared as shown in Scheme 4 below.

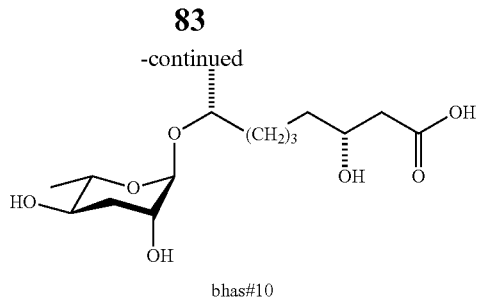

bhas#10

Figure 19:
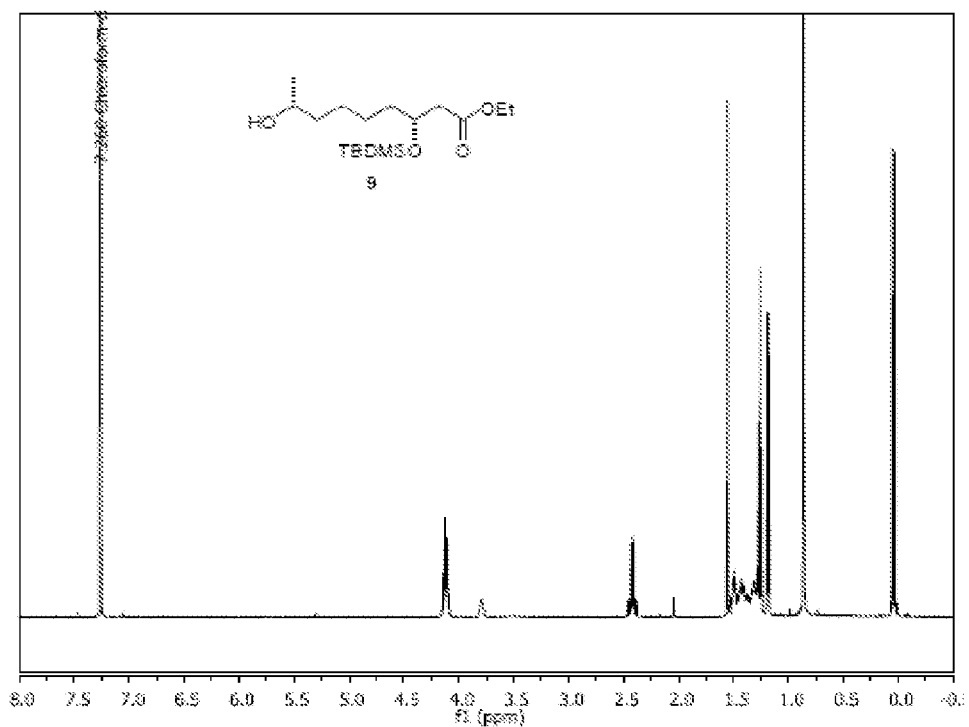
FIG. 19 is the $^1$H NMR spectrum (500 MHz, chloroform-dl) of Ethyl (8R)-hydroxy-(3R)-tert-butyldimethylsilyloxynonanoate (9).

To prepare 9, a solution of 6 (366 mg, 1.91 mmol, Guan & Greenberg, *J. Am. Chem. Soc.* 131:15225-31 (2009), which is hereby incorporated by reference in its entirety) and 7 (104 mg, 380 µmol, Evans & Andrews, *Angew. Chem. Int. Ed.* 47:5426-29 (2008), which is hereby incorporated by reference in its entirety) in dry DCM (10 ml) was treated with 1,4-benzoquinone (4 mg, 38 µmol) in DCM (0.5 ml) and stirred for 10 minutes. A solution of Grubbs $2^{nd}$ generation catalyst (16 mg, 19 µmol) in DCM (0.5 ml) was added. The resulting mixture was stirred at 40° C. After 20 hours, the mixture was filtered over a small layer of silica and concentrated in vacuum. Flash column chromatography on silica using a gradient of 0-20% ethyl acetate in hexane afforded a mixture of the desired product 8 and the homodimer of 6. The mixture was not purified further; instead, the crude mixture (160 mg) was dissolved in ethanol (2 ml), treated with Pd/C (15 mg, 10%, w/w), and hydrogenated for 40 hours. The resulting mixture was filtered, concentrated in vacuum, and purified by flash column chromatography on silica gel using a gradient of 10-30% ethyl acetate in hexane to afford Ethyl (8R)-hydroxy-(3R)-tert-butyldimethylsilyloxynonanoate (9) (48 mg, 144 µmol, 38% over two steps) as a colorless oil. $^1$H NMR (500 MHz, chloroform-$d_1$): δ (ppm) 0.03 (s, 3H), 0.06 (s, 3H), 0.86 (s, 9H), 1.19 (d, J=6.2 Hz, 3H), 1.26 (t, J=7.2 Hz, 3H), 1.29-1.47 (m, 6H), 1.47-1.53 (m, 2H), 2.40 (dd, J=14.6 Hz, J=5.7 Hz, 1H), 2.44 (dd, J=14.6 Hz, J=7.0 Hz, 1H), 3.75-3.83 (m, 1H), 4.09-4.15 (m, 3H). See FIG. 19.

Figure 20:
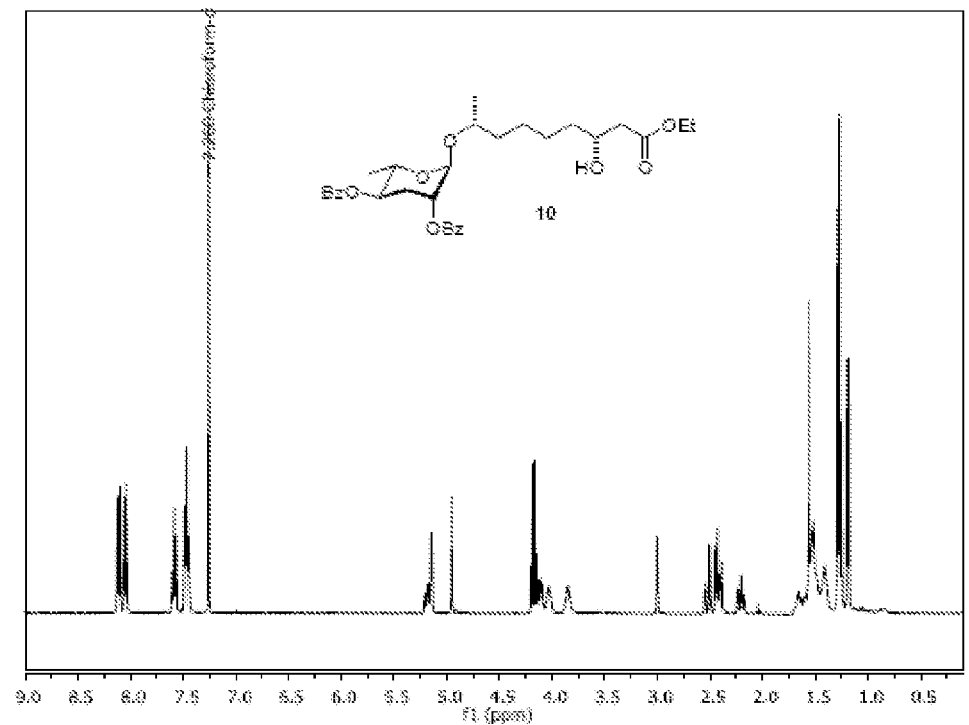
FIG. 20 is the $^1$H NMR spectrum (400 MHz, chloroform-dl) of Ethyl (8R)-(3'R,5'R-dibenzoyloxy-6'S-methyl-(2H)-tetrahydropyran-2'-yloxy)-(3R)-hydroxynonanoate (10).
Figure 21A:
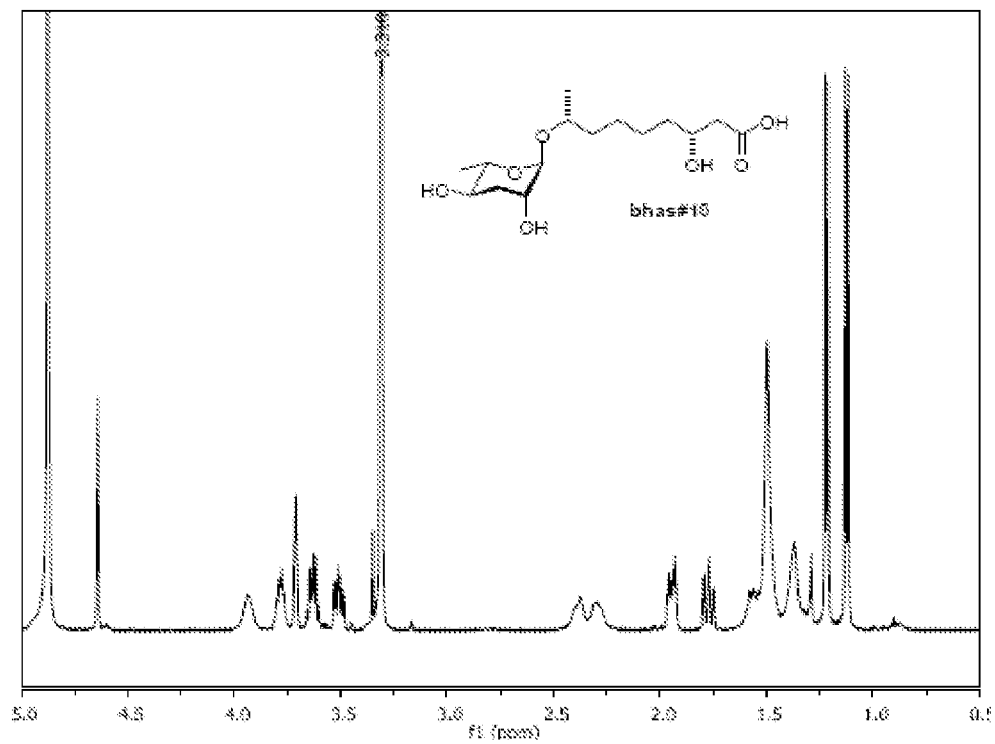
FIGS. 21A-D are the $^1$H NMR spectrum (FIG. 21A), $^{13}$C NMR spectrum (FIG. 21B), HSQC spectrum (FIG. 21C), and HMBC spectrum (FIG. 21D) of (8R)-(3'R,5'R-dihydroxy-6'S-methyl-(2H)-tetrahydropyran-2'-yloxy)-(3R)-hydroxynonanoic acid (bhas#10). $^1$H NMR: 500 MHz, methanol-d$_4$; $^{13}$C NMR: 125 MHz, methanol-d$_4$; HSQC: 600 MHz for $^1$H, 151 MHz for $^{13}$C, methanol-d$_4$; HMBC: 600 MHz for $^1$H, 151 MHz for $^{13}$C, methanol-d$_4$.
Figure 21B:
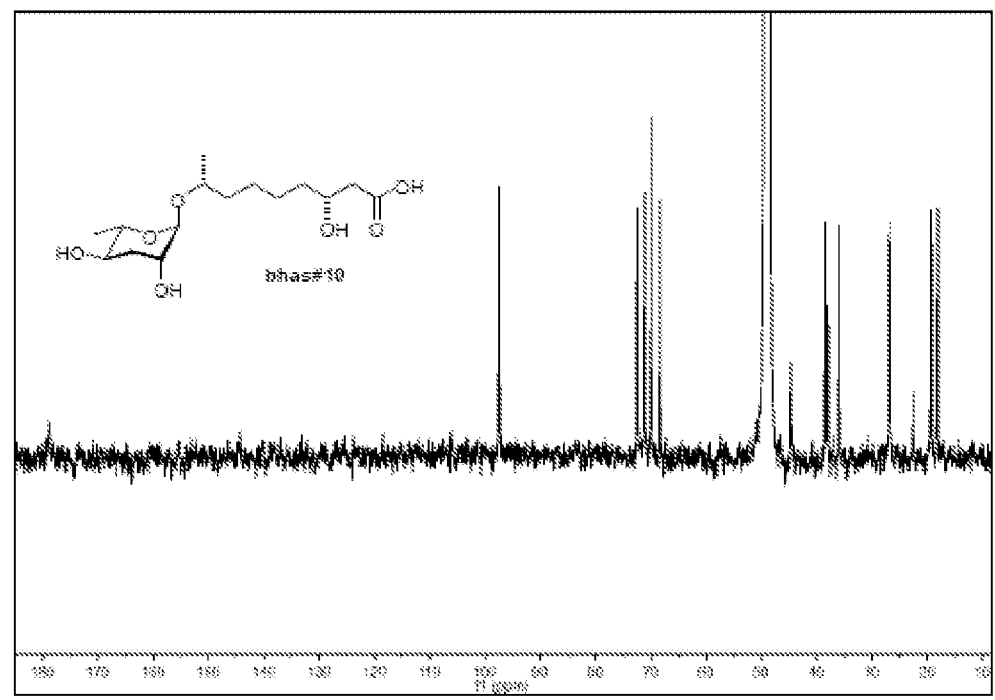
Figure 21C:
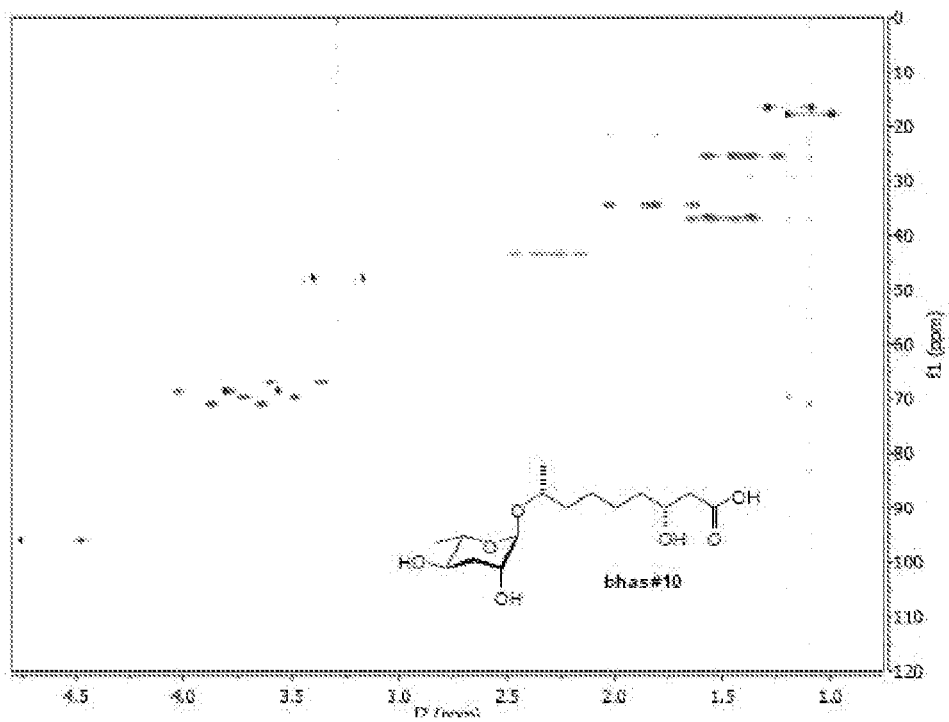
Figure 21D:
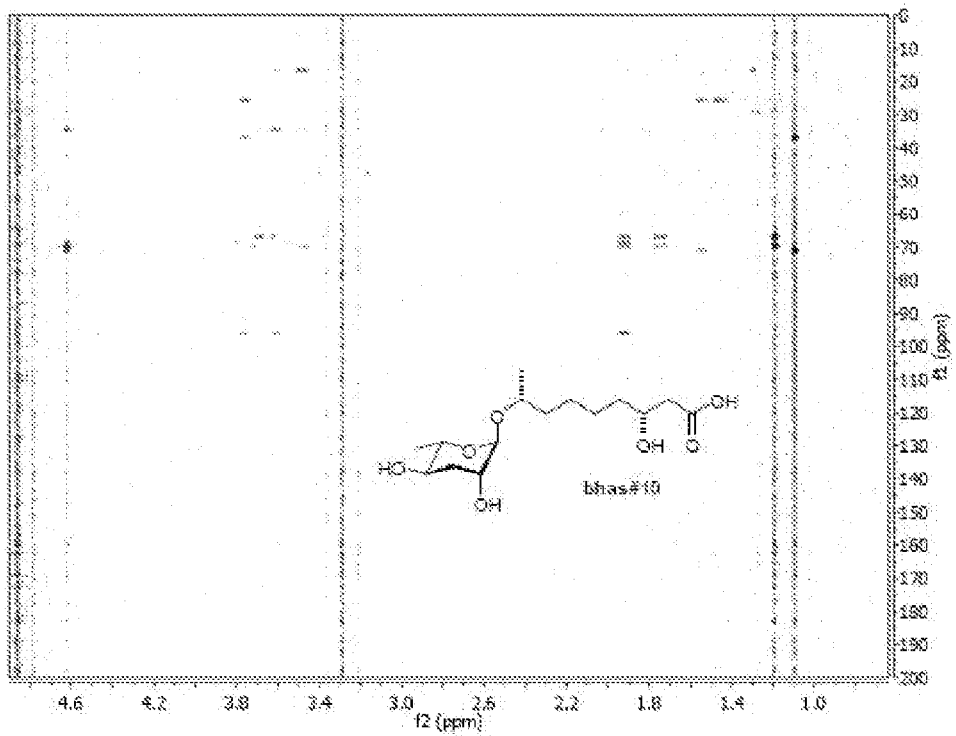

To prepare 10, a solution of 2,4-di-O-benzoyl-ascarylose-1-(2,2,2-trichloroacetimide) (1, 62 mg, 120 µmol, Butcher et al., *Nat. Chem. Biol.* 3:420-22 (2007), which is hereby incorporated by reference in its entirety) in dry DCM (2 ml) at −10° C. was treated with 9 (47 mg, 141 µmol) and trimethylsilyloxy triflate (10 µl). After 3.5 hours, the solution was washed with saturated aqueous NaHCO$_3$ solution (0.5 ml), dried over Na$_2$SO$_4$, and concentrated in vacuum. Flash column chromatography on silica using a gradient of 10-40% ethyl acetate in hexane afforded Ethyl (8R)-(3'R,5'R-Dibenzoyloxy-6'S-methyl-(2H)-tetrahydropyran-2'-yloxy)-(3R)-hydroxynonanoate (10) (4.0 mg, 7.2 µmol, 6%) as a colorless oil. $^1$H NMR (400 MHz, chloroform-$d_1$): δ (ppm) 1.19 (d, J=6.1 Hz, 3H), 1.27 (t, J=7.2 Hz, 3H), 1.28 (d, J=6.4 Hz, 3H), 1.33-1.72 (m, 8H), 2.20 (ddd, J=14.3 Hz, J=11.6 Hz, J=3.2 Hz, 1H), 2.42 (dd, J=16.5 Hz, J=9.0 Hz, 1H), 2.38-2.45 (m, 1H), 2.52 (dd, J=16.5 Hz, J=3.0 Hz, 1H), 3.00 (d, J=3.9 Hz, 1H), 3.80-3.89 (m, 1H), 3.98-4.07 (m, 1H), 4.11 (dq, J=9.7 Hz, J=6.1 Hz, 1H), 4.17 (q, J=7.2 Hz, 2H), 4.95 (s.br, 1H), 5.12-5.22 (m, 2H), 7.43-7.50 (m, 4H), 7.55-7.62 (m, 2H), 8.05 (d, J=7.5 Hz, 2H), 8.11 (d, J=7.5 Hz, 2H). See FIG. 20.

To prepare bhas#10, a solution of 10 (4 mg, 7.2 µmol) in THF (150 µl) was treated with LiOH (7 mg, 290 µl) in water (100 µl) and 1,4-dioxane (250 ml) at 67° C. for 5 hours. The reaction mixture was acidified with acetic acid (100 µl), concentrated in vacuum, treated with methanol (2 ml), and concentrated in vacuum. Flash column chromatography on silica using a gradient of 5-25% methanol in DCM with 0.5% glacial acetic acid afforded (8R)-(3'R,5'R-Dihydroxy-6'S-methyl-(2H)-tetrahydropyran-2'-yloxy)-(3R)-hydroxynonanoic acid (bhas#10) (1.5 mg, 4.7 µmol; 65%) as a colorless oil.

$^1$H (600 MHz), $^{13}$C (151 MHz), and HMBC NMR spectroscopic data for bhas#10 were obtained using methanol-$d_4$ and are shown in Table 4 below. Chemical shifts are referenced to (CD$_2$HOD)=3.31 ppm and ($\underline{C}$D$_2$HOD)=49.05 ppm. See FIGS. 21A-D.

TABLE 4

NMR spectroscopic data of bhas#10

| Position | δ $^{13}$C [ppm] | δ $^1$H [ppm] | $^1$H—$^1$H-coupling constants [Hz] | Relevant HMBC correlations |
|---|---|---|---|---|
| 1 | 178.5 | | | |
| 2 | 44.8 | 2.23-2.33 | | |
|   |      | 2.34-2.44 | | |
| 3 | 70.0 | 3.89-3.98 | | |
| 4 | 38.0 | 1.44-1.52 | | |
| 5-6 | 26.8, 27.0 | 1.33-1.52 | | |
| 7 | 38.4 | 1.44-1.63 | | C6, C8, |
| 8 | 72.5 | 3.78 | | C1', C-7, C-9 |
| 9 | 19.3 | 1.12 | $J_{8,9}$ = 6.2 | C-8, C-7 |
| 1' | 97.5 | 4.64 | | C-3', C-5', C-8 |
| 2' | 70.0 | 3.71 | | |
| 3' | 35.9 | 1.77 (ax) | $J_{3'ax, 3'eq}$ = 13.2, $J_{3'ax, 4'}$ = 11.5, $J_{2', 3'ax}$ = 3.1 | C-4', C-5' |
|   |      | 1.95 (eq) | $J_{2', 3'eq}$ = 13.2, $J_{3'eq, 4'}$ = 4.7 | C-1', C-2', C-4', C-5' |
| 4' | 68.4 | 3.51 | $J_{4', 5'}$ = 9.4 | C-3', C-5', C-6' |
| 5' | 71.2 | 3.63 | | C-1', C-3', C-4', C-6' |
| 6' | 18.1 | 1.22 | $J_{5', 6'}$ = 6.2 | C4', C-5' |

Example 38

Synthesis of Ascaroside bhas #22

Ascaroside bhas#22 was prepared as shown in Scheme 5 below.

Scheme 5

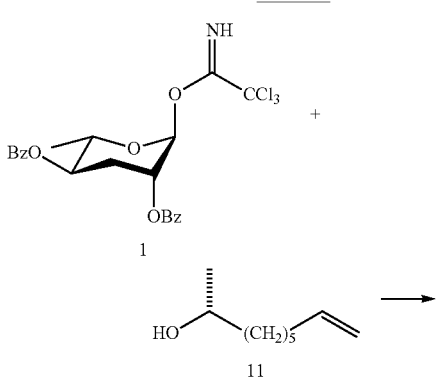

85
-continued

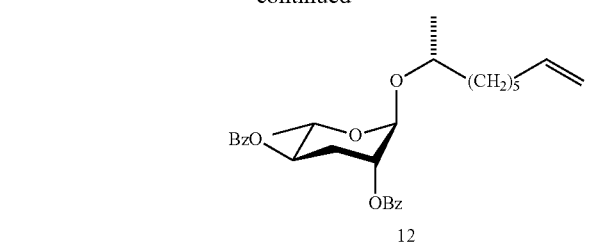
12

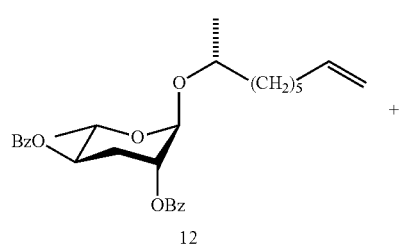
12

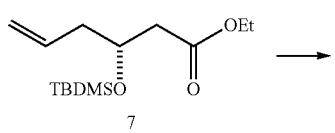
7

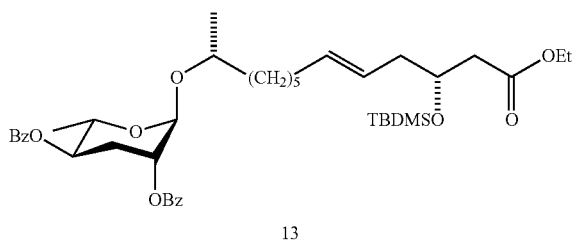
13

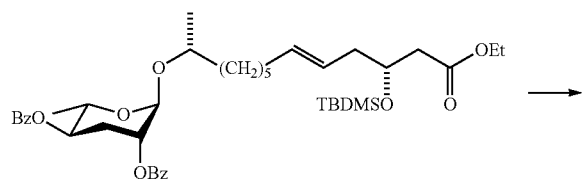
13

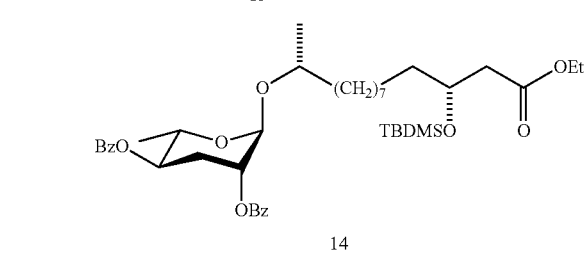
14

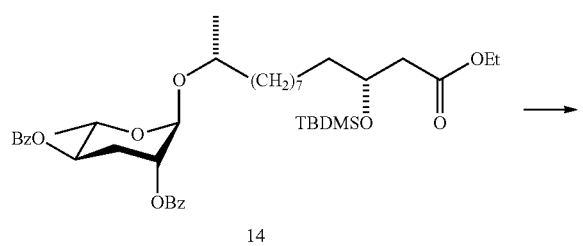
14

86
-continued

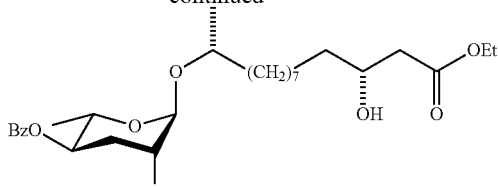
15

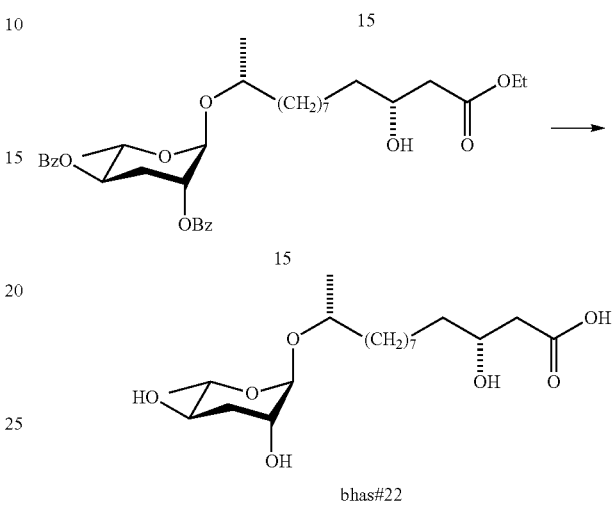
15 bhas#22

Figure 22A:
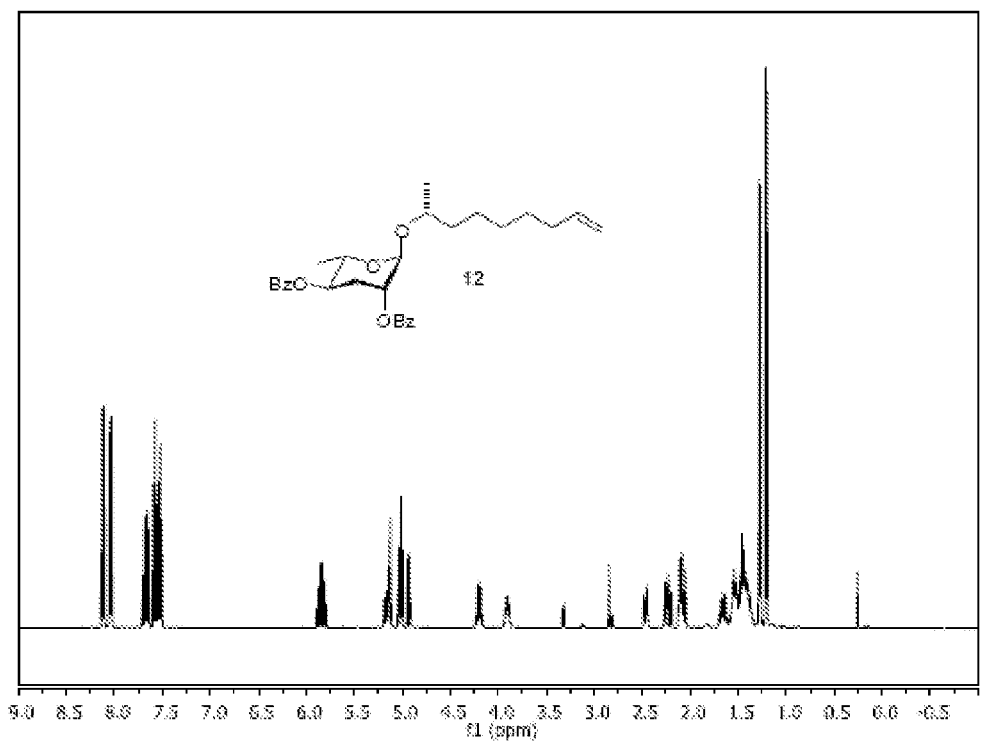
FIGS. 22A-B are the $^1$H NMR spectrum (FIG. 22A) and $^{13}$C NMR spectrum (FIG. 22B) of (8R)-(3'R,5'R-dibenzoyloxy-6'S-methyl-(2H)-tetrahydropyran-2'-yloxy)non-1-ene (12). $^1$H NMR: 400 MHz, acetone-d$_6$; $^{13}$C NMR: 100 MHz, acetone-d$_6$.
Figure 22B:
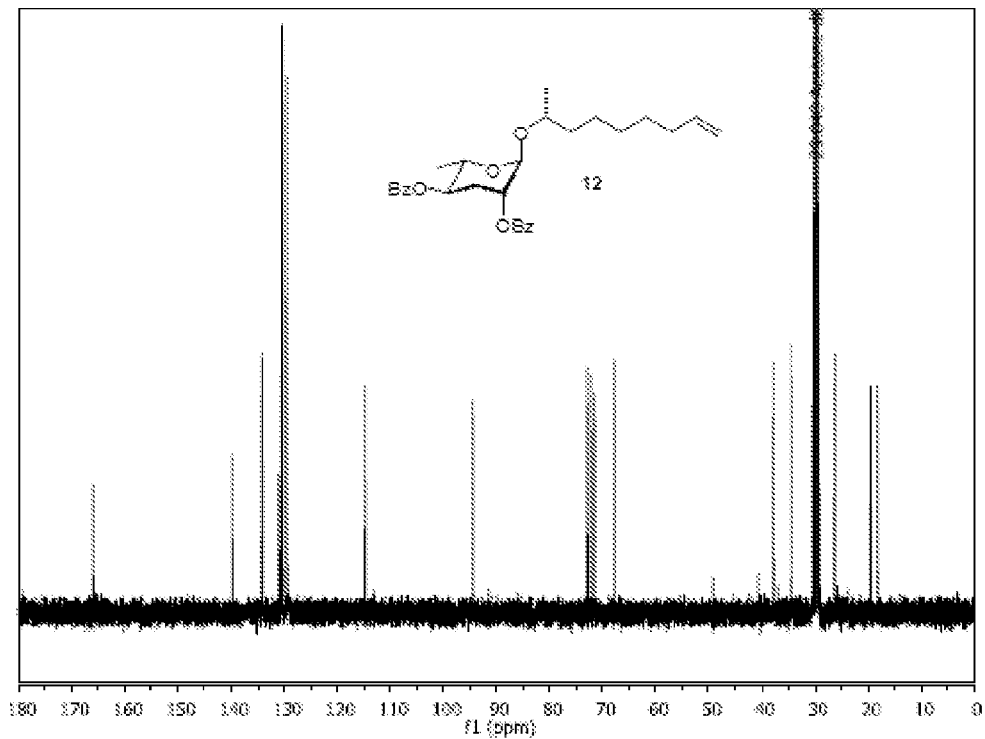

To prepare 12, a solution of 2,4-di-O-benzoyl-ascarylose-1-(2,2,2-trichloroacetimide) (1, 132 mg, 263 µmol, Butcher et al., *Nat. Chem. Biol.* 3:420-22 (2007), which is hereby incorporated by reference in its entirety) in dry DCM (3 ml) at 0° C. was treated with (8R)-hydroxynon-1-ene (11, 85.2 mg, 600 µmol, Ferrie et al., *Synlett* 18:2891-93 (2007), which is hereby incorporated by reference in its entirety) and trimethylsilyloxy triflate (5 µl). After 3 hours, the solution was washed with saturated aqueous NaHCO$_3$ solution (0.5 ml), dried over Na$_2$SO$_4$, and concentrated in vacuum. Flash column chromatography on silica using a gradient of 10-30% ethyl acetate in hexanes afforded (8R)-(3'R,5'R-Dibenzoyloxy-6'S-methyl-(2H)-tetrahydropyran-2'-yloxy) non-1-ene (12) (71.0 mg, 148 µmol, 56%) as a colorless oil. $^1$H NMR (400 MHz, acetone-d$_6$): δ (ppm) 1.20 (d, J=6.1 Hz, 3H), 1.27 (d, J=6.3 Hz, 3H), 1.33-1.72 (m, 8H), 2.09 (m, 2H), 2.23 (ddd, J=13.5 Hz, J=11.4 Hz, J=3.2 Hz, 1H), 2.47 (m, 1H), 3.91 (m, 1H), 4.20 (dq, J=9.6 Hz, J=6.1 Hz, 1H), 4.93 (ddt, J=10.2 Hz, J=2.2 Hz, J=1.3 Hz, 1H), 5.01 (s.br, 1H), 5.02 (ddt, J=17.1, Hz, J=2.2 Hz, J=1.6 Hz, 1H), 5.13 (m, 1H), 5.16 (ddd, J=11.3 Hz, J=9.8 Hz, J=4.6 Hz, 1H), 5.84 (ddt, J=17.1 Hz, J=10.3 Hz, J=6.8 Hz, 1H), 7.50-7.60 (m, 4H), 7.63-7.71 (m, 2H), 8.04 (m, 2H), 8.12 (m, 2H); $^{13}$C NMR (100 MHz, acetone-d$_6$): δ (ppm) 18.3, 19.5, 26.3, 29.7, 29.7, 30.4, 34.4, 37.8, 67.7, 71.5, 72.1, 72.9, 94.4, 114.8, 129.4, 129.5, 130.2, 130.4, 131.0, 131.0, 134.1, 134.2, 139.8, 165.9, 166.0. See FIGS. 22A-B.

Figure 23:
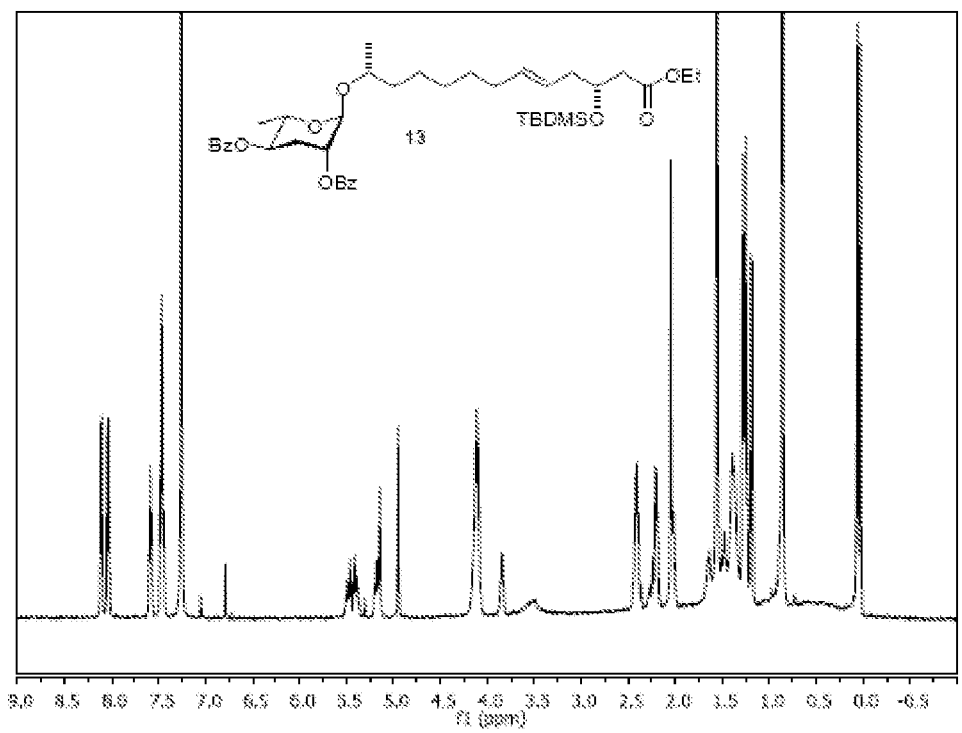
FIG. 23 is the $^1$H NMR spectrum (400 MHz, chloroform-d$_1$) of (12R)-(3'R,5'R-dibenzoyloxy-6'S-methyl-(2H)-tetrahydropyran-2'-yloxy)-(3R)-tert-butyldimethylsilyloxytridec-5-enoic acid ethyl ester (13).

To prepare 13, a solution of 12 (38 mg, 80 µmol) and 7 (65 mg, 240 µmol, Evans & Andrews, *Angew. Chem. Int. Ed.* 47:5426-29 (2008), which is hereby incorporated by reference in its entirety) in dry DCM (2 ml) was treated with 1,4-benzoquinone (1 mg, 8 µmol) in DCM (0.5 ml) and stirred for 10 minutes. A solution of Grubbs 2$^{nd}$ generation catalyst (3 mg, 4 µmol) in DCM (0.5 ml) was added. The resulting mixture was stirred at 40° C. After 20 hours, the mixture was filtered over a small layer of silica and concentrated in vacuum. Flash column chromatography on silica using a 5:1 mixture of hexanes and ethyl acetate afforded Ethyl (12R)-(3'R,5'R-dibenzoyloxy-6'S-methyl-(2H)-tetrahydropyran-2'-yloxy)-(3R)-tert-butyldimethylsilyloxytridec-5-enoate (13) (17.0 mg, 23 µmol, 29%) as a colorless oil. $^1$H NMR (400 MHz, chloroform-d$_1$): δ (ppm) 0.03 (s, 3H), 0.06 (s, 3H), 0.86 (s, 9H), 1.19 (d, J=6.2 Hz, 3H), 1.25 (t, J=7.1 Hz, 3H), 1.28 (d, J=6.3 Hz, 3H), 1.32-1.44 (m, 4H), 1.44-1.52 (m, 2H), 1.61-1.68 (m, 2H), 1.99-2.06 (m, 2H), 2.17-2.22 (m, 3H), 2.38-2.43 (m, 3H), 3.84 (m, 1H), 4.06-4.18 (m, 4H), 4.95 (s, 1H), 5.14 (s.br, 1H), 5.18 (dt, J=4.2 Hz, J=10.6 Hz, 1H), 5.39 (dt, J=15.2 Hz, J=6.8 Hz, 1H), 5.47 (dt, J=15.2 Hz, J=6.3 Hz, 1H), 7.43-7.49 (m, 4H), 7.56-7.61 (m, 2H), 8.04 (d, J=7.4 Hz, 2H), 8.11 (d, J=7.2 Hz, 2H). See FIG. 23.

Figure 24:
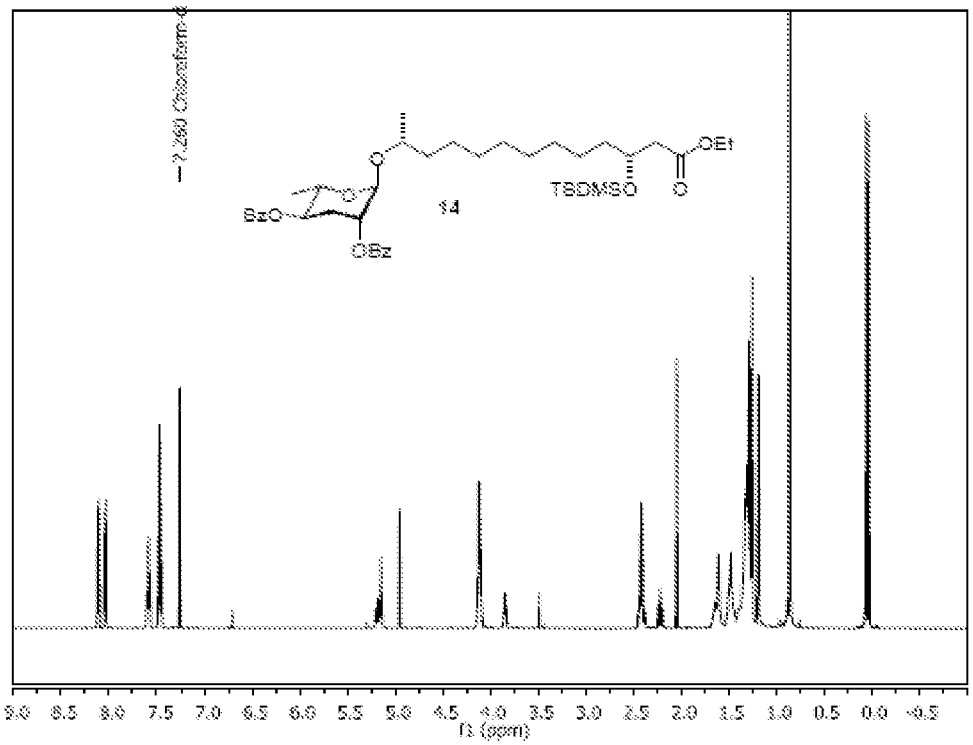
FIG. 24 is the $^1$H NMR spectrum (400 MHz, chloroform-d$_1$) of (12R)-(3'R,5'R-dibenzoyloxy-6'S-methyl-(2H)-tetrahydropyran-2'-yloxy)-(3R)-tert-butyldimethylsilyloxytridecanoic acid ethyl ester (14).

To prepare 14, a solution of 13 (14.2 mg, 18.9 µmol) in methanol (1.5 ml) was treated with Pd/C and hydrogenated for 24 hours. The mixture was filtered and concentrated in vacuum to afford Ethyl (12R)-(3'R,5'R-dibenzoyloxy-6'S-methyl-(2H)-tetrahydropyran-2'-yloxy)-(3R)-tert-butyldimethylsilyloxytridecanoate (14) (12.8 mg, 17.0 µmol, 90%) as a colorless oil. $^1$H NMR (600 MHz, chloroform-d$_1$): δ (ppm) 0.03 (s, 3H), 0.05 (s, 3H), 0.86 (s, 9H), 1.19 (d, J=6.1 Hz, 3H), 1.25 (t, J=7.1 Hz, 3H), 1.28 (d, J=6.3 Hz, 3H), 1.29-1.40 (m, 10H), 1.42-1.53 (m, 4H), 1.58-1.68 (m, 2H), 2.21 (ddd, J=14.0 Hz, J=11.7 Hz, J=2.8 Hz, 1H), 2.37-2.45 (m, 3H), 3.84 (m, 1H), 4.08-4.15 (m, 4H), 4.95 (s, 1H), 5.14 (s.br, 1H), 5.18 (dt, J=4.2 Hz, J=10.6 Hz, 1H), 7.43-7.49 (m, 4H), 7.56-7.61 (m, 2H), 8.04 (d, J=7.4 Hz, 2H), 8.11 (d, J=7.2 Hz, 2H). See FIG. 24.

Figure 25:
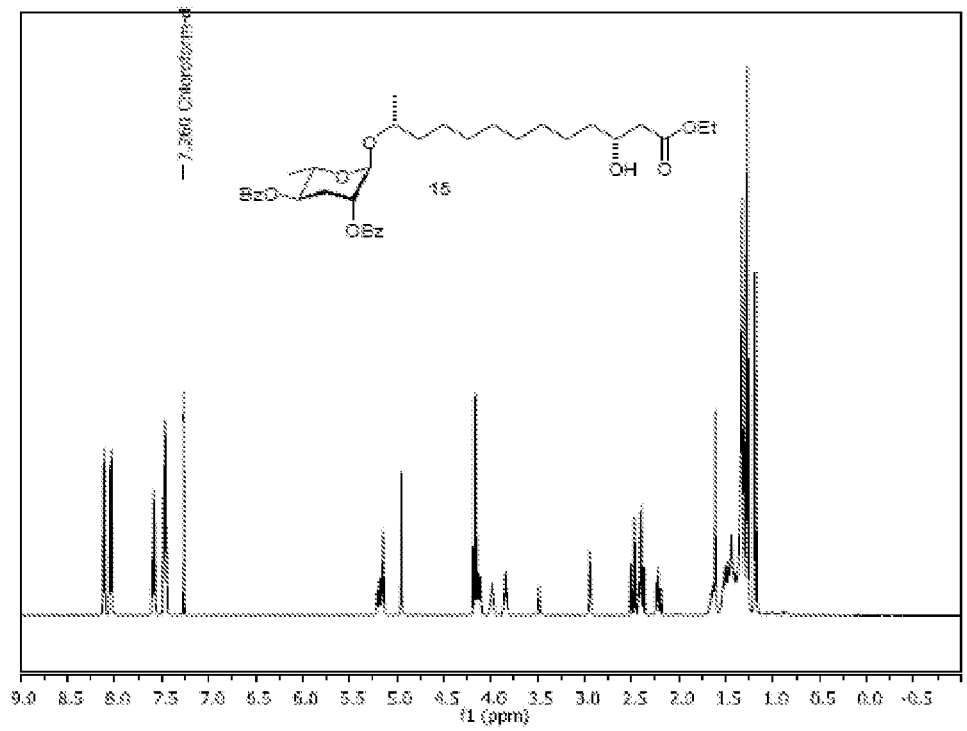
FIG. 25 is the $^1$H NMR spectrum (400 MHz, chloroform-d$_1$) of (12R)-(3'R,5'R-dibenzoyloxy-6'S-methyl-(2H)-tetrahydropyran-2'-yloxy)-(3R)-hydroxytridecanoic acid ethyl ester (15).
Figure 26A:
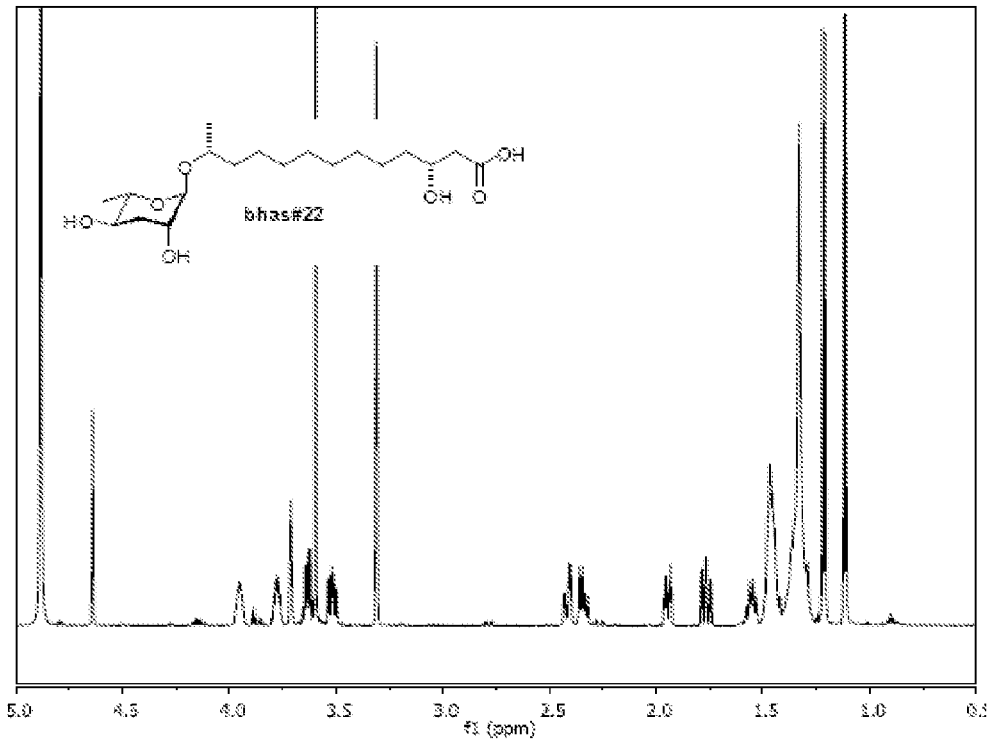
FIGS. 26A-D are the $^1$H NMR spectrum (FIG. 26A), dqfCOSY spectrum (FIG. 26B), HSQC spectrum (FIG. 26C), and HMBC spectrum (FIG. 26D) of (12R)-(3'R,5'R-dihydroxy-6'S-methyl-(2H)-tetrahydropyran-2'-yloxy)-(3R)-hydroxytridecanoic acid (bhas#22). $^1$H NMR: 600 MHz, methanol-d$_4$; dqfCOSY: 600 MHz, methanol-d$_4$; HSQC: 600 MHz for $^1$H, 151 MHz for $^{13}$C, methanol-d$_4$; HMBC: 600 MHz for $^1$H, 151 MHz for $^{13}$C, methanol-d$_4$.
Figure 26B:
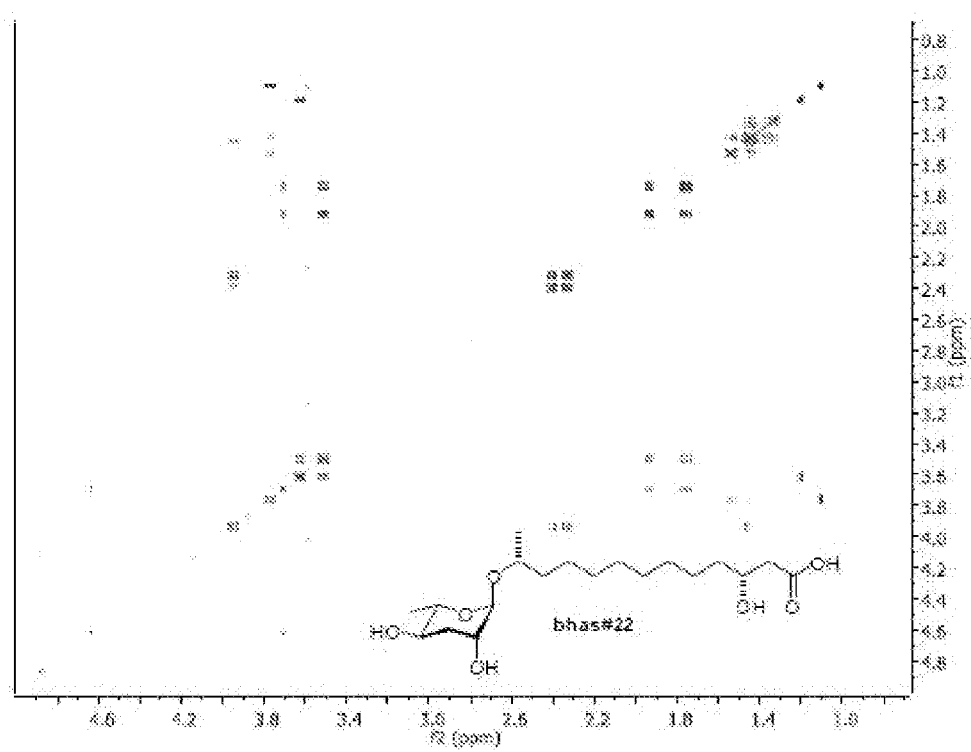
Figure 26C:
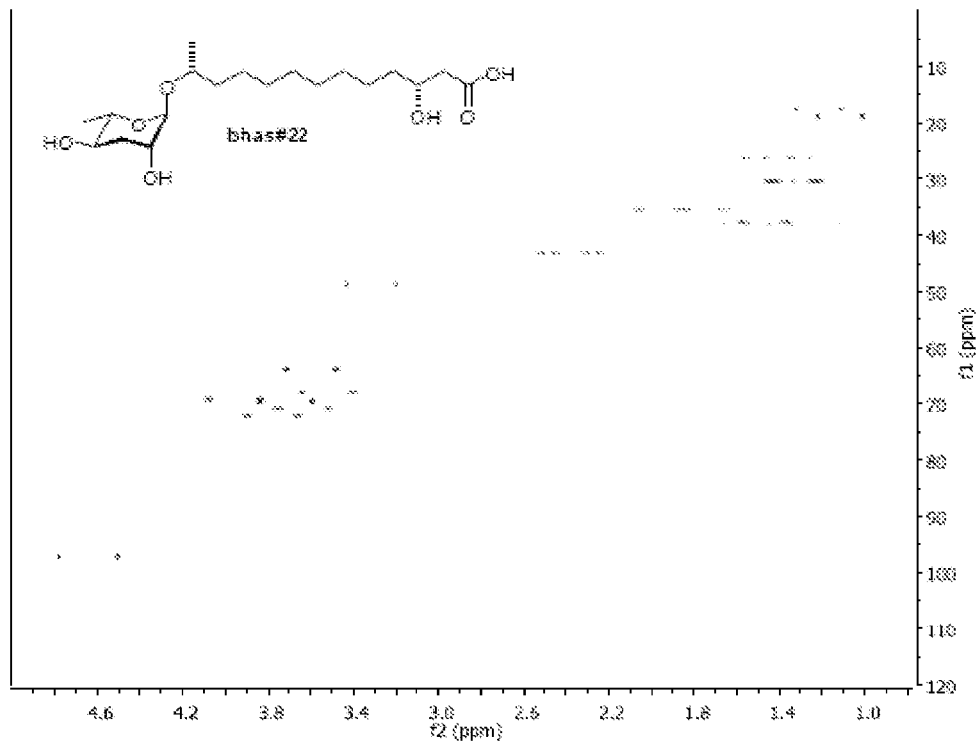
Figure 26D:
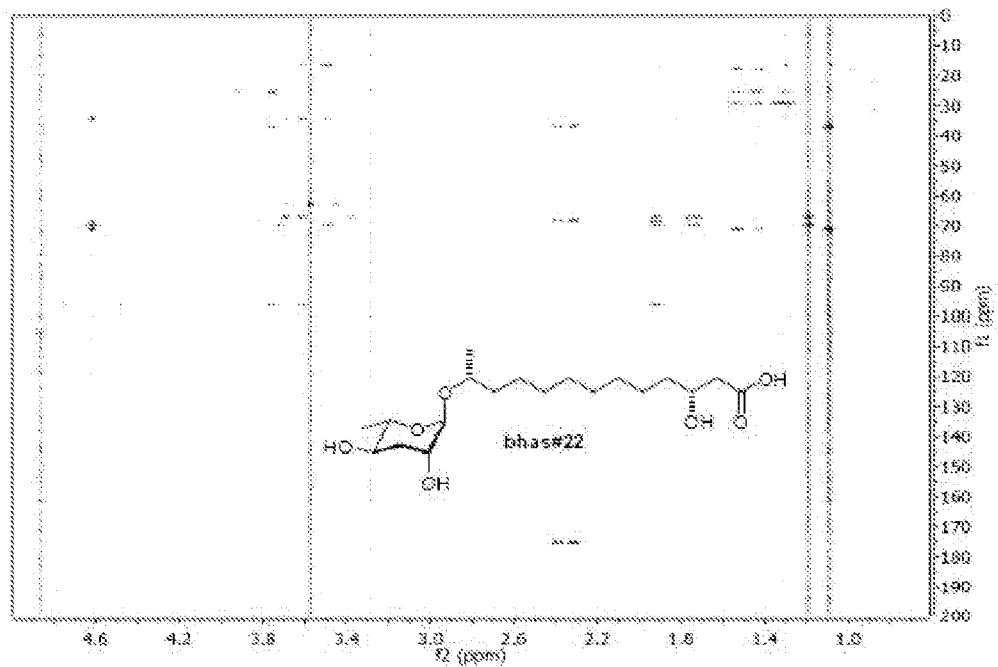

To prepare 15, a solution of 14 (19.5 mg, 26.8 µmol) in acetonitrile (1 ml) was treated with 40% aqueous hydrofluoric acid (10 µl) in acetonitrile (100 µl). After stirring for 1 hour, the solution was treated with NaHCO$_3$ (100 mg) for 15 minutes, dried over Na$_2$SO$_4$, and concentrated in vacuum. Flash column chromatography on silica using a gradient of 5-80% ethyl acetate in hexanes afforded Ethyl (12R)-(3'R,5'R-dibenzoyloxy-6'S-methyl-(2H)-tetrahydropyran-2'-yloxy)-(3R)-hydroxytridecanoate (15) (12.0 mg, 19.6 µmol; 73%) as a colorless oil. $^1$H NMR (501 MHz, chloroform-d$_1$): δ (ppm) 1.19 (d, J=6.1 Hz, 3H), 1.27 (t, J=7.2 Hz, 3H), 1.28 (d, J=6.4 Hz, 3H), 1.30-1.55 (m, 14H), 1.60-1.68 (m, 2H), 2.21 (ddd, J=13.5 Hz, J=11.6 Hz, J=3.1 Hz, 1H), 2.38 (dd, J=16.4 Hz, J=9.2 Hz, 1H), 2.41 (m, 1H), 2.49 (dd, J=16.3 Hz, J=3.1 Hz, 1H), 3.84 (m, 1H), 3.99 (m, 1H), 4.12 (dq, J=9.8 Hz, J=6.2 Hz, 1H), 4.17 (q, J=7.1 Hz, 2H), 4.95 (s, 1H), 5.15 (s.br, 1H), 5.18 (ddd, J=11.2 Hz, J=9.9 Hz, J=4.5 Hz, 1H), 7.43-7.49 (m, 4H), 7.56-7.61 (m, 2H), 8.04 (m, 2H), 8.11 (m, 2H). See FIG. 25.

To prepare bhas#22, a solution of 15 (12 mg, 19.6 µmol) in THF (1 ml) was treated with LiOH (15 mg) in water (200 µl) and 1,4-dioxane (2 ml) at 67° C. for 3 hours. The reaction mixture was acidified with acetic acid (100 µl), concentrated in vacuum, treated with methanol (2 ml), and concentrated in vacuum. Flash column chromatography on silica using a gradient of 5-30% methanol in DCM with 0.2% acetic acid afforded (12R)-(3'R,5'R-Dihydroxy-6'S-methyl-(2H)-tetrahydropyran-2'-yloxy)-(3R)-hydroxytridecanoic acid (bhas#22) (7.3 mg, 19.4 µmol; 99%) as a colorless oil.

$^1$H (600 MHz), $^{13}$C (151 MHz), and HMBC NMR spectroscopic data for bhas#22 were obtained using methanol-d$_4$ and are shown in Table 5 below. Chemical shifts were referenced to (CD$_2$HOD)=3.31 ppm and (CD$_2$HOD)=49.05 ppm. See FIGS. 26A-D.

TABLE 5

NMR spectroscopic data of bhas#22

| Position | δ $^{13}$C [ppm] | δ $^1$H [ppm] | $^1$H—$^1$H-coupling constants [Hz] | Relevant HMBC correlations |
|---|---|---|---|---|
| 1 | 176.4 | | | |
| 2 | 43.4 | 2.34, 2.42 | $J_{2,2}$ = 15.2, $J_{2,3}$ = 8.1 | C-1, C-3, C-4 |
| 3 | 69.2 | 3.95 | | C-4, C-5 |
| 4 | 37.8 | 1.45 | | |
| 5-10 | 26.4-30.4 | 1.26-1.39 | | |
| 11 | 38.0 | 1.40-1.50 | | C9, C10, C12, C13 |
| 12 | 72.2 | 3.78 | | C1', C-9, C-10, C11 |
| 13 | 18.9 | 1.12 | $J_{12,13}$ = 6.2 | C-11, C-12 |
| 1' | 97.2 | 4.64 | | C-2', C-3', C-5', C-12 |
| 2' | 69.6 | 3.71 | | C-3', C-4' |
| 3' | 35.5 | 1.77 (ax) | $J_{3'ax, 3'eq}$ = 13.1, $J_{3'ax, 4'}$ = 11.4, $J_{2', 3'ax}$ = 3.0 | C-2', C-4', C-5' |
| | | 1.95 (eq) | $J_{2', 3'eq}$ = 3.2, $J_{3'eq, 4'}$ = 4.7 | C-1', C-2', C-4', C-5' |
| 4' | 68.0 | 3.52 | $J_{4', 5'}$ = 9.6 | C-1', C-3', C-6' |
| 5' | 70.9 | 3.63 | $J_{5', 6'}$ = 6.3 | C-1', C-3', C-4', C-6' |
| 6' | 17.8 | 1.21 | | C4', C-5' |

Example 39

Synthesis of Ascarolside bhos#26

Ascaroside bhos#26 was prepared as shown in Scheme 6 below.

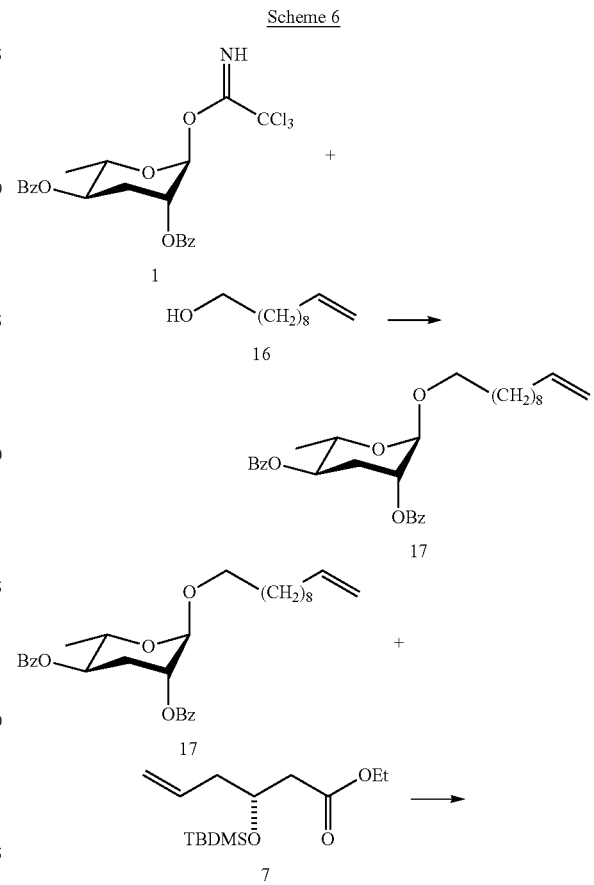

Scheme 6

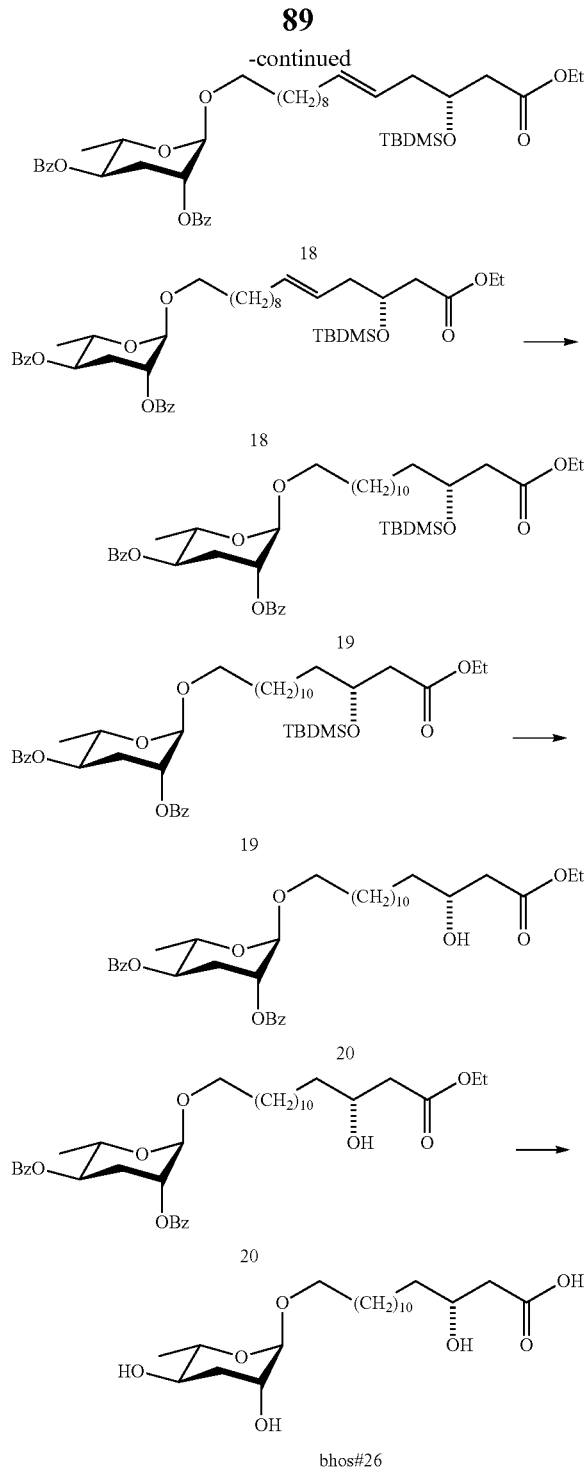

Figure 27A:
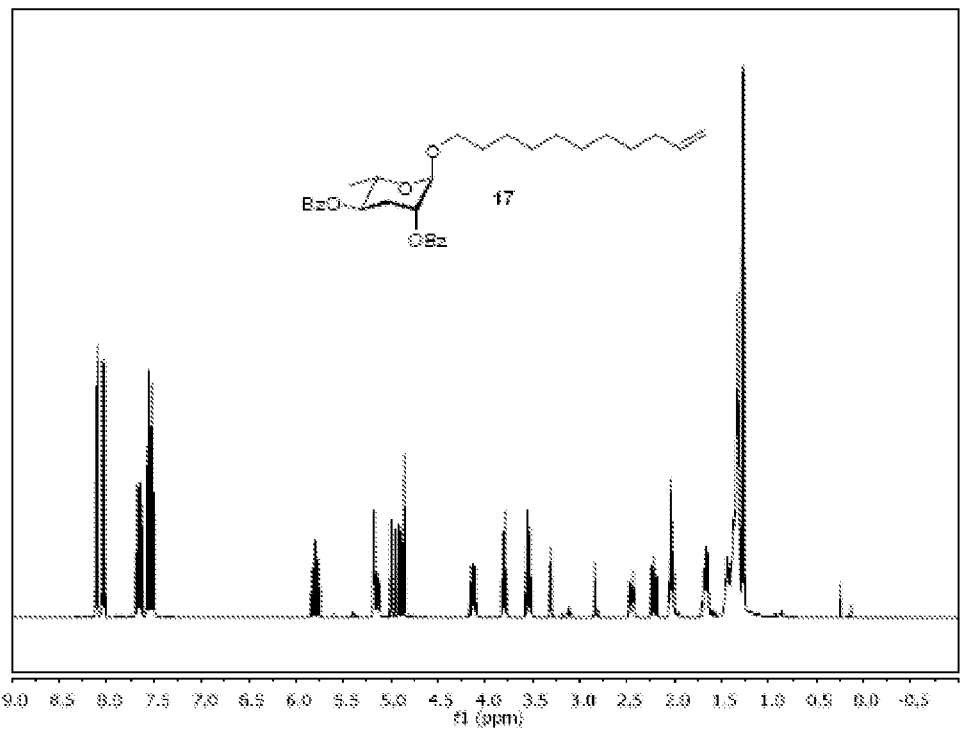
FIGS. 27A-B are the $^1$H NMR spectrum (FIG. 27A) and $^{13}$C NMR spectrum (FIG. 27B) of 11-(3'R,5'R-dibenzoyloxy-6'S-methyl-(2H)-tetrahydropyran-2'-yloxy)undec-1-ene (17). $^1$H NMR: 400 MHz, acetone-d$_6$; $^{13}$C NMR: 100 MHz, acetone-d$_6$.
Figure 27B:
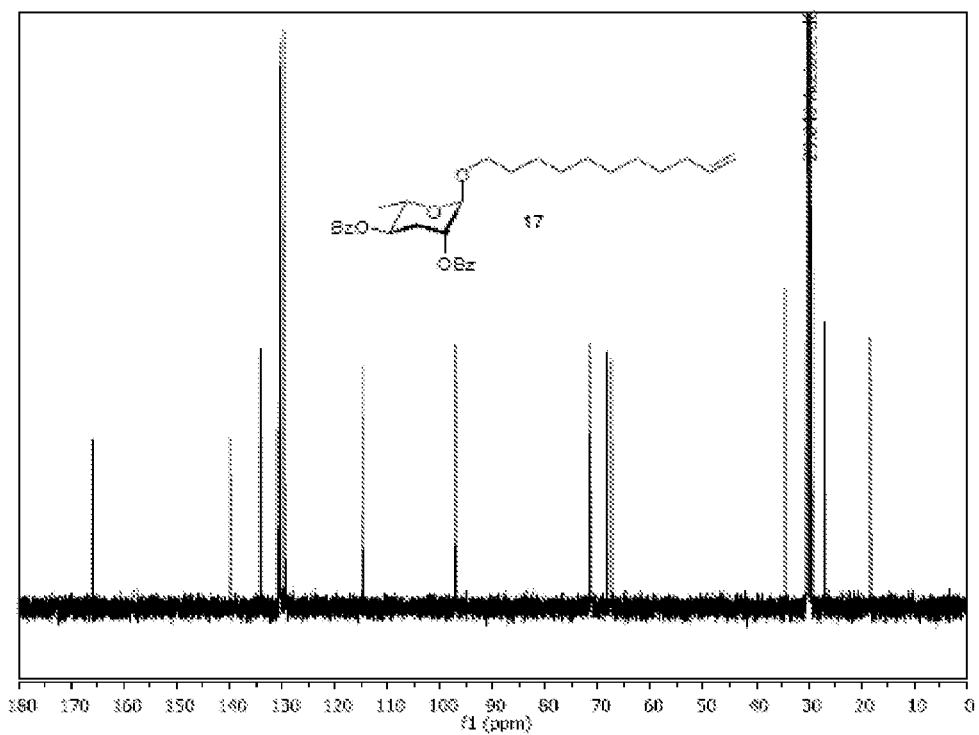

To prepare 17, a solution of 2,4-di-O-benzoyl-ascarylose-1-(2,2,2-trichloroacetimide) (1, 132 mg, 263 μmol, Butcher et al., *Nat. Chem. Biol.* 3:420-22 (2007), which is hereby incorporated by reference in its entirety) in dry DCM (3 ml) at 0° C. was treated with 11-hydroxyundec-1-ene (16, 102 mg, 600 μmol) and trimethylsilyloxy triflate (5 μl). After 3 hours, the solution was washed with saturated aqueous NaHCO₃ solution (0.5 ml), dried over Na₂SO₄, and concentrated in vacuum. Flash column chromatography on silica using gradient of 10-30% (v/v) ethyl acetate in hexanes afforded 11-(3'R,5'R-Dibenzoyloxy-6'S-methyl-(2H)-tetrahydropyran-2'-yloxy)undec-1-ene (17) (92.3 mg, 182 μmol, 69%) as a colorless oil. ¹H NMR (400 MHz, acetone-d₆): δ (ppm) 1.28 (d, J=6.2 Hz, 3H), 1.30-1.49 (m, 11H), 1.63-1.72 (m, 2H), 2.03 (m, 2H), 2.22 (ddd, J=13.5 Hz, J=11.3 Hz, J=3.2 Hz, 1H), 2.46 (m, 1H), 3.55 (dt, J=9.7 Hz, J=6.5 Hz, 1H), 3.80 (dt, J=9.8 Hz, J=6.7 Hz, 1H), 4.13 (dq, J=9.8 Hz, J=6.3 Hz, 1H), 4.86 (s.br, 1H), 4.90 (ddt, J=10.2 Hz, J=2.2 Hz, J=1.3 Hz, 1H), 5.98 (ddt, J=17.1, Hz, J=2.2 Hz, J=1.6 Hz, 1H), 5.15 (ddd, J=11.3 Hz, J=9.8 Hz, J=4.6 Hz, 1H), 5.18 (m, 1H), 5.80 (ddt, J=17.1 Hz, J=10.3 Hz, J=6.8 Hz, 1H), 7.49-7.59 (m, 4H), 7.62-7.71 (m, 2H), 8.04 (m, 2H), 8.11 (m, 2H); ¹³C NMR (100 MHz, acetone-d₆): δ (ppm) 18.28, 26.88, 29.67, 29.83, 30.10, 30.16, 30.28, 34.46, 67.43, 68.25, 71.43, 71.53, 97.00, 114.66, 129.42, 129.48, 130.23, 130.35, 130.95, 130.96, 134.08, 134.19, 139.78, 165.89, 165.91. See FIGS. 27A-B.

Figure 28:
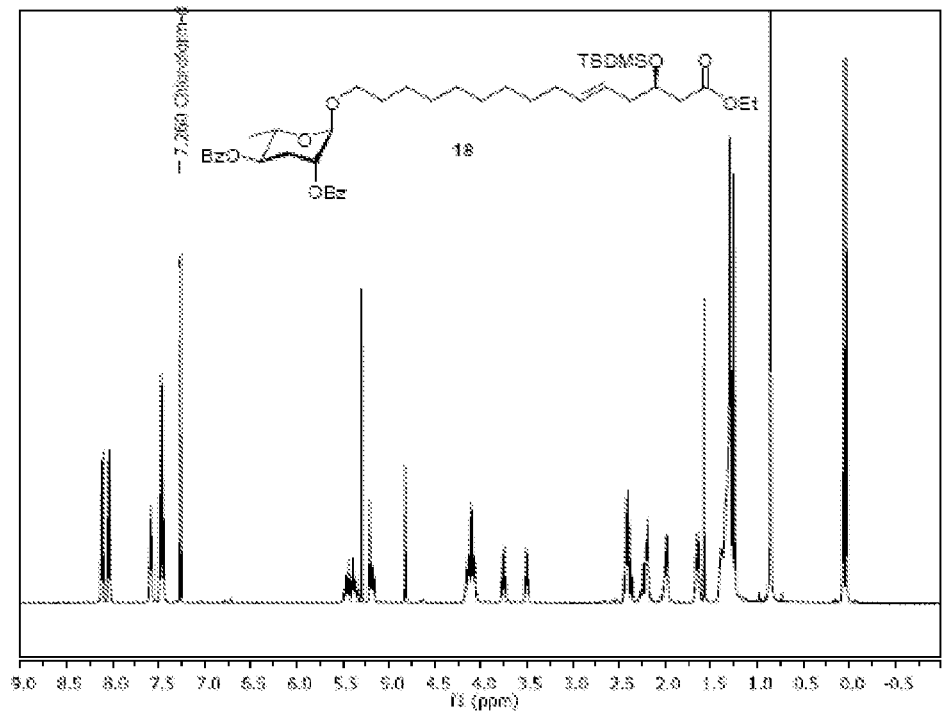
FIG. 28 is the $^1$H NMR spectrum (400 MHz, chloroform-d$_1$) of 15-(3'R,5'R-dibenzoyloxy-6'S-methyl-(2H)-tetrahydropyran-2'-yloxy)-(3R)-tert-butyldimethylsilyloxypentadec-5-enoic acid ethyl ester (18).

To prepare 18, a solution of 17 (30.8 mg, 60 μmol) and 7 (50 mg, 180 μmol, Evans & Andrews, *Angew. Chem. Int. Ed.* 47:5426-29 (2008), which is hereby incorporated by reference in its entirety) in dry DCM (2 ml) was treated with 1,4-benzoquinone (1 mg, 8 μmol) in DCM (0.5 ml) and stirred for 10 minutes. A solution of Grubbs 2$^{nd}$ generation catalyst (3 mg, 4 μmol) in DCM (0.5 ml) was added. The resulting mixture was stirred at 40° C. After 20 hours, the mixture was filtered over a small layer of silica and concentrated in vacuum. Flash column chromatography on silica using a 5:1 mixture of hexanes and ethyl acetate afforded Ethyl 15-(3'R,5'R-dibenzoyloxy-6'S-methyl-(2H)-tetrahydropyran-2'-yloxy)-(3R)-tert-butyldimethylsilyloxy-pentadec-5-enoate (18) (14.2 mg, 18.9 μmol, 31%) as a colorless oil. ¹H NMR (400 MHz, chloroform-d₁): δ (ppm) 0.03 (s, 3H), 0.06 (s, 3H), 0.86 (s, 9H), 1.25 (t, J=7.2 Hz, 3H), 1.30 (d, J=6.2 Hz, 3H), 1.27-1.43 (m, 12H), 1.61-1.68 (m, 2H), 1.95-2.02 (m, 2H), 2.16-2.25 (m, 2H), 2.35-2.46 (m, 3H), 3.50 (dt, J=9.6 Hz, J=6.5 Hz, 1H), 3.76 (dt, J=9.6 Hz, J=6.8 Hz, 1H), 4.04-4.18 (m, 4H), 4.82 (s, 1H), 5.18 (ddd, J=11.2 Hz, J=9.9 Hz, J=4.7 Hz, 1H), 5.21 (s.br, 1H), 5.37 (dt, J=15.2 Hz, J=7.0 Hz, 1H), 5.45 (dt, J=15.3 Hz, J=6.9 Hz, 1H), 7.43-7.50 (m, 4H), 7.56-7.61 (m, 2H), 8.04 (m, 2H), 8.11 (m, 2H). See FIG. 28.

Figure 29:
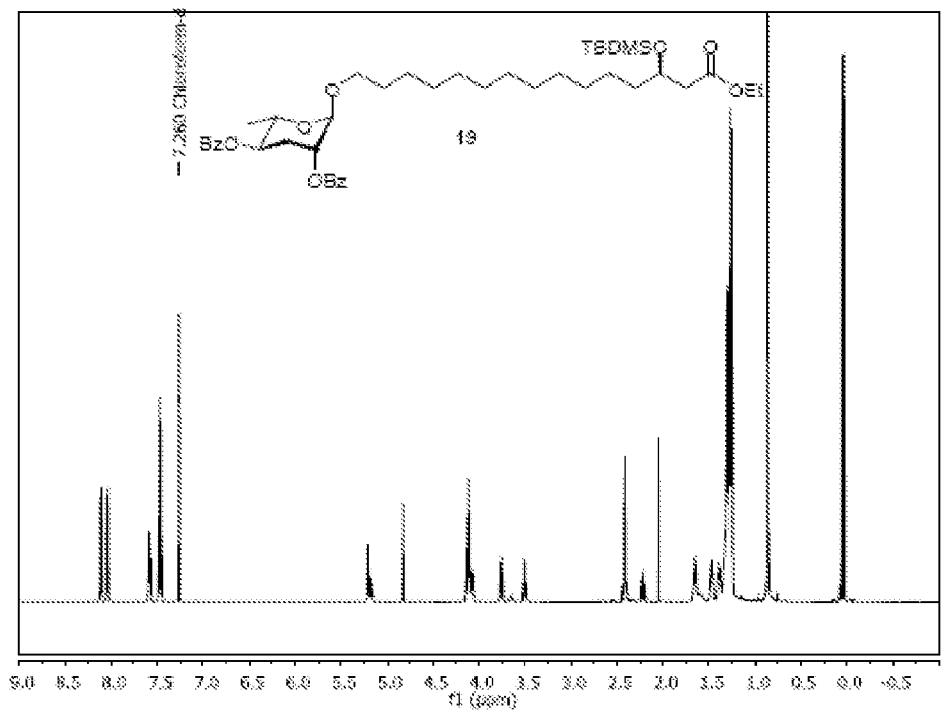
FIG. 29 is the $^1$H NMR spectrum (400 MHz, chloroform-d$_1$) of 15-(3'R,5'R-dibenzoyloxy-6'S-methyl-(2H)-tetrahydropyran-2'-yloxy)-(3R)-tert-butyldimethylsilyloxypentadecanoic acid ethyl ester (19).

To prepare 19, a solution of 18 (14.2 mg, 18.9 μmol) in methanol (1.5 ml) was treated with Pd/C (10 mg, 10%, w/w) and hydrogenated for 24 hours. The mixture was filtered and concentrated in vacuum. Flash column chromatography on silica using a gradient of 5-80% ethyl acetate in hexanes afforded Ethyl 15-(3'R,5'R-dibenzoyloxy-6'S-methyl-(2H)-tetrahydropyran-2'-yloxy)-(3R)-tert-butyldimethylsilyloxy-pentadecanoate (19) (12.8 mg, 17.0 μmol, 90%) as a colorless oil. ¹H NMR (400 MHz, chloroform-d₁): δ (ppm) 0.03 (s, 3H), 0.06 (s, 3H), 0.86 (s, 9H), 1.25 (t, J=7.2 Hz, 3H), 1.30 (d, J=6.2 Hz, 3H), 1.25-1.36 (m, 14H), 1.36-1.42 (m, 2H), 1.45-1.51 (m, 2H), 1.61-1.68 (m, 2H), 2.21 (ddd, J=14.3 Hz, J=11.4 Hz, J=3.2 Hz, 1H), 2.35-2.46 (m, 3H), 3.50 (dt, J=9.6 Hz, J=6.5 Hz, 1H), 3.76 (dt, J=9.6 Hz, J=6.8 Hz, 1H), 4.04-4.18 (m, 4H), 4.82 (s, 1H), 5.18 (ddd, J=11.2 Hz, J=9.9 Hz, J=4.7 Hz, 1H), 5.20 (s.br, 1H), 7.43-7.50 (m, 4H), 7.56-7.61 (m, 2H), 8.04 (m, 2H), 8.11 (m, 2H). See FIG. 29.

To prepare 20, a solution of 19 (9.2 mg, 12.2 μmol) in acetonitrile (2 ml) was treated with 40% hydrofluoric acid (20 μl). After stirring for 1 hour, the solution was treated with NaHCO₃ (100 mg) for 15 minutes, dried over Na₂SO₄, and concentrated in vacuum. Flash column chromatography on silica using a gradient of 5-80% ethyl acetate in hexanes afforded Ethyl 15-(3'R,5'R-dibenzoyloxy-6'S-methyl-(2H)-tetrahydropyran-2'-yloxy)-(3R)-hydroxypentadecanoate (20) (4.4 mg, 6.9 μmol; 57%). ¹H NMR (400 MHz, chloroform-d₁): δ (ppm) 1.27 (t, J=7.2 Hz, 3H), 1.30 (d, J=6.2 Hz, 3H), 1.25-1.36 (m, 16H), 1.36-1.42 (m, 2H), 1.45-1.51 (m, 2H), 1.61-1.68 (m, 2H), 2.21 (ddd, J=14.3 Hz, J=11.4

Figure 30:
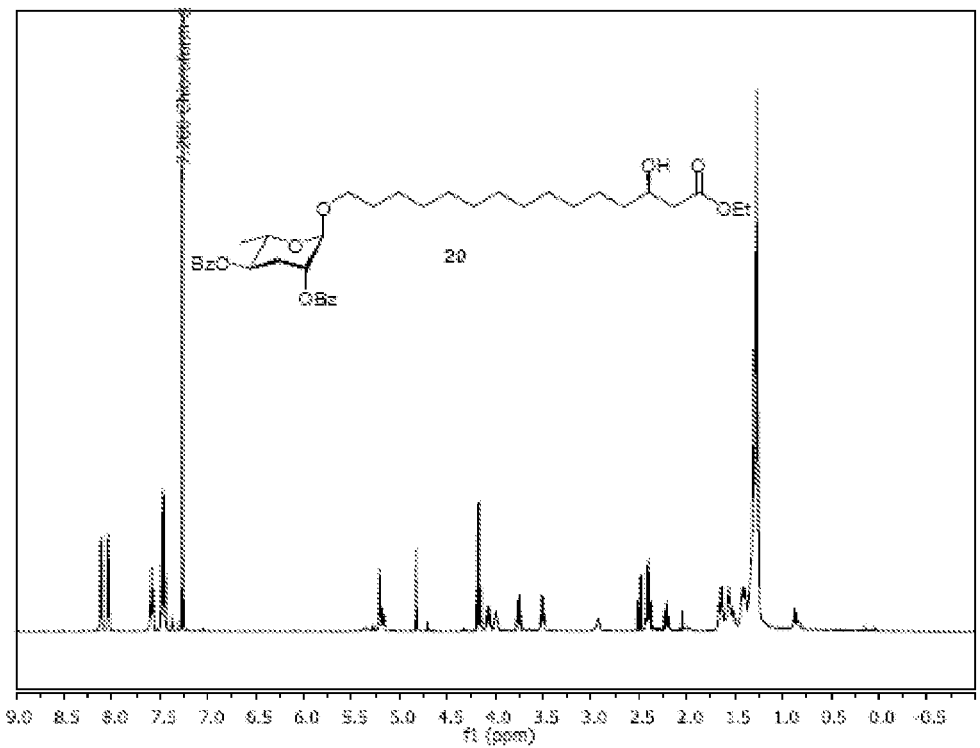
FIG. 30 is the $^1$H NMR spectrum (400 MHz, chloroform-d$_1$) of 15-(3'R,5'R-dibenzoyloxy-6'S-methyl-(2H)-tetrahydropyran-2'-yloxy)-(3R)-hydroxypentadecanoic acid ethyl ester (20).
Figure 31A:
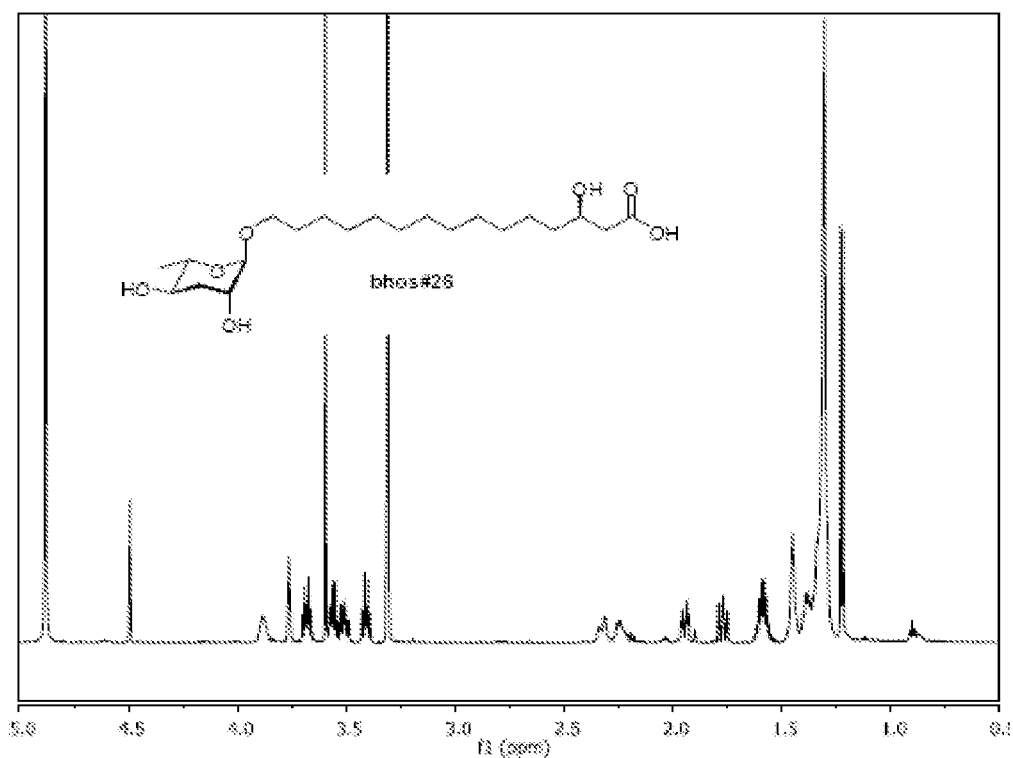
FIGS. 31A-D are the $^1$H NMR spectrum (FIG. 31A), dqfCOSY spectrum (FIG. 31B), HSQC spectrum (FIG. 31C), and HMBC spectrum (FIG. 31D) of 15-(3'R,5'R-dihydroxy-6'S-methyl-(2H)-tetrahydropyran-2'-yloxy)-(3R)-hydroxypentadecanoic acid (bhos#26). $^1$H NMR: 400 MHz, methanol-d$_4$; dqfCOSY: 600 MHz, methanol-d$_4$; HSQC: 600 MHz for $^1$H, 151 MHz for $^{13}$C, methanol-d$_4$; HMBC: 600 MHz for $^1$H, 151 MHz for $^{13}$C, methanol-d$_4$.
Figure 31B:
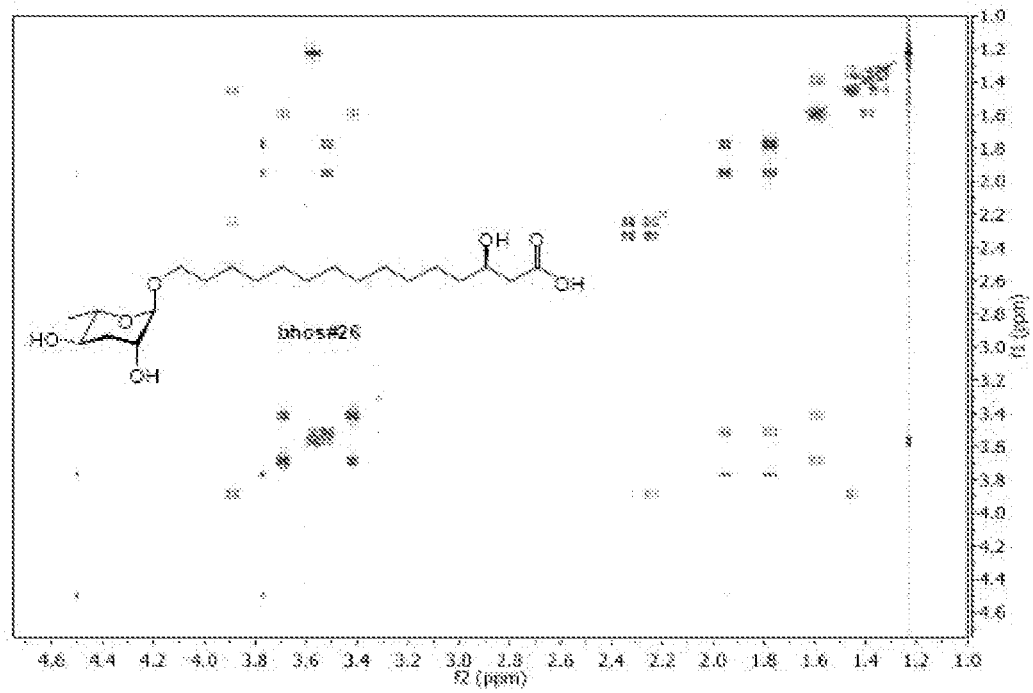
Figure 31C:
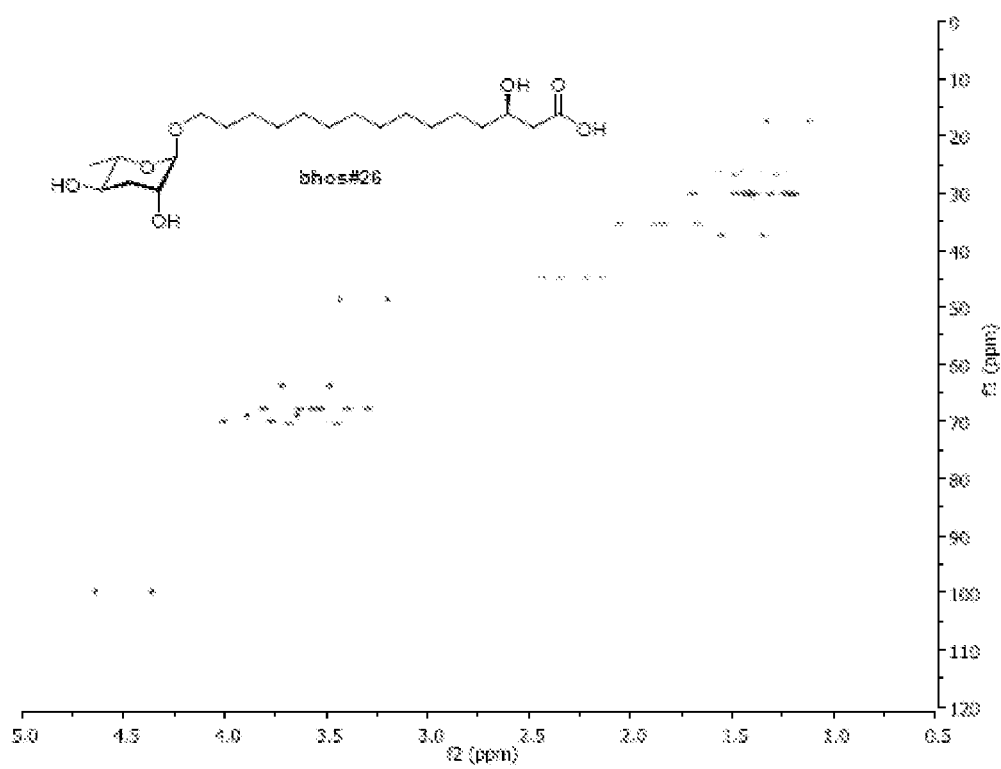
Figure 31D:
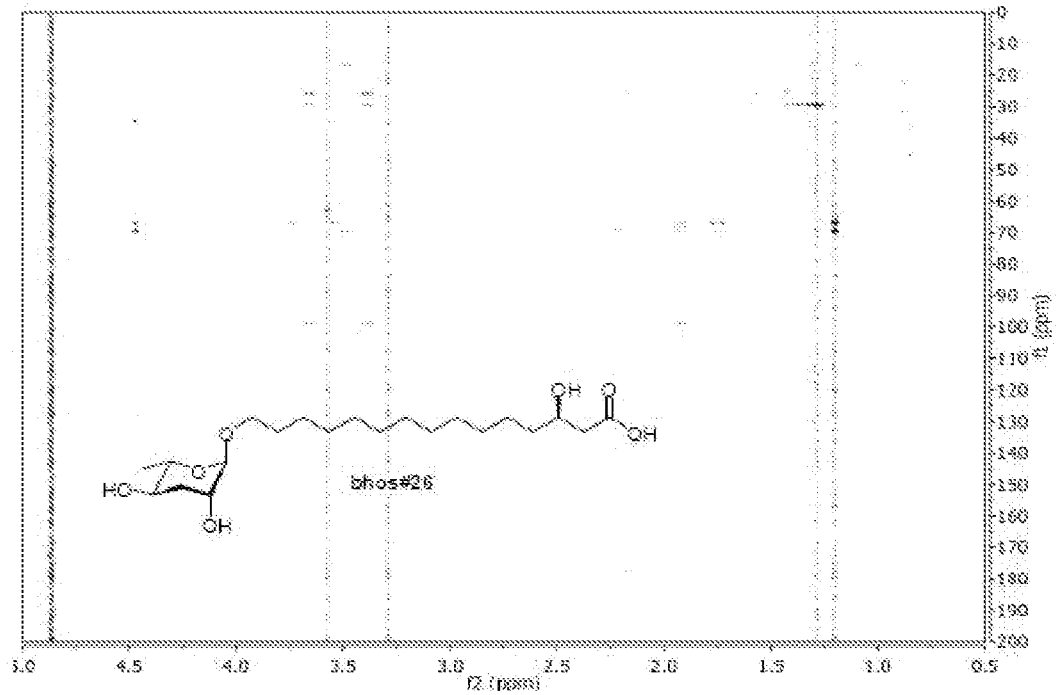
Figure 32A:
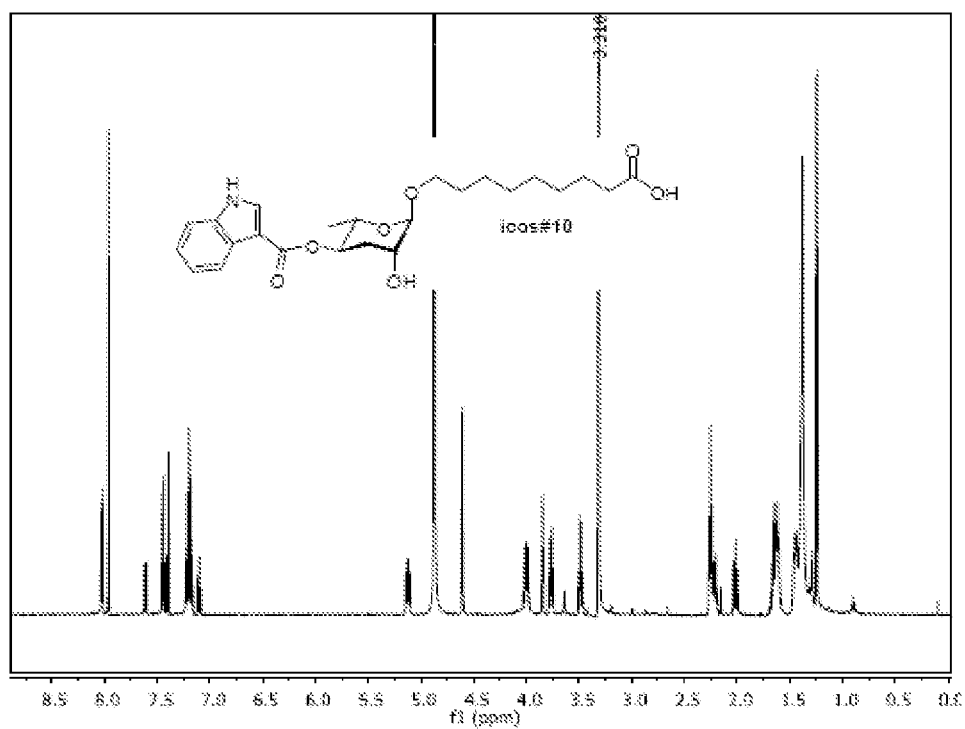
FIGS. 32A-D are the $^1$H NMR spectrum (FIG. 32A), dqfCOSY spectrum (FIG. 32B), HSQC spectrum (FIG. 32C), and HMBC spectrum (FIG. 32D) of 9-(5'R-(1H-indole-3-carbonyloxy)-3'R-hydroxy-6'S-methyl-tetrahydro-(2H)-pyran-2'-yloxy)nonanoic acid (icos#10). $^1$H NMR: 600 MHz, methanol-d$_4$; dqfCOSY: 600 MHz, methanol-d$_4$; HSQC: 600 MHz for $^1$H, 151 MHz for $^{13}$C, methanol-d$_4$; HMBC: 600 MHz for $^1$H, 151 MHz for $^{13}$C, methanol-d$_4$.
Figure 32B:
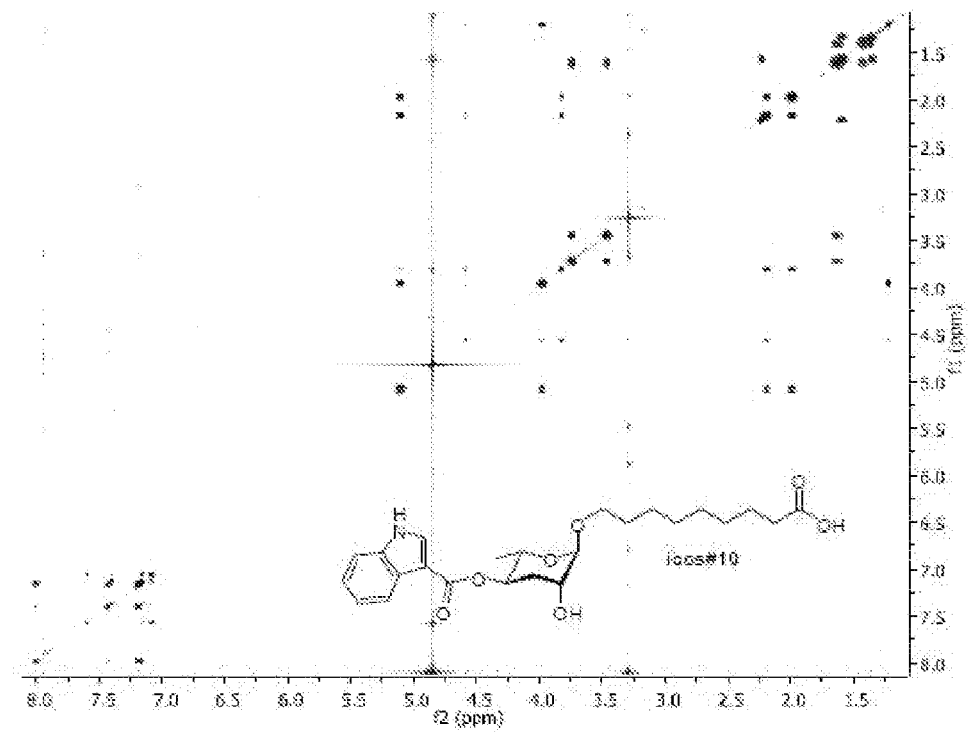
Figure 32C:
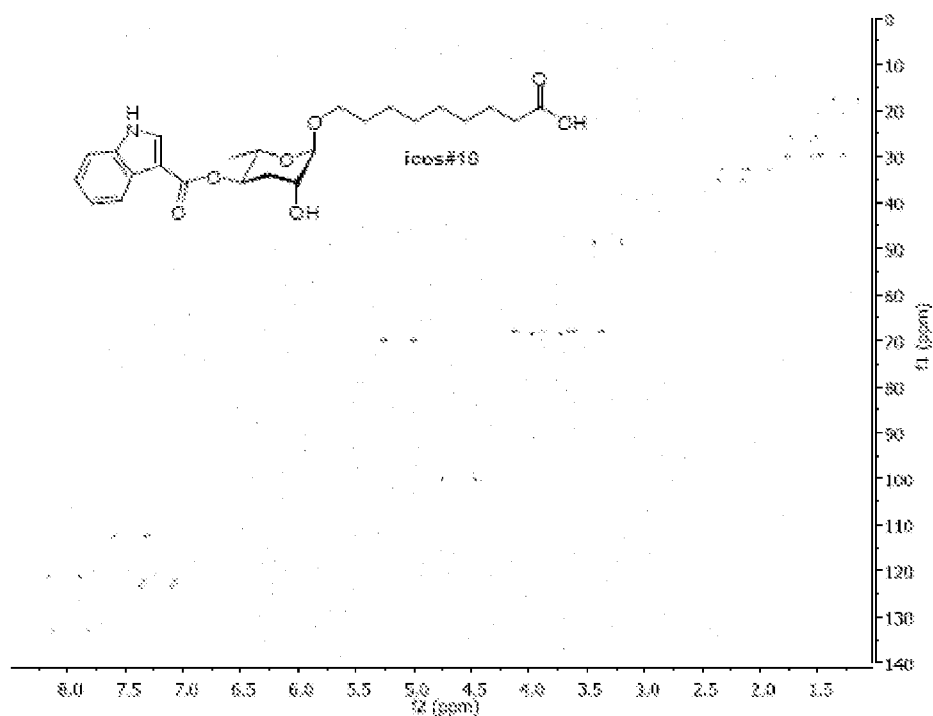
Figure 32D:
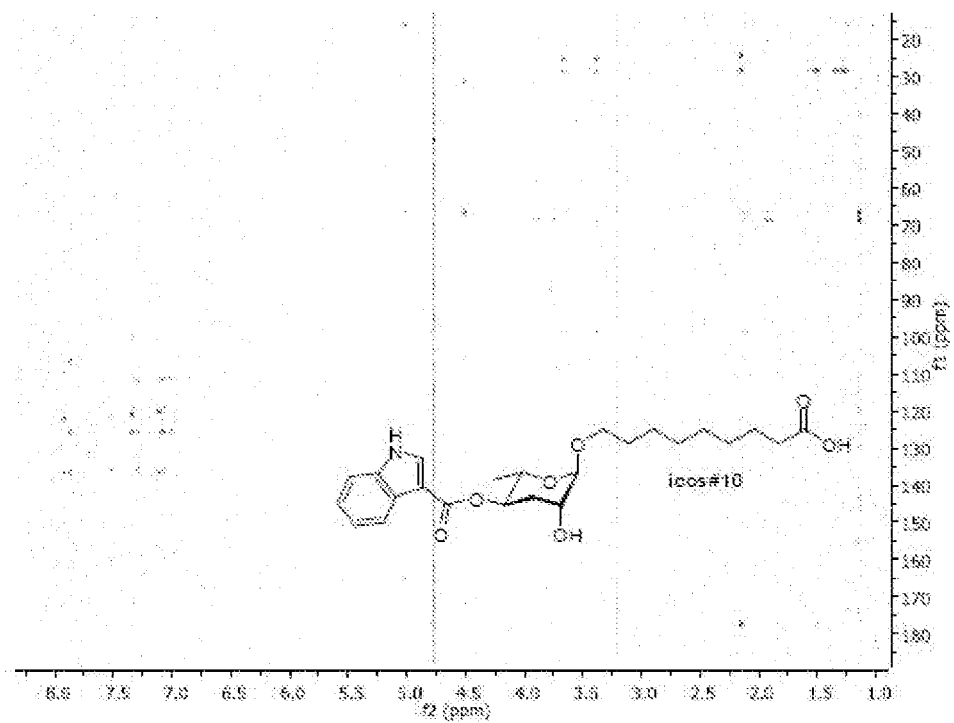

Hz, J=3.2 Hz, 1H), 2.39 (dd, J=16.4 Hz, J=9.0 Hz, 1H), 2.41 (m, 1H), 2.50 (dd, J=16.4 Hz, J=3.0 Hz, 1H), 3.50 (dt, J=9.6 Hz, J=6.5 Hz, 1H), 3.76 (dt, J=9.6 Hz, J=6.8 Hz, 1H), 3.99 (m, 1H), 4.07 (dq, J=10.0 Hz, J=6.2 Hz, 1H), 4.17 (q, J=7.1 Hz, 2H), 4.82 (s, 1H), 5.18 (ddd, J=11.2 Hz, J=9.9 Hz, J=4.7 Hz, 1H), 5.20 (s.br, 1H), 7.43-7.50 (m, 4H), 7.56-7.61 (m, 2H), 8.04 (m, 2H), 8.11 (m, 2H). See FIG. 30.

To prepare bhos#26, a solution of 20 (4.4 mg, 6.9 μmol) in THF (1 ml) was treated with a solution of LiOH (5 mg) in water (200 μl) and 1,4-dioxane (2 ml) and stirred at 67° C. After 3 hours, the solution was acidified with glacial acetic acid (50 μl) and concentrated in vacuum. Flash column chromatography on silica using a gradient of 5-50% methanol in DCM with 0.2% acetic acid afforded 15-(3'R, 5'R-Dihydroxy-6'S-methyl-(2H)-tetrahydropyran-2'-yloxy)-(3R)-hydroxypentadecanoic acid (bhos#26) (2.3 mg, 5.7 μmol; 83%).

$^1$H (600 MHz), $^{13}$C (151 MHz), and HMBC NMR spectroscopic data for bhos#26 were obtained using methanol-$d_4$ and are shown in Table 6 below. Chemical shifts are referenced to (CD$_2$HOD)=3.31 ppm and (CD$_2$HOD)=49.05 ppm. See FIGS. 31A-D.

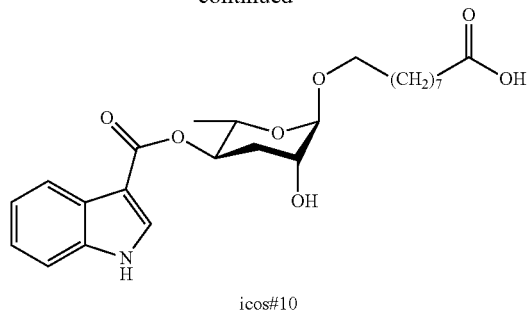

icos#10

To prepare icos#10, a solution of oscr#10 (12 mg, 39.5 μmol) in a mixture of methanol (1 ml) and toluene (1 ml) was treated with 2.0 M TMS-diazomethane in diethyl ether (23 μl, 46 μmol). After stirring for 30 minutes, excess reagent was quenched by addition of acetic acid (20 μl) and the solution was concentrated in vacuum. Flash column chromatography on silica using a gradient of 5-10% metha-

TABLE 6

NMR spectroscopic data of bhos#26

| Position | δ $^{13}$C [ppm] | δ $^1$H [ppm] | $^1$H—$^1$H-coupling constants [Hz] | Relevant HMBC correlations |
|---|---|---|---|---|
| 1 | 180.0 | | | |
| 2 | 45.0 | 2.23, 2.33 | $J_{2,2}$ = 16.0, $J_{2,3}$ = 7.0 | C-1, C-3, C-4 |
| 3 | 70.0 | 3.88 | | C-4, C-5 |
| 4 | 37.7 | 1.44, 1.59 | | |
| 5-12 | 30.40-30.50 | 1.30-1.59 | | |
| 13 | 27.2 | 1.37 | | |
| 14 | 30.5 | 1.57 | | |
| 15 | 68.0 | 3.41, 3.68 | $J_{15,15}$ = 9.6 Hz, $J_{15,14}$ = 6.3 | C-1', C-14, |
| 1' | 100.0 | 4.49 | | C-2', C-3', C-5', C-15 |
| 2' | 69.1 | 3.76 | | C-3', C-4' |
| 3' | 35.6 | 1.77 (ax) | $J_{3'ax,3'eq}$ = 13.1, $J_{3'ax,4'}$ = 11.3, $J_{2',3'ax}$ = 3.1 | C-2', C-4',C-5' |
| | | 1.95 (eq) | $J_{2',3'eq}$ = 3.2, $J_{3'eq,4'}$ = 4.7 | C-2', C-4',C-5' |
| 4' | 68.0 | 3.51 | $J_{4',5'}$ = 9.6 | C-5', C-6' |
| 5' | 70.5 | 3.56 | $J_{5',6'}$ = 6.1 | C-3', C-4',C-6' |
| 6' | 17.8 | 1.23 | | C4', C-5' |

Example 40

Synthesis of Ascaroside icos#10

Ascaroside icos#10 was prepared as shown in Scheme 7 below.

Scheme 7

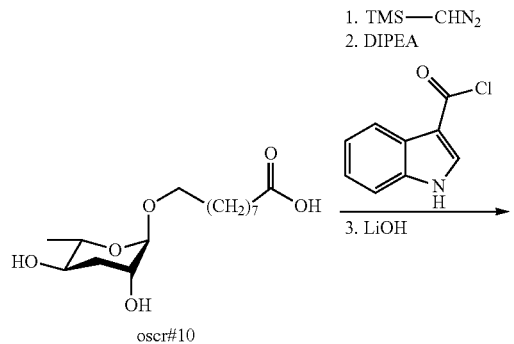

1. TMS—CHN$_2$
2. DIPEA
3. LiOH oscr#10 nol in DCM afforded the methyl ester (11.3 mg, 35.5 μmol, 90%) as a colorless solid.

A solution of the methyl ester in DCM (1 ml) at −20° C. was treated with DIPEA (175 μl, 1 mmol) and indolecarboxylic acid chloride. Indolecarboxylic acid chloride was freshly prepared by treatment of indole-3-carboxylic acid (68 mg, 420 μmol) in DCM (2 ml) at 0° C. with DMF (10 μl) and SOCl$_2$ (72 μl, 840 μmol). After stirring the reaction mixture for 20 minutes at room temperature, the solution was concentrated in vacuum and DCM (2 ml) was added drop wise. The solution was allowed to reach −7° C. and was then quenched with saturated aqueous NaHCO$_3$ solution (2 ml). The aqueous phase was extracted with DCM (2 ml, three times). The combined organic phases were dried over Na$_2$SO$_4$ and concentrated in vacuum. Flash column chromatography on silica using a gradient of 5-10% methanol in DCM afforded an isomeric mixture of indole carboxylate esters (8.4 mg, 18.2 μmol, 51%). The resulting isomeric mixture of indole carboxylate esters was dissolved in THF (1 ml) and treated with a solution of LiOH (2.8 mg, 116 μmol) in water (0.5 ml) and 1,4-dioxane (2 ml) at 67° C.

After stirring for 2 hours, the solution was acidified with acetic acid (30 µl) and concentrated in vacuum. Flash column chromatography on silica using a gradient of 5-20% methanol in DCM containing 0.2% acetic acid afforded an isomeric mixture of icos#10 isomers. HPLC afforded pure samples of 9-(5'R-((1H)-Indole-3-carbonyloxy)-3'R-hydroxy-6'S-methyl-tetrahydro-(2H)-pyran-2'-yloxy)nonanoic acid (icos#10) (0.6 mg, 1.3 µmol, 7%) and its isomer (0.3 mg, 0.67 µmol, 3.7%).

$^1$H (600 MHz), $^{13}$C (151 MHz), and HMBC NMR spectroscopic data for icos#10 were obtained using methanol-d$_4$ and are shown in Table 7 below. Chemical shifts are referenced to (CD$_2$HOD)=3.31 ppm and (CD$_2$HOD)=49.05 ppm. See FIGS. 32A-D.

TABLE 7

NMR spectroscopic data of icos#10

| Position | δ $^{13}$C [ppm] | δ $^1$H [ppm] | $^1$H—$^1$H-coupling constants [Hz] | Relevant HMBC correlations |
|---|---|---|---|---|
| 1 | 176.4 | | | |
| 2 | 35.5 | 2.26 | $J_{2,3}$ = 7.5 | C-1, C-3, C-4 |
| 3 | 26.1 | 1.62 | | |
| 4-5 | 30.1 | 1.38 | | |
| 6 | 21.0 | 1.38 | | |
| 7 | 27.1 | 1.43 | | |
| 8 | 30.4 | 1.65 | | |
| 9 | 68.2 | 3.49, 3.77 | $J_{9,9}$ = 9.7, $J_{9,8}$ = 6.5 | C-1' |
| 1' | 100.2 | 4.60 | | C-3', C-9 |
| 2' | 68.8 | 3.85 | | |
| 3' | 33.2 | 2.02 (ax) | $J_{3'ax, 3'eq}$ = 13.1, $J_{3'ax, 4'}$ = 11.3, $J_{2', 3'ax}$ = 3.0 | C-4', C-5' |
| | | 2.21 (eq) | $J_{3'ax, 3'eq}$ = 12.9, $J_{3'eq, 4'}$ = 4.0 | C-1', C-4', C-5' |
| 4' | 70.3 | 5.13 | $J_{4', 5'}$ = 9.8 | C-5', C-6', C3" |
| 5' | 68.2 | 4.00 | $J_{5', 6'}$ = 6.3 | |
| 6' | 17.8 | 1.25 | | C4', C-5' |
| 2" | 133.1 | 7.96 | | C-3", C3a", C7a" |
| 3" | 108.1 | | | |
| 3"-CO | 166.0 | | | |
| 3a" | 137.9 | | | |
| 4" | 121.5 | 8.02 | | C5", C3a" |
| 5" | 123.4 | 7.20 | | C4", C3a" |
| 6" | 122.3 | 7.20 | | C7", C7a" |
| 7" | 112.7 | 7.45 | | C6", C7a" |
| 7a" | 127.0 | | | |

Example 41

Synthesis of Ascaroside hbas#3

Ascaroside hbas#3 was prepared as shown in Scheme 8 below.

Scheme 8

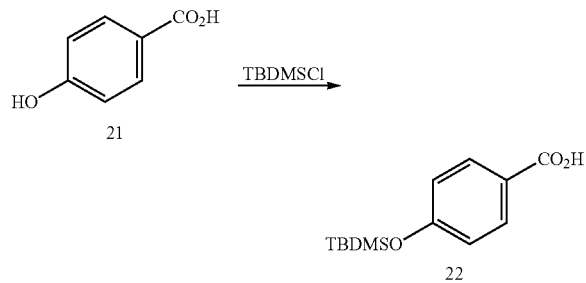

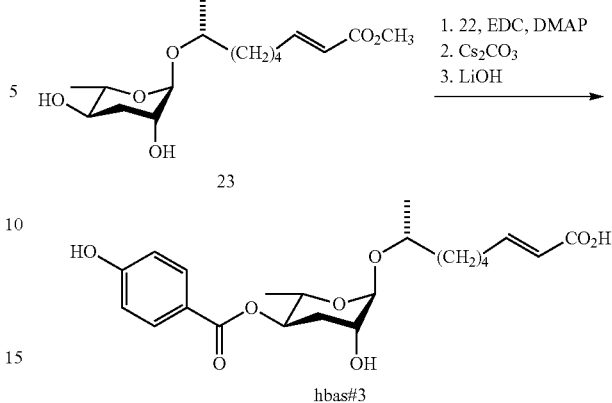

hbas#3

Figure 33A:
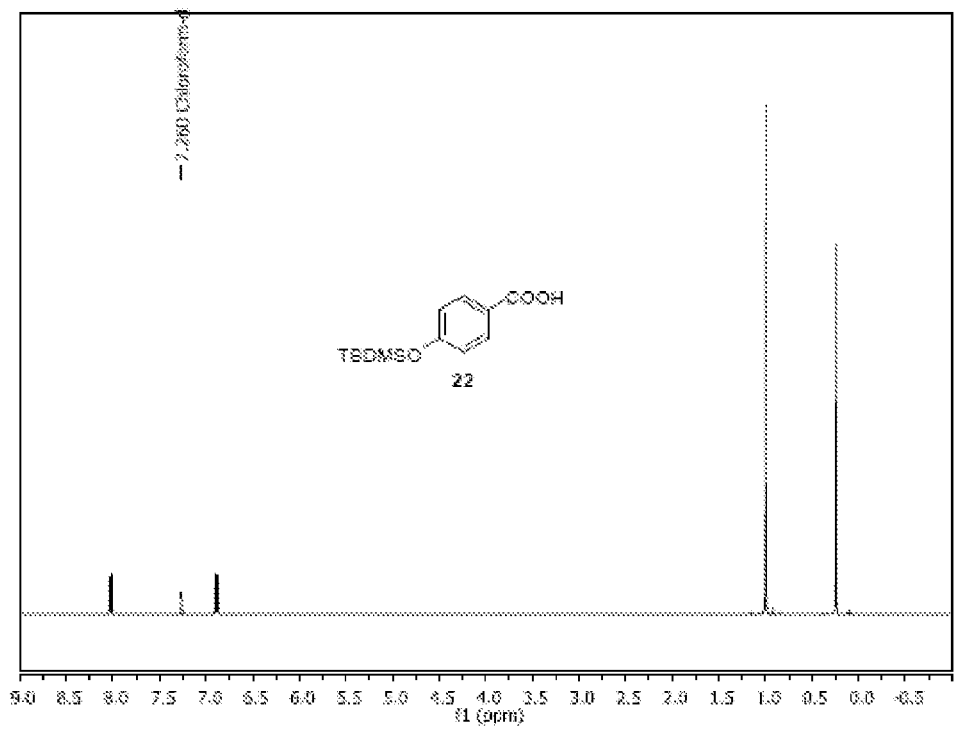
FIGS. 33A-B are the $^1$H NMR spectrum (FIG. 33A) and $^{13}$C NMR spectrum (FIG. 33B) of 4-tert-butyldimethylsilyloxybenzoic acid (22). $^1$H NMR: 400 MHz, chloroform-d$_1$; $^{13}$C NMR: 100 MHz, chloroform-d$_1$.
Figure 33B:
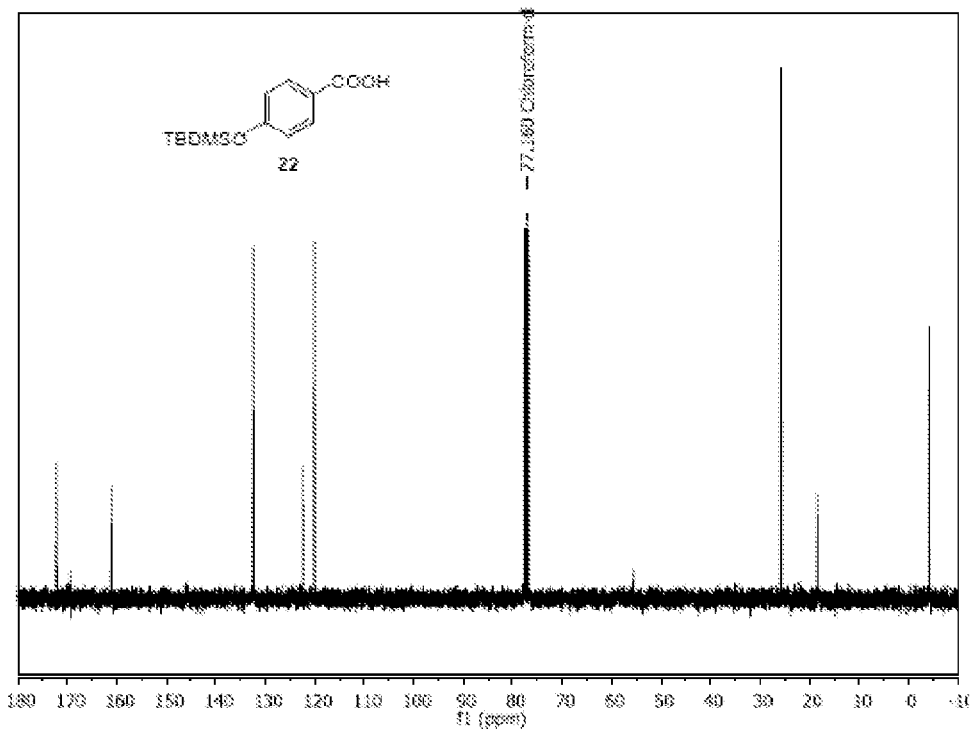

To prepare 22, a solution of 4-hydroxybenzoic acid (21, 1.52 g, 10 mmol) in DMF (7 ml) was treated with DIPEA (5.2 ml, 30 mmol) and tert-butyldimethylsilyl chloride (3.7 g, 24.5 mmol). After 12 hours, the mixture was brought to a pH of 4 by addition of 1 M H$_3$PO$_4$. The mixture was extracted twice with hexanes (15 ml). The organic phase was washed twice with water (15 ml), dried over Na$_2$SO$_4$, and concentrated in vacuum. The residue (3.7 g) was dissolved in THF (10 ml), and treated with water (7 ml) and glacial acetic acid (21 ml). After stirring for 90 minutes, the mixture was added to ice water and extracted twice with a 1:1 mixture (v/v) of diethyl ether and hexanes (30 ml). The organic phase was washed with water (30 ml), dried over Na$_2$SO$_4$, and concentrated in vacuum. Flash column chromatography on silica using a gradient of 5-20% methanol in DCM containing 0.2% acetic acid afforded 4-tert-butyldimethylsilyloxybenzoic acid (22, 1.42 g, 5.3 mol, 53%) as a white solid. $^1$H NMR (400 MHz, chloroform-d$_1$): δ (ppm) 0.24 (s, 6H), 0.99 (s, 9H), 6.89 (d, J=8.8 Hz, 2H), 8.02 (d, J=8.8 Hz, 2H); $^{13}$C NMR (100 MHz, chloroform-d$_1$): δ (ppm)-4.22, 18.40, 25.73, 120.08, 122.39, 132.46, 132.46, 161.01, 172.23. See FIGS. 33A-B.

To prepare hbas#3, a solution of ascaroside#3 methyl ester (23, 5.7 mg, 18 µmol, Srinivasan et al., *Pub. Lib. Sci. Biol.* 10:e1001237 (2012), which is hereby incorporated by reference in its entirety) in dry DCM (500 µl) was treated with 22 (11.0 mg, 41 µmol), 1-ethyl-3-(3-dimethylaminopropyl) carbodiimide hydrochloride (EDC, 9.0 mg, 47 µmol), and 4-dimethylaminopyridine (DMAP, 6.2 mg, 51 µmol). After stirring for 48 hours, the solution was concentrated in vacuum and treated with H$_2$O (500 µL). The resulting products were extracted with DCM (1 ml, three times), dried over Na$_2$SO$_4$, and concentrated in vacuum. Flash column chromatography on silica using a gradient of 0-30% methanol in DCM afforded an isomeric mixture of 4-tert-butyldimethylsilyloxybenzoyl-ascaroside#3 methyl esters (7.3 mg, 12.9 µmol; 72%).

For deprotection of the aromatic tert-butyldimethylsilyloxy group (Jiang & Wang, *Tetrahedron Lett.* 44:3859-61 (2003), which is hereby incorporated by reference in its entirety), a mixture of (4-tert-butyldimethylsilyloxybenzoyl)-ascaroside#3 methyl esters (6.0 mg, 10.7 µmol) in DMF (360 µl) was treated with Cs$_2$CO$_3$ (1.9 mg, 5.4 µmol) in H$_2$O (36 µl) and stirred for 3.5 hours. The resulting products were extracted with DCM (1 ml, twice), dried over Na$_2$SO$_4$, and concentrated in vacuum. Flash column chromatography on silica gel using a gradient of 0-30% methanol in DCM afforded an isomeric mixture of 4-hydroxybenzoyl-ascaroside#3 methyl esters (4.5 mg, 10.0 µmol; 93%).

For cleavage of the methyl ester group, a mixture of 4-hydroxybenzoyl-ascaroside#3 methyl esters (4.5 mg, 10.0 µmol) in THF (100 µl) was treated with LiOH (2.3 mg) in H$_2$O (30 µl) and 1,4-dioxane (500 µl) at 67° C. After 2 hours, the reaction was quenched by addition of glacial acetic acid (50 µl). The solution was concentrated in vacuum. Flash column chromatography on silica using a gradient of 5-20% methanol in DCM with 0.2% acetic acid afforded an isomeric mixture of hbas#3 isomers (1.2 mg, 2.8 µmol, 28%). HPLC afforded pure samples of (8R)-(3'R-Hydroxy-5'R-(4-hydroxybenzoyloxy)-6'S-methyl-(2H)-tetrahydropyran-2'-yloxy)non-(2E)-enoic acid (hbas#3) (0.6 mg, 1.4 µmol; 14%) and its isomer (0.6 mg, 1.4 µmol; 14%).

Figure 34A:
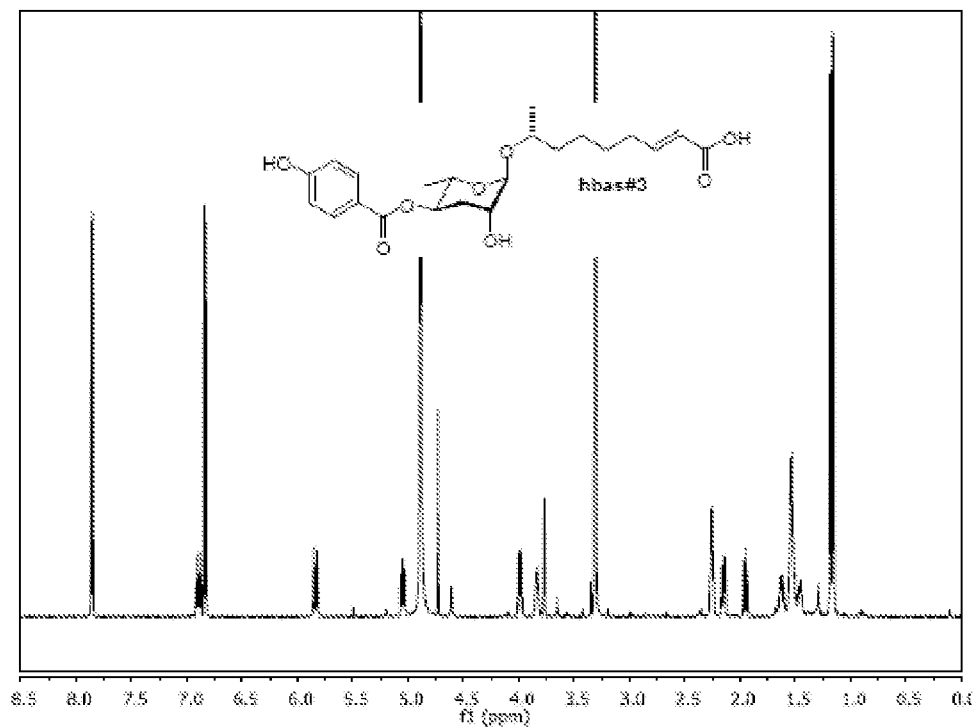
FIGS. 34A-C are the $^1$H NMR spectrum (FIG. 34A), dqfCOSY spectrum (FIG. 34B), and HMBC spectrum (FIG. 34C) of (8R)-(3'R-hydroxy-5'R-(4-hydroxybenzoyloxy)-6'S-methyl-(2H)-tetrahydropyran-2'-yloxy)non-(2E)-enoic acid (hbas#3). $^1$H NMR: 600 MHz, methanol-d$_4$; dqfCOSY: 600 MHz, methanol-d$_4$; HMBC: 600 MHz for $^1$H, 151 MHz for $^{13}$C, methanol-d$_4$.
Figure 34B:
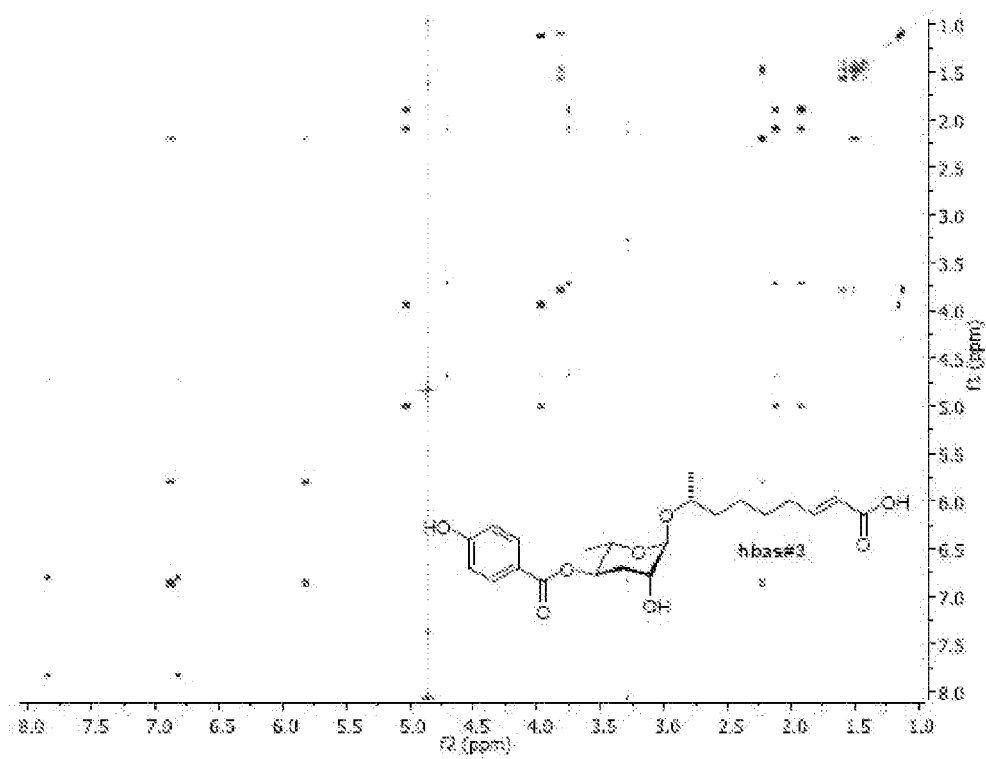
Figure 34C:
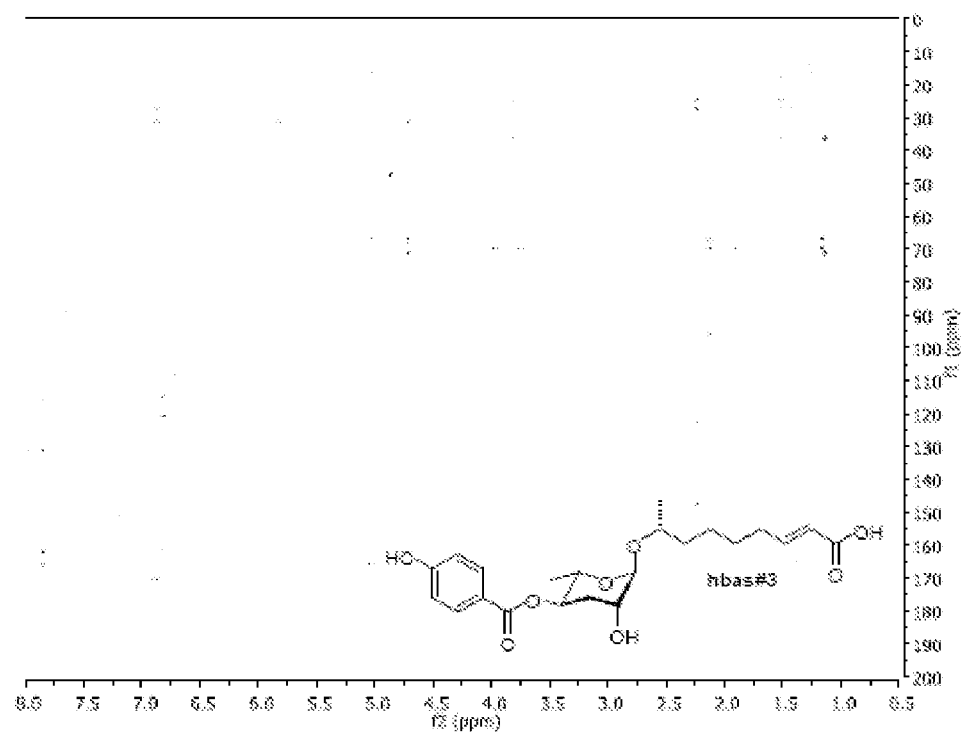

$^1$H (600 MHz), $^{13}$C (151 MHz), and HMBC NMR spectroscopic data for hbas#3 were obtained using methanol-d$_4$ and are shown in Table 8 below. Chemical shifts are referenced to (CD$_2$HOD)=3.31 ppm and (CD$_2$HOD)=49.05 ppm. See FIGS. 34A-C.

TABLE 8

NMR spectroscopic data of hbas#3

| Position | δ $^{13}$C [ppm] | δ $^1$H [ppm] | $^1$H—$^1$H-coupling constants [Hz] | Relevant HMBC correlations |
|---|---|---|---|---|
| 1 | 171.7 | | | |
| 2 | 124.4 | 5.83 | J$_{2,3}$ = 15.6 | C-4 |
| 3 | 149.0 | 6.90 | J$_{3,4}$ = 7.0 | C-1, C-4, C-5 |
| 4 | 33.1 | 2.26 | | C-2, C-3, C5, C-6 |
| 5, 6 | 29.2, 26.5 | 1.40-1.54 | | C-4, C-6 |
| 7 | 38.1 | 1.53, 1.62 | | C-5, C-6, C-8 |
| 8 | 72.7 | 3.83 | | C-6, C-7, C-9 |
| 9 | 19.4 | 1.16 | J$_{8,9}$ = 6.1 | C-7, C-8 |
| 1' | 97.5 | 4.73 | | C-3', C-5', C-8 |
| 2' | 69.5 | 3.77 | | C-4' |
| 3' | 33.1 | 1.95 (ax) | J$_{3'ax, 3'eq}$ = 12.9, J$_{3'ax, 4'}$ = 11.2, J$_{2', 3'ax}$ = 2.9 | C-4', C-5' |
| | | 2.15 (eq) | J$_{2', 3'eq}$ = 3.2, J$_{3'eq, 4'}$ = 4.7 | C-2', C-4', C-5' |
| 4' | 71.5 | 5.05 | J$_{4', 5'}$ = 9.6 | C-5', C-6', C-7'' |
| 5' | 68.4 | 3.98 | J$_{5', 6'}$ = 6.3 | C-4', C-6' |
| 6' | 18.1 | 1.18 | | C4', C-5' |
| 7''-COO | 167.2 | | | |
| 1'' | 122.1 | | | |
| 2'', 6'' | 132.8 | 7.85 | J = 8.9 | C-1'', C-3'', 5'', C-4'', C-7'' |
| 3'', 5'' | 116.2 | 6.83 | | C-2'', 6'', C-4'' |
| 4'' | 163.6 | | | |

Example 42

Synthesis of Ascaroside mbas#3

Ascaroside mbas#3 was prepared as shown in Scheme 9 below.

Scheme 9

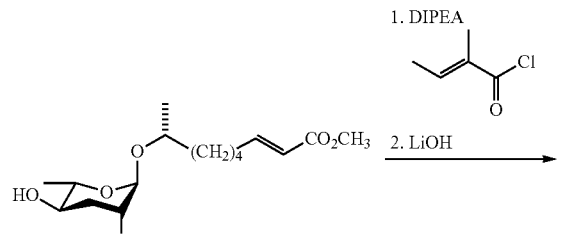

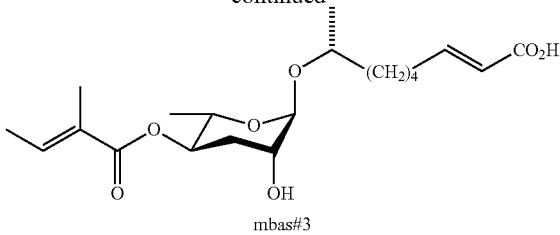

mbas#3

To prepare mbas#3, a solution of ascaroside#3 methyl ester (23, 10 mg, 31.4 µmol, Srinivasan et al., *Pub. Lib. Sci. Biol.* 10:e1001237 (2012), which is hereby incorporated by reference in its entirety) in dry DCM (1 ml) at 0° C. was treated with DIPEA (110 µl, 630 µmol). (E)-2-methylbut-2-enoic acid chloride (35 µl, 316 µmol) in DCM (0.5 ml) was added drop wise. After stirring at 0° C. for 1 hour, the solution was allowed to return to room temperature and treated with saturated aqueous NaHCO$_3$ solution (0.5 ml). The product was extracted with ethyl acetate, dried over Na$_2$SO$_4$, and concentrated in vacuum. Flash chromatography on silica using a gradient of 5-25% ethyl acetate in hexanes afforded the di-tiglate ester (5.2 mg, 10.8 µmol, 34%) as a yellowish solid.

The product (4.5 mg, 9.4 µmol) was dissolved in THF (1 ml) and treated with LiOH (0.5 mg, 22 µmol) in water (100 µl) and 1,4-dioxane (2 ml). After stirring at 67° C. for 3 hours, the reaction was quenched by addition of glacial acetic acid (100 µl). The solution was concentrated in vacuum. The residue was dissolved in methanol and concentrated in vacuum. Flash column chromatography on silica gel using a gradient of 0-20% methanol in DCM containing 0.2% acetic acid afforded a mixture of mbas#3 isomers (2.1 mg, 5.45 µmol). HPLC provided a pure sample of (8R)-(3'R-Hydroxy-5'R-(E)-(2-methylbut-2-enoyloxy)-6'S-methyl-(2H)-tetrahydropyran-2'-yloxy)non-(2E)-enoic acid (mbas#3) (1.2 mg, 3.1 µmol; 33% yield) identical to the natural product from *C. elegans*.

Figure 35A:
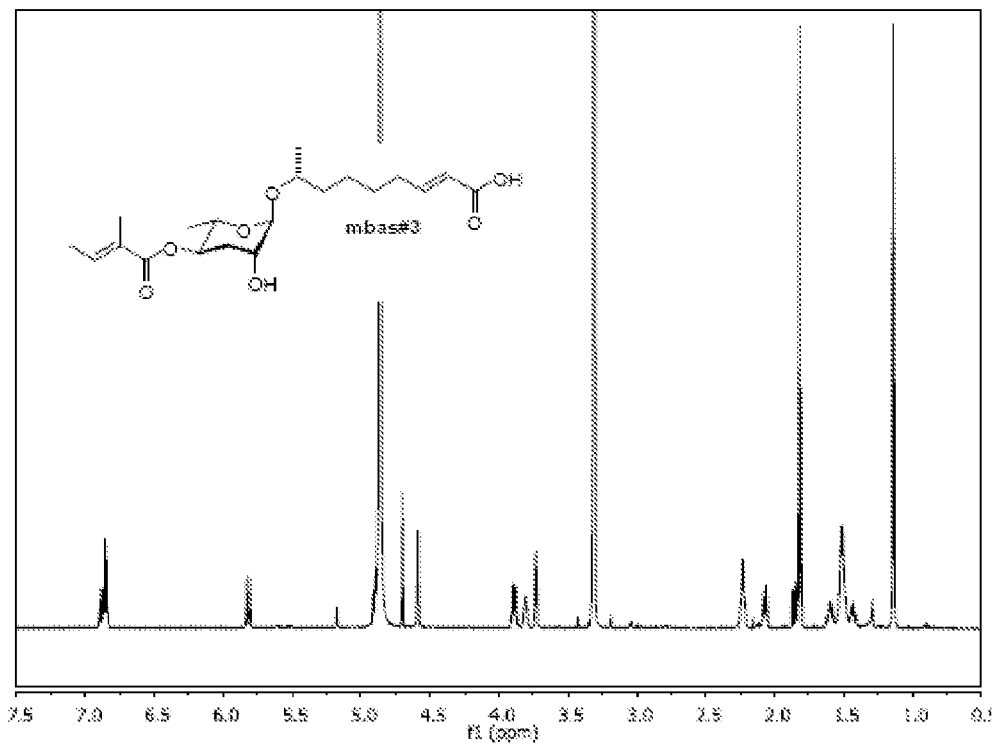
FIGS. 35A-B are the $^1$H NMR spectrum (FIG. 35A) and dqfCOSY spectrum (FIG. 35B) of (8R)-(3'R-hydroxy-5'R-(E)-(2-methylbut-2-enoyloxy)-6'S-methyl-(2H)-tetrahydropyran-2'-yloxy)non-(2E)-enoic acid (mbas#3). $^1$H NMR: 600 MHz, methanol-d$_4$; dqfCOSY: 600 MHz, methanol-d$_4$.
Figure 35B:
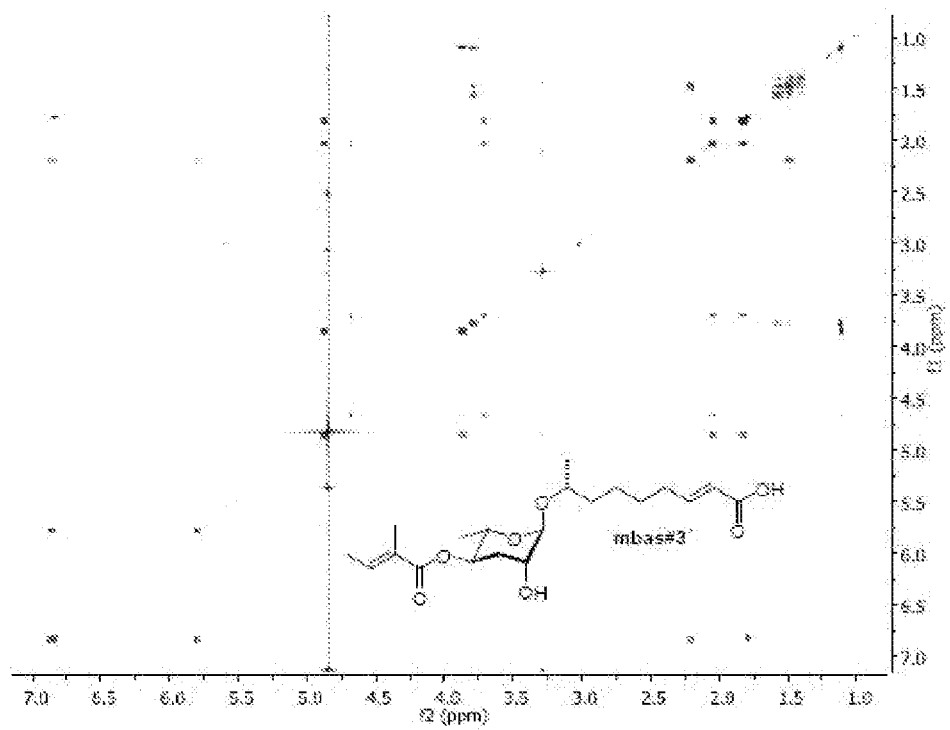
Figure 36A:
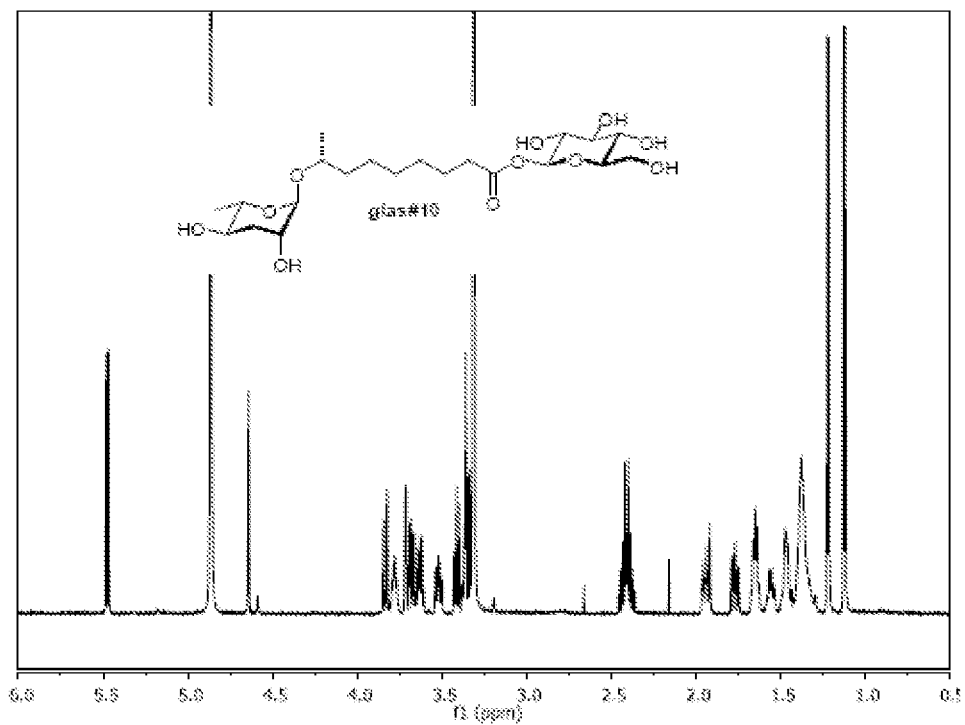
FIGS. 36A-D are the $^1$H NMR spectrum (FIG. 36A), dqfCOSY spectrum (FIG. 36B), HMQC spectrum (FIG. 36C), and HMBC spectrum (FIG. 36D) of 2-(8R)-(3'R,5'R-di-hydroxy-6'S-methyl-(2H)-tetrahydropyran-2'-yloxy) nonanoyl-3,4,5-trihydroxy-6-hydroxymethyl-(2H)-tetrahydropyran (glas#10). $^1$H NMR: 600 MHz, methanol-d$_4$; dqfCOSY: 600 MHz, methanol-d$_4$; HMQC: 600 MHz for $^1$H, 151 MHz for $^{13}$C, methanol-d$_4$; HMBC: 600 MHz, methanol-d$_4$.
Figure 36B:
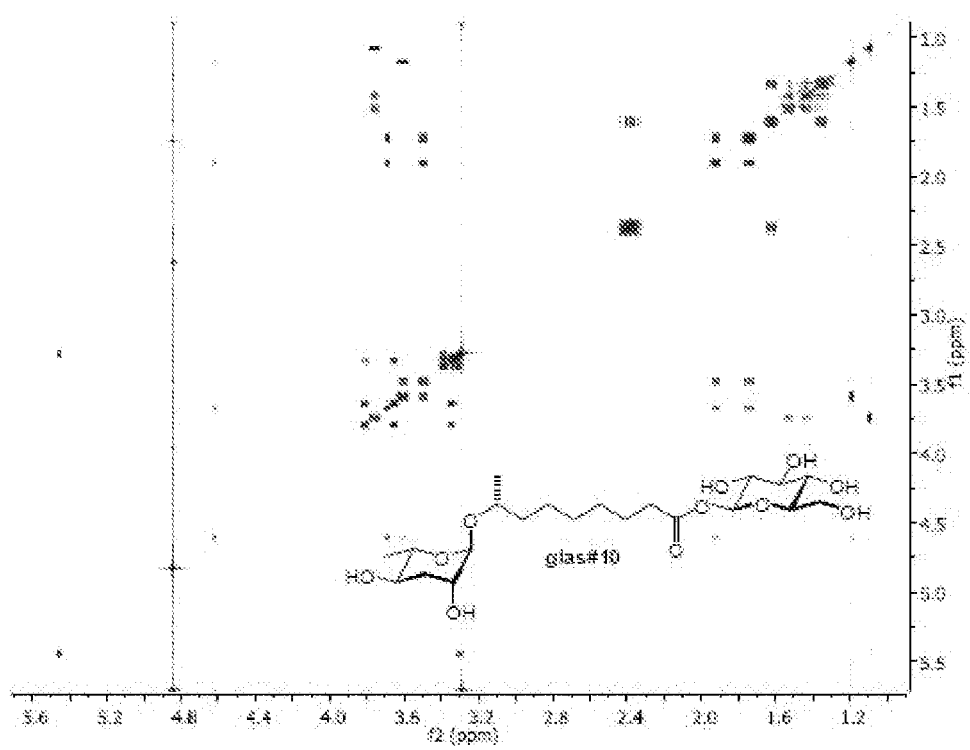
Figure 36C:
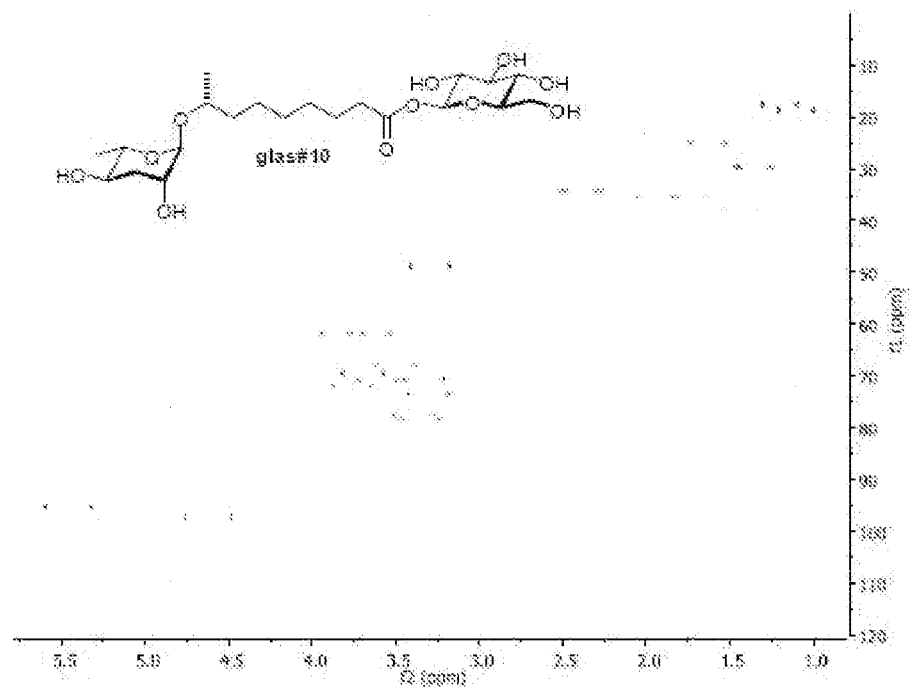
Figure 36D:
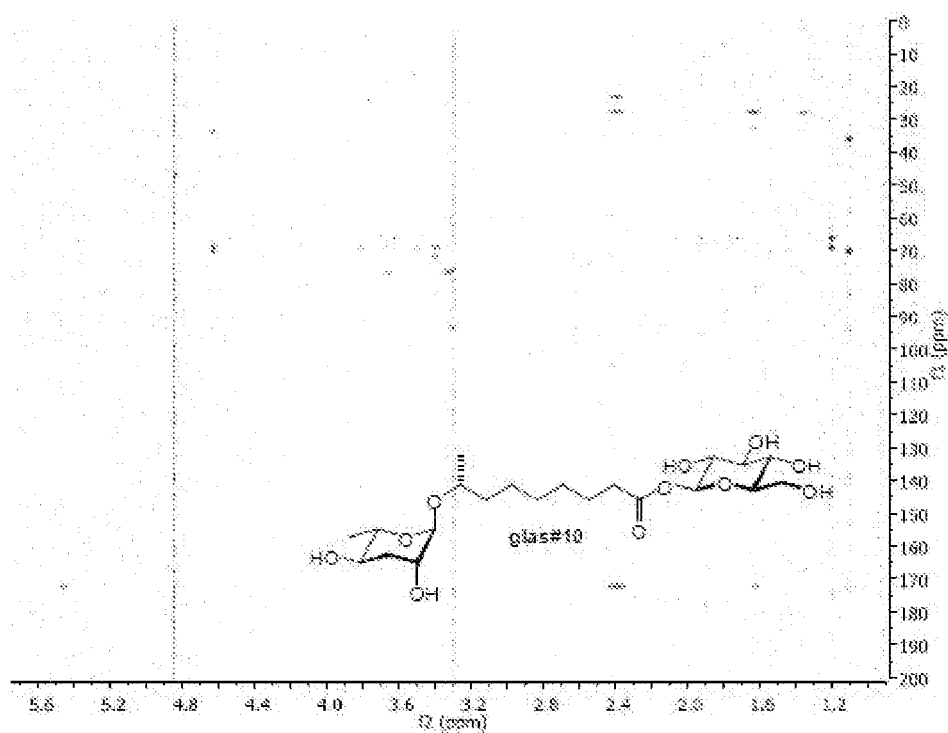

$^1$H (600 MHz), $^{13}$C (151 MHz), and HMBC NMR spectroscopic data for mbas#3 were obtained using methanol-d$_4$ and are shown in Table 9 below. Chemical shifts are referenced to (CD$_2$HOD)=3.31 ppm and (CD$_2$HOD)=49.05 ppm. See FIGS. 35A-B.

TABLE 9

NMR spectroscopic data of mbas#3

| Position | δ $^{13}$C [ppm] | δ $^1$H [ppm] | 1H—1H-coupling constants [Hz] | Relevant HMBC correlations |
|---|---|---|---|---|
| 1 | 171.7 | | | |
| 2 | 124.4 | 5.82 | J$_{2,3}$ = 15.6 | |
| 3 | 149.0 | 6.88 | J$_{3,4}$ = 7.0 | |
| 4 | 33.0 | 2.23 | | C-5, C-6 |
| 5, 6 | 29.3, 26.4 | 1.42-1.55 | | |
| 7 | 37.9 | 1.60 1.52 | | |
| 8 | 72.4 | 3.81 | | |
| 9 | 18.9 | 1.14 | J$_{8,9}$ = 6.1 | C-7, C-8 |
| 1' | 97.4 | 4.70 | | C-3', C-5', C-8' |
| 2' | 69.3 | 3.73 | | |
| 3' | 32.8 | 1.85 (ax) | J$_{3'ax, 3'eq}$ = 12.9, J$_{3'ax, 4'}$ = 11.2, J$_{2', 3'ax}$ = 2.9 | |
| | | 2.07 (eq) | J$_{2', 3'eq}$ = 3.2, J$_{3'eq, 4'}$ = 4.7 | |
| 4' | 71.4 | 4.90 | J$_{4', 5'}$ = 9.6 | |
| 5' | 68.2 | 3.89 | J$_{5', 6'}$ = 6.1 | |

TABLE 9-continued

NMR spectroscopic data of mbas#3

| Position | δ $^{13}$C [ppm] | δ $^1$H [ppm] | 1H—1H-coupling constants [Hz] | Relevant HMBC correlations |
|---|---|---|---|---|
| 6' | 17.8 | 1.13 | | C-4', C-5' |
| 1"-COO | 168.5 | | | |
| 2" | 129.2 | | | |
| 3" | 138.8 | 6.85 | $J_{3", 4"} = 7.0$ | |
| 4" | 14.2 | 1.81 | | C-2", C-3" |
| 5" | 11.8 | 1.82 | | C-1", C-2", C-3" |

Example 43

Synthesis of Ascaroside glas#10

Ascaroside glas#10 was prepared as shown in Scheme 10 below.

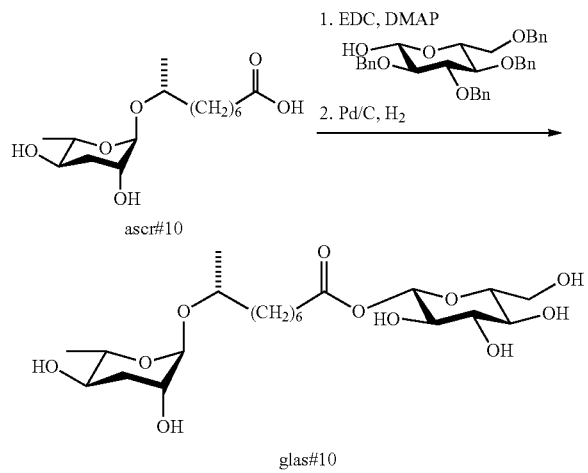

Scheme 10

To prepare glas#10, a solution of ascr#10 (3 mg, 9.9 µmol) in dry DMF (2 ml) was treated with 2,3,4,6-tetra-O-benzyl-D-glucose (11 mg, 20 µmol), DMAP (12.2 mg, 100 µmol), and EDC (19.2 mg, 100 µmol). After stirring at room temperature for 18 hours, the solution was concentrated in vacuum. The residue was treated with aqueous acetic acid (200 µl), concentrated, and purified by flash column chromatography on silica using a gradient of 5-50% methanol in DCM.

The product was dissolved in ethanol (1 ml), treated with Pd/C (10 mg, 10% Pd (w/w)), and hydrogenated for 24 hours. The mixture was filtered and concentrated in vacuum. HPLC provided pure samples of β-D-glucosyl-ascaroside#10 (1.5 mg, 3.22 µmol, 33%) and α-D-glucosyl-ascaroside#10 (1.2 mg, 2.58 µmol, 26%).

$^1$H (600 MHz), $^{13}$C (151 MHz), and HMBC NMR spectroscopic data for glas#10 were obtained using methanol-d$_4$ and are shown in Table 10 below. Chemical shifts are referenced to (CD$_2$HOD)=3.31 ppm and (CD$_2$HOD)=49.05 ppm. See FIGS. 36A-D.

TABLE 10

NMR spectroscopic data of glas#10

| Position | δ $^{13}$C [ppm] | δ $^1$H [ppm] | $^1$H—$^1$H-coupling constants [Hz] | Relevant HMBC correlations |
|---|---|---|---|---|
| 1 | 173.8 | | | |
| 2 | 34.7 | 2.41 | $J_{2, 2} = 15.4$, $J_{2, 3} = 7.8$ | C-1 |
| 3 | 25.5 | 1.64 | | C-1, C-2 |
| 4 | | 1.37 | | |
| 5, 6 | 29.8, 30.1 | 1.30-1.50 | | |
| 7 | 26.6 | 1.45-1.55 | | |
| 8 | 72.3 | 3.78 | | |
| 9 | 19.2 | 1.12 | $J_{8, 9} = 6.1$ | C-8, C-7 |
| 1' | 97.4 | 4.60 | | C-9, C-3', C-5' |
| 2' | 69.8 | 3.71 | | |
| 3' | 35.8 | 1.77 (ax) | $J_{3'ax, 3'eq} = 13.0$, $J_{3'ax, 4'} = 11.4$, $J_{2', 3'ax} = 2.9$ | |
| | | 1.95 (eq) | $J_{2', 3'eq} = 3.2$, $J_{3'eq, 4'} = 4.7$ | |
| 4' | 68.2 | 3.52 | $J_{4', 5'} = 9.5$ | |
| 5' | 71.0 | 3.63 | $J_{5', 6'} = 6.3$, $J_{5', 4'} = 9.3$ | |
| 6' | 18.0 | 1.22 | | C-5', C-4' |
| 1" | 95.4 | 5.47 | $J_{1", 2"} = 8.1$ | C-1 |
| 2" | 73.8 | 3.32 | $J_{2", 3"} = 9.1$ | |
| 3" | 77.8 | 3.41 | $J_{3", 4"} = 9.7$ | |
| 4" | 70.9 | 3.35 | $J_{4", 5"} = 9.7$ | |
| 5" | 78.7 | 3.36 | | |
| 6" | 62.2 | 3.67 | $J_{6", 6"} = 12.0$, $J_{6", 5"} = 4.8$ | |
| | | 3.83 | $J_{6", 6"} = 12.0$, $J_{6", 5"} = 1.9$ | |

Example 44

Identification and Quantification of Ascarosides

Figure 37K:
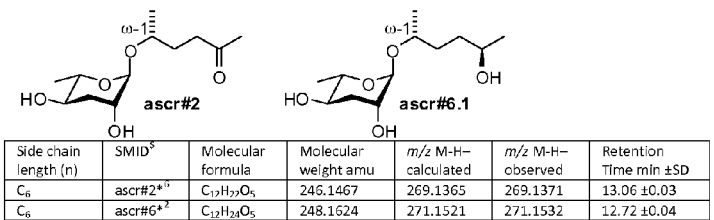
Figure 38:
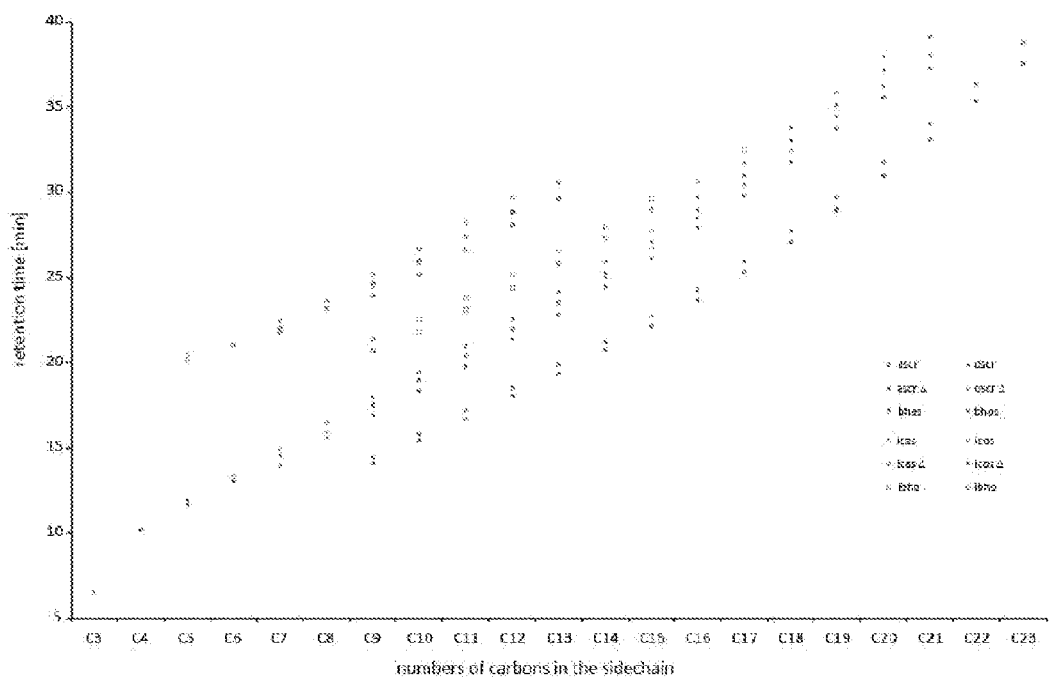
FIG. 38 shows the HPLC elution profiles of ascarosides identified in wild-type and mutant excretome extracts of *C. elegans* (Δ indicates components with (E)-configured α,β-unsaturated sidechains).
Figure 39:
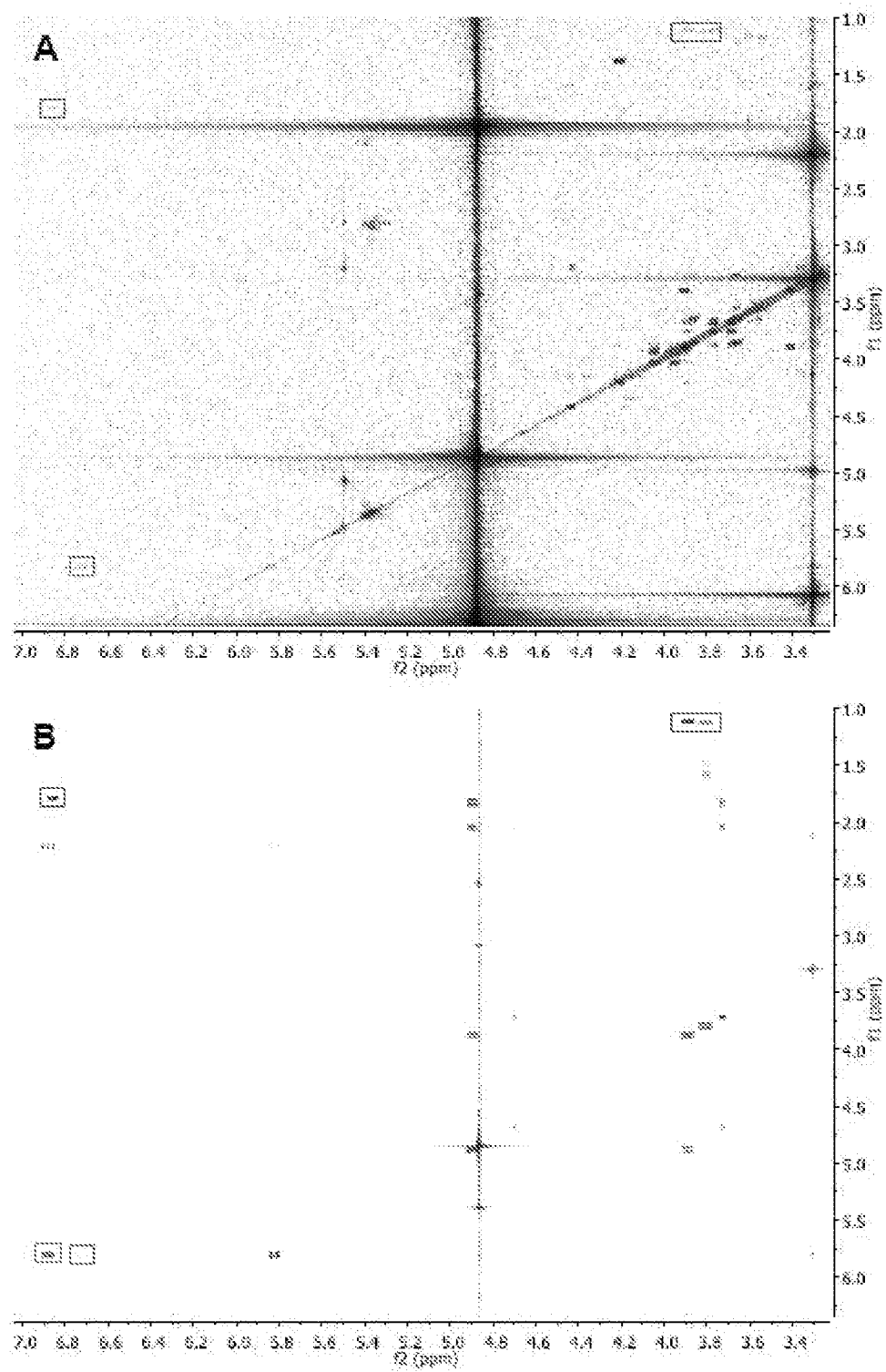
FIGS. 39A-B are sections of dqfCOSY spectra (600 MHz, methanol-$d_4$) of mbas#3-enriched fraction from wild-type *C. elegans* media extracts (FIG. 39A) and synthetic mbas#3 (FIG. 39B) showing characteristic signals for methyl groups of the ascarylose ring and the side chain (blue), the allylic methyl group of the tiglate unit (red), and the pH dependant signal for the side chain double bond (green).
Figure 40:
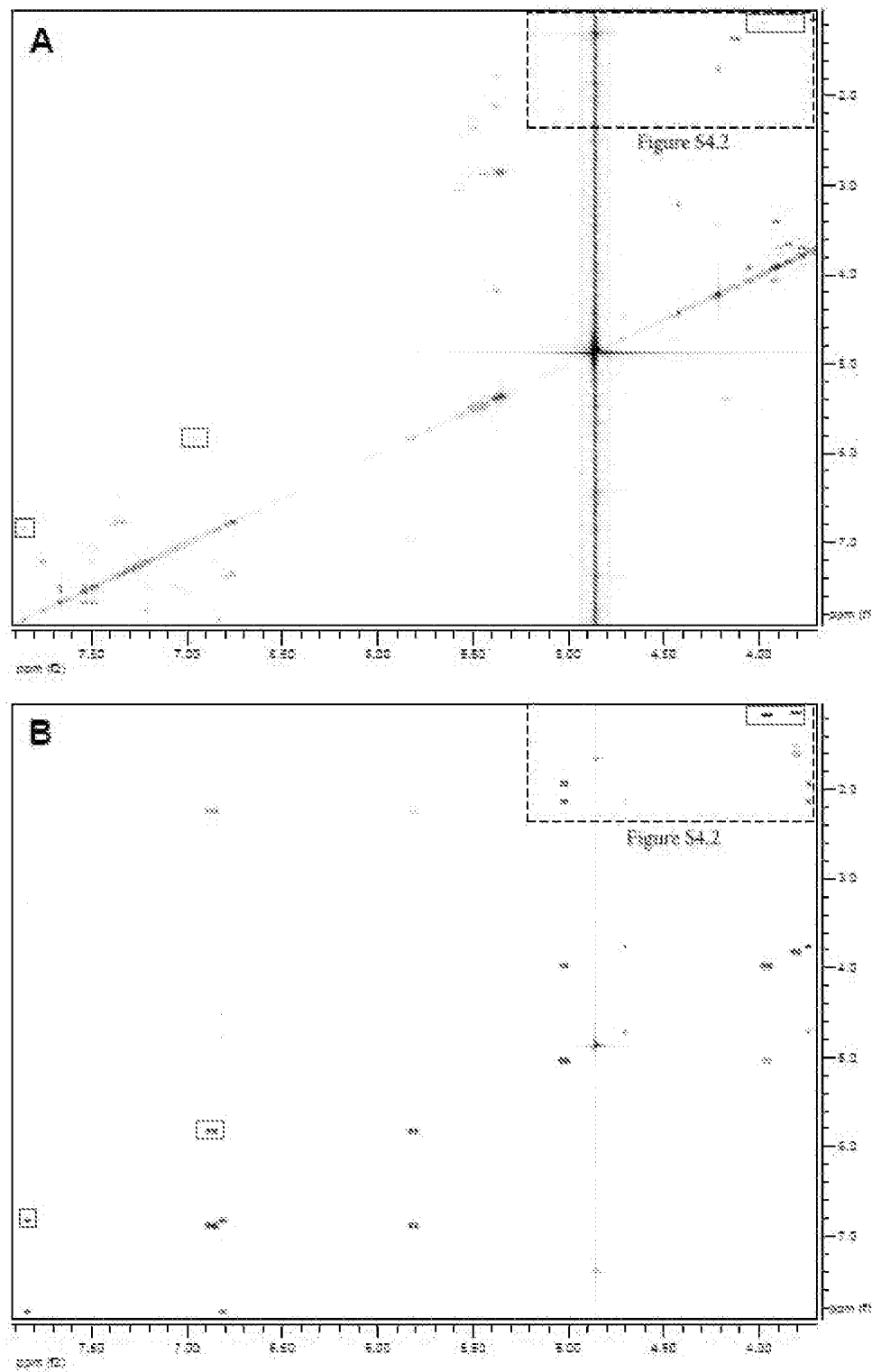
FIGS. 40A-B are sections of dqfCOSY spectra (600 MHz, methanol-$d_4$) of hbas#3-enriched fraction from wild-type *C. elegans* media extracts (FIG. 40A) and synthetic hbas#3 (FIG. 40B) showing characteristic signals for methyl groups of the ascarylose ring and the side chain (blue), the para-substituted 4-hydroxybenzoyl unit (red), and the side chain double bond (green).
Figure 41:
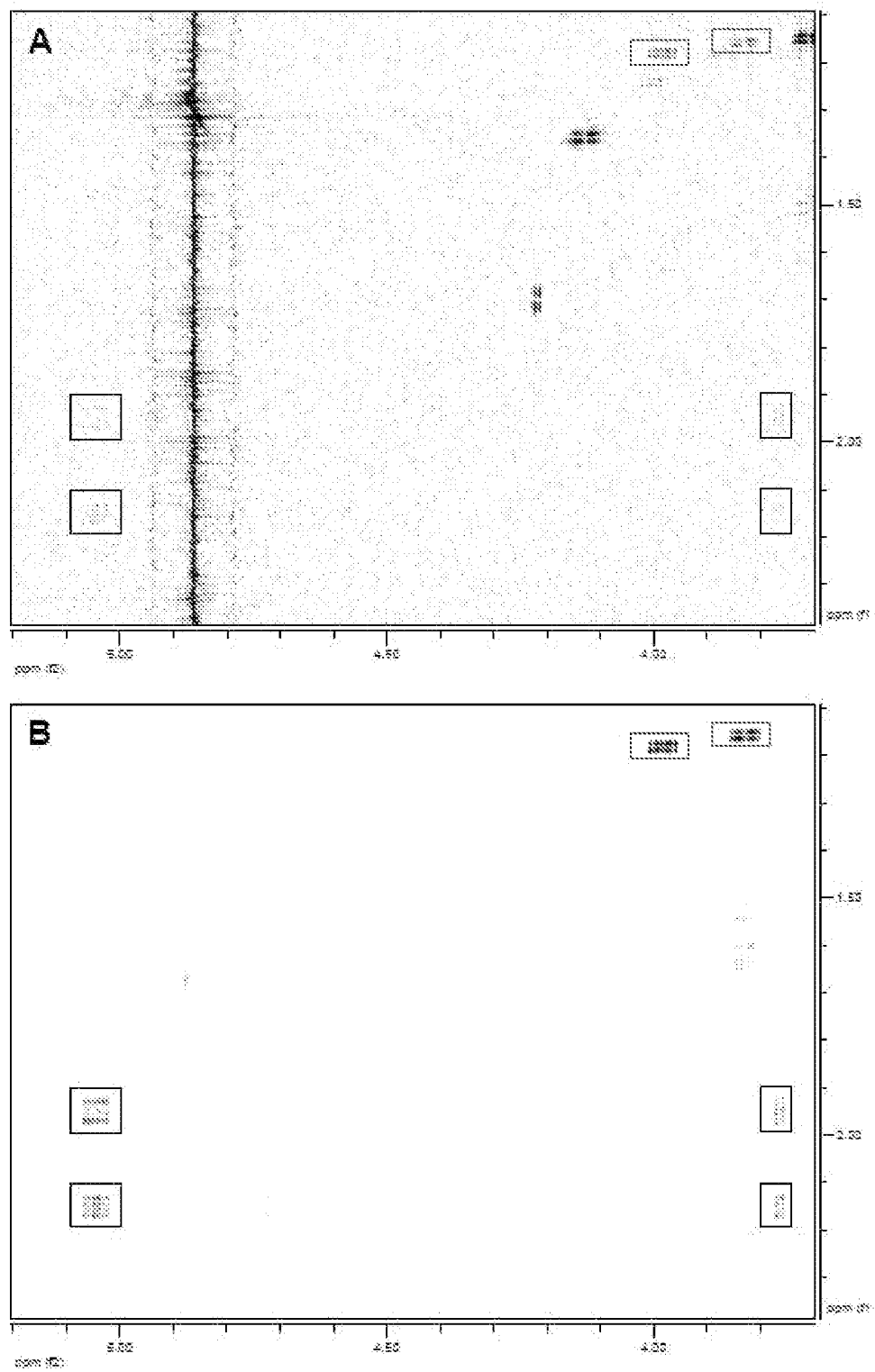
FIGS. 41A-B are enlarged sections of dqfCOSY spectra (600 MHz, methanol-$d_4$) of hbas#3-enriched fraction from wild-type *C. elegans* media extracts (FIG. 41A) and synthetic hbas#3 (FIG. 41B) showing characteristic signals for methyl groups of the ascarylose ring (blue), and the ascarylose spin system (black).
Figure 45:
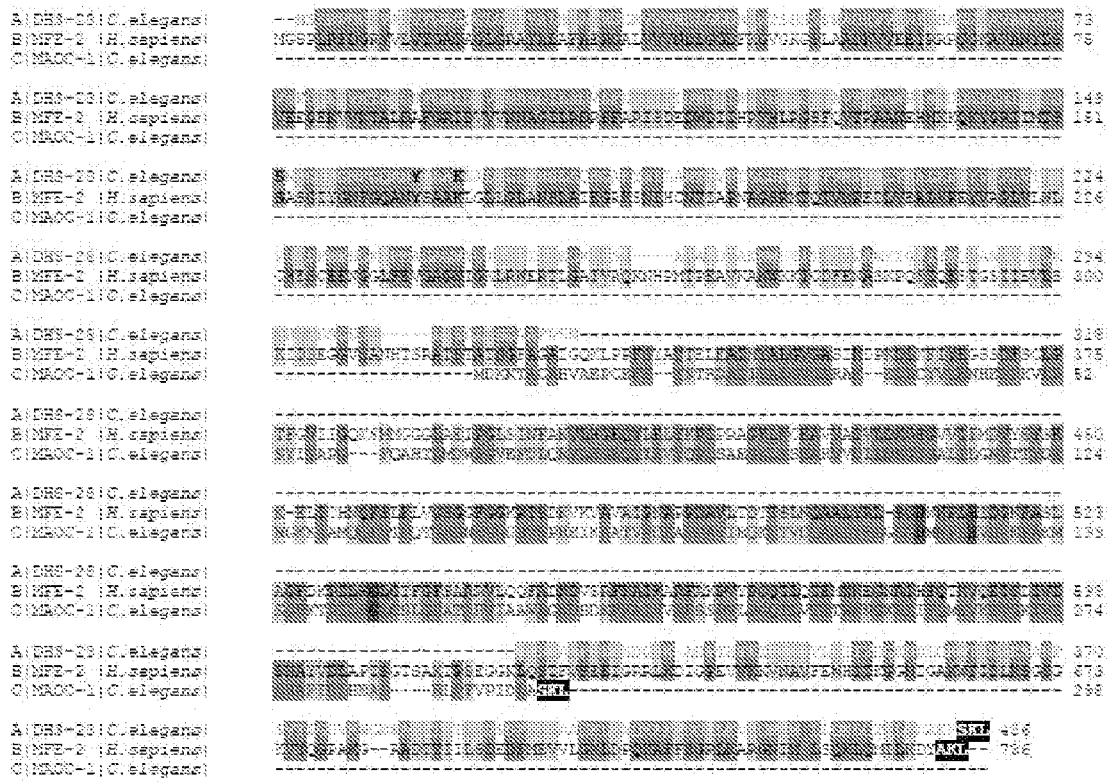
FIG. 45 shows the alignment of human MFE-2 isoform 2 (NP_000405.1) with *C. elegans* MAOC-1 (NP_495494.1 (red)) and DHS-28 (NP_509146.1; oxidoreductase domain (green), SCP-2 sterol carrier protein domain (yellow)) performed using ClustalW. Amino acids constituting the catalytic sites are marked with green and red boxes and the peroxisomal targeting signal in black. Identical amino acids are marked in grey and similar amino acids are marked in light grey.

For the identification of ascarosides detected in wild type and mutants (ascr, oscr, bhas, bhos, icas, icos, ibha, ibho and glas), HPLC-retention times were plotted versus m/z (or chain length). (For HPLC-EMI-MS data, see FIG. 37A ((ω-1)-oxygenated ascarosides (ascr)), FIG. 37B ((ω)-oxygenated ascarosides (oscr)), FIG. 37C ((ω-1)-oxygenated β-hydroxyascarosides (bhas)), FIG. 37D ((ω)-oxygenated β-hydroxyascarosides (bhos)), FIG. 37E ((ω-1)-oxygenated indole ascarosides (icas)), FIG. 37F ((ω)-oxygenated indole ascarosides (icos)), FIG. 37G ((ω-1)-oxygenated indole β-hydroxy ascarosides (ibha)), FIG. 37H ((ω)-oxygenated indole β-hydroxy ascarosides (ibho)), FIG. 37I (glucosyl ascaroside esters (glas)), FIG. 37J (ascr#8, and 4-(4-hydroxybenzoyl)- and 4-(2-(E)-methyl-2-butenoyl)-ascarosides (hbas and mbas)), and FIG. 37K (ascr#2 and ascr#6.1).) Components belonging to a homologous series exhibited almost linear elution profiles (FIG. 38), indicating that components within a series share the same relative stereochemistry. The structure and stereochemistry of the various series were then identified based on the (1) isolation of representative examples and NMR analysis (for example see FIGS. 39A-B, 40A-B, 41A-B, 42, and 43A-B), (2) comparison of representative examples with synthetic standards, (3) molecular formula as established from high-resolution MS, (4) characteristic MS/MS fragmentation (see FIGS. 44A-P), and (5) HPLC-retention times that matched retention time values extrapolated from those of the synthetic samples. The (E)-configuration of α,β-unsaturated ascarosides was established by comparison with ascr#3, (Z)-configured ascr#3, and ascr#7, and was also suggested by the stereoselectivity of acyl-CoA-oxidase (ACOX) activity. The (3R)-stereochemistry of the β-hydroxyascarosides (bhas and bhos series) was deduced from comparison with synthetic standards of bhas#10, bhas#22, and bhos#26 as representative examples, and was also suggested from the sequence homology of MAOC-1 and DHS-28 with (R)-selective MFE-2 (FIG. 45).

Quantification of ascarosides was performed by integration of LC-MS signals from the corresponding ion traces. Ascaroside concentrations were calculated using response factors determined for synthetic standards of ascr#1, ascr#3, ascr#5, ascr#7, ascr#9, ascr#10, oscr#9, oscr#10, bhas#22, bhos#26, icas#3, icas#9, icos#10, and glas#10. For most compounds, mass spectrometer response was roughly linear (less than 10% error) for amounts of 1 pmol to 2 nmol per injection. Response factors for ascarosides that were not synthesized were extrapolated based on data observed for the available standards. Generally, strong differences were observed between the response factors of short-chained members of each series (side chains less than C7), whereas differences between response factors of longer-chained homologs were small. Since not all short-chained members of all series were synthesized, the systematic errors of the absolute amounts reported for some short-chain ascarosides could be larger than for longer-chained compounds.

In order to roughly account for culture duration and worm biomass, ascaroside content of the excretome and worm pellet samples were recorded in fmol ascarosides produced per hour of culture time per mg of worm pellet dry weight. All quantitative data reported in FIGS. 37-62 were derived from at least two independent biological repeats.

Example 45

Spot Attraction Assays

Attraction assays with hbas#3 were conducted as previously reported (Srinivasan et al., Nature 454:1115-18 (2008); Pungaliya et al., Proc. Natl. Acad. Sci. U.S.A. 106:7708-13 (2009), which are hereby incorporated by reference in their entirety). For the attraction assays, 50-60 hermaphrodite worms were harvested daily at the early fourth larval stage (L4) and stored at 20° C. overnight to be used as young adults the following day. Hbas#3 was dissolved in water containing 10% ethanol. Aliquots were stored at −20° C. in 20 μL tubes. 10% ethanol in water was used as control.

Example 46

Quadrant Assays for Measuring Chemotaxis

Chemotaxis to hbas#3 was assessed on 10 cm four-quadrant petri plates (Wicks et al., Dev. Biol. 221:295-307 (2000), which is hereby incorporated by reference in its entirety). Each quadrant was separated from adjacent ones by plastic spacers. Pairs of opposite quadrants were filled with nematode growth medium (NGM) agar containing different concentrations of hbas#3. Animals were washed gently in an S-basal buffer and placed in the center of a four-quadrant plate with ascarosides in alternating quadrants, and scored after 15 minutes and 30 minutes. A chemotaxis index was calculated as: (the number of animals on ascaroside quadrants minus the number of animals on buffer quadrants)/(total number of animals).

Example 47

Statistical Analyses

Unpaired student's t tests with Welch's correction were used for comparing ascaroside profiles between wild-type and mutant metabolomes and for comparing attraction of hermaphrodites on hbas#3 (*: $P<0.05$, : $P<0.001$, *: $P<0.0001$). One-factor ANOVA followed by Dunnett's post-test (*: $P<0.05$, **: $P<0.01$) was used for comparing the chemotaxis indices of the different concentrations of hbas#3.

Example 48

LC-MS/MS Reveals New Ascarosides in Wild Type C. elegans

It was desirable to develop an analysis method that would (1) facilitate sensitive detection and quantitation of the known ascarosides in the metabolomes of different C. elegans strains and mutants and (2) aid with the discovery of new ascaroside derivatives.

Because of the vast complexity of the C. elegans metabolome, HPLC-MS analysis of metabolite extracts results in extremely crowded chromatograms that are difficult to interpret (FIG. 46A). However, it seemed likely that structurally related ascarosides would exhibit characteristic MS/MS fragmentation patterns, which provide a much more selective and sensitive means for their detection. Therefore, ESI-MS/MS fragmentation of a series of synthetic ascarosides was investigated.

It was found that with negative-ion electrospray ionization (ESI$^-$), ascarosides gave rise to an intense and highly diagnostic product ion at m/z 73.02939 [$C_3H_5O_2$], which originated from the ascarylose unit (FIGS. 44A-P and 46B). This detection method proved suitable for all known ascarosides, except for ascr#2 and ascr#4, which do not ionize well under ESI$^-$ conditions. For detection of ascarosides that ionize only under ESI$^+$ conditions, neutral loss of 130.0663 amu [$C_6H_{10}O_3$] due to cleavage of the ascarylose unit was monitored. However, it was found that ESI$^+$ MS/MS detection of ascarosides was generally less sensitive than ESI$^-$ MS/MS detection, as ascarosides fragment less predictably under ESI$^+$ conditions. Tests were conducted then to determine whether a screen for precursor ions of m/z 73 could be used to detect known as well as yet unidentified ascarosides in the C. elegans wild-type metabolome. Liquid culture metabolite extracts, which contain accumulated excreted metabolites from large numbers of worms (the worm "excretome"), were used. The resulting HPLC-MS/MS chromatograms showed a large number of well-resolved peaks, most of which were found to represent ascarosides, including several families of previously undetected compounds.

The identities of the known ascarosides were confirmed using synthetic standards. In addition, it was found that the known saturated ascarosides ascr#1, ascr#9, and ascr#10 are accompanied by substantial quantities of homologs with six- to fifteen-carbon side chains (FIGS. 46C and 47A). Identification of this homologous series was based on high-resolution MS/MS, LC-retention times, and the synthesis of representative members (see Example 44 and FIG. 38]). The LC-MS/MS screen further revealed that ascarosides with side chains of 5 to 11 carbons were accompanied by smaller quantities of slightly less polar isomers. These ascaroside isomers were produced more abundantly by acox-1 mutant worms.

Several additional peaks in the wild-type MS/MS chromatograms could not be assigned to any of the known ascaroside classes. For two of these compounds, MS/MS product ions at m/z 301.1651 [$C_{15}H_{25}O_6$] suggest that they represent ascr#3 derivatives. The putative ascr#3 derivatives were isolated by preparative HPLC and analyzed using 2D NMR spectroscopy (dqfCOSY, see FIGS. 39A-B, 40A-B, and 41A-B), which confirmed that these compounds were ascr#3-based and further indicated the presence of a 4-hydroxybenzoyl or (E)-2-methyl-2-butenoyl (tigloyl) moiety attached to the 4-position of the ascarylose (FIG. 47C). These structural assignments were corroborated via total synthesis of authentic samples (see Examples 41-42). In analogy to the recently reported indole-3-carboxy derivative of ascr#3 ("icas#3") (Srinivasan et al., Publ. Lib. Sci. Biol. 10(1):e1001237 (2012), which is hereby incorporated by reference in its entirety), the 4-hydroxybenzoyl and (E)-2-methyl-2-butenoyl derivatives of ascr#3 were named with SMIDs, "hbas#3" and "mbas#3", respectively. Hbas#3 and mbas#3 were the first ascarosides to incorporate 4-hydroxybenzoyl and (E)-2-methyl-2-butenoyl moieties, which, in analogy to the indole-3-carboxy moiety in icas#3 (Srinivasan et al., Publ. Lib. Sci. Biol. 10(1):e1001237 (2012), which is hereby incorporated by reference in its entirety), could be derived from amino acid precursors. Because of its structural similarity to the aggregation-inducing indole ascarosides (Srinivasan et al., Publ. Lib. Sci. Biol. 10(1): e1001237 (2012), which is hereby incorporated by reference in its entirety), hbas#3 was tested for its effect on worm behavior. It was found that hbas#3 strongly attracted *C. elegans* at concentrations as low as 10 femtomolar (see FIGS. 48A-B), which exceeds the potency of any previously known *C. elegans* small molecule signal (Srinivasan et al., Nature 454:1115-18 (2008); Srinivasan et al., Publ. Lib. Sci. Biol. 10(1):e1001237 (2012), which are hereby incorporated by reference in their entirety). Low femtomolar activity is unusual for small molecule signals in animals, but matches that of some classes of peptide hormones (Rittschof & Cohen, Peptides 25:1503-16 (2004); Gozes et al., CNS Drug Rev. 11:353-68 (2005), which are hereby incorporated by reference in their entirety).

Example 49

Peroxisomal β-Oxidation in Ascaroside Biosynthesis

Comparative LC-MS/MS was used to investigate ascaroside biogenesis. Studies have indicated that the side chains of the ascarosides are derived from peroxisomal β-oxidation of longer-chained precursors and that the acyl-CoA oxidase ACOX-1 participates in the first step of ascaroside side chain β-oxidation, introducing α,β-unsaturation (FIGS. 49A-B) (Joo et al., J. Biol. Chem. 285:29319-25 (2010), which is hereby incorporated by reference in its entirety). In vertebrates as well as in *Drosophila*, the next two steps in peroxisomal β-oxidation-hydration of the double bond and subsequent dehydrogenation to the β-ketoacyl-CoA ester are catalyzed by one protein, e.g., the multifunctional enzyme type 2 (MFE-2). These two enzymatic functions appear to be separated in *C. elegans* such that the dehydratase and dehydrogenase are distinct proteins (FIG. 45) (Haataja et al., Biochem. J. 435:771-81 (2011), which is hereby incorporated by reference in its entirety). Studies have shown that *C. elegans* DHS-28, a protein with homology to the (R)-selective β-hydroxyacyl-CoA dehydrogenase domain of human MFE-2, likely participates in converting β-hydroxyacyl-CoA-derivatives into the corresponding β-ketoacyl-CoA intermediates, which are subsequently cleaved by the β-ketoacyl-CoA thiolase DAF-22 (Butcher et al., PNAS 106: 1875-79 (2009); Joo et al., Biochem. J. 422:61-71 (2009), which are hereby incorporated by reference in their entirety). However, it remained unclear which enzyme serves as the enoyl-CoA hydratase that catalyzes the essential second step of the β-oxidation cascade.

Using the MS/MS-based ascaroside screening method described herein, the ascaroside profiles of acox-1(ok2257), dhs-28(hj8), and daf-22(ok693) mutant worms were re-investigated. Additionally, another study indicated that maoc-1 encoded a peroxisomal 2-enoyl-CoA hydratase (Zhang et al., PNAS 10:4640-45 (2010), which is hereby incorporated by reference in its entirety), which was hypothesized to participate in the hydration step of ascaroside β-oxidation. Thus, the excretomes of several other peroxisomal mutants, including maoc-1(hj13) worms, were analyzed.

Example 50

Side-Chain Functionalization Precedes β-Oxidation

LC-MS/MS analysis of the excretome of acox-1(ok2257) mutant worms revealed that abundance of the α,β-unsaturated ascr#3, the dominating component of wild-type media, was greatly reduced (FIGS. 50A-E). This decrease in ascr#3 and other α,β-unsaturated ascarosides did not appear to be the result of overall down regulation in ascaroside production, but instead was accompanied by accumulation of a series of saturated ascarosides. For example, ascr#10, the dihydro-derivative and direct precursor of ascr#3, was 13.6 times more abundant in acox-1(ok2257) than in the wild-type excretome. The corresponding homologs with 11- and 13-carbon side chains, ascr#18 and ascr#22, were 29 times and 66 times more abundant in acox-1 than in the wild-type excretome, respectively. The build-up of longer-chained saturated ascarosides in the acox-1(ok2257) excretome confirmed the importance of ACOX-1 in α,β-dehydrogenation of the ascaroside side chain (FIG. 49A). Because ascaroside biosynthesis is not abolished in acox-1(ok2257) worms, it seems likely that other, yet unidentified ACOX-enzymes contribute to peroxisomal β-oxidation of long chain ascaroside precursors. However, LC-MS/MS analysis of the excretome of several other peroxisomal acox mutants (see Examples 29-34 and 44-47 and FIG. 51]) revealed largely wild-type like ascaroside profiles.

Figure 42:
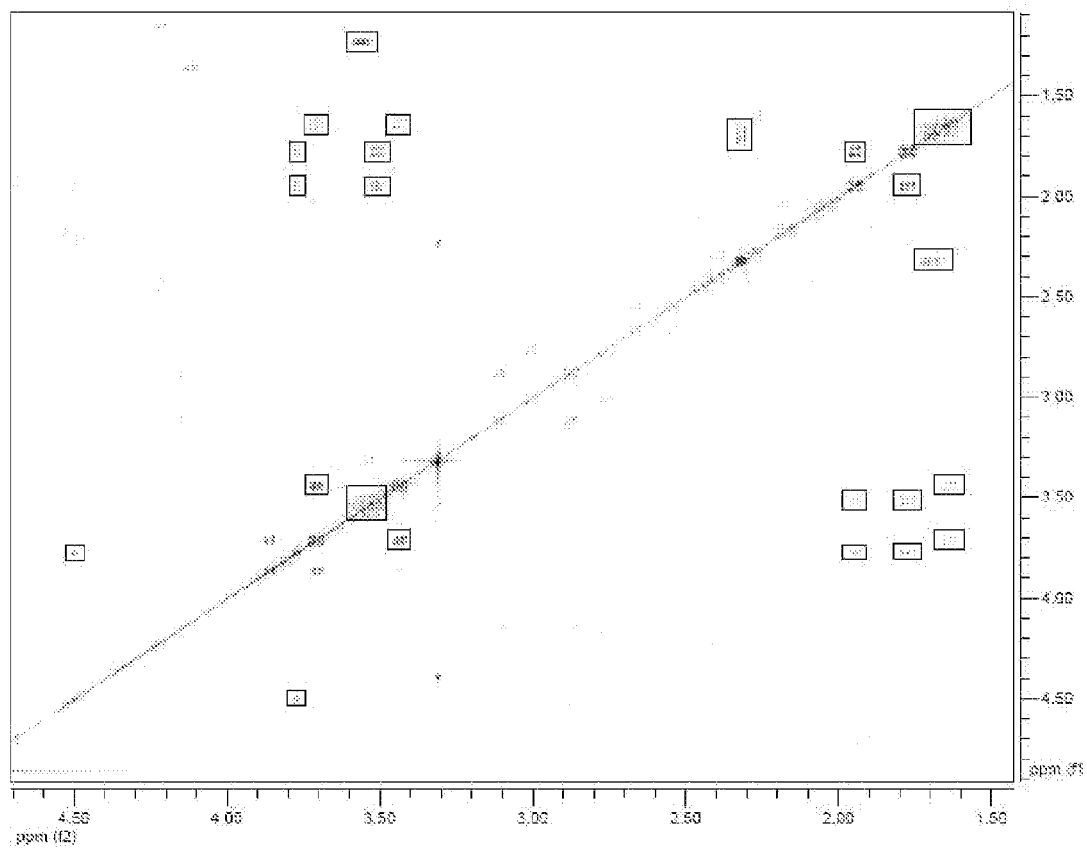
FIG. 42 is the dqfCOSY spectrum (600 MHz, methanol-$d_4$) of oscr#9-enriched fraction from acox-1 (ok2257) media extracts.
Figure 52:
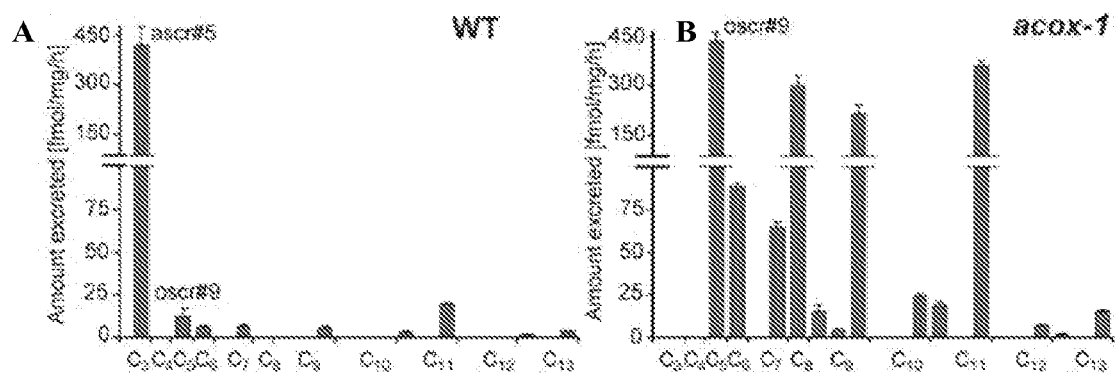
FIGS. 52A-B show the amount of (ω)-oxygenated ascarosides in wild-type (FIG. 52A) and acox-1 mutants (FIG. 52B) (see also FIGS. 53A-E).
Figure 53:
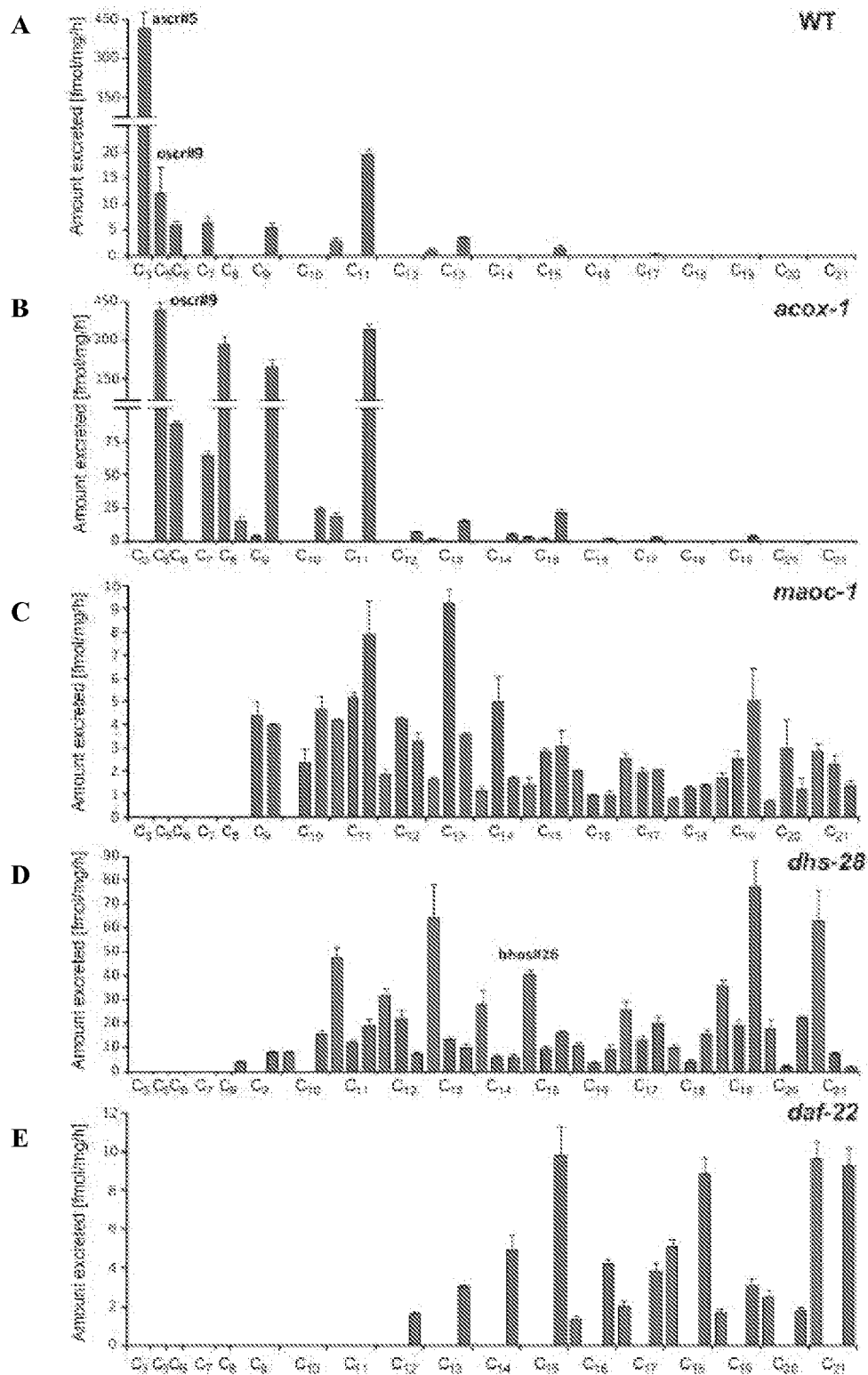
FIGS. 53A-E are the profiles of (ω)-oxygenated ascaroside in wild-type (N2) (FIG. 53A) and β-oxidation mutants (acox-1 (FIG. 53B), maoc-1 (FIG. 53C), dhs-28 (FIG. 53D), daf-22 (FIG. 53E) showing saturated (blue), α,β-unsaturated (red), and β-hydroxylated (green) ascarosides. (For (ω-1)-oxygenated ascarosides, see FIGS. 50A-E).
Figure 54:
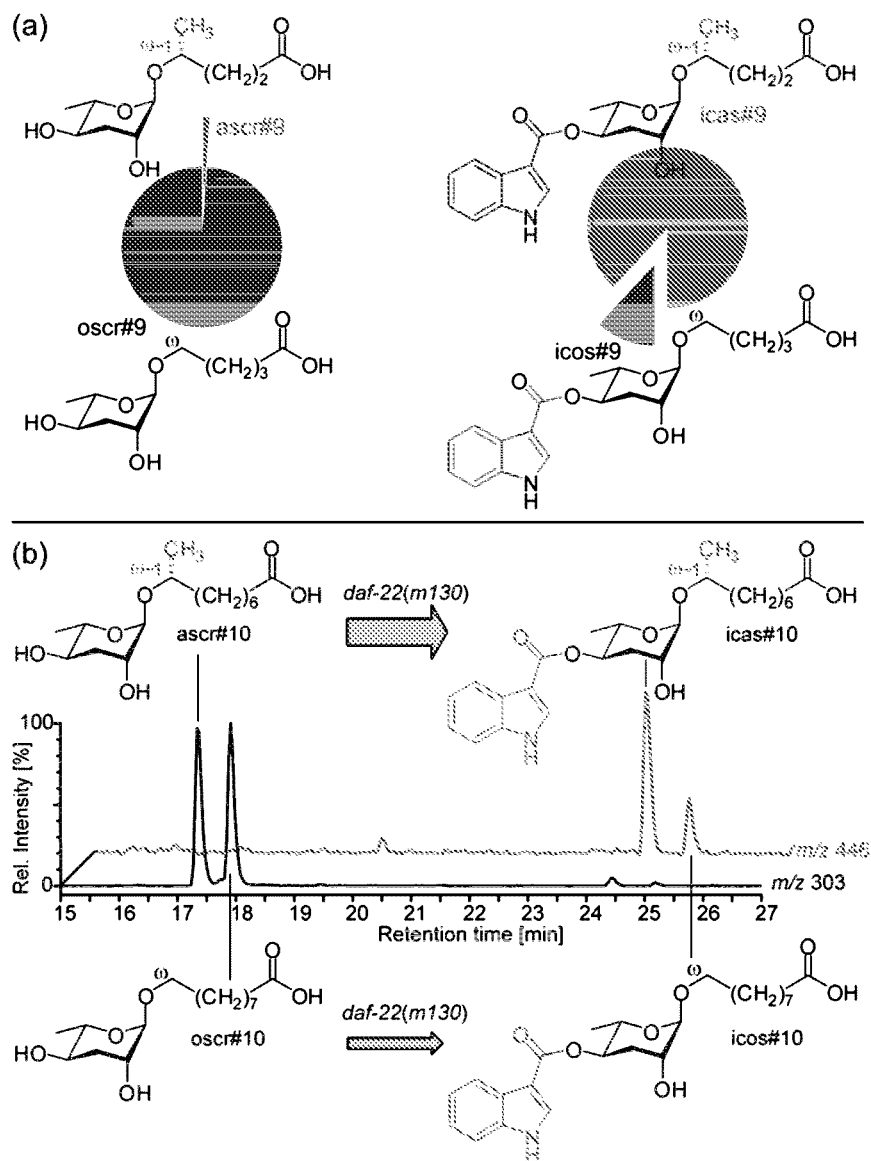
FIGS. 54A-B relate to indole ascaroside biosynthesis. Relative abundance of (ω-1) and (ω)-oxygenated $C_5$-ascarosides ascr#9 and oscr#9 and their corresponding indole ascarosides icas#9 and icos#9 in acox-1 indicates that indole-3-carbonyl attachment is highly specific (FIG. 54A).

Further analysis of the acox-1(ok2257) excretome revealed the complete absence of ascr#5, one of the major dauer inducing ascarosides produced abundantly in wild type worms (FIG. 52]). Ascr#5 differs from all other previously identified ascarosides in that its side chain is attached to the ascarylose sugar via the terminal carbon ("ω linkage"), and not the penultimate carbon ("ω-1 linkage") (FIG. 47B). Instead of ascr#5, large quantities of a new homologous series of saturated ascarosides in acox-1(ok2257) were detected, smaller amounts of which were also present in the wild-type excretome (FIG. 52]). The most abundant component of this series of isomers was isolated via preparative HPLC, and identified by NMR spectroscopy to be an ω-linked ascaroside with a $C_5$ side chain (FIGS. 42 and 47B). This suggests that the additional series of compounds observed in acox-1 represents a series of ω-linked saturated ascarosides (FIG. 37B), which were confirmed by synthesis of $C_5$ and $C_9$ ω-linked ascarosides (see Examples 35-36). To differentiate the (ω)-linked ascarosides from their previously described (ω-1)-linked isomers, the newly found (ω)-linked compounds were named with the SMID "oscr", e.g., the synthesized (ω)-linked isomers of ascr#9 and ascr#10 were named oscr#9 and oscr#10 (FIG. 47]).

Thus, production of (ω)-linked ascr#5 was abolished in acox-1(ok2257) worms, whereas production of longer chain homologs with 5-13 carbon side chains, e.g., oscr#9, was starkly upregulated (FIG. 52). These results indicate that β-oxidation in acox-1(ok2257) worms is strongly dependent on whether the side chain is (ω-1)- or (ω)-functionalized. Chain shortening of (ω-1)-oxygenated substrates appeared to stall at a chain length of 9 carbons as in ascr#10, whereas (ω)-oxygenated substrates were processed for two additional rounds of β-oxidation to afford large quantities of (ω)-oxygenated oscr#9 featuring a 5-carbon side chain. This suggests that side chain oxygenation precedes peroxisomal β-oxidation. In contrast, the time point of ascarylose attachment seemed less certain. The absence of any (ω-1)- or (ω)-hydroxylated fatty acids in the investigated *C. elegans* mutant metabolome samples suggests a biosynthetic model in which very long-chain ascarosides serve as substrates for peroxisomal β-oxidation. However, it may be possible that β-oxidation occurs prior to ascarylose attachment.

Example 51

MAOC-1 and DHS-28 are Functional Homologs of Human MFE-2

In contrast to wild-type and acox-1(ok2257) worms, short-chain ($<C_9$) ascarosides were not detected in maoc-1 (hj13) and dhs-28(hj8) worms, which instead accumulated several series of (ω-1)- and (ω)-oxygenated medium and long chain ascarosides ($\geq C_9$). The ascaroside profile of the maoc-1(hj13) excretome was dominated by α,β-unsaturated ascarosides such as ascr#21 ($C_{13}$) and ascr#25 ($C_{15}$) (FIGS. 50A-E), supporting the hypothesis that MAOC-1 functions as an enoyl-CoA hydratase in the ascaroside biosynthetic pathway (FIG. 49A). In addition, the maoc-1(hj13) excretome contained smaller amounts of the corresponding saturated ascarosides, along with a third homologous series of compounds, whose high-resolution mass spectrometry (HRMS) and MS/MS fragmentation suggested that they represent a series of long chain β-hydroxylated ascarosides (FIGS. 37C-D, 44A-P, and 50A-E). These structural assignments were confirmed via synthesis of representative members of this series (see Examples 37-39), the $C_9$ and $C_{13}$ β-hydroxylated (ω-1)-ascarosides bhas#10 and bhas#22, as well as the $C_{15}$ β-hydroxylated (ω)-ascaroside bhos#26 (SMIDs for (ω-1)- and (ω)-oxygenated β-hydroxylated ascarosides: "bhas" and "bhos"). Since β-hydroxylated ascarosides are putative products of enoyl-CoA hydratases such as MAOC-1, their presence in the excretomes of both studied maoc-1 mutant strains, maoc-1(hj13), which carries a point mutation in the active site (D186N), and the 2110 base pair deletion mutant maoc-1(ok2645) (FIG. 49B) suggests that additional enoyl-CoA hydratases may participate in ascaroside biosynthesis.

Similar to the results for maoc-1(hj13), the dhs-28(hj8) ascaroside profile was found to be dominated by compounds with side chains ranging from $C_9$-$C_{21}$ (FIGS. 50A-E). However, in contrast to maoc-1(hj13), saturated and α,β-unsaturated ascarosides constituted a relatively smaller portion of total ascarosides in dhs-28(hj8). Further, (ω-1)- and (ω)-oxygenated β-hydroxy ascarosides (bhas and bhos) with odd numbered side chains from $C_{13}$-$C_{21}$ were found to be major components (FIGS. 50A-E and 53A-E), which is consistent with the proposed biosynthetic role of DHS-28 as a β-hydroxyacyl-CoA dehydrogenase (Butcher et al., *PNAS* 106: 1875-79 (2009); Joo et al., *Biochem. J.* 422:61-71 (2009), which are hereby incorporated by reference in their entirety). Analysis of the daf-22(ok693) excretome revealed the absence of all ascarosides with side chains shorter than 12 carbons, as reported earlier (Pungaliya et al., *PNAS* 106: 7708-13 (2009); Butcher et al., *PNAS* 106:1875-79 (2009); Joo et al., *Biochem. J.* 422:61-71 (2009), which are hereby incorporated by reference in their entirety) (FIGS. 50A-E and 53A-E). The daf-22(ok693) excretome contained small amounts of homologous series of (ω-1)- and (ω)-oxygenated long chain ascarosides featuring saturated (ascr and oscr) and β-hydroxylated side chains (bhas and bhos). In addition, the daf-22(ok693) excretome contained very long chain ascarosides (VLCA, $>C_{22}$) with side chain lengths of up to 33 carbons, as reported earlier (Pungaliya et al., *PNAS* 106:7708-13 (2009); Zagoriy et al., *Chem. Biodivers.* 7:2016-22 (2010), which are hereby incorporated by reference in their entirety).

Example 52

Identification of New Indole Ascarosides

Indole-3-carbonylated ascarosides were much less abundant than the corresponding unfunctionalized ascarosides and have been shown to function as highly potent aggregation signals (Srinivasan et al., *Publ. Lib. Sci. Biol.* 10(1): e1001237 (2012), which is hereby incorporated by reference in its entirety). LC-MS/MS screening revealed several new types of indole ascarosides (FIGS. 37E-H and 47C). The results of synthetic samples of icas#3, icas#9, and icas#1 (Srinivasan et al., *Publ. Lib. Sci. Biol.* 10(1):e1001237 (2012), which is hereby incorporated by reference in its entirety) show that indole ascarosides exhibit a characteristic fragmentation pattern that includes neutral loss of 143 amu [$C_9H_5NO$] due to cleavage of the indole-3-carbonyl unit, as well as the ascaroside-diagnostic product ion at m/z 73 (see FIGS. 44A-P). LC-MS/MS screening for components with this fragmentation pattern revealed that known (ω-1)-oxygenated isomers icas#1, icas#9, and icas#10 in acox-1 (ok2257) are accompanied by a series of (ω)-oxygenated indole ascarosides (SMID: icos#1, icos#9, and icos#10), which was confirmed by chemical synthesis of icos#10 as a representative example (see Example 40). Peroxisomal β-oxidation mutants that do not produce short chain ascarosides (<9 carbon side chains), for example maoc-1 and dhs-28 worms, also did not produce any of the corresponding indole ascarosides. Instead, the maoc-1 and dhs-28 excretomes contained significant amounts of (ω-1)- and (ω)-oxygenated long chain indole ascarosides (SMIDs icas and icos) and indole β-hydroxy ascarosides (SMIDs ibha and ibho) with side chains from 9-17 carbons (see FIGS. 37E-H).

Example 53

Indole Ascaroside Biogenesis

Experiments with deuterium-labeled tryptophan and axenic in vitro cultures have shown that the indole-3-carbonyl moiety of indole ascarosides originates from L-tryptophan (Srinivasan et al., *Publ. Lib. Sci. Biol.* 10(1): e1001237 (2012), which is hereby incorporated by reference in its entirety). A similar L-tyrosine or L-phenylalanine origin seems likely for the 4-hydroxybenzoyl moiety of hbas#3, whereas the tigloyl group of mbas#3 could be derived from L-isoleucine (Attygalle et al., *J. Chem. Ecol.* 33:963-70 (2007), which is hereby incorporated by reference in its entirety). However, it remained unclear at what stage in ascaroside biosynthesis the indole-3-carbonyl moiety is attached.

Figure 55:
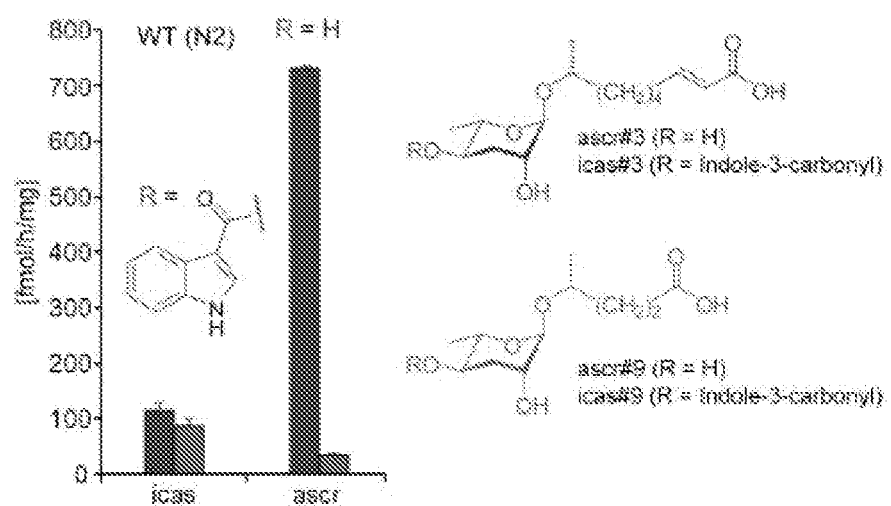
FIG. 55 shows the relative abundance of ascarosides ascr#3 and ascr#9 and their corresponding indole ascarosides icas#3 and icas#9 in wild-type excretome extracts, and indicates that indole attachment is highly dependent on side chain length.
Figure 59:
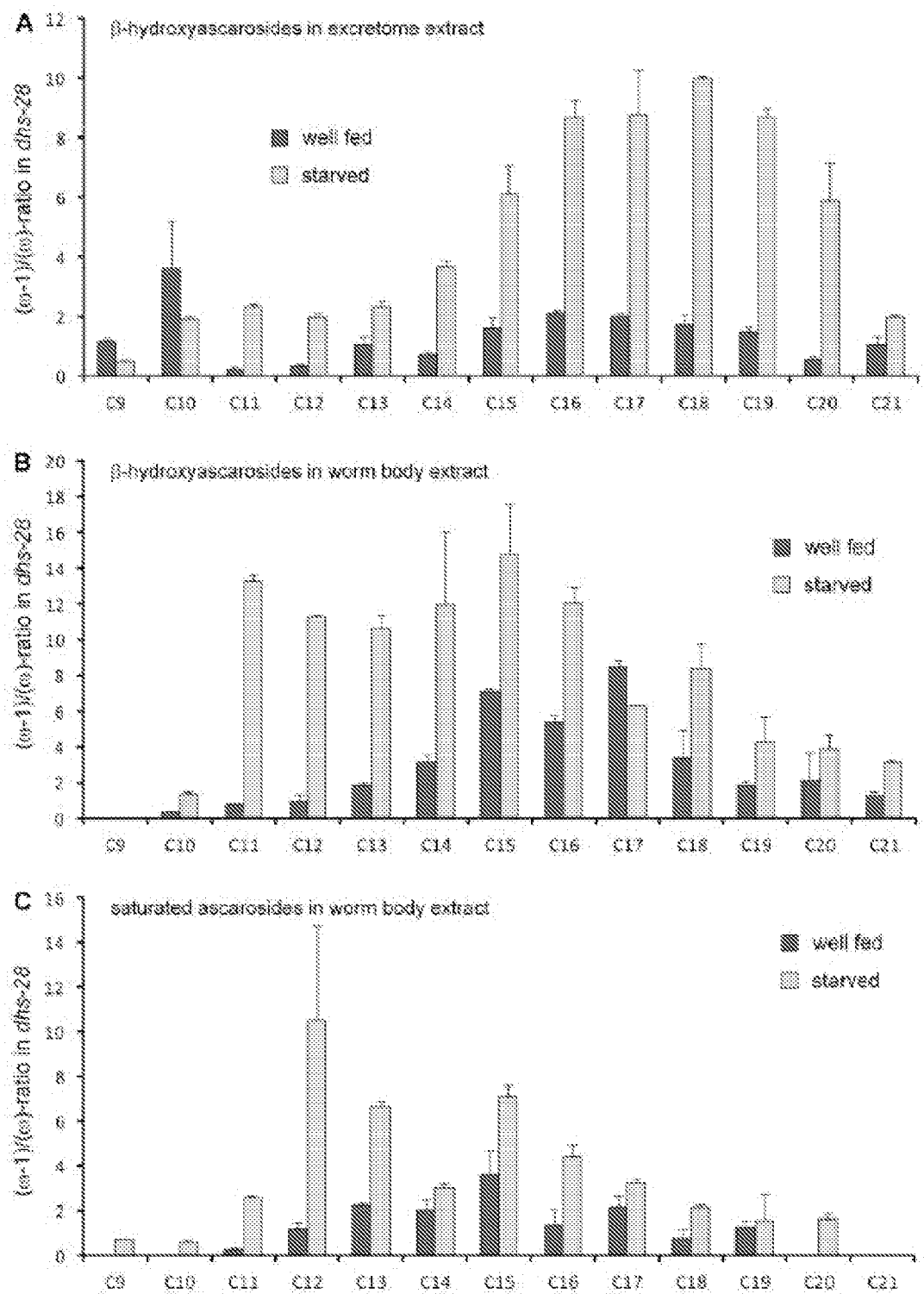
FIGS. 59A-C show the ratio of (ω-1) to (ω)-linked ascarosides in dhs-28(hj8) mutant worms and show strong dependence on nutritional conditions.

Comparison of ascaroside and indole ascaroside profiles revealed that indole ascaroside biosynthesis is tightly controlled. For example, it was found that in acox-1 mutants, the (ω)-ascaroside oscr#9 was over 100 times more abundant than the (ω-1)-ascaroside ascr#9, whereas (ω-1)-indole ascaroside icas#9 was much more prominent than (ω)-indole ascaroside icos#9 (FIG. 54A). Similarly, icas#3 and icas#9, the dominating indole ascarosides in the wild type excretome, were produced in roughly equal amounts, whereas ascr#3 was about 20 times more abundant than ascr#9 (FIG. 55). This strong dependence of indole ascaroside biosynthesis on side chain length and (ω-1)- vs. (ω)-oxygenation suggests that these compounds originate from specific attachment of an indole-3-carbonyl unit to the corresponding non-indole ascaroside.

To test whether non-indole ascarosides serve as precursors for indole ascarosides, daf-22(m130) worms (which are devoid of all short-chained indole and non-indole ascarosides) were incubated with a 1:1 mixture of ascr#10 and oscr#10 for 5 days. Subsequent analysis by LC-MS shows partial conversion into icas#10 and icos#10 (FIG. 54B), indicating that non-indole ascarosides serve as specific precursors to their corresponding indole derivatives. Moreover, conversion of (ω-1)-ascaroside ascr#10 was preferred over conversion of (ω)-ascaroside oscr#10, reflecting the ratios of these compounds in wild type and acox-1 mutants. Similarly, daf-22(m130) worms were found to convert added ascr#3 into icas#3. Further conversion of indole or non-indole ascarosides into shorter chain derivatives (e.g., ascr#1 or icas#1) was not observed. These results indicate that attachment of an L-tryptophan-derived indole-3-carbonyl unit represents the final step in indole ascaroside biosynthesis.

Example 54

Ascaroside Excretion is Selective

Despite detailed investigations of ascaroside function, little was known about how ascarosides are released and transported from their site of biosynthesis. The ascaroside profiles of the wild-type excretomes (liquid culture supernatant extracts) and worm body metabolomes (worm pellet extracts) were compared to identify possible non-excreted ascaroside derivatives and to determine quantitative differences. Ascaroside profiles of worm pellet extracts differed significantly from those excreted into the media, indicating that ascarosides are differentially released by *C. elegans* (FIG. 56A). In the worm pellets, the most abundant ascarosides, such as ascr#3 in wild-type and ascr#10 in acox-1 worms, were accompanied by significantly more polar derivatives, which were absent from the media extracts (FIG. 57). MS/MS analysis suggested that these components represent ascaroside O-glycoside esters. Isolation of the putative ascr#10 glycoside from acox-1(ok2257) worm pellet extracts and subsequent NMR spectroscopic analysis (FIGS. 43A-B) indicate esterification of ascr#10 with the anomeric hydroxy group of β-glucose, which was subsequently confirmed via synthesis (SMID for 1-β-D-glucosyl ascr#10: glas#10, FIG. 56A). The fact that large quantities of highly polar glas#10 and other ascaroside glucosides (see FIG. 37I) were retained in the worm bodies but not excreted suggests that they represent transport or storage forms of the ultimately excreted signaling molecules.

In addition, saturated ascarosides were retained in the worm bodies to a much greater extent than their α,β-unsaturated derivatives (FIG. 56A). Differential release was also observed for (ω)-oxygenated components (FIG. 58). Therefore, it appears that *C. elegans* exhibits remarkable control over the release of ascaroside signals.

Example 55

Nutritional State Affects Ascaroside Biosynthesis

Ascaroside biosynthesis has been reported to depend on various environmental factors, including food availability (Butcher et al., *PNAS* 106:1875-79 (2009), which is hereby incorporated by reference in its entirety), developmental stage (Kaplan et al., *Publ. Lib. Sci. ONE* 6:e17804 (2011), which is hereby incorporated by reference in its entirety), and temperature (Joo et al., *J. Biol. Chem.* 285:29319-25 (2010), which is hereby incorporated by reference in its entirety).

Figure 60:
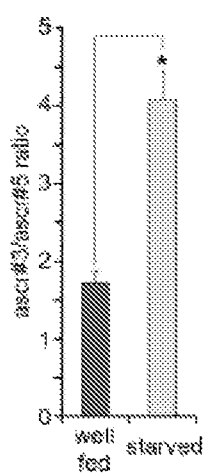
FIG. 60 shows the starvation dependence of ascr#3/ascr#5 ratio in wild type excretome.

LC-MS was used to investigate the effect of nutritional state on ascaroside biosynthesis by comparing the excretomes of well-fed and starved cultures of wild-type and mutant worms. The results indicate that the ratio of (ω-1) to (ω)-linked ascarosides strongly depends on nutritional state. Production of long-chain (ω-1)-oxygenated ascarosides in starved cultures of dhs-28 was about 5 times higher than those of well fed cultures (FIGS. 56B and 59A-C). Similarly, starved wild-type worms excreted significantly larger amounts of the (ω-1)-linked ascr#3 than well-fed worms, relative to the amounts of (ω)-linked ascr#5 (FIG. 60). Both ascr#5 and ascr#3 are major components of the dauer pheromone; however, they affect worm behavior differently (Jeong et al., *Nature* 433:541-45 (2005); Srinivasan et al., *Nature* 454:1115-18 (2008); Butcher et al., *PNAS* 105: 14288-92 (2008); Macosko et al., *Nature* 458:1171-75 (2009), which are hereby incorporated by reference in their entirety).

Therefore, it appears that ascaroside signaling is actively regulated in response to changes in nutrient availability via modulation of (ω-1)- and (ω)-functionalization of very long-chain fatty acids upstream of peroxisomal β-oxidation. Together with the recent finding that (ω)- and (ω-1)-functionalized ascarosides are sensed by different families of G-protein coupled receptors (Kim et al., *Science* 326:994-98 (2009); McGrath et al., *Nature* 477:321-25 (2011), which are hereby incorporated by reference in their entirety), these results suggest that (ω)- and (ω-1)-functionalized ascarosides target separate downstream signaling pathways.

Discussion of Examples 29-55

Ascarosides play important roles for several different aspects of *C. elegans* biology. This functional diversity is paralleled by corresponding structural diversity and a complex biosynthetic pathway. The MS/MS-based study described in Examples 34-43 and FIGS. 37A-37K revealed 146 ascarosides, including 124 previously unreported analogs, which show several unexpected features including (ω)-oxygenation of the fatty acid-derived side chains, 4-hydroxybenzoylation or (E)-2-methyl-2-butenoylation of the ascarylose unit, and glucosyl esters. Most ascarosides occur as members of homologous series of compounds with (ω-1)- or (ω)-linked saturated, α,β-unsaturated, or β-hydroxylated side chains ranging from 3 to 21 (occasionally more) carbons. Importantly, only a few members of each series are produced abundantly in wild type nematodes, and incorporation of specific structural features such as modification in position 4 of the ascarylose (e.g., as in indole ascarosides) or the incorporation of α,β-unsaturation appears to be tightly controlled.

Given their assembly from carbohydrate, lipid, and amino acid-derived building blocks, the ascarosides appear as a modular library of small molecule signals that integrate inputs from three basic metabolic pathways (FIG. 61A). The ascarosides then transduce input from these pathways via their diverse signaling functions in *C. elegans*' behavior and development, including dauer formation, mate attraction, hermaphrodite repulsion, and aggregation (Srinivasan et al., *Publ. Lib. Sci. Biol.* 10(1):e1001237 (2012); Edison, A. S., *Curr. Opin. Neurobiol.* 19:378-88 (2009), which are hereby incorporated by reference in their entirety). Their specific biosyntheses suggest that many of the newly identified ascarosides also contribute to known or as yet undetermined functions in *C. elegans*. As an example, hbas#3 was shown to act as an attraction signal whose potency exceeds that of all previously known small molecules in this model organism.

A working model for ascaroside biogenesis is proposed in FIG. 61B. The finding that ascarosides are members of several homologous series with side chains up to 21 (and more) carbons suggests their origin from peroxisomal β-oxidation of very long chain precursors. Previous studies reported the presence of very long chain ascarosides (VLCA) with $C_{29}$ and $C_{31}$ side chains in wild-type and daf-22 mutants, which could represent precursors or intermediates in ascaroside biosynthesis (Pungaliya et al., *PNAS* 106:7708-13 (2009); Zagoriy et al., *Chem. Biodivers.* 7:2016-22 (2010), which are hereby incorporated by reference in their entirety). Alternatively, very long chain fatty acids (VLCFAs) could undergo peroxisomal β-oxidation prior to (ω-1)- or (ω)-functionalization and subsequent attachment of the ascarylose. The observation that the acox-1 mutation affected (ω-1)- and (ω)-oxygenated ascarosides differently suggests that (ω-1)- and (ω)-functionalization of VLCFA precursors occur upstream of their breakdown by peroxisomal β-oxidation. Given the large range in side chain lengths, it seems likely that the resulting (ω-1)- and (ω)-hydroxy VLCFAs are linked to ascarylose prior to entering the β-oxidation pathway, though the presence of a promiscuous ascarosyl transferase may also be possible (FIG. 61B).

Chain shortening of VLCA can then progress via repetitive cycles of peroxisomal β-oxidation. The results from the LC-MS/MS screening allows for the proposal of precise roles for enzymes participating in each of the four-step β-oxidation cycle: the acyl-CoA oxidase ACOX-1, enoyl-CoA hydratase MAOC-1, β-hydroxyacyl-CoA dehydrogenase DHS-28, and β-ketoacyl-CoA thiolase DAF-22. Mutations in acox-1, maoc-1, and dhs-28 were shown to result in specific changes of the corresponding ascaroside profiles, in agreement with their proposed functions.

The acyl-CoA oxidase ACOX-1 has been the subject of a previous study that indicates that mutations in acox-1 primarily affect the biosynthesis of ascr#2 and ascr#3, but not of ascr#1 (Joo et al., *J. Biol. Chem.* 285:29319-25 (2010), which is hereby incorporated by reference in its entirety). However, the results described in Example 50 indicate that acox-1(ok2257) mutants have a reduced ability to process $C_9$ (ω-1)-functionalized ascarosides, resulting in diminished production of all shorter-chained ascarosides and build-up of $C_9$ and longer chained saturated ascarosides. Mutations of maoc-1 (as well as dhs-28 and daf-22) have been shown to result in expansion of intestinal lipid droplets and cause an increase in fasting- and lipolysis-resistant triglycerides (Zhang et al., *PNAS* 10:4640-45 (2010), which is hereby incorporated by reference in its entirety). The results described in Example 51 show that MAOC-1 participates in ascaroside biosynthesis, acting as the previously unidentified enoyl-CoA hydratase. These findings further demonstrate that hydration of enoyl-CoAs and dehydrogenation of β-hydroxyacyl-CoAs in *C. elegans* are catalyzed by two distinct enzymes, MAOC-1 and DHS-28, as had been indicated by their homology to separate functional domains of human MFE-2 (Zhang et al., *PNAS* 10:4640-45 (2010), which is hereby incorporated by reference in its entirety).

The results described in Examples 52-53 further show that attachment of the tryptophan-derived indole-3-carbonyl unit in indole ascarosides likely represents the last step in their biosynthesis, and that this step is highly specific. As attachment of an indole-3-carbonyl group to ascarosides can dramatically alter their biological function, such tight regulation makes sense. For example, indole-3-carbonyl addition to the dauer-inducing and strongly repulsive signal ascr#3 results in the potent hermaphrodite attractant icas#3 (Srinivasan et al., *Publ. Lib. Sci. Biol.* 10(1):e1001237 (2012), which is hereby incorporated by reference in its entirety).

The biosynthesis of ascarylose in *C. elegans* has not been investigated. However, the detection of ascarosides in axenic *C. elegans* cultures demonstrates that *C. elegans* produces ascarylose endogenously (Srinivasan et al., *Publ. Lib. Sci. Biol.* 10(1):e1001237 (2012), which is hereby incorporated by reference in its entirety). Ascarylose biosynthesis in bacteria is well understood and the *C. elegans* genome includes several homologs of bacterial genes in this pathway, for example ascE from *Yersinia pseudotuberculosis* (FIG. 62) (Thorson et al., *J. Bacteriol.* 176:5483-93 (1994), which is hereby incorporated by reference in its entirety), providing potential entry points for the study of ascarylose biosynthesis and its regulation in nematodes. Moreover, the oxidases catalyzing (ω-1)- or (ω)-functionalization of VLCFA precursors remain to be identified. The finding that the ratio of (ω-1)/(ω)-oxygenated ascarosides in wild type and peroxisomal β-oxidation mutants was strongly affected by starvation indicates that this step may encode information about nutritional state. In addition, ascaroside excretion was shown to be surprisingly specific. Given the high sensitivity and selectivity of LC-MS/MS, ascaroside profiling using the method described in Examples 29-55 can aid in identifying additional genes and environmental factors that participate in ascaroside biosynthesis and homeostasis.

Example 56

Dauer Production

*C. elegans* were cultured under dauer inducing liquid culture conditions (Kaplan et al., *Publ. Lib. Sci. ONE* 6:e17804 (2011), which is hereby incorporated by reference in its entirety) in S-complete with 20,000 worms/ml and 0.5% (wet weight) *E. coli* (HB101). Nematodes were incubated at 22° C. in a shaker (250 rpm) for 112 hours after feeding L1 larvae nematodes. Thereafter, nematodes were treated with 1% sodium dodecyl sulphate (SDS) for 15 minutes. Surviving nematodes were allowed to be separated from dead nematodes on an agar plate prior to collection.

After removal of the dead nematodes by vacuum, dauer animals were collected using M9 buffer and placed at 4° C.

Example 57

Rearing of *S. feltiae*

*S. feltiae* was ordered from ARBICO Organics (Tucson, Ariz.). *G. mellonella* larvae (Wax worms, Grubco, Hamilton, Ohio) were infected with 50 *S. feltiae* dauer juveniles per larvae. After two days, the infected larvae were placed into new 6 cm diameter petri dishes and the white trap method was used to collect infective juveniles (IJs) (LAWRENCE LACEY: MANUAL OF TECHNIQUES IN INSECT PATHOLOGY (1997), which is hereby incorporated by reference in its entirety).

*S. feltiae* IJs were verified by polymerase chain reaction (PCR) using species specific primers from the ITS rDNA region as described in Campos-Herrera et al., *Ann. Appl. Biol.* 158:55-68 (2011), which is hereby incorporated by reference in its entirety. PCR amplifications were performed in an MJ Research PTC 200 Peltier Thermal Cycler. Amplifications were conducted as described in Campos-Herrera et al., *Ann. Appl. Biol.* 158:55-68 (2011), which is hereby incorporated by reference in its entirety, in a 25 µL final volume containing 1 µL DNA template, using sterile deionized water and DNA prepared from *Steinernema riobrave* as negative controls. Cycling parameters were 94° C. for 15 minutes followed by 35 cycles of denaturation at 94° C. for 30 seconds, annealing at 59° C. for 20 seconds, and extension at 72° C. for 20 seconds with a final extension of 72° C. for 10 minutes. Amplicon sizes were verified through electrophoresis on a tris-acetate-EDTA (TAE) 2% agarose gel and visualized in the UVP BioDoc-It™ System.

The *S. feltiae* primer produced specific amplification for all samples containing IJs from lab populations in conventional PCR. The primers showed no amplification for *S. riobrave* and deionized water controls.

Example 58

Rearing of Root Knot Nematodes

Infected tomato plants were collected from field sites in Florida. Roots were inspected for root knot infection, and root knot nematode eggs were collected as described by in Hussey & Barker, *Plant Dis. Rep.* 57:1025-28 (1973), which is hereby incorporated by reference in its entirety, with modifications. The infected roots were treated with 1% bleach for 2 minutes. Eggs released from egg mass matrices were collected with a nested filter system (85 µm) to collect plant debris and with 25 µm nylon filters (Nytex) to collect eggs. Eggs were washed thoroughly with MILLI-Q water and placed at room temperature for 3 days onto a 20 µm filter on an 8 cm diameter petri dish with a small amount of water to hatch.

Root-knot nematodes extracted from infested tomato roots were identified based on morphology and isozyme phenotyping for esterase (EST) and malate dehydrogenase (MDH). Morphological identifications were conducted using perineal patterns of mature females is described in JOSEPH NEAL SASSER & CATHY CAMERON CARTER: AN ADVANCED TREATISE ON MELOIDOGYNE (1985), which is hereby incorporated by reference in its entirety. Briefly, isozyme phenotyping was conducted using 25 young egg-laying females. Extracts of females dissected directly from the root system were run on two polyacrylamide gel electrophoresis (PAGE) (Brito et al., *Nematology* 10:757-66 (2008), which is hereby incorporated by reference in its entirety). One gel was stained for both MDH and EST activities (KENNETH REECE BARKER, CATHY CAMERON CARTER & JOSEPH NEAL SASSER: AN ADVANCED TREATISE ON MELOIDOGYNE (1985), which is hereby incorporated by reference in its entirety), whereas a second was stained only for EST.

Example 59

Identification of *C. elegans* Dispersal Blend

Liquid cultures that induced 60% dauer (2 experiments) and 40% dauer after 67 hours of feeding L1s were analyzed using LC-MS. Four ascarosides were common to all three liquid media. The concentrations of each were measured from the liquid cultures that produced 60% dauers.

Example 60

Dispersal Assay

*S. feltiae* IJs were washed with MILLI-Q water three times and incubated in 6 cm petri dishes for 36 hours with a small amount (4-5 ml) of MILLI-Q water. Nematodes were placed the following day on a 10.7 g/L agar with 1010 g/cm$^2$ gel strength (PhytoTechnology Lab. Shawnee Mission, Kans.). Nematode behavior was assayed on multiple plates with internal plate replicates to rule out the possibility that behavior was affected by plate composition. Approximately 300 IJs in 10 µl water were placed on an agar medium and the test compounds or extracts (1-2 µl) were placed into the nematode suspension. Upon absorption (~15 minutes) of the liquid, the freely moving nematodes were video recorded for 5-10 minutes. Dispersal behavior is temperature and season dependent. During winter, the assay is effective at room temperature (22±1° C.). During summer, the assay requires a temperature controlled environment due to the effects on nematode behavior above 23° C.

*C. elegans* dauer juveniles were washed with MILLI-Q water 3 times, placed into 6 cm petri dishes with a small amount of water, and rested overnight. Approximately 200-300 nematodes in 10 µl of water were placed on an agar plate, to which 2 µl of treatment was added. The liquid culture that produced 60% dauer animals was centrifuged, filtered with a 0.45 µm filter, and used as a positive control for dispersal. Thereafter, media were lyophilized and resuspended in MILLI-Q water 5 times. 2 µl to 10 µl of nematode suspension was used for the assay. As a negative control, 0.5% *E. coli* (HB101) was prepared in S-complete, lyophilized, and adjusted to the final volume of 0.25% *E. coli* in the assay. The dispersal behavior was observed for 12-15 minutes.

To assay the dispersal of root knot nematodes, the root knot nematodes that hatched within 1-3 days were collected and washed with MILLI-Q water 3 times using 10 µm nylon filters (Nytex). Thereafter, they were placed into a 1.5 ml Eppendorf tube. The nematodes in 10 µl water were placed on an agar plate. Nematodes found at locations away from where they were originally placed were counted at 1 hour and 2 hours. Each treatment was normalized using the total number of nematodes that were deployed. For each treatment, 20 experiments were conducted on three different days. The nematode density was ~30 per plate in 14 experiments and 100 per plate in 6 experiments. The experiments were conducted in the morning.

Example 61

Quantifying of C. elegans Dispersal

Figure 63:
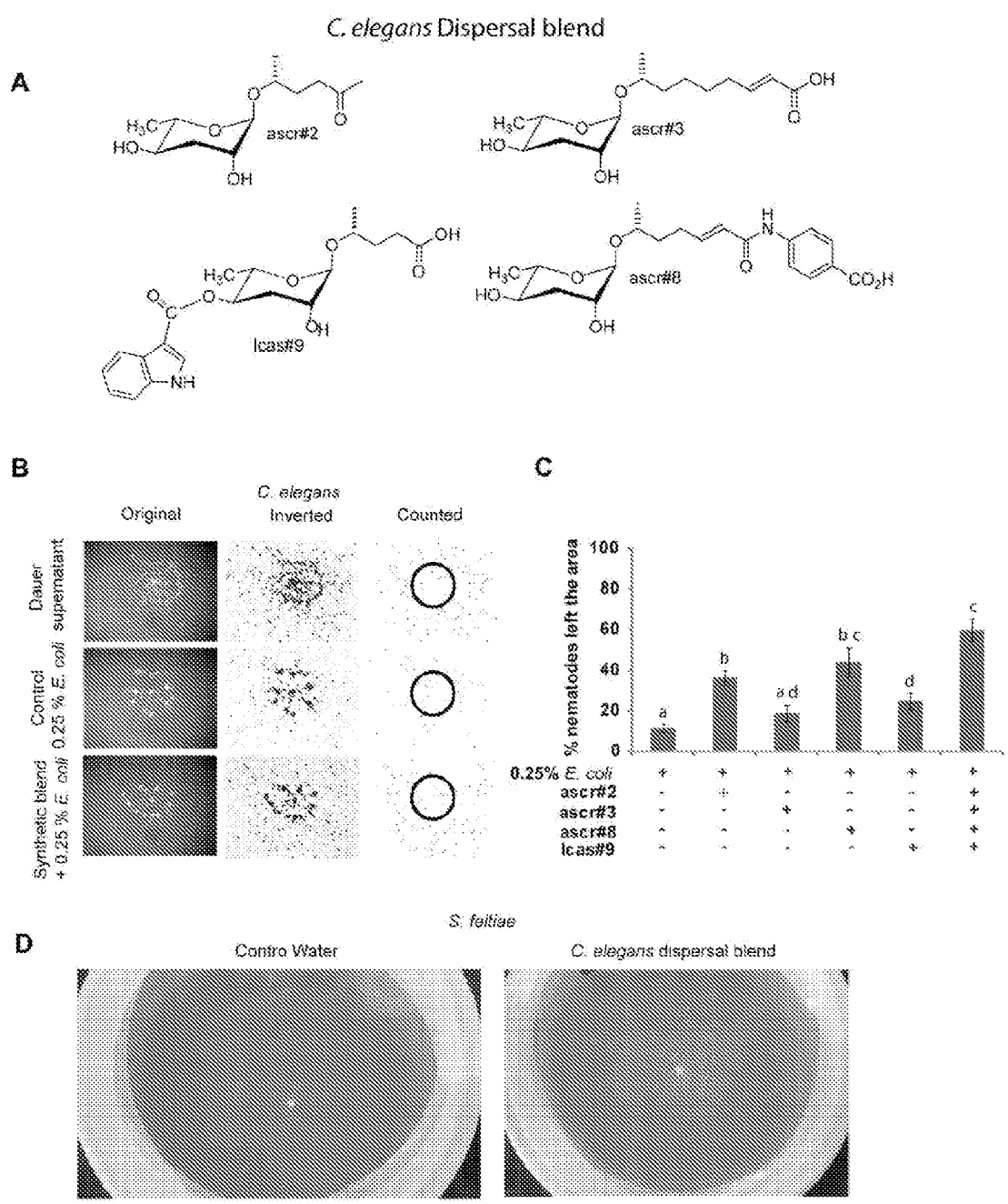
FIGS. 63A-D relate to the quantification and response of S. feltiae to the C. elegans dispersal blend.

Nematodes were quantified using Image J software (Image Processing and Analysis in Java, National Institutes of Health). The number of nematodes visualized and counted using Image J is illustrated in FIG. 63B. Nematodes inside the circle were subtracted manually from the total number of worms counted because of the location of their placement. Each treatment was replicated 9-11 times. The graph was normalized to the positive control, the dauer conditioned medium.

Example 62

Purification of the S. feltiae Dispersal Blend

Activity-guided fractionation was conducted as reported in Srinivasan et al., Nature 454:1115-18 (2008), which is hereby incorporated by reference in its entirety, with modifications. A total of 33 insect host cadavers (G. mellonella larvae) were placed into 70% EtOH and stored at −20° C. until extraction. The insect cadavers were homogenized using 1 g of ceramic zirconium beads (1.25 mm) (ZIRMIL) in 2 ml tubes for 37 seconds using a Precellys24 homogenizer. Samples were centrifuged for 15 minutes at 18400 relative centrifugal force (rcf), and the supernatant was lyophilized and resuspended in MILLI-Q water. The dispersal activity of nematodes was tested using the dispersal assay described in Example 60 and a physiologically relevant concentration of insect host cadaver extract or fractionated extract. To facilitate calculations for physiologically relevant concentration of the ascarosides, wax worm volume was estimated at ~200 µl; the average weight of wax worms was 232+57 mg (n=19).

The first reverse-phase solid-phase extraction was performed using Sep-Pak Plus C18 cartridges (Waters corporation, Milford, Mass.). The initially collected flow through was termed Fraction A. Thereafter, the column was washed with water, collected, and saved. Subsequently, the column was eluted with 50% (Fraction B) and 90% (Fraction C) MeOH. The fractions were tested for dispersal activity both individually and in combination. Also, individual fractions were analyzed by LC-MS. Fraction A contained ascr#9, which was collected by LC-MS and tested for activity with Fraction B+C.

Example 63

Time Course Study of S. feltiae Ascaroside Production

The one-on-one assay method (LAWRENCE LACEY: MANUAL OF TECHNIQUES IN INSECT PATHOLOGY (1997), which is hereby incorporated by reference in its entirety) was used. One wax worm was placed in one well of a 24 well plate. For infection, 50 S. feltiae IJ were placed in 25 µl of water in each well. After 24 hours, the plates were examined for infected insect larvae. Those that were infected were placed in a white trap (LAWRENCE LACEY: MANUAL OF TECHNIQUES IN INSECT PATHOLOGY (1997), which is hereby incorporated by reference in its entirety) and those that were infected after 48 hours were placed on a separate white trap. Initial sampling was made after 48 hours. Thereafter, samples were taken every day for 9 days and once at day 14. For each experiment, samples comprised six insect host cadavers. The insect cadavers were placed into a 2 ml Eppendorf tube with 1 ml of water. The cadavers were punctured with a needle to allow dissipation of internal contents and then vortexed. Samples were centrifuged at 3380 rcf for 10 minutes, and 0.5-1 ml of the supernatant was recovered. The supernatant was frozen at −20° C. and then lyophilized. Thereafter, it was resuspended in 200 µl of 50% MeOH and diluted 1:1 with 0.1% formic acid. Sample pH was 4.3. At this point, 20 µl of each sample was subjected to LC-MS for analysis of ascr#9.

Example 64

Asrc#9 in Insect Host Cadavers of Steinernema spp and Heterorhabditis spp

Insect hosts (G. mellonella) were infected with H. bacteriophora, H. zealandica, H. floridensis, S. carpocapsae, S. riobrave, or S. diaprepesi. When nematodes began to emerge from insect cadavers, they were placed into 1.5 ml of 70% EtOH and stored at −20° C. until use. Thereafter, insect cadavers were homogenized using 1 g of ceramic zirconium beads (1.25 mm) (ZIRMIL) in 2 ml tubes for 39 seconds using a Precellys24 homogenizer. The homogenized cadavers were centrifuged at 3380 rcf for 10 minutes. The supernatant was diluted with 1 ml of HPLC water, placed at −20° C., and then placed into a SpeedVac® (Speed Vac Plus SC210A, Savant) overnight. Each cadaver extract was resuspended in 1 ml of 50% MeOH and centrifuged at 18400 rcf for 15-20 minutes. Thereafter, samples were diluted in a 1:1 ratio with 0.1% formic acid, yielding a sample pH of 4.2. Presence or absence of arc#9 was determined by LC-MS.

Example 65

LC-MS Analysis

Ascaroside analysis was carried out using the method reported in Kaplan et al., Publ. Lib. Sci. ONE 6:e17804 (2011), which is hereby incorporated by reference in its entirety.

Example 66

Dispersal Assay

Figure 64:
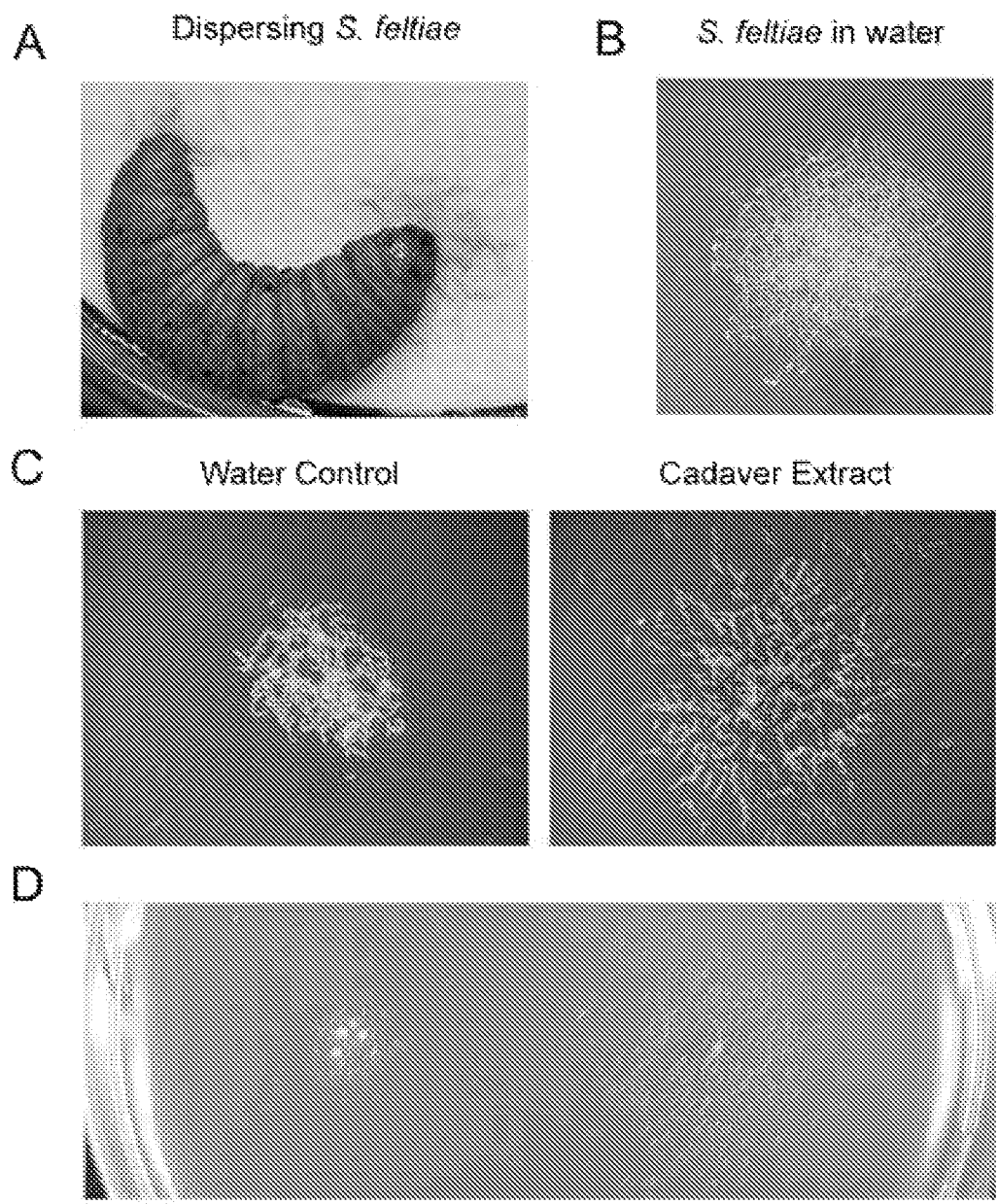
FIGS. 64A-D relate to the dispersal assay.

For entomopathogenic nematodes (EPN), insect cadavers are known to promote dispersal behavior of the IJ stage (Shapiro-Ilan et al., J. Invertebr. Pathol. 83:270-72 (2003), which is hereby incorporated by reference in its entirety). An assay was therefore developed to identify compounds in consumed insect cadavers that promote dispersal. Approximately 300 IJs of S. feltiae in 10 µl of water were placed on an agar plate (FIG. 64B). Then, either 2 µl water (FIG. 64C) or an aqueous extract of Galleria mellonella larval cadavers infected with S. feltiae (FIG. 64D) was placed into the nematode suspension. After absorption of water into the media, nematodes were able to move freely. The water-treated nematodes remained near the site of deployment with no dispersal behavior. In contrast, cadaver extract-treated nematodes were very active and moved away from the point of release. This was the same distinct dispersal behavior observed for nematodes leaving a cadaver. LC-MS analyses of the cadaver extract revealed the presence of an ascaroside (ascr#9) (Srinivasan et al., Publ. Lib. Sci. Biol. 10(1): e1001237 (2012), which is hereby incorporated by reference in its entirety), supporting the hypothesis that *S. feltiae* might utilize ascarosides as dispersal signals.

Example 67

C. elegans Dispersal is Regulated by a Blend of Ascarosides

Figure 65:
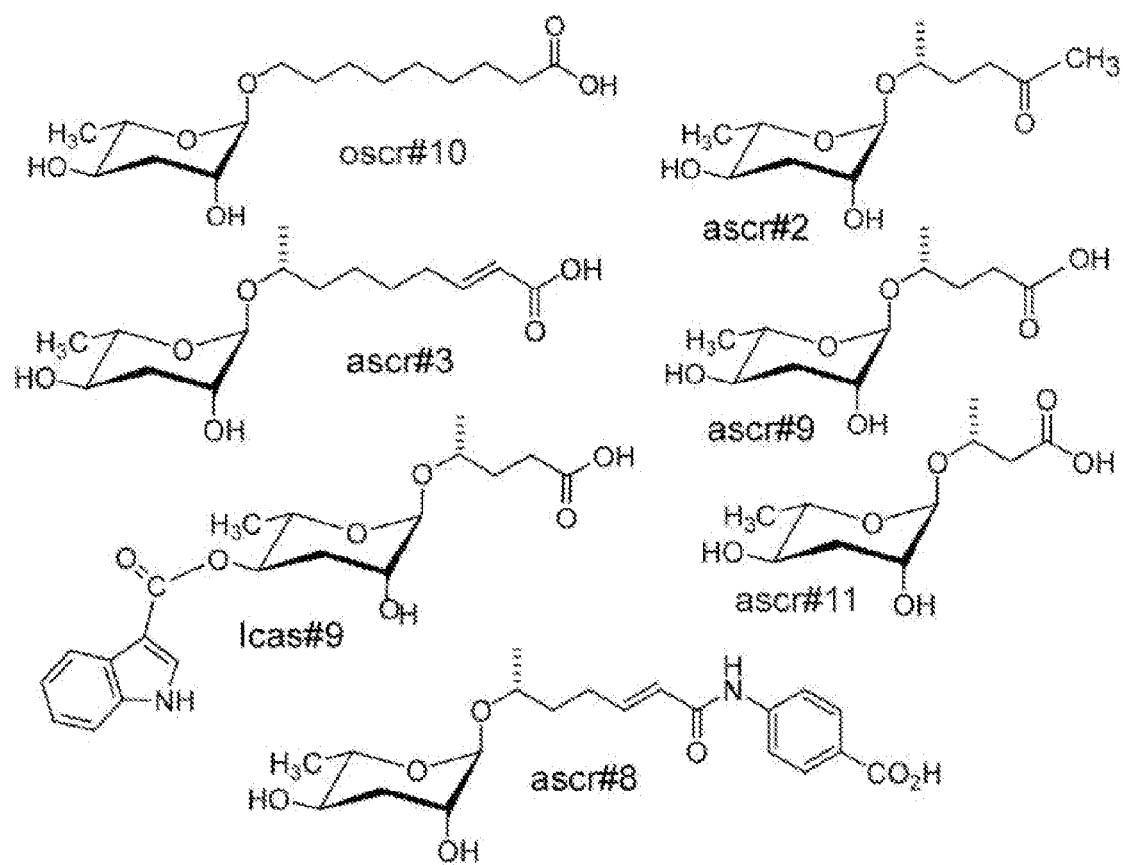
FIG. 65 shows the structures of several ascarosides.

The dispersal bioassay in Example 66 was then investigated to determine whether it could also be used to test for dispersal of *C. elegans* dauer larvae. For this assay, a growth medium from a *C. elegans* liquid culture that had produced 60% dauer larvae was used. Following removal of all nematodes, this dauer-conditioned medium strongly induced dispersal behavior in the *C. elegans* dauer. Using LC-MS, the dauer forming medium was found to contain four known ascarosides (ascr#2, ascr#3, ascr#8, and icas#9) (Butcher et al., *Nat. Chem. Biol.* 3:420-22 (2007); Pungaliya et al., *PNAS* 106:7708-13 (2009); Srinivasan et al., *Publ. Lib. Sci. Biol.* 10(1):e1001237 (2012), which are hereby incorporated by reference in their entirety) (FIGS. 63A and 65), which were shown previously to individually promote dauer entry in *C. elegans* (Butcher et al., *Nat. Chem. Biol.* 3:420-22 (2007); Butcher et al., *Org. Lett.* 11:3100-03 (2009); Pungaliya et al., *PNAS* 106:7708-13 (2009), which are hereby incorporated by reference in their entirety). The concentrations of the ascarosides in the dauer forming culture medium were estimated to be ascr#2 (3.68 pmol/µl), ascr#3 (0.165 pmol/µl), ascr#8 (0.25 pmol/µl), and icas#9 (0.005 pmol/µl).

A synthetic blend of these ascarosides was then tested for dispersal activity, using the dauer conditioned medium as a positive control. The media was estimated to contain approximately half of the original 0.5% *E. coli* (HB101) food source. Thus 0.25% *E. coli* was added to the synthetic test samples as well as to a water control to prevent food searching behavior induced by the absence of food. The number of dispersing nematodes was normalized to the percent of the positive control response. In the presence of just the food (negative control), approximately 35% of the dauer larvae left the release location. However, with the addition of the synthetic ascaroside blend, nearly twice as many nematodes (62%) moved away from the release location (FIGS. 63B and 66A-B). Tested individually at physiological concentration, ascr#8 (50%) and ascr#2 (40%) gave the strongest response, but all four were less active than the blend (FIG. 63C). This suggests that *C. elegans* dauer larvae were able to perceive and respond to single components of the dispersal blend, but the complete four-component blend was necessary to restore the activity.

Example 68

EPNs and Plant Parasitic Nematodes Sense the *C. elegans* Dispersal Blend

It was hypothesized that many nematode species might be able to sense and respond to signals released by other nematode species. Thus, ascaroside released by *C. elegans* could function as valid avoidance signals. In the dispersal assay, IJs of *S. feltiae* exhibited no noticeable movement when exposed to water, but were very active and moved away from the release location when exposed to the *C. elegans* dispersal blend (FIGS. 63D and 66C). The mobile J2 form of wild root knot nematodes (a mixture of *Meloidogyne* spp; *M. javanica*, *M. floridensis*, and *M. incognita*) isolated from tomato roots were also tested for response to the *C. elegans* dispersal blend (FIG. 66D). Again, more nematodes (10-12%) left the area where the *C. elegans* blend was introduced as compared to the control. This suggests that at least some nematode species can respond to dispersal blends of distantly related nematode species.

Example 69

The Major Components of *S. feltiae* and *C. elegans* Blends are Structural Analogs For characterization of the *S. feltiae* dispersal pheromone, insect host cadavers were extracted with 70% EtOH, fractionated by reverse phase (C18) chromatography, and assayed (FIGS. 67A-D). The bioassay revealed that a combination of all three fractions (A, B, and C) was necessary for activity (FIG. 67A). Analysis of the fractions by LC-MS (FIGS. 68A-C) revealed 2 ascarosides in fraction A, which were identified to be ascr#9 and ascr#11 with the help of a synthetic standard (Srinivasan et al., *Publ. Lib. Sci. Biol.* 10(1):e1001237 (2012); von Reuss et al., *J. Am. Chem. Soc.* 134(3):1817-24 (2012), which are hereby incorporated by reference in their entirety). Bioassays showed that ascr#9 and ascr#11 did not have activity by themselves at physiologically relevant concentrations (FIG. 67B). This is because the natural fraction A was inactive when tested alone (FIG. 67A). However, combining synthetic ascr#9 at the biologically relevant concentration (40 pmol/µl) with natural fractions B and C restored the original dispersal activity (FIG. 67C), confirming ascr#9 as an active component of the *S. feltiae* dispersal blend. The second ascaroside found in fraction A, ascr#11, also restored the full activity when combined with fractions B and C (FIG. 67D), indicating that either ascr#9 or ascr#11 were by themselves sufficient to reconstitute full dispersal activity in combination with fractions B and C.

A developmental profile has been previously established (Kaplan et al., *Publ. Lib. Sci. ONE* 6:e17804 (2011), which is hereby incorporated by reference in its entirety) for the principle *C. elegans* dispersal pheromone component, ascr#2. The primary ascaroside of fraction A in the *S. feltiae* dispersal blend, ascr#9, is a structural analog to ascr#2 (FIG. 67C). The accumulation of ascr#9 in *S. feltiae* infected insect cadavers was thus analyzed in a time course experiment (FIG. 69). The results show that ascr#9 had a very similar accumulation profile as previously established for ascr#2 in *C. elegans*. Furthermore, the accumulation of ascr#9 was highest directly prior to IJ dispersal and remained constant for at least 6 days in the IJ-depleted cadaver. This is very similar to observation of ascr#2 and dauer formation for *C. elegans* (Kaplan et al., *Publ. Lib. Sci. ONE* 6:e17804 (2011), which is hereby incorporated by reference in its entirety). In contrast, the ascr#11 profile (FIG. 69) differed from that of ascr#9. It initially became detectable but not quantifiable at day 8 (dispersal day), and could not be quantified in the insect host cadaver until day 14, which is 6 days after dispersal.

Ascr#9 was also tested and was found to be able to substitute for its structural analog ascr#2 in the *C. elegans* dispersal blend (FIG. 70). Thus, a cross species perception, as found with *S. feltiae*, may also be true for *C. elegans*.

Example 70

Ascr#9 could be a Common Component in Dispersal Blends of Phylogenetically Related EPNs In beetles and flies, phylogenetically related species share components in their aggregation pheromone blends (Symonds & Elgar, *Proc. Biol. Sci.* 271:839-46 (2004); Symonds & Wertheim, *J. Evol. Biol.* 18:1253-63 (2005), which are hereby incorporated by reference in their entirety). To further test to what degree dispersal blend components were shared by phylogenetically related nematode species, insect host cadavers infected with *Steinernema* spp. and *Heterorhabditis* spp. were analyzed for presence of ascr#9, ascr#2 and ascr#11 (FIGS. 71A-B).

The insect host cadavers for both species were found to contain ascr#9 (FIGS. 71A-B), which suggests that ascr#9 may be used by a broad range of EPN species as part of their dispersal blends. Ascr#11 was found in all tested *Steinernema* spp., but not in *Heterorhabditis* spp, suggesting that ascr#11 may be specific for *Steinernema* spp.

Discussion of Examples 56-70

For *C. elegans*, shared and unique compositions of ascarosides regulate different behaviors. For example, the mating and dispersal blends share ascr#2, ascr#3, and ascr#8 (Srinivasan et al., *Nature* 454:1115-18 (2008); Pungaliya et al., *PNAS* 106:7708-13 (2009); Kaplan et al., *Publ. Lib. Sci. ONE* 6:e17804 (2011), which are hereby incorporated by reference in their entirety). The *C. elegans* mating blend is characterized by a unique component, ascr#4 (Srinivasan et al., *Nature* 454:1115-18 (2008), which is hereby incorporated by reference in its entirety), and the dispersal blend has a unique component, icas#9 (Srinivasan et al., *Publ. Lib. Sci. Biol.* 10(1):e1001237 (2012), which is hereby incorporated by reference in its entirety). It is therefore thought that this can be common for many nematode species.

It was not yet clear whether *Meloidogyne* spp. also utilizes dispersal blends, but it has been shown herein that these nematode species can detect and respond to signals released by other nematode species that are indicative of decomposing and decaying plant material. The *C. elegans* dispersal blend shows similar activity in developmentally analogous stages of phylogenetically related species, suggesting that it can be used to identify genetic targets as well as to formulate dispersal blends for control of species parasitic to plants, humans, and livestock. Examples 56-70 not only demonstrate that several nematode species utilize species-specific small molecule signals to regulate dispersal behavior, but also that nematode dispersal behavior may be broadly induced by interspecies communication.

Example 71

Retention Assay

OP50 *E. coli* was grown on a standard 5 cm agar plate (made with standard Nematode Growth Medium). The bacterial lawn was 16 mm in diameter and was grown overnight at 20° C. before being used in trials. Two 4 mm spots (0.6 µL) were placed on opposite sides of the bacterial lawn (using a transparent template to guide spot placement), and several minutes elapsed for the liquid to settle in before placing nematodes down on the assay. Recording began immediately upon worm placement. 0.6 µL of the control was placed on one side of the lawn, and 0.6 µL of the experimental cue was placed on the other side of the lawn, changing the location of the cue throughout trials between left/right and top/bottom to avoid bias.

Nematodes were isolated by gender at the L4 stage the day before being used in trials as developed adults. Worms were evenly divided and placed at two points equidistant from the foci of the scoring region. Trials were recorded for 20 minutes, and frames were collected for analysis at 1 frame per second. Results were averaged from at least three different trials. For every nematode species in this study, a different total number of worms (using water in both scoring regions) was tested to determine the minimum number of worms necessary for consistent unbiased results over a 20 minute trial. The total number of worms used in the multiple species assays depended on that species' optimal parameters. 10 worms were used for *P. redivivus* males and females, 20 worms were used for *C. elegans* males and *O. dolichuridae* males, and 14 worms were used for *S. glaseri* males. The Automated Software was used to compare worm occupancy in each scoring region over time, and the Chemotaxis Index (Bargmann et al., *Cell* 74:515-27 (1993), which is hereby incorporated by reference in its entirety) was adapted to score preference or avoidance to each ascaroside.

Example 72

Attraction Assay 10 cm standard chemotaxis plates were prepared (Bargmann et al., *Cell* 74:515-27 (1993), which is hereby incorporated by reference in its entirety) and stored at 4° C. until the day before use. Standard 1 cm-diameter copper pipes were sectioned into 1 cm-tall segments to use for the holding chambers. The females/hermaphrodites were isolated overnight, washed 3 times in M9 buffer, and then allowed to wander on a plate pre-conditioned with 50 uL of 1000× streptomycin for 2 hours to kill any bacteria that might produce a false positive attractant. The nematodes were then washed 3 times, and the supernatant from the last wash was placed in a copper chamber, as the control, 1 cm from the border of the 10 cm plate. The nematodes were suspended in M9 within the copper chamber, 1 cm from the border opposite the control chamber. After 6 hours, they were subsequently removed and replaced with 3 µL of 1M sodium azide. 100 *C. elegans* adult males were isolated overnight, washed several times in ddH$_2$O, and placed at the center of the agar plate. After several hours, males paralyzed within 2 cm of each region were scored. The Chemotaxis Index (Bargmann et al., *Cell* 74:515-27 (1993), which is hereby incorporated by reference in its entirety) was then used to score male chemotaxis to either point source.

Example 73

Mating Assay

The mating assay described in Peden et al., *Curr. Biol.* 15:394-404 (2005), which is hereby incorporated by reference in its entirety, was adapted. Briefly, 40 young adult hermaphrodites/females were placed on an 8 mm bacterial lawn. *C. elegans* L4 males were isolated overnight. 5 males were placed on the hermaphrodite/female-rich plate. The number of males that responded to a hermaphrodite within a 3-minute period were counted (a single male only being counted once). Response was defined when a male stopped at the hermaphrodite and affixed their ventral tail on the potential mate for more than 10 consecutive seconds. They were scored for their Response Efficiency, also adapted from Peden et al., *Curr. Biol.* 15:394-404 (2005), which is hereby incorporated by reference in its entirety, which was calculated using the formula: Response Efficiency=[# males responding/5 males]×100%.

Example 74

Automated Software (for Retention Assay)

A video camera attached to the microscope produced a digital video stream, which was then analyzed. The ratio of the time the average worm spent in each region of interest was calculated for every trial. For ease of implementation, all worms in a single experiment were assumed to be roughly the same size. Thus worm pixels were counted instead of whole worms, allowing fractions of a worm in the region of interest to be taken into account. It also eliminated the need for a shape-based worm identification algorithm, and allowed each frame to be analyzed independently. A band-pass filter was applied to each frame to eliminate the effect of uneven lighting and also accentuate the worms against the background. The worm was then identified after thresholding the filtered image. Throughout each experiment, the locations and sizes of the regions of interest were known. Through the filtering described above, it is known which pixels are occupied by worms and which ones are not. Thus, the ratio of worm-pixels to all pixels inside the region of interest can be calculated to produce the worm-occupancy ratio. This calculation was done for every frame, giving a plot output of worm-occupancy ratio vs. time for each region.

Example 75

HPLC Analysis

A Thermo Finnigan LCQ Deca XP Max was used with electrospray ionization in positive ion mode in the 50-1000 AMU range. The Thermo Separation spectra HPLC system consisted of a P4000 quaternary pump, an AS 3000 auto sampler, and a UV 6000 diode array detector. The solvents were water with (a) 0.1% formic acid and (b) 90% acetonitrile-10% water with 10 mM ammonium formate. The column temperature was maintained at 60° C. and a solvent flow of 1.0 ml/min. The reversed phase column (PLRP-S Polymeric reversed phase column, 250×4.6 mmid, Varian Inc.) was eluted with a solvent composition starting with 90:10 (a,b) for 2 minutes, followed by a gradient to 5:95 in 20 minutes and an additional 5 minutes at 5:95. Ultraviolet absorption was monitored at 190 and 400 nm. Solvent flow between the ultraviolet detector and mass spectroscopy electrospray interface split 9:1 with a low-volume micro needle P450 splitter valve (Upchurch Scientific, Oak Harbor, Wash.), making it possible to obtain spectra of eluted compounds and simultaneously collect 90% of the injected material for bioassay. The purified peak with retention time of 9.7 minutes was active to males in the bioassay. LC-MS with chemical ionization (positive mode) shows that the major peak had an m/z of 294(M+NH$_4$). This was confirmed to be ascr#1 using NMR analysis.

Example 76

Construction of the Phylogenetic Tree

Small subunit ribosomal DNA (SSU rDNA) sequences for this analysis were obtained from GenBank. The sequences were first aligned using MUSCLE and then subsequently trimmed to facilitate comparison of sequences with varying lengths. The trimmed alignment resulted in 690 characters represented for all taxa. The Neighbor-Joining (N-J) analysis was done using the "Dnadist" and "Neighbor" programs from the PHYLIP 3.68 package, using "Consense" to produce a majority-rule consensus tree.

Example 77

Culture of Nematodes and Collection of Worm Excretions and Secretions

C. elegans, Rhabditis sp., O. tipulae, C. sp. 7, P. pacificus, P. redivivus, Koernia sp., and P. strongyloides were maintained on standard 6 cm agar plates with E. coli OP50. To grow large amounts, they were grown in liquid culture—S complete medium with E. coli HB101 at 20° C. at 250 rpm in an incubator shaker. The worms were exposed to several wash and filtration steps, using S Basal to remove bacteria. The worms were collected between the washes by centrifugation at 3000 rpm for 5 minutes. The worms were incubated at 1 worm/µL in S Basal for 6 hours. The worms were then filtered out and the remaining supernatant was passed through a 0.22 µm filter before being stored at −20° C.

S. carpocapsae, S. glaseri, S. riobrave, and H. bacteriophora were maintained as reported in Hallem, et al., Curr. Biol. 21(5):377-83 (2011), which is hereby incorporated by reference in its entirety. Briefly, several last-instar Galleria mellonella larvae were placed on a 6 cm Petri dish with a 55 mm Whatman 1 filter paper. Approximately 500-1000 IJs were placed on this filter paper. After 7 days, the insect cadavers were placed on an inverted 6 cm Petri plate carrying a Whatman 1 filter paper and immersed in a small volume of ddH$_2$O in a 10 cm Petri dish. Emerging IJs were collected and washed several times as described above, before being incubated in ddH$_2$O at 1 worm/µL for 6 hours. Adults were dissected out of insect cadavers after 3 days post-infection, and washed/incubated as described above.

N. brasiliensis, A. suum, P. penetrans, and Romanomermis spp. were provided by the collaborators identified in Table 11 below. All strains used in this Example are listed. Species without a strain identification are labeled "no designation".

TABLE 11

Source of nematode strains

| Species | Strain | Source or References |
|---|---|---|
| Nippostrongylus brasiliensis | no designation | Edward G. Platzer |
| Heterorhabditis bacteriophora | M31e | Sternberg collection |
| Rhabditis sp. | AF5 | Caenorhabditis Genetics Center |
| Oscheius tipulae | PS1305 | Sternberg collection |
| Caenorhabditis elegans | N2 | Sternberg collection |
| Caenorhabditis sp. 7 | JU1325 | Marie-Anne Felix |
| Ascaris suum | no designation | Robin Gasser |
| Pristionchus pacificus | RS2333 | Ralf Sommer |
| Koernia sp. | RS1982 | Ralf Sommer |
| Pratylenchus penetrans | 3/C | Antoon T. Ploeg |
| Panagrellus redivivus | PS2298 | Sternberg collection |
| Pelodera strongyloides | DF5022 | Caenorhabditis Genetics Center |
| Steinernema carpocapsae | ALL | Sternberg collection |
| Steinernema riobrave | no designation | Sternberg collection |
| Steinernema glaseri | VII | S. Patricia Stock |
| Romanomermis iyengari | no designation | Edward G. Platzer |
| Romanomermis culicivorax | 3B4 | Edward G. Platzer |

N. brasiliensis was incubated in 0.85% saline at 1 worm/5 µL (given their large size) at 30° C. A. suum were washed in sterile saline before being incubated in DMEM for 3, 6, and 13 hours at 37° C. The supernatants were tested individually and then subsequently pooled for combined analysis. P.

*penetrans* and *Romanomermis* spp. were incubated in ddH$_2$O at 20° C. at 250 rpm overnight.

Example 78

Worm Sample Preparation

Worm water samples were lyophilized, extracted with 1-10 ml methanol twice, and filtered over cotton wool. Extracts were concentrated in vacuum. Resulting residues were resuspended in 150 μL methanol and then filtered.

Example 79

MS Analysis

Figure 73:
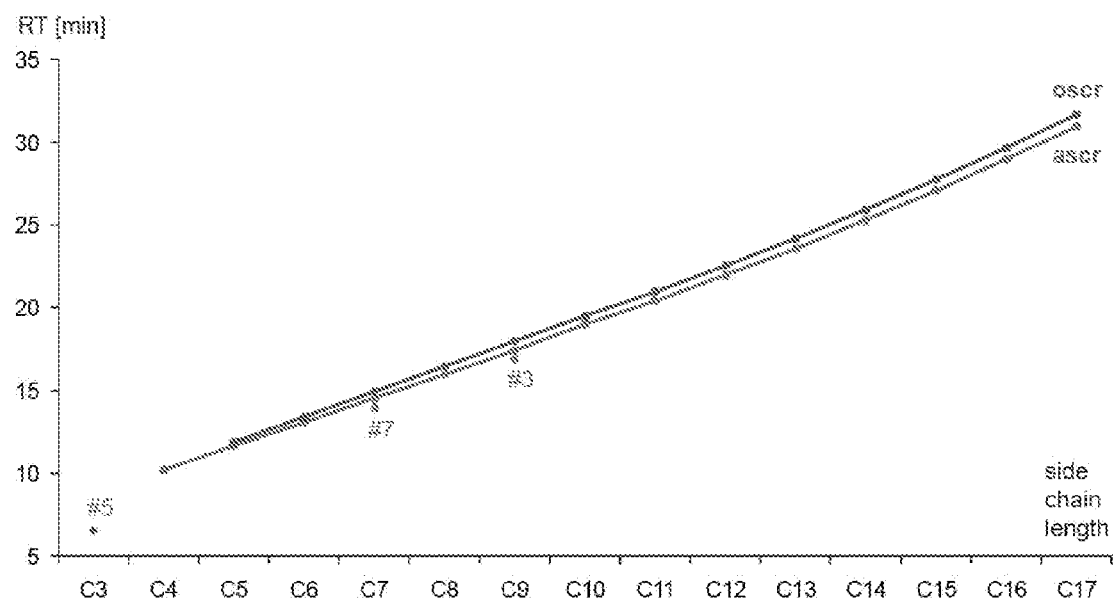
FIG. 73 shows the HPLC retention times of ascarosides (ascr's) and omega-ascarosides (oscr's). Side chains range from 3-17 carbons, derived from analysis of wild-type and peroxisomal beta-oxidation mutants of *C. elegans* and synthetic standards.

HPLC-MS was performed using an Agilent 1100 Series HPLC system equipped with an Agilent Eclipse XDB-C18 column (9.4×250 mm, 5 μm particle diameter) connected to a Quattro II spectrometer (Micromass/Waters) using a 10:1 split. A 0.1% acetic acid-acetonitrile solvent gradient was used at a flow rate of 3.6 ml/min, starting with an acetonitrile content of 5% for 5 minutes and then increased to 100% over a period of 40 minutes. Metabolite extracts were analyzed by HPLC-ESI-MS in negative and positive ion modes using a capillary voltage of 3.5 kV and a cone voltage of −40 V and +20 V, respectively. Ascarosides were identified by comparison of quasi molecular ion signals (FIGS. 72A-D) and HPLC retention times (FIG. 73) with those of a library of 150 components identified from wild-type and peroxisomal beta-oxidation mutants of *C. elegans*. To confirm the assignment of ascaroside structures, MS/MS screen was used for precursor ions of m/z=73.0 (FIGS. 74A-B), because previous work indicated that all ascarosides afforded an intensive C$_3$H$_5$O$_2$ product ion upon MS/MS (argon as collision gas at 2.1 mtorr and 30 eV). Quantification of ascarosides was performed by integration of LC-MS signals from the corresponding ion-traces. Relative ascaroside concentrations were finally calculated using response factors determined for synthetic standards of ascr#1, ascr#2, ascr#3, ascr#5, ascr#7, ascr#9, ascr#10, oscr#9, oscr#10, and icas#9. Response factors for the ascarosides which have not been synthesized yet were extrapolated based on data observed for the available standards.

Example 80

Synthesis of Ascaroside oscr #9

Ascaroside oscr#9 was prepared as shown in Scheme 11 below.

Scheme 11

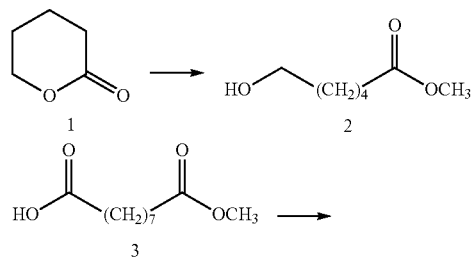

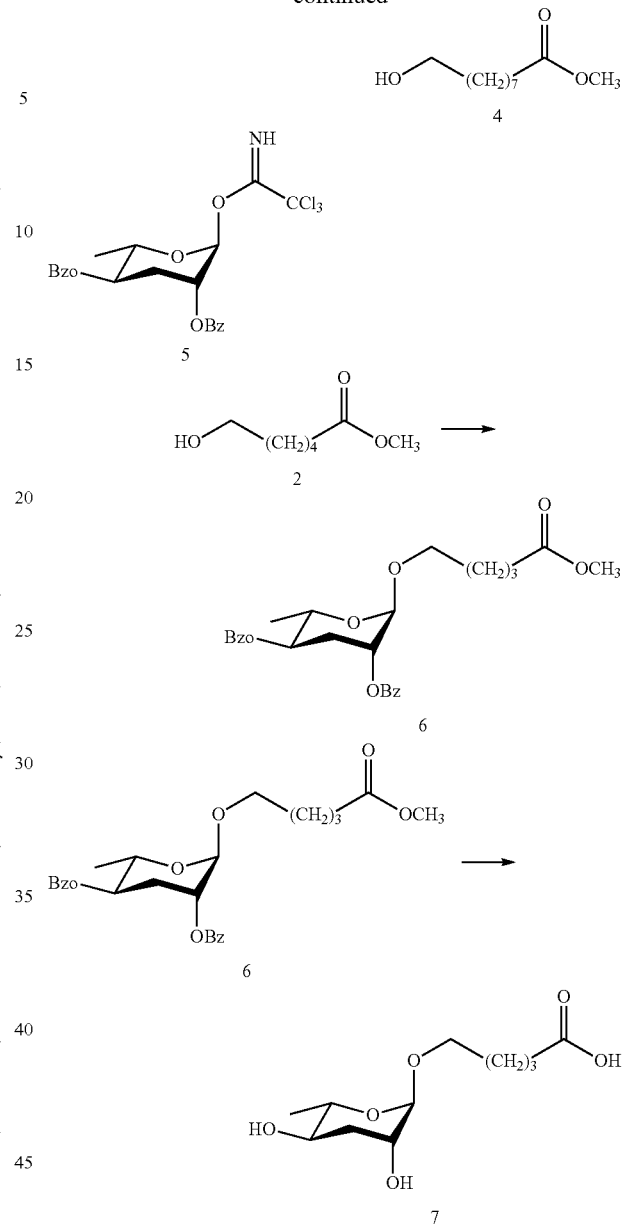

To prepare 2, freshly distilled δ-valerolactone (1) (856 mg) in methanol (17 ml) was treated with concentrated H$_2$SO$_4$ (100 μl) and refluxed for 12 hours. The solution was cooled to −20° C., treated with NaHCO$_3$ (80 mg), and stirred for 10 minutes. The reaction mixture was filtered and the solvent was removed in vacuum. The residue was taken up in DCM (10 ml), dried over Na$_2$SO$_4$, filtered, and concentrated in vacuum to give methyl 5-hydroxypentanoate (2) (Huckstep et al., *Synthesis* 10:881-82 (1982), which is hereby incorporated by reference in its entirety) (1071 mg, 94%) as a colorless oil, which was used directly without any further purification. $^1$H NMR (400 MHz, acetone-d$_6$): δ 1.55 (2H, m), 1.68 (2H, m), 2.35 (2H, t, J=7.4 Hz), 3.57 (2H, m), 3.64 (3H, s); $^{13}$C NMR (100 MHz, acetone-d$_6$): δ 22.2, 32.9, 34.1, 51.5, 61.9, 174.2. See FIGS. 75A-B.

To prepare 4, a solution of nonanedioic acid monomethyl ester (3) (923 mg, 4.6 mmol) in dry THF (3 ml) at −20° C. was treated with 1 M BH$_3$ in THF (4.6 ml, 4.6 mmol) over 10 minutes. After stirring at room temperature for 4 hours, the reaction was quenched with 0.77 M aqueous K$_2$CO$_3$ solution (10 ml) at 0° C. The product was extracted with diethyl ether (3×20 ml), washed with saturated aqueous NaCl solution, dried over Na$_2$SO$_4$, and concentrated in vacuum to afford methyl 9-hydroxynonanoate (4) (Kai K. et al., *Tetrahedron* 64:6760-69 (2008), which is hereby incorporated by reference in its entirety) (850 mg, 99% yield) as a colorless oil, which was used directly without any further purification. $^1$H NMR (400 MHz, chloroform-d$_1$): δ 1.27-1.37 (8H, m), 1.50-1.66 (4H, m), 2.29 (2H, t, J=7.5 Hz), 3.62 (2H, t, J=6.5 Hz), 3.66 (3H, s). See FIG. 75C.

To prepare 6, a solution of 2,4-di-O-benzoyl-ascarylose-1-(2,2,2-trichloroacetimide) (5) (11116) (132 mg, 263 μmol) and 2 (125 mg, 950 μmol) in dry DCM (3 ml) at 0° C. was treated with trimethylsilyloxy triflate (5 μl). After 3 hours, the solution was washed with saturated aqueous NaHCO$_3$ solution (0.5 ml), dried over Na$_2$SO$_4$, and concentrated in vacuum. Flash column chromatography on silica gel using a 20-40% (v/v) ethyl acetate gradient in n-hexane afforded 5-(3'R,5'R-dibenzoyloxy-6'S-methyl-(2H)-tetrahydropyran-2-yloxy)-pentanoic acid methyl ester (6) (66.8 mg, 142 μmol, 47%) as a colorless oil. $^1$H NMR (400 MHz, acetone-d$_6$): δ 1.28 (3H, d, J=6.2 Hz), 1.67-1.80 (4H, m), 2.23 (1H, m), 2.40 (2H, t, J=6.9 Hz), 2.48 (1H, m), 3.58 (1H, m), 3.64 (3H, s), 3.83 (1H, m), 4.13 (1H, dq, J=9.8 Hz, J=6.0 Hz), 4.87 (1H, s.br), 5.15 (1H, ddd, J=11.0 Hz, J=10.4 Hz, J=4.5 Hz), 5.18 (1H, s.br), 7.50-7.60 (4H, m), 7.62-7.72 (2H, m), 8.05 (2H, d, J=7.5 Hz), 8.11 (2H, d, J=7.5 Hz); $^{13}$C NMR (100 MHz, acetone-d$_6$): δ 18.3, 22.5, 29.6, 34.0, 51.5, 67.5, 67.9, 71.4, 71.5, 97.0, 129.4, 129.5, 130.03, 130.4, 131.0 (2×), 134.1, 134.2, 165.9, 166.0, 174.0. See FIGS. 75D-E.

To prepare oscr#9 (7), a solution of 6 (66.8 mg, 142 μmol) in dry THF (0.5 ml) was added to a mixture of LiOH (28 mg, 1.4 mmol) and water (0.6 ml) in 1,4-dioxane (4 ml). After stirring at 66° C. for 2 hours, the solution was acidified with glacial acetic acid and concentrated in vacuum. Flash column chromatography on silica gel using a 5-30% (v/v) methanol gradient in DCM containing 1% glacial acetic acid afforded 5-(3'R,5'R-dihydroxy-6'S-methyl-(2H)-tetrahydropyran-2-yloxy)-pentanoic acid (oscr#9) (7) (26 mg, 105 μmol, 74%) as a colorless oil. $^1$H NMR (400 MHz, methanol-d$_4$): δ 1.22 (3H, d, J=6.0 Hz), 1.58-1.72 (4H, m), 1.77 (1H, ddd, J=13.1 Hz, J=11.1 Hz, J=3.2 Hz), 1.95 (1H, ddt, J=13.1 Hz, J=3.7 Hz, J=0.9 Hz), 2.33 (2H, t, J=7.2 Hz), 3.43 (1H, dt, J=9.6 Hz, J=6.0 Hz) 3.47-3.59 (2H, m), 3.71 (1H, dt, J=9.8 Hz, J=6.2 Hz), 3.77 (1H, m), 4.50 (1H, s); $^{13}$C NMR (100 MHz, methanol-d$_4$): δ 18.1, 23.0, 30.1, 34.7, 36.0, 67.9, 68.3, 69.4, 70.9, 100.4, 177.5; ESI-MS (negative mode) m/z=247.1 [M-H]. See FIGS. 75F-G.

Example 81

Synthesis of Ascaroside oscr #10

Ascaroside oscr#10 was prepared as shown in Scheme 12 below.

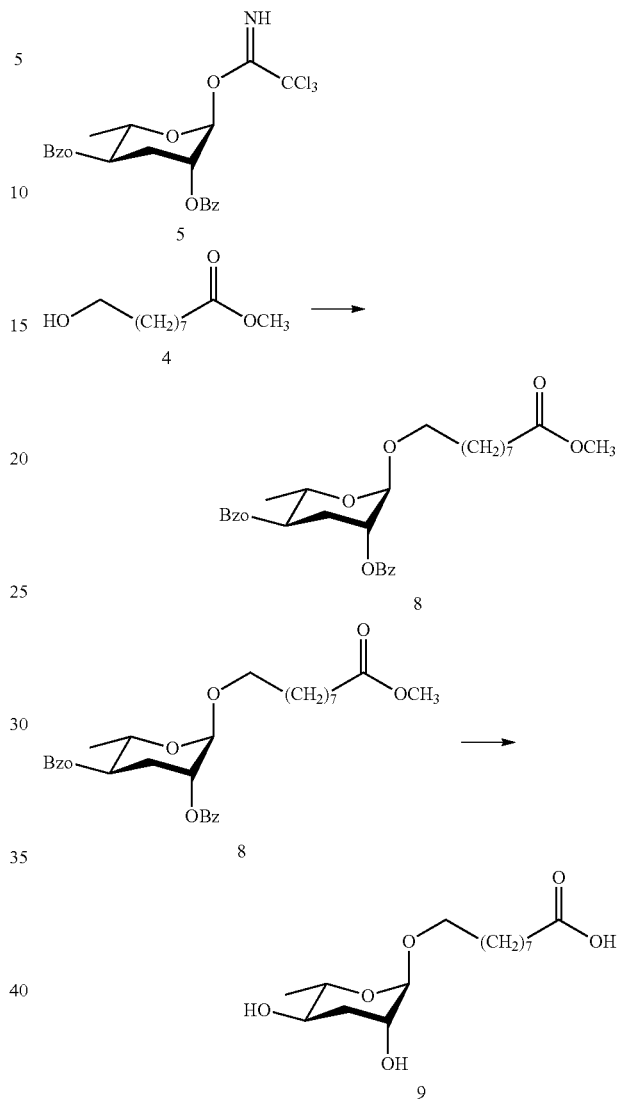

Scheme 12

To prepare 8, a solution of 2,4-di-O-benzoyl-ascarylose-1-(2,2,2-trichloroacetimide) (5) (132 mg, 263 μmol, Hallem, et al., *Curr. Biol.* 21(5):377-83 (2011), which is hereby incorporated by reference in its entirety) and 4 (112.8 mg, 600 μmol) in dry DCM (3 ml) at 0° C. was treated with trimethylsilyloxy triflate (5 μl). After 3 hours, the solution was washed with saturated aqueous NaHCO$_3$ solution (0.5 ml), dried over Na$_2$SO$_4$, and concentrated in vacuum. Flash column chromatography on silica gel using 20-40% (v/v) ethyl acetate gradient in n-hexane afforded 99.3 mg 9-(3'R, 5'R-dibenzoyloxy-6'S-methyl-(2H)-tetrahydropyran-2-yloxy)-nonanoic acid methyl ester (8) (190 μmol, 72% yield) as a colorless oil. $^1$H NMR (400 MHz, acetone-d$_6$): δ 1.28 (3H, d, 6.2 Hz), 1.30-1.40 (6H, m), 1.40-1.49 (2H, m), 1.56-1.72 (2H, m), 2.22 (1H, ddd, J=13.6 Hz, J=11.5 Hz, J=3.2 Hz), 2.30 (2H, t, J=7.5 Hz), 2.46 (1H, m), 3.55 (1H, dt, J=9.8 Hz, J=6.5 Hz), 3.60 (3H, s), 3.81 (1H, dt, J=9.6 Hz, J=6.6 Hz), 4.13 (1H, dq, J=9.7 Hz, J=6.2 Hz), 4.86 (1H, s.br), 5.15 (1H, ddd, J=11.4 Hz, J=9.8 Hz, J=4.6 Hz), 5.18 (1H, m), 7.50-7.60 (4H, m), 7.63-7.71 (2H, m), 8.04 (2H, m), 8.11 (2H, m); $^{13}$C NMR (100 MHz, acetone-d$_6$): δ 18.3, 25.6, 26.8, 29.7, 29.9, 30.0, 30.2, 30.4, 34.4, 51.4, 67.4, 68.2, 71.4, 71.5, 97.0, 129.4, 129.5, 130.2, 130.3, 130.9, 131.0, 134.1, 134.2, 165.9 (2C), 174.3. See FIGS. 75H-I.

To prepare oscr#10, a solution of 8 (99.3 mg, 190 μmol) in THF (500 μl) was added to a mixture of LiOH (38 mg, 1.9 mmol) and water (800 μl) in 5 ml 1,4-dioxane (5 ml). After stirring at 66° C. for 3 hours, the solution was acidified with acetic acid and concentrated in vacuum. Flash column chromatography on silica gel using a 5-30% (v/v) methanol gradient in DCM containing 1% glacial acetic acid afforded 9-(3'R,5'R-dihydroxy-6'S-methyl-(2H)-tetrahydropyran-2-yloxy)-nonanoic acid (oscr#10) (9) (49 mg, 161 μmol, 85%) as a colorless oil. $^1$H NMR (400 MHz, methanol-$d_4$): δ 1.22 (3H, d, J=6.1 Hz), 1.32-1.43 (8H, m), 1.56-1.63 (4H, m), 1.77 (1H, ddd, J=13.1 Hz, J=11.1 Hz, J=3.2 Hz), 1.96 (1H, ddt, J=13.1 Hz, J=3.7 Hz, J=0.9 Hz), 2.28 (2H, t, J=7.4 Hz), 3.41 (1H, dt, J=9.6 Hz, J=6.2 Hz) 3.49-3.59 (2H, m), 3.68 (1H, dt, J=9.8 Hz, J=5.5 Hz), 3.76 (1H, m), 4.49 (1H, s); $^{13}$C NMR (100 MHz, methanol-$d_4$): δ 17.3, 25.2, 26.4, 28.0, 29.3, 29.5, 29.6, 30.5, 34.1, 61.1, 67.4, 68.5, 69.9, 99.4, 176.8; ESI-MS (negative ion mode) m/z=303.2 [M-H]. See FIGS. 75J-K.

Example 82

Many Nematode Species Produce Ascarosides

A mass spectrometry-based screen was initiated for ascarosides (FIGS. 76A-D) in a varied selection of nematode species, including both free-living and parasitic (plant, insect, and mammal) nematodes. Previous studies have shown that *C. elegans* ascaroside production is developmental stage-specific (Kaplan et al., *Pub. Lib. Sci. ONE* 6(3): e17804 (2011), which is hereby incorporated by reference in its entirety). To obtain comprehensive samples, exudates from a developmentally mixed culture were tested, thus containing an accumulation of ascarosides released by all larval and adult stages. When feasible, parasitic infective juveniles and adults were tested separately, for the purpose of identifying ascarosides uniquely associated with host seeking or mate finding, respectively. Nematode secretions were analyzed via HPLC-MS using a protocol optimized for the detection of ascarosides in complex metabolome samples (Example 79). These analyses revealed the presence of ascarosides in most of the nematode samples. Samples were compared with mass spectroscopic data from a library of 150 ascarosides previously identified from both wild-type and mutant strains of *C. elegans*. These analyses revealed the presence of ascarosides in most of the analyzed nematode samples.

Ascarosides generally occurred as mixtures, including compounds with saturated and unsaturated side chains. Side-chain lengths were highly variable and ranged from the shorter chains also found in *C. elegans* to compounds with considerably longer side chains in *Pelodera strongyloides* and *Heterorhabditis bacteriophora*. As in *C. elegans*, most of the identified ascarosides bear the ascarylose sugar at the penultimate carbon of the side chain ("ω-1-functionalization"), except for *Caenorhabditis* sp. 7 and *Rhabditis* sp., which produce ascarosides in which the ascarylose is attached to the terminal carbon of the side chain ("ω-functionalization", e.g. oscr#9 and oscr#10 in FIG. 76D). Indole ascarosides, e.g. icas#9 (FIG. 76A), which were recently shown to act as aggregation signals in *C. elegans* (Srinivasan et al., *Pub. Lib. Sci. Biol.* 10(1):e1001237 (2012), which is hereby incorporated by reference in its entirety), were found only in *Caenorhabitis* spp. However, in *C. elegans*, indole ascaroside concentrations were much lower than those of simple ascarosides ("ascr" and "oscr" in FIG. 76A). As the available metabolite sample sizes for most of the species studied herein were much smaller than those available for *Caenorhabditis* spp., it is possible that indole ascarosides could not be detected in some nematodes because the amounts were too small for detection by HPLC-MS.

Ascaroside profiles generally varied between species (FIG. 77). However, species from very different ecologies in some cases produced the same ascarosides. For example, ascr#9 is produced by the compost-dwelling *Panagrellus redivivus, Rhabditis* sp., and *Caenorhabditis* spp.; soil-dwelling *Oschieus tipulae*; insect-associated *Pristionchus pacificus*; and insect-infective *Heterorhabditis bacteriophora, Steinernema carpocapsae, Steinernema riobrave*, and *Steinernema glaseri*.

No known ascarosides were detected in 3 of the 17 analyzed nematode species, namely *Pratylenchus penetrans, Ascaris suum*, and *Romanomermis* species. It is possible that these species produce only very small quantities of ascarosides, or that they produce ascarosides with unexpected structural features that could not be detected with the used method, given that ascarosides similar to those identified from wild-type and mutant strains of *C. elegans* were screened for. Previous studies have reported the presence of lipid-like long-chain ascarosides in *Ascaris sum*; however, they were limited to oocytes and eggs (Bartley et al., *J. Nat. Prod.* 59(10):921-26 (1996); Tarr, *Comp. Biochem. Physiol.* 46B:167-76 (1973), which are hereby incorporated by reference in their entirety). Given their highly lipophilic character, these compounds are poorly soluble in aqueous media, which explains their absence in the above analysis herein, and thus are unlikely to serve as pheromones. Mermithid species, such as *Romanomermis* spp., have the unique ability to store a lifetime supply of lipid-composed sustenance (Platzer, *J. Am. Mosquito Contr. Association* Bulletin 7:58-64 (2007); Ittycheriah et al., *Nematologica* 23:165-71 (1977), which are hereby incorporated by reference in their entirety). It is possible that they have a different mechanism of fatty acid metabolism or perhaps ascaroside synthesis has not yet evolved, given that the *Romanomermis* spp. were the most ancestral species tested.

Example 83

Ascarosides Mediate Distinct Nematode Behaviors

Nematode behavioral responses to a series of synthesized ascarosides were tested using several different behavior assays. A retention assay (FIG. 78) using automated software to detect preference or avoidance of regions conditioned with individual ascarosides (FIG. 79) was used. Nematode species in the HPLC/MS study were screened for compatibility with this bioassay, which requires adequate movement across a bacterial lawn. Parasitic nematodes were largely excluded due to their requirement of substrates similar to their host environment. This investigation was further limited to males, because in most species, males are much more mobile than females or hermaphrodites, with the exception of *P. redivivus* females, which move well and were therefore included. *Oscheius tipulae* was excluded due to the fact that males are only occasionally present in this hermaphroditic species; instead, the closely related male-female species, *Oscheius dolichuroides*, was added. In a previous study, samples of ~1 pmol (from 1 μM concentration) of ascr#2 and ascr#3 proved to be the most active concentration for attraction in *C. elegans* (Srinivasan et al., *Nature* 454:1115-18 (2008), which is hereby incorporated by reference in its entirety). Thus, available synthetic ascarosides were tested at the concentration of 1 nM, 1 µM, and 1 mM.

Several of the tested nematode species preferred areas conditioned by many of the same ascarosides, particularly ascr#1, ascr#3, ascr#7, ascr#8, ascr#9, and ascr#10 (FIG. 78). However, activity thresholds varied between species. For example, *C. elegans* males preferred 1 µM-conditioned regions of ascr#10, whereas *S. glaseri* and *P. redivivus* males only preferred 1 mM-conditioned regions of ascr#10. Furthermore, several nematode species responded to ascarosides that were not produced by their own species, suggesting possible interspecies communication. One of the tested species, *O. dolichuroides*, did not respond to any of the assayed ascarosides. It is possible that this species responds to other ascarosides or that specific environmental conditions are required to elicit its response to ascarosides.

Further, *P. redivivus* males and females were observed to respond to different sets of ascarosides, a phenomenon previously described in *C. elegans* (Srinivasan et al., *Nature* 454:1115-18 (2008), which is hereby incorporated by reference in its entirety). These gender-specific responses demonstrate that ascarosides may serve different roles both between and within species. For example, icas#9 acted as an aggregating stimulant in *C. elegans* (Srinivasan et al., *Pub. Lib. Sci. Biol.* 10(1):e1001237 (2012), which is hereby incorporated by reference in its entirety); however, it repeled *P. redivivus* females and elicited no response from *P. redivivus* males. Because icas#9 was not produced by *P. redivivus*, it could serve as an interspecies cue.

The ability of *C. elegans* hermaphrodites to attract *C. elegans* males from a distance was also tested. Previous studies have reported that *C. elegans* hermaphrodites failed to attract males on a 5 cm plate containing a point source conditioned by a single hermaphrodite or on an agar-mounted slide holding hermaphrodite-incubated supernatant (Bargmann et al., *Cell.* 74:515-27 (1993), which is hereby incorporated by reference in its entirety). In the experiments described herein, both the diameter of the assay arena and the number of hermaphrodites were expanded, using a 10 cm plate and testing 1-300 hermaphrodites (FIG. 80A). The results demonstrate that *C. elegans* hermaphrodites indeed attracted males from a distance (FIG. 80B). The ability of *C. elegans* males to chemotax towards 50 *C. elegans* hermaphrodites was compared to that of equal numbers of females or hermaphrodites from other species. Because it was found that *C. elegans* males were attracted to 7 different ascarosides (FIG. 78), it was predicted that species producing these ascarosides would attract *C. elegans* males, whereas those producing few or none of these ascarosides would fail to attract *C. elegans* males. The results herein show that *C. elegans* males demonstrated partial attraction to *P. redivivus* females (FIGS. 80A-C), whose species produced 3 of the 7 known *C. elegans* male attractants (FIG. 77) (Srinivasan et al., *Nature* 454:1115-18 (2008); Pungaliya et al., *PNAS* 19:7708-13 (2009), which are hereby incorporated by reference in their entirety). It was also found that *C. elegans* males did not show long-range attraction to females or hermaphrodites from the species *S. carpocapsae, P. pacificus*, or *P. strongyloides*, which produced two, one, and none of the known *C. elegans* male attractants, respectively. These findings provide further evidence for the possibility of ascaroside-mediated interactions between different nematode species. The individual roles of three previously described *C. elegans* mate-finding pheromones (ascr#2, ascr#3, and ascr#8) (Srinivasan et al., *Nature* 454:1115-18 (2008); Butcher et al., *Nat. Chem. Biol.* 7:420-22 (2007), which are hereby incorporated by reference in their entirety) were also tested to elicit male attraction from a distance. The results show that ascr#2 and ascr#3 elicited *C. elegans* male attraction, with amounts as low as 500 attomol and 5 femtomol, respectively, whereas ascr#8 was not active in this assay. These results suggest that ascr#2 and ascr#3 serve to attract *C. elegans* males from a distance, whereas ascr#8 serves to hold males within vicinity upon arrival to a point source.

Mating between *C. elegans* males and conspecific hermaphrodites as well as females/hermaphrodites of different nematode species were also investigated. The mating assay described in Peden & Barr, *Curr. Biol.* 15:394-404 (2005), which is hereby incorporated by reference in its entirety, which scores the percentage of males that attempt to copulate with hermaphrodites/females, was adapted (FIG. 81). The investigation was to test whether *C. elegans* would mate with distantly related nematode species. The results show that they did not attempt to copulate with *P. redivivus, S. carpocapsae, P. pacificus*, or *P. stronglyoides* for 10 seconds (FIG. 81). Furthermore, the addition of a blend of ascarosides did not induce mating to any of these nematode species. Previous studies indicated that *C. elegans* male mating behavior was guided primarily by hermaphrodite recognition via mechanosensory or local chemical cues (Liu et al., *Neuron* 14:79-89 (1995), which is hereby incorporated by reference in its entirety). The results herein suggest that ascaroside sex pheromones serve to assist *C. elegans* mate location, but do not affect physical mating.

Discussion of Examples 71-83

The findings of Examples 71-83 indicate that ascarosides comprise a broad nematode lexicon, given their widespread production and recognition by different nematode species. These findings are evocative of bacterial quorum sensing, where acyl homoserine lactones (AHLs) are both produced and sensed by many species of Gram-negative bacteria (Miller et al., *Annu. Rev. Microbiol.* 55:165-99 (2001), which is hereby incorporated by reference in its entirety) (FIG. 82). Different AHLs are structurally very similar but have species-specific variations in the N-acyl chain (Miller et al., *Annu. Rev. Microbiol.* 55:165-99 (2001), which is hereby incorporated by reference in its entirety). Ascarosides are organized in a very similar fashion: they are composed of the same ascarylose sugar ring but have variations in the attached fatty acid side chain (Dickschat, *Nat. Prod. Rep.* 27:343-69 (2010), which is hereby incorporated by reference in its entirety) (FIG. 82). The results herein indicate that nematodes secrete combinations from the same repertoire of ascarosides to present a specific chemical signature to their surrounding environment.

The shared structural organization and broad-reaching nature of both ascarosides and AHLs provide new insight into the syntax of biochemical communication networks. Many bacterial behaviors are mediated by quorum sensing, such as bioluminescence, biofilm formation, virulence factor expression, antibiotic production, and motility (Boyer & Wisnieski-Dye, *FEMS Microbiol. Ecol.* 1:1-19 (2009), which is hereby incorporated by reference in its entirety). Similarly, many *C. elegans* behaviors are mediated by ascarosides, such as mate finding, repulsion, aggregation, olfactory plasticity, and entry into a diapausal life stage (Srinivasan et al., *Nature* 454:1115-18 (2008); Jeong, et al., *Nature* 433:541-45 (2005); Butcher et al., *Nat. Chem. Biol.*

7:420-22 (2007); Pungaliya et al., *PNAS* 19:7708-13 (2009); Niblack et al., *Annu. Rev. Phytopathol.* 44:283-303 (2006); Macosko et al., *Nature* 458:1171-75 (2009); Yamada et al., *Science* 329:1647-50 (2010); Butcher et al., *Nat. Chem. Biol.* 3:420-22 (2007); Golden & Riddle, *Science* 218:578-80 (1982), which are hereby incorporated by reference in their entirety).

Furthermore, the ascaroside profile of *C. elegans* changes in response to growth and environmental perturbation (Kaplan et al., *Pub. Lib. Sci. ONE* 6(3):e17804 (2011), which is hereby incorporated by reference in its entirety). Considering the broad diversity of nematodes and nematode behaviors, the modular nature of ascarosides seems an appropriate strategy for using a single mechanism to convey the changing needs of an individual or population. Molecules that are structurally similar to bacterial AHLs can be synthesized to develop a new class of antimicrobial drugs that interfere with bacterial communication (Schauder et al., *Genes Dev.* 15:1468-80 (2001), which is hereby incorporated by reference in its entirety). Similar studies in nematodes can enable the design of synthetic ascaroside blends to interfere with nematode reproduction and survival in parasite-host models.

Because nematodes are currently responsible for about $100 billion of losses to global agriculture annually (JOSEPH A. VEECH: VISTAS ON NEMATOLOGY (Society of Nematologists, Inc., Hyatsville, Md., 1987), which is hereby incorporated by reference in its entirety) and infect 3 billion humans worldwide (Blumenthal & Davis, *Nat. Genet.* 36:1246-47 (2004), which is hereby incorporated by reference in its entirety), there exists significant need for parasitic control. The concept of using species-specific pheromones for the management of insect pests has driven over 50 years of insect pheromone research with >100 pheromones utilized in pest management (Witzgall et al., *J. Chem. Ecol.* 36:80-100 (2010), which is hereby incorporated by reference in its entirety). However, pheromone-mediated interruption has only been practically applied to a single nematode pheromone, vanillic acid, towards control of the soybean parasitic nematode *Heterodera glycines* (Meyer et al., *J. Nematol.* 29:282-88 (1997), which is hereby incorporated by reference in its entirety). This is most likely attributed to the lack of nematode pheromone identification, aside from those discovered in *H. glycines* and *C. Elegans* (Jaffe et al., *J. Chem. Ecol.* 15:2031-43 (1989); Srinivasan et al., *Nature* 454:1115-18 (2008); Jeong, et al., *Nature* 433:541-45 (2005); Butcher et al., *Nat. Chem. Biol.* 7:420-22 (2007); Pungaliya et al., *PNAS* 19:7708-13 (2009), which are hereby incorporated by reference in their entirety). The discovery of this broad-reaching, modular library of nematode pheromones can undoubtedly prove useful towards this necessary effort, while interpretation of the syntax can provide new insight into the evolution of biochemical signatures.

Example 84

Ascaroside Production in Root Knot Nematodes

Ascarosides ascr#10, ascr#16, ascr#18, ascr#20, and ascr#22 were detected in certain species of *Meloidogyne* plant parasitic nematodes (FIG. 83) and identified using high-resolution mass spectrometry (FIGS. 84-88). It is predicted that these ascarosides and/or structural derivatives thereof (alone, in concert, and/or in concert with ascr#9 or other ascarosides) act as dispersants and repellants in *Meloidogyne* species. (It is also predicted that ascr#18 and ascr#22 and/or structural derivatives thereof (alone, in concert, and/or in concert with ascr#9 or other ascarosides) act as dispersants and repellants in *Heterorhabditis*.)

Example 85

*P. pacificus* Metabolite Naming

All newly identified compounds are named with four letter SMIDs, as described in Example 3. New four-letter SMIDs (pasc (phenylethanolamide ascaroside), ubas (3-ureido isobutyrate ascaroside), dasc (dimeric ascaroside), part (paratoside), and npar (nucleoside-based paratoside)) are introduced here.

Example 86

Analytical Instrumentation

NMR spectra were recorded on a Varian INOVA-600 (600 MHz for $^1$H, 151 MHz for $^{13}$C), INOVA-500 (500 MHz for $^1$H and 125 MHz for $^{13}$C), and INOVA-400 (400 MHz for $^1$H, 100 MHz for $^{13}$C) instruments. HPLC-MS and flash chromatography were performed as described in Example 1. HPLC fractionation was performed using an Agilent 1100 Series HPLC system equipped with an Agilent Eclipse XDB-C18 column (9.4×250 mm, 5 µm particle diameter) coupled to a Teledyne ISCO Foxy 200 fraction collector. High resolution mass spectra were acquired using a Xevo G2 QTOF mass spectrometer.

Example 87

*P. pacificus* Strains and Culture Conditions

*Pristionchus pacificus* strains RS2333 (exo-metabolome preparation), RS5134 (dauer formation assay), and RSB020 (mouth-form dimorphism assay) were used. Plates and liquid cultures of worms were prepared as described in Ogawa et al., *Curr. Biol.* 19:67-71 (2009), which is hereby incorporated by reference in its entirety.

Example 88

Preparation of Exo-Metabolome Extracts and Preliminary Fractionation

3 L of the culture supernatant of *P. pacificus* strain RS2333 was filtered and centrifuged at 10,000 rpm for 10 minutes. The culture supernatant was applied to a C18 column (Chromabond, Macherey Nagel), which was followed by elution with 50% MeOH in H$_2$O. This step removed strongly lipophilic components (e.g. triglycerides, long-chain fatty acids) but did not reduce bioactivity. The eluate was evaporated and resuspended with mixture of chloroform and methanol (2:1). The sample was applied to a SiOH column (Chromabond, Macherey Nagel) equilibrated with chloroform/methanol (2:1). The column was washed with chloroform/methanol (2:1, fraction I), chloroform/methanol (1:5, fraction II), and chloroform/methanol/water (6:10:1, fraction III). Fraction II showed the most activity in subsequent dauer formation assays and was used for preliminary 2D-NMR spectroscopy-based analyses. Several additional 1 L-batches of culture supernatant were processed analogously to obtain larger quantities of the compounds detected in the initial 2D NMR spectroscopic analysis.

For additional high-resolution HPLC-MS analysis of unfractionated material, 100 ml sample of culture supernatant were lyophilized to a fine powder, which was subsequently extracted with 50 ml of a 95:5 mixture of ethanol and water for 16 hours. The extract was concentrated in vacuo, filtered, and used for HPLC-MS without further processing. For bacterial control experiments, 1 L of E. coli OP50 bacteria culture grown overnight was lyophilized and treated as described above.

Example 89

2D NMR Spectroscopic Metabolome Analyses

Non-gradient phase-cycled dqfCOSY spectra were acquired using the parameters: 0.8 s acquisition time, 400-600 complex increments, 8-32 scans per increment. dqfCOSY spectra were zero-filled to 8 k×4 k and a cosine bell-shaped window function was applied in both dimensions before Fourier transformation. Gradient and non-gradient HSQCAD and HMBC spectra were acquired using 0.25 s acquisition time and 256-500 complex increments. NMR spectra were processed using Varian VNMR, MestreLabs' MestReC, and MNova software packages.

Example 90

HPLC Protocol and LC-MS/MS Analysis

HPLC-MS was performed using an Agilent 1100 Series HPLC system equipped with an Agilent Eclipse XDB-C18 column (9.4×250 mm, 5 µm particle diameter) connected to a Quattro II spectrometer (Micromass/Waters) using a 10:1 split. A 0.1% acetic acid-acetonitrile solvent gradient was used at a flow rate of 3.6 mL/min, starting with an acetonitrile content of 5% for 5 minutes which was increased to 100% over a period of 40 minutes. Exo-metabolome fractions were analyzed by HPLC-ESI-MS in negative and positive ion modes using a capillary voltage of 4.0 kV and a cone voltage of −40 V and +20 V respectively. LC-MS/MS screening for precursor ions of m/z=73.0 (negative mode) was performed using argon as the collision gas at 2.1 mtorr and 40 eV. This HPLC protocol was also used for synthetic sample purification as well as enrichment of minor components of the P. pacificus exo-metabolome.

Example 91

General Methods for Chemical Synthesis

Thin-layer chromatography (TLC) was used to monitor progress of reactions unless stated otherwise using J. T. Baker Silica Gel IB2-F. Unless stated otherwise, reagents were purchased from Sigma-Aldrich and used without further purification. N,N-dimethylformamide (DMF) and dichloromethane (DCM) were dried over 4 Å molecular sieves prior to use. Tetrahydrofuran (THF) and 1,4-dioxane were distilled prior to use. Optical rotations were measured on a Perkin Elmer 241 polarimeter. Solvent used for taking optical rotations (methanol) was not further purified prior to use.

Example 92

Dauer Formation Assay

Dauer formation assays were performed as described in Ogawa et al., Curr. Biol. 19:67-71 (2009), which is hereby incorporated by reference in its entirety, using heat- or kanamycin-killed E. coli OP50. Synthetic compounds were dissolved in ethanol (0.5 mM, stock solution) and combined with water to make a 100l solution and subsequently added to 3 mL NGM-agar without peptone (3 µl, 0.3, 0.1 µM final concentrations).

Example 93

Mouth-Form Dimorphism Assay

Mouth-form dimorphism assays were performed using P. pacificus strain RSB020. The synthetic compounds dissolved in ethanol (0.5 mM) were diluted with water to make 100 µl solution and subsequently added to 3 mL NGM-agar (1 µM final concentration). The assay plates were seeded with 50 µl OP50 culture in LB medium and incubated overnight at 20° C. to allow bacterial growth. Each replicate included the progeny of two mothers, which were picked as adult hermaphrodites of a consistent age (carrying 4-6 eggs) and which were all from the same P. pacificus culture plate. Following the placement of mothers on assay plates, plates were kept at 20° C. for six days, such that the entire broods were adults at the time of screening. A random sample of 50 hermaphrodite progeny was screened per plate. All animals were screened by differential interference contrast (DIC) microscopy on a Zeiss Axiskop. The following discrete characters were used to discriminate eurystomatous from stenostomatous individuals, respectively: (1) claw-shaped vs. flint-shaped (i.e. dorsoventrally symmetrical) dorsal tooth; (2) presence vs. absence of a subventral tooth; (3) strongly vs. weakly sclerotized stomatal walls. No intermediate mouth-forms were observed. Experiments were conducted in triplicate for each treatment.

In assays of responses to compounds of several concentrations (1, 0.3, 0.1, 0.03, 0.01 µM final concentrations), experiments were performed as described above, with the following modifications. To allow greater resolution of responses to lower concentrations, 60 randomly screened individuals in each of five replicates per concentration per compound were assayed. All concentration-curve experiments were performed in parallel using mothers picked randomly from the same two source populations. To prepare large numbers of individual mothers for these experiments, source populations were established from virgin hermaphrodites to constrain the presence of males and were conditioned to well-fed and ambient conditions for at least one generation before mothers were picked for the assays.

Example 94

Statistical Analysis

Error bars represent a 95% confidence interval in FIGS. 122A-D. All experiments were conducted in triplicate (or in five replicates for mouth-form concentration-curve assays) for each treatment. Significant differences (*P<0.05 and **P<0.001) between each chemical treatment and the control (EtOH) treatment in FIGS. 122A-B were determined using Fisher's exact test in the program R.

Example 95
Synthesis of Ascaroside pasc#9
To prepare 11, a solution of ascr#9 (Srinivasan et al., *PLoS Biol.* 10:e1001237 (2012), which is hereby incorporated by reference in its entirety) (30 mg, 121 µmol) in a 3:2
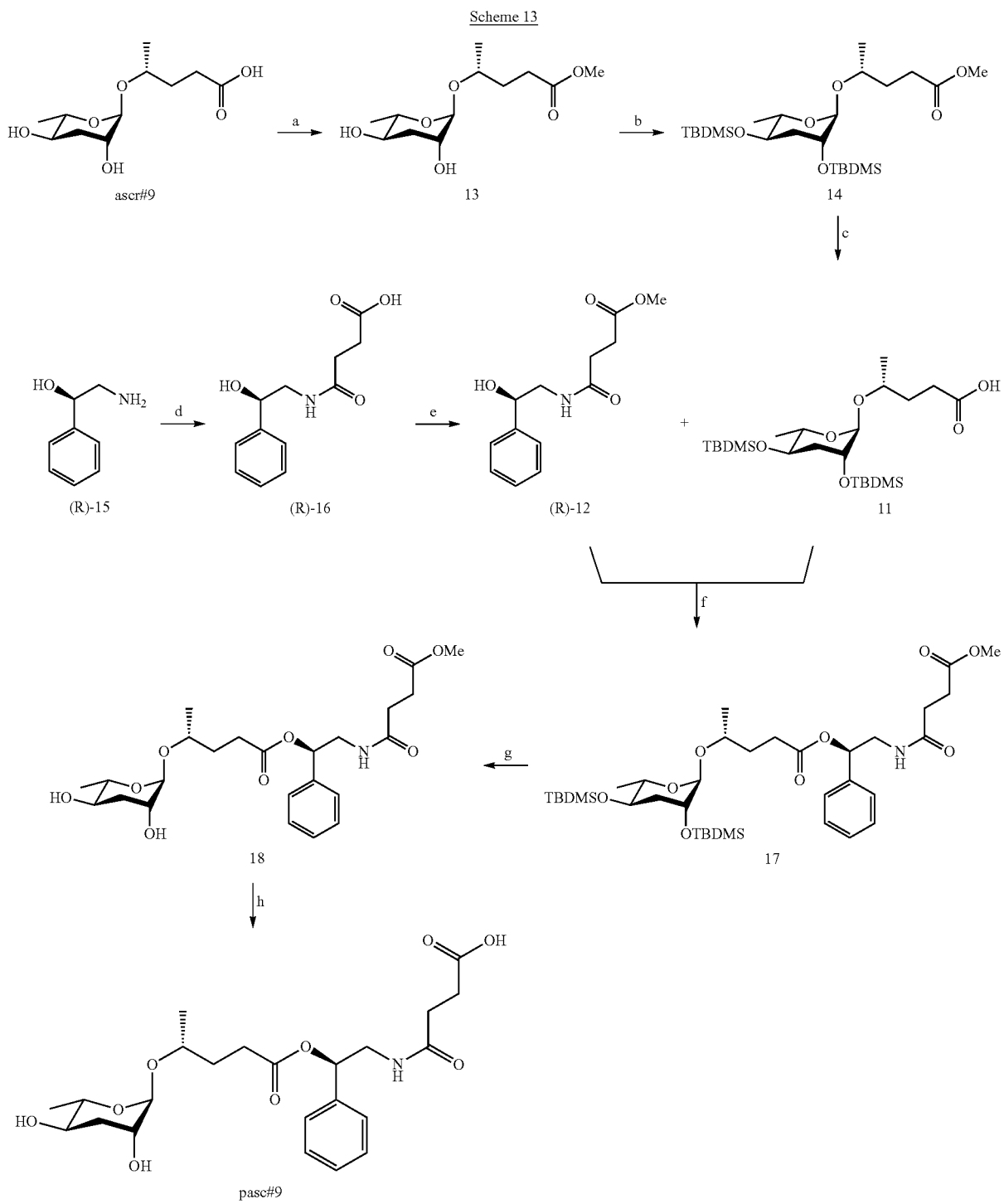
Scheme 13
(a) TMSCHN2, toluene/MeOH
(b) TBDMSCl, imidazole, DMF
(c) LiOH, THF/dioxane/H2O, 67° C.
(d) succinic anhydride, DCM
(e) TMSCHN2, toluene/MeOH
(f) EDC, DMAP, DCM
(g) 40% HF, MeCN
(h) LiOH, THF/dioxane/H2O, 60° C.

mixture (v/v) of methanol and toluene (2 mL) was treated with 2.0 M (trimethylsilyl)diazomethane solution (120 µl) in diethyl ether. After stirring for 30 minutes, excess reagent was destroyed by addition of acetic acid and the solution was concentrated in vacuo. The crude residue was used in the next step without further purification. The residue 13 was dissolved in dry DMF (1.5 mL), cooled to 0° C., and treated with imidazole (91 mg, 1.34 mmol) and stirred for 5 minutes. This mixture was treated with tert-butylchlorodimethylsilane (182 mg, 1.21 mmol) and left to stir overnight. The reaction was quenched with brine (5 mL), extracted with diethyl ether, dried over $Na_2SO_4$, and concentrated in vacuo. Flash column chromatography on silica using a gradient of 0-25% ethyl acetate in hexanes afforded 14 (55 mg, 112 µmol, 93% over two steps) as a colorless oil. A solution of 14 (55 mg, 112 µmol) in dry tetrahydrofuran (1 mL) was added to a mixture of LiOH (11 mg, 457 µmol) and water (0.4 mL) in 1,4-dioxane (2 mL). After stirring at 67° C. for 3 hours the solution was acidified with glacial acetic acid and concentrated in vacuo. Flash column chromatography on silica using a gradient of 0-30% ethyl acetate with 0.1% acetic acid in hexanes afforded (R)-4-(((2R,3R,5R,6S)-3,5-bis((tert-butyldimethylsilyl)oxy)-6-methyltetrahydro-2H-pyran-2-yl)oxy)pentanoic acid (11) (50 mg, 105 µmol, 94%) as a colorless oil. $^1H$ NMR (600 MHz, chloroform-d): δ (ppm) 4.55 (s, 1H), 3.87-3.80 (m, 1H), 3.78-3.75 (m, 1H), 3.68-3.61 (m, 1H), 3.58-3.52 (m, 1H), 2.56-2.42 (m, 2H), 1.89-1.71 (m, 4H), 1.18 (d, J=6.3 Hz, 3H), 1.13 (d, J=6.2 Hz, 3H), 0.91-0.87 (m, 18H), 0.07-0.03 (m, 12H). See FIG. 89.

To prepare (R)-12, a solution of (R)(−)-2-amino-1-phenylethanol ((R)-15) (281 mg, 2.05 mmol) and succinic anhydride (220 mg, 2.2 mmol) in dry dichloromethane (7 mL) was stirred overnight. The reaction was then concentrated in vacuo. Flash column chromatography on silica using a gradient of 0-30% methanol in dichloromethane containing 0.25% acetic acid afforded (R)-16 (470 mg, 1.98 µmol, 97%) as a white powder. A solution of (R)-16 (288 mg, 1.22 mmol) in a 3:2 mixture (v/v) of methanol and toluene (10 mL) was treated with 2.0 M (trimethylsilyl) diazomethane solution (900 µl) in diethyl ether. After stirring for 30 minutes, excess reagent was destroyed by addition of acetic acid and the solution was concentrated in vacuo. Crude (R)-methyl 4-((2-hydroxy-2-phenylethyl) amino)-4-oxobutanoate ((R)-12) was obtained and used in the next step without further purification. (300 mg, 1.20 mmol, 98%). $^1H$ NMR (400 MHz, acetone-$d_6$): δ (ppm) 7.41-7.20 (m, 5H), 4.76 (dd, J=7.7 Hz, J=3.8 Hz, 1H), 3.62 (s, 3H), 3.50 (ddd, J=13.6 Hz, J=6.4 Hz, J=4.0 Hz, 1H), 3.26 (ddd, J=13.6 Hz, J=8.0 Hz, J=5.2 Hz, 1H), 2.60-2.54 (m, 2H), 2.52-2.46 (m, 2H). $^{13}C$ NMR (100 MHz, acetone-$d_6$): δ (ppm) 173.7, 172.7, 144.3, 128.9, 127.9, 126.8, 73.6, 51.7, 48.5, 31.0, 29.7. See FIGS. 90A-B.

To prepare 18, a solution of 11 (17 mg, 36 µmol) in 3 mL dry dichloromethane was treated with 4-dimethylaminopyridine (1 mg, 8.2 µmol) and EDC hydrochloride (11 mg, 57 µmol). After stirring for 30 minutes, (R)-12 (18 mg, 71 µmol) in 1 mL dry dichloromethane was added to the mixture. After stirring for 2 hours, the reaction was concentrated in vacuo. Flash column chromatography on silica using a gradient of 10-70% ethyl acetate in hexanes afforded 17 (17 mg, 24 µmol, 67%) as a colorless oil. A solution of 17 (17 mg, 24 µmol) in acetonitrile (750 µL) was cooled to 0° C. and was treated with 1 drop of 40% HF while stirring. The reaction was allowed to warm to room temperature and stirred for 1.5 hours. The reaction was re-cooled to 0° C. and quenched with saturated aqueous $NaHCO_3$ solution (4 drops) and immediately acidified with glacial acetic acid. The reaction was concentrated in vacuo and flash column chromatography on silica using a gradient of 0-30% methanol in dichloromethane afforded (R)—(R)-2-(4-methoxy-4-oxobutanamido)-1-phenylethyl 4-(((2R,3R,5R,6S)-3,5-dihydroxy-6-methyltetrahydro-2H-pyran-2-yl)oxy)pentanoate (18) (6.6 mg, 13.7 µmol, 57%) as a colorless oil. $^1H$ NMR (500 MHz, methanol-$d_4$): δ (ppm) 7.41-7.27 (m, 5H), 5.84 (dd, J=8.4 Hz, J=4.4 Hz, 1H), 4.64 (s, 1H), 3.84-3.76 (m, 1H), 3.73-3.68 (m, 1H), 3.66 (s, 3H), 3.61-3.45 (m, 4H), 2.6-2.44 (m, 6H), 1.98-1.91 (m, 1H), 1.88-1.71 (m, 3H), 1.20 (d, J=6.1 Hz, 3H), 1.14 (d, J=6.1 Hz, 3H). $^{13}C$ NMR (125 MHz, methanol-$d_4$): δ (ppm) 174.7, 174.6, 174.3, 139.7, 129.6, 129.3, 127.5, 97.4, 75.7, 71.6, 71.4, 69.9, 68.3, 52.2, 45.4, 36.0, 33.3, 31.6, 31.3, 30.1, 19.1, 18.1. See FIGS. 91A-B.

To prepare pasc#9, a solution of 18 (6.6 mg, 14 µmol) in dry tetrahydrofuran (200 µl) was treated with a mixture of LiOH (0.3 mg, 12 µmol) and water (80 µl) in 1,4-dioxane (400 µl). After stirring at 60° C. for 5 minutes, the solution was acidified with glacial acetic acid and concentrated in vacuo. HPLC purification (see Methods) of the crude reaction mixture afforded 4-(((R)-2-(((R)-4-(((2R,3R,5R,6S)-3,5-dihydroxy-6-methyltetrahydro-2H-pyran-2-yl)oxy)pentanoyl)oxy)-2-phenylethyl)amino)-4-oxobutanoic acid (pasc#9) (1.8 mg, 4 µmol, 29%) as a colorless oil.

$$\alpha_D^{20} = -110.0$$

(c. 0.18, methanol).

$^1H$ (600 MHz), $^{13}C$ (151 MHz), and HMBC NMR spectroscopic data for pasc#9 were obtained using methanol-$d_4$ and are shown in Table 12 below. Chemical shifts were referenced to (C$\underline{D_2H}$OD)=3.31 ppm and ($\underline{C}D_3$OD)=49.00 ppm. See FIGS. 92A-D.

TABLE 12

NMR spectroscopic data for pasc#9

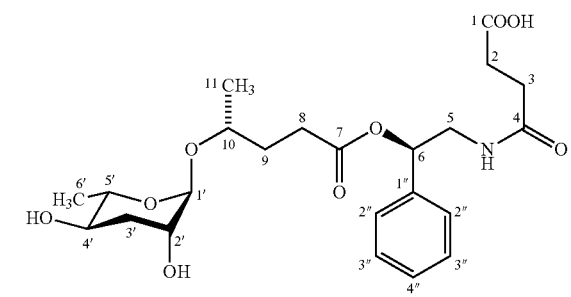

pasc#9

| Position | δ $^{13}C$ [ppm] | δ $^1H$ [ppm] | $^1H$—$^1H$-coupling constants (Hz) | Key HMBC correlations |
|---|---|---|---|---|
| 1 | 175.8 | — | | |
| 2 | 31.3 | 2.44 | $J_{2,3}$ = 7.2 | C-1 |
| 3 | 30.1 | 2.56 | | C-4 |
| 4 | 174.4 | — | | |
| 5 | 45.1 | 5a = 3.51 | $J_{5a, 5b}$ = 13.7, $J_{5a, 6}$ = 8.5 | C-4 |
| | | 5b = 3.58 | $J_{5b, 6}$ = 4.4 | |
| 6 | 75.4 | 5.84 | | C-7, C-1" |
| 7 | 173.8 | — | | |
| 8 | 31.3 | 2.54 | | C-7 |
| 9 | 33.0 | 1.81 | | |

TABLE 12-continued

NMR spectroscopic data for pasc#9

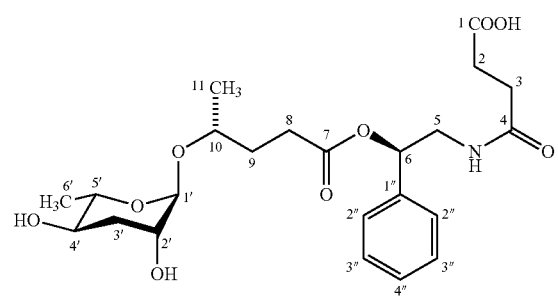

pasc#9

| Position | δ $^{13}$C [ppm] | δ $^1$H [ppm] | $^1$H—$^1$H-coupling constants (Hz) | Key HMBC correlations |
|---|---|---|---|---|
| 10 | 71.3 | 3.80 | $J_{10, 11}$ = 6.6 | C-1' |
| 11 | 18.8 | 1.14 | | |
| 1' | 97.0 | 4.64 | $J_{1', 2'}$ = 2.3 | C-2', C-3', C-5' |
| 2' | 69.4 | 3.72 | $J_{2', 3'(ax)}$ = 6.6, $J_{2', 3'(eq)}$ = 6.6 | |
| 3' | 35.6 | 1.70 (ax) | $J_{3'(ax), 3'(eq)}$ = 13.0, $J_{3'(ax), 4'}$ = 11.8 | |
| | | 1.95 (eq) | $J_{3'(eq), 4'}$ = 4.9 | |
| 4' | 67.8 | 3.51 | $J_{4', 5'}$ = 11.8 | |
| 5' | 71.0 | 3.58 | $J_{5', 6'(eq)}$ = 6.4 | |
| 6' | 17.8 | 1.20 | | |
| 1" | 139.4 | — | | |
| 2" | 127.3 | 7.29-7.37 | | C-1", C-6 |
| 3" | 129.1 | 7.29-7.37 | | |
| 4" | 128.9 | 7.29-7.37 | | |

Example 96

Synthesis of 4-(((S)-2-(((R)-4-(((2R,3R,5R,6S)-3,5-Dihydroxy-6-Methyltetrahydro-2H-Pyran-2-yl)oxy)pentanoyl)oxy)-2-Phenylethyl)amino)-4-Oxobutanoic Acid 4-(((S)-2-(((R)-4-(((2R,3R,5R,6S)-3,5-dihydroxy-6-methyltetrahydro-2H-pyran-2-yl)oxy)pentanoyl)oxy)-2-phenylethyl)amino)-4-oxobutanoic acid (19), a non-natural isomer of pasc#9, was prepared following analogous reaction steps to those described in Example 95 but starting from (S)(+)-2-amino-1-phenylethanol (S)-15, as shown in Scheme 14 below. $^1$H NMR (600 MHz, methanol-d$_4$): δ (ppm) 7.40-7.34 (m, 4H), 7.32-7.28 (m, 1H), 5.86 (dd, J=8.5 Hz, J=4.3 Hz, 1H), 4.63 (s, 1H), 3.84-3.78 (m, 1H), 3.67-3.64 (m, 1H), 3.60-3.53 (m, 2H), 3.52-3.47 (m, 2H), 2.62-2.43 (m, 6H), 1.95-1.89 (m, 1H), 1.88-1.77 (m, 2H), 1.77-1.71 (m, 1H), 1.16 (d, J=6.2 Hz, 3H), 1.14 (d, J=6.1 Hz, 3H). $^{13}$C NMR (151 MHz, methanol-d$_4$): δ (ppm) 176.1, 174.6, 174.1, 139.4, 129.4, 129.0, 127.3, 97.0, 75.4, 71.3, 71.1, 69.6, 68.0, 45.3, 35.6, 33.0, 31.29, 31.25, 30.2, 18.8, 17.9. See FIGS. 93A-C.

Scheme 14

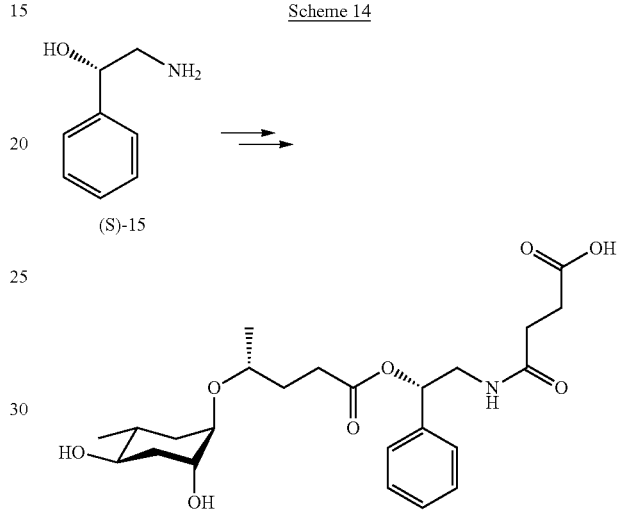

Example 97

Synthesis of Ascaroside part#9

Ascaroside part#9 was prepared as shown in Scheme 15.

Scheme 15

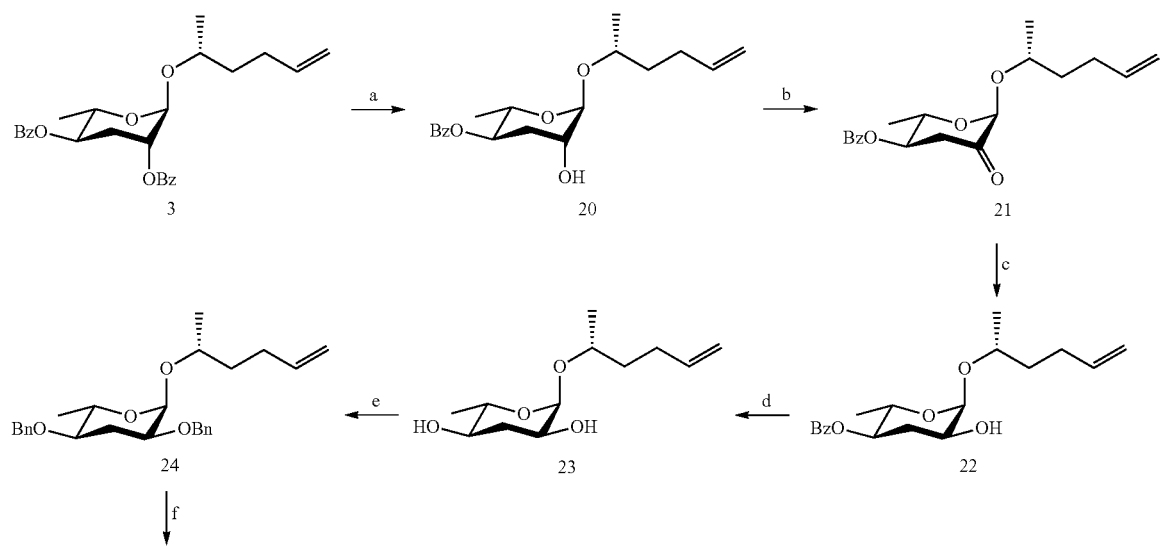

-continued

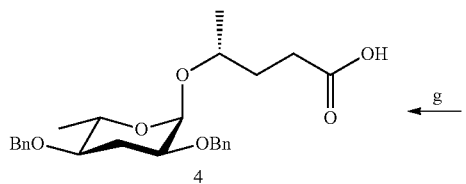
4

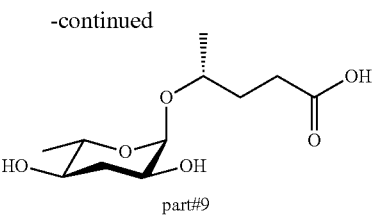
part#9

Reagents and conditions:
(a) LiOH, THF/dioxane/H2O, 67° C.;
(b) Dess-Martin periodinane, DCM;
(c) NaBH4, DCM/MeOH;
(d) LiOH, THF/dioxane/H2O, 67° C.;
(e) BnBr, NaH, DMF;
(f) RuCl3•H2O, NaIO4, DCM/MeCN/H2O;
(g) 10% Pd/C, H2 (g), 10% formic acid in MeOH To prepare 22, a solution of 3 (Srinivasan et al., *PLoS Biol.* 10:e1001237 (2012), which is hereby incorporated by reference in its entirety) (181.5, 413 μmol) in dry tetrahydrofuran (0.5 mL) was added to a mixture of LiOH (8.9 mg, 371 μmol) and water (0.2 mL) in 1,4-dioxane (1 mL). After stirring at 67° C. for 40 minutes the solution was acidified with few drops of glacial acetic acid and concentrated in vacuo. Flash column chromatography on silica using a gradient of 10-40% ethyl acetate in hexanes afforded 20 (48.5 mg, 145 μmol, 35%) as a colorless oil. A solution of 20 (48.5 mg, 145 μmol) in dry dichloromethane (2 mL) was treated with Dess-Martin periodinane (88 mg, 208 μmol). After 5 hours the solution was diluted with 10 mL dichloromethane and washed three times with a solution of 5% Na2S2O3 in H2O. The organic layer was dried over Na2SO4 and concentrated in vacuo. Flash column chromatography on silica using a gradient of 0-30% ethyl acetate in hexanes afforded 21 (26.8 mg, 81 μmol, 56%) as a colorless oil. A solution of 21 (24.5 mg, 74 μmol) in 1:1 dichloromethane:methanol (0.7 mL) was treated with NaBH4 (12 mg, 317 μmol). After 10 minutes the solution was acidified with glacial acetic acid and diluted with dichloromethane and concentrated in vacuo. Flash column chromatography on silica using a gradient of 0-40% ethyl acetate in hexanes afforded (2S,3R,5S,6R)-6-((R)-hex-5-en-2-yloxy)-5-hydroxy-2-methyltetrahydro-2H-pyran-3-yl benzoate (22) (18.2 mg, 54 μmol, 74%) as a colorless oil. $^1$H NMR (600 MHz, acetone-d6): δ (ppm) 8.04-8.01 (m, 2H), 7.67-7.63 (m, 1H), 7.55-7.50 (m, 2H), 5.89 (ddt, J=17.1 Hz, J=10.3 Hz, J=6.6 Hz, 1H), 5.09-5.04 (m, 1H), 4.99-4.95 (m, 1H), 4.84 (d, J=3.7, 1H), 4.69 (ddd, J=11.4 Hz, J=9.8 Hz, J=4.6 Hz, 1H), 4.04-3.98 (m, 1H), 3.89-3.82 (m, 1H), 3.78-3.71 (m, 1H), 2.29-2.16 (m, 3H), 1.93-1.86 (m, 1H), 1.79-1.72 (m, 1H), 1.65-1.58 (m, 1H), 1.19 (d, J=6.1 Hz, 3H), 1.16 (d, J=6.3 Hz, 3H). $^{13}$C NMR (151 MHz, acetone-d6): δ (ppm) 165.9, 139.6, 134.1, 131.1, 130.2, 129.5, 114.9, 96.4, 73.7, 72.9, 67.8, 66.8, 37.3, 34.3, 30.7, 19.5, 17.9. See FIGS. 94A-B.

To prepare 24, a solution of 22 (18.2 mg, 54 μmol) in dry tetrahydrofuran (0.5 mL) was added to a mixture of LiOH (13.5 mg, 563 μmol) and water (0.2 mL) in 1,4-dioxane (1 mL). After stirring at 67° C. for 3 hours the solution was acidified with glacial acetic acid and concentrated in vacuo. Flash column chromatography on silica using a gradient of 0-30% methanol in dichloromethane afforded 23 (8.5 mg, 37 μmol, 67%) as a colorless oil. A solution of 23 (8.5 mg, 37 μmol) in DMF (700 μl), cooled to 0° C., was treated with sodium hydride (10 mg, 60% suspension in mineral oil, 250 μmol). After stirring for 20 minutes, benzylbromide (15 μl) was added and the mixture stirred overnight. Excess reagent was destroyed by addition of methanol (300 μl), the residue diluted with ethyl acetate (2 mL), and the organic phase washed with water (3×0.5 mL), dried over Na2SO4, and concentrated in vacuo. Flash column chromatography on silica using a gradient of 0-25% ethyl acetate in hexanes afforded (2R,3S,5R,6S)-3,5-bis(benzyloxy)-2-((R)-hex-5-en-2-yloxy)-6-methyltetrahydro-2H-pyran (24) (13 mg, 32 μmol, 80%) as a colorless oil. $^1$H NMR (400 MHz, chloroform-d): δ (ppm) 7.38-7.25 (m, 10H), 5.82 (ddt, J=17.1 Hz, J=10.4 Hz, J=6.5 Hz, 1H), 5.06-4.99 (m, 1H), 4.98-4.93 (m, 1H), 4.89 (d, J=3.4 Hz, 1H), 4.65 (d, J=11.6 Hz, 1H), 4.59 (s, 2H), 4.46 (d, J=11.6 Hz, 1H), 3.86-3.74 (m, 2H), 3.51-3.43 (m, 1H), 3.07 (ddd, J=11.1 Hz, J=9.4 Hz, J=4.3 Hz, 1H), 2.33-2.06 (m, 3H), 1.93-1.82 (m, 1H), 1.83-1.73 (m, 1H), 1.63-1.52 (m, 1H), 1.22 (d, J=6.2 Hz, 3H), 1.19 (d, J=6.1 Hz, 3H). 34H total. $^{13}$C NMR (100 MHz, chloroform-d): δ (ppm) 138.6, 138.41, 138.38, 128.55 (2C), 127.92, 127.89, 127.85 (2C), 114.7, 93.2, 78.2, 74.1, 71.6, 70.90, 70.86, 67.6, 52.4, 36.5, 30.3, 19.7, 17.9. See FIGS. 95A-B.

To prepare part#9, a solution of 24 (5.4 mg, 13 μmol) in a 1:1:1 mixture (v/v/v) of dichloromethane:acetonitrile:H2O (300 μL) was first treated with NaIO4 (13 mg, 61 μmol) and then with a solution of RuCl3.H2O (145 μg, 0.7 μmol) in H2O (50 μL). After 1.75 hours, the mixture was diluted with H2O (1 mL), extracted with dichloromethane (3×1 mL), dried over Na2SO4, and concentrated in vacuo. Flash column chromatography on silica using a gradient of 0-20% methanol in dichloromethane containing 0.25% glacial acetic acid afforded 4 (4.6 mg, 11 μmol, 81%) as a colorless oil. A solution of Pd/C (11 mg, 10%, w/w) in 500 μL of methanol containing 10% formic acid was first flushed with argon for 5 minutes and subsequently with a moderate flow of H2 gas. To this stirring solution was added a solution 4 (4.1 mg, 9.3 μmol) in 500 μL methanol. After 4.5 hours, the reaction was filtered over a pad of silica and concentrated in vacuo. HPLC purification (see Example 90) afforded (R)-4-(((2R,3S,5R, 6S)-3,5-dihydroxy-6-methyltetrahydro-2H-pyran-2-yl)oxy) pentanoic acid (part#9) (1.5 mg, 6.0 μmol, 65%) as a colorless oil.

$$\alpha_D^{22} = -128.6$$

(c. 0.15, methanol).

$^1$H (600 MHz), $^{13}$C (151 MHz), and HMBC NMR spectroscopic data for part#9 were obtained using methanol-d4 and are shown in Table 13 below. Chemical shifts were referenced to (CD2HOD)=3.31 ppm and (CD3OD)=49.00 ppm. See FIGS. 96A-D.

TABLE 13

NMR spectroscopic data for part#9

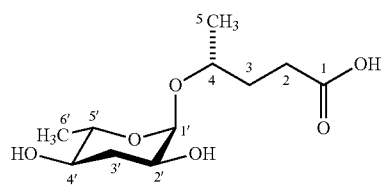

part#9

| Position | δ $^{13}$C [ppm] | δ $^1$H [ppm] | $^1$H—$^1$H-coupling constants (Hz) | Key HMBC correlations |
|---|---|---|---|---|
| 1 | 178.3 | — | | |
| 2 | 31.8 | 2.43 | $J_{2,3}$ = 7.1 | C-1, C-3 |
| 3 | 33.5 | 1.85 | | |
| 4 | 72.4 | 3.83 | $J_{4,5}$ = 6.3 | C-1' |
| 5 | 19.0 | 1.179 | | |
| 1' | 95.9 | 4.74 | $J_{1',2'}$ = 3.9 | C-2', C-3', C-5' |
| 2' | 68.4 | 3.60 | $J_{2',3'(ax)}$ = 12.1; $J_{2',3'(eq)}$ = 5.5 | |
| 3' | 36.8 | 1.74 (ax) | $J_{3'(eq),3'(ax)}$ = 12.3; $J_{3'(eq),4'}$ = 4.7 | |
|  |  | 2.02 (eq) | $J_{3'(ax),4'}$ = 10.9 | |
| 4' | 71.6 | 3.15 | $J_{4',5'}$ = 9.4 | |
| 5' | 69.9 | 3.58 | $J_{5',6'(eq)}$ = 6.1 | |
| 6' | 17.5 | 1.18 | | C-4, C-5 |

Example 98

Synthesis of D-Paratosyl-4R-Hydroxypentanoic Acid ((R)-30)

(R)-30, a non-natural diastereomer of part#9, was prepared as shown in Scheme 16 below.

Scheme 16

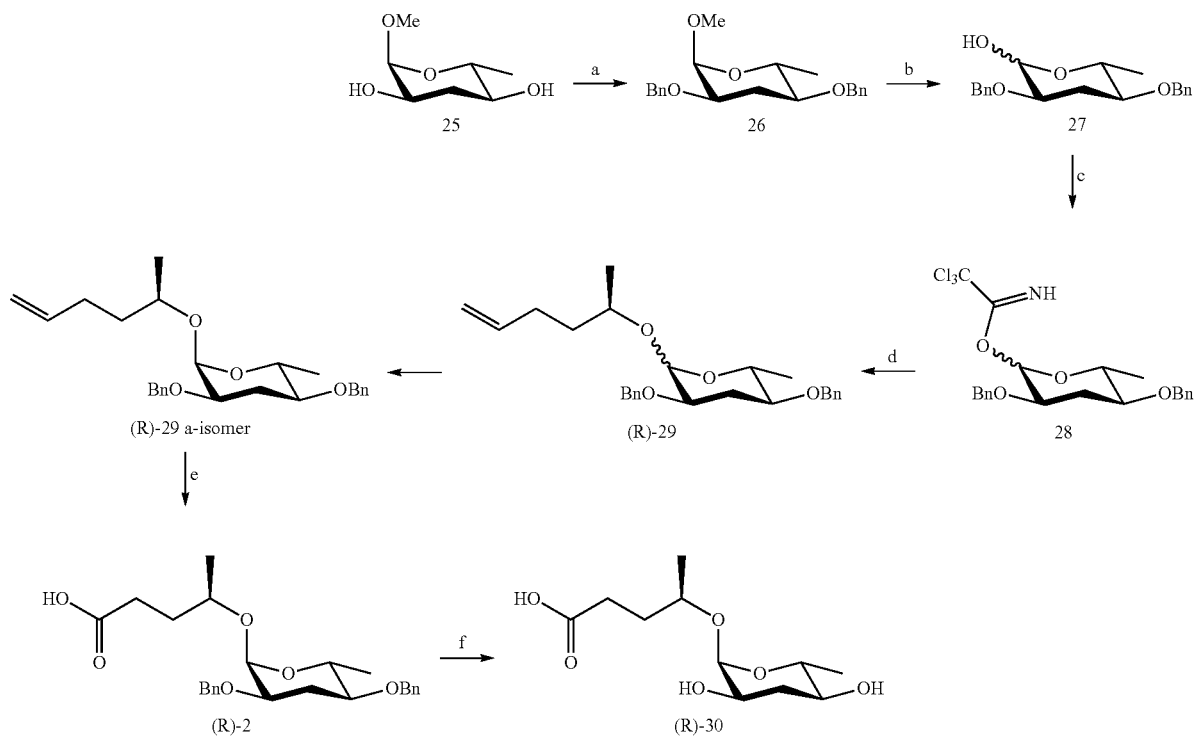

(a) BnBr, NaH, DMF
(b) H2SO4, AcOH
(c) CCl3CN, DBU, DCM
(d) (R)-5-hexen-2-ol, TMSOTf, DCM, 0° C.
(e) RuCl3•H2O, NaIO4, DCM/MeCN/H2O
(f) 10% Pd/C, H2 (g), 10% formic acid in MeOH To prepare 26, a solution of 25 (Zhao & Liu, *J. Org. Chem.* 66:6810-15 (2001), which is hereby incorporated by reference in its entirety) (137 mg, 845 μmol) in DMF (2 mL) was cooled to 0° C., and treated with sodium hydride (203 mg, 60% suspension in mineral oil, 5.1 mmol). After 30 minutes benzyl bromide (630 μL) was added and the mixture stirred overnight. After cooling the reaction mixture to 0° C., excess reagent was destroyed by addition of methanol (3 mL), the residue diluted with diethyl ether (5 mL), and the organic phase washed with water (3×2 mL), dried over $Na_2SO_4$, and concentrated in vacuo. Flash column chromatography on silica using a gradient of 0-25% ethyl acetate in hexanes afforded (2S,3R,5S,6R)-3,5-bis(benzyloxy)-2-methoxy-6-methyltetrahydro-2H-pyran (26) (217 mg, 634 μmol, 75%) as a colorless oil. $^1$H NMR (400 MHz, chloroform-d): δ (ppm) 7.41-7.27 (m, 10H), 4.68-4.56 (m, 4H), 4.46 (d, J=11.6 Hz, 1H), 3.75-3.66 (m, 1H), 3.53-3.45 (m, 1H), 3.43 (s, 3H), 3.12-3.03 (m, 1H), 2.36-2.29 (m, 1H), 1.92-1.81 (m, 1H), 1.26 (d, J=6.4 Hz, 3H). $^{13}$C NMR (100 MHz, chloroform-d): δ (ppm) 138.3, 138.2, 128.49, 128.46, 127.90, 127.86, 127.78, 127.75, 97.1, 77.9, 74.1, 71.1, 70.7, 67.0, 54.8, 30.0, 17.8. See FIGS. 97A-B.

To prepare (R)-29, a solution of 26 (217 mg, 634 μmol) in a mixture of 3 M $H_2SO_4$ (0.5 mL) and acetic acid (2 mL) was heated at 100° C. for 2 hours. After cooling, the reaction mixture was dried in vacuo and to it was added saturated aq. $NaHCO_3$ (5 mL), stirred for 10 minutes, and extracted with dichloromethane (3×2 mL). Flash column chromatography on silica using a gradient of 0-30% ethyl acetate in hexanes afforded 27 (177 mg, 539 μmol, 85%) as a colorless oil. A solution of 27 (177 mg, 539 μmol) in dry dichloromethane (4 mL) was treated with trichloroacetonitrile (115 μL, 1.15 mmol) and 1,8-diazabicyclo[5.4.0]undec-7-ene (9 μL, 60.3 μmol). After 30 minutes, the reaction was concentrated in vacuo. Flash column chromatography on silica using a gradient of 10-20% ethyl acetate in hexanes afforded 28 (110 mg, 233 μmol, 43%) as a colorless oil. A solution of 28 (110 mg, 233 μmol) in dry dichloromethane (2 mL) was cooled to 0° C. and treated with (R)-2-hexenol (60 μL, 500 μmol) and trimethylsilyl trifluoromethanesulfonate (5 μL, 28 μmol). After stirring at 0° C. for 3 hours, the reaction was quenched with saturated aqueous $NaHCO_3$, dried over $Na_2SO_4$, and concentrated in vacuo. Flash column chromatography on silica using a gradient of 0-20% ethyl acetate in hexanes afforded (3R,5S,6R)-3,5-bis(benzyloxy)-2-((R)-hex-5-en-2-yloxy)-6-methyltetrahydro-2H-pyran ((R)-29) α-anomer (40.5 mg, 99 μmol, 43%) and β-anomer (35 mg, 85 μmol, 37%) as colorless oils. For (R)-29 α-anomer, $^1$H NMR (500 MHz, chloroform-d): δ (ppm) 7.38-7.26 (m, 10H), 5.82 (ddt, J=17.0 Hz, 10.3 Hz, 6.6 Hz, 1H), 5.04-4.98 (m, 1H), 4.97-4.93 (m, 1H), 4.87 (d, J=3.4 Hz, 1H), 4.65 (d, J=11.5 Hz, 1H), 4.59 (s, 2H), 4.46 (d, J=11.5 Hz, 1H), 3.86-3.78 (m, 1H), 3.78-3.72 (m, 1H), 3.49-3.43 (m, 1H), 3.80 (ddd, J=11.1 Hz, 9.4 Hz, 4.4 Hz, 1H), 2.34-2.28 (m, 1H), 2.25-2.11 (m, 2H), 1.94-1.85 (m, 1H), 1.75-1.66 (m, 1H), 1.58-1.49 (m, 1H), 1.25 (d, J=6.3 Hz, 3H), 1.22 (d, J=6.3 Hz, 3H). $^{13}$C NMR (125 MHz, chloroform-d): δ (ppm) 138.7, 138.39, 138.37, 128.54, 128.52, 127.91, 127.86, 127.84, 127.80, 114.6, 95.7, 78.2, 74.5, 74.4, 71.0, 70.9, 67.4, 35.9, 30.2, 29.7, 21.5, 17.9. See FIGS. 98A-B.

To prepare (R)-30, a solution of (R)-29α-anomer (20.3 mg, 49 μmol) in a 1:1:1 mixture (v/v/v) of dichloromethane:acetonitrile:$H_2O$ (360 μL) was first treated with $NaIO_4$ (43 mg, 203 μmol) and then with a solution of $RuCl_3 \cdot H_2O$ (547 μg, 2.6 μmol) in $H_2O$ (80 μL). After 2.75 hours, the mixture was diluted with $H_2O$ (1.2 mL), extracted with dichloromethane (3×1 mL), dried over $Na_2SO_4$, and concentrated in vacuo. Flash column chromatography on silica using a gradient of 0-20% methanol in dichloromethane containing 0.25% glacial acetic acid afforded (R)-2 (16 mg, 37 μmol, 76%) as a colorless oil. A solution of Pd/C (20 mg, 10%, w/w) in 500 μL of methanol containing 10% formic acid was first flushed with argon for 5 minutes and subsequently with a moderate flow of $H_2$ gas. To this stirring solution was added a solution (R)-2 (7.0 mg, 16.3 μmol) in 500 μL methanol. After 1 hour, the reaction was filtered over a pad of silica and concentrated in vacuo, affording (R)-4-(((2S,3R,5S,6R)-3,5-dihydroxy-6-methyltetrahydro-2H-pyran-2-yl)oxy)pentanoic acid ((R)-30) (4.0 mg, 16.1 μmol, 98%) as a colorless oil. $^1$H NMR (500 MHz, methanol-$d_4$): δ (ppm) 4.70 (d, J=3.6 Hz, 1H), 3.81-3.72 (m, 1H), 3.63-3.54 (m, 2H), 3.16 (ddd, J=11.4 Hz, 9.4 Hz, 4.6 Hz, 1H), 2.45 (t, J=7.6 Hz, 2H), 2.04-1.97 (m, 1H), 1.85-1.77 (m, 2H), 1.77-1.69 (m, 1H), 1.26 (d, J=6.2 Hz, 3H), 1.17 (d, J=6.3 Hz, 3H). $^{13}$C NMR (125 MHz, methanol-$d_4$): δ (ppm) 178.0, 99.6, 76.1, 71.9, 69.9, 69.0, 37.0, 33.1, 31.0, 21.8, 17.7. See FIGS. 99A-B.

Example 99

Synthesis of (S)-4-(((2S,3R,5S,6R)-3,5-Dihydroxy-6-Methyltetrahydro-2H-Pyran-2-yl)oxy)pentanoic Acid ((S)-30)

(S)-30, an enantiomer of part#9, was prepared following analogous reaction steps to those described in Example 98 but using (S)-2-hexenol, as shown in Scheme 17 below. The NMR spectroscopic characterization of (S)-30 was identical to that of part#9.

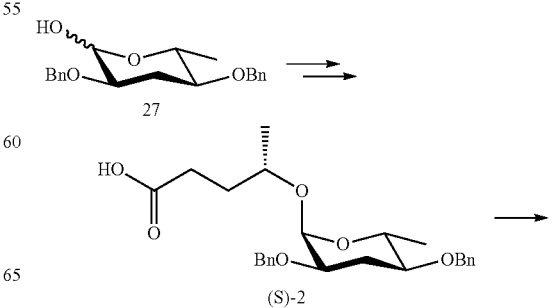

Scheme 17

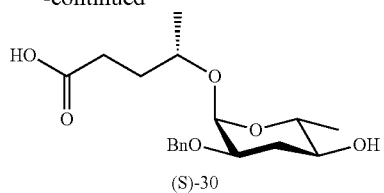
(S)-30
Example 100
Synthesis of Ascaroside npar#1
Ascaroside npar#1 was prepared as shown in Scheme 18 below.
Scheme 18
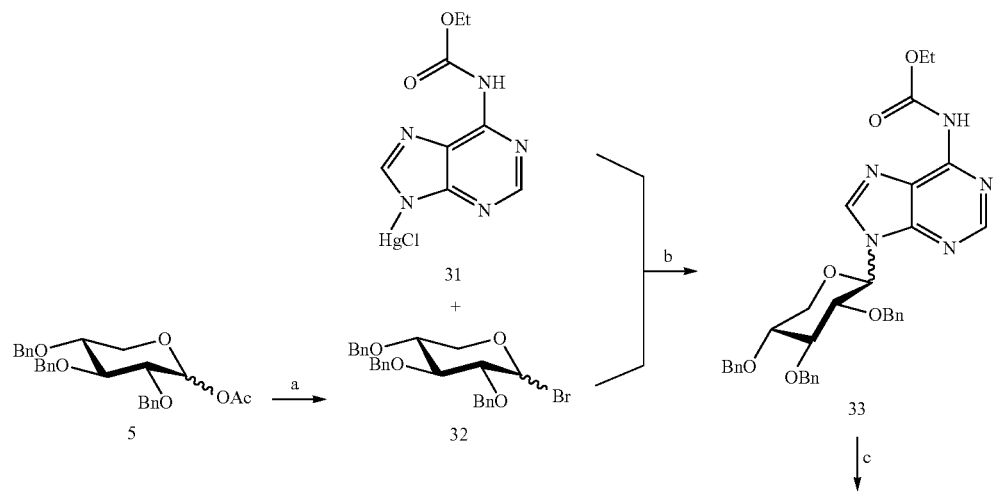
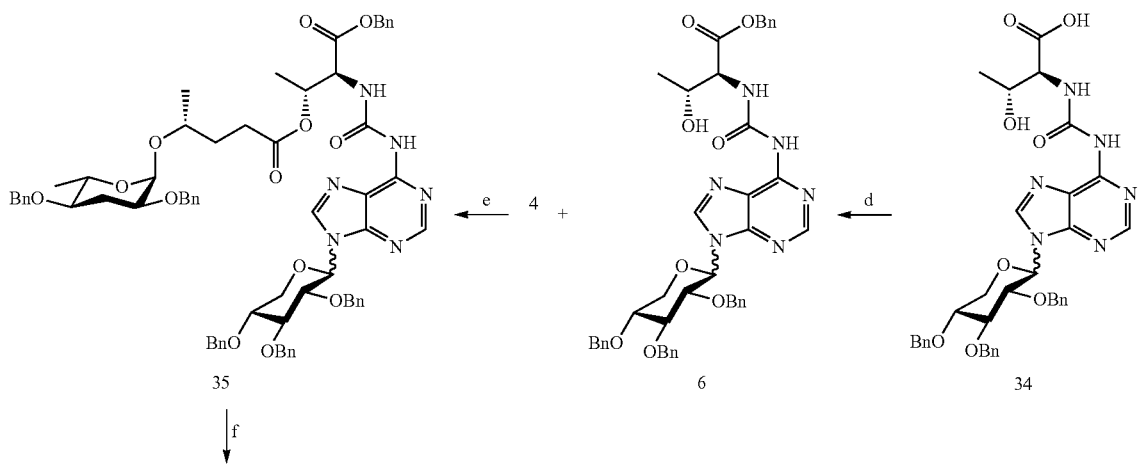

-continued

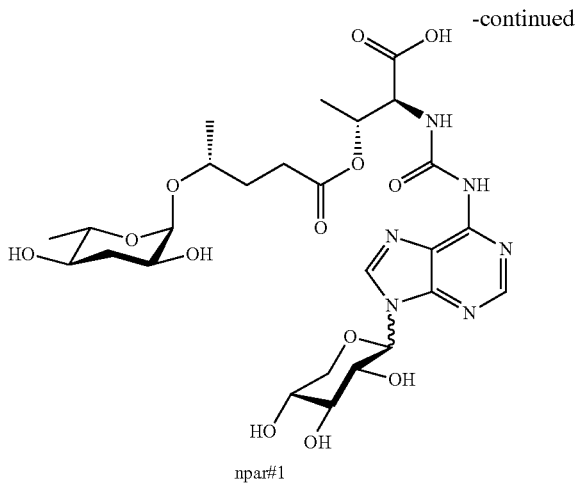

npar#1

(a) TMSBr, DCM, -40° C. to room temperature
(b) toluene, reflux
(c) L-threonine, pyridine, 107° C.
(d) 2-benzyloxy-1-methylpyridinium triflate4, Et3N, PhCF3, 83° C.
(e) EDC, DMAP, DCM
(f) 10% Pd/C, H2 (g) 10% formic acid in MeOH To prepare 32, a solution of 5 (Lucero & Woerpel, *J. Org. Chem.* 71:2641-47 (2006), which is hereby incorporated by reference in its entirety) (550 mg, 1.19 mmol) in dry dichloromethane (1.5 mL) cooled to -40° C. was added trimethylsilyl bromide (3.2 mL, 24.2 mmol) dropwise with constant stirring. The reaction mixture was then allowed to warm up to room temperature and stirred for 45 minutes. The excess reagent and solvent was removed in vacuo. The product ((3R,4S,5R)-3,4,5-tris(benzyloxy)-2-bromotetrahydro-2H-pyran (32)) was not characterized further and was used for the next step directly, because the product decomposed in contact to moisture.

To prepare 6, 31 (Chheda & Hong, *J. Med. Chem.* 14:748-53 (1971), which is hereby incorporated by reference in its entirety) (500 mg, 1.12 mmol) was dried thoroughly in vacuo and added to a solution of 32 in 12 mL dry toluene. The reaction mixture was refluxed for 2.5 hours. Toluene was evaporated to reduce the volume to ~3 mL in vacuo and 3 mL of petroleum ether was added to it. The resulting brown suspension was filtered and the precipitate washed with warm chloroform (3×10 mL). The filtrate and the washings were combined and washed with 10 mL 30% aq. KI solution, 10 mL water, dried over $Na_2SO_4$, and concentrated in vacuo. Flash column chromatography on silica using a gradient of 0-20% methanol in dichloromethane afforded 33 (160 mg, 262 μmol, 22% over two steps, mixture of α and β anomers in ratio ~2:3) as a pale yellow oil. 33 was reacted with L-threonine and worked up following conditions reported for the corresponding 2,3,5-tri-O-acetylribofuranoside-derivative (Chheda & Hong, *J. Med. Chem.* 14:748-53 (1971), which is hereby incorporated by reference in its entirety). Flash column chromatography on silica using a gradient of 0-30% methanol in dichloromethane containing 0.25% acetic acid afforded 34 (117 mg, 172 μmol, 66%, mixture of α and β-anomers in ratio ~2:3) as a yellow solid. A mixture of 34 (72 mg, 106 μmol) and 15 μl triethylamine (210 μmol) in 300 μl trifluoromethylbenzene was treated with 2-benzyloxy-1-methylpyridinium triflate (Tummatorn et al., *J. Org. Chem.* 72:8962-64 (2007), which is hereby incorporated by reference in its entirety) (71 mg, 210 μmol) and stirred at 83° C. for 15 hours. The products were partitioned between 2 mL ethyl acetate and 2 mL water, the organic phase washed with 1 mL water, 1 mL brine, dried over $Na_2SO_4$, and concentrated in vacuo. Flash column chromatography on silica using a gradient of 0-20% isopropanol in dichloromethane afforded (2S,3R)-benzyl 3-hydroxy-2-(3-(9-((3R,4S,5R)-3,4,5-tris(benzyloxy)tetrahydro-2H-pyran-2-yl)-9H-purin-6-yl)ureido)butanoate (6) (8.1 mg, 10 μmol, 10%, β-anomer) as a yellow solid. $^1$H NMR (500 MHz, methanol-$d_4$): δ (ppm) 8.39 (s, 1H), 8.27 (s, 1H), 7.43-7.25 (m, 15H), 6.99-6.95 (m, 1H), 6.91-6.86 (m, 2H), 6.67-6.62 (m, 2H), 5.53 (d, J=8.9 Hz, 1H), 5.25 (d, J=12.7 Hz, 1H), 5.23 (d, J=12.7 Hz, 1H), 5.01 (d, J=11.2 Hz, 1H), 4.88 (d, J=11.2 Hz, 1H), 4.74 (s, 2H), 4.62-4.56 (m, 2H), 4.48 (dq, J=6.4 Hz, 2.5 Hz, 1H), 4.26-4.15 (m, 3H), 3.94-3.88 (m, 1H), 3.84-3.79 (m, 1H), 3.53-3.46 (m, 1H), 1.31 (d, J=6.5 Hz, 3H). 3C NMR (125 MHz, methanol-$d_4$): δ (ppm) 172.2, 156.6, 152.1, 151.5, 151.4, 143.7, 139.9, 139.7, 138.4, 137.2, 129.65, 129.53, 129.46, 129.37, 129.24, 129.13, 129.08, 129.06, 128.90, 128.88, 128.74, 128.71, 121.5, 86.5, 85.6, 79.6, 78.8, 76.5, 75.7, 74.1, 68.5, 68.1, 67.7, 60.6, 20.7. See FIGS. 100A-B.

To prepare npar#1, a solution of 4 (4 mg, 9 μmol) in 450 μL dry dichloromethane was treated with 4-dimethylaminopyridine (2.5 mg, 20 μmol) and EDC hydrochloride (4 mg, 21 μmol). After stirring for 15 minutes, 6 (7.3 mg, 9 μmol) in 300 μL dry dichloromethane was added to the mixture. After stirring for 12 hours, the reaction was concentrated in vacuo. Flash column chromatography on silica using a gradient of 0-15% isopropanol in dichloromethane afforded 35 (5.5 mg, 4.6 μmol, 51%). A solution of Pd/C (7 mg, 10%, w/w) in 500 μL of methanol containing 10% formic acid was first flushed with argon for 5 minutes and subsequently with a moderate flow of $H_2$ gas. To this stirring solution was added a solution 35 (5.5 mg, 4.6 μmol) in 500 μL methanol. After 4 hours, the reaction was filtered over a pad of silica and concentrated in vacuo. HPLC purification (see Example 90) afforded (2S,3R)-3-(((R)-4-(((2R,3S,5R,6S)-3,5-dihydroxy-6-methyltetrahydro-2H-pyran-2-yl)oxy)pentanoyl)oxy)-2-(3-(9-((2R,3R,4S,5R)-3,4,5-trihydroxytetrahydro-2H-pyran-2-yl)-9H-purin-6-yl)ureido)butanoic acid (npar#1) (1.1 mg, 1.7 μmol, 37%) as a colorless oil.

$\alpha_D^{20} = -14.5$ (c. 0.11, methanol).

$^1$H (600 MHz), $^{13}$C (151 MHz), and HMBC NMR spectroscopic data for npar#1 were obtained using methanol-$d_4$ and are shown in Table 14 below. Chemical shifts were referenced to (C$\underline{D_2H}$OD)=3.31 ppm and ($\underline{C}D_3$OD)=49.00 ppm. See FIGS. 101A-E.

TABLE 14

NMR spectroscopic data for npar#1

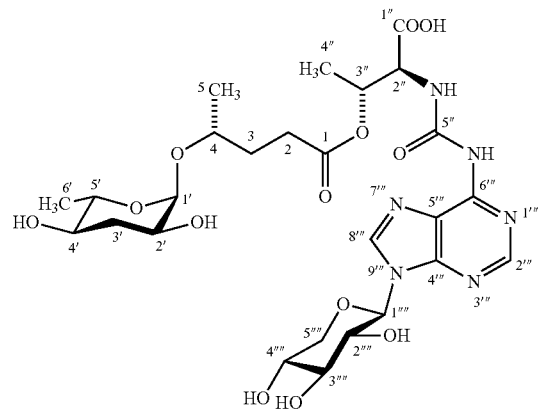

npar#1

| Position | δ $^{13}$C [ppm] | δ $^1$H [ppm] | $^1$H—$^1$H-coupling constants (Hz) | Key HMBC correlations |
|---|---|---|---|---|
| 1 | 173.6 | — | | |
| 2 | 31.5 | 2.59, 2.49 | | C-1 |
| 3 | 33.1 | 1.84-1.97 | | |
| 4 | 72.6 | 3.82 | $J_{4,5} = 6.2$ | C-1' |
| 5 | 19.0 | 1.17 | | |
| 1' | 96.1 | 4.73 | $J_{1',2'} = 3.9$ | C-2', C-3', C-5' |
| 2' | 68.3 | 3.61 | $J_{2',3'(ax)} = 12.1$; $J_{2',3'(eq)} = 5.8$ | |
| 3' | 36.7 | 1.73 (ax) | $J_{3'(eq),3'(ax)} = 12.4$; $J_{3'(eq),4'} = 4.6$ | |
|  |  | 2.02 (eq) | $J_{3'(ax),4'} = 11.7$ | |
| 4' | 71.5 | 3.15 | $J_{4',5'} = 9.7$ | |
| 5' | 69.9 | 3.53 | $J_{5',6'(eq)} = 6.3$ | |
| 6' | 17.6 | 1.173 | | C-5' |
| 1″ | 174.7 | — | | |
| 2″ | 58.4 | 4.69 | $J_{2'',3''} = 6.3$ | C-1″, C-3″, C-5″ |
| 3″ | 71.7 | 5.58 | $J_{3'',4''} = 6.8$ | |
| 4″ | 17.4 | 1.38 | | |
| 5″ | 154.7 | — | | |
| 2‴ | 152.1 | 8.66 | | C-6‴ |
| 4‴ | 151.9 | — | | |
| 5‴ | 121.2 | — | | |
| 6‴ | 151.6 | — | | |
| 8‴ | 143.3 | 8.47 | | C-4‴, C-5‴ |
| 1″″ | 85.7 | 5.56 | $J_{1'''',2''''} = 9$ | C-4‴, C-8‴, C-2″″, C-3″″ |
| 2″″ | 72.8 | 4.15 | $J_{2'''',3''''} = 9.2$ | |
| 3″″ | 78.6 | 3.53 | $J_{3'''',4''''} = 9.2$ | |
| 4″″ | 70.4 | 3.76 | $J_{4'''',5''''(ax)} = 10.4$, $J_{4'''',5''''(eq)} = 5.5$ | |
| 5″″ | 69.7 | 3.50 (ax) | $J_{5''''(ax),5''''(eq)} = 11.5$ | |
|  |  | 4.04 (eq) | | |

Example 101

Synthesis of (2S,3R)-3-(((S)-4-(((2S,3R,5S,6R)-3,5-Dihydroxy-6-Methyltetrahydro-2H-Pyran-2-yl)oxy)pentanoyl)oxy)-2-(3-(9-((2R,3R,4S,5R)-3,4,5-Trihydroxytetrahydro-2H-Pyran-2-yl)-9H-Purin-6-yl)ureido)butanoic Acid (36)

36 was prepared following analogous reaction steps to those described for npar#1 in Example 100 but using (S)-2, as shown in Scheme 19 below. $^1$H NMR (600 MHz, methanol-$d_4$): δ (ppm) 8.65 (s, 1H), 8.46 (s, 1H), 5.59-5.54 (m, 1H), 5.55 (d, J=9.4 Hz, 1H), 4.71 (d, J=3.8 Hz, 1H), 4.67-4.63 (m, 1H), 4.14 (t, J=9.1 Hz, 1H), 4.04 (dd, J=11.3 Hz, 5.5 Hz, 1H), 3.84-3.73 (m, 2H), 3.62-3.56 (m, 1H), 3.55-3.47 (m, 3H), 3.13 (ddd, J=11.3 Hz, 9.3 Hz, 4.4 Hz, 1H), 2.60-2.47 (m, 2H), 2.04-1.98 (m, 1H), 1.94-1.84 (m, 2H), 1.75-1.68 (m, 1H), 1.37 (d, J=6.3 Hz, 3H), 1.16 (d, J=6.1 Hz, 3H), 1.15 (d, J=6.3 Hz, 3H). $^{13}$C NMR (151 MHz, methanol-$d_4$): δ (ppm) 173.7, 173.5, 153.5, 152.3, 151.8, 151.5, 143.3, 121.1, 96.0, 85.7, 78.6, 72.8, 72.4, 71.9, 71.6, 70.5, 70.1, 69.7, 68.4, 58.5, 36.8, 33.2, 31.5, 19.1, 17.61, 17.57. See FIGS. 102A-C.

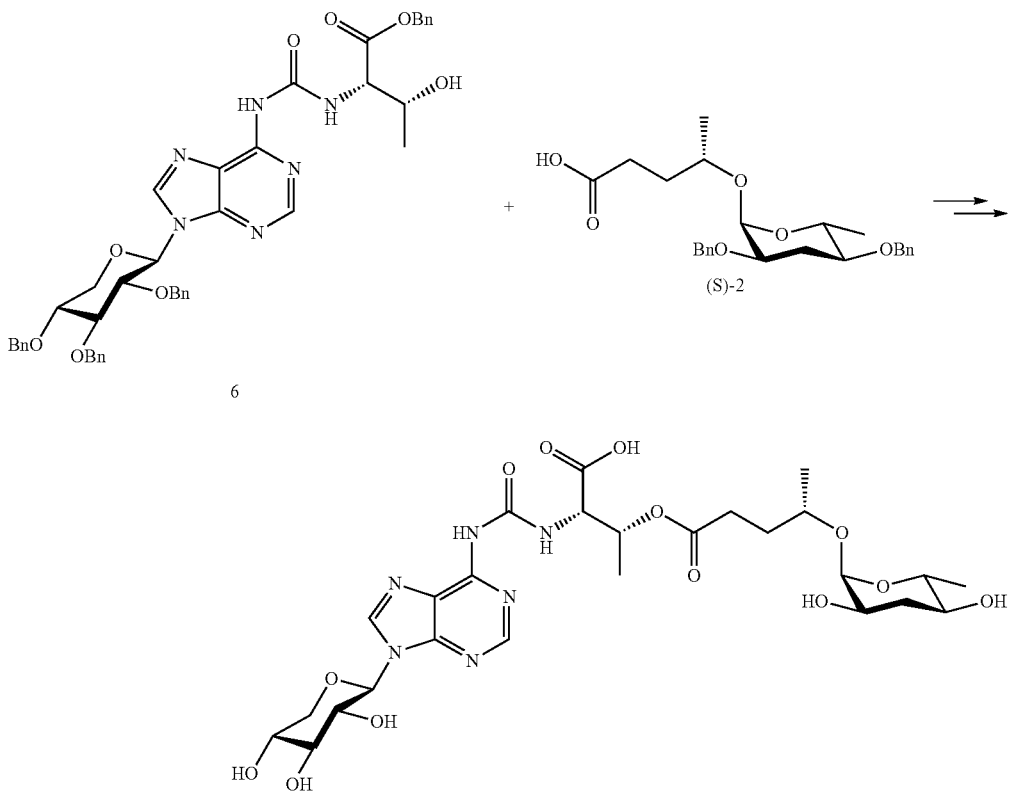

Scheme 19

Example 102

Synthesis of Ascaroside dasc#1

Ascaroside dasc#1 was prepared as shown in Scheme 20 below.

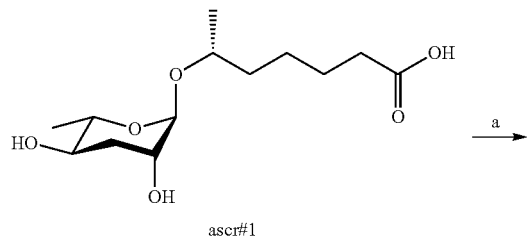

Scheme 20 ascr#1

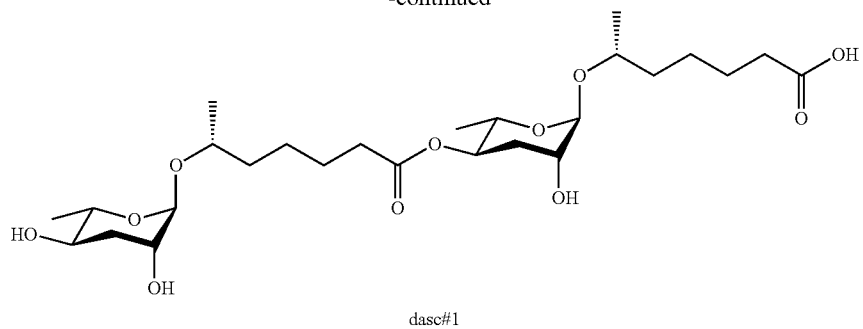

dasc#1

(a) EDC, DMAP, DMF

To prepare dasc#1, a solution of ascr#1 (15 mg, 54 μmol) in 15 mL dry DMF was added to a solution of 4-dimethylaminopyridine (13.5 mg, 110.7 μmol) and EDC hydrochloride (11 mg, 57.3 μmol) in 7 mL dry DMF. The reaction was monitored by ESI⁻ MS and was quenched with few drops of glacial acetic acid and concentrated in vacuo when polymer peaks (m/z=791 etc.) were observed in significant quantities. Flash column chromatography on silica using a gradient of 0-30% methanol in dichloromethane containing 0.25% and further HPLC purification (see Example 90) of crude product mixture afforded (R)-6-(((2R,3R,5R,6S)-5-(((R)-6-(((2R,3R,5R,6S)-3,5-dihydroxy-6-methyltetrahydro-2H-pyran-2-yl)oxy)heptanoyl)oxy)-3-hydroxy-6-methyltetrahydro-2H-pyran-2-yl)oxy)heptanoic acid (dasc#1) (1.1 mg, 2.1 μmol, 7.8%) as a colorless oil.

$$\alpha_D^{20} = -115.0$$

(c. 0.11, methanol).

$^1$H (600 MHz), $^{13}$C (151 MHz), and HMBC NMR spectroscopic data for dasc#1 were obtained using methanol-d$_4$ and are shown in Table 15 below. Chemical shifts were referenced to (CD$_2$HOD)=3.31 ppm and (CD$_3$OD)=49.00 ppm. See FIGS. 103A-D.

TABLE 15

NMR spectroscopic data for dasc#1

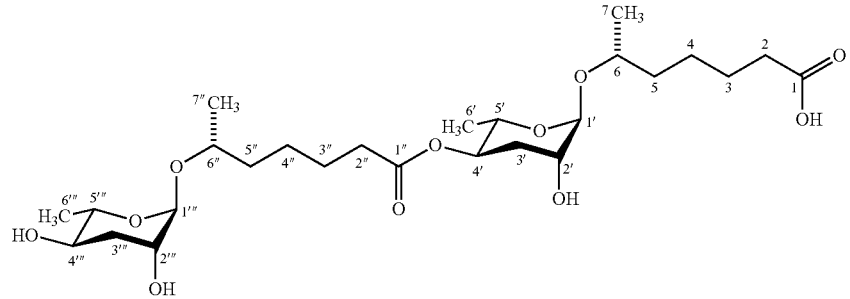

dasc#1

| Position | δ $^{13}$C [ppm] | δ $^1$H [ppm] | $^1$H—$^1$H-coupling constants (Hz) | Key HMBC correlations |
|---|---|---|---|---|
| 1 | 177.0 | — | | |
| 2 | 37.8 | 2.25 | $J_{2,3}$ = 7.7 | C-1 |
| 3 | 25.9 or 26.2 | 1.64 | | |
| 4 | 26.4 or 27.1 | 1.36-1.68 | | |
| 5 | 37.9 | 1.45-1.62 | | |
| 6 | 71.9 or 72.7 | 3.79 | $J_{6,7}$ = 6.3 | C-1' |
| 7 | 19.0 | 1.13 | | |
| 1' | 97.4 | 4.68 | $J_{1',2'}$ = 2.0 | C-2', C-3', C-5' |
| 2' | 69.4 | 3.72 | $J_{2',3'\,(ax)}$ = 6.3; $J_{2',3'\,(eq)}$ = 5.9 | |
| 3' | 32.8 | 1.83 (ax) 2.04 (eq) | $J_{3'(eq),3'(ax)}$ = 13.5; $J_{3'(eq),4'}$ = 5.0; $J_{3'(ax),4'}$ = 11.7 | |
| 4' | 71.1 | 4.86 | $J_{4',5'}$ = 10.1 | C-1" |
| 5' | 68.0 | 3.84 | $J_{5',6'(eq)}$ = 6.4 | |
| 6' | 17.9 | 1.14 | | C-4', C-5' |
| 1" | 174.4 | — | | |
| 2" | 34.9 | 2.35 | $J_{2",3"}$ = 7.5 | C-1" |
| 3" | 25.9 or 26.2 | 1.64 | | |
| 4" | 26.4 or 27.1 | 1.36-1.68 | | |
| 5" | 37.9 | 1.45-1.62 | | |

TABLE 15-continued
NMR spectroscopic data for dasc#1
dasc#1
| Position | δ $^{13}$C [ppm] | δ $^1$H [ppm] | $^1$H—$^1$H-coupling constants (Hz) | Key HMBC correlations |
|---|---|---|---|---|
| 6″ | 71.9 or 72.7 | 3.79 | $J_{6″, 7″} = 6.3$ | C-1‴ |
| 7″ | 19.0 | 1.13 | | |
| 1‴ | 97.2 | 4.64 | $J_{1‴, 2‴} = 2.4$ | C-2‴, C-3‴, C-5‴ |
| 2‴ | 69.4 | 3.71 | $J_{2‴, 3‴(ax)} = 6.2$; $J_{2‴, 3‴(eq)} = 6.0$ | |
| 3‴ | 35.7 | 1.76 (ax) | $J_{3‴(eq), 3‴(ax)} = 13.4$; $J_{3‴(eq), 4‴} = 4.7$ | |
| | | 1.95 (eq) | $J_{3‴(ax), 4‴} = 11.8$ | |
| 4‴ | 68.1 | 3.51 | $J_{4‴, 5‴} = 9.4$ | |
| 5‴ | 70.9 | 3.61 | $J_{5‴, 6‴(eq)} = 6.4$ | |
| 6‴ | 17.9 | 1.22 | | C-4‴, C-5‴ |
Example 103
Synthesis of Ascaroside ubas#1
Ascaroside ubas#1 was prepared as shown in Scheme 21 below.
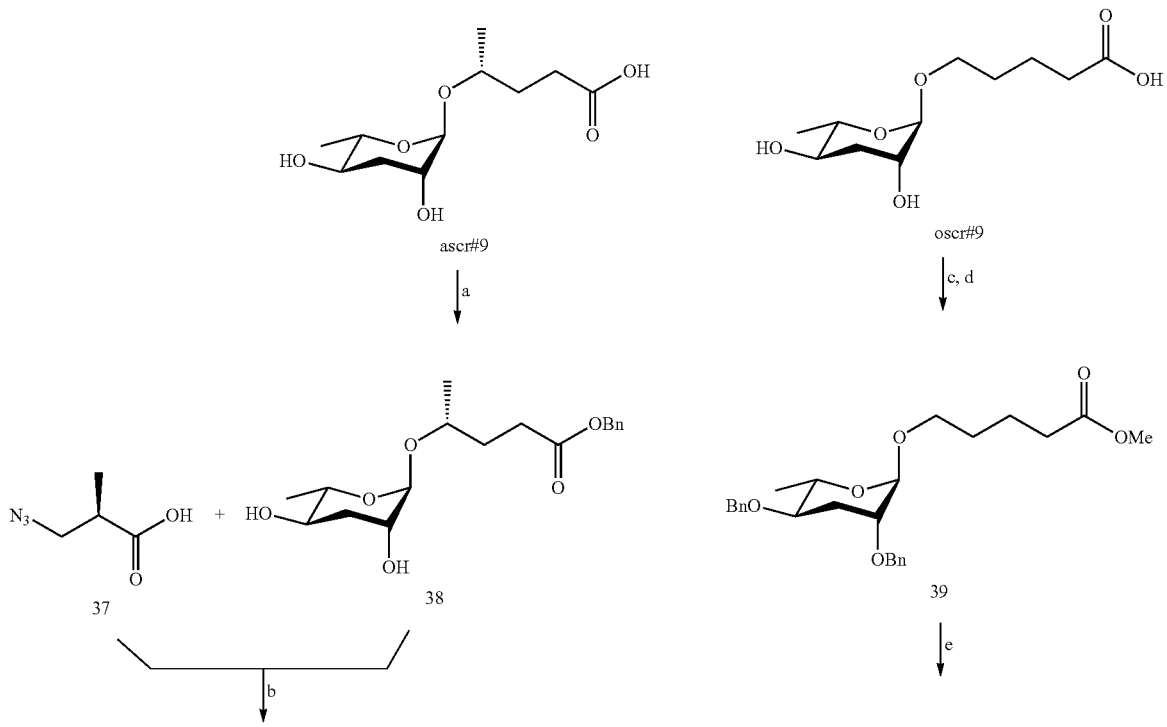

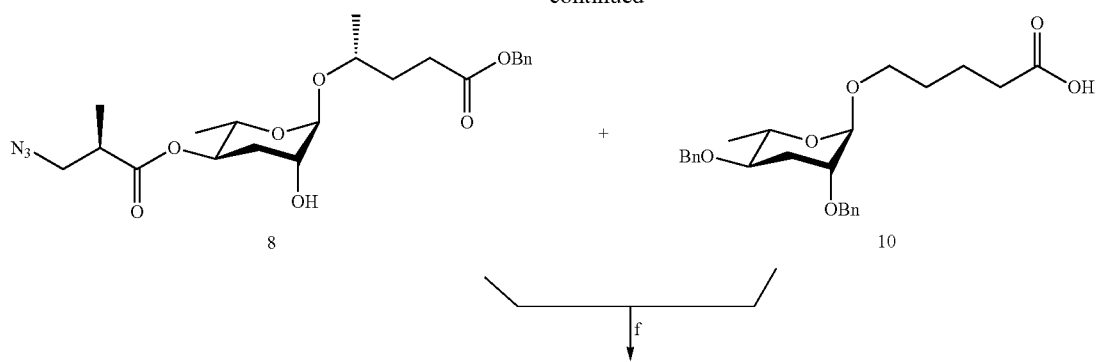
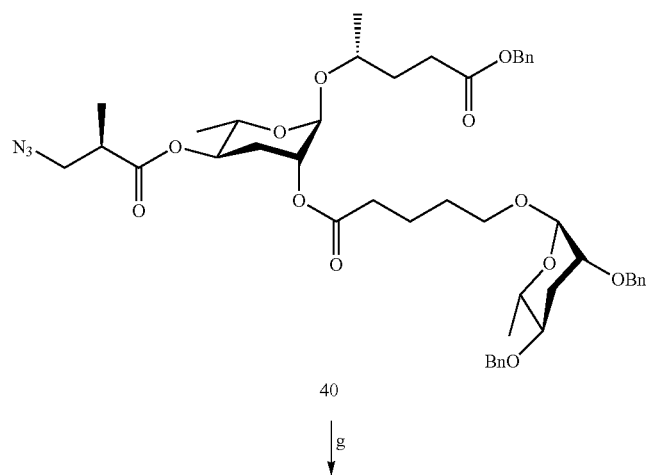
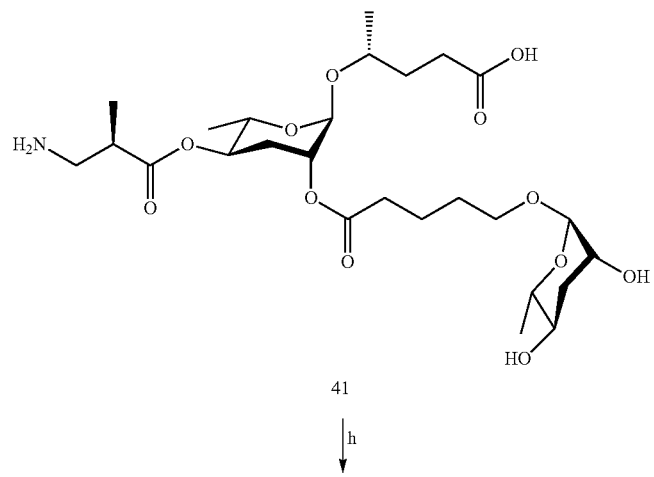

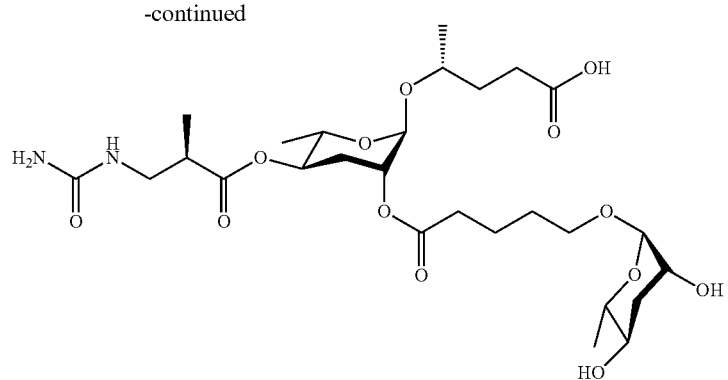

unbas#1

(a) 2-benzyloxy-1-methylpyridinium triflate Et3N, PhCF3, 83° C.
(b) EDC, DMAP, DCM
(c) TMSCHN2, toluene/MeOH
(d) BnBr, NaH, DMF
(e) LiOH, THF/dioxane/H2O, 67° C.
(f) EDC, DMAP DCM
(g) 10% Pd/C, H2 (g), 5% HCl in MeOH
(h) KCNO, HCl H2O, 75° C.

To prepare 38, a mixture of ascr#9 (Srinivasan et al., *PLoS Biol.* 10:e1001237 (2012), which is hereby incorporated by reference in its entirety) (24.0 mg, 97 µmol) and 28 µl triethylamine (200 µmol) in 300 µl trifluoromethyl benzene was treated with 70 mg 2-benzyloxy-1-methylpyridinium triflate (Tummatorn et al., *J. Org. Chem.* 72:8962-64 (2007), which is hereby incorporated by reference in its entirety) (200 µmol) and stirred at 83° C. for 18 hours. The products were partitioned between 2 mL ethylacetate and 2 mL water, the organic phase washed with 1 mL water, 1 mL saturated aq. NaCl solution, dried over $Na_2SO_4$, and concentrated in vacuo. Flash column chromatography on silica using a gradient of 0-10% methanol in dichloromethane afforded (R)-benzyl 4-(((2R,3R,5R,6S)-3,5-dihydroxy-6-methyltetrahydro-2H-pyran-2-yl)oxy)pentanoate (38) (22.6 mg, 66.8 µmol, 69%) as a colorless oil. $^1$H NMR (500 MHz, chloroform-d): δ (ppm) 7.39-7.30 (m, 5H), 5.12 (s, 2H), 4.68 (s, 1H), 3.88-3.80 (m, 1H), 3.80-3.74 (m, 1H), 3.63-3.52 (m, 2H), 2.54-2.41 (m, 2H), 2.06-2.01 (m, 1H), 1.90-1.84 (m, 2H), 1.82-1.75 (m, 1H), 1.24 (d, J=6.1 Hz, 3H), 1.14 (d, J=6.2 Hz, 3H). $^{13}$C NMR (125 MHz, chloroform-d): δ (ppm) 173.6, 136.0, 128.7, 128.39, 128.37, 95.8, 70.3, 70.1, 69.3, 68.1, 66.5, 35.3, 32.2, 30.8, 18.8, 17.8. See FIGS. 104A-B.

To prepare 8, a solution of 38 (22.6 mg, 66.8 µmol) and 3-azido-(2R)-methylpropanoic acid (Rej et al., *J. Org. Chem.* 61:6289-95 (1996), which is hereby incorporated by reference in its entirety) (37, 8.6 mg, 66.8 µmol) in 2 mL dichloromethane was treated with 4-dimethylaminopyridine (16.3 mg, 133.6 µmol) and EDC hydrochloride (25.7 mg, 133.6 µmol). After stirring at room temperature for 12 hours the reaction was quenched by addition of 5% aqueous acetic acid (100 µl), dried over $Na_2SO_4$, and concentrated in vacuo. Flash column chromatography on silica using a gradient of 0-10% isopropanol in dichloromethane afforded (R)-benzyl 4-(((2R,3R,5R,6S)-5-(((R)-3-azido-2-methylpropanoyl)oxy)-3-hydroxy-6-methyltetrahydro-2H-pyran-2-yl)oxy)pentanoate (8) (5.2 mg, 11.6 µmol, 17%) as a colorless oil. $^1$H NMR (400 MHz, chloroform-d): δ (ppm) 7.40-7.31 (m, 5H), 5.15 (d, J=13.6 Hz, 1H), 5.11 (d, J=13.6 Hz, 1H), 4.86 (ddd, J=10.9 Hz, 9.4 Hz, 4.6 Hz, 1H), 4.73-4.70 (m, 1H), 3.90-3.76 (m, 3H), 3.52 (dd, J=12.2 Hz, 7.5 Hz, 1H), 3.38 (dd, J=12.2 Hz, 5.6 Hz, 1H), 2.71-2.60 (m, 1H), 2.57-2.42 (m, 2H), 2.13-2.05 (m, 2H), 1.93-1.83 (m, 3H), 1.20 (d, J=7.0 Hz, 3H), 1.17 (d, J=6.3 Hz, 3H), 1.16 (d, J=6.2 Hz, 3H). See FIG. 105.

To prepare 10, a solution of oscr#9 (von Reuss et al., *J. Am. Chem. Soc.* 134:1817-24 (2012), which is hereby incorporated by reference in its entirety) (17.6 mg, 71 µmol) in a 1:1 mixture (v/v) of methanol and toluene (2 mL) was treated with 2.0 M (trimethylsilyl)diazomethane solution (200 µl) in diethyl ether. After stirring for 30 minutes excess reagent was destroyed by addition of acetic acid and the solution concentrated in vacuo. The residue was dissolved in DMF (500 µl), cooled to 0° C., and treated with sodium hydride (17 mg, 60% suspension in mineral oil, 425 µmol). After 10 minutes benzyl bromide (51 µl) was added and the mixture stirred overnight. Excess reagent was destroyed by addition of methanol (300 µl), the residue diluted with ethyl acetate (2 mL), and the organic phase washed with water (3×1 mL), dried over $Na_2SO_4$, and concentrated in vacuo. Flash column chromatography on silica using a gradient of 0-40% ethyl acetate in hexanes afforded 39 (14.4 mg, 33 µmol, 46% over two steps) as a colorless oil. A solution of 39 (14.4 mg, 33 µmol) in THF (1 mL) was treated with 3.3 M aq. lithium hydroxide solution (100 µl, 330 µmol) in dioxane (2 mL) at 67° C. After 3 hours the reaction was quenched by addition of acetic acid, and concentrated in vacuo. Flash column chromatography on silica using a gradient of 0-20% methanol in dichloromethane afforded 5-(((2R,3R,5R,6S)-3,5-bis(benzyloxy)-6-methyltetrahydro-2H-pyran-2-yl)oxy)pentanoic acid (10) (11.8 mg, 28 µmol, 85%) as a colorless oil. $^1$H NMR (500 MHz, acetone-d$_6$): δ (ppm) 7.32-7.38 (m, 8H), 7.30-7.25 (m, 2H), 4.69 (s, 1H), 4.62 (d, J=11.8 Hz, 1H), 4.58 (s, 2H), 4.48 (d, J=11.8 Hz, 1H), 3.73-3.64 (m, 2H), 3.64-3.60 (m, 1H), 3.46-3.38 (m, 2H), 2.37-2.30 (m, 3H), 1.73-1.57 (m, 5H), 1.21 (d, J=6.2 Hz, 3H). $^{13}$C NMR (125 MHz, acetone-d$_6$): δ (ppm) 174.6, 140.0, 139.9, 129.1, 129.0, 128.6, 128.4, 128.19, 128.21, 97.7, 76.4, 76.0, 71.4, 71.2, 68.9, 67.3, 33.9, 30.2, 29.8, 22.6, 18.6. See FIGS. 106A-B.

To prepare 40, a solution of 8 (5.2 mg, 11.6 µmol) and 10 (6.4 mg, 14.9 µmol) in 1 mL dichloromethane was treated with 4-dimethylaminopyridine (3.7 mg, 30 µmol) and EDC hydrochloride (5.8 mg, 30 µmol). After stirring at room temperature for 12 hours the reaction was quenched by addition of 5% aqueous acetic acid (50 µl), dried over $Na_2SO_4$, and concentrated in vacuo. Flash column chromatography on silica using a gradient of 0-50% ethyl acetate in hexane afforded (2R,3R,5R,6S)-5-(((R)-3-azido-2-methylpropanoyl)oxy)-2-(((R)-5-(benzyloxy)-5-oxopentan-2-yl)

oxy)-6-methyltetrahydro-2H-pyran-3-yl 5-(((2R,3R,5R,6S)-3,5-bis(benzyloxy)-6-methyltetrahydro-2H-pyran-2-yl)oxy)pentanoate (40) (9.6 mg, 11.2 μmol, 97%) as a colorless oil. $^1$H NMR (500 MHz, acetone-d$_6$): δ (ppm) 7.40-7.25 (m, 15H), 5.15 (d, J=12.3 Hz, 1H), 5.12 (d, J=12.3 Hz, 1H), 4.84-4.78 (m, 2H), 4.66 (s, 1H), 4.74 (s, 1H), 4.58 (d, J=12.3 Hz, 1H), 4.57 (d, J=11.4 Hz, 1H), 4.53 (d, J=12.3 Hz, 1H), 4.46 (d, J=11.4 Hz, 1H), 3.87-3.80 (m, 2H), 3.75-3.67 (m, 2H), 3.60-3.56 (m, 1H), 3.51 (dd, J=12.2 Hz, 7.6 Hz, 1H), 3.47-3.34 (m, 3H), 2.68-2.60 (m, 1H), 2.55-2.41 (m, 2H), 2.38 (t, J=7.4 Hz, 2H), 2.24-2.18 (m, 1H), 2.12-2.06 (m, 1H), 1.96-1.85 (m, 3H), 1.77-1.65 (m, 3H), 1.64-1.55 (m, 2H), 1.29 (d, J=6.2 Hz, 3H), 1.19 (d, J=7.1 Hz, 3H), 1.16 (d, J=6.2 Hz, 3H), 1.15 (d, J=6.1 Hz, 3H). $^{13}$C NMR (125 MHz, acetone-d$_6$): δ (ppm) 173.4, 173.2, 172.9, 138.6, 138.5, 136.0, 128.7, 128.52, 128.51, 128.45, 128.38, 128.0, 127.79, 127.77, 97.2, 93.5, 75.6, 75.4, 71.4, 71.24, 71.22, 70.5, 70.4, 68.3, 67.0, 66.8, 66.5, 55.8, 40.1, 34.1, 32.1, 30.6, 29.9, 29.7, 29.5, 29.1, 21.8, 18.9, 18.3, 17.7, 14.9. ESI$^+$ MS: m/z=882.5 [M+Na$^+$] and 898.5 [M+K$^+$]. See FIGS. 107A-B.

To prepare ubas#1, a solution of Pd/C (5.4 mg, 10%, w/w) in 0.7 mL of methanol containing 5% 1 M aq. HCl was flushed with argon gas for 5 minutes and subsequently with a moderate flow of H$_2$ gas for 5 minutes. To this stirring solution was added a solution of 40 (4.3 mg, 5.0 μmol) in 1.3 mL methanol via syringe and the H$_2$ gas was continuously flowed through the reaction. The reaction was monitored by direct injection ESI$^-$ MS. After 20 minutes, the reaction was filtered over a pad of silica with additional methanol. The product was concentrated in vacuo and the crude mixture of 40 and 41 (3.7 mg) was used in the next step without further purification. A solution of aqueous HCl (200 μL, 50 μmol), aq. KCNO (200 μL, 50 μmol) and H$_2$O (100 μL) was prepared. This aq. HCl/KCNO solution was added to the crude mixture of 40 and 41 (3.7 mg) and was placed in a 75° C. oil bath for 5 minutes. Additional aqueous HCl solution (50 μL, 12.5 μmol) was added to the reaction and this was allowed to stir for an additional 2.5 minutes. The pH of the reaction mixture was periodically checked to ensure the pH was not basic. The reaction was monitored by direct injection ESI$^-$ MS. The mixture was concentrated in vacuo and HPLC purification (see Example 90) afforded (R)-4-(((2R,3R,5R,6S)-3-((5-(((2R,3R,5R,6S)-3,5-dihydroxy-6-methyltetrahydro-2H-pyran-2-yl)oxy)pentanoyl)oxy)-6-methyl-5-(((R)-2-methyl-3-ureidopropanoyl)oxy)tetrahydro-2H-pyran-2-yl)oxy)pentanoic acid (ubas#1) (200 μg, 0.3 μmol, 7% over two steps) as a colorless oil.

$^1$H (600 MHz), $^{13}$C (151 MHz), and HMBC NMR spectroscopic data for ubas#1 were obtained using methanol-d$_4$ and are shown in Table 16 below. Chemical shifts were referenced to (CD$_2$HOD)=3.31 ppm and (CD$_3$OD)=49.00 ppm. See FIGS. 108A-D.

TABLE 16

NMR spectroscopic data for ubas#1

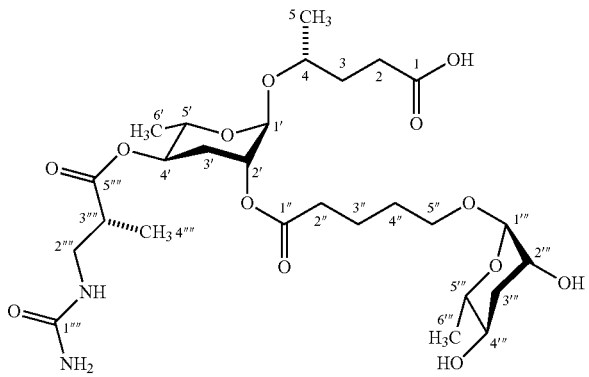

ubas#1

| Position | δ $^{13}$C [ppm] | δ $^1$H [ppm] | $^1$H—$^1$H-coupling constants (Hz) | Key HMBC correlations |
|---|---|---|---|---|
| 1 | 174.6 | — | | |
| 2 | 35.0 | 2.31 | $J_{2,3}$ = 7.4 | C-1 |
| 3 | 34.3 | 1.83 | $J_{3,4}$ = 6.2 | |
| 4 | 72.7 | 3.84 | $J_{4,5}$ = 6.4 | C-1' |
| 5 | 18.9 | 1.16 | | |
| 1' | 94.2 | 4.77 | $J_{1',2'}$ = 2.4 | C-2', C-3', C-5' |
| 2' | 71.8 | 4.80 | $J_{2',3'(ax)}$ = 6.4; $J_{2',3'(eq)}$ = 5.8 | C-1" |
| 3' | 30.7 | 2.01(ax) 2.10(eq) | $J_{3'(eq),3'(ax)}$ = 13.7; $J_{3'(eq),4'}$ = 4.2 $J_{3'(ax),4'}$ = 11.7 | |
| 4' | 71.1 | 4.73 | $J_{4',5'}$ = 9.2 | C-5"" |
| 5' | 67.9 | 3.99 | $J_{5',6'}$(eq) = 6.4 | |
| 6' | 17.8 | 1.16 | | |
| 1" | 173.9 | — | | |
| 2" | 34.5 | 2.43 | $J_{2",3"}$ = 7.0 | C-1" |
| 3" | 22.7 | 1.75 | | |
| 4" | 29.6 | 1.67 | $J_{4",5"}$ = 6.2 | |
| 5" | 67.6 | 5a" = 3.45 5b" = 3.76 | | C-1''' |
| 1''' | 100.1 | 4.51 | $J_{1''',2'''}$ = 2.6 | C-2''', C-3''', C-5''' |
| 2''' | 69.1 | 3.79 | $J_{2''',3'''(ax)}$ = 6.1, $J_{2''',3'''}$ (eq) = 5.9 | |
| 3''' | 35.7 | 1.78 (ax) | $J_{3'''(eq),3'''(ax)}$ = 13.1, $J_{3'''(eq),4'''}$ = 4.3 | |

TABLE 16-continued

NMR spectroscopic data for ubas#1

[Structure of ubas#1 shown]

ubas#1

| Position | δ $^{13}$C [ppm] | δ $^1$H [ppm] | $^1$H—$^1$H-coupling constants (Hz) | Key HMBC correlations |
|---|---|---|---|---|
| 4''' | 68.1 | 1.95 (eq) 3.51 | $J_{3'''(ax), 4'''}$ = 11.2 | |
| 5''' | 70.5 | 3.57 | $J_{4''', 5'''}$ = 9.5 | |
| 6''' | 17.9 | 1.23 | $J_{5''', 6'''(eq)}$ = 6.4 | |
| 1'''' | 161.7 | — | | |
| 2'''' | 43.4 | 3.26 | $J_{2'''', 3''''}$ = 6.8 | C-1'''' |
| 3'''' | 41.5 | 2.68 | $J_{3'''', 4''''}$ = 6.9 | C-5'''' |
| 4'''' | 14.7 | 1.14 | | C-5'''' |
| 5'''' | 175.6 | | | |

Example 104

Enrichment of ubas#2

An enriched sample of (R)-4-(((2R,3R,5R,6S)-3-(((R)-5-(((2R,3R,5R,6S)-3,5-dihydroxy-6-methyltetrahydro-2H-pyran-2-yl)oxy)hexanoyl)oxy)-6-methyl-5-(((R)-2-methyl-3-ureidopropanoyl)oxy)tetrahydro-2H-pyran-2-yl)oxy) pentanoic acid (ubas#2) was obtained following HPLC enrichment of crude *P. pacificus* exo-metabolome extract. $^1$H NMR (600 MHz, methanol-d$_4$): δ (ppm) 4.80 (m, 1H), 4.79 (s, 1H), 4.74 (m, 1H), 4.65 (s, 1H), 3.99 (m, 1H), 3.84 (m, 1H), 3.82 (m, 1H), 3.72 (m, 1H), 3.62 (m, 1H), 3.51 (m, 1H), 3.26 (m, 2H), 2.68 (m, 1H), 2.42 (m, 2H), 2.34 (m, 2H), 2.10 (m, 1H), 2.01 (m, 1H), 1.95 (m, 1H), 1.83 (m, 2H), 1.78 (m, 1H), 1.64-1.57 (m, 4H), 1.23 (d, J=6.3 Hz, 3H), 1.157 (d, J=6.2 Hz, 3H), 1.156 (d, J=6.3 Hz, 3H), 1.147 (d, J=6.2 Hz, 3H), 1.142 (d, J=7.0 Hz, 3H). See FIG. 109.

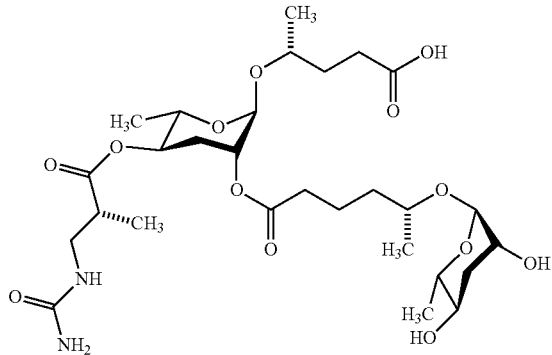

ubas#2

Discussion of Examples 85-104

Small molecules serve a wide variety of essential biological functions (Meinwald, *J. Nat. Prod.* 74:305-09 (2011), which is hereby incorporated by reference in its entirety). They facilitate inter- and intra-specific chemical communication, are used for chemical defense and predation, function as hormones and second messengers in animals and plants, and serve as building blocks for biological macromolecules. In contrast to most groups of microorganisms and plants, whose genomes have revealed a great variety of "secondary" small-molecule biosynthetic pathways, e.g. polyketides and non-ribosomal peptides (Walsh, *Acc. Chem. Res.* 41:4-10 (2008), which is hereby incorporated by reference in its entirety), most metazoans are not known to have dedicated biosynthetic machinery to generate structurally complex small molecules. Correspondingly, most unusual metabolites isolated from animal sources have been shown to be diet-derived. Exceptions include compounds isolated from basal animals (e.g. sponges) and arthropods, some of which, however, may also be of microbial origin (Piel, *Nat. Prod. Rep.* 26:338-62 (2009); Dossey, *Nat. Prod. Rep.* 27:1737-57 (2010); Gronquist & Schroeder, in 2 COMPREHENSIVE NATURAL PRODUCTS II—CHEMISTRY AND BIOLOGY 67-108 (Bradley S. Moore & Phillip Crews eds., 2010), which are hereby incorporated by reference in their entirety). Studies in the model organism elegans showed that this nematode produces a family of small molecule signals, the ascarosides, e.g. ascr#1-ascr#3, and hbas#3 (FIG. 110A), which control multiple aspects of *C. elegans* life history, including larval development, mating, and social behaviors (Srinivasan et al., *Nature* 454:1115-18 (2008); Butcher et al., *Nat. Chem. Biol.* 3:420-22 (2007); Srinivasan et al., *PLoS Biol.* 10:e1001237 (2012); von Reuss et al., *J. Am. Chem. Soc.* 134:1817-24 (2012), which are hereby incorporated by reference in their entirety). The structures of these *C. elegans* signaling molecules derive from combination of the dideoxysugar ascarylose with a variety of lipid- and amino acid-metabolism derived moieties, suggesting that nematodes, and perhaps other animals, harbor yet unrecognized biosynthetic capabilities.

As part of a broad 2D NMR-spectroscopic screen of nematode metabolomes, the exo-metabolome (the entirety of all secreted and excreted metabolites) of the necromenic roundworm *Pristionchus pacificus* was analyzed. Like *C. elegans, P. pacificus* is a free-living nematode that has been established as a model organism for the study of developmental and evolutionary biology (Hong & Sommer, *Bioessays* 28:651-59 (2006), which is hereby incorporated by reference in its entirety). *P. pacificus* forms a necromenic association with beetles, which may represent a pre-adaptation to the evolution of true parasitism (Rae et al., *J. Exp. Biol.* 211:1927-36 (2008), which is hereby incorporated by reference in its entirety). *P. pacificus* exhibits two types of phenotypic plasticity that are key to its survival in the wild. Like in many other nematode species, harsh environmental conditions, for example food shortage, trigger developmental arrest as dauer worms, a highly stress-resistant alternate larval stage (Weller et al., *J. Parasitol.* 96:525-31 (2010), which is hereby incorporated by reference in its entirety). *P. pacificus* further exhibits a unique dimorphism in mouth development, representing an example for phenotypic plasticity of morphology in an adult metazoan (FIG. 110B). Adult worms can have either a narrow ("stenostomatous") or a wide and more complex ("eurystomatous") mouth opening, the latter developing in response to conditions of low food availability. The two different mouth forms are associated with different feeding habits: stenostomatous worms are considered to feed primarily on bacteria, whereas the eurystomatous form is suited for predatory behavior toward other nematodes. Previous studies showed that both dauer formation and mouth dimorphism are regulated by population density, suggesting that these two examples of phenotypic plasticity are driven by inter-organismal small-molecule signaling (FIG. 110B) (Bento et al., *Nature* 466:494-97 (2010), which is hereby incorporated by reference in its entirety).

2D NMR-based metabolomics of *P. pacificus* exo-metabolome fractions with dauer-inducing activity revealed a striking diversity of signals suggestive of primary metabolites, for example xylose, threonine, adenosine, short-chain fatty acids, succinate, phenylethanolamine, and several dideoxysugar derivatives (FIG. 110C); however, their NMR data indicated that most of these moieties are part of larger assemblies. The dideoxysugar derivatives fell into two chemically different subgroups. One group was based on ascarylose, a sugar that is widely produced by nematodes (Choe et al., *Curr. Biol.* 22:772-80 (2012), which is hereby incorporated by reference in its entirety), whereas a second group of compounds appeared to include a related sugar, paratose, which previously had been reported only from bacteria (FIG. 110C). Analyzing the *P. pacificus* exo-metabolome by HPLC-MS/MS for the presence of any of the ~150 ascarosides recently identified from *C. elegans* (von Reuss et al., *J. Am. Chem. Soc.* 134:1817-24 (2012), which is hereby incorporated by reference in its entirety), ascr#1, ascr#9, and ascr#12 were detected, as previously reported (FIG. 111A) (Choe et al., *Curr. Biol.* 22:772-80 (2012), which is hereby incorporated by reference in its entirety). However, these three compounds accounted only for a small portion of the structures detected by 2D NMR spectroscopy.

Combining results from NMR and high resolution HPLC-MS/MS analyses (FIGS. 111A, 112, and 113), structures for the major unknown components of the *P. pacificus* exo-metabolome were proposed, in some cases after additional fractionation to increase the content of minor components (FIG. 111B). The most abundant ascaroside derivative, named pasc#9 was proposed as an N-succinyl 1-phenylethanolamide linked to ascarylose via a 4-hydroxypentanoic acid chain (FIG. 111B). This compound was accompanied by two dimeric ascaroside derivatives, a dimer (dasc#1) of the known ascr#1 in which one ascr#1-unit is attached to carbon 4 of the other ascr#1 unit, and second dimer (ubas#1) consisting of ascr#9 to which the (ω)-oxygenated ascaroside oscr#9 is attached in position 2 (FIG. 111B). This second dimer, ubas#1, additionally bears a 3-ureido isobutyrate moiety attached to carbon 4. Neither dimeric ascarosides nor ureido isobutyrate-substituted metabolites appear to have previously been reported from nature.

These ascarosides were accompanied by two abundant metabolites that included paratose instead of ascarylose, npar#1 and part#9 (FIG. 111B). In npar#1, the paratose moiety was linked to a short lipid side chain, which in turn was connected to threonine. This amino acid was connected further via a carbamoyl group to a derivative of the nucleoside adenosine (FIG. 111B). Strikingly, this adenosine was found to include a xylopyranose, and not ribofuranose or deoxyribofuranose as in DNA, RNA, and known nucleoside-based signaling molecules. The accompanying part#9 represents the paratose and side-chain portions of npar#1 (FIG. 111B).

To confirm these structural assignments, for determining stereochemistry, and to explore biological functions, syntheses for the proposed structures were developed, taking advantage of their modular nature (FIG. 111C, see Examples 95-104). Comparison of NMR spectra of the synthetic and natural samples established the configuration of the N-succinyl 1-phenylethanolamide moiety in natural pasc#9 as R (FIG. 114). Similarly, comparison of NMR spectroscopic data and HPLC retention times enabled assigning the stereochemistry of the dimeric ascarosides dasc#1 and ubas#1 (FIGS. 115 and 116). The R-configuration of the 3-ureido isobutyrate moiety in ubas#1 is consistent with its likely origin from thymine catabolism (van Kuilenburg et al., *Biochem. J.* 379:119-24 (2004), which is hereby incorporated by reference in its entirety). Lastly samples of the paratoside part#9 and the unusual xyloadenosine derivative, npar#1 were synthesized. Comparing HPLC-retention times of natural part#9 and several synthetic part#9 diastereomers it was found that natural part#9 must be either D-paratosyl-4S-hydroxypentanoic acid or L-paratosyl-4R-hydroxypentanoic acid (FIG. 117). It was initially assumed that part#9 and npar#1 contained D-paratose, which had previously been described from bacteria whereas L-paratose had not been found in nature. Furthermore, D-paratose is a putative intermediate in the biosynthesis of L-ascarylose (Thorson et al., *J. Bacteriol.* 176:5483-93 (1994), which is hereby incorporated by reference in its entirety), on which all ascarosides in nematodes are based. However, the HPLC retention time and NMR spectra of a synthetic npar#1 diasteromer including D-paratosyl-4S-hydroxypentanoic acid did not match the data obtained for natural npar#1 (FIG. 118A). Therefore, it was concluded that npar#1 must be based on L-paratosyl-4R-hydroxypentanoic acid, which was confirmed via synthesis of this diastereomer and comparison of its spectroscopic data with those of natural npar#1 (FIGS. 118B-C). The sugar L-paratose has not previously been found in nature; however, its occurrence in nematodes could plausibly result from epimerization of L-ascarylose at position 2.

Whether the identified combinations of sugar, amino acid, lipid, and nucleoside-derived building blocks are specific was next asked. To address this, the entire *P. pacificus* exo-metabolome was carefully re-analyzed by high resolution HPLC-MS/MS and screened for homologues or alternative combinations of the primary metabolism-derived building blocks in the already-identified structures. pasc#9 was found to be accompanied by trace amounts of two homologues including six- and seven-carbon side chains, which were also detected by NMR spectroscopy (FIG. 119). In addition, a small amount of a homologue of ubas#1 (ubas#2 in FIG. 113) as well as a derivative of npar#1, whose MS data indicated loss of the xylose (npar#2 in FIG. 113), were detected. Importantly, no non-specific or seemingly random combinations of building blocks that would suggest non-enzymatic genesis of the identified compounds were observed. These results show that modular assembly of the identified compounds is highly specific. To exclude the possibility that the identified compounds are bacterial metabolites, the metabolome of the *E. coli* OP50 bacteria used as food for *P. pacificus* was also analyzed. None of the identified compounds were found to be present in the bacterial metabolome (FIG. 120). Furthermore, all of the identified compounds were detected in *P. pacificus* cultures fed with *Pseudomonas* sp. instead of *E. coli*.

Synthetic samples of the identified compounds were then tested for their activity in the *P. pacificus* dauer and mouth-form dimorphism assays. As expected from previous studies that showed that *C. elegans* exo-metabolome samples are not active in the *P. pacificus* mouth-form dimorphism and dauer assays (Ogawa et al., *Curr. Biol.* 19:67-71 (2009), which is hereby incorporated by reference in its entirety), it was found that ascr#1, a compound abundantly excreted by *C. elegans* (Jeong et al., *Nature* 433:541-45 (2005), which is hereby incorporated by reference in its entirety), has no dauer-inducing activity in *P. pacificus*, even at very high concentrations (FIG. 121). In contrast, the nucleoside derivative npar#1 strongly induced dauer formation and appears to account for most of the reported dauer-inducing activity of unfractionated exo-metabolome (Mayer & Sommer, *Proc. Biol. Sci.* 278:2784-90 (2011), which is hereby incorporated by reference in its entirety) (FIGS. 122A and 122C). Additionally, weaker dauer inducation with part#9 was observed, whereas all other compounds tested were inactive in this assay. Testing the synthetic compounds in the mouth dimorphism assay, the dimeric compound dasc#1, which was inactive in the dauer formation assay, was found to strongly induce the eurystomatous mouth form (FIGS. 122B and 122D). In addition, weaker induction of the eurystomatous mouth form was observed for high concentrations of pasc#9, ascr#1, and npar#1, whereas dimeric ubas#1 as well as monomeric ascr#9 and part#9 were inactive.

These results show that adult phenotypic plasticity and larval development in *P. pacificus* are controlled by distinct yet partially overlapping sets of signaling molecules. Whereas mouth-form dimorphism is primarily regulated by dasc#1, the product of highly specific ascaroside dimerization, dauer formation is controlled by a molecule combining a paratoside with an unusual nucleoside. Previous work showed that the signaling molecules controlling phenotypic plasticity in *P. pacificus* act upstream of evolutionarily conserved transcription factors including DAF-16/FOXO and the nuclear hormone receptor DAF-12 (FIG. 122E) (Ogawa et al., *Development* 138:1281-84 (2011); Sommer & Ogawa, *Curr. Biol.* 21:R758-R66 (2011), which are hereby incorporated by reference in their entirety), whereby daf-12 is required for both dauer induction and mouth-form dimorphism, whereas daf-16, is required for dauer induction but dispensable for regulation of mouth-form dimorphism (Ogawa et al., *Development* 138:1281-84 (2011), which is hereby incorporated by reference in its entirety). Therefore, the different subsets of small molecules regulating dauer formation and mouth-form dimorphism appear to target different downstream effectors. The present Examples further demonstrate species-specific co-option of small molecule biosynthetic pathways for regulating different types of phenotypic plasticity, as ascr#1 contributes to dauer in *C. elegans*, whereas its dimer dasc#1 regulates adult morphology in *P. pacificus*. Based on the recent identification of GPCRs as receptors of the *C. elegans* dauer pheromone (McGrath et al., *Nature* 477:321-25 (2011), which is hereby incorporated by reference in its entirety), it is probable that specific GPCRs in *P. pacificus* connect npar#1, dasc#1 with their respective downstream pathways.

The structures of the identified small-molecule signals appear to integrate specific inputs from the major primary metabolic pathways: fatty acid, carbohydrate, amino acid, and nucleoside metabolism (FIG. 122E). Modular assembly of building blocks from these pathways generates diverse molecular architectures, which are further distinguished from any previously known animal metabolites by an unusual nucleoside modification, resulting in a xylopyranose-based adenosine. This unprecedented nucleoside is likely derived from metabolism of canonical (ribo)-threonylcarbamoyl adenosine (t6A), a highly conserved nucleoside found directly adjacent to the anticodon triplet of a subset of tRNAs (Deutsch et al., *J. Biol. Chem.* 287:13666-73 (2012), which is hereby incorporated by reference in its entirety). t6A plays an important role for maintaining translational fidelity; however, it usually accounts for only a very small fraction of tRNA, and the production of large quantities of a xylopyranose derivative in *P. pacificus* is surprising.

The present Examples provide direct evidence for small-molecule control of adult phenotypic plasticity in a metazoan that relies on conserved endocrine signaling pathways. Whether the biosynthesis of the identified signaling molecules also involves conserved pathways or depends on dedicated enzymes specific to *P. pacificus* (and perhaps other nematodes) is not known. However, the finding that the *P. pacificus* compounds are derived from assembly of modified primary metabolites suggests that their biosynthesis is largely based on conserved biochemical pathways (FIG. 122E). Notably, the *P. pacificus* genome contains more than 25,000 gene predictions with many specific gene duplication events among genes encoding primary metabolic enzymes (Dieterich et al., *Nat. Genet.* 40:1193-98 (2008); Borchert et al., *Genome Res.* 20:837-46 (2010), which are hereby incorporated by reference in their entirety). Supporting the involvement of primary metabolism in the biosynthesis of nematode signaling molecules, recent investigations of ascaroside biogenesis in *C. elegans* showed that the lipid-like ascaroside side chains are derived from conserved peroxisomal-β-oxidation (von Reuss et al., *J. Am. Chem. Soc.* 134:1817-24 (2012); Butcher et al., *Proc. Nat'l Acad. Sci. U.S.A.* 106:1875-79 (2009), which are hereby incorporated by reference in their entirety). Known signaling molecules and co-factors in higher animals, e.g. S-adenosyl methionine or phosphatidylinositols, often rely on combination of building blocks derived from one or two different primary metabolic pathways. The present Examples demonstrate that metazoans may extend such strategies to produce signaling molecules of much greater structural complexity, suggesting that detailed spectroscopic re-analysis of metabolomes from higher animals, including mammals, may also reveal novel types of modular small-molecule signals.

Example 105

C. elegans Strains and General Culture Methods

Wild-type C. elegans (N2, Bristol), daf-22(m130), daf-22(ok693), acox-1(ok2257), maoc-1 (hj13), and dhs-28 (hj8) mutant strains were obtained from the Caenorhabditis Genetics Center (CGC). Strains were maintained at 20° C. on NGM plates with bacteria (E. coli OP50) as food.

Example 106

Preparation of C. elegans Metabolite Extracts

Liquid cultures were grown as reported in (Pungaliya et al., Proc. Nat'l Acad. Sci. U.S.A. 106:7708 (2009), which is hereby incorporated by reference in its entirety). Briefly, wild-type or daf-22 mutant worms were grown for two generations on NGM plates seeded with OP50. Three crowded 6 cm NGM plates were washed into 100 mL solution of S-medium in a 500 mL Erlenmeyer flask and grown at 22° C. and 220 pm. Concentrated OP50 from 1 L bacterial cultures, grown overnight, were given on day 1 and day 3. On day 5 the liquid culture was split into two 500 mL Erlenmeyer flasks and the growth media volume was maintained at 100 mL. An additional 1 L OP50 pellet was given as food upon splitting. The cultures were harvested on day 7 by centrifugation at 4750 rpm. The supernatant was lyophilized and the residue extracted with 95% ethanol (300 mL) at room temperature for 12 hours. The resulting suspension was filtered and evaporated in vacuo at room temperature to yield the crude extracts. In this manner four extracts each of wild-type (N2), daf-22(m130), and daf-22 (ok693) cultures were prepared. For NAE quantification, mutant strains were grown as above in duplicate. Liquid cultures for ascaroside mixture experiments were prepared as described above with addition of 2.5 µM of ascr#3 and 2.5 µM of ascr#9 at day 0.

In preparation for NMR-spectroscopic analysis, the crude extracts were suspended in 1:8 methanol (MeOH):dichloromethane (DCM), using 7.5 mL of this solvent mixture per 1 gram of crude extract. Following centrifugation, 2 ml aliquots of supernatant of each sample were filtered over 1 g of silica (EMD Chemicals Inc.) using 10 mL of 1:8 MeOH:DCM for elution. The filtrate was evaporated to dryness in vacuo prior to analysis. For NMR spectroscopic analysis, 10-20 mg of the resulting metabolite extracts was used.

Example 107

Preparation of Bacterial Metabolite Extracts

E. coli OP50 was grown overnight at 37° C. and 220 rpm to an OD of 1.2 in 2 L of Lysogeny broth (LB). The bacterial broth was spun for 20 minutes at 4750 rpm. The supernatant was then lyophilized, crushed with mortar and pestle, and extracted with 150 mL 95% ethanol (2 times). The extract was filtered through a sintered crucible and concentrated in vacuo prior to analysis.

Example 108

Mass Spectrometric Analysis

Metabolite extracts prepared as described above were resuspended in 1.5 mL methanol, centrifuged, and 30 µL of this sample was injected into HPLC-MS for analysis. HPLC-MS analysis was performed using the Agilent 1100 Series HPLC system with an Agilent Eclipse XDB-C18 column (9.4×250 mm, 5 µm particle diameter) connected to the Quattro II mass spectrometer using a 10:1 split. For short chain ascarosides, a 0.1% aqueous acetic acid-acetonitrile gradient was used. The gradient started with 5% acetonitrile for 5 minutes, then increased to 100% acetonitrile over 32 minutes. For long chain ascarosides, an acetonitrile-isopropanol gradient was used, starting with 5% isopropanol in acetonitrile for 5 minutes; then isopropanol was increased to 75% over 32 minutes. Samples were analyzed by HPLC-ESI-MS in negative and positive ion modes using a capillary voltage of 3.5 kV and a cone voltage of −40 V and +20 V, respectively. The elemental composition of the long chain ascarosides was performed by high resolution MS and HPLC-MS using the Xevo G2 QT of.

EPEA and AEA (14) were quantified by HPLC-MS (using the Quattro II) using a water (0.1% acetic acid)—acetonitrile gradient as described above for short chain ascarosides. The retention time of EPEA and AEA were established by injection of an authentic standard (Enzo Life Sciences and Cayman Chemicals, respectively). Relative endocannabinoid content in wild type and mutant strains was quantified by integration of LC-MS signals from corresponding ion traces for $(M-H)^-$ or $(M+Cl)^-$. All integration values were normalized by the mass of the liquid culture pellet. All quantitative data reported in FIG. 123 were from at least two independent biological repeats.

Example 109

NMR Spectrometric Analysis

NMR samples sample were prepared by dissolving 10-20 mg portions of metabolite extract (see Example 107) in 0.6 ml of $CD_3OD$. Samples were analyzed using a Varian INOVA 600 MHz NMR spectrometer. Non-gradient phase-cycled dqfCOSY spectra were acquired using the following parameters: 0.8 s acquisition time, 600 complex increments, 16 scans per increment. For processing with mvaDANS, spectra were zero-filled to 2048×1024 data points, a sine-square-shaped window function was applied in both dimensions prior to Fourier transformation, and spectra converted to magnitude mode prior to transfer to MATLAB.

For detailed analysis in phase-sensitive mode, dqfCOSY spectra were zero-filled to 8192×4096 data points and a cosine bell-shaped window function was applied in both dimensions before Fourier transformation. Gradient and non-gradient HSQCAD and HMBC spectra of purified fractions of daf-22-upregulated metabolites were acquired using 8-32 scans, 0.25 s acquisition time, and 256-500 complex increments. NMR spectra were processed using Bruker TopSpin, Varian VNMR, MestreLabs' MestReC, and MNova software packages.

Example 110

Isolation of Major daf-22-Upregulated Metabolites

To 8 g of Celite (prewashed with ethyl acetate) was added a solution of daf-22 metabolite extract from 16 100-ml liquid cultures. After evaporation of the solvent, the material was dry-loaded into an empty 25 g RediSep® Rf loading cartridge. Fractionation was performed using a Teledyne ISCO CombiFlash® system over a RediSep® Rf GOLD 40 g HP Silica Column using a normal phase dichloromethane-methanol solvent system, starting with 6 minutes of 100% dichloromethane, followed by a linear increase of methanol content up to 10% at 24 minutes, followed by another linear increase of methanol content up to 40% at 40 minutes, followed by another linear increase of methanol content up to 95% at 45 minutes which was then continued to 48 minutes. This yielded 70 fractions (~20 mL each) which were individually evaporated in vacuo and analyzed by NMR spectroscopy ($^1$H NMR, dqfCOSY) and HPLC-MS. $^1$H NMR-spectroscopic signals identified via mvaDANS as representing daf-22-upregulated metabolites were detected in fractions 35-45. Isolation of major daf-22-upregulated metabolites was achieved by preparative HPLC using the same HPLC method described in Example 90 for HPLC-MS analysis of long chain ascarosides. Isolated fractions were characterized further by dqfCOSY, HSQC, and HMBC as well as high-resolution HPLC-MS using the Xevo G2 QT of.

Example 111

Statistical Analysis

Unpaired student's t-tests with Welch's correction for comparing the relative abundance of EPEA and AEA in wild type and mutant strains was used. *P<0.05, P<0.01, *P<0.001. See FIG. 123D and FIG. 124.

Example 112 mvaDANS Analysis

Figure 130:
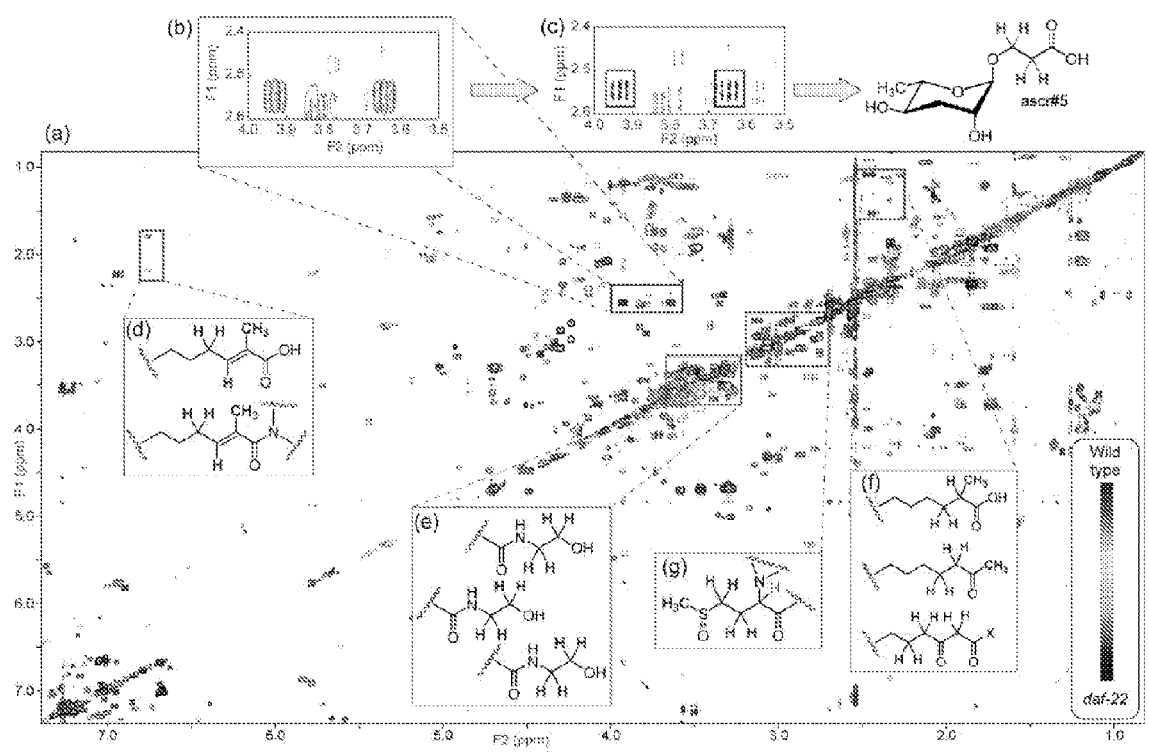

For identification of daf-22-upregulated metabolites via mvaDANS, dqfCOSY spectra were acquired for metabolome extracts obtained from two different daf-22 alleles (m130, ok693) and wild-type *C. elegans* (FIGS. 125, 126, and 127). dqfCOSY spectra from four independent biological replicates were processed in magnitude mode using the mvaDANS algorithm in Matlab, which incorporated dynamic binning and multivariate pattern recognition analysis (FIG. 128). Automatic cross peak identification and binning converted each of the dqfCOSY spectra into a set of crosspeak integrals which were corrected for dilution using Probabilistic Quotient Normalization (Dieterle et al., *Anal. Chem.* 78:4281 (2006), which is hereby incorporated by reference in its entirety), mean-centered, and scaled to unit variance. This matrix of bin integrals was then subjected to statistical analysis including two-way hierarchical clustering, Principal Component Analysis (PCA) (FIG. 125A) (Wold et al., *Chemometr. Intell. Lab. Syst.* 2:37 (1987), which is hereby incorporated by reference in its entirety), and Partial Least Squares—Discriminant Analysis (PLS-DA) (FIG. 129) (de Jong, *Chemometr. Intell. Lab. Syst.* 18:251 (1993), which is hereby incorporated by reference in its entirety). Coefficients from PCA loadings and PLS-DA predictors were back-projected onto the dqfCOSY spectra to enable the detection of NMR spectroscopic signals representing compounds differentially expressed in the three *C. elegans* strains (FIGS. 130 and 131).

Automatic Cross Peak Identification and Integration for mvaDANS

Spectral segments are detected from a representative pseudo-spectrum-here, an average spectrum calculated from the mean along the third dimension of the spectral stack. To identify segments of the pseudo-spectrum corresponding to crosspeak regions, a local noise surface is calculated using the AUTOPSY (Koradi, *J. Magnetic Res.* 135:288 (1998), which is hereby incorporated by reference in its entirety) method (equations 1-4). AUTOPSY calculates a point-wise estimation of underlying noise as follows.

$$d_x = \min\left(\sqrt{\frac{1}{n}\sum_{i=1}^{n}(\delta_{xi} - \overline{\delta_x})^2}\right) \quad (1)$$

$$d_y = \min\left(\sqrt{\frac{1}{n}\sum_{i=1}^{n}(\delta_{iy} - \overline{\delta_y})^2}\right) \quad (2)$$

$$b = \min([d_x, d_y]) \quad (3)$$

$$p_{xy} = \sqrt{\left(\sqrt{d_x^2 - b^2}\right)^2 + \left(\sqrt{d_y^2 - b^2}\right)^2 + b^2} \quad (4)$$

Here, $d_x$ and $d_y$ are noise values for each slice x and y in the direct and indirect dimensions of the 2D NMR spectrum, respectively. The noise value for a given slice $\delta_x$ or $\delta_y$ is calculated by splitting the slice up into 16 regions of size n=F1/16 for the direct dimension and n=F2/16 for the indirect dimension. The noise for that trace is then the standard deviation of the region with the minimum standard deviation as shown in equations 1 and 2. Each point p in the spectrum is intersected by two slices x and y whose noise values are $d_x$ and $d_y$. The noise at point $p_{xy}$ combines the noise in slice x with the noise in slice y with a baseline noise value b as in equations 3 and 4. This method of calculating noise is very well suited to the noise structure of 2D NMR data, which is characterized by vertical noise such as T1 and water noise.

Once the noise surface $p_{xy}$ has been calculated, peaks can be detected by identifying local maxima above a certain multiple of the noise surface. While the exact threshold can vary, values of 5-10 detect the large majority of cross-peaks. A threshold of 10 was used for the high-concentration *C. elegans* samples used here. Segments are then defined as regions adjacent to detected peaks.

Initial spectral segments are identified as regions within 0.04 ppm of a peak in the $^1$H dimension of homonuclear spectra. In the case of multiplicity, local maxima are grouped together into a single initial segment. Each segment is then labeled with a unique integer value and iterated minimum and maximum filtering expand these initial segments. Min/max filtering has the effect of growing the segments until they encounter another spectral segment or until they reach a maximum frequency range of approximately 0.2 ppm for $^1$H. This procedure creates spectral segments with non-rectangular bounds that are bounded by nearby resonances yet avoid close cropping of cross-peak line shapes. These segments are then integrated using a trapezoidal numerical integration.

Pattern Recognition Using Spectral Bins

Integration of detected spectral segments transforms the 2D NMR dataset from a three-dimensional stack of full resolution 2D spectra ($\omega_1, \omega_2, N$) to a two-dimensional matrix of features (N,P) where P is the number of detected segments. The resulting matrix of bin intensities is then normalized using Probabilistic Quotient Normalization (Dieterle et al., *Anal. Chem.* 78:4281 (2006), which is hereby incorporated by reference in its entirety) and variance stabilized using univariate scaling. These approaches, sometimes referred to as column-wise and row-wise normalization, are frequently applied in metabolomic data processing to account for dilution between samples or receiver gain differences between spectra and balance the variance of high and low intensity signals. Pattern recognition methods PCA and PLS-DA were then applied directly to the transformed bin matrix. The result of pattern recognition is, for each component in the model, a set of N scores showing the similarity of the samples to each other and a vector of P coefficients (referred to as loadings or predictors) that indicate the contribution of each bin to the separation between the samples.

The matrix of peak integrals was also represented as a $\log_2$-fold-change vs. median heatmap. The heatmap was clustered using the UPGMA hierarchical clustering algorithm (Gordon, *J. Royal Stat. Soc. Ser. A Stat. Soc.* 150:119 (1987), which is hereby incorporated by reference in its entirety). Representing the bin matrix as a clustered heatmap allows rapid identification of groups of cross-peaks whose differential levels differentiate experimental classes. Additionally, PLS-DA predictors and PCA loadings were ordered using the clustered indices of the cross peak regions. This representation displays the features of the data that are identified by pattern recognition.

To interpret the model and identify important metabolites, coefficients are back projected onto the full resolution spectra by using the spectral segments. For all segments in the full resolution matrix, the data points within the segment are replaced with the value of the coefficient from pattern recognition of the bin extracted from that segment to produce a full resolution loadings matrix. For stabilized data, loading coefficients are independent of signal intensity and thus peak shape is not visible. To produce full-resolution back-projected loadings that look like 2D NMR spectra, this matrix is then multiplied point-wise by the standard deviation along the third dimension of the 2D NMR stack. To visualize the loadings, contour lines are defined by the back-projected loadings, and the colors of these lines are defined by the coefficients themselves. While the mvaDANS algorithm was applied to dqfCOSY data processed in magnitude mode to reduce the number of local minima/maxima, regions of interest identified by mvaDANS were cross-referenced with the original phase-sensitive data for greater structural detail. mvaDANS is natively compatible with other $^1$H-$^1$H NMR experiments, including TOCSY, COSY, and NOESY, and is compatible with only a few changes in parameters to heteronuclear experiments, including $^1$H-$^{13}$C HSQC.

Validation and Spectral Interpretation

For analysis of daf-22 specific crosspeaks, the back projection spectrum was overlaid with the original daf-22 dqfCOSY spectra, processed in phase-sensitive mode. Spin systems including chemical shift and coupling constant values were obtained via manual interpretation of the original phase-sensitive spectra. Using available databases (Reaxys, Beilstein, Scifinder, HMDB, NMRshiftDB, BMRB), hypotheses about partial structures representing the identified spin systems were developed. Partial fractionation of daf-22 exo-metabolome was used to generate enriched samples of the identified metabolites for further NMR-spectroscopic analysis via HMQC and HMBC (see Example 110).

Back projections from PCA analysis were used to identify daf-22 specific crosspeaks. PLS-DA analysis was used to validate the statistically based separation of wild-type and daf-22 metabolomes (FIG. 129). Back projections from PLS-DA predictors (FIG. 131) largely matched the back projection from PC 1 loadings (FIG. 130). Peaks prominently present in dqfCOSY spectra of *E. coli* OP-50 metabolite extract (FIG. 132) were excluded from further analysis.

Example 113 daf-22 Mutant-Specific Very Long Chain Ascarosides daf-22 mutant-specific VLCAs 24R)-(3'R,5'R-dihydroxy-6'S-methyl-(2H)-tetrahydropyran-2'-yloxy)-2-methyl-3-oxopentacosanoic acid ethanolamide (7), (26R)-(3'R,5'R-dihydroxy-6'S-methyl-(2H)-tetrahydropyran-2'-yloxy)-3-oxo-heptacosanoic acid ethanolamide (8), 24R)-(3'R,5'R-dihydroxy-6'S-methyl-(2H)-tetrahydropyran-2'-yloxy)-2-methyl-2E-pentacosenoic acid ethanolamide (9), 24R)-(3'R, 5'R-dihydroxy-6'S-methyl-(2H)-tetrahydropyran-2'-yloxy)-2-methyl-2E-pentacosenoic acid (10), and (24R)-(3'R,5'R-dihydroxy-6'S-methyl-(2H)-tetrahydropyran-2'-yloxy)-2-methyl-pentacosanoic acid (11) (see FIG. 123B) were identified using the methods described in Examples 105-112. Their structures and spectroscopic data are shown in Table 17 below.

TABLE 17

Spectroscopic data for VLCAs 7-11

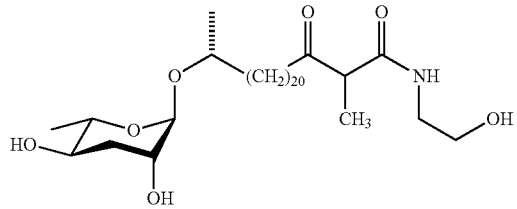

7

$^1$H NMR*: δ 4.69 (m, 1H, 2'-H); 3.81 (m, 1H, 3'-H); 1.86 (ddd, J = 13.5, J = 11.0, J = 3.1, 1H, 4'-H$_{ax}$); 2.08
(ddd, J = 13.5, J = 4.5, J = 3.3, 1H, 4'-H$_{eq}$); 3.60 (ddd, J = 11.0, J = 9.2, J = 4.5, 1H, 5'-H); 3.70 (dq, J = 9.2,
J = 6.3, 1H, 6'-H); 1.27 (d, J = 6.3, 3H, 6'-CH$_3$); 1.12 (d, J = 6.2, 3H, 25-H); 3.79 (m, 1H, 24-H); 1.56 (m,
1H, 23-H); 1.43 (m, 1H, 23-H); 1.30-1.20 (m, 34H, 6-22H); 1.56 (m, 2H, 5-H); 2.55 (td, J = 7.3, J = 2.3,
2H, 4-H, 3.45 (qd, J = 6.5, J = 2.3, 1H, 2-H); 1.40 (d, J = 6.5, 3H, 2-CH$_3$); 3.43 (q, J = 5.2, 2H, 1''-H);
3.72 (t,
J = 5.0, 2H, 2''-H); 6.72 (t, J = 5.5, 1H, N-H).

TABLE 17-continued

Spectroscopic data for VLCAs 7-11

$^{13}$C NMR**: δ 96.0 (C-2'); 69.4 (C-3'); 35.1 (C-4'); 68.1 (C-5'); 69.7 (C-6'); 17.6 (6'-$\underline{C}$H$_3$); 18.9 (C-25); 71.7
(C-24); 37.2 (C-23); 28.9-30.5 (C-22-C-6); 23.3 (C-5); 41.7 (C-4); 210.3 (C-3); 54.0 (C-2); 15.3 (2-$\underline{C}$H$_3$) 171.1 (C-1); 42.5 (C-1''); 62.3 (C-2'').
HR-MS (ESI$^+$): calculated for C$_{34}$H$_{65}$NO$_7$Na [M + Na]$^+$ 622.4653, observed 622.4728.

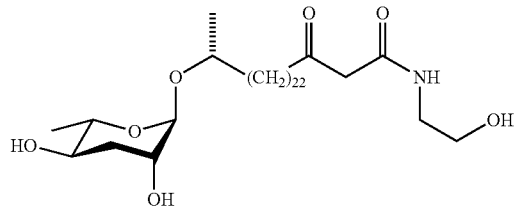

8

$^1$H NMR*: δ 4.70 (m, 1H, 2'-H); 3.81 (m, 1H, 3'-H); 1.84 (ddd, J = 13.5, J = 11.0, J = 3.1, 1H, 4'-H$_{ax}$); 2.07
(ddd, J = 13.5, J = 4.5, J = 3.3, 1H, 4'-H$_{eq}$); 3.61 (ddd, J = 11.0, J = 9.3, J = 4.5, 1H, 5'-H); 3.69 (dq, J = 9.3,
J = 6.2, 1H, 6'-H); 1.27 (d, J = 6.3, 3H, 6'-C$\underline{H}$$_3$); 1.12 (d, J = 6.2, 3H, 27-H); 3.79 (m, 1H, 26-H); 1.56 (m,
1H, 25-H); 1.42 (m, 1H, 25-H); 1.30-1.20 (m, 38H, 6-24H); 1.57 (m, 2H, 5-H), 2.53 (t, J = 7.5, 2H, 4-H),
(3.43, s, 2H, 2-H), 3.46 (q, J = 5.2, 2H, 1''-H); 3.74 (t, J = 5.0, 2H, 2''-H); 7.42 (t, J = 5.5, 1H, N-H).
$^{13}$C NMR**: δ 96.1 (C-2'); 69.4 (C-3'); 35.1 (C-4'); 68.1 (C-5'); 69.7 (C-6'); 17.6 (6'-$\underline{C}$H$_3$); 18.9 (C-27); 71.7
(C-26); 37.2 (C-25); 28.9-30.5 (C-24-C-6); 23.3 (C-5); 44.0 (C-4); 207.4 (C-3); 48.4 (C-2); 167.0 (C-1); 42.6 (C-1''); 62.3 (C-2'').
HR-MS (ESI$^+$): calculated for C$_{35}$H$_{67}$NO$_7$Na [M + Na]$^+$ 636.4810, observed 636.4851.

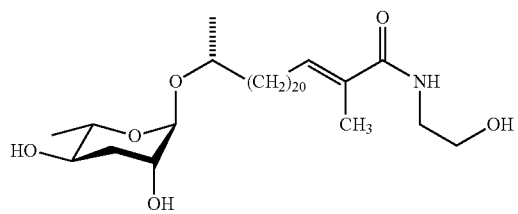

9

$^1$H NMR*: δ 4.70 (m, 1H, 2'-H); 3.81 (m, 1H, 3'-H); 1.84 (ddd, J = 13.5, J = 11.0, J = 3.1, 1H, 4'-H$_{ax}$); 2.07
(ddd, J = 13.5, J = 4.5, J = 3.3, 1H, 4'-H$_{eq}$); 3.61 (ddd, J = 11.0, J = 9.4, J = 4.5, 1H, 5'-H); 3.70 (dq, J = 9.4,
J = 6.2, 1H, 6'-H); 1.28 (d, J = 6.2, 3H, 6'-C$\underline{H}$$_3$); 1.12 (d, J = 6.2, 3H, 25-H); 3.79 (m, 1H, 24-H); 1.56 (m,
1H, 23-H); 1.42 (m, 1H, 23-H); 1.34-1.20 (m, 34H, 6-22H); 1.41 (m, 2H, 5-H); 2.14 (q, J = 7.2, 2H, 4-H);
6.41 (tq, J = 7.2, J = 1.2, 1H, 3-H); 1.86 (m, 3H, 2-C$\underline{H}$$_3$); 3.50 (q, J = 5.2, 2H, 1''-H); 3.77 (t, J = 5.0, 2H, 2''-H); 6.15 (t, J = 5.5, 1H, N-H).
$^{13}$C NMR**: δ 96.1 (C-2'); 69.4 (C-3'); 35.1 (C-4'); 68.1 (C-5'); 69.7 (C-5'); 17.6 (6'-$\underline{C}$H$_3$); 18.9 (C-25); 71.7
(C-24); 37.2 (C-23); 28.9-30.5 (C-22-C-5); 28.4 (C-4); 137.3 (C-3); 129.9 (C-2); 12.6 (2-$\underline{C}$H$_3$); 170.7 (C-1);
42.8 (C-1''); 62.9 (C-2'').
HR-MS (ESI$^+$): calculated for C$_{34}$H$_{65}$NO$_7$Na [M + Na]$^+$ 622.4653, observed 622.4728.

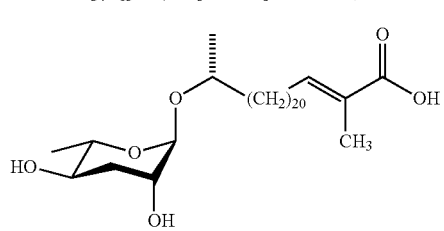

10

$^1$H NMR*: δ 4.71 (m, 1H, 2'-H); 3.81 (m, 1H, 3'-H); 1.84 (ddd, J = 13.5, J = 11.0, J = 3.1, 1H, 4'-H$_{ax}$); 2.07
(ddd, J = 13.5, J = 4.5, J = 3.3, 1H, 4'-H$_{eq}$); 3.61 (ddd, J = 11.0, J = 9.4, J = 4.5, 1H, 5'-H); 3.70 (dq, J = 9.4,
J = 6.2, 1H, 6'-H); 1.27 (d, J = 6.2, 3H, 6'-C$\underline{H}$$_3$); 1.12 (d, J = 6.2, 3H, 25-H); 3.79 (m, 1H, 24-H); 1.56 (m,
1H, 23-H); 1.42 (m, 1H, 23-H); 1.34-1.20 (m, 34H, 6-22H); 1.45 (m, 2H, 5-H); 2.18 (q, J ≈ 7, 2H, 4-H);
6.87 (tq, J = 7.2, J = 1.4, 1H, 3-H); 1.82 (m, 3H, 2-C$\underline{H}$$_3$).
$^{13}$C NMR**: δ 96.2 (C-2'); 69.4 (C-3'); 35.1 (C-4'); 68.1 (C-5'); 69.7 (C-6'); 17.6 (6'-$\underline{C}$H$_3$); 18.9 (C-25); 71.7

TABLE 17-continued

Spectroscopic data for VLCAs 7-11

(C-24); 37.2 (C-23); 29-30.5 (C-22-C-5); 28.5 (C-4); 145.0 (C-3); 126.6 (C-2); 12.2 (CH$_3$-C2); 170.5 (C-1).
HR-MS (ESI$^+$): calculated for C$_{32}$H$_{60}$NO$_6$Na [M + Na]$^+$ 563.4282, observed 563.4283.

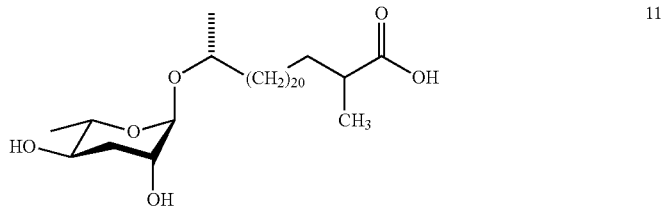

11

$^1$H NMR*: δ 4.71 (m, 1H, 2'-H); 3.81 (m, 1H, 3'-H); 1.84 (ddd, J = 13.5, J = 11.0, J = 3.1, 1H, 4'-H$_{ax}$); 2.07
(ddd, J = 13.5, J = 4.5, J = 3.3, 1H, 4'-H$_{eq}$); 3.60 (ddd, J = 11.0, J = 9.4, J = 4.5, 1H, 5'-H); 3.70 (dq, J = 9.4,
J = 6.3, 1H, 6'-H); 1.27 (d, J = 6.3, 3H, 6'-CH$_3$); 1.12 (d, J = 6.2, 3H, 25-H); 3.79 (m, 1H, 24-H); 1.56 (m,
1H, 23-H); 1.42 (m, 1H, 23-H); 1.35-1.20 (m, 38H, 4-22H); 1.67 (m, 1H, 3-H); 1.42 (m, 1H, 3-H); 2.46
(sext., J = 7, 1H, 2-H); 1.17 (d, J = 6.8, 3H, 2-CH$_3$).
$^{13}$C NMR**: δ 96.2 (C-2'); 69.4 (C-3'); 35.1 (C-4'); 68.1 (C-5'); 69.7 (C-6'); 17.6 (6'-CH$_3$); 18.9 (C-25); 71.7
(C-24); 37.2 (C-23); 29.0-30.5 (C-22-C-4); 28.5 (C-4); 33.8 (C-3); 39.2 (C-2); 17.0 (2-CH$_3$); 179.5 (C-1).
HR-MS (ESI$^+$): calculated for C$_{32}$H$_{60}$NO$_6$Na [M + Na]$^+$ 563.4282, observed 563.4283.

*(CDCl$_3$, 600 MHz)
**(CDCl$_3$, 151 MHz)

Example 114 daf-22 Mutant-Specific Very Long Chain Ascaroside (ω-1)-O-Ascarosyl 2-Ketones (12)

A series of daf-22 mutant-specific VLCA (ω-1)-O-ascarosyl 2-ketones (12) (see FIG. 123C), including (23R)-(3'R, 5'R-Dihydroxy-6'S-methyl-(2H)-tetrahydropyran-2'-yloxy)-tetracosan-2-one (12a), were identified using the methods described in Examples 105-112. The structure and spectroscopic data of 12a are shown in Table 18 below.

TABLE 18

Spectroscopic data for VLCA 12a

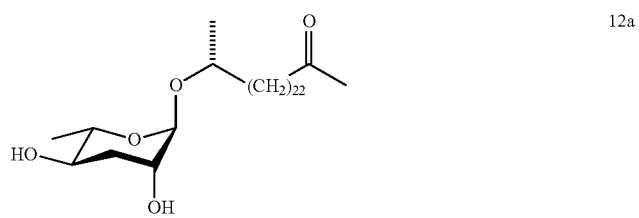

12a $^1$H NMR (CDCl$_3$, 600 MHz): δ 4.70 (m, 1H, 2'-H); 3.81 (m, 1H, 3'-H); 1.84 (ddd, J = 13.5, J = 11.0, J = 3.1,
1H, 4'-H$_{ax}$); 2.07 (ddd, J = 13.5, J = 4.5, J = 3.3, 1H, 4'-H$_{eq}$); 3.59 (ddd, J = 11.0, J = 9.2, J = 4.5, 1H, 5'-H);
3.69 (dq, J = 9.2, J = 6.2, 1H, 6'-H); 1.27 (d, J = 6.2, 3H, 6'-CH$_3$); 1.12 (d, J = 6.2, 3H, 26-H); 3.79 (m, 1H,
25-H); 1.56 (m, 1H, 24-H); 1.42 (m, 1H, 24-H); 1.35-1.20 (m, 38H, 5-23H); 1.56 (m, 2H, 4-H); 2.41 (t, J =
7.5, 2H, 3-H); 2.13 (s, 3H, 1-H).
$^{13}$C NMR (CDCl$_3$, 151 MHz): δ 96.2 (C-2'); 69.4 (C-3'); 35.1 (C-4'); 68.1 (C-5'); 69.7 (C-6'); 17.6 (6'-CH$_3$);
18.9 (C-24); 71.7 (C-23); 37.2 (C-22); 29.0-30.5 (C-21-C-5); 23.9 (C-4); 43.8 (C-3); 209.6 (C-2); 29.9 (C-1).
HR-MS (ESI$^+$): calculated for C$_{32}$H$_{62}$O$_5$Na [M + Na]$^+$ 549.4495, observed 549.4501.

The structure and HPLC/HR-MS (ESI⁺) data of the series of VLCA (ω-1)-O-ascarosyl 2-ketones (12) are shown in Table 19 below.

TABLE 19

HPLC/HR-MS (ESI⁺) data of (ω-1)-ascarosyl-2-oxoalkanes (12)

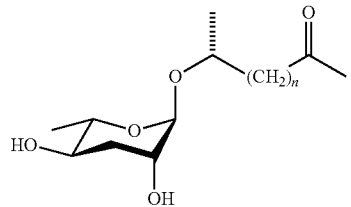

12

| Side chain length (n) | Molecular formula | Molecular weight [amu] | m/z [M + Na]⁺ calculated | m/z [M + Na]⁺ observed | Retention time [min] |
|---|---|---|---|---|---|
| 18 | $C_{28}H_{54}O_5$ | 470.3971 | 493.3869 | 493.3869 | 6.55 |
| 19 | $C_{29}H_{56}O_5$ | 484.4128 | 507.4025 | 507.4024 | 7.33 |
| 20 | $C_{30}H_{58}O_5$ | 498.4284 | 521.4182 | 521.4178 | 8.39 |
| 21 | $C_{31}H_{60}O_5$ | 512.4441 | 535.4338 | 535.4346 | 9.52 |
| 22 | $C_{32}H_{62}O_5$ | 526.4597 | 549.4495 | 549.4501 | 11.14 |
| 23 | $C_{33}H_{64}O_5$ | 540.4754 | 563.4651 | 563.4650 | 12.95 |
| 24 | $C_{34}H_{66}O_5$ | 554.491 | 577.4808 | 577.4807 | 15.06 |
| 25 | $C_{35}H_{68}O_5$ | 568.5067 | 591.4964 | 591.4967 | 17.50 |
| 26 | $C_{36}H_{70}O_5$ | 582.5223 | 605.5121 | 605.5116 | 20.55 |

Discussion of Examples 105-114

Analyses of the *C. elegans* metabolome revealed a family of structurally diverse small molecules, the ascarosides, as products of conserved peroxisomal β-oxidation (von Reuss et al., *J. Am. Chem. Soc.* 134:1817 (2012); Butcher et al., *Proc. Nat'l Acad. Sci. U.S.A.* 106:1875 (2009); Pungaliya et al., *Proc. Nat'l Acad. Sci. U.S.A.* 106:7708 (2009), each of which is hereby incorporated by reference in its entirety) (see FIGS. 133 and 134). The ascarosides form a modular compound library, integrating building blocks from lipid, carbohydrate, and amino acid metabolism into small molecule signals that regulate key aspects of *C. elegans* biology (Butcher et al., *Nat. Chem. Biol.* 3:420 (2007); Srinivasan et al., *Nature* 454:1115 (2008); Srinivasan et al., *PLoS Biol.* 10:e1001237 (2012); Macosko et al., *Nature* 458:1171 (2009), each of which is hereby incorporated by reference in its entirety). Previous work used mass spectrometry-based comparative metabolomics to characterize the functions of three enzymes in ascaroside biosynthesis, the acyl-CoA oxidase ACOX-1, the enoyl-CoA hydratase MAOC-1, and the 3-hydroxyacyl-CoA dehydrogenase DHS-28 (von Reuss et al., *J. Am. Chem. Soc.* 134:1817 (2012), which is hereby incorporated by reference in its entirety) (see FIG. 134). However, the predicted role of the fourth enzyme in the peroxisomal β-oxidation cascade, which is encoded by the gene daf-22, a close homolog of mammalian 3-keto-acyl-CoA thiolases, could not be confirmed because no characteristic shunt metabolites were found. Given the central role of daf-22 in the proposed peroxisomal β-oxidation pathway, it was hypothesized that other, yet unidentified metabolites accumulate in daf-22 mutants, which may help confirm the biochemical function of this enzyme.

Figure 125:
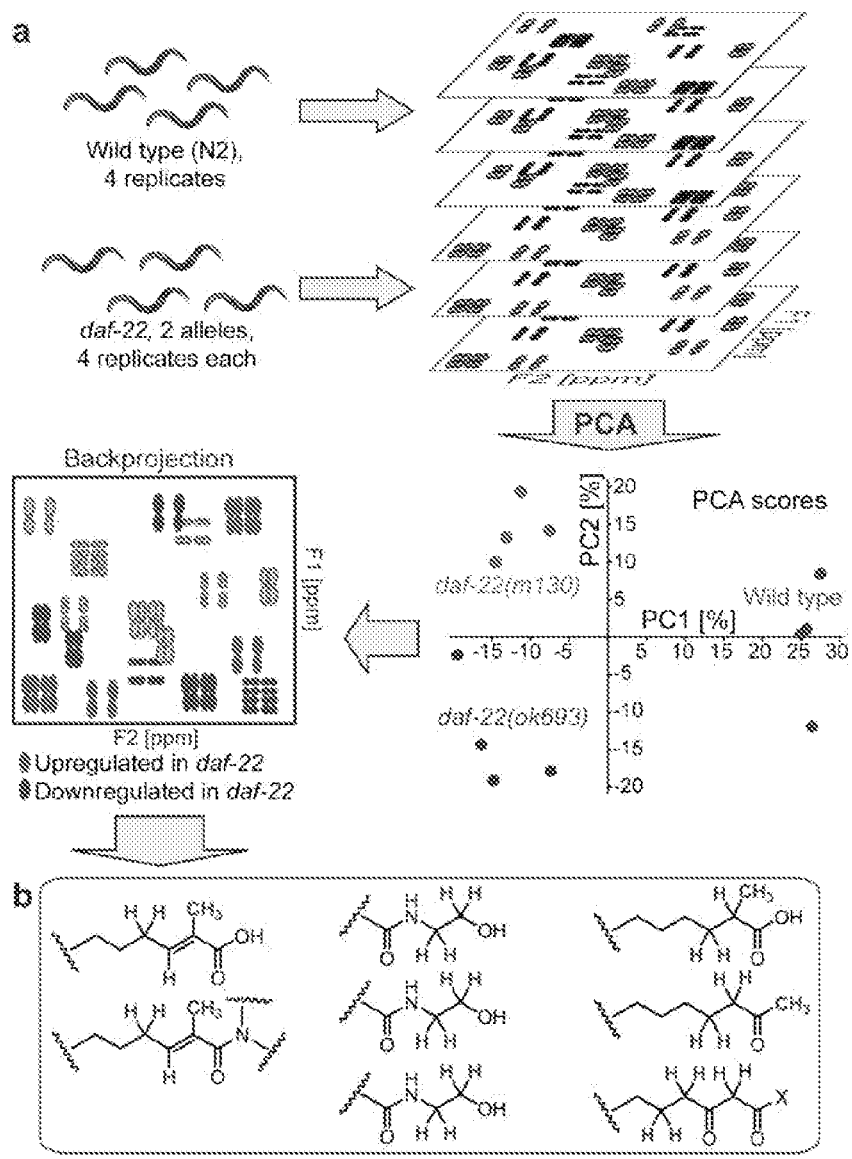

Therefore, the daf-22 metabolome was reinvestigated using unbiased NMR spectroscopy-based metabolomics. Previously, manual comparisons of 2D NMR spectra of wild-type and daf-22 metabolomes had been employed to identify additional members of the ascaroside family of signaling molecules (Pungaliya et al., *Proc. Nat'l Acad. Sci. U.S.A.* 106:7708 (2009); Srinivasan et al., *PLoS Biol.* 10:e1001237 (2012); Robinette et al., *Acc. Chem. Res.* 45:288 (2012), each of which is hereby incorporated by reference in its entirety). These studies highlighted the utility of 2D NMR spectra for comparative metabolomics, but also demonstrated the need for computational tools that would enable statistical analysis of series of spectra from different mutants. For this purpose, multivariate Differential Analysis by 2D NMR Spectroscopy (mvaDANS), which enables automated processing and comparative computational analysis for sets of 2D NMR spectra, was developed.

mvaDANS builds on previous efforts to use 2D NMR for metabolomic analysis by incorporating dynamic signal detection and pattern recognition (Hedenstrom et al., *Mol. Plant.* 2:933 (2009); Hedenstrom et al., *Chemometr. Intell. Lab.* 92:110 (2008); Robinette et al., *Anal. Chem.* 83:1649 (2011); Robinette et al., *Anal. Chem.* 80:3606 (2008); Zhang et al., *Anal. Chem.* 79:7748 (2007); Zhang & Bruschweiler, *Angew. Chem. Int. Ed.* 46:2639 (2007); Zhang et al., *Anal. Chem.* 80:7549 (2008), each of which is hereby incorporated by reference in its entirety) (see Example 112). FIG. 125 summarizes the use of this approach for identifying compounds that are upregulated in daf-22 mutants and thus may represent shunt metabolites or biosynthetic intermediates. dqfCOSY spectra were acquired for metabolome extracts obtained from two different daf-22 alleles (m130, ok693) and wild-type *C. elegans*, including four independent biological replicates (FIGS. 125, 126, and 127). Automatic crosspeak identification and binning (FIG. 128) prepared the dqfCOSY spectra for statistical analysis via Principal Component Analysis ("PCA") (Wold et al., *Chemometr. Intell. Lab.* 2:37 (1987), which is hereby incorporated by reference in its entirety) (see Example 112), which clustered the data by genotype (FIG. 125A). Coefficients from the PCA loadings were back-projected onto the dqfCOSY spectra, which revealed a large number of crosspeaks that are up- or down-regulated in daf-22 mutants relative to wild-type (FIGS. 125A, 130, and 135).

For this study, analysis was restricted to crosspeaks that were strongly featured in spectra from both daf-22 alleles but were very weak or undetectable in wild-type. Furthermore, crosspeaks also present in the *E. coli* food source were excluded. Manual analysis of the remaining strongly daf-22-upregulated crosspeaks and inputs from corresponding HMBC spectra suggested a series of partial structures, including methyl ketones, α-methyl branched fatty acids and corresponding ethanolamides, as well as 3-keto fatty acid derivatives (FIG. 125B). Considering the proposed role of daf-22 in ascaroside biosynthesis (FIG. 134), it was hypothesized that these structural features belong to accumulated shunt metabolites. Subsequent fractionation of the daf-22 metabolome guided by the daf-22-specific NMR signals led to isolation of six different very long-chain ascarosides (VLCA) that account for all of the predicted structural features (FIG. 123; see Examples 113-114 for full spectroscopic data). Most prominent are a series of (ω-1)-O-ascarosyl 2-ketones (12) as well as (ω-1)-O-ascarosyl 3-keto fatty acid ethanolamides, which include the 2-methyl pentacosanoic acid derivative 7 and the straight-chain heptacosanoic acid derivative 8. Compounds 7 and 8 are accompanied by smaller amounts of the corresponding bis-norhomologues. Similarly, the 2-methyl pentacos-2-enoic acid ethanolamide 9 and the two fatty acids 10 and 11 are accompanied by bis-norhomologues. In contrast, chain lengths of the (ω-1)-O-ascarosyl 2-ketones (12) vary more broadly and are not preferentially odd-numbered (FIG. 123C). HPLC-MS analysis confirmed the absence of these components in wild-type samples (FIG. 123A).

The incorporation of ethanolamine in the daf-22 specific VLCAs was unexpected and suggested the possibility of interactions between peroxisomal β-oxidation and ethanolamide-based signaling pathways. Recently, N-acyl-ethanolamines (NAEs) were identified as endocannabinoid-like signaling molecules in C. elegans and linked to dietary restriction-dependent lifespan regulation (Lucanic et al., Nature 473:226 (2010), which is hereby incorporated by reference in its entirety). Whether the upregulation of VLCAs in daf-22 mutants affects NAE levels was evaluated. It was found that NAE production, including the most active endocannabinoid, eicosapentaenoyl ethanolamide (13, EPEA), and arachidonoyl ethanolamide (AEA), was dramatically downregulated in both daf-22 alleles (FIGS. 123D and 124) suggesting a shift of ethanolamine utilization from the NAEs to VLCAs. Similarly, greatly reduced EPEA and AEA production was found in mutants of maoc-1 and dhs-28 (FIGS. 123D and 124) which act directly upstream of daf-22 (FIG. 134). EPEA-levels in acox-1 mutant worms were not significantly affected and AEA levels only slightly decreased, corresponding to the much weaker effect of the acox-1 mutation on peroxisomal β-oxidation (von Reuss et al., J. Am. Chem. Soc. 134:1817 (2012), which is hereby incorporated by reference in its entirety). EPEA and AEA production was not rescued by growing daf-22 worms with addition of synthetic ascarosides (FIGS. 123D and 124), suggesting that the observed reduction of NAE levels in peroxisomal β-oxidation mutants is not an indirect effect of the lack of ascaroside pheromone. These findings indicate that in C. elegans specific defects in peroxisomal β-oxidation result in depletion of endocannabinoid pools (FIG. 123E). It is unknown whether conditions that reduce expression of peroxisomal β-oxidation genes in healthy animals trigger down-regulation of endocannabinoids, which could serve as a regulatory mechanism tying fat metabolism and ascaroside signaling to dietary restriction pathways. Ethanolamides of short-chain ascarosides serve as pheromones in a parasitic nematode species (Noguez et al., ACS Chem. Biol. 7:961 (2012), which is hereby incorporated by reference in its entirety), suggesting that interactions of peroxisomal β-oxidation and ethanolamide metabolism also exist in other nematode genera.

Mammalian homologs of daf-22 are thought to be specifically required for chain shortening of branched-chain fatty acids such as phytanic acid (Wanders & Waterham, Annu. Rev. Biochem. 75:295 (2006); Wanders, Mol. Genet. Metab. 83:16 (2004), each of which is hereby incorporated by reference in its entirety). However, the co-occurrence of straight-chain and methyl-branched derivatives among the daf-22 mutant-specific VLCAs suggests that daf-22 is involved in processing of both branched and straight-chain fatty acids. The chain lengths of the daf-22 mutant-specific VLCAs indicates that 23- to 27-carbon fatty acids may represent endpoints of C. elegans fatty acid biogenesis, in which the last chain-extension step incorporates either malonate or methylmalonate. Notably, the present metabolomic analyses provided no evidence for incorporation of methylmalonate at earlier stages in the biosynthesis of these fatty acid derivatives. The chain lengths of the daf-22 mutant upregulated VLCAs in C. elegans are similar to those of very long-chain fatty acids that accumulate in human disorders involving defects in peroxisomal β-oxidation such as Zellweger syndrome (Wanders & Waterham, Annu. Rev. Biochem. 75:295 (2006); Wanders, Mol. Genet. Metab. 83:16 (2004), each of which is hereby incorporated by reference in its entirety). However, human fatty acid biosynthesis is not known to selectively incorporate propionate or methylmalonate in the last chain-extension step to form α-methyl-branched variants.

In a biosynthetic model (FIGS. 134 and 123E), the identified daf-22 mutant-specific compounds plausibly represent shunt metabolites derived from fatty-acid and β-ketoacid CoA esters, in which the α,β-unsaturation and β-keto functionalities result from upstream action of ACOX-1, MAOC-1, and DHS-28. The daf-22-upregulated long-chain methyl ketones may derive from corresponding β-keto fatty acids, which are highly prone to decarboxylation. Although described in an earlier study (Butcher et al., Proc. Nat'l Acad. Sci. U.S.A. 106:1875 (2009), which is hereby incorporated by reference in its entirety), no evidence for β-keto fatty acids in the present metabolite extracts was found by either NMR spectroscopy or HPLC-MS. The odd-numbered side-chain lengths of the daf-22-upregulated ascarosyl-fatty acids are consistent with the structures of the known end products of peroxisomal β-oxidation, the short-chain ascaroside pheromones, most of which include side chains with 3, 5, 7, or 9 carbons (FIG. 133) (von Reuss et al., J. Am. Chem. Soc. 134:1817 (2012), which is hereby incorporated by reference in its entirety). These odd-numbered side chains further suggest that ascaroside side-chain biosynthesis starts with a three-carbon (methylmalonate) template or that C. elegans elongates odd-numbered fatty acids obtained from food.

In conclusion, mvaDANS-based comparison of daf-22 and wild-type metabolomes revealed long-chain ascarosylethanolamides as an unexpected class of shunt metabolites in daf-22 mutant worms. The abundance of β-keto derivatives and methyl ketones among the identified long-chain ascarosides supports that daf-22 acts as a thiolase in ascaroside pheromone biosynthesis, as had been suspected based on homology to mammalian peroxisomal thiolases.

Untargeted comparative metabolomics will form an important tool for reinvestigating metazoan biochemistry. mvaDANS extends the scope of 2D NMR-based metabolomic analysis (Wishart, Brief Bioinform. 8(5):279-93 (2007); Nicholson et al., Nature Rev. Drug Discov. 1:153 (2002); Gartland et al., Mol. Pharmacol. 39:629 (1991), each of which is hereby incorporated by reference in its entirety) by introducing automated cross-peak identification and integration. Whereas pattern recognition techniques have been applied previously to 2D NMR spectra, these approaches have either relied on manual peak selection (Van et al., J. Proteome Res. 7:630 (2008), which is hereby incorporated by reference in its entirety), parametric approaches (Chylla et al., Anal. Chem. 83:4871 (2011), which is hereby incorporated by reference in its entirety) or used spectral unfolding/refolding techniques (Robinette et al., Anal. Chem. 83:1649 (2011); Hedenstrom et al., Chemometr. Intell. Lab. 92:110 (2008), each of which is hereby incorporated by reference in its entirety). It is expected that advances in statistical spectroscopy will continue to accelerate the structural and functional characterization of biogenic small molecules.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of modifying behavior of a nematode, comprising:

providing a composition comprising a compound of Formula I, or a salt thereof; and administering an effective dosage of the composition to the nematode:

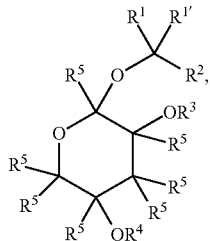

wherein:

each $R^1$ is independently H, —C(R)$_3$, —OR, —N(R)$_2$, halogen, an alkyl, a haloalkyl, an alkenyl, or a haloalkenyl; wherein each R is independently H, halogen, an alkyl, or an alkenyl;

$R^{1'}$ is absent, H, —C(R)$_3$, —OR, —N(R)$_2$, halogen, an alkyl, a haloalkyl, an alkenyl, or a haloalkenyl; wherein each R is independently H, halogen, an alkyl, or an alkenyl;

$R^2$ is a moiety of formula:

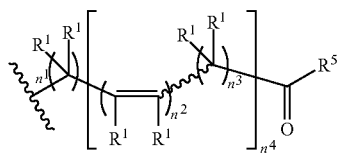

$R^{5'}$ is selected from H, —OH, —OR$^6$, —OCR$^6$R$^7$R$^8$, —CR$^6$R$^7$R$^8$, —NH$_2$, —NHR$^6$, —NR$^6$R$^7$, —CR$^6$R$^7$C(O)NHR$^8$, halogen, alkyl, haloalkyl, alkenyl, haloalkenyl, aryl, heteroaryl, arylalkyl, heterocyclyl, cycloalkyl, cycloalkenyl, acyl, amino acid, nucleoside, monosaccharide having 5 or 6 carbon atoms, a bond connecting to $R^3$ or $R^4$ of another unit of Formula I,

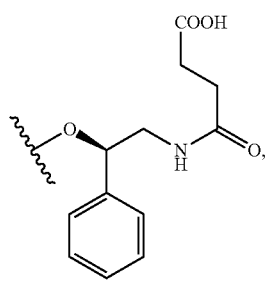

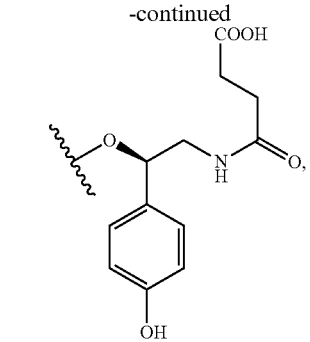

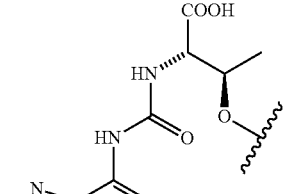

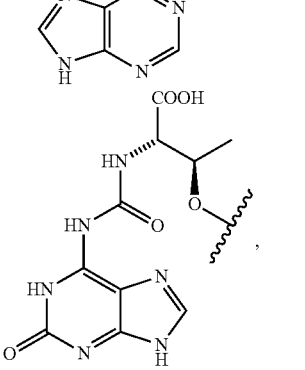

and

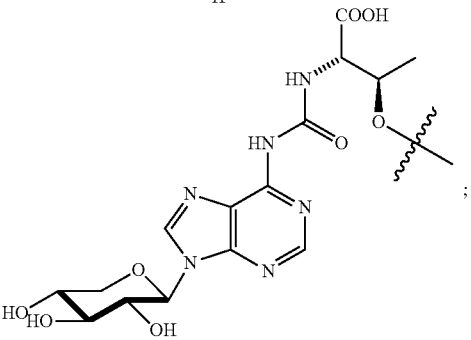

each $R^5$ is independently H, —OH, —OR$^6$, —OCR$^6$R$^7$R$^8$, —CR$^6$R$^7$R$^8$, —NH$_2$, —NHR$^6$, —NR$^6$R$^7$, —CR$^6$R$^7$C(O)NHR$^8$, halogen, an alkyl, a haloalkyl, an alkenyl, a haloalkenyl, an aryl, a heteroaryl, an arylalkyl, a heterocyclyl, a cycloalkyl, a cycloalkenyl, an acyl, an amino acid, a nucleoside, a monosaccharide having 5 or 6 carbon atoms, or a bond connecting to $R^3$ or $R^4$ of another unit of Formula I;

$R^6$ and $R^7$ are each independently H, —CR$_3$, —OR, —N(R)$_2$, halogen, an alkyl, a haloalkyl, an alkenyl, a haloalkenyl, an aryl, a heteroaryl, a heterocyclyl, a cycloalkyl, or a cycloalkenyl, wherein the alkyl, alkenyl, aryl, heteroaryl, heterocyclyl, cycloalkyl, or cycloalkenyl is optionally substituted with one or more substituents independently selected from the group consisting of —OR$^8$, —C(O)R$^8$, —NHC(O)R$^8$, an alkyl, a haloalkyl, an aryl, a heteroaryl, a heterocyclyl, and a cycloalkyl;

each R is independently H, halogen, an alkyl, or an alkenyl;

each $R^8$ is H, —$C(R)_3$, —$[C(R)_2]_{n4}NHC(O)R^9$, —$[C(R)_2]_{n4}C(O)(NH)R^9$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, wherein the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —$OR^9$, —$C(O)R^9$, —$NHC(O)R^9$, halogen, an alkyl, a haloalkyl, an aryl, a heteroaryl, a heterocyclyl, a cycloalkyl, and a monosaccharide having 5 or 6 carbon atoms;

each $R^9$ is H, —$C(R)_3$, —OR, —$N(R)_2$, halogen, an alkyl, a haloalkyl, an alkenyl, a haloalkenyl, an aryl, a heteroaryl, a heterocyclyl, a cycloalkyl, a cycloalkenyl, a purine, a pyrimidine, or a monosaccharide having 5 or 6 carbon atoms, wherein the alkyl, alkenyl, aryl, heteroaryl, heterocyclyl, cycloalkyl, cycloalkenyl, purine, pyrimidine, or monosaccharide is optionally substituted with one or more substituents independently selected from the group consisting of —$C(R)_3$, —OR, —C(O)R, halogen, an alkyl, a haloalkyl, an aryl, a heteroaryl, a heterocyclyl, and a cycloalkyl; wherein each R is independently H, halogen, an alkyl, or an alkenyl; and $n^1$, $n^2$, and $n^3$ are each independently an integer of 0 to 30;

$n^4$ is an integer of 1 to 30;

the sum of $n^1$, each $n^2$, and each $n^3$ is 1 to 30; and $R^3$ and $R^4$ are each independently H, —$CR^6R^7R^8$, —$C(O)R^8$, an alkyl, a haloalkyl, an alkenyl, a haloalkenyl, an aryl, a heteroaryl, a heterocyclyl, a cycloalkyl, a cycloalkenyl, an acyl, an amino acid, a nucleoside, a monosaccharide having 5 or 6 carbon atoms, or a bond connecting to $R^5$ of another unit of Formula I;

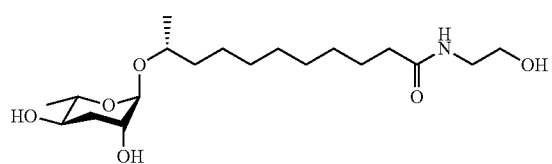

wherein either:

A) $R^{5'}$ is selected from

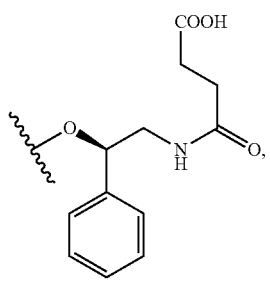

-continued

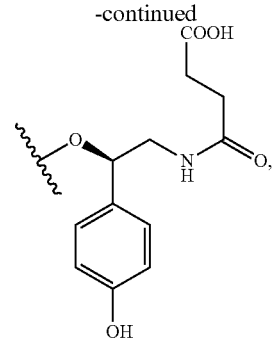

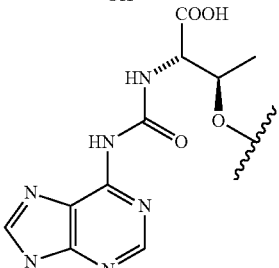

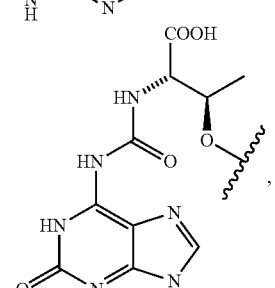

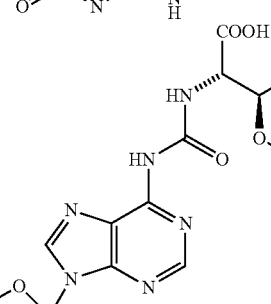

, and

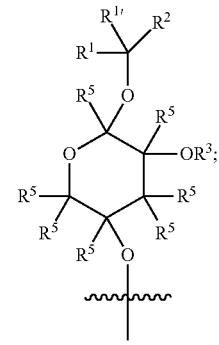

or

B) $R^3$ is C(O)alkyl, substituted with a monosaccharide having 5 or 6 carbon atoms, and
$R^4$ is C(O)alkyl substituted with —$NHC(O)NH_2$.

2. The method according to claim 1, wherein $R^{5'}$ is selected from

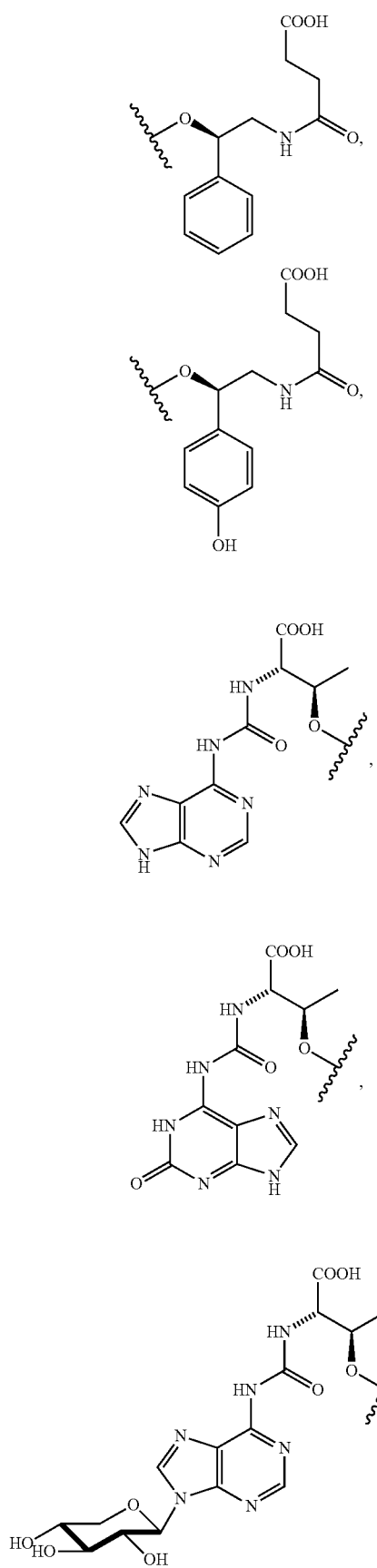
-continued
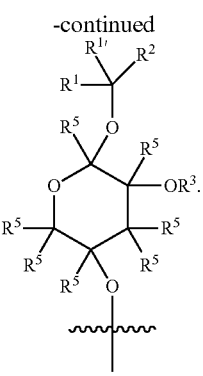
3. The method according to claim 2, wherein the compound is a compound of formula:
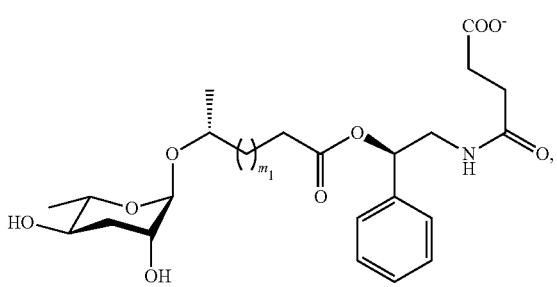
wherein $m_1$ is an integer of 1 to 3.
4. The method according to claim 1, wherein the compound is a compound of Formula IE, IE', IF, or IF':
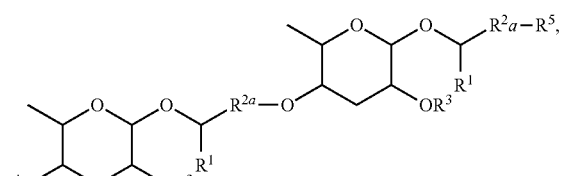
IE
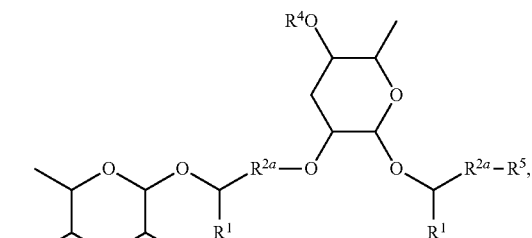
IF
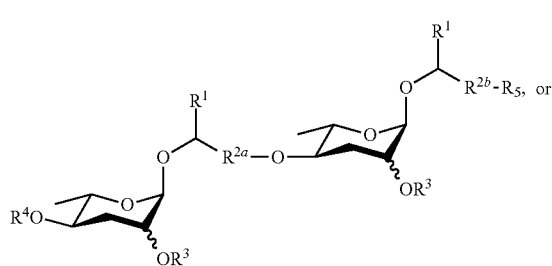
IE'

-continued

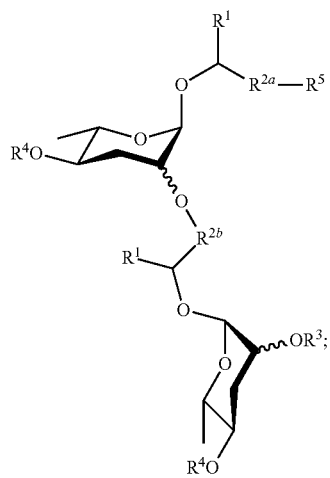

wherein:
R$^{2a}$ and R$^{2b}$ are each independently a moiety of formula IF′

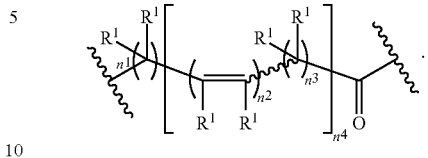

5. The method of claim 1, wherein:
R$^3$ is C(O)alkyl substituted with a monosaccharide having 5 or 6 carbon atoms, and
R$^4$ is C(O)alkyl substituted with —NHC(O)NH$_2$.

6. The method of claim 1, wherein the nematode behavior is selected from reproduction, development, dauer formation, aggregation, attraction, repulsion, dispersal, deterrence, feeding, host finding, and host invasion.

7. A method of modifying behavior of a nematode, comprising:
providing a composition comprising a compound selected from:

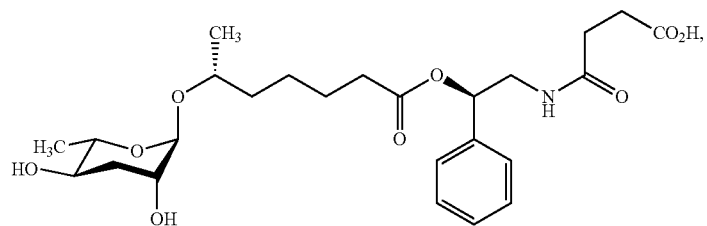

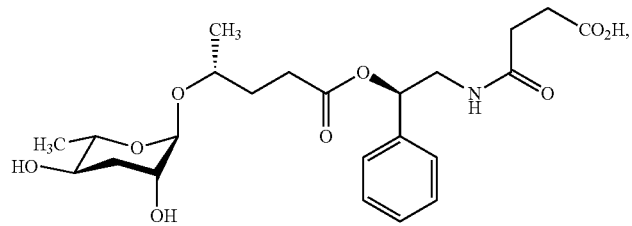

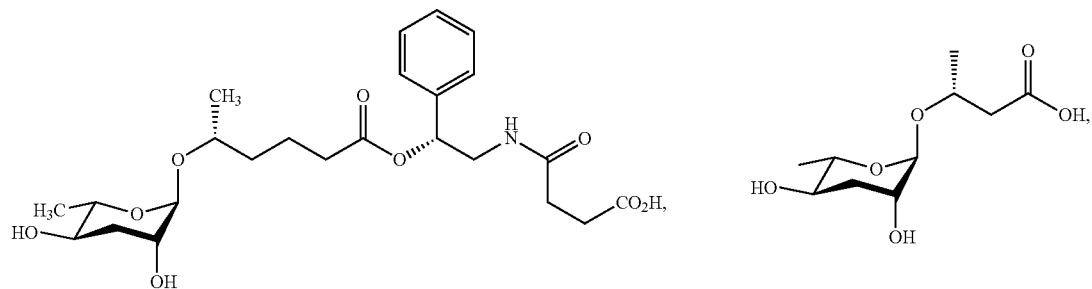

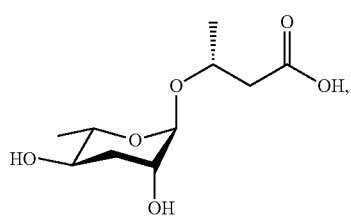

189 190
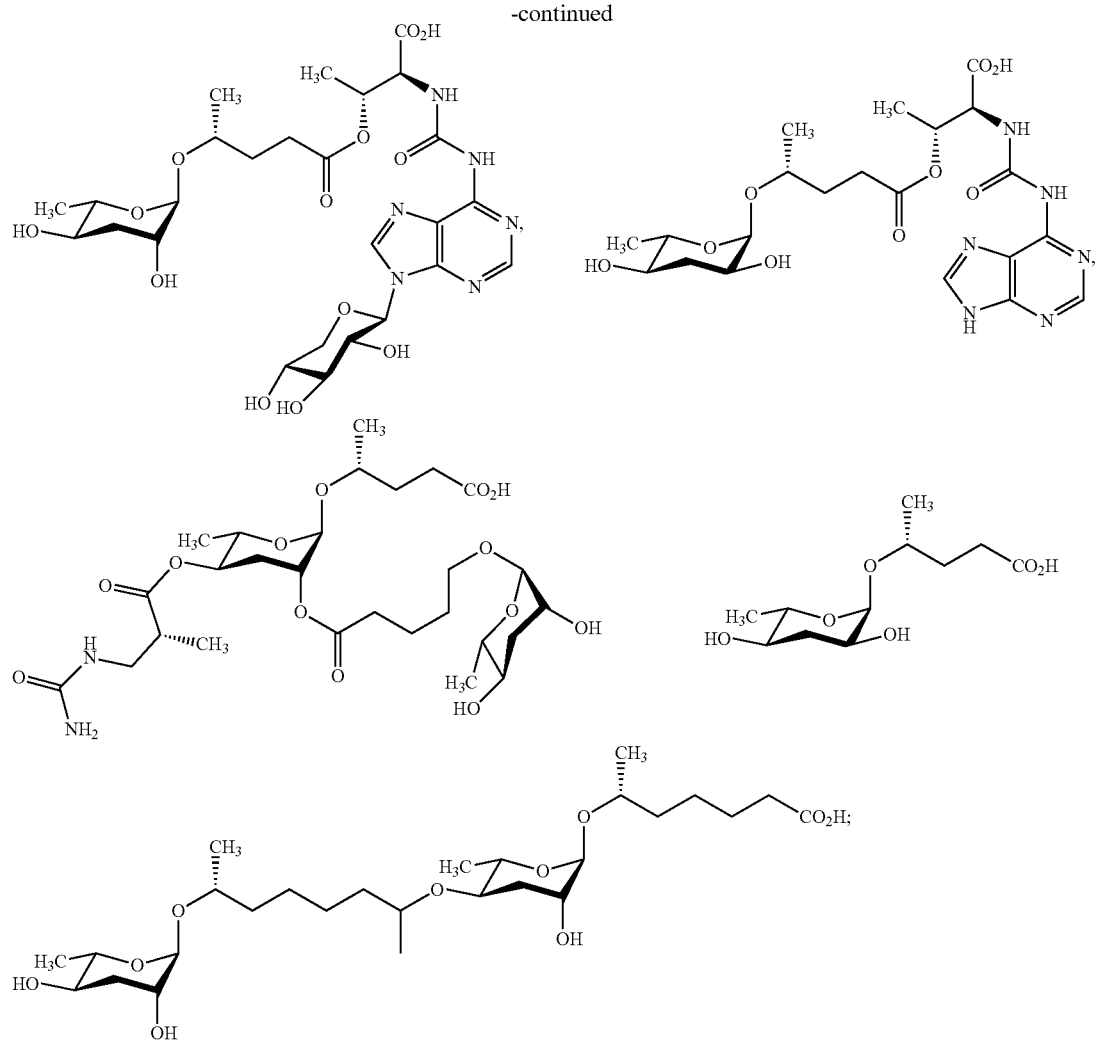
-continued
and administering an effective dosage of the composition to the nematode.
* * * * *